US011370827B2

(12) United States Patent
Chhabra et al.

(10) Patent No.: US 11,370,827 B2
(45) Date of Patent: *Jun. 28, 2022

(54) CHIMERIC FACTOR VIII POLYPEPTIDES AND USES THEREOF

(71) Applicant: BIOVERATIV THERAPEUTICS INC., Waltham, MA (US)

(72) Inventors: Ekta Seth Chhabra, Framingham, MA (US); Tongyao Liu, Lexington, MA (US); Robert T Peters, Needham, MA (US); Haiyan Jiang, Belmont, MA (US)

(73) Assignee: BIOVERATIV THERAPEUTICS INC., Waltham, MA (US)

( * ) Notice: Subject to any disclaimer, the term of this patent is extended or adjusted under 35 U.S.C. 154(b) by 1008 days.

This patent is subject to a terminal disclaimer.

(21) Appl. No.: 14/371,948

(22) PCT Filed: Jan. 12, 2013

(86) PCT No.: PCT/US2013/021330
§ 371 (c)(1),
(2) Date: Jul. 11, 2014

(87) PCT Pub. No.: WO2013/106787
PCT Pub. Date: Jul. 18, 2013

(65) Prior Publication Data
US 2015/0023959 A1 Jan. 22, 2015

Related U.S. Application Data

(60) Provisional application No. 61/586,099, filed on Jan. 12, 2012, provisional application No. 61/586,654, filed on Jan. 13, 2012, provisional application No. 61/667,901, filed on Jul. 3, 2012, provisional application No. 61/734,954, filed on Dec. 7, 2012.

(51) Int. Cl.
*A61K 38/37* (2006.01)
*C07K 14/755* (2006.01)
*A61K 47/62* (2017.01)
*C07K 16/00* (2006.01)

(52) U.S. Cl.
CPC ............ *C07K 14/755* (2013.01); *A61K 47/62* (2017.08); *C07K 16/00* (2013.01); *A61K 38/37* (2013.01); *C07K 2317/94* (2013.01); *C07K 2319/00* (2013.01); *C07K 2319/31* (2013.01)

(58) Field of Classification Search
None
See application file for complete search history.

(56) References Cited

U.S. PATENT DOCUMENTS 4,179,337 A 12/1979 Davis et al.
4,215,051 A 7/1980 Palmer et al.
4,683,195 A 7/1987 Mullis et al.
4,683,202 A 7/1987 Mullis
4,713,339 A 12/1987 Levinson et al.
4,757,006 A 7/1988 Toole, Jr. et al.
4,800,159 A 1/1989 Mullis et al.
4,868,112 A 9/1989 Toole, Jr.
4,965,188 A 10/1990 Mullis et al.
4,965,199 A 10/1990 Capon et al.
4,970,300 A 11/1990 Fulton et al.
4,994,371 A 2/1991 Davie et al.
5,004,803 A 4/1991 Kaufman et al.
5,112,950 A 5/1992 Meulien et al.
5,171,844 A 12/1992 Van Ooyen et al.
5,364,771 A 11/1994 Lollar et al.
5,543,502 A 8/1996 Nordfang et al.
5,595,886 A 1/1997 Chapman et al.
5,610,278 A 3/1997 Nordfang et al.
5,643,575 A 7/1997 Martinez et al.
5,648,260 A 7/1997 Winter et al.
5,658,570 A 8/1997 Newman et al.
5,739,277 A 4/1998 Presta et al.

(Continued)

FOREIGN PATENT DOCUMENTS

CA 2728012 A1 12/2009
CA 2780542 A1 5/2011

(Continued)

OTHER PUBLICATIONS

Counts et al., J Clin Invest. Sep. 1978;62(3):702-9.*
Instructions for Imidoester crosslinkers from Thermo Scientific, 2012, 2 pages.*
Nogami et al., Blood. Jun. 1, 2002;99(11):3993-8.*
Nogami et al., Int J Hematol. May 2007;85(4):317-22.*
Agersoe, H., et al., "Prolonged Effect of N8-Gp in Haemophilia A Dogs Supports Less Frequent Dosing," Journal of Thrombosis and Haemostasis 9(Suppl. 2): 115, Abstract P-MO-181, Abstracts from 2011 ISTH Congress, International Society on Thrombosis and Haemostasis, United States (Jul. 31, 2011).

(Continued)

*Primary Examiner* — Michael Szperka
(74) *Attorney, Agent, or Firm* — Lathrop GPM LLP; James H. Velema, Esq.; James V. DeGiulio, Esq.

(57) ABSTRACT

The present invention provides a VWF fragment comprising the D' domain and D3 domain of VWF, a chimeric protein comprising the VWF fragment and a heterologous moiety, or a chimeric protein comprising the VWF fragment and a FVIII protein and methods of using the same. A polypeptide chain comprising a VWF fragment of the invention binds to or is associated with a polypeptide chain comprising a FVIII protein and the polypeptide chain comprising the VWF fragment can prevent or inhibit binding of endogenous VWF to the FVIII protein. By preventing or inhibiting binding of endogenous VWF to the FVIII, which is a half-life limiting factor for FVIII, the VWF fragment can induce extension of half-life of the FVIII protein. The invention also includes nucleotides, vectors, host cells, methods of using the VWF fragment, or the chimeric proteins.

48 Claims, 32 Drawing Sheets
Specification includes a Sequence Listing.

(56) References Cited

U.S. PATENT DOCUMENTS

| | | |
|---|---|---|
| 5,789,203 A | 8/1998 | Chapman et al. |
| 5,834,250 A | 11/1998 | Wells et al. |
| 5,846,951 A | 12/1998 | Gregoriadis |
| 5,859,204 A | 1/1999 | Lollar |
| 5,869,046 A | 2/1999 | Presta et al. |
| 5,972,885 A | 10/1999 | Spira et al. |
| 5,981,216 A | 11/1999 | Kenten et al. |
| 6,030,613 A | 2/2000 | Blumberg et al. |
| 6,037,452 A | 3/2000 | Minamino et al. |
| 6,048,720 A | 4/2000 | Dalborg et al. |
| 6,060,447 A | 5/2000 | Chapman et al. |
| 6,086,875 A | 7/2000 | Blumberg et al. |
| 6,096,871 A | 8/2000 | Presta et al. |
| 6,121,022 A | 9/2000 | Presta et al. |
| 6,194,551 B1 | 2/2001 | Idusogie et al. |
| 6,228,620 B1 | 5/2001 | Chapman et al. |
| 6,242,195 B1 | 6/2001 | Idusogie et al. |
| 6,251,632 B1 | 6/2001 | Lillicrap et al. |
| 6,277,375 B1 | 8/2001 | Ward |
| 6,316,226 B1 | 11/2001 | Van Ooyen et al. |
| 6,346,513 B1 | 2/2002 | Van Ooyen et al. |
| 6,358,703 B1 | 3/2002 | Cho et al. |
| 6,376,463 B1 | 4/2002 | Lollar |
| 6,458,563 B1 | 10/2002 | Lollar |
| 6,485,726 B1 | 11/2002 | Blumberg et al. |
| 6,528,624 B1 | 3/2003 | Idusogie et al. |
| 6,538,124 B1 | 3/2003 | Idusogie et al. |
| 6,696,245 B2 | 2/2004 | Winter et al. |
| 6,737,056 B1 | 5/2004 | Presta |
| 6,818,439 B1 | 11/2004 | Jolly et al. |
| 6,821,505 B2 | 11/2004 | Ward |
| 6,998,253 B1 | 2/2006 | Presta et al. |
| 7,041,635 B2 | 5/2006 | Kim et al. |
| 7,083,784 B2 | 8/2006 | Dall'Acqua et al. |
| 7,199,223 B2 | 4/2007 | Bossard et al. |
| 7,211,559 B2 | 5/2007 | Saenko et al. |
| 7,317,091 B2 | 1/2008 | Lazar et al. |
| 7,348,004 B2 | 3/2008 | Peters et al. |
| 7,404,956 B2 | 7/2008 | Peters et al. |
| 7,566,701 B2 | 7/2009 | Diener et al. |
| 7,846,445 B2 | 12/2010 | Schellenberger et al. |
| 7,862,820 B2 | 1/2011 | Peters et al. |
| 10,138,291 B2 * | 11/2018 | Chhabra ............. C07K 14/755 |
| 2003/0069395 A1 | 4/2003 | Sato et al. |
| 2003/0143697 A1 | 7/2003 | Stahl et al. |
| 2003/0235536 A1 | 12/2003 | Blumberg |
| 2004/0101740 A1 | 5/2004 | Sanders |
| 2005/0100990 A1 | 5/2005 | Saenko et al. |
| 2005/0147618 A1 | 7/2005 | Rivera et al. |
| 2006/0074199 A1 | 4/2006 | Hirata et al. |
| 2007/0191597 A1 | 8/2007 | Jain et al. |
| 2007/0231329 A1 | 10/2007 | Lazar et al. |
| 2007/0237765 A1 | 10/2007 | Lazar et al. |
| 2007/0237766 A1 | 10/2007 | Lazar et al. |
| 2007/0237767 A1 | 10/2007 | Lazar et al. |
| 2007/0243188 A1 | 10/2007 | Lazar et al. |
| 2007/0248603 A1 | 10/2007 | Lazar et al. |
| 2007/0286859 A1 | 12/2007 | Lazar et al. |
| 2008/0004206 A1 | 1/2008 | Rosen et al. |
| 2008/0057056 A1 | 3/2008 | Lazar et al. |
| 2008/0146782 A1 | 6/2008 | DeFrees et al. |
| 2008/0153751 A1 | 6/2008 | Rosen et al. |
| 2008/0161243 A1 | 7/2008 | Rosen et al. |
| 2008/0194481 A1 | 8/2008 | Rosen et al. |
| 2008/0261877 A1 | 10/2008 | Ballance et al. |
| 2009/0092582 A1 * | 4/2009 | Bogin ................. A61P 5/00 424/85.5 |
| 2009/0118185 A1 | 5/2009 | Fay et al. |
| 2009/0192076 A1 | 7/2009 | Matthiessen et al. |
| 2010/0120664 A1 | 5/2010 | Schulte et al. |
| 2010/0189682 A1 * | 7/2010 | Schellenberger ...... C07K 14/53 424/85.2 |
| 2010/0239554 A1 | 9/2010 | Schellenberger et al. |
| 2010/0285021 A1 | 11/2010 | Jacquemin et al. |
| 2010/0292130 A1 | 11/2010 | Skerra et al. |
| 2010/0323956 A1 | 12/2010 | Schellenberger et al. |
| 2011/0046060 A1 | 2/2011 | Schellenberger et al. |
| 2011/0046061 A1 | 2/2011 | Schellenberger et al. |
| 2011/0077199 A1 | 3/2011 | Schellenberger et al. |
| 2011/0172146 A1 | 7/2011 | Schellenberger et al. |
| 2011/0183907 A1 | 7/2011 | Weimer et al. |
| 2011/0287517 A1 | 11/2011 | Steward et al. |
| 2011/0288005 A1 | 11/2011 | Silverman et al. |
| 2012/0121706 A1 | 5/2012 | Kuliopulos et al. |
| 2012/0178691 A1 | 7/2012 | Schellenberger et al. |
| 2012/0289468 A1 | 11/2012 | Barnett |
| 2013/0017997 A1 | 1/2013 | Schellenberger et al. |
| 2013/0108629 A1 | 5/2013 | Dumont et al. |
| 2015/0023959 A1 | 1/2015 | Chhabra et al. |
| 2015/0266943 A1 | 9/2015 | Chhabra et al. |
| 2016/0229903 A1 | 8/2016 | Chhabra et al. |
| 2016/0251408 A1 | 9/2016 | Chhabra et al. |
| 2017/0073393 A1 | 3/2017 | Chhabra et al. |

FOREIGN PATENT DOCUMENTS

| | | | |
|---|---|---|---|
| CN | 101163506 A | 4/2008 | |
| CN | 101415445 A | 4/2009 | |
| CN | 101480490 A | 7/2009 | |
| CN | 102076855 A | 5/2011 | |
| CN | 102088999 A | 6/2011 | |
| CN | 102348715 A | 2/2012 | |
| EP | 0295597 A2 | 12/1988 | |
| EP | 1867660 A1 | 12/2007 | |
| EP | 1935430 A1 | 6/2008 | |
| JP | 2006-518985 A | 10/2003 | |
| JP | 2010-531135 A | 9/2010 | |
| JP | 2011-528562 A | 11/2011 | |
| WO | WO-8704187 A1 | 7/1987 | |
| WO | WO-8800831 A1 | 2/1988 | |
| WO | WO-8803558 A1 | 5/1988 | |
| WO | WO-8807089 A1 | 9/1988 | |
| WO | WO-8808035 A1 | 10/1988 | |
| WO | WO-9109122 A1 | 6/1991 | |
| WO | WO-9320093 A1 | 10/1993 | |
| WO | WO-9411503 A2 | 5/1994 | |
| WO | WO-9614339 A1 | 5/1996 | |
| WO | WO-9805787 A1 | 2/1998 | |
| WO | WO-9823289 A1 | 6/1998 | |
| WO | WO-9951642 A1 | 10/1999 | |
| WO | WO-9958572 A1 | 11/1999 | |
| WO | WO-0009560 A2 | 2/2000 | |
| WO | WO-0032767 A1 | 6/2000 | |
| WO | WO-0042072 A2 | 7/2000 | |
| WO | WO-0187922 A2 | 11/2001 | |
| WO | WO-0244215 A2 | 6/2002 | |
| WO | WO-02060919 A2 | 8/2002 | |
| WO | WO-03074569 A2 | 9/2003 | |
| WO | WO-03077834 A2 | 9/2003 | |
| WO | WO-2004016750 A2 | 2/2004 | |
| WO | WO-2004029207 A2 | 4/2004 | |
| WO | WO-2004035752 A2 | 4/2004 | |
| WO | WO-2004044859 A1 | 5/2004 | |
| WO | WO-2004063351 A2 | 7/2004 | |
| WO | WO-2004067566 A1 * | 8/2004 | ........... C07K 14/755 |
| WO | WO-2004074455 A2 | 9/2004 | |
| WO | WO-2004099249 A2 | 11/2004 | |
| WO | WO-2005040217 A2 | 5/2005 | |
| WO | WO-2005047327 A2 | 5/2005 | |
| WO | WO-2005070963 A1 | 8/2005 | |
| WO | WO-2005077981 A2 | 8/2005 | |
| WO | WO-2005092925 A2 | 10/2005 | |
| WO | WO-2005123780 A2 | 12/2005 | |
| WO | WO-2006019447 A1 | 2/2006 | |
| WO | WO-2006047350 A2 | 5/2006 | |
| WO | WO-2006085967 A2 | 8/2006 | |
| WO | WO-2007021494 A2 | 2/2007 | |
| WO | WO-2007103515 A2 * | 9/2007 | ......... C12N 15/1044 |
| WO | WO-2007144173 A1 | 12/2007 | |
| WO | WO-2008033413 A2 | 3/2008 | |
| WO | WO-2008057683 A2 | 5/2008 | |
| WO | WO-2008077616 A1 | 7/2008 | |
| WO | WO 2008/151258 A2 | 12/2008 | |
| WO | WO-2008155134 A1 | 12/2008 | |

(56) References Cited

FOREIGN PATENT DOCUMENTS

| | | | | |
|---|---|---|---|---|
| WO | WO-2009023270 A2 * | 2/2009 | | A61P 17/02 |
| WO | WO-2009023270 A3 | 2/2009 | | |
| WO | WO-2009058322 A1 | 5/2009 | | |
| WO | WO-2009062100 A1 | 5/2009 | | |
| WO | WO-2009156137 A1 | 12/2009 | | |
| WO | WO 2010/010051 A1 | 1/2010 | | |
| WO | WO-2010060081 A1 | 5/2010 | | |
| WO | WO-2010091122 A1 * | 8/2010 | | A61P 5/10 |
| WO | WO 2010111414 A1 * | 9/2010 | | C07K 14/755 |
| WO | WO-2010144502 A2 | 12/2010 | | |
| WO | WO-2010144508 A1 | 12/2010 | | |
| WO | WO-2011020866 A2 | 2/2011 | | |
| WO | WO-2011028228 A1 | 3/2011 | | |
| WO | WO-2011028229 A1 | 3/2011 | | |
| WO | WO-2011028344 A2 | 3/2011 | | |
| WO | WO 2011060242 A2 * | 5/2011 | | C07K 14/755 |
| WO | WO-2011060242 A2 | 5/2011 | | |
| WO | WO 2011069164 A2 * | 6/2011 | | A61K 38/37 |
| WO | WO-2011069164 A2 * | 6/2011 | | A61K 47/643 |
| WO | WO-2011101242 A1 | 8/2011 | | |
| WO | WO-2011101284 A1 | 8/2011 | | |
| WO | WO-2012006623 A1 | 1/2012 | | |
| WO | WO-2012006633 A1 | 1/2012 | | |
| WO | WO-2012006635 A1 | 1/2012 | | |
| WO | WO-2013106787 A1 | 7/2013 | | |
| WO | WO-2013122617 A1 | 8/2013 | | |
| WO | WO-2013123457 A1 | 8/2013 | | |
| WO | WO-2014011819 A2 | 1/2014 | | |
| WO | WO-2014210547 A1 | 12/2014 | | |
| WO | WO-2014210558 A1 | 12/2014 | | |
| WO | WO-2015106052 A1 | 7/2015 | | |

OTHER PUBLICATIONS

Armour, K.L., et al., "Recombinant Human IgG Molecules Lacking Fc Gamma Receptor I Binding and Monocyte Triggering Activities," European Journal of Immunology 29(8):2613-2624, Wiley-VCH, Germany (1999).

Arnau, J., et al., "Current strategies for the Use of Affinity Tags and Tag Removal for the Purification of Recombinant Proteins," Protein Expression and Purification 48(1):1-13, Elsevier Inc., United States (2006).

Benhar, I. and Pastan, I., "Cloning, Expression and Characterization of the Fv Fragments of the Anti-Carbohydrate mAbs B1 and B5 as Single-Chain Immunotoxins," Protein Engineering Design and Selection 7(11):1509-1515, Oxford University Press, England (1994).

Burmeister, W.P., et al., "Crystal Structure of the Complex of Rat Neonatal Fc Receptor with Fc," Nature 372(6504):379-383, Nature Publishing Group, England (1994).

Caliceti, P., et al., "Biopharmaceutical Properties of Uricase Conjugated to Neutral and Amphiphilic Polymers," Bioconjugate Chemistry 10(4):638-646, American Chemical Society, United States (1999).

Cameron, C., et al., "The Canine Factor VIII cDNA and 5' Flanking Sequence," Thrombosis and Haemostasis 79(2):317-322, Schattauer, Germany (1998).

Capon, D.J., et al., "Designing CD4 Immunoadhesins for AIDS Therapy," Nature 337(6207):525-531, Nature Publishing Group, England (1989).

Cho, J.W. and Troy, F.A. II, "Polysialic Acid Engineering: Synthesis of Polysialylated Neoglycosphingolipids by Using the Polysialyltransferase from Neuroinvasive *Escherichia coli* K1," Proceedings of the National Academy of Sciences USA 91(24):11427-11431, National Academy of Sciences, United States (1994).

Delgado, C., et al., "The Uses and Properties of PEG-Linked Proteins," Critical Reviews in Therapeutic Drug Carrier Systems 9(3-4):249-304, CRC Press, Inc., United States (1992).

Dennis, M.S., et al., "Albumin Binding as a General Strategy for Improving the Pharmacokinetics of Proteins," The Journal of Biological Chemistry 277(38):35035-35043, American Society for Biochemistry and Molecular Biology, United States (2002).

Dumont, J.A., et al., "Prolonged Activity of a Recombinant Factor VIII-Fc Fusion Protein in Hemophilia A Mice and Dogs," Blood 119(13):3024-3030, The American Society of Hematology, United States (Mar. 29, 2012).

Eaton, D.L., et al., "Construction and Characterization of an Active Factor VIII Variant Lacking the Central One-Third of the Molecule," Biochemistry 25(26):8343-8347, American Chemical Society, United States (1986).

Friend, P.J., et al., "Phase I Study of an Engineered Aglycosylated Humanized CD3 Antibody in Renal Transplant Rejection," Transplantation 68(11):1632-1637, Lippincott Williams & Wilkins, Inc., United States (1999).

GenBank, "*Homo sapiens* Transferrin (TF), mRNA," Accession No. NM001063.3 published on May 25, 2014, accessed at http://www.ncbi.nlm.nih.gov/nuccore/NMJ01063, accessed on Sep. 24, 2014, 5 pages.

GenBank, "*Homo sapiens* Transferrin (TF), mRNA," Accession No. XM002793 published on May 13, 2002, accessed at https://www.ncbi.nlm.nih.gov/nuccore/XM_002793.7?report=genbank, accessed on Sep. 24, 2014, 2 pages.

GenBank, "*Homo sapiens* Transferrin (TF), mRNA," Accession No. XM039847 published on Jul. 16, 2001, accessed at http://www.ncbi.nlm.nih.gov/nuccore/XM_039847.1?report=genbank, accessed on Sep. 24, 2014, 2 pages.

GenBank, "*Homo sapiens* Transferrin (TF), mRNA," Accession No. XM039845 published Jul. 16, 2001, accessed at https://www.ncbi.nlm.nih.gov/nuccore/XM_039845.1?report=genbank, accessed on Sep. 24, 2014, 2 pages.

Genbank, "*Homo sapiens* von Willebrand factor (VWF), mRNA" NCBI Reference Sequence: NM_000552.3, accessed at http://www.ncbi.nlm.nih.gov/nuccore/NM_000552.3, accessed on Mar. 29, 2016, 10 pages.

GenBank, "Human Transferrin mRNA, Complete cds," Accession No. M12530.1, published on Jan. 14, 1995, accessed at http://www.ncbi.nlm.nih.gov/nuccore/M1253014, accessed on Jan. 15, 2015, 2 pages.

GenBank, "Transferrin [human, liver, mRNA, 2347 nt]," Accession No. 595936.1, published on May 7, 1993, accessed at http://www.ncbi.nlm.nih.gov/nuccore/S95936, accessed on Sep. 24, 2014, 2 pages.

Genbank, "transferrin precursor [*Homo sapiens*]" Accession No. AAA61140.1, accessed at http://www.ncbi.nlm.nih.gov/protein/AAA61140, accessed on Mar. 29, 2016, 3 pages.

Genbank, "Von Willebrand factor preproprotein [*Homo sapiens*]," NCBI Reference Sequence: NP_000543.2, accessed at http://www.ncbi.nlm.nih.gov/protein/NP_000543.2, accessed on Mar. 29, 2016, 6 pages.

Gitschier, J., et al., "Characterization of the Human Factor VIII Gene," Nature 312(5992):326-330, Nature Publishing Group, England (1984).

Goudemand, J., et al., "Pharmacokinetic Studies on Wilfactin, a Von Willebrand Factor Concentrate with a Low Factor VIII Content Treated with Three Virus-inactivation/removal Methods," Journal of Thrombosis and Haemostasis 3(10):2219-2227, Blackwell Publishers, England (2005).

Graw, J., et al., "Haemophilia A: From Mutation Analysis to New Therapies," Nature Reviews. Genetics 6(6):488-501, Nature Publishing Group, England (2005).

Healey, J.F., et al., "The cDNA and Derived Amino Acid Sequence of Porcine Factor VIII," Blood 88(11):4209-4214, The American Society of Hematology, United States (1996).

Ho, S.N., et al., "Site-Directed Mutagenesis by Overlap Extension Using the Polymerase Chain Reaction," Gene 77(1):51-59, Elsevier Science Publishers B.V., Netherlands (1989).

Hoeben, R.C., et al, "Expression of Functional Factor VIII in Primary Human Skin Fibroblasts after Retrovirus-mediated Gene Transfer," The Journal of Biological Chemistry 265(13):7318-7323, The American Society for Biochemistry and Molecular Biology, United States (1990).

Horton, R.M., et al., "Gene Splicing by Overlap Extension," Methods in Enzymology 217:270-279, Academic Press, United States (1993).

(56) References Cited

OTHER PUBLICATIONS

International Search Report and Written Opinion for International Application No. PCT/US2015/010738, ISA/US, Alexandria, Virginia, United States, dated May 15, 2015, 4 pages.
International Search Report and Written Opinion for International Patent Application No. PCT/US2013/021330, United States Patent Office, Alexandria, Virginia, dated Apr. 29, 2013, 4 pages.
International Search Report and Written Opinion for International Patent Application No. PCT/US2013/049989, United States Patent Office, Alexandria, Virginia, dated Dec. 16, 2013, 5 pages.
International Search Report and Written Opinion for International Patent Application No. PCT/US2014/044731, United States Patent Office, Alexandria, Virginia, dated Nov. 4, 2014, 4 pages.
International Search Report and Written Opinion and Written Opinion for International Patent Application No. PCT/US2014/044718, United States Patent Office, Alexandria, Virginia, dated Nov. 4, 2014, 10 pages.
Israel, E.J., et al., "Expression of the neonatal Fc receptor, FcRn, on human intestinal epithelial cells," Immunology 92(1):69-74, Blackwell Sciences, England (1997).
Kasuda, S., et al., "Establishment of Embryonic Stem Cells Secreting Human Factor VIII for Cell-Based Treatment of Hemophilia A," Journal of Thrombosis and Haemostasis 6(8):1352-1359, International Society on Thrombosis and Haemostasis, England (2008).
Kobayashi, N., et al., "FcRn-Mediated Transcytosis of Immunoglobulin G in Human Renal Proximal Tubular Epithelial Cells," American Journal of Physiology 282(2):F358-F365, American Physiological Society, United States (2002).
Konig, T. and Skerra, A., "Use of an Albumin-Binding Domain for the Selective Immobilisation of Recombinant Capture Antibody Fragments on ELISA Plates," Journal of Immunological Methods 218(1-2):73-83, Elsevier Science B.V., Netherlands (1998).
Langner, K-D., et al., "Synthesis of Biologically Active Deletion Mutants of Human Factor VIII:C," Behring Institute Mitteilungen 82:16-25, Behringwerke AG, Germany (1988).
Larrick, J.W., et al., "Rapid Cloning of Rearranged Immunoglobulin Genes from Human Hybridoma Cells using Mixed Primers and the Polymerase Chain Reaction," Biochemical and Biophysical Research Communications 160(3):1250-1256, Academic Press, United States (1989).
Lee, M.T, "Ch. 12: Disorders of Coagulation" in Pediatric Hematology Secrets, Weiner M.A. and Cario, M.S. eds., pp. 47-52, Hanley & Belfus, United States (2001).
Lenting, P.J., et al., "Clearance Mechanisms of Von Willebrand Factor and Factor VIII," Journal of Thrombosis and Haemostasis 5(7):1353-1360, International Society on Thrombosis and Haemostasis, England (2007).
Lenting, P.J., et al., "The Life Cycle of Coagulation Factor VIII in View of its Structure and Function," Blood, 92(11):3983-3996, American Society of Hematology, United States (1998).
Leyte, A.,et al., "Sulfation of Tyr1680 of Human Blood Coagulation. Factor VIII is Essential for the Interaction of Factor VIII with Von Willebrand factor," The Journal of Biological Chemistry 266(2):740-746, The American Society for Biochemistry and Molecular Biology,Inc., United States (1991).
Lillicrap, D., "Extending Half-life in Coagulation Factors: Where do We Stand?," Thrombosis Research, 122 Suppl 4:S2-S8, Pergamon Press, United States (2008).
Liu, T. et al., "Evaluation of Peg-FVIII Molecules with Prolonged Half-lives in a Murine FVIII-Dependent Bleeding Model," Journal of Thrombosis and Haemostasis 5(Suppl. 2): Abstract P-M-035, Abstracts from 2007 ISTH Congress, International Society on Thrombosis and Haemostasis, United States (2007).
Liu, T., et al., "Recombinant FVIII Fc Fusion Protein is Fully Active in Treating Acute Injury and Demonstrates Prolonged Prophylactic Efficacy in Hemophilia a Mice," Journal of Thrombosis and Haemostasis 9(Suppl. 2): 561, Abstract P-WE-131, Abstracts from 2011 ISTH Congress, International Society on Thrombosis and Haemostasis, United States (Jul. 27, 2011).

Logan, J., et al., "Adenovirus Tripartite Leader Sequence Enhances Translation of mRNAs Late After Infection," Proceedings of the National Academy of Sciences USA 81(12):3655-3659, National Academy of Sciences, United States (1984).
Mackett, M., et al., "General Method for Production and Selection of Infectious Vaccinia Virus Recombinants Expressing Foreign Genes," Journal of Virology 49(3):857-864, American Society for Microbiology, United States (1984).
Mackett, M., et al., "Vaccinia Virus: A Selectable Eukaryotic Cloning and Expression Vector," Proceedings of the National Academy of Sciences USA 79(23):7415-7419, National Academy of Sciences, United States (1982).
McCue, J.T., et al., "Application of a Novel Affinity Adsorbent for the Capture and Purification of Recombinant Factor VIII Compounds," Journal of Chromatography A 1216(45):7824-7830, Elsevier, Netherlands (2009).
Mei, B., et al., "Expression of Human Coagulation Factor VIII in a Human Hybrid Cell Line, HKB11," Molecular Biotechnology 34(2):165-178, Humana Press Inc., United States (2006).
Meulien, P., et al., "A New Recombinant Procoagulant Protein Derived from the cDNA Encoding Human Factor VIII," Protein Engineering 2(4):301-306, IRL Press Ltd., England (1988).
Miao, H.Z., et al., "Bioengineering of Coagulation Factor VIII for Improved Secretion," Blood 103(9):3412-3419, The American Society of Hematology, United States (2004).
Morpurgo, M., et al., "Covalent Modification of Mushroom Tyrosinase with Different Amphiphic Polymers for Pharmaceutical and Biocatalysis Applications," Applied Biochemistry and Biotechnology 56(1):59-72, Humana Press, Inc., United States (1996).
Mount, J.D., et al., "Sustained Phenotypic Correction of Hemophilia B dogs with a Factor IX Null Mutation by Liver-Directed Gene Therapy," Blood 99(8):2670-2676, The American Society of Hematology, United States (2002).
National Heart Lung and Blood Institute, "The Diagnosis, Evaluation and Management of von Willebrand Disease Scientific Overview," accessed at http://www.nhlbi.nih.gov/guidelines/vwd/2scientificoverview.htm, accessed on Oct. 22, 2011.
Neumann, E., et al., "Gene Transfer into Mouse Lyoma Cells by Electroporation in High Electric Fields," The EMBO Journal 1(7):841-845, IRL Press Limited, England (1982).
Ngo, J.C., et al., "Crystal Structure of Human Factor VIII: implications for the Formation of the Factor IXa-factor VIIIa Complex," Structure 16(4):597-606, Elsevier Ltd., United States (2008).
Panicali, D., et al., "Construction of Poxviruses as Cloning Vectors: Insertion of the Thymidine Kinase Gene from Herpes Simplex Virus into the DNA of Infectious Vaccinia Virus," Proceedings of the National Academy of Sciences of the United States of America 79(16):4927-4931, The National Academy of Sciences of the United States (1982).
Peters, R.T., et al., "Biochemical and Functional Characterization of a Recombinant Monomeric Factor VIII-Fc Fusion Protein," Journal of Thrombosis and Haemostasis 11(1):132-141, Blackwell Pub, England (Jan. 2013).
Pipe, S.W., et al., "Functional Factor VIII made with Von Willebrand Factor at High Levels in Transgenic Milk," Journal of Thrombosis and Haemostasis 9(11):2235-2242, International Society on Thrombosis and Haemostasis, England (Nov. 2011).
Powell, J.S., et al., "Safety and Prolonged Activity of Recombinant Factor VIII Fc Fusion Protein in Hemophilia a Patients," Blood 119(13):3031-3037, The American Society of Hematology, United States (Mar. 29, 2012).
Roth, J. et al., "From Microbes to Man" in Polysialic Acid, Roth J., Rutishauser U., Troy F.A., eds., pp. 335-348, BirkhauserVerlag, Basel, Switzerland (1993).
Routledge, E.G., et al., "The Effect of Aglycosylation on the Immunogenicity of a Humanized Therapeutic CD3 Monoclonal Antibody," Transplantation 60(8):847-853, Williams & Wilkins, United States (1995).
Ruberti, F., et al., "The Use of the RACE Method to Clone Hybridoma cDNA When V Region Primers Fail," Journal of Immunological Methods 173(1):33-39, Elsevier, United States (1994).

(56) References Cited

OTHER PUBLICATIONS

Ruther, U. and Muller-Hill, B., "Easy Identification of cDNA Clones," The EMBO Journal 2(10):1791-1794, IRL Press Ltd, England (1983).
Saenko, E.L., et al., "A Role for the C2 Domain of Factor VIII in Binding to Von Willebrand Factor," Journal of Biological Chemistry 269(15):11601-11605, American Society for Biochemistry and Molecular Biology, United States (1994).
Sambrook, J., et al., "Molecular Cloning: A Laboratory Manual," Second Edition, Cold Spring Harbor Laboratory Press, United States (1989).
Sarver, N., et al., "Stable Expression of Recombinant Factor VIII Molecules Using a Bovine Papillomavirus Vector," DNA 6(6):553-564, Mary Ann Liebert, Inc., United States (1987).
Schellenberger, V., et al., "A Recombinant Polypeptide Extends the in Vivo Half-Life of Peptides and Proteins in a Tunable Manner," Nature Biotechnology 27(12):1186-1190, Nature America, Inc., United States (2009).
Schlapschy, M., et al., "Fusion of a Recombinant Antibody Fragment with a Homo-amino-acid Polymer: Effects on Biophysical Properties and Prolonged Plasma Half-Life," Protein Engineering Design and Selection 20(6):273-284, Oxford University Press, England (2007).
Shen, B.W., et al., "The Tertiary Structure and Domain Organization of Coagulation Factor VIII," Blood 111(3):1240-1247, The American Society of Hematology, United States (2008).
Shields, R.L., et al., "High Resolution Mapping of the Binding Site on Human IgG1 for Fc gamma RI, Fc gamma RII, Fc gamma RIII, and FcRn and Design of IgG1 Variants with Improved Binding to the Fc gamma R," The Journal of Biological Chemistry 276(9):6591-6604, American Society for Biochemistry and Molecular Biology, United States (2001).
Simonsen, C.C., et al., "Isolation and Expression of an Altered Mouse Dihydrofolate Reductase cDNA," Proceedings of the National Academy of Sciences 80(9):2495-2499, National Academy of Sciences, United States (1983).
Smith, G.E., et al., "Molecular Engineering of the Autographa Californica Nuclear Polyhedrosis Virus Genome: Deletion Mutations Within the Polyhedrin Gene," Journal of Virology 46(2):584-593, American Society for Microbiology, United States (1983).
Smith, T.F. and Waterman, M.S., "Comparison of Biosequences," Advances in Applied Mathematics 2(4):482-489, Academic Press, Inc., United States (1981).
Sommermeyer, V.K., et al., "Klinisch Verwendete Hydroxyethylstarke: Physikalisch-Chemische Charakterisierung," Krankenhauspharmazie 8(8):271-278, Deutscher Apotheker Verlag, Birkenwaldstr, Germany (1987).
Story, C.M., et al., "A Major Histocompatibility Complex Class I-like Fc Receptor Cloned from Human Placenta: Possible Role in Transfer of Immunoglobulin G from Mother to Fetus," The Journal of Experimental Medicine 180(6):2377-2381, The Rockefeller University Press, United States (1994).
Toole, J.J., et al., "A Large Region (≈95 kDa) of Human Factor VIII is Dispensable for in vitro Procoagulant Activity," Proceedings of the National Academy of Sciences USA 83(16):5939-5942, National Academy of Sciences, United States (1986).
Toole, J.J., et al., "Molecular Cloning of a cDNA Encoding Human Antihaemophilic Factor," Nature 312(5992):342-347, Nature Publishing Group, England (1984).
Vehar, G.A., et al., "Structure of Human Factor VIII," Nature 312(5992):337-342, Nature Publishing Group, England (1984).
Vorobjev, P.E., et al., "Oligonucleotide Conjugated to Linear and Branched High Molecular Weight Polyethylene Glycol as Substrates for RNase H," Nucleosides & Nucleotides 18(11-12):2745-2750, Marcel Dekker, Inc., United States (1999).
Ward, E.S. and Ghetie, V., "The Effector Functions of Immunoglobulins: Implications for Therapy," Therapeutic Immunology 2(2):77-94, Blackwell Science Ltd., England (1995).
Weidler, B., et al., "Pharmakokinetische Merkmale als Kriterien fur den klinischen Einsatz von Hydroxyethylstarke," Arzneimittel-Forschung 41(5):494-498, Editio Cantor, Germany (1991).
Wigler, M., et al., "Biochemical Transfer of Single-Copy Eucaryotic Genes Using Total Cellular DNA as Donor," Cell 14(3):725-731, Cell Press, United States (1978).
Wood, W.I., et al., "Expression of Active Human Factor VIII from Recombinant DNA Clones," Nature 312(5992):330-337, Nature Publishing Group, England (1984).
Zhou, Y.F., et al., "Sequence and Structure Relationships within von Willebrand Factor," Blood 120(2):449-458, American Society of Hematology, United States (Jul. 12, 2012).
Co-pending U.S. Appl. No. 15/110,673, inventors Chhabra, E.S. et al., filed Jan. 9, 2015 (Not Published).
Alvarez, P., et al., "Improving Protein Pharmacokinetics by genetics Fusion to Simple Amino Acid Sequences," The Journal of Biological Chemistry 279(5):3375-3381, American Society for Biochemistry and Molecular Biology, United States (2003).
Proft, T., "Sortase-mediated protein ligation: an emerging biotechnology tool for protein modification and immobilization," Biotechnology Letters 32:1-10, Springer Science+Business Media B.V., Netherlands (Sep. 2009).
Counts, R. B., et al., "Disulfide Bonds and the Quaternary Structure of Factor VIII/von Willebrand Factor," J. Clin. Invest. 62(3):702-09, The American Society for Clinical Investigation, Inc. (1978).
Thermo Scientific, "Instructions: Imidoester Crosslinkers: DMA, DMP, DMS, DTBP," available at https://tools.thermofisher.com/content/sfs/manuals/MAN0011314_ImidoesterCrsLnk_DMA_DMP_DMS_DTBP_UG.pdf, 2 pages (2012).
Nogami, K., et al., "A novel mechanism of factor VIII protection by von Willebrand factor from activated protein C-catalyzed inactivation," Blood 99(11):3993-98, American Society of Hematology (2002).
Nogami, K., et al., "Relationship between the binding sites for von Willebrand factor, phospholipid, and human factor VIII C2 inhibitor alloantibodies within the factor VIII C2 domain," Int. J. Hematol. 85(4):317-22, Springer (2007).
Office Action dated Jul. 21, 2017, in U.S. Appl. No. 14/413,765, inventor Ekta Seth Chhabra, filed Jul. 10, 2013.
Office Action dated Mar. 29, 2017, in U.S. Appl. No. 14/413,765, inventor Ekta Seth Chhabra, filed Jul. 10, 2013.
Office Action dated May 23, 2017, in U.S. Appl. No. 14/894,108, inventor Ekta Seth Chhabra, filed May 3, 2016.
Engels, et al., "Gene Synthesis," Angewandte Chemie International Edition, 28(6):716-734, VCH Verlagsgesellschaft mbH, Germany (1989).
Pool, J.G., et al., "Ineffectiveness of intramuscularly injected Factor 8 concentrate in two hemophilic patients," The New England Journal of Medicine 275(10):547-548, Massachusetts Medical Society, United States (1966).
Office Action dated Sep. 27, 2017, in U.S. Appl. No. 14/379,192, inventor Ekta Seth Chhabra, filed Feb. 20, 2015.
Meloun, B., et al., "Complete Amino Acid Sequence of Human Serum Albumin," FEBS Letter 58(1):134-137, John Wiley & Sons, United States (1975).
Office Action dated May 30, 2017, in U.S. Appl. No. 14/379,192, inventor Ekta Seth Chhabra, filed Feb. 20, 2015.
Office Action dated Nov. 1, 2016, in U.S. Appl. No. 14/379,192, inventor Ekta Seth Chhabra, filed Feb. 20, 2015.
Li, X., et al., "The Physical Exchange of Factor VIII (FVIII) between von Willebrand factor and Activated Platelets and the Effect of the FVIII B-Domain on Platelet Binding," Biochemistry 36:10760-10767, Portland Press, United States (1997).
Woof, J.M., et al., "Human antibody-Fc receptor interactions illuminated by crystal structures.," Nat Rev Immunology 4(2):89-99, Nature Publishing Group, United States (2004).
Office Action dated Dec. 15, 2017, in U.S. Appl. No. 14/894,108, inventor Ekta Seth Chhabra, filed May 3, 2016.
Office Action dated Jan. 26, 2018, in U.S. Appl. No. 14/895,264, inventor Ekta Seth Chhabra, filed Dec. 2, 2015.
Office Action dated Mar. 16, 2018, in U.S. Appl. No. 14/379,192, inventor Schellenberger V., filed Feb. 20, 2015.

(56) References Cited

OTHER PUBLICATIONS

Office Action dated Apr. 30, 2018, in U.S. Appl. No. 14/379,196 , inventor Kulman, J , filed Aug. 15, 2014.
Office Action dated Sep. 7, 2018, in U.S. Appl. No. 14/895,264, inventor Ekta Seth Chhabra, filed Dec. 2, 2015.
Office Action dated Aug. 7, 2018, in U.S. Appl. No. 14/379,192 , inventor Schellenberger V., filed Feb. 20, 2015.
Office Action dated Sep. 5, 2018, in U.S. Appl. No. 14/379,196 , inventor Kulman, J , filed Aug. 15, 2014.
Nieman, M.T., et al., "Interaction of thrombin with PAR1 and PAR4 at the thrombin cleavage site," *Biochemistry* 46(29):8603-8610, American Chemistry Society, United States (2007).
Extended European Search report received for European Application No. 13735649.9, dated Nov. 3, 2015, 8 pages.

\* cited by examiner

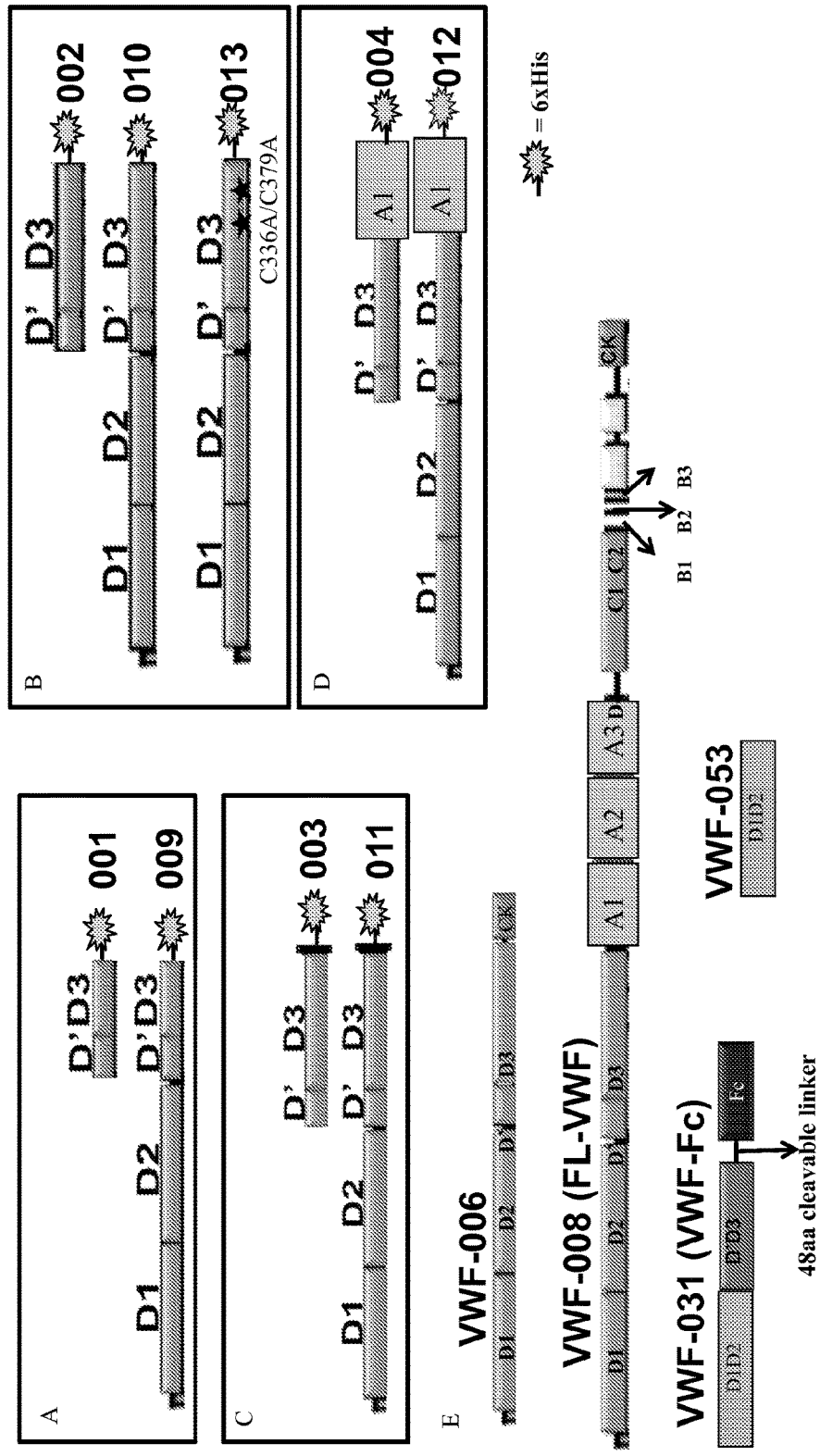
Figure 1: Different VWF Constructs

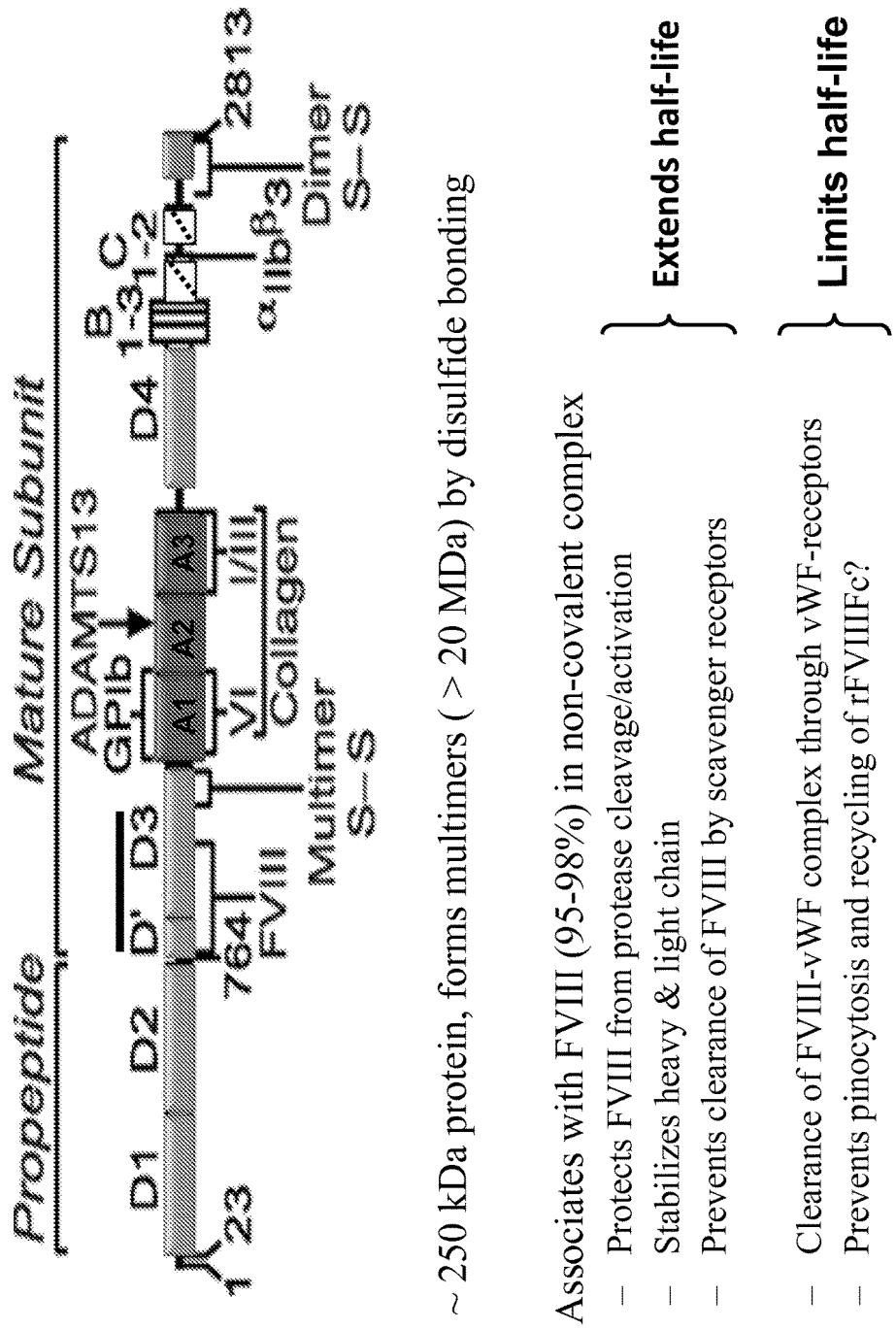
Figure 1F: Von Willebrand Factor

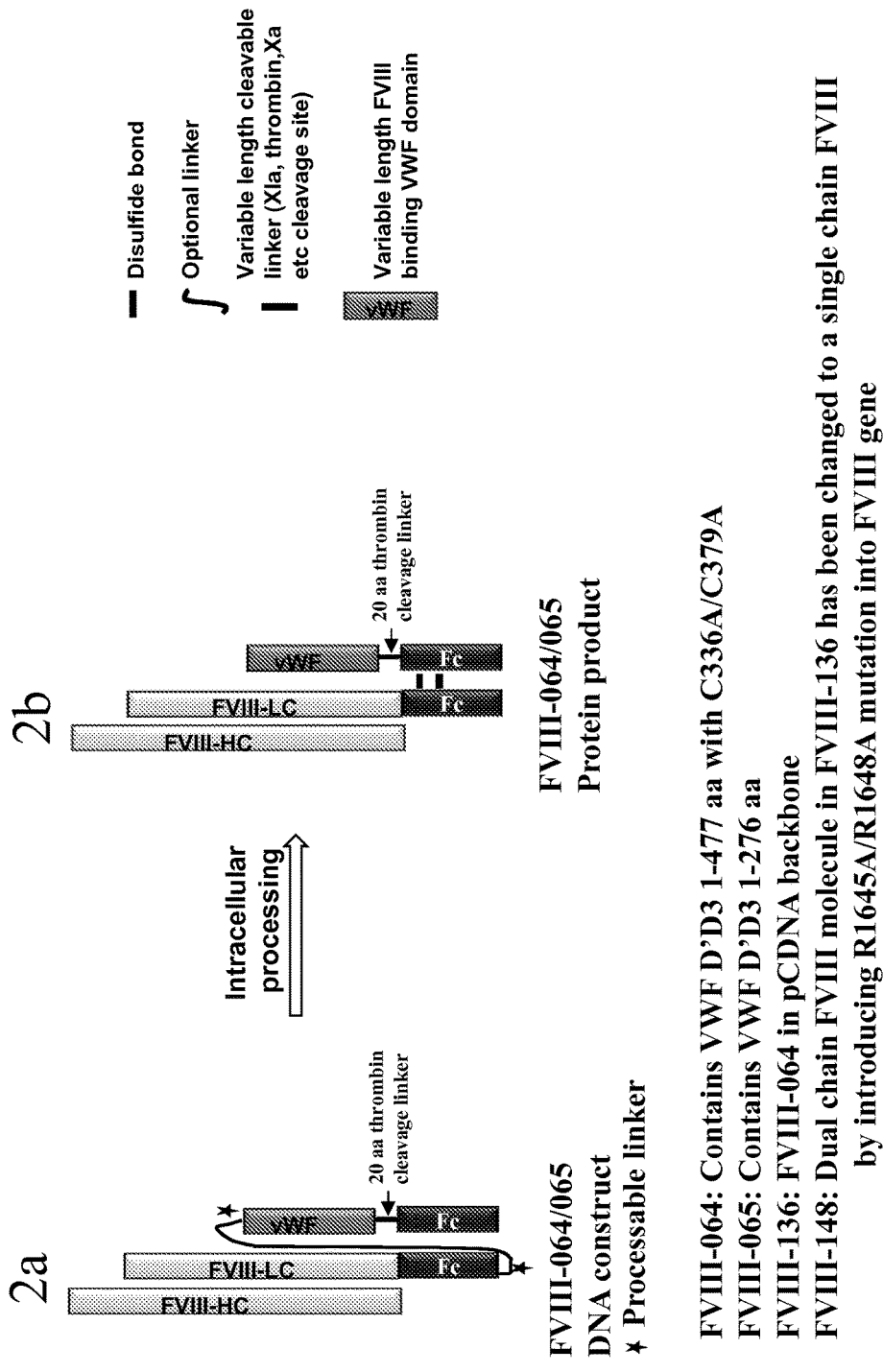

Figure 3: FVIII Constructs (variable linker)

| DNA construct | Linker between VWF and Fc |
|---|---|
| FVIII-064 | 20 aa= ID {2X(GGGGS)}LVPRGSGG |
| FVIII-159 | 35 aa= IS{5X(GGGGS)}LVPRGSGG |
| FVIII-160 and its derivatives | FVIII-160: 48 aa= IS{6X(GGGGS)}LVPRGSGGGSGGGGS |
| | FVIII-180: FVIII-160 with K2092A mutation in FVIII C1 domain |
| | FVIII-181: FVIII-160 with F2093A mutation in FVIII C1 domain |
| | FVIII-182: FVIII-160 with K2092A/F2093A mutations in FVIII C1 domain |
| FVIII-178 | 73 aa= IS{11X(GGGGS)}LVPRGSGGGSGGGGS |
| FVIII-179 | 98 aa= IS{16X(GGGGS)}LVPRGSGGGSGGGGS |
| VWF= D'D3 (1-477aa with C336A/C379A) | |

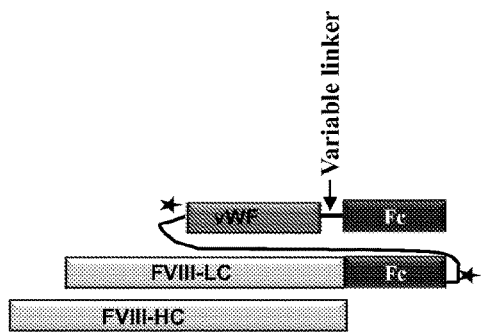

FVIII-064, 159, 160, 178, 179
★ In vivo processable linker

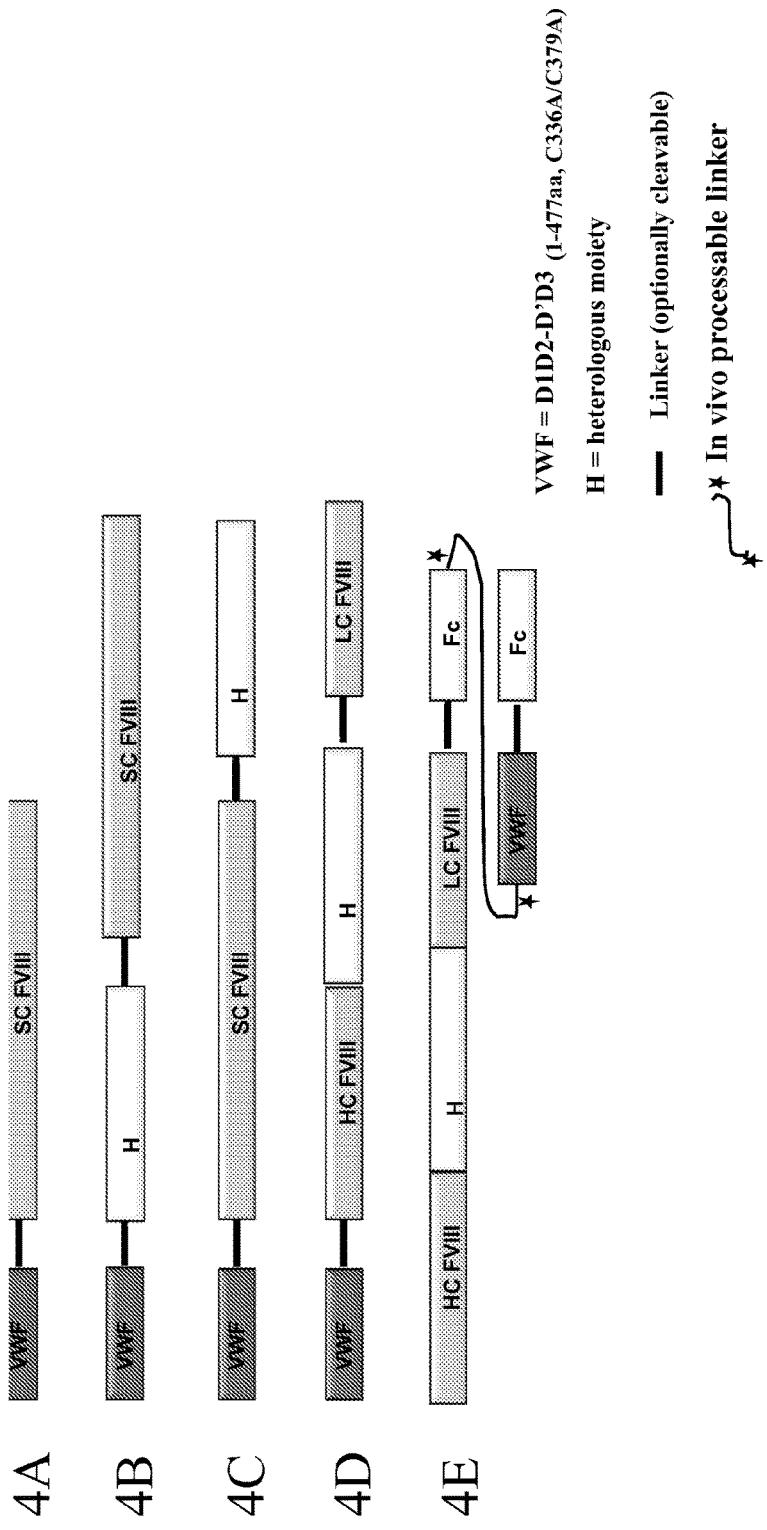
Figure 4: FVIII Constructs

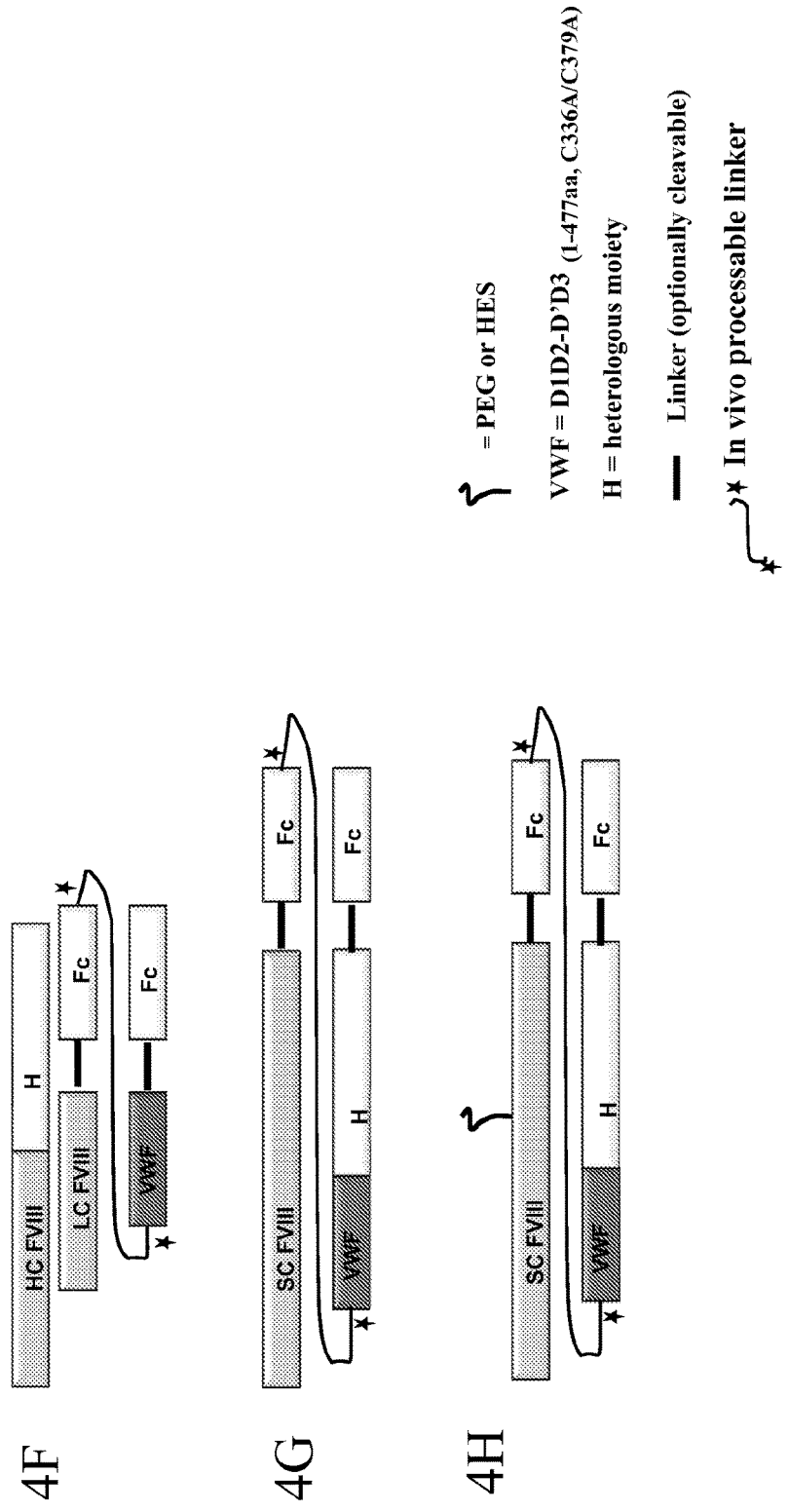
Figure 4: FVIII Constructs (continued)

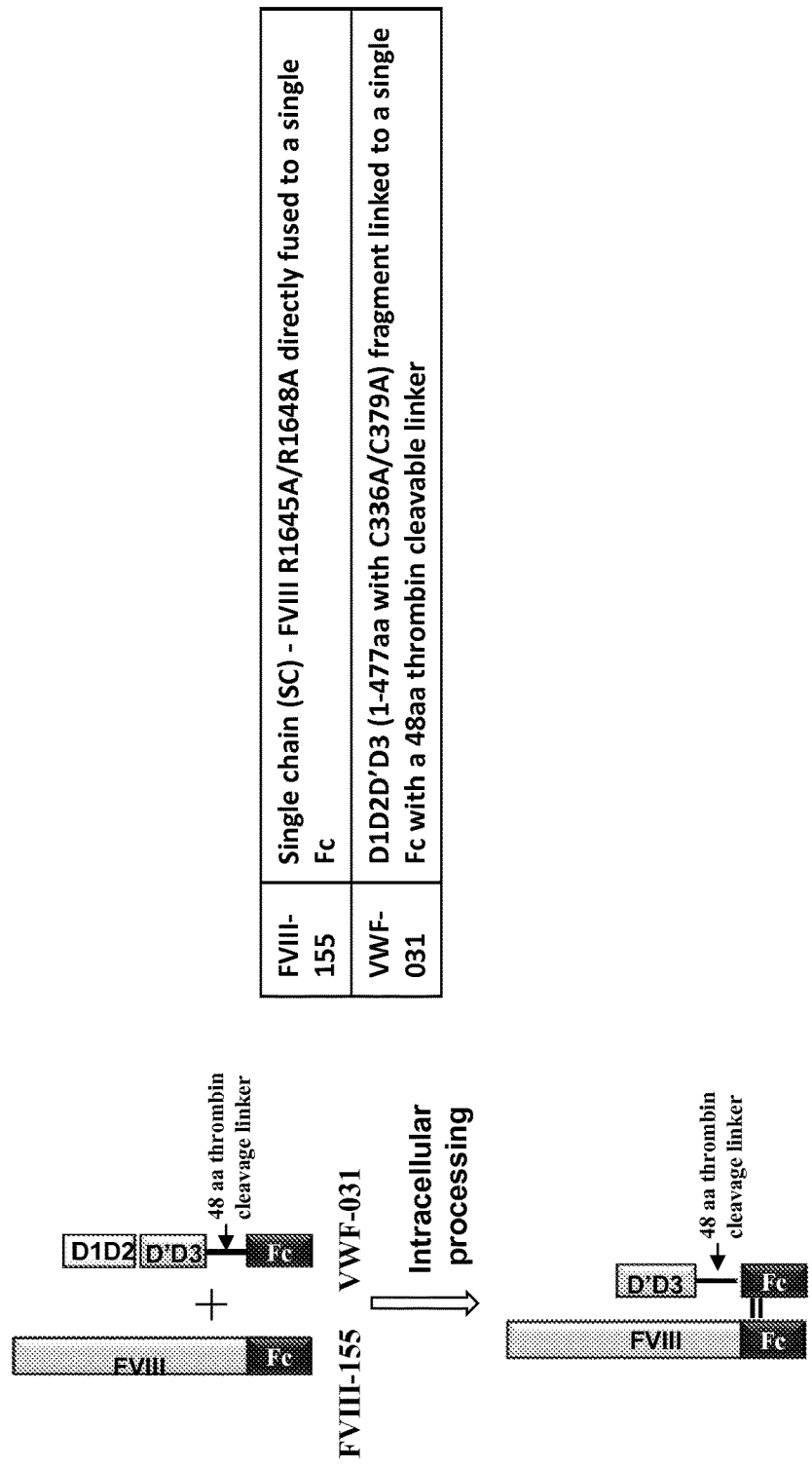
Figure 5: FVIII Constructs (Co-transfection system)

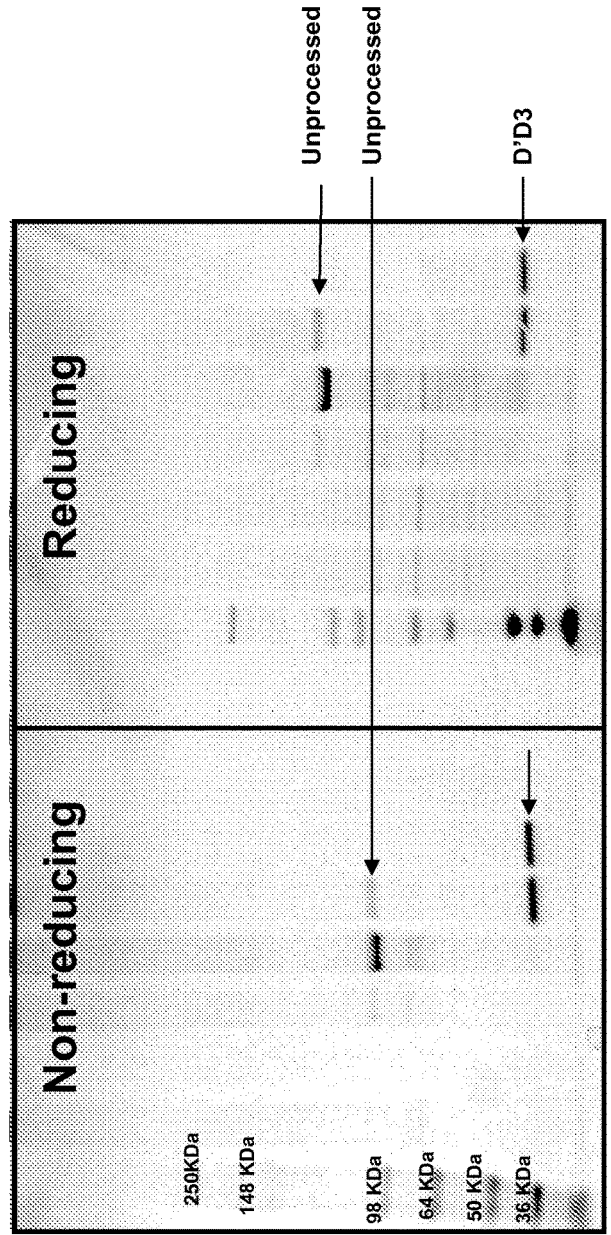
Figure 6: Purification of VWF 009 (D1D2D'D3 $_{1-276\,aa}$ x 6 his)

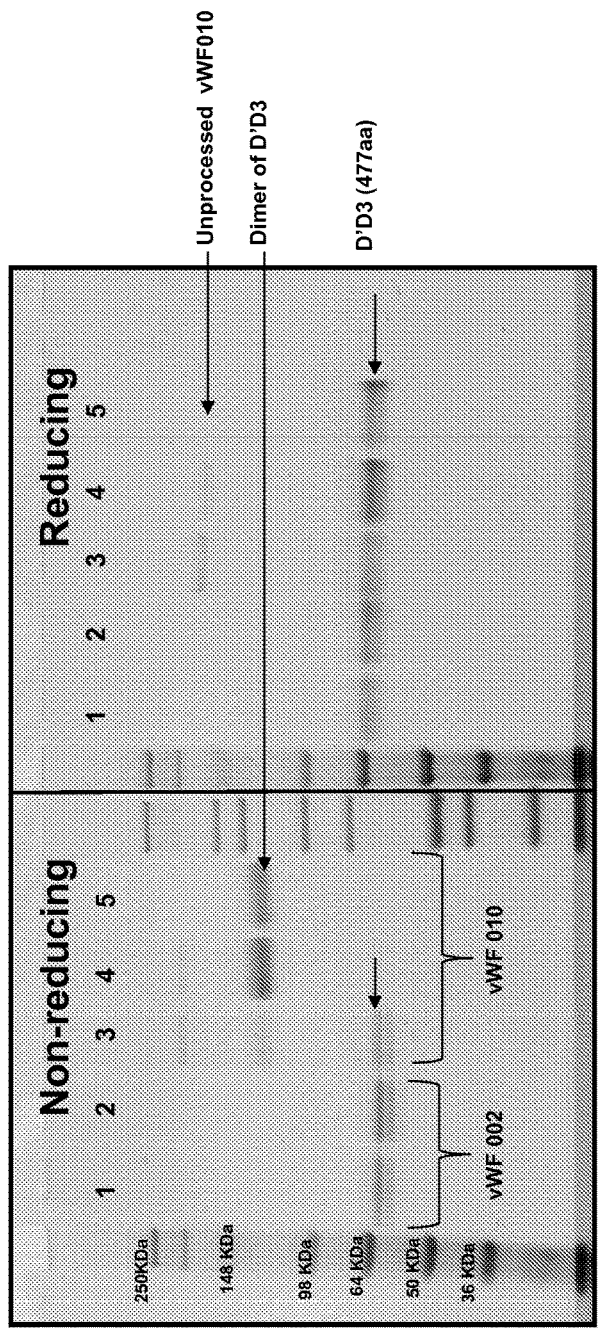
Figure 7: Purified vWF 002 and 010 (D'D3 $_{1-477\,aa}$ x 6 his)
Doublet around 60kDa shows different glycosylation state
1- vWF -002 IMAC Fraction 1A3
2- vWF -002 IMAC Fraction 1B1
3- vWF -010 IMAC Fraction 1B3
4- vWF -010 IMAC Fraction 2A1
5- vWF -010 IMAC Fraction 2A2

Figure 8: Thrombin digestion of FVIII-VWF heterodimer
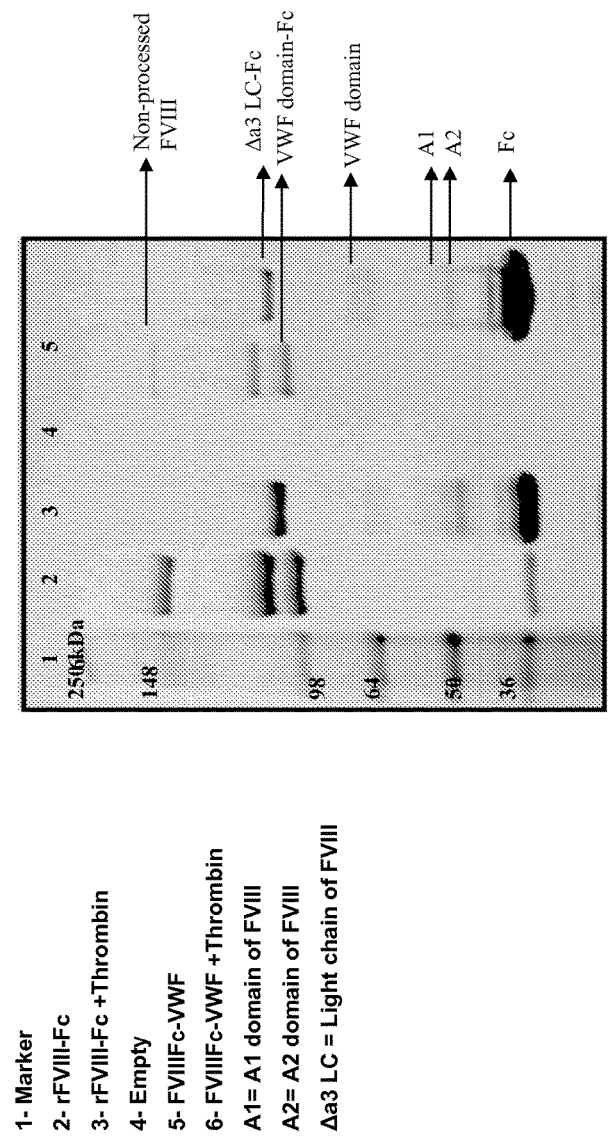
1- Marker
2- rFVIII-Fc
3- rFVIII-Fc +Thrombin
4- Empty
5- FVIIIFc-VWF
6- FVIIIFc-VWF +Thrombin
A1= A1 domain of FVIII
A2= A2 domain of FVIII
Δa3 LC = Light chain of FVIII

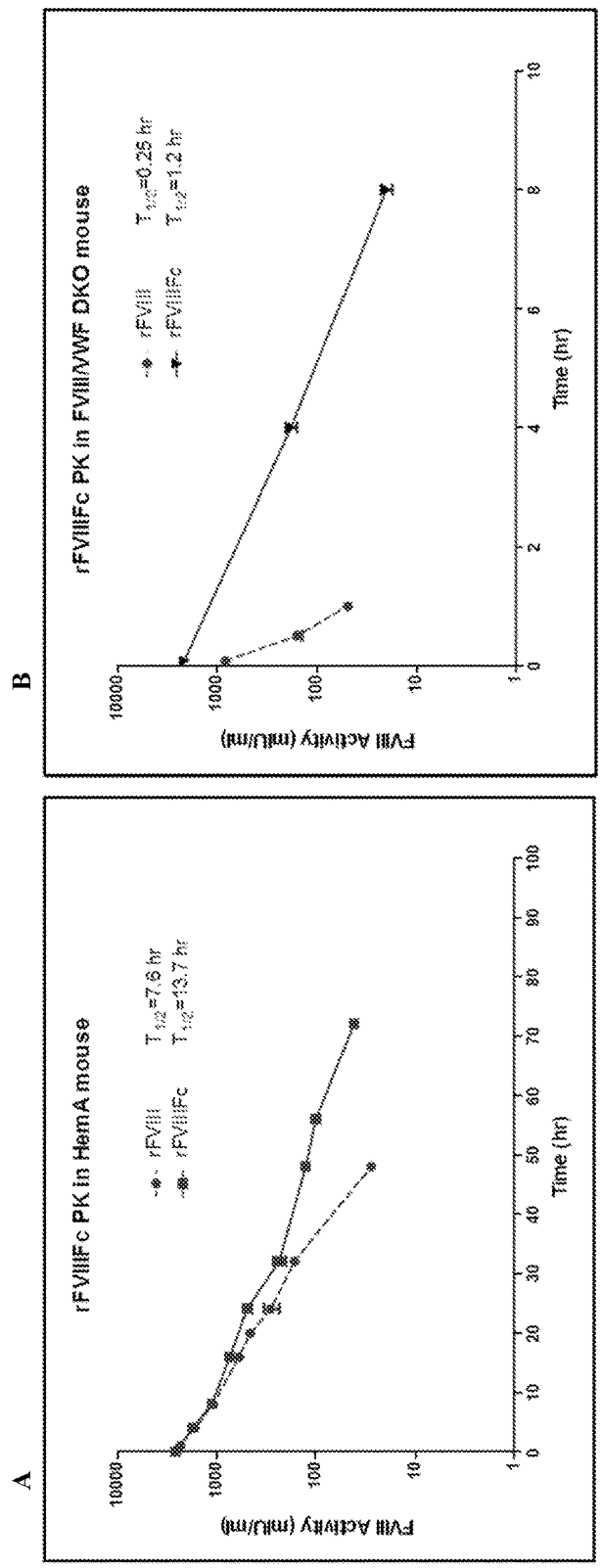
Figure 9: FVIII-VWF interaction is a limiting factor for FVIII half-life extension

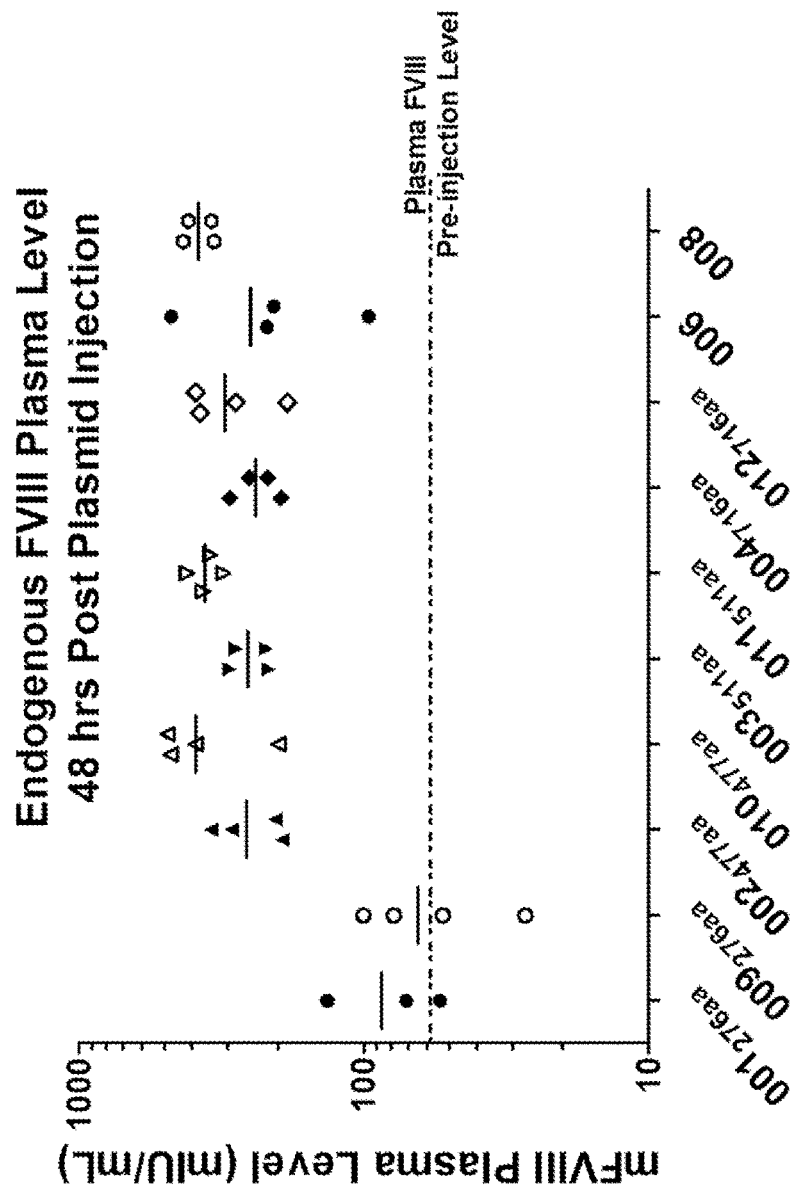
Figure 10A: Full length D'D3 dimer provides same FVIII protection as the Full length VWF molecule

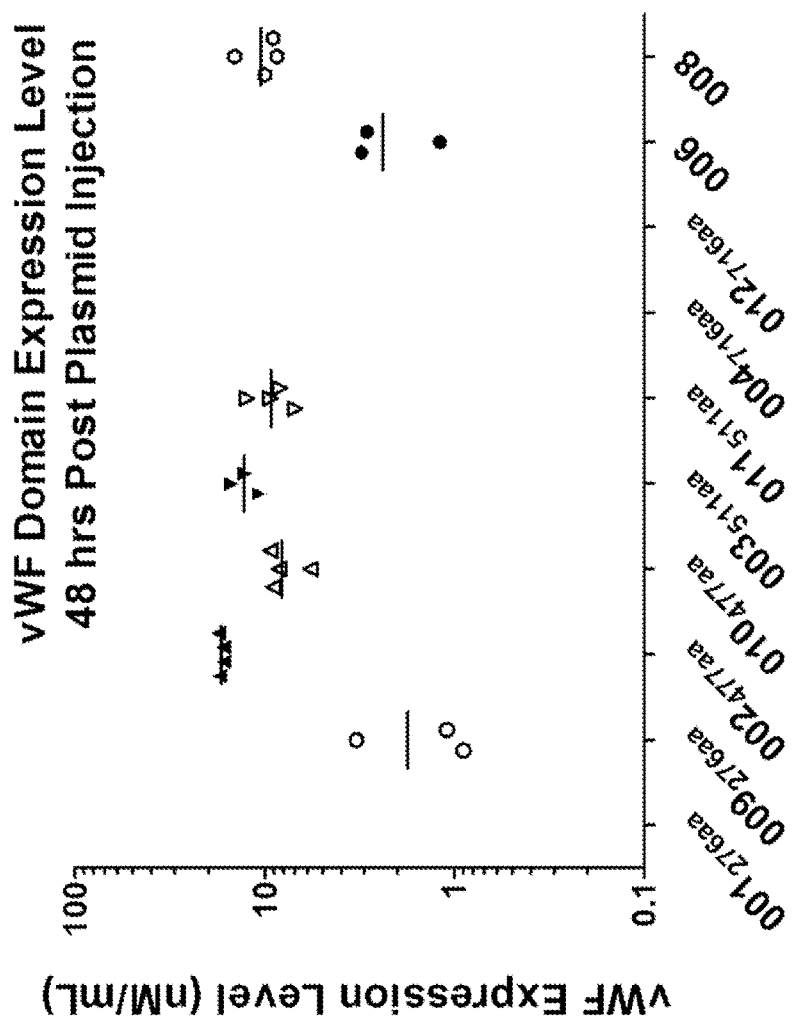
Figure 10B: Full length D'D3 dimer provides same FVIII protection as the Full length VWF

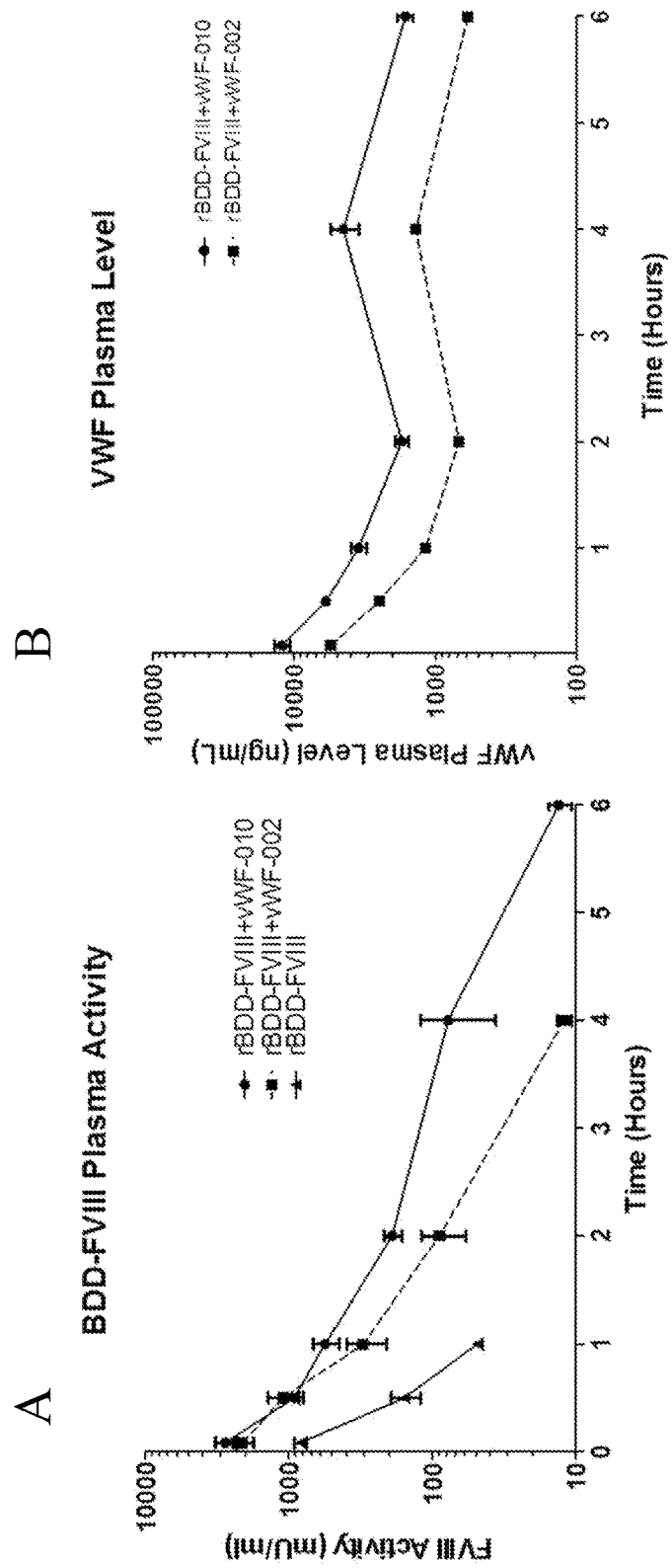
Figure 11: BDD-FVIII PK in FVIII-VWF DKO mice with VWF-010 or VWF-002 co-injection

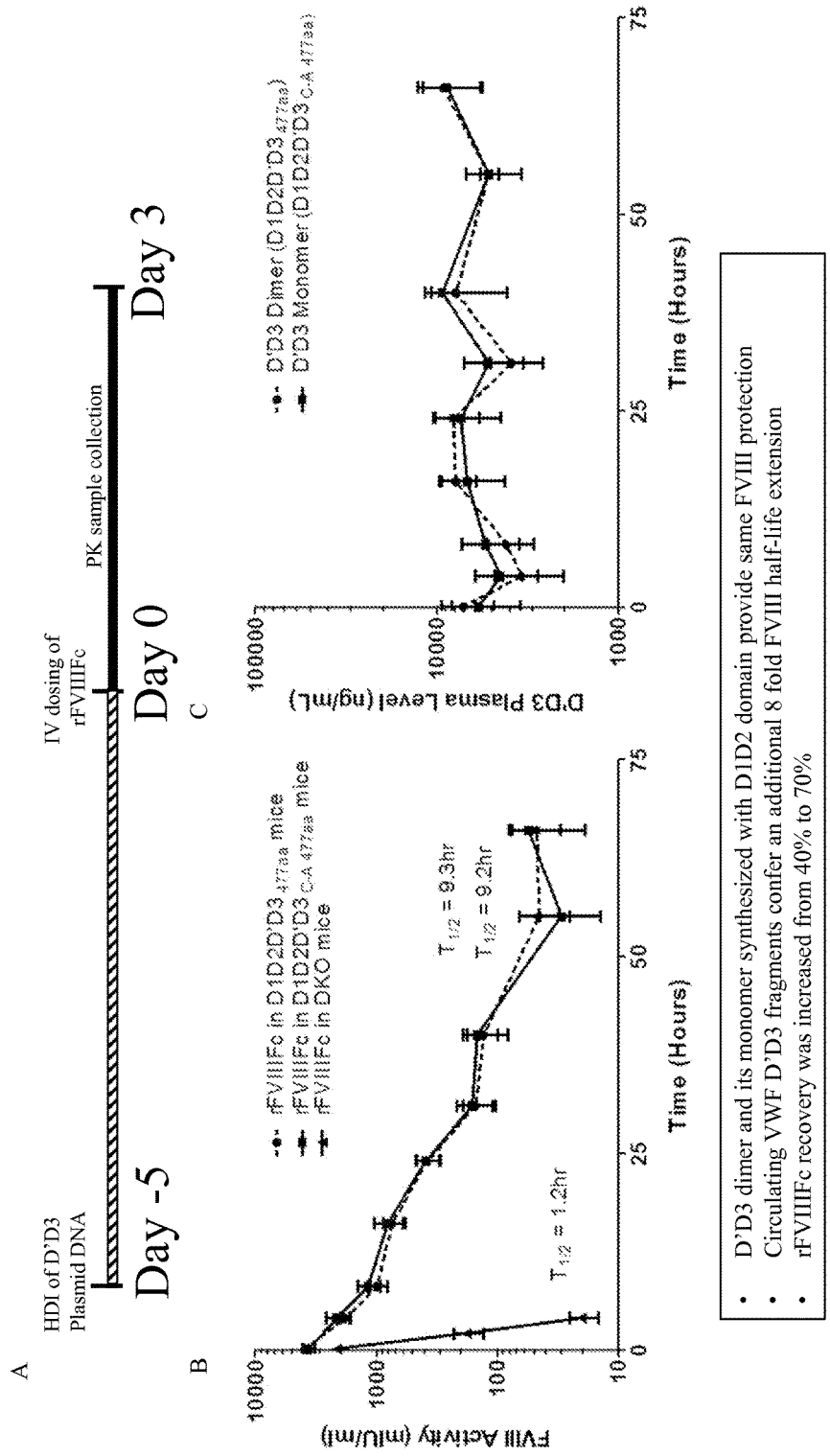
Figure 12: rFVIIIFc PK in VWF D'D3 Expressing Mice

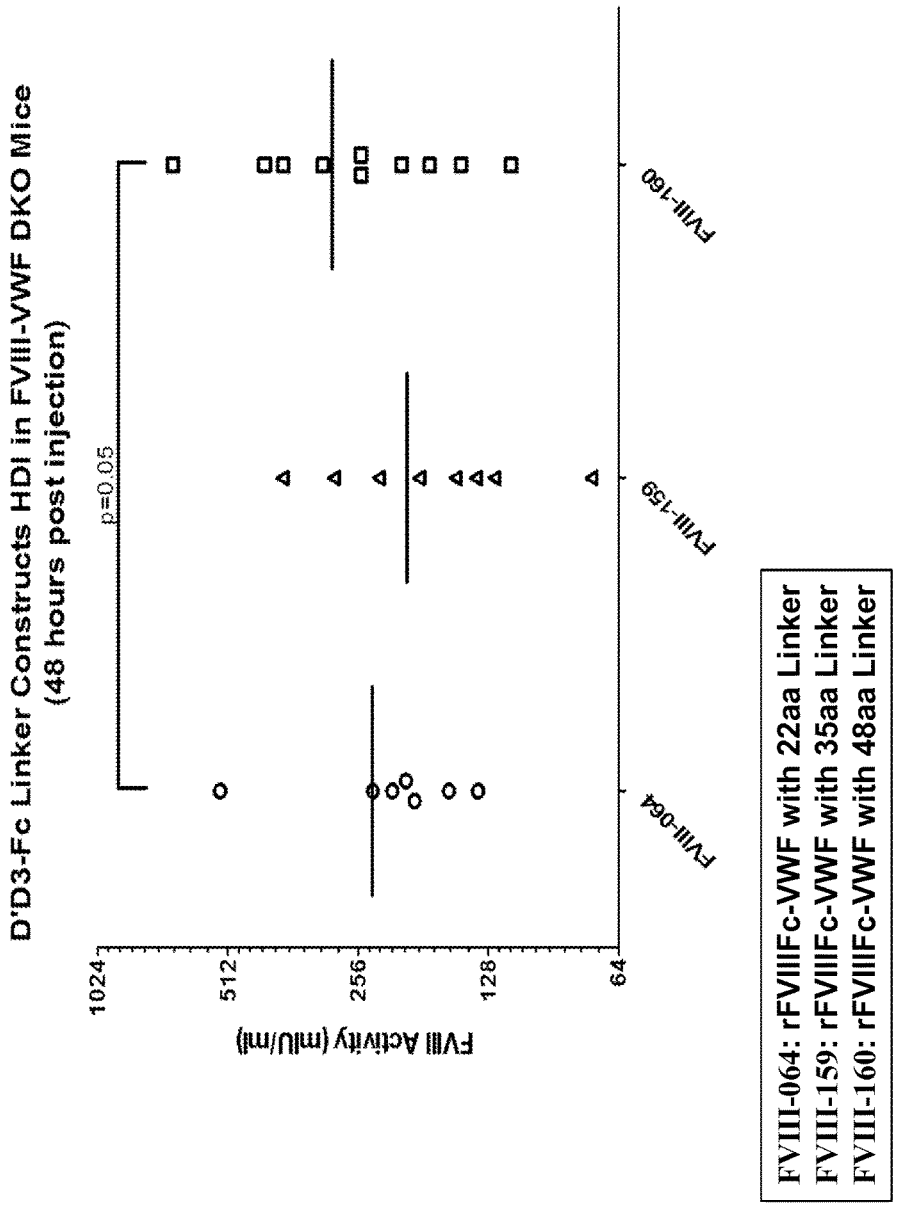
Figure 13: D'D3-Fc linker selection by HDI in FVIII/VWF DKO mice

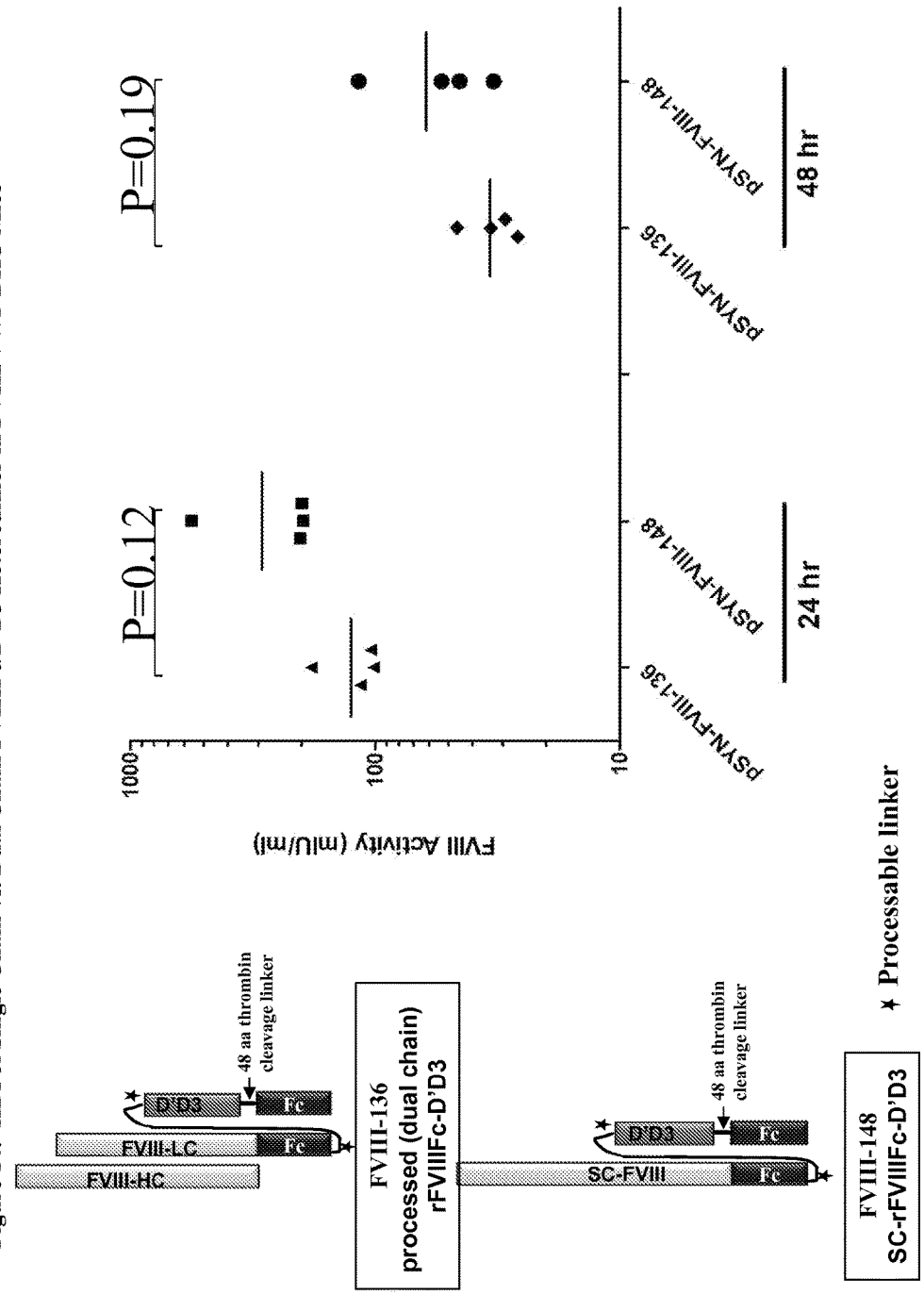
Figure 14: HDI of Single Chain vs. Dual Chain FVIIIFc/D'D3 Heterodimer in FVIII/VWF DKO Mice

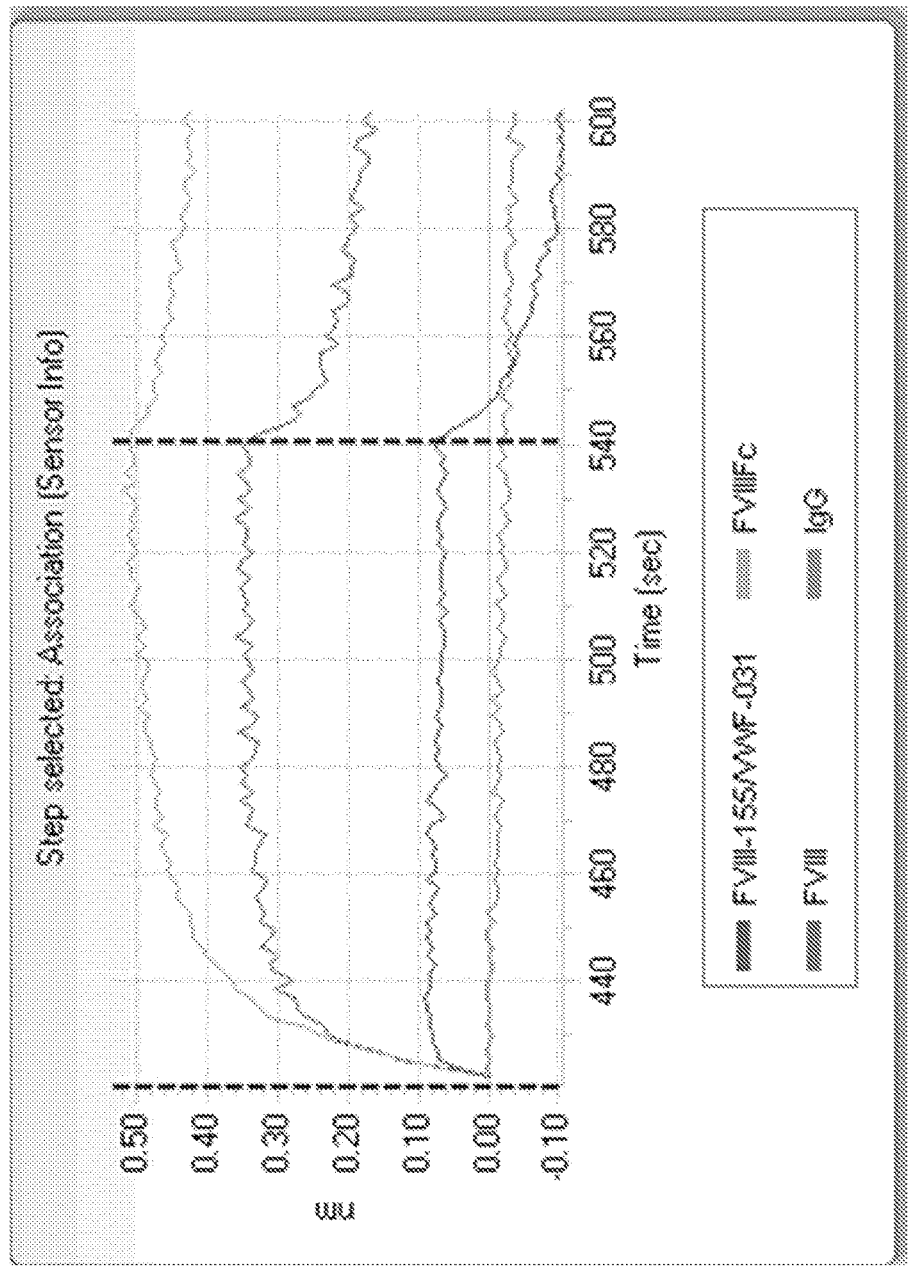
Figure 15: FVIII-155/VWF-031 binding to immobilized VWF by Octet assay

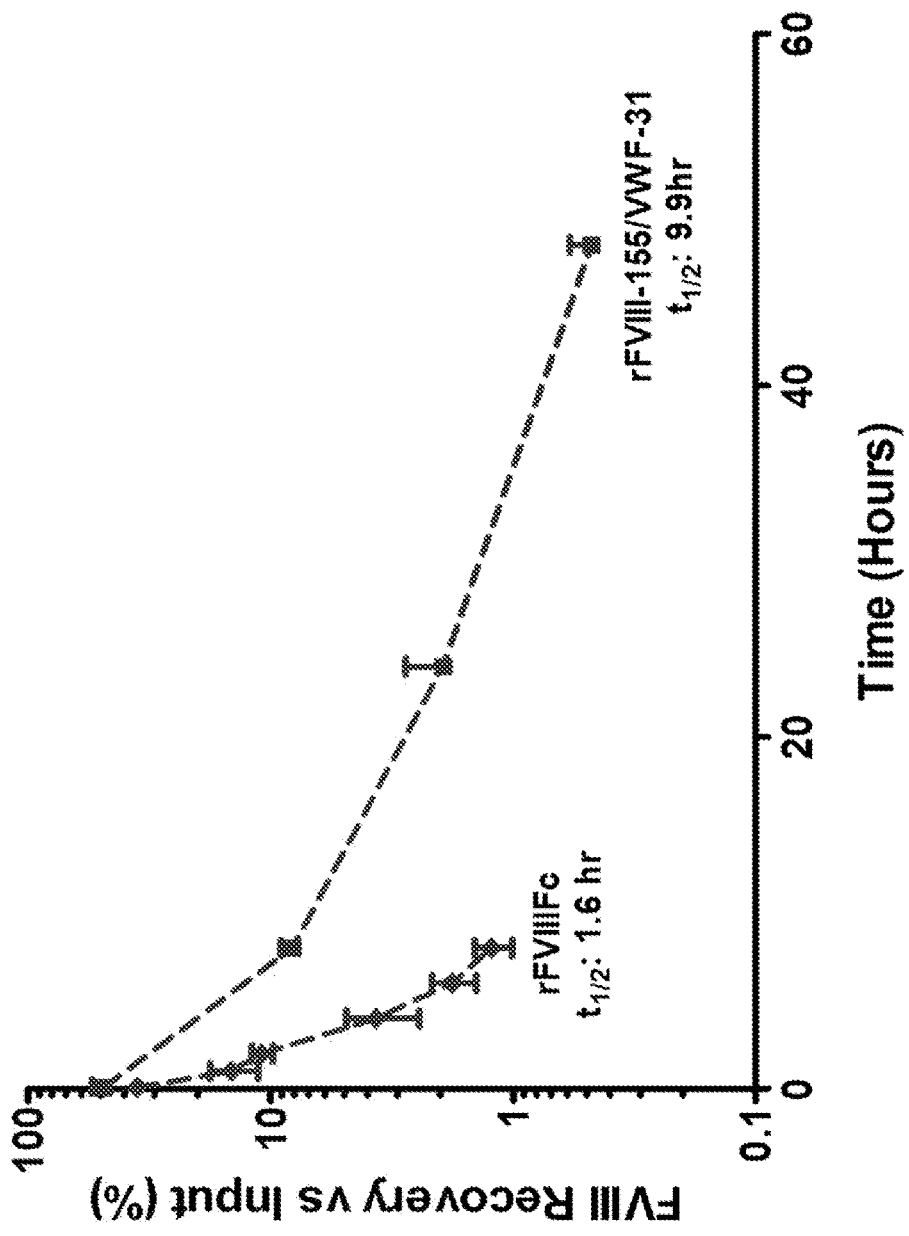
Figure 16: FVIII-155/VWF-031 and FVIIIFc PK in FVIII/VWF DKO mice

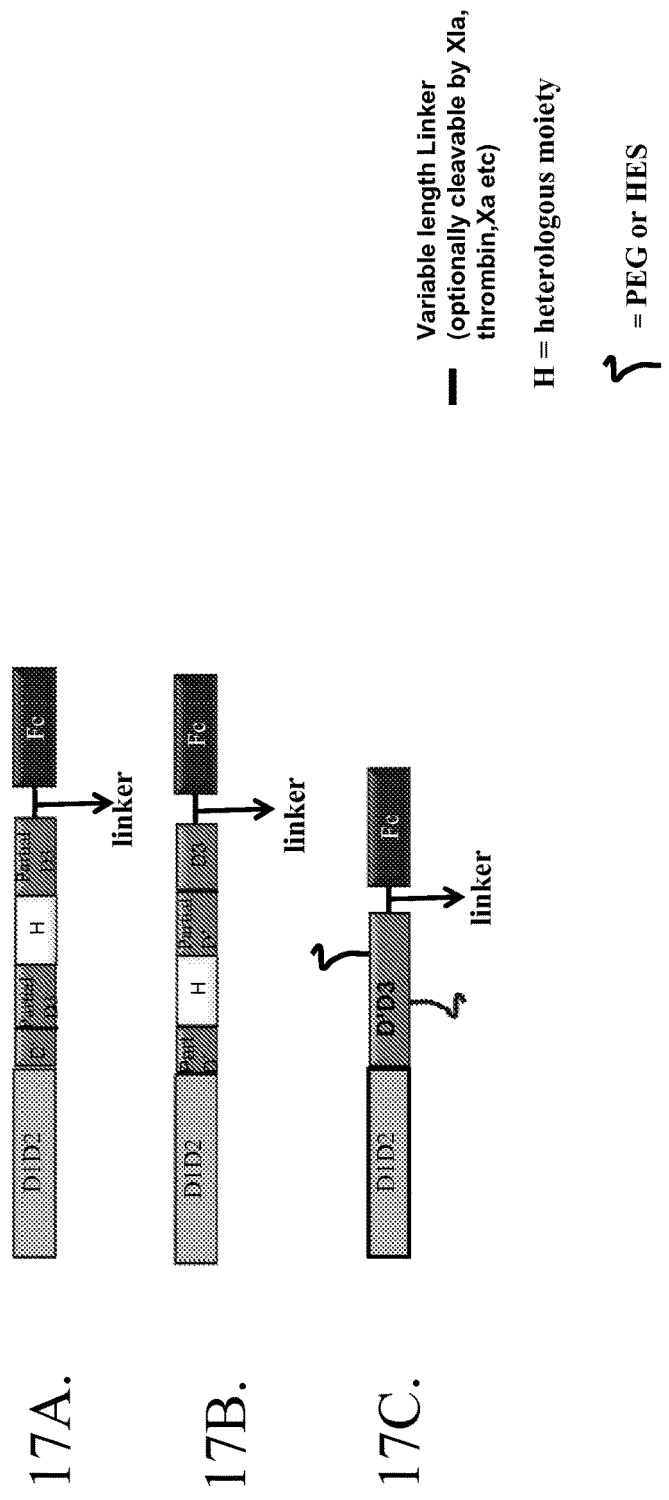
Figure 17: VWF Constructs

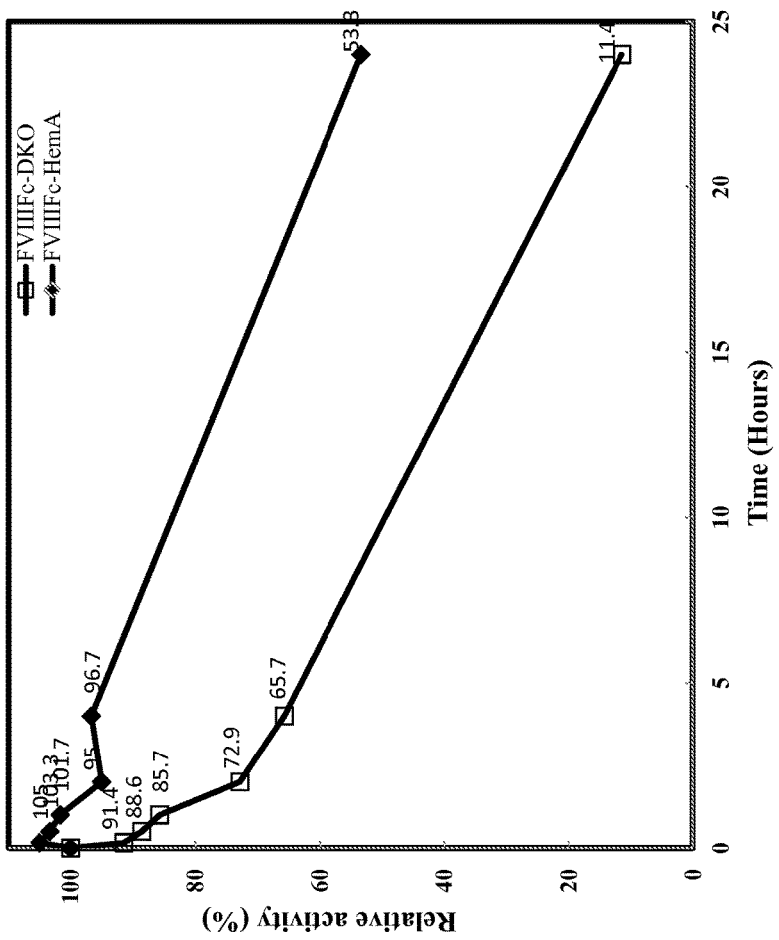
Figure 18A: Loss of FVIIIFc activity in both HemA and DKO plasma by Chromogenic Assay

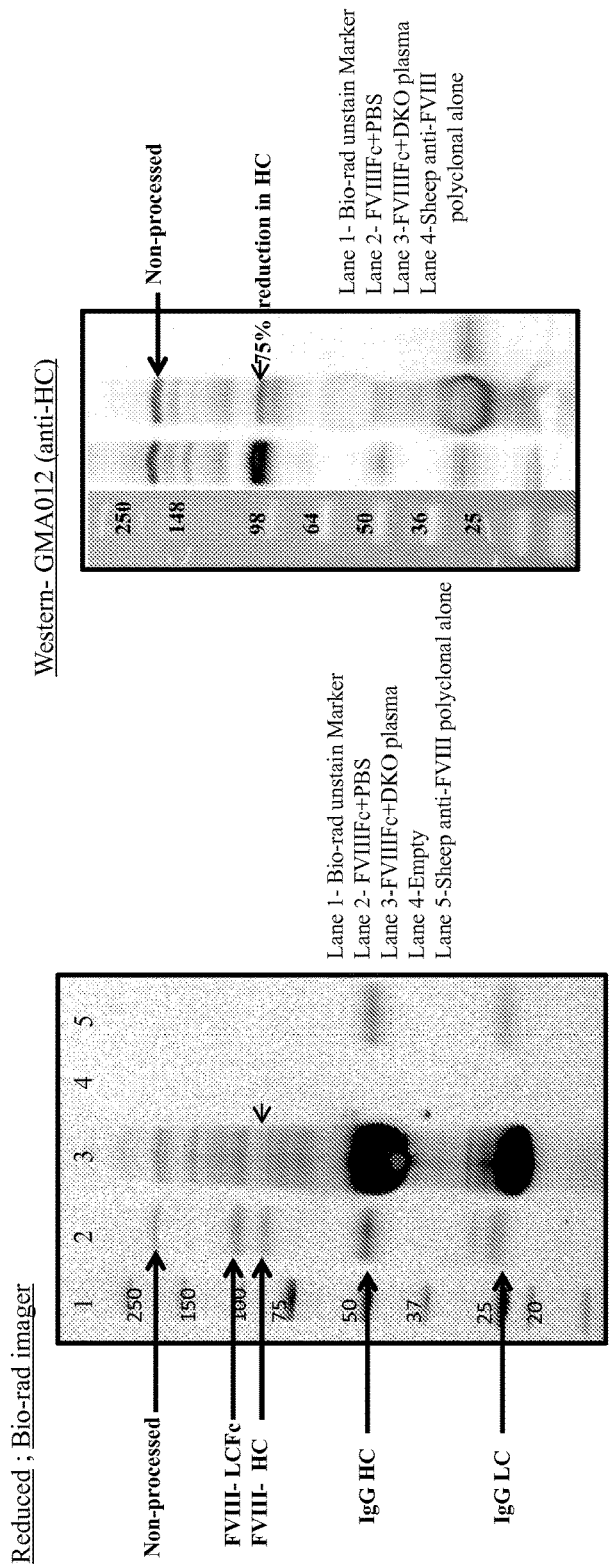

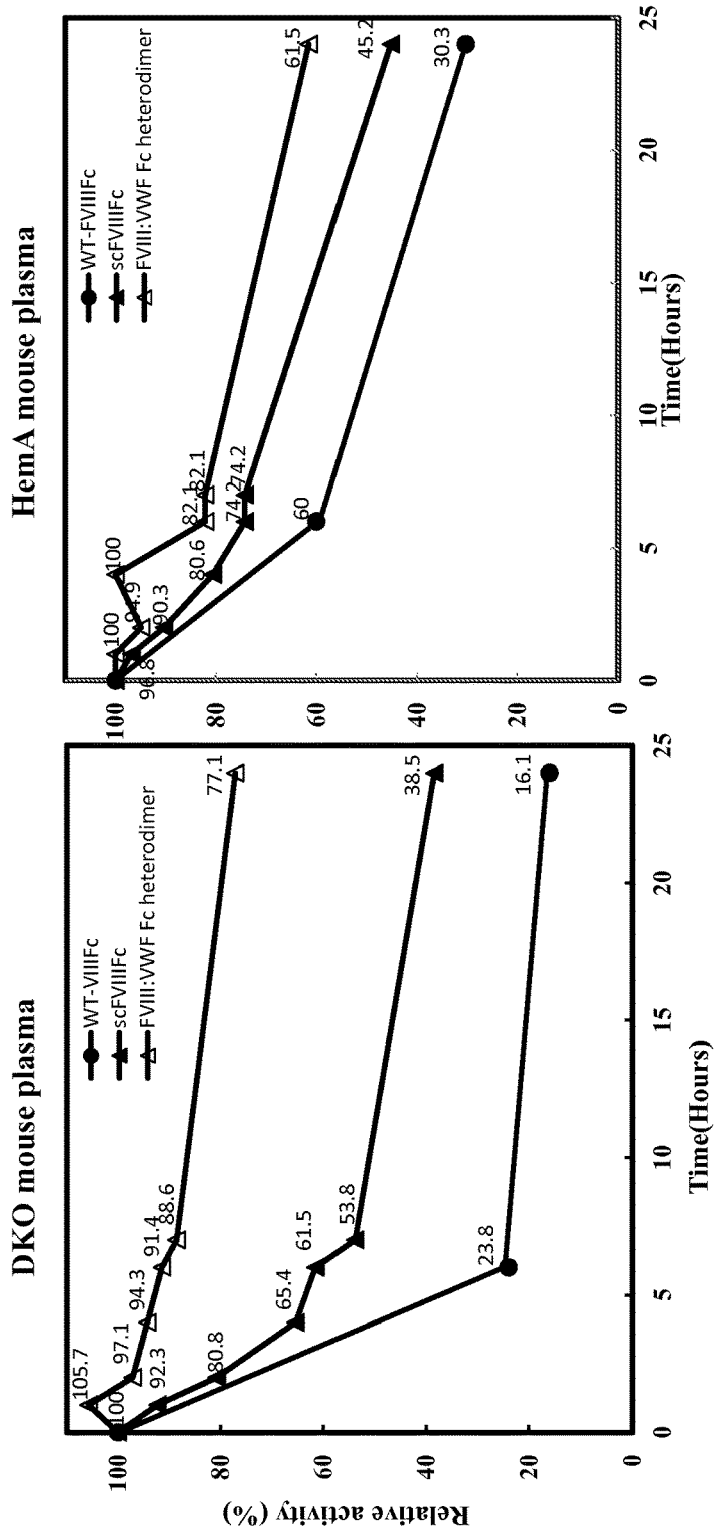
Figure 19: FVIIIFc activity by chromogenic assay

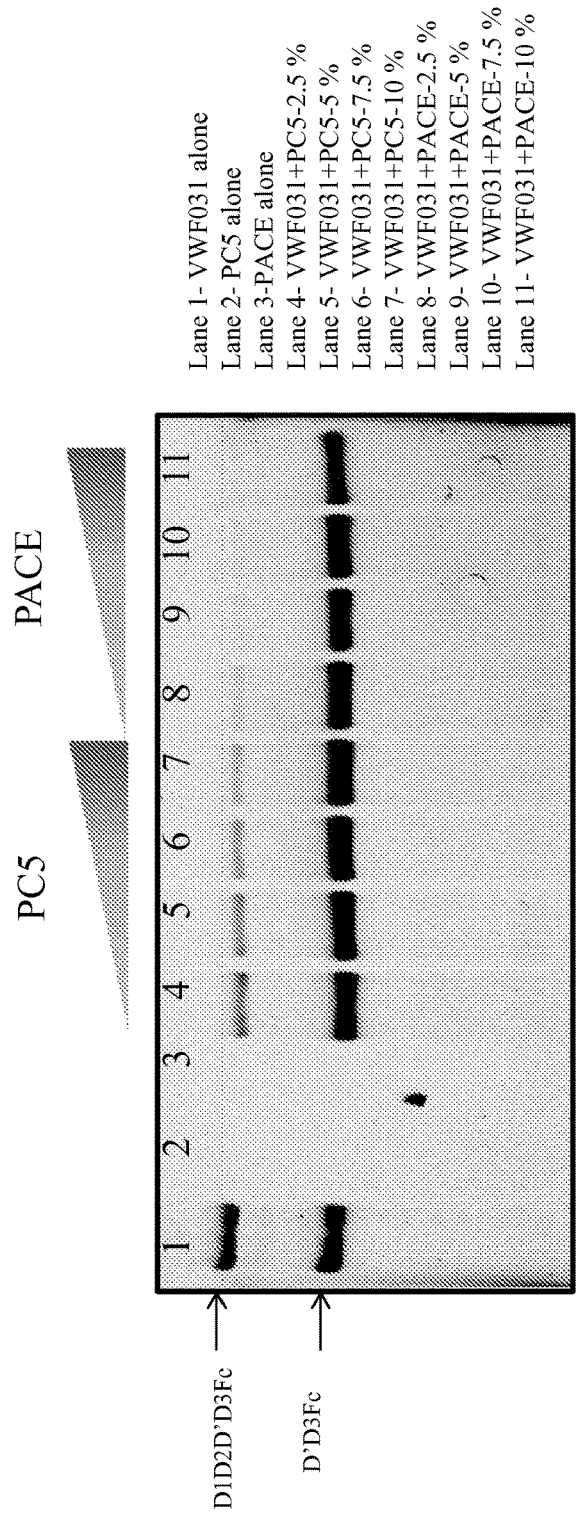
Figure 20: PC5 vs PACE Processing Of VWF-031(D1D2D'D3Fc)

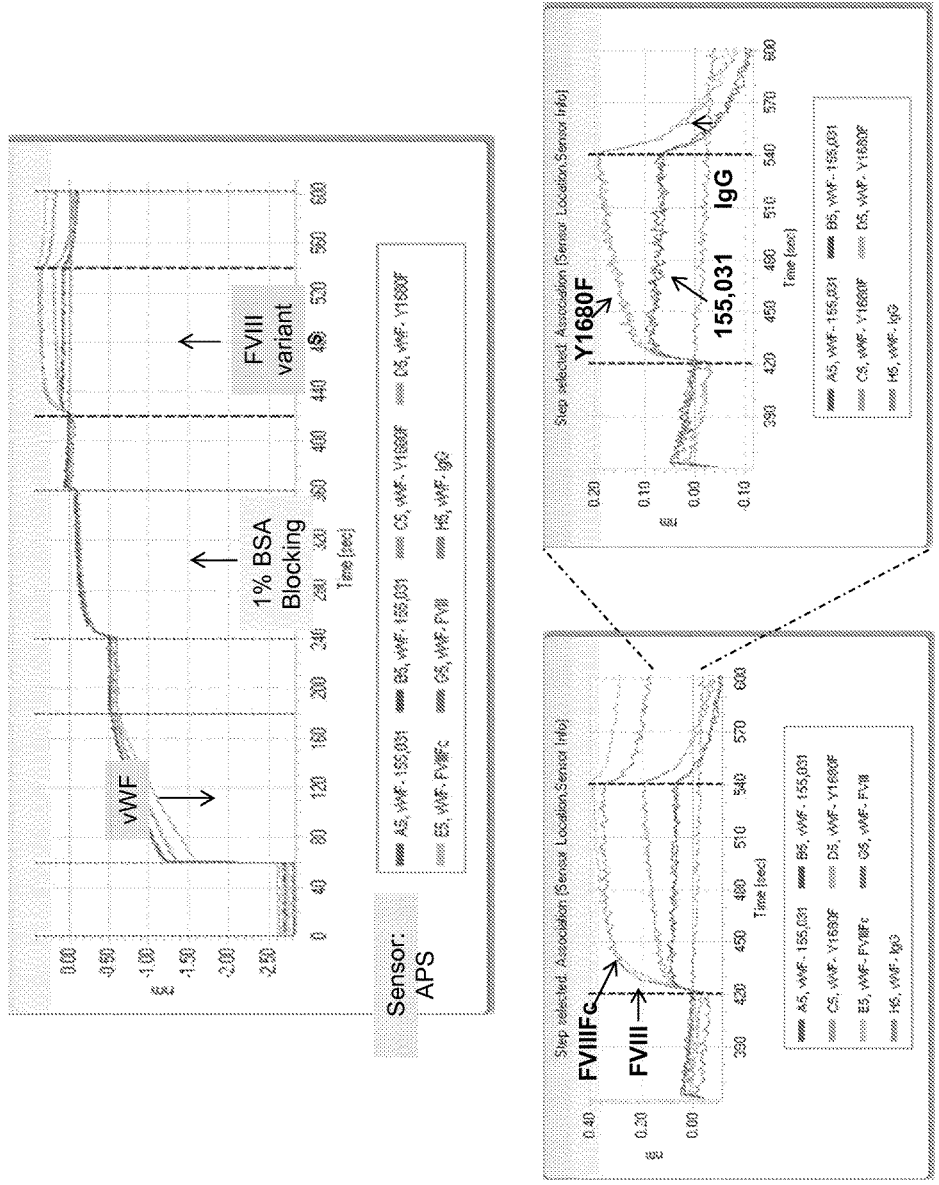
Figure 21A: No Binding Of FVIII-155/VWF-031 To VWF

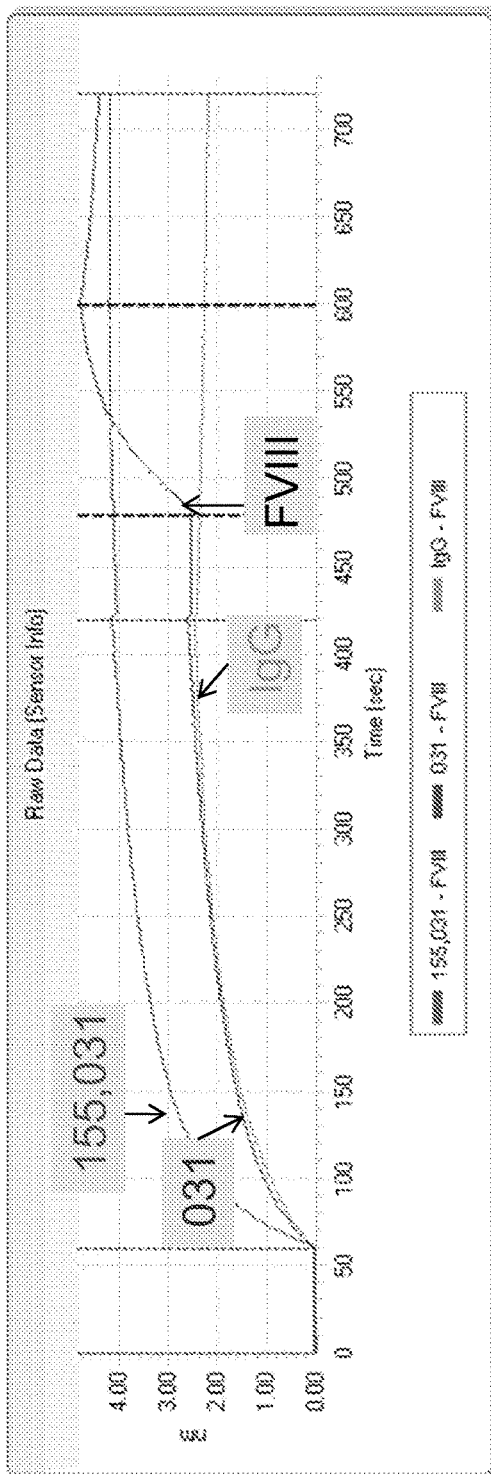
Figure 21B: FVIII-155/VWF-031 Does Not Bind To FVIII

Figure 22: Interaction Of FVIII With VWF-031
- 1000 RU of goat anti-human IgG immobilized
- 100 RU of VWF-031
- FVIII (B-domain deleted) applied in single-cycle kinetics mode
- 1:1 fit ; n=4
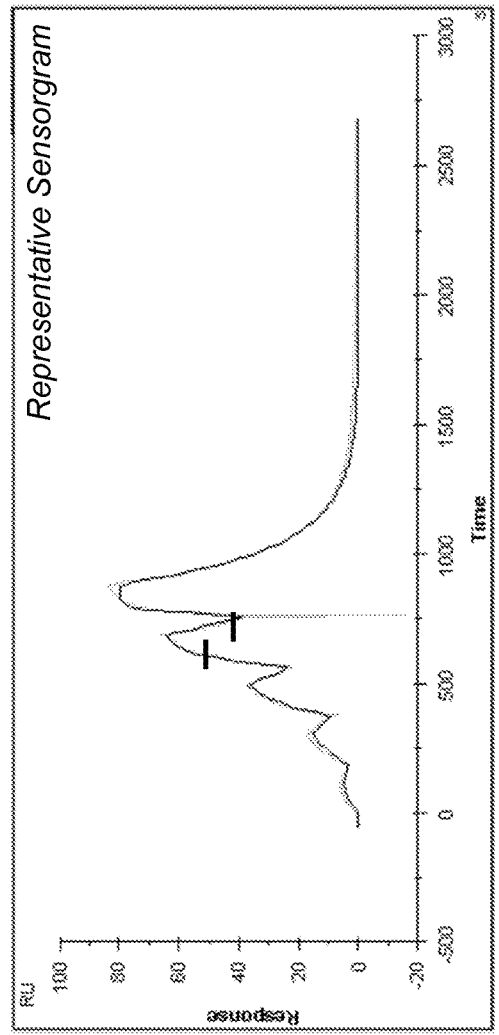
$K_D = 10 \pm 1$ nM
(25-fold weaker than FL-VWF as ligand)

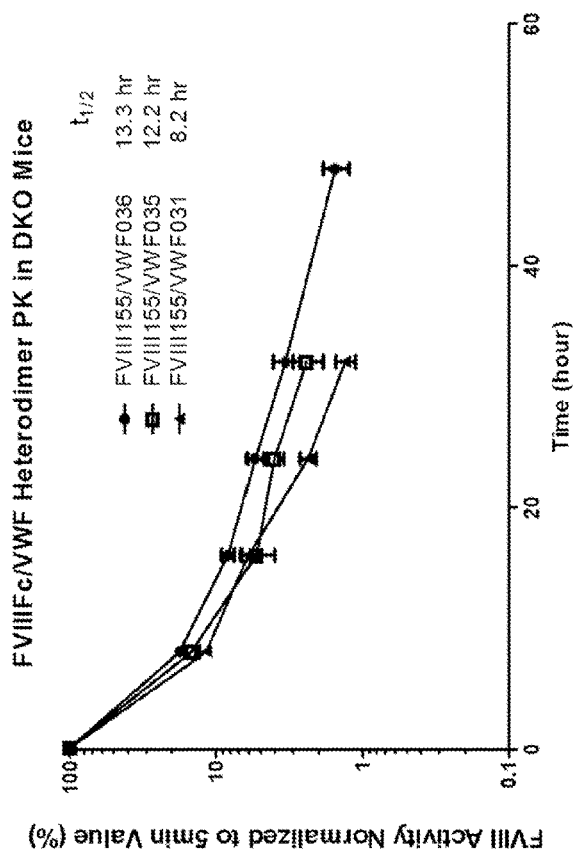
Figure 23: Effect of different linker length of FVIIIFc/VWF heterodimer on PK in FVIII/VWF DKO mice

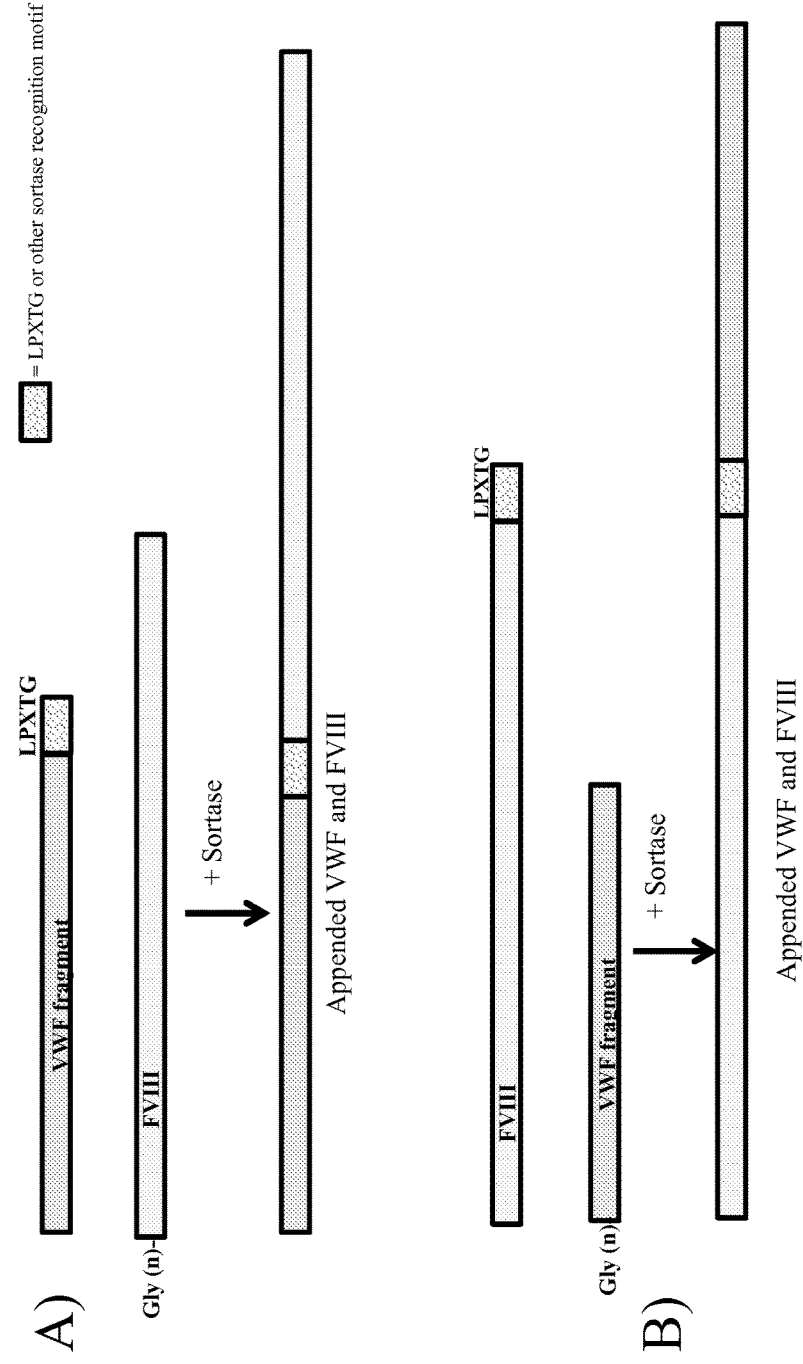
Figure 24: Example of sortase ligation

Figure 24: Example of sortase ligation
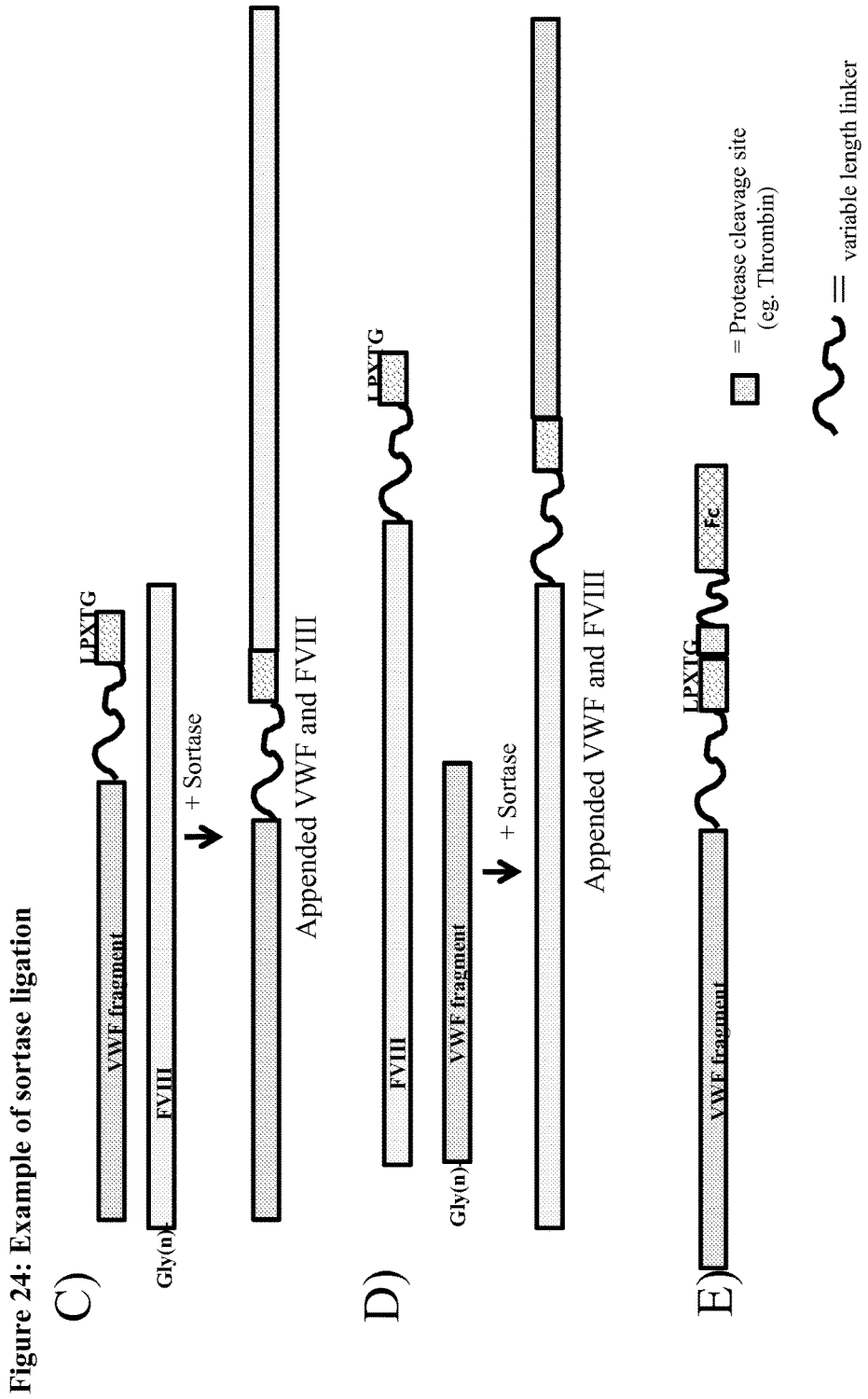

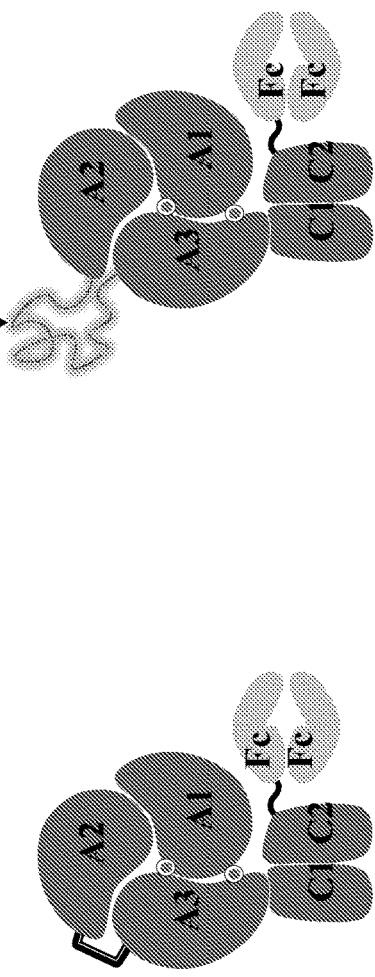
Figure 25: Schematic comparison of single chain FVIIIFc (FVIII155) and partial B-domain containing single chain FVIIIFc (FVIII198)

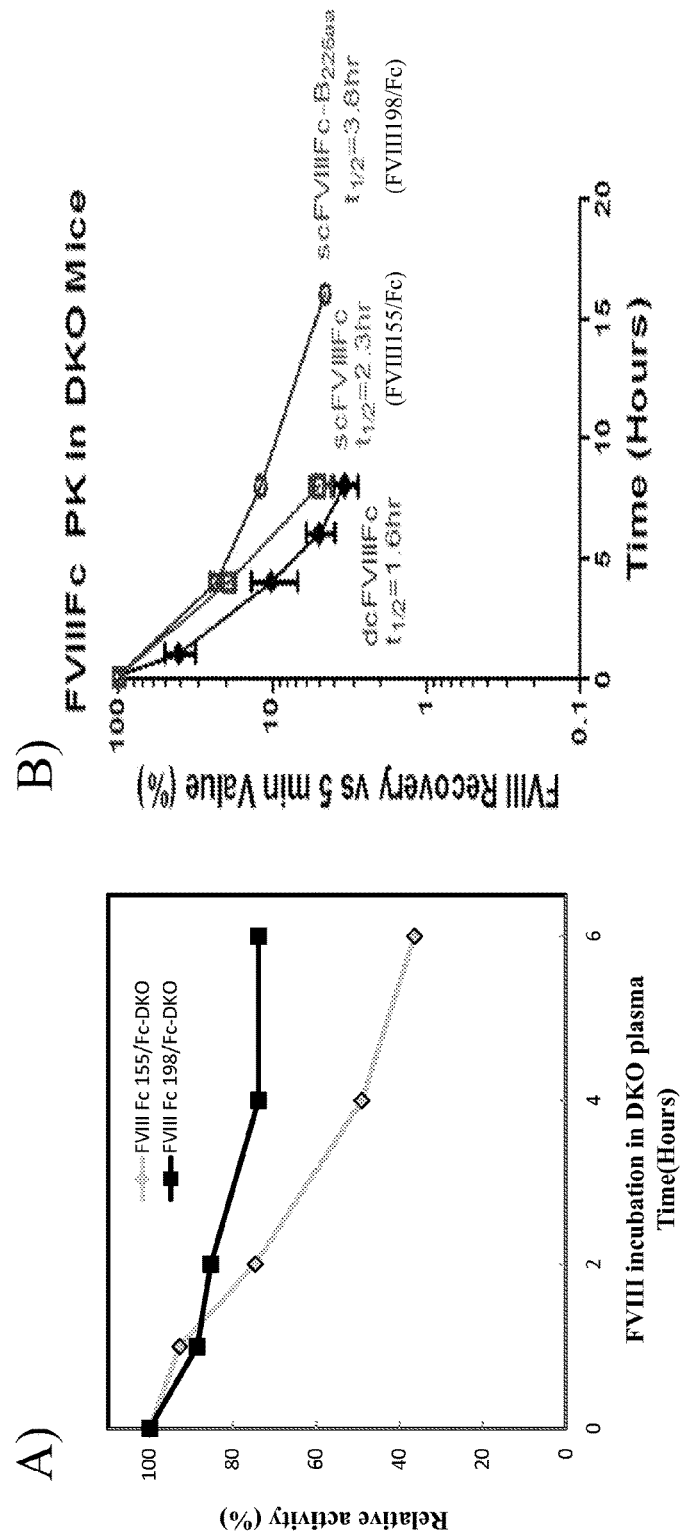
Figure 26: The partial B-Domain increases the half-life of FVIII198 1.5 fold in comparison to FVIII155

CHIMERIC FACTOR VIII POLYPEPTIDES AND USES THEREOF

CROSS-REFERENCE TO RELATED APPLICATIONS

This application is the National Stage of International Application Number PCT/US2013/021330, filed Jan. 12, 2013, which claims the benefit of U.S. Provisional Application Nos. 61/586,099, filed Jan. 12, 2012, 61/586,654, filed Jan. 13, 2012, 61/667,901, filed Jul. 3, 2012, and 61/734,954, filed Dec. 7, 2012, which are incorporated by reference herein in their entireties.

REFERENCE TO A SEQUENCE LISTING SUBMITTED ELECTRONICALLY VIA EFS-WEB

The content of the electronically submitted sequence listing (Name: 21593590004-SequenceListing.txt; Size: 288,526 bytes; Date of Creation: Jul. 10, 2014) is herein incorporated by reference in its entirety.

BACKGROUND OF THE INVENTION

Coagulation is a complex process by which blood forms clots. It is an important part of hemostasis, the cessation of blood loss from a damaged vessel, wherein a damaged blood vessel wall is covered by a platelet and fibrin-containing clot to stop bleeding and begin repair of the damaged vessel. Disorders of coagulation can lead to an increased risk of bleeding (hemorrhage) or obstructive clotting (thrombosis).

Coagulation begins almost instantly after an injury to the blood vessel has damaged the endothelium lining of the vessel. Exposure of the blood to proteins such as tissue factor initiates changes to blood platelets and the plasma protein fibrinogen, a clotting factor. Platelets immediately form a plug at the site of injury; this is called primary hemostasis. Secondary hemostasis occurs simultaneously: Proteins in the blood plasma, called coagulation factors or clotting factors, respond in a complex cascade to form fibrin strands, which strengthen the platelet plug. Non-limiting coagulation factors include, but are not limited to, factor I (fibrinogen), factor II (prothrombin), Tissue factor, factor V (proaccelerin, labile factor), factor VII (stable factor, proconvertin), factor VIII (Antihemophilic factor A), factor IX (Antihemophilic factor B or Christmas factor), factor X (Stuart-Prower factor), factor XI (plasma thromboplastin antecedent), factor XII (Hageman factor), factor XIII (fibrin-stabilizing factor), VWF, prekallikrein (Fletcher factor), high-molecular-weight kininogen (HMWK) (Fitzgerald factor), fibronectin, antithrombin III, heparin cofactor II, protein C, protein S, protein Z, plasminogen, alpha 2-antiplasmin, tissue plasminogen activator (tPA), urokinase, plasminogen activator inhibitor-1 (PAI1), and plasminogen activator inhibitor-2 (PAI2).

Haemophilia A is a bleeding disorder caused by defects in the gene encoding coagulation factor VIII (FVIII) and affects 1-2 in 10,000 male births. Graw et al., Nat. Rev. Genet. 6(6): 488-501 (2005). Patients affected with hemophilia A can be treated with infusion of purified or recombinantly produced FVIII. All commercially available FVIII products, however, are known to have a half-life of about 8-12 hours, requiring frequent intravenous administration to the patients. See Weiner M. A. and Cairo, M. S., Pediatric Hematology Secrets, Lee, M. T., 12. Disorders of Coagulation, Elsevier Health Sciences, 2001; Lillicrap, D. Thromb. Res. 122 Suppl 4:S2-8 (2008). In addition, a number of approaches have been tried in order to extend the FVIII half-life. For example, the approaches in development to extend the half-life of clotting factors include pegylation, glycopegylation, and conjugation with albumin. See Dumont et al., Blood. 119(13): 3024-3030 (Published online Jan. 13, 2012). Regardless of the protein engineering used, however, the long acting FVIII products currently under development have improved half-lives, but the half-lives are reported to be limited-only to about 1.5 to 2 fold improvement in preclinical animal models. See Id. Consistent results have been demonstrated in humans, for example, rFVIIIFc was reported to improve half-life up to ~1.7 fold compared with ADVATE® in hemophilia A patients. See Id. Therefore, the half-life increases, despite minor improvements, may indicate the presence of other T1/2 limiting factors. See Liu, T. et al., 2007 ISTH meeting, abstract #P-M-035; Henrik, A. et al., 2011 ISTH meeting, abstract #P=MO-181; Liu, T. et al., 2011 ISTH meeting abstract #P-WE-131.

Plasma von Willebrand Factor (VWF) has a half-life of approximately 12 hours (ranging from 9 to 15 hours). http://www.nhlbi.nih.gov/guidelines/vwd/2_scientificoverview.htm (last visited Oct. 22, 2011). The VWF half-life may be affected by a number of factors: glycosylation pattern, ADAMTS-13 (a disintegrin and metalloprotease with thrombospondin motif-13), and various mutations in VWF.

In plasma, 95-98% of FVIII circulates in a tight non-covalent complex with full-length VWF. The formation of this complex is important for the maintenance of appropriate plasma levels of FVIII in vivo. Lenting et al., Blood. 92(11): 3983-96 (1998); Lenting et al., J. Thromb. Haemost. 5(7): 1353-60 (2007). The full-length wild-type FVIII is mostly present as a heterodimer having a heavy chain (MW 200 kd) and a light chain (MW 73 kd). When FVIII is activated due to proteolysis at positions 372 and 740 in the heavy chain and at position 1689 in the light chain, the VWF bound to FVIII is removed from the activated FVIII. The activated FVIII, together with activated factor IX, calcium, and phospholipid ("tenase complex"), involves in the activation of factor X, generating large amounts of thrombin. Thrombin, in turn, then cleaves fibrinogen to form soluble fibrin monomers, which then spontaneously polymerize to form the soluble fibrin polymer. Thrombin also activates factor XIII, which, together with calcium, serves to crosslink and stabilize the soluble fibrin polymer, forming cross-linked (insoluble) fibrin. The activated FVIII is cleared fast from the circulation by proteolysis.

Due to the frequent dosing and inconvenience caused by the dosing schedule, there is still a need to develop FVIII products requiring less frequent administration, i.e., a FVIII product that has a half-life longer than the 1.5 to 2 fold half-life limitation.

BRIEF SUMMARY OF THE INVENTION

The present invention is drawn to a chimeric protein comprising a Factor VIII ("FVIII") protein and an adjunct moiety ("AM"), wherein the adjunct moiety inhibits or prevents endogenous VWF from binding to the FVIII protein. The FVIII protein and the adjunct moiety are linked to each other by a covalent bond in order to prevent dissociation of the adjunct moiety in the presence of endogenous VWF. In one embodiment, the covalent bond is a peptide bond, a disulfide bond, or a linker, which is strong enough to prevent dissociation of the adjunct moiety from the FVIII protein in the presence of endogenous VWF. In another embodiment, the adjunct moiety prevents the FVIII protein from being cleared through a VWF clearance pathway. In other embodiments, the adjunct moiety inhibits or prevents endogenous VWF from binding to the FVIII protein by shielding or blocking a VWF binding site on the FVIII protein. For example, VWF binding site is located in the A3 domain or the C2 domain of the FVIII protein or both the A3 domain and the C2 domain.

In some embodiments, the chimeric protein includes a construct comprising a FVIII protein and an adjunct moiety linked to each other by a covalent bond, wherein the chimeric protein does not comprise a FVIII half-life limiting factor, which induces a half-life limitation of the FVIII protein, e.g., a full-length VWF protein or a mature VWF protein. Therefore, in some embodiments, the half-life of the FVIII protein of the chimeric protein is extendable beyond the half-life limitation of the FVIII protein in the presence of endogenous VWF.

In certain embodiments, the adjunct moiety has at least one VWF-like FVIII protecting property. Examples of the VWF-like FVIII protecting property include, but are not limited to, protecting the FVIII protein from one or more protease cleavages, protecting the FVIII protein from activation, stabilizing the heavy chain and/or the light chain of the FVIII protein, or preventing clearance of the FVIII protein by one or more scavenger receptors. In one embodiment, the adjunct moiety comprises a polypeptide, a non-polypeptide moiety, or both. In another embodiment, the adjunct moiety can be a polypeptide comprising an amino acid sequence of at least about 40, at least about 50, at least about 60, at least about 70, at least about 80, at least about 90, at least about 100, at least about 110, at least about 120, at least about 130, at least about 140, at least about 150, at least about 200, at least about 250, at least about 300, at least about 350, at least about 400, at least about 450, at least about 500, at least about 550, at least about 600, at least about 650, at least about 700, at least about 750, at least about 800, at least about 850, at least about 900, at least about 950, or at least about 1000 amino acids in length. In certain embodiments, the adjunct moiety comprises a VWF fragment, an immunoglobulin constant region or a portion thereof, albumin or a fragment thereof, an albumin binding moiety, a PAS sequence, a HAP sequence, transferrin or a fragment thereof, or any combinations thereof. In other embodiments, the adjunct moiety is a non-polypeptide moiety comprising polyethylene glycol (PEG), polysialic acid, hydroxyethyl starch (HES), a derivative thereof, or any combinations thereof.

In certain embodiments, the adjunct moiety comprises a VWF fragment comprising a D' domain and a D3 domain of VWF, wherein the VWF fragment is associated with the FVIII protein by a non-covalent bond in addition to the covalent bond between the FVIII protein and the adjunct moiety (VWF fragment). In one example, the VWF fragment is a monomer. In another example, the VWF fragment comprises two, three, four, five, or six VWF fragments linked to one or more of each other.

In one aspect, the chimeric protein comprises an adjunct moiety, e.g., a VWF fragment, and at least one heterologous moiety (H1) and an optional linker between the adjunct moiety, e.g., VWF fragment, and the heterologous moiety (H1). In one embodiment, the heterologous moiety (H1) can comprise a moiety that extends the half-life of the FVIII protein, e.g., a polypeptide selected from the group consisting of an immunoglobulin constant region or a portion thereof, albumin or a fragment thereof, an albumin binding moiety, a PAS sequence, a HAP sequence, transferrin or a fragment thereof, and any combinations thereof or a non-polypeptide moiety selected from the group consisting of polyethylene glycol (PEG), polysialic acid, hydroxyethyl starch (HES), a derivative thereof, and any combinations thereof. In one embodiment, the heterologous moiety (H1) comprises a first Fc region. In another embodiment, the heterologous moiety (H1) comprises an amino acid sequence comprising at least about 50 amino acids, at least about 100 amino acids, at least about 150 amino acids, at least about 200 amino acids, at least about 250 amino acids, at least about 300 amino acids, at least about 350 amino acids, at least about 400 amino acids, at least about 450 amino acids, at least about 500 amino acids, at least about 550 amino acids, at least about 600 amino acids, at least about 650 amino acids, at least about 700 amino acids, at least about 750 amino acids, at least about 800 amino acids, at least about 850 amino acids, at least about 900 amino acids, at least about 950 amino acids, or at least about 1000 amino acids. In other embodiments, the chimeric protein comprises a linker between the adjunct moiety, e.g., a VWF fragment, and the heterologous moiety (H1), which is a cleavable linker.

In another aspect, the FVIII protein in the chimeric protein comprises FVIII and at least one heterologous moiety (H2). In one embodiment, the heterologous moiety (H2) is capable of extending the half-life of the FVIII protein, e.g., a polypeptide selected from the group consisting of an immunoglobulin constant region or a portion thereof, albumin or a fragment thereof, an albumin binding moiety, a PAS sequence, a HAP sequence, transferrin or a fragment thereof, and any combinations thereof or a non-polypeptide moiety comprising polyethylene glycol (PEG), polysialic acid, hydroxyethyl starch (HES), a derivative thereof, and any combinations thereof. In a particular embodiment, the heterologous moiety (H2) comprises a second Fc region.

In some embodiments, the chimeric protein comprises a first polypeptide chain comprising the VWF fragment, a first heterologous moiety, and a linker and a second polypeptide chain comprising the FVIII protein and a second heterologous moiety, wherein the first polypeptide chain and the second polypeptide chain are linked to each other by a covalent bond. In one example, the first heterologous moiety and the second heterologous moiety are linked to each other by the covalent bond, e.g., a disulfide bond, a peptide bond, or a linker, wherein the covalent bond prevents replacement of the VWF fragment in the first polypeptide chain with endogenous VWF in vivo. In some embodiments, the linker between the FVIII protein and the second heterologous moiety is a cleavable linker.

In certain embodiments, the first heterologous moiety (H1) linked to the VWF fragment and the second heterologous moiety (H2) linked to the FVIII protein are linked by a linker, e.g., a scFc linker, which is a processable linker.

In yet other embodiments, the FVIII protein in the chimeric protein further comprises a third heterologous moiety (H3), a fourth heterologous moiety (H4), a fifth heterologous moiety (H5), a sixth heterologous moiety (H6), or any combinations thereof. In one embodiment, one or more of the third heterologous moiety (H3), the fourth heterologous moiety (H4), the fifth heterologous moiety (H5), the sixth heterologous moiety (H6) are capable of extending the half-life of the FVIII protein. In another embodiments, the third heterologous moiety (H3), the fourth heterologous moiety (H4), the fifth heterologous moiety (H5), and the sixth heterologous moiety (H6) are linked to the C terminus or N terminus of FVIII or inserted between two amino acids of FVIII. In other embodiments, one or more of the third heterologous moiety (H3), the fourth heterologous moiety (H4), the fifth heterologous moiety (H5), or the sixth heterologous moiety (H6) comprises an amino acid sequence comprising at least about 50 amino acids, at least about 100 amino acids, at least about 150 amino acids, at least about 200 amino acids, at least about 250 amino acids, at least about 300 amino acids, at least about 350 amino acids, at least about 400 amino acids, at least about 450 amino acids, at least about 500 amino acids, at least about 550 amino acids, at least about 600 amino acids, at least about 650 amino acids, at least about 700 amino acids, at least about 750 amino acids, at least about 800 amino acids, at least about 850 amino acids, at least about 900 amino acids, at least about 950 amino acids, or at least about 1000 amino acids.

In some embodiments, the linker between the FVIII protein and the second heterologous moiety or the linker between the VWF fragment and the first heterologous moiety further comprises a first cleavage site (P1) at the N-terminal region of the linker, a second cleavage site (P2) at the C-terminal region of the linker, or both. In other embodiments, one or more of the linker between the FVIII protein and the adjunct moiety, the linker between the FVIII protein and the second heterologous moiety, and the linker between the VWF fragment and the first heterologous moiety have a length of about 1 to about 2000 amino acids.

In other embodiments, the chimeric protein comprises a FVIII protein and an adjunct moiety, which are linked by a linker between the FVIII protein and the adjunct moiety, wherein the linker further comprises a sortase recognition motif, e.g., the sequence of LPXTG (SEQ ID NO: 106).

The present invention is directed to a von Willebrand Factor (VWF) fragment comprising the D' domain and the D3 domain of VWF, wherein the VWF fragment binds to Factor VIII (FVIII) and inhibits binding of endogenous VWF to a FVIII protein. In one embodiment, the VWF fragment of the invention is not amino acids 764 to 1274 of SEQ ID NO: 2. In one embodiment, the FVIII protein, without the VWF fragment, has a half-life comparable to wild-type FVIII. In another embodiment, the FVIII protein is a fusion protein comprising FVIII and a heterologous moiety that is capable of extending half-life of FVIII. The heterologous moiety can be a polypeptide, a non-polypeptide moiety, or both. The heterologous polypeptide moiety can be selected from the group consisting of an immunoglobulin constant region or a portion thereof, albumin or a fragment thereof, an albumin binding moiety, a PAS sequence, a HAP sequence, transferrin or a fragment thereof, and any combination thereof. In other embodiments, the heterologous moiety is an immunoglobulin constant region or a portion thereof, e.g., an Fc region. In still other embodiments, the non-polypeptide moiety is selected from the group consisting of polyethylene glycol (PEG), polysialic acid, hydroxyethyl starch (HES), a derivative thereof, and any combinations thereof. In certain embodiments, The FVIII protein comprises a first polypeptide chain and a second polypeptide chain, wherein the first polypeptide chain comprises FVIII and a first Fc region and the second polypeptide chain comprises a second Fc region without FVIII.

In another embodiment, the VWF fragment extends a half-life of FVIII. The amino acid sequence of the D' domain can be at least 90%, 95%, 96%, 97%, 98%, 99%, or 100% identical to amino acids 764 to 866 of SEQ ID NO: 2. Also, the amino acid sequence of the D3 domain can be at least 90%, 95%, 96%, 97%, 98%, 99%, or 100% identical to amino acids 867 to 1240 of SEQ ID NO: 2. In certain embodiments, the VWF fragment contains at least one amino acid substitution at a residue corresponding to residue 1099, residue 1142, or both of SEQ ID NO: 2. In a particular embodiment, a VWF fragment comprises, consisting essentially of, or consists of amino acids 764 to 1240 of SEQ ID NO: 2. The VWF fragment can further comprise the D1 domain, the D2 domain, or the D1 and D2 domains of VWF. In some embodiments, the VWF fragment further comprises a VWF domain selected from the group consisting of the A1 domain, the A2 domain, the A3 domain, the D4 domain, the B1 domain, the B2 domain, the B3 domain, the C1 domain, the C2 domain, the CK domain, one or more fragments thereof, and any combinations thereof. In other embodiments, the VWF fragment is pegylated, glycosylated, hesylated, or polysialylated.

The present invention is also directed to a chimeric protein comprising a VWF fragment described herein, a heterologous moiety, and an optional linker between the VWF fragment and the heterologous moiety. The heterologous moiety can be a polypeptide, a non-polypeptide moiety, or both. In one embodiment, the heterologous polypeptide moiety is selected from the group consisting of an immunoglobulin constant region or a portion thereof, albumin or a fragment thereof, an albumin binding moiety, a PAS sequence, a HAP sequence, transferrin or a fragment thereof, and any combination thereof. In another embodiment, the heterologous non-polypeptide moiety is selected from group consisting of polyethylene glycol (PEG), polysialic acid, hydroxyethyl starch (HES), a derivative thereof, and any combinations thereof. In a particular embodiment, the heterologous moiety is a first Fc region. The chimeric protein can further comprise a second Fc region, wherein the second Fc region is linked to or associated with the first Fc region or linked to or associated with the VWF fragment.

In one aspect, a chimeric protein of the invention comprises a formula selected from the group consisting of:
(aa) V-L1-H1-L2-H2,
(bb) H2-L2-H1-L1-V,
(cc) H1-L1-V-L2-H2, and
(dd) H2-L2-V-L1-H1,
wherein the V is one or more of the VWF fragments described herein,
each of L1 and L2 is an optional linker;
H1 is a first heterologous moiety;
(-) is a peptide bond or one or more amino acids; and
H2 is an optional second heterologous moiety.

In one embodiment, H1 is a first heterologous moiety, e.g., a half-life extending molecule which is known in the art. In one embodiment, the first heterologous moiety is a polypeptide. The first heterologous polypeptide moiety is selected from the group consisting of an immunoglobulin constant region or a portion thereof, albumin or a fragment thereof, an albumin binding moiety, a PAS sequence, a HAP sequence, transferrin or a fragment thereof, and any combinations thereof. In another embodiment, H1 is a non-polypeptide moiety selected from the group consisting of polyethylene glycol (PEG), polysialic acid, hydroxyethyl starch (HES), a derivative thereof, and any combinations thereof. H2 is an optional second heterologous moiety, e.g., a half-life extending molecule which is known in the art. In one embodiment, the second heterologous moiety can be selected from the group consisting of an immunoglobulin constant region or a portion thereof, albumin or a fragment thereof, an albumin binding moiety, a PAS sequence, a HAP sequence, transferrin or a fragment thereof, and any combination thereof. In another embodiment, H2 is a non-polypeptide moiety, which is selected from the group consisting of polyethylene glycol (PEG), polysialic acid, hydroxyethyl starch (HES), a derivative thereof, and any combinations thereof. In certain embodiments, H1 is a first Fc region and H2 is a second Fc region. The first Fc region and the second Fc region can be the same or different and can be linked to each other by a linker or a covalent bond, e.g., a disulfide bond. In another embodiment, the second Fc region is linked to or associated with a Factor VIII protein. Optionally, there could be a third heterologous moiety, H3, which is a half-life extender, which is linked to the VWF fragment, the first heterologous moiety, or the second heterologous moiety. Non-limiting examples of the third heterologous moiety can include a polypeptide or a non-polypeptide moiety or both. In one embodiment, the third heterologous polypeptide moiety can be selected from the group consisting of an immunoglobulin constant region or a portion thereof, albumin or a fragment thereof, an albumin binding moiety, a PAS sequence, a HAP sequence, transferrin or a fragment thereof, or any combinations thereof. In another embodiment, H2 is a non-polypeptide moiety, which is be selected from the group consisting of polyethylene glycol (PEG), polysialic acid, hydroxyethyl starch (HES), a derivative thereof, and any combinations thereof. In some embodiments, H3 is linked to the VWF fragment or the first or the second heterologous moiety by a cleavable linker, e.g., a thrombin cleavable linker. Non-limiting examples of the linkers are disclosed elsewhere herein.

In another aspect, the invention provides a chimeric protein comprising a VWF fragment described herein, a FVIII protein, and an optional linker between the VWF fragment and the FVIII protein. The VWF fragment can be bound to the FVIII protein. In one embodiment, a chimeric protein comprises a VWF fragment described herein, which is linked to a heterologous moiety. The heterologous moiety can be a moiety that extends the half-life of the protein, which comprises a polypeptide, a non-polypeptide moiety, or both. Examples of such a heterologous polypeptide moiety include, e.g., an immunoglobulin constant region or a portion thereof, albumin or a fragment thereof, an albumin binding moiety, a PAS sequence, a HAP sequence, any derivatives or variants thereof, or any combinations thereof. Examples of a non-polypeptide moiety include, e.g., polyethylene glycol (PEG), polysialic acid, hydroxyethyl starch (HES), a derivative thereof, or any combinations thereof. In another embodiment, the heterologous moiety is a first Fc region linked to the VWF fragment. In other embodiments, the chimeric protein further comprises a second Fc region linked to the FVIII protein. The VWF fragment or the FVIII protein can be linked to the first Fc region or the second Fc region, respectively, by a linker. In still other embodiments, a chimeric protein comprises a VWF fragment described herein linked to a first heterologous moiety, e.g., first Fc region, and a FVIII protein linked to a second heterologous moiety, e.g., second Fc region, wherein the VWF fragment is further linked to the second heterologous moiety (e.g., second Fc region) or the FVIII protein by a linker or by covalent bond or the first heterologous moiety (e.g., Fc region) is further linked to the FVIII protein or the second heterologous moiety (e.g., second Fc region) by a linker or a covalent bond. In some embodiments, the FVIII of the chimeric protein has a partial B-domain. In some embodiments, the FVIII protein with a partial B-domain is FVIII198 (SEQ ID NO: 105). In other embodiments, the chimeric protein further comprises a sortase recognition motif.

In some embodiments, as a result of the invention the half-life of the FVIII protein is extended compared to a FVIII protein without the VWF fragment or wildtype FVIII. The half-life of the FVIII protein is at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the half-life of a FVIII protein without the VWF fragment. In one embodiment, the half-life of FVIII is about 1.5-fold to about 20-fold, about 1.5 fold to about 15 fold, or about 1.5 fold to about 10 fold longer than the half-life of wild-type FVIII. In another embodiment, the half-life of the FVIII is extended about 2-fold to about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, about 2-fold to about 3-fold, about 2.5-fold to about 10-fold, about 2.5-fold to about 9-fold, about 2.5-fold to about 8-fold, about 2.5-fold to about 7-fold, about 2.5-fold to about 6-fold, about 2.5-fold to about 5-fold, about 2.5-fold to about 4-fold, about 2.5-fold to about 3-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 3-fold to about 4-fold, about 4-fold to about 6 fold, about 5-fold to about 7-fold, or about 6-fold to about 8 fold as compared to wild-type FVIII or a FVIII protein without the VWF fragment. In other embodiments, the half-life of FVIII is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours. In still other embodiments, the half-life of FVIII is about 15 hours to about two weeks, about 16 hours to about one week, about 17 hours to about one week, about 18 hours to about one week, about 19 hours to about one week, about 20 hours to about one week, about 21 hours to about one week, about 22 hours to about one week, about 23 hours to about one week, about 24 hours to about one week, about 36 hours to about one week, about 48 hours to about one week, about 60 hours to about one week, about 24 hours to about six days, about 24 hours to about five days, about 24 hours to about four days, about 24 hours to about three days, or about 24 hours to about two days.

In some embodiments, the average half-life of the FVIII protein per subject is about 15 hours, about 16 hours, about 17 hours, about 18 hours, about 19 hours, about 20 hours, about 21 hours, about 22 hours, about 23 hours, about 24 hours (1 day), about 25 hours, about 26 hours, about 27 hours, about 28 hours, about 29 hours, about 30 hours, about 31 hours, about 32 hours, about 33 hours, about 34 hours, about 35 hours, about 36 hours, about 40 hours, about 44 hours, about 48 hours (2 days), about 54 hours, about 60 hours, about 72 hours (3 days), about 84 hours, about 96 hours (4 days), about 108 hours, about 120 hours (5 days), about six days, about seven days (one week), about eight days, about nine days, about 10 days, about 11 days, about 12 days, about 13 days, or about 14 days.

In another aspect, a chimeric protein of the invention comprises a formula selected from the group consisting of:
(a) V-L1-H1-L3-C-L2-H2,
(b) H2-L2-C-L3-H1-L1-V, (c) C-L2-H2-L3-V-L1-H1,
(d) H1-L1-V-L3-H2-L2-C,
(e) H1-L1-V-L3-C-L2-H2,
(f) H2-L2-C-L3-V-L1-H1,
(g) V-L1-H1-L3-H2-L2-C,
(h) C-L2-H2-L3-H1-L1-V,
(i) H2-L3-H1-L1-V-L2-C,
(j) C-L2-V-L1-H1-L3-H2,
(k) V-L2-C-L1-H1-L3-H2, and
(l) H2-L3-H1-L1-C-L2-V,
  wherein V is a VWF fragment described herein;
  each of L1 or L2, is an optional linker, e.g., a thrombin cleavable linker;
  L3 is an optional linker, e.g., scFc linker, e.g., a processable linker;
  each of H1 or H2 is an optional heterologous moiety; and
  C is a FVIII protein; and
  (-) is a peptide bond or one or more amino acids.

In other aspects, a chimeric protein of the invention comprises a formula selected from the group consisting of:
(m) V-L1-H1: H2-L2-C,
(n) V-L1-H1:C-L2-H2,
(o) H1-L1-V:H2-L2-C,
(p) H1-L1-V:C-L2-H2,
(q) V:C-L1-H1:H2,
(r) V:H1-L1-C:H2,
(s) H2:H1-L1-C:V,
(t) C:V-L1-H1:H2, and
(u) C:H1-L1-V:H2,
  wherein V is a VWF fragment described herein;
  each of L1 or L2, is an optional linker, e.g., a thrombin cleavable linker;
  each of H1 or H2 is an optional heterologous moiety; and
  C is a FVIII protein;
  (-) is a peptide bond or one or more amino acids; and
  (:) is a chemical or physical association between H1 and H2, between V and C, and between V and H1 and C and H2.

(:) represents a chemical association, e.g., at least one non-peptide bond. In certain embodiments, the chemical association, i.e., (:) is a covalent bond. In some embodiments, the association between H1 and H2 is a covalent bond, e.g., a disulfide bond. In other embodiments, the chemical association, i.e., (:) is a non-covalent interaction, e.g., an ionic interaction, a hydrophobic interaction, a hydrophilic interaction, a Van der Waals interaction, a hydrogen bond. In certain embodiments, the association between the FVIII protein and the VWF fragment is a non-covalent bond. In other embodiments, (:) is a non-peptide covalent bond. In still other embodiments, (:) is a peptide bond. In one embodiment, H1 is a first heterologous moiety. In one embodiment, the first heterologous moiety is capable of extending half-life of the FVIII activity. In another embodiment, the first heterologous moiety is a polypeptide, a non-polypeptide moiety, or both. In one embodiment, the first heterologous polypeptide moiety can be selected from the group consisting of an immunoglobulin constant region or a portion thereof, albumin or fragment thereof, an albumin binding moiety, a PAS sequence, a HAP sequence, transferrin or a fragment thereof, and any combinations thereof. In another embodiment, the non-polypeptide moiety is selected from the group consisting of polyethylene glycol (PEG), polysialic acid, hydroxyethyl starch (HES), a derivative thereof, and any combinations thereof. In some embodiments, H2 is a second heterologous moiety. The second heterologous moiety can also be a half-life extender known in the art and can be a polypeptide, a non-polypeptide moiety, or a combination of both. In one embodiment, the second heterologous moiety is selected from the group consisting of an immunoglobulin constant region or a portion thereof, albumin or fragment thereof, an albumin binding moiety, a PAS sequence, a HAP sequence, transferrin or a fragment thereof, and any combinations thereof. In certain embodiments, the non-polypeptide moiety is selected from the group consisting of polyethylene glycol (PEG), polysialic acid, hydroxyethyl starch (HES), a derivative thereof, and any combinations thereof. In a particular embodiment, H1 is a first Fc region. In some embodiments, H2 is a second Fc region. Optionally, there could be a third heterologous moiety, H3, which is a half-life extender. H3 can be linked to one or more of V, C, H1, or H2 by an optional linker, e.g., a cleavable linker, e.g., a thrombin cleavable linker. Non-limiting examples of the third heterologous moiety can include an immunoglobulin constant region or a portion thereof, albumin or a fragment thereof, polyethylene glycol (PEG), a PAS sequence, and hydroxyethyl starch (HES) or a derivative thereof.

In certain embodiments, one or more of the linkers used to connect the VWF fragment, the FVIII protein, the first heterologous moiety, and/or the second heterologous moiety of formulas (a) to (u) to each other is a cleavable linker. One or more of the cleavage sites used in the chimeric protein can be cleaved by a protease selected from the group consisting of factor XIa, factor XIIa, kallikrein, factor VIIa, factor IXa, factor Xa, factor IIa (thrombin), Elastase-2, Granzyme-B, TEV, Enterokinase, Protease 3C, Sortase A, MMP-12, MMP-13, MMP-17, and MMP-20. In other embodiments, one or more linkers used in formulas (a) to (l) (e.g., L3) comprise a processable linker. The processable linkers can be cleaved by an intracellular enzyme upon secretion. The processable linker can comprise a first cleavage site (P1) at the N-terminal region of the linker, a second cleavage site (P2) at the C-terminal region of the linker, or both.

In some embodiments, one or more of the linkers used in the invention have a length of at least about 1 to 2000 amino acids. In a specific embodiment, one or more of the linkers used in the invention have a length of at least about 20, 35, 42, 48, 73, 98, 144, 288, 324, 576, or 864 amino acids. In a particular embodiment, one or more of the linkers comprise a gly/ser peptide. The gly/ser peptide can be (Gly4 Ser)$_3$ or (Gly4 Ser)$_4$.

In other aspects, a FVIII protein in a chimeric protein is a functional Factor VIII protein. The FVIII protein can comprise one or more domains of FVIII selected from the group consisting of the A1 domain, the A2 domain, the B domain, the A3 domain, the C1 domain, the C2 domain, one or more fragment thereof, and any combinations thereof. In one embodiment, the FVIII protein comprises the B domain or a portion thereof. In another embodiment, the FVIII protein is SQ B domain deleted FVIII. In other embodiments, the FVIII protein comprises single chain FVIII. In still other embodiments, the FVIII protein comprises a heavy chain of FVIII and a light chain of Factor VIII, wherein the heavy chain and the light chain are associated with each other by a metal bond. In certain embodiments, the FVIII protein has a low affinity to or does not bind to a low-density lipoprotein receptor-related protein (LRP). For example, a FVIII protein useful for the invention can contain at least one amino acid substitution that lowers the affinity to or eliminates the binding to the LRP. Non-limiting examples of the at least one amino acid substitution is at a residue corresponding to residue 471, residue 484, residue 487, residue 490, residue 497, residue 2092, residue 2093 or two or more combinations thereof of full-length mature FVIII. In some embodiments, the FVIII protein in a chimeric protein of this invention contains at least one amino acid substitution, which induces the FVIII protein to be more stable than a FVIII protein without the substitution. In other embodiments, the FVIII protein contains at least one amino acid substitution in the A2 domain and at least one amino acid substitution in the A3 domain, wherein the A2 domain and the A3 domain are associated to each other by a covalent bond. Non-limiting examples of the amino acid substitution in the A2 domain is at a residue corresponding residue 662 or 664 of full-length mature FVIII. In addition, non-limiting examples of the amino acid substitution in the A3 domain is at a residue corresponding to residue 1826 or 1828 of full-length mature FVIII is polysialylated.

In further aspects, the invention provides a polynucleotide encoding a VWF fragment described herein or a chimeric protein described herein, or a set of polynucleotides comprising a first nucleotide chain and a second nucleotide chain, wherein the first nucleotide chain encodes the VWF fragment and the second nucleotide chain encodes the second Fc region or the clotting factor or fragment thereof of the chimeric protein. In one embodiment, the set of polynucleotides further comprises a third polynucleotide chain, which encodes a proprotein convertase belongs to the subtilisin-like proprotein convertase family. Non-limiting examples of the proprotein convertase include proprotein convertase subtilisin/kexin type 3 (PACE or PCSK3), proprotein convertase subtilisin/kexin type 5 (PCSK5 or PC5), proprotein convertase subtilisin/kexin type 7 (PCSK7 or PC7), or a yeast Kex 2. In still other aspects, the invention includes a vector comprising the polynucleotide or the set of polynucleotides and one or more promoters operably linked to the polynucleotide or the set of polynucleotides or a set of vectors comprising a first vector and a second vector, wherein the first vector encodes the first polynucleotide chain of the set of polynucleotides and the second vector encodes the second polynucleotide chain of the set of polynucleotides. The set of vectors can further comprise a third vector, which comprises a third polynucleotide chain encoding PC5 or PC7. In some embodiments, the vector further comprises PACE. In some embodiments, PACE cleaves the D1D2 domains of the VWF fragment.

In some aspects, the invention is directed to a pharmaceutical composition comprising the VWF fragment, the chimeric protein, the polynucleotide, the set of polynucleotides, the vector, or the set of vectors, and a pharmaceutically acceptable carrier. The composition of this invention can extend the half-life of Factor VIII. In other aspects, the invention includes a host cell comprising the polynucleotide, the set of polynucleotides, the vector, or the sets of vectors.

In other aspects, the present invention is drawn to a chimeric protein comprising a FVIII protein, an adjunct moiety and an optional linker, wherein the adjunct moiety inhibits or prevents endogenous VWF from binding to the FVIII protein and has at least one VWF-like FVIII protecting property. The VWF-like FVIII protecting property comprises protecting the FVIII protein from one or more protease cleavages, protecting the FVIII protein from activation, stabilizing the heavy chain and/or the light chain of the FVIII protein, or preventing clearance of the FVIII protein by one or more scavenger receptors.

The adjunct moiety in the chimeric protein can inhibit or prevent endogenous VWF from binding to the FVIII protein by shielding or blocking a VWF binding site on the FVIII protein. In some embodiments, the VWF binding site is located in the A3 domain or the C2 domain of the FVIII protein or both A3 domain and C2 domain of the FVIII protein. In another embodiment, the VWF binding site is the amino acid sequence corresponding to amino acids 1669 to 1689 and 2303 to 2332 of SEQ ID NO: 16. In some embodiments, the adjunct moiety is a polypeptide, a non-polypeptide moiety, or both. The polypeptide useful as the adjunct moiety can comprise an amino acid sequence of at least 40, 50, 60, 70, 80, 90, 100, 110, 120, 130, 140, 150, 200, 250, 300, 350, 400, 450, 500, 550, 600, 650, 700, 750, 800, 850, 900, 950, or 1000 amino acids in length. For example, the polypeptide useful as an adjunct moiety can be selected from the group consisting of a VWF fragment, an immunoglobulin constant region or a portion thereof, albumin or a fragment thereof, an albumin binding moiety, a PAS sequence, a HAP sequence, other half-life extending technologies, and any combinations thereof. The non-polypeptide moiety useful as an adjunct moiety can be selected from the group consisting of polyethylene glycol (PEG), polysialic acid, hydroxyethyl starch (HES) or a derivative thereof, and any combinations thereof. In one embodiment, the adjunct moiety is the VWF fragment described herein. The adjunct moiety and the FVIII protein can be linked, e.g., by a linker, or associated with each other. The linker can comprise a cleavable linker, e.g., a thrombin cleavable linker.

In one aspect, the invention provides a method of preventing or inhibiting binding of a FVIII protein with endogenous VWF comprising adding an effective amount of the VWF fragment, the chimeric protein, the polynucleotide, or the set of polynucleotides to a cell comprising a FVIII protein or a polynucleotide encoding the FVIII protein, wherein the VWF fragment binds to the FVIII protein. In another aspect, the invention includes a method of preventing or inhibiting binding of the FVIII protein with endogenous VWF comprising adding an effective amount of the chimeric protein, the polynucleotide, or the set of polynucleotides to a subject in need thereof, wherein the VWF fragment binds to the FVIII protein and thus prevents or inhibits binding of the FVIII protein. In some aspects, the invention includes a method of extending or increasing half-life of a FVIII protein, wherein the method comprises adding an effective amount of the VWF fragment, the chimeric protein, the polynucleotide, or the set of polynucleotides to a cell comprising a FVIII protein or a polynucleotide encoding the FVIII protein or to a subject in need thereof, wherein the VWF fragment binds to the FVIII protein. In other aspects, the invention is drawn to a method of preventing or inhibiting clearance of a FVIII protein from a cell, wherein the method comprises adding an effective amount of the VWF fragment, the chimeric protein, the polynucleotide, or the set of polynucleotides to a cell comprising a FVIII protein or a polynucleotide encoding the FVIII protein or to a subject in need thereof, wherein the VWF fragment binds to the FVIII protein.

In another aspect, the invention is directed to a method of treating a bleeding disease or disorder in a subject in need thereof comprising administering an effective amount of the VWF fragment, the chimeric protein, the polynucleotide, or the set of polynucleotides, wherein the bleeding disease or disorder is selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath. In other embodiments, the treatment is prophylactic or on-demand. In still other embodiments, the invention is a method of treating a disease or disorder associated with Type 2N von Willebrand's disease to a subject in need thereof, comprising administering an effective amount of the VWF fragment, the chimeric protein, the polynucleotide, or the set of polynucleotides, wherein the disease or disorder is treated.

BRIEF DESCRIPTION OF THE DRAWINGS/FIGURES

FIG. 1A-F. Schematic diagrams of VWF proteins. FIG. 1A shows two VWF fragments containing amino acids 1 to 276 of SEQ ID NO: 73 (amino acids 764 to 1039 of SEQ ID NO: 2). VWF-001 is synthesized without the pre/propeptide sequences of VWF, while VWF-009 is synthesized with the pre/propeptide sequences (D1 and D2 domains). The prepeptide of VWF-009 is cleaved during synthesis, and VWF-009 contains the propeptide with the D' and D3 domain sequences. FIG. 1B shows three VWF fragments containing amino acids 1 to 477 of SEQ ID NO: 73 (amino acids 764 to 1240 of SEQ ID NO: 2). VWF-002 is synthesized without the pre/propeptide sequences. VWF-010 contains the D1D2 domains in addition to the D'D3 domains. VWF-013 contains the D1D2D'D3 domains in addition to alanine residues substituting cysteines at residues 336 and 379 of SEQ ID NO: 72. FIG. 1C shows two VWF fragments containing the D'D3 domains and a portion of the A1 domain. VWF-003 has amino acids 764 to 1274 of SEQ ID NO: 2). VWF-011 contains the D1D2 domains in addition to the D'D3 domains. FIG. 1D shows two constructs, VWF-004 and VWF-012. VWF-004 contains the D'D3 domains and the complete sequence of A1 domain. VWF-012 contains the D1D2D'D3 domains and the complete sequence of A1 domain. FIG. 1E shows three constructs. VWF-006 contains the D1D2D'D3 domains and the CK domain of VWF (cysteine knot domain). VWF-008 is the full-length VWF. VWF-031 (VWF-Fc) shows a construct containing the D1D2D'D3 domains linked to a single Fc region by a cleavable linker. VWF-053 is the D1D2 domains. FIG. 1F shows full-length VWF protein comprising propeptide (the D1 and D2 domains) and mature subunits (the D', D3, A1, A2, A3, D4, B1-3, C1-2 domains). The VWF protein is about 250 kDa protein and forms multimers (>20 MDa) by disulfide bonding. The VWF protein associates with FVIII (95-98%) in non-covalent complex and then extends half-life of FVIII by protecting FVIII from protease cleavage/activation, stabilizing heavy & light chain, and preventing clearance of FVIII by scavenger receptors. The VWF protein also can limit half-life of FVIII by clearance of FVIII-VWF complex through VWF receptors and preventing pinocytosis and recycling of rFVIIIFc.

FIG. 2. Schematic diagrams of examples of VWF:FVIII heterodimer constructs. The left construct shows a VWF fragment having the D'D3 domains of full-length VWF (amino acids 1-477 of SEQ ID NO: 73) and containing alanine substitutions at residues 336 and 379 of SEQ ID NO: 72. The chimeric protein construct (FVIII 064/065) comprises the C-terminus of a VWF fragment linked to a first Fc region by a linker and FVIII is linked to a second Fc region, wherein the second Fc region is further linked to the N-terminus of a VWF fragment by a linker (e.g., formula C-H1-L1-V-L2-H2, wherein V is a VWF fragment, C is FVIII, H1 and H2 are Fc regions, and L1 and L2 are cleavable linkers). The construct in FIG. 2b is an intracellularly processed VWF:FVIII heterodimer construct where the linker between the second Fc and the N-terminus of the VWF fragment has been cleaved. FVIII-064 contains the D'D3 domains of VWF (amino acids 1 to 477 of SEQ ID NO: 73 with C336A and C379A substitutions). FVIII-065 contains the D'D3 domains of VWF (amino acids 1 to 276 of SEQ ID NO: 73). FVIII-136 contains FVIIIFc linked to the D'D3 fragment-Fc by a linker that can be processed by an intracellular protease enzyme. When FVIII-136 is expressed, the enzyme cleaves the linker between the second Fc (fused to FVIII-LC) and the VWF D'D3 fragment (fused to the first Fc), while the Fc region fused to (or linked to) FVIII-LC forms a covalent bond (e.g., a disulfide bond) with the first Fc fused to (or linked to) the VWF fragment. FVIII-148 is single chain FVIIIFc with the D'D3 fragment (a single chain FVIII by introducing R1645A/R1648A mutation into FVIII gene).

FIG. 3. Schematic diagrams of examples of VWF:FVIII heterodimer constructs containing examples of variable linkers between VWF and Fc. The constructs (FVIII-064, FVIII-159, FVIII-160, FVIII-178, and FVIII-179) have the common structure represented as formula C-H1-L1-V-L2-H2, but contain examples of different linkers or amino acid substitutions. The constructs shown contain the same VWF fragment, which is the D' and D3 domains of VWF (i.e., amino acids 1 to 477 of SEQ ID NO: 73 with amino acid substitutions C336A and C379A). Construct FVIII 64 has a thrombin cleavable linker (i.e., L2) between the VWF fragment and the Fc (i.e., H2), which has 20 amino acids. Construct FVIII 159 has a thrombin cleavable linker (i.e., L2) between the VWF fragment and the Fc (i.e., H2), which has 35 amino acids. Construct FVIII 160 has a thrombin cleavable linker (i.e., L2) between the VWF fragment and the Fc (i.e., H2), which has 48 amino acids. Constructs FVIII-180, FVIII-181, and FVIII-182 are derivatives of FVIII-160 containing K2092A mutation in FVIII C1 domain, K2093A mutation in FVIII C1 domain, and K2092A/K2093A mutations in FVIII C1 domain, respectively. Construct FVIII-178 has a thrombin cleavable linker (i.e., L2) between the VWF fragment and the Fc (i.e., H2), which has 73 amino acids. Construct FVIII-179 has a thrombin cleavable linker (i.e., L2) between the VWF fragment and the Fc (i.e., H2), which has 98 amino acids.

FIG. 4: Schematic diagrams of examples of FVIII-VWF constructs, in which VWF is D1D2D'D3 fragment of VWF, the Linker is a variable length linker containing a cleavage site, e.g., a thrombin cleavage site, SC FVIII is a single chain FVIII, which contains the R1645A/R1648A substitutions, H is a heterologous moiety, e.g., an immunoglobulin constant region or a portion thereof, a moiety for conjugating polyethylene glycol (PEG) and/or PEG, an albumin or albumin fragment, an albumin binding moiety, a HAP sequence, a moiety for polysialylation and/or polysialic acid, a moiety for hydroxyethyl starch (HES) and/or HES, or a PAS sequence, etc., HC FVIII is a heavy chain of FVIII, LC FVIII is a light chain of FVIII, and Fc is an Fc region of an immunoglobulin constant region. FIG. 4A has a formula of VWF-Linker-SC FVIII. FIG. 4B has a formula of VWF-Linker-H-Linker-SC FVIII. The linkers (the first linker between VWF and H and the second linker between H and SC FVIII) can be identical or different. FIG. 4C has a formula of VWF-Linker-SC FVIII-Linker-H. The linkers (the first linker between VWF and SC FVIII and the second linker between SC FVIII and H) can be identical or different. FIG. 4D has a formula of VWF-Linker-HC FVIII-H-Linker-LC FVIII. The linkers (the first linker between VWF and HC FVIII and the second linker between H and LC FVIII) can be identical or different. FIG. 4E has a formula of HC FVIII-H-LC FVIII-Linker-first Fc-Linker-VWF-Linker-second Fc. The linkers (the first linker between LC FVIII and first Fc, the second linker between first Fc and VWF, and the third linker between VWF and second Fc) can be identical or different. The linkers can be a cleavable linker. For example, the linker between first Fc and VWF can be a cleavable linker comprising a cleavage site at the N-terminus and/or the C-terminus of the linker. The first Fc and the second Fc can be identical or different. FIG. 4F has a formula of HC FVIII-H-LC FVIII-Linker-first Fc-Linker-VWF-Linker-second Fc. The linkers (the first linker between LC FVIII and first Fc, the second linker between first Fc and VWF, and the third linker between VWF and second Fc) can be identical or different. One or more linkers can be a cleavable linker. For example, the linker between the first Fc and VWF can be a cleavable linker comprising a cleavage site at the N-terminus and/or the C-terminus of the linker. The first Fc and the second Fc can be identical or different. FIG. 4G has a formula of SC FVIII-Linker-Fc-Linker-VWF-H-Linker-Fc. FIG. 4H has a formula of Pegylated or Hesylated SC FVIII-Linker-Fc-Linker-VWF-H-Linker-Fc. The linkers (the first linker between SC FVIII and first Fc, the second linker between first Fc and VWF, and the third linker between H and second Fc) can be identical or different. One or more linkers can be a cleavable linker. For example, the linker between the first Fc and VWF can be a cleavable linker comprising a cleavage site at the N-terminus and/or the C-terminus of the linker. The first Fc and the second Fc can be identical or different.

FIG. 5. Schematic diagrams of FVIII-VWF heterodimer co-transfection system. Construct FVIII-155 contains the full-length FVIII sequence (with an alanine residue substituting the arginine residues at 1645 and 1648) linked to an Fc region. VWF-031 contains the D1D2D'D3 fragment (with an alanine residue substituting the Cysteine residues at 336 and 379) which is linked to another Fc region with a 48 thrombin cleavable linker. After intracellular processing, construct FVIII-155 produces a full length single chain FVIII (SCFVIII) fused to one Fc fragment, construct VWF-031 produces a 477 amino acids D'D3 fragment linked to another Fc fragment. Two covalent bonds can be formed between the Fc fragments that are linked to the SC FVIII or the D'D3 fragment, this in turn allows a covalent association of FVIII and D'D3, which is the main character of the desired final product.

FIG. 6 is the non-reducing and reducing SDS PAGE of VWF-009 (D1D2D'D3 1-276 aa×6 HIS), which shows VWF-009 exists as a monomer. Unprocessed means VVF-009 with the propeptide (the D1D2 domains).

FIG. 7 is the non-reducing and reducing SDS PAGE of VWF-002 (D'D3 1-477 aa×6 his) or VWF-010 (D1D2D'D3 1-477 aa×6 his), which shows VWF-002 exists as a monomer and VWF-010 exists as a dimer.

FIG. 8 shows thrombin digestion of FVIII-VWF heterodimer shown in FIG. 2(b). Lane 1 shows marker. Lane 2 is rFVIII-Fc without thrombin. Lane 3 is rFVIII-Fc with thrombin. Lane 5 is FVIIIFc-VWF. Lane 6 shows FVIIIFc-VWF and thrombin. A1 indicates A1 domain of FVIII, A2 indicates A2 domain of FVIII, and Δa3 LC indicates the light chain of FVIII.

FIG. 9A-B shows the FVIII activity measured by a FVIII chromogenic assay. FIG. 9A shows pharmacokinetic profile of rFVIII and rFVIIIFc in HemA mouse. FIG. 9B shows PK profile of rFVIII and rFVIIIFc in FVIII/VWF Double knock-out (DKO) mouse. The Y axis shows FVIII activity in mIU/mL, and the X axis shows time.

FIG. 10A-B shows FVIII protection by the D'D3 fragments as shown by mFVIII plasma level (mIU/mL) and VWF expression level (nM/mL) 48 hours post plasmid injection. The VWF fragments used to show FVIII protection are VWF-001 (276aa, monomer), VWF-009 (276aa, monomer), VWF-002 (477aa, monomer), VWF-010 (477aa, dimer), VWF-003 (511aa, monomer), VWF-011 (511aa, dimer), VWF-004 (716aa, monomer), VWF-012 (716aa, dimer), VWF-006, and VWF-008.

FIG. 11 shows the pharmacokinetic profile of rBDD-FVIII in FVIII-VWF DKO mice when co-administered with D'D3 fragments. FIG. 11A shows FVIII activity (mIU/mL) measured by a FVIII chromogenic assay after co-administration of rBDD-FVIII and VWF-002 or rBDD-FVIII and VWF-010 or rBDD-FVIII alone in FVIII/VWF DKO mice. FIG. 11B shows VWF-002 and VWF-010 plasma level (ng/mL) after administration. The X axis represents time in hours.

FIG. 12 shows pharmacokinetic profile of rFVIIIFc in VWF D'D3 expressing mice. FIG. 12A shows the timeline of hydrodynamic injection (HDI) of the D'D3 domain encoding plasmid DNA (day −5), intravenous dosing of rFVIIIFc (day 0), and PK sample collection (day0-day3). FIG. 12B shows post rFVIIIFc infusion plasma FVIII activity (mIU/mL) measured by a FVIII chromogenic assay in FVIII/VWF DKO mice with HDI of the D1D2D'D3 domains (477aa) (circle) and the D1D2D'D3 domains (477aa) with cysteine substitutions (rectangle) in FVIII/VWF DKO mice. The FVIII activity in control mice without HDI of the D'D3 domains is shown as triangle. FIG. 10C show the D'D3 plasma level (ng/mL) after HDI administration of the D1D2D'D3 dimer or the D1D2D'D3 monomer DNA construct. The X axis represents time in hours.

FIG. 13 shows D'D3-Fc linker selection by HDI in FVIII/VWF DKO mice. Different lengths of the linkers (20aa (FVIII-064), 35aa (FVIII-159), or 48aa (FVIII-160)) were inserted between the D'D3 domains and the Fc region. The FVIII activity (mIU/ml) was measured by a FVIII chromogenic assay after HDI in FVIII/VWF DKO mice.

FIG. 14 shows HDI of Single Chain FVIIIFc/D'D3 heterodimer in FVIII/VWF DKO mice. The FVIII activities of processed (dual chain) rFVIIIFc-D'D3 (pSYN-FVIII-136) and Single Chain rFVIIIFc-D'D3 (pSYN-FVIII-148) were measured 24 hours and 48 hours after HDI.

FIG. 15 shows binding affinity of FVIII-155/VWF-031 heterodimer to immobilized hVWF by Octet assay. FVIIIFc, FVIII, and IgG were also used as controls. The x-axis shows time in seconds, and the y-axis shows the binding in nanometer (nm).

FIG. 16 shows FVIII-155/VWF-031 pharmacokinetics in FVIII/VWF deficient (FVIII/VWF DKO) mice. The x-axis indicates time in hours, and the y-axis indicates FVIII recovery v. input in percent.

FIG. 17: Schematic diagrams of examples of VWF fragment constructs, in which VWF is D1D2D'D3 fragment of VWF; the Linker is a variable length linker containing a cleavage site, e.g., a thrombin cleavage site; H is a heterologous moiety, e.g., an immunoglobulin constant region or a portion thereof, a moiety for conjugating polyethylene glycol (PEG) and/or PEG, an albumin or albumin fragment, an albumin binding moiety, a HAP sequence, a moiety for polysialylation and/or polysialic acid, a moiety for hydroxyethyl starch (HES) and/or HES, or a PAS sequence, etc.; and Fc is an Fc region of an immunoglobulin. FIG. 17A has a formula of D1D2-D' partial D3-H-Partial D3-Linker-Fc. FIG. 17B has a formula of D1D2-Partial D'-H-partial D'D3-Linker-Fc. FIG. 17C has a formula of D1D2-Pegylated or Hesylated D'D3-Linker-Fc. The linker can be optionally cleaved.

FIG. 18: A) shows FVIIIFc loses FVIII activity in both HemA (diamond) and DKO (square) plasma over time. FVIII activity is measured by chromogenic assay. X-axis shows time in hours, and y-axis shows relative activity. B) shows that the loss in FVIII activity is due to the dissociation or degradation of the heavy chain (HC). The left panel shows an immuno-precipitation assay using sheep anti-FVIII polyclonal antibody in Bio-rad 4-15% gel. The gel was reduced and imaged by Bio-rad system. Lane 1 shows Bio-rad unstain marker; lane 2 shows FVIIIFc and PBS; lane 3 shows FVIIIFc and DKO plasma; and lane 5 shows sheep anti-FVIII polyclonal antibody alone. The right panel shows Western analysis of the gel using FVIII anti-heavy chain antibody (GMA012). Lane 1 shows Bio-rad unstain marker; lane 2 shows FVIIIFc and PBS; lane 3 shows FVIIIFc and DKO plasma; and lane 4 shows sheep anti-FVIII polyclonal antibody alone.

FIG. 19: shows FVIII activity of wild type FVIIIFc (circle), scFVIIIFc (single chain FVIII) (filled triangle), or FVIII:VWF heterodimer (e.g., FVIII155/VWF31) (empty triangle) by chromogenic assay in DKO mouse plasma (left panel) and HemA mouse plasma (right panel) as a function of time. Y axis shows relative FVIII activity. Wild type FVIIIFc contains dual chain of FVIII (i.e., FVIII heavy chain and FVIII light chain held together non-covalently) and thus has three chains, a FVIII heavy chain, a FVIII light chain fused to an Fc, and an Fc alone. ScFVIIIFc contains a FVIII single chain and thus has two chains, one with a single chain FVIII fused to an Fc and another with an Fc alone. The FVIII:VWF heterodimer (e.g., FVIII155/VWF031) contains single chain FVIII fused to an Fc and a VWF fragment (D'D3) fused to an Fc.

FIG. 20 shows processing of D1D2 domain from VWF fragment (e.g., VWF-031(D1D2D'D3Fc)) by PC5 or PACE (Furin) at different concentrations. The D1D2 processing is shown on a Bio-rad 4-15% gel at a reduced condition by Bio-rad imager. Lane 1 shows VWF031 alone; lane 2 shows PC5 alone; lane 3 shows PACE alone; lane 4 shows VWF031 and PC5 at 2.5%; lane 5 shows VWF031 and PC5 at 5%; lane 6 shows VWF031 and PC5 at 7.5%; lane 7 shows VWF031 and PC5 at 10%; lane 8 shows VWF031 and PACE at 2.5%; lane 9 shows VWF031 and PACE at 5%; lane 10 shows VWF031 at 7.5%; and lane 11 shows VWF031 and PACE at 10%.

FIG. 21: A) shows that a binding assay of a FVIII:VWF heterodimer (e.g., FVIII-155/VWF-031) by ForteBio octet instrument. For the assay, full length VWF was captured by using APS sensor. The binding of FVIIIFc and FVIII to the full-length VWF is shown at the lower left panel. The lack of binding of FVIIIY1680 (a mutant having no affinity for VWF) and FVIII:VWF heterodimer (FVIII155/VWF031) is shown at the lower right panel. B) shows another binding assay of a FVIII:VWF heterodimer (e.g., FVIII-155/VWF-031). In this assay, the constructs (VWF031 construct, FVIII-155/VWF031, or FVIII) were immobilized on protein G sensor. The binding of the constructs to FVIII was measured.

FIG. 22 shows binding affinity of VWF D'D3 domains with FVIII molecule measured by a surface plasma resonance experiment. The VWF031 construct (100RU) was captured by 1000RU anti-human IgG. B-domain deleted FVIII was applied in single cycle kinetics mode in 1:1 fit. The total number was 4.

FIG. 23 shows effects of different linker length in the FVIIIFc/VWF heterodimer constructs on pharmacokinetics when administered in FVIII/VWF DKO mice. Three different linkers (48 aa, 73aa, or 98aa) were inserted between the D'D3 and the Fc, i.e., VWF031, VWF035, and VWF036. The FVIII activity normalized to 5 min value (%) is shown in Y-axis.

FIG. 24 shows examples of sortase ligation of a VWF fragment with FVIII. A) shows two ligation constructs, (1) a VWF fragment fused to a sortase recognition motif (e.g., LPXTG) at the C-terminus and (2) FVIII having glycine (n) at the N-terminus. After reaction with sortase, the VWF fragment and the sortase recognition motif are ligated to the N-terminus of FVIII. B) shows two ligation constructs, (1) FVIII fused to a sortase recognition motif at its C-terminus and (2) a VWF fragment having glycine (n) at its N-terminus. After reaction with sortase, FVIII and the sortase recognition motif are fused to the VWF fragment at the N-terminus of the VWF fragment. C) shows two ligation constructs, (1) a VWF fragment fused to a sortase recognition motif by a variable length linker and (2) FVIII fused to glycine (n) at its N-terminus. After reaction with sortase, the VWF fused by a linker to the sortase recognition motif is ligated to the N-terminus of FVIII. D) shows two ligation constructs, (1) FVIII fused by a variable length linker to a sortase recognition motif and (2) a VWF fragment fused to glycine (n) at its N-terminus. After reaction with sortase, FVIII fused by a linker to the sortase recognition motif is ligated to the N terminus of VWF fragment. E) shows a ligation construct containing a VWF fragment fused by a variable length linker to a sortase recognition motif, which is also fused to a protease cleavage site (e.g., Thrombin cleavage site) fused by a variable length linker to an Fc.

FIG. 25 shows a schematic comparison of FVIII155 and FVIII198. FVIII155 encodes a single chain FVIIIFc protein. FVIII198 is a partial B-domain containing single chain FVIIIFc molecule-226N6. 226 represents the N-terminus 226 amino acid of the FVIII B-domain, and N6 represents six N-glycosylation sites in the B-domain.

FIG. 26 A) shows a stability assay measuring the relativity activity of FVIII155 and FVIII198 in DKO plasma as a function of time. As can be seen in the figure, the presence of the partial B-domain in FVIII198 increased the stability of single chain FVIIIFc in comparison to FVIII155; B) shows a comparison of the half-lives of FVIII198, FVIII155, and dual chain (dcFVIIIFc) in DKO mice. As can be seen in the figure, single chain FVIII (FVIII155) has a 1.5 fold increase in half life in comparison to dual chain FVIII. Single chain FVIII with the 266N6 B-domain (FVIII198) had a further 1.5 fold increase in half life. The graph shows the FVIII recovery v. the 5 minute value (%) as a function of time.

DETAILED DESCRIPTION OF THE INVENTION

Definitions

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

The term "polynucleotide" or "nucleotide" is intended to encompass a singular nucleic acid as well as plural nucleic acids, and refers to an isolated nucleic acid molecule or construct, e.g., messenger RNA (mRNA) or plasmid DNA (pDNA). In certain embodiments, a polynucleotide comprises a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a Factor VIII polypeptide contained in a vector is considered isolated for the purposes of the present invention. Further examples of an isolated polynucleotide include recombinant polynucleotides maintained in heterologous host cells or purified (partially or substantially) from other polynucleotides in a solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid can include regulatory elements such as promoters, enhancers, ribosome binding sites, or transcription termination signals.

As used herein, a "coding region" or "coding sequence" is a portion of polynucleotide which consists of codons translatable into amino acids. Although a "stop codon" (TAG, TGA, or TAA) is typically not translated into an amino acid, it may be considered to be part of a coding region, but any flanking sequences, for example promoters, ribosome binding sites, transcriptional terminators, introns, and the like, are not part of a coding region. The boundaries of a coding region are typically determined by a start codon at the 5' terminus, encoding the amino terminus of the resultant polypeptide, and a translation stop codon at the 3'terminus, encoding the carboxyl terminus of the resulting polypeptide. Two or more coding regions of the present invention can be present in a single polynucleotide construct, e.g., on a single vector, or in separate polynucleotide constructs, e.g., on separate (different) vectors. It follows, then, that a single vector can contain just a single coding region, or comprise two or more coding regions, e.g., a single vector can separately encode a binding domain-A and a binding domain-B as described below. In addition, a vector, polynucleotide, or nucleic acid of the invention can encode heterologous coding regions, either fused or unfused to a nucleic acid encoding a binding domain of the invention. Heterologous coding regions include without limitation specialized elements or motifs, such as a secretory signal peptide or a heterologous functional domain.

Certain proteins secreted by mammalian cells are associated with a secretory signal peptide which is cleaved from the mature protein once export of the growing protein chain across the rough endoplasmic reticulum has been initiated. Those of ordinary skill in the art are aware that signal peptides are generally fused to the N-terminus of the polypeptide, and are cleaved from the complete or "full-length" polypeptide to produce a secreted or "mature" form of the polypeptide. In certain embodiments, a native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, e.g., a human tissue plasminogen activator (TPA) or mouse β-glucuronidase signal peptide, or a functional derivative thereof, can be used.

The term "downstream" refers to a nucleotide sequence that is located 3' to a reference nucleotide sequence. In certain embodiments, downstream nucleotide sequences relate to sequences that follow the starting point of transcription. For example, the translation initiation codon of a gene is located downstream of the start site of transcription.

The term "upstream" refers to a nucleotide sequence that is located 5' to a reference nucleotide sequence. In certain embodiments, upstream nucleotide sequences relate to sequences that are located on the 5' side of a coding region or starting point of transcription. For example, most promoters are located upstream of the start site of transcription.

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions may include promoters, translation leader sequences, introns, polyadenylation recognition sequences, RNA processing sites, effector binding sites and stem-loop structures. If a coding region is intended for expression in a eukaryotic cell, a polyadenylation signal and transcription termination sequence will usually be located 3' to the coding sequence.

A polynucleotide which encodes a gene product, e.g., a polypeptide, can include a promoter and/or other transcription or translation control elements operably associated with one or more coding regions. In an operable association a coding region for a gene product, e.g., a polypeptide, is associated with one or more regulatory regions in such a way as to place expression of the gene product under the influence or control of the regulatory region(s). For example, a coding region and a promoter are "operably associated" if induction of promoter function results in the transcription of mRNA encoding the gene product encoded by the coding region, and if the nature of the linkage between the promoter and the coding region does not interfere with the ability of the promoter to direct the expression of the gene product or interfere with the ability of the DNA template to be transcribed. Other transcription control elements, besides a promoter, for example enhancers, operators, repressors, and transcription termination signals, can also be operably associated with a coding region to direct gene product expression.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

The term "expression" as used herein refers to a process by which a polynucleotide produces a gene product, for example, an RNA or a polypeptide. It includes without limitation transcription of the polynucleotide into messenger RNA (mRNA), transfer RNA (tRNA), small hairpin RNA (shRNA), small interfering RNA (siRNA) or any other RNA product, and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage.

A "vector" refers to any vehicle for the cloning of and/or transfer of a nucleic acid into a host cell. A vector may be a replicon to which another nucleic acid segment may be attached so as to bring about the replication of the attached segment. A "replicon" refers to any genetic element (e.g., plasmid, phage, cosmid, chromosome, virus) that functions as an autonomous unit of replication in vivo, i.e., capable of replication under its own control. The term "vector" includes both viral and nonviral vehicles for introducing the nucleic acid into a cell in vitro, ex vivo or in vivo. A large number of vectors are known and used in the art including, for example, plasmids, modified eukaryotic viruses, or modified bacterial viruses. Insertion of a polynucleotide into a suitable vector can be accomplished by ligating the appropriate polynucleotide fragments into a chosen vector that has complementary cohesive termini.

Vectors may be engineered to encode selectable markers or reporters that provide for the selection or identification of cells that have incorporated the vector. Expression of selectable markers or reporters allows identification and/or selection of host cells that incorporate and express other coding regions contained on the vector. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like. Examples of reporters known and used in the art include: luciferase (Luc), green fluorescent protein (GFP), chloramphenicol acetyltransferase (CAT), -galactosidase (LacZ), -glucuronidase (Gus), and the like. Selectable markers may also be considered to be reporters.

The term "plasmid" refers to an extra-chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Eukaryotic viral vectors that can be used include, but are not limited to, adenovirus vectors, retrovirus vectors, adeno-associated virus vectors, poxvirus, e.g., vaccinia virus vectors, baculovirus vectors, or herpesvirus vectors. Non-viral vectors include plasmids, liposomes, electrically charged lipids (cytofectins), DNA-protein complexes, and biopolymers.

A "cloning vector" refers to a "replicon," which is a unit length of a nucleic acid that replicates sequentially and which comprises an origin of replication, such as a plasmid, phage or cosmid, to which another nucleic acid segment may be attached so as to bring about the replication of the attached segment. Certain cloning vectors are capable of replication in one cell type, e.g., bacteria and expression in another, e.g., eukaryotic cells. Cloning vectors typically comprise one or more sequences that can be used for selection of cells comprising the vector and/or one or more multiple cloning sites for insertion of nucleic acid sequences of interest.

The term "expression vector" refers to a vehicle designed to enable the expression of an inserted nucleic acid sequence following insertion into a host cell. The inserted nucleic acid sequence is placed in operable association with regulatory regions as described above.

Vectors are introduced into host cells by methods well known in the art, e.g., transfection, electroporation, microinjection, transduction, cell fusion, DEAE dextran, calcium phosphate precipitation, lipofection (lysosome fusion), use of a gene gun, or a DNA vector transporter.

"Culture," "to culture" and "culturing," as used herein, means to incubate cells under in vitro conditions that allow for cell growth or division or to maintain cells in a living state. "Cultured cells," as used herein, means cells that are propagated in vitro.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced recombinant technology, but is not necessarily translated from a designated nucleic acid sequence. It can be generated in any manner, including by chemical synthesis.

An "isolated" polypeptide or a fragment, variant, or derivative thereof refers to a polypeptide that is not in its natural milieu. No particular level of purification is required. For example, an isolated polypeptide can simply be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

Also included in the present invention are fragments or variants of polypeptides, and any combination thereof. The term "fragment" or "variant" when referring to polypeptide binding domains or binding molecules of the present invention include any polypeptides which retain at least some of the properties (e.g., FcRn binding affinity for an FcRn binding domain or Fc variant, coagulation activity for an FVIII variant, or FVIII binding activity for the VWF fragment) of the reference polypeptide. Fragments of polypeptides include proteolytic fragments, as well as deletion fragments, in addition to specific antibody fragments discussed elsewhere herein, but do not include the naturally occurring full-length polypeptide (or mature polypeptide). Variants of polypeptide binding domains or binding molecules of the present invention include fragments as described above, and also polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions.

The term "VWF fragment" or "VWF fragments" used herein means any VWF fragments that interact with FVIII and retain at least one or more properties that are normally provided to FVIII by full-length VWF, e.g., preventing premature activation to FVIIIa, preventing premature proteolysis, preventing association with phospholipid membranes that could lead to premature clearance, preventing binding to FVIII clearance receptors that can bind naked FVIII but not VWF-bound FVIII, and/or stabilizing the FVIII heavy chain and light chain interactions. The term "VWF fragment" as used herein does not include full length- or mature VWF protein. In a particular embodiment, the "VWF fragment" as used herein comprises a D' domain and a D3 domain of the VWF protein, but does not include the A1 domain, the A2 domain, the A3 domain, the D4 domain, the B1 domain, the B2 domain, the B3 domain, the C1 domain, the C2 domain, and the CK domain of the VWF protein.

The term "half-life limiting factor" or "FVIII half-life limiting factor" as used herein indicates a factor that prevents the half-life of a FVIII protein from being longer than 1.5 fold or 2 fold compared to wild-type FVIII (e.g., ADVATE® or REFACTO®). For example, full length or mature VWF can act as a FVIII half-life limiting factor by inducing the FVIII and VWF complex to be cleared from system by one or more VWF clearance pathways. In one example, endogenous VWF is a FVIII half-life limiting factor. In another example, a full-length recombinant VWF molecule non-covalently bound to a FVIII protein is a FVIII-half-life limiting factor.

The term "endogenous VWF" as used herein indicates VWF molecules naturally present in plasma. The endogenous VWF molecule can be multimer, but can be a monomer or a dimer. Endogenous VWF in plasma binds to FVIII and forms a non-covalent complex with FVIII.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

As known in the art, "sequence identity" between two polypeptides is determined by comparing the amino acid sequence of one polypeptide to the sequence of a second polypeptide. When discussed herein, whether any particular polypeptide is at least about 50%, 60%, 70%, 75%, 80%, 85%, 90%, 95%, 99%, or 100% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full-length of the reference polypeptide sequence and that gaps in homology of up to 5% of the total number of amino acids in the reference sequence are allowed.

As used herein, an "amino acid corresponding to" or an "equivalent amino acid" in a VWF sequence or a FVIII protein sequence is identified by alignment to maximize the identity or similarity between a first VWF or FVIII sequence and a second VWF or FVIII sequence. The number used to identify an equivalent amino acid in a second VWF or FVIII sequence is based on the number used to identify the corresponding amino acid in the first VWF or FVIII sequence.

A "fusion" or "chimeric" protein comprises a first amino acid sequence linked to a second amino acid sequence with which it is not naturally linked in nature. The amino acid sequences which normally exist in separate proteins can be brought together in the fusion polypeptide, or the amino acid sequences which normally exist in the same protein can be placed in a new arrangement in the fusion polypeptide, e.g., fusion of a Factor VIII domain of the invention with an immunoglobulin Fc domain. A fusion protein is created, for example, by chemical synthesis, or by creating and translating a polynucleotide in which the peptide regions are encoded in the desired relationship. A chimeric protein can further comprises a second amino acid sequence associated with the first amino acid sequence by a covalent, non-peptide bond or a non-covalent bond.

As used herein, the term "half-life" refers to a biological half-life of a particular polypeptide in vivo. Half-life may be represented by the time required for half the quantity administered to a subject to be cleared from the circulation and/or other tissues in the animal. When a clearance curve of a given polypeptide is constructed as a function of time, the curve is usually biphasic with a rapid $\alpha$-phase and longer $\beta$-phase. The $\alpha$-phase typically represents an equilibration of the administered Fc polypeptide between the intra- and extra-vascular space and is, in part, determined by the size of the polypeptide. The $\beta$-phase typically represents the catabolism of the polypeptide in the intravascular space. In some embodiments, FVIII and chimeric proteins comprising FVIII are monophasic, and thus do not have an alpha phase, but just the single beta phase. Therefore, in certain embodiments, the term half-life as used herein refers to the half-life of the polypeptide in the $\beta$-phase. The typical $\beta$ phase half-life of a human antibody in humans is 21 days.

The term "heterologous" as applied to a polynucleotide or a polypeptide, means that the polynucleotide or polypeptide is derived from a distinct entity from that of the entity to which it is being compared. Therefore, a heterologous polypeptide linked to a VWF fragment means a polypeptide chain that is linked to a VWF fragment and is not a naturally occurring part of the VWF fragment. For instance, a heterologous polynucleotide or antigen can be derived from a different species, different cell type of an individual, or the same or different type of cell of distinct individuals.

The term "linked" as used herein refers to a first amino acid sequence or nucleotide sequence covalently or non-covalently joined to a second amino acid sequence or nucleotide sequence, respectively. The term "covalently linked" or "covalent linkage" refers to a covalent bond, e.g., a disulfide bond, a peptide bond, or one or more amino acids, e.g., a linker, between the two moieties that are linked together. The first amino acid or nucleotide sequence can be directly joined or juxtaposed to the second amino acid or nucleotide sequence or alternatively an intervening sequence can covalently join the first sequence to the second sequence. The term "linked" means not only a fusion of a first amino acid sequence to a second amino acid sequence at the C-terminus or the N-terminus, but also includes insertion of the whole first amino acid sequence (or the second amino acid sequence) into any two amino acids in the second amino acid sequence (or the first amino acid sequence, respectively). In one embodiment, the first amino acid sequence can be joined to a second amino acid sequence by a peptide bond or a linker. The first nucleotide sequence can be joined to a second nucleotide sequence by a phosphodiester bond or a linker. The linker can be a peptide or a polypeptide (for polypeptide chains) or a nucleotide or a nucleotide chain (for nucleotide chains) or any chemical moiety (for both polypeptide and polynucleotide chains). The covalent linkage is sometimes indicated as (-) or hyphen.

As used herein the term "associated with" refers to a covalent or non-covalent bond formed between a first amino acid chain and a second amino acid chain. In one embodiment, the term "associated with" means a covalent, non-peptide bond or a non-covalent bond. In some embodiments this association is indicated by a colon, i.e., (:). In another embodiment, it means a covalent bond except a peptide bond. In other embodiments, the term "covalently associated" as used herein means an association between two moieties by a covalent bond, e.g., a disulfide bond, a peptide bond, or one or more amino acids (e.g., a linker). For example, the amino acid cysteine comprises a thiol group that can form a disulfide bond or bridge with a thiol group on a second cysteine residue. In most naturally occurring IgG molecules, the CH1 and CL regions are associated by a disulfide bond and the two heavy chains are associated by two disulfide bonds at positions corresponding to 239 and 242 using the Kabat numbering system (position 226 or 229, EU numbering system). Examples of covalent bonds include, but are not limited to, a peptide bond, a metal bond, a hydrogen bond, a disulfide bond, a sigma bond, a pi bond, a delta bond, a glycosidic bond, an agnostic bond, a bent bond, a dipolar bond, a Pi backbond, a double bond, a triple bond, a quadruple bond, a quintuple bond, a sextuple bond, conjugation, hyperconjugation, aromaticity, hapticity, or antibonding. Non-limiting examples of non-covalent bond include an ionic bond (e.g., cation-pi bond or salt bond), a metal bond, an hydrogen bond (e.g., dihydrogen bond, dihydrogen complex, low-barrier hydrogen bond, or symmetric hydrogen bond), van der Walls force, London dispersion force, a mechanical bond, a halogen bond, aurophilicity, intercalation, stacking, entropic force, or chemical polarity.

The term "monomer-dimer hybrid" used herein refers to a chimeric protein comprising a first polypeptide chain and a second polypeptide chain, which are associated with each other by a disulfide bond, wherein the first chain comprises a clotting factor, e.g., Factor VIII, and an Fc region and the second chain comprises, consists essentially of, or consists of an Fc region without the clotting factor. The monomer-dimer hybrid construct thus is a hybrid comprising a monomer aspect having only one clotting factor and a dimer aspect having two Fc regions.

As used herein, the term "cleavage site" or "enzymatic cleavage site" refers to a site recognized by an enzyme. Certain enzymatic cleavage sites comprise an intracellular processing site. In one embodiment, a polypeptide has an enzymatic cleavage site cleaved by an enzyme that is activated during the clotting cascade, such that cleavage of such sites occurs at the site of clot formation. Exemplary such sites include e.g., those recognized by thrombin, Factor XIa or Factor Xa. Exemplary FXIa cleavage sites include, e.g, TQSFNDFTR (SEQ ID NO: 47) and SVSQTSKLTR (SEQ ID NO: 48). Exemplary thrombin cleavage sites include, e.g, DFLAEGGGVR (SEQ ID NO: 49), TTKIKPR (SEQ ID NO: 50), LVPRG (SEQ ID NO: 55) and ALRPR (amino acids 1 to 5 of SEQ ID NO: 51). Other enzymatic cleavage sites are known in the art.

As used herein, the term "processing site" or "intracellular processing site" refers to a type of enzymatic cleavage site in a polypeptide which is the target for enzymes that function after translation of the polypeptide. In one embodiment, such enzymes function during transport from the Golgi lumen to the trans-Golgi compartment. Intracellular processing enzymes cleave polypeptides prior to secretion of the protein from the cell. Examples of such processing sites include, e.g., those targeted by the PACE/furin (where PACE is an acronym for Paired basic Amino acid Cleaving Enzyme) family of endopeptidases. These enzymes are localized to the Golgi membrane and cleave proteins on the carboxy terminal side of the sequence motif Arg-[any residue]-(Lys or Arg)-Arg. As used herein the "furin" family of enzymes includes, e.g., PCSK1 (also known as PC1/Pc3), PCSK2 (also known as PC2), PCSK3 (also known as furin or PACE), PCSK4 (also known as PC4), PCSK5 (also known as PC5 or PC6), PCSK6 (also known as PACE4), or PCSK7 (also known as PC7/LPC, PC8, or SPC7). Other processing sites are known in the art.

The term "Furin" refers to the enzymes corresponding to EC No. 3.4.21.75. Furin is subtilisin-like proportion convertase, which is also known as PACE (Paired basic Amino acid Cleaving Enzyme). Furin deletes sections of inactive precursor proteins to convert them into biologically active proteins. During its intracellular transport, pro-peptide is cleaved from mature VWF molecule by a Furin enzyme in the Golgi.

In constructs that include more than one processing or cleavage site, it will be understood that such sites may be the same or different.

Hemostatic disorder, as used herein, means a genetically inherited or acquired condition characterized by a tendency to hemorrhage, either spontaneously or as a result of trauma, due to an impaired ability or inability to form a fibrin clot. Examples of such disorders include the hemophilias. The three main forms are hemophilia A (factor VIII deficiency), hemophilia B (factor IX deficiency or "Christmas disease") and hemophilia C (factor XI deficiency, mild bleeding tendency). Other hemostatic disorders include, e.g., Von Willebrand disease, Factor XI deficiency (PTA deficiency), Factor XII deficiency, deficiencies or structural abnormalities in fibrinogen, prothrombin, Factor V, Factor VII, Factor X or factor XIII, Bernard-Soulier syndrome, which is a defect or deficiency in GPIb. GPIb, the receptor for VWF, can be defective and lead to lack of primary clot formation (primary hemostasis) and increased bleeding tendency), and thrombasthenia of Glanzman and Naegeli (Glanzmann thrombasthenia). In liver failure (acute and chronic forms), there is insufficient production of coagulation factors by the liver; this may increase bleeding risk.

The chimeric molecules of the invention can be used prophylactically. As used herein the term "prophylactic treatment" refers to the administration of a molecule prior to a bleeding episode. In one embodiment, the subject in need of a general hemostatic agent is undergoing, or is about to undergo, surgery. The chimeric protein of the invention can be administered prior to or after surgery as a prophylactic. The chimeric protein of the invention can be administered during or after surgery to control an acute bleeding episode. The surgery can include, but is not limited to, liver transplantation, liver resection, dental procedures, or stem cell transplantation.

The chimeric protein of the invention is also used for on-demand (also referred to as "episodic") treatment. The term "on-demand treatment" or "episodic treatment" refers to the administration of a chimeric molecule in response to symptoms of a bleeding episode or before an activity that may cause bleeding. In one aspect, the on-demand (episodic) treatment can be given to a subject when bleeding starts, such as after an injury, or when bleeding is expected, such as before surgery. In another aspect, the on-demand treatment can be given prior to activities that increase the risk of bleeding, such as contact sports.

As used herein the term "acute bleeding" refers to a bleeding episode regardless of the underlying cause. For example, a subject may have trauma, uremia, a hereditary bleeding disorder (e.g., factor VII deficiency) a platelet disorder, or resistance owing to the development of antibodies to clotting factors.

Treat, treatment, treating, as used herein refers to, e.g., the reduction in severity of a disease or condition; the reduction in the duration of a disease course; the amelioration of one or more symptoms associated with a disease or condition; the provision of beneficial effects to a subject with a disease or condition, without necessarily curing the disease or condition, or the prophylaxis of one or more symptoms associated with a disease or condition. In one embodiment, the term "treating" or "treatment" means maintaining a FVIII trough level at least about 1 IU/dL, 2 IU/dL, 3 IU/dL, 4 IU/dL, 5 IU/dL, 6 IU/dL, 7 IU/dL, 8 IU/dL, 9 IU/dL, 10 IU/dL, 11 IU/dL, 12 IU/dL, 13 IU/dL, 14 IU/dL, 15 IU/dL, 16 IU/dL, 17 IU/dL, 18 IU/dL, 19 IU/dL, or 20 IU/dL in a subject by administering a chimeric protein or a VWF fragment of the invention. In another embodiment, treating or treatment means maintaining a FVIII trough level between about 1 and about 20 IU/dL, about 2 and about 20 IU/dL, about 3 and about 20 IU/dL, about 4 and about 20 IU/dL, about 5 and about 20 IU/dL, about 6 and about 20 IU/dL, about 7 and about 20 IU/dL, about 8 and about 20 IU/dL, about 9 and about 20 IU/dL, or about 10 and about 20 IU/dL. Treatment or treating of a disease or condition can also include maintaining FVIII activity in a subject at a level comparable to at least about 1%, 2%, 3%, 4%, 5%, 6%, 7%, 8%, 9%, 10%, 11%, 12%, 13%, 14%, 15%, 16%, 17%, 18%, 19%, or 20% of the FVIII activity in a non-hemophiliac subject. The minimum trough level required for treatment can be measured by one or more known methods and can be adjusted (increased or decreased) for each person.

Chimeric Proteins

The present invention is directed to extending the half-life of a Factor VIII protein by preventing or inhibiting a FVIII half-life limiting factor (e.g. endogenous VWF) in vivo from associating with the FVIII protein. Endogenous VWF associates with about 95% to about 98% of FVIII in non-covalent complexes. The endogenous VWFs bound to a FVIII protein are known to protect FVIII in various ways. For example, full length VWF (as a multimer having about 250 kDa) can protect FVIII from protease cleavage and FVIII activation, stabilize the FVIII heavy chain and/or light chain, and prevent clearance of FVIII by scavenger receptors. However, at the same time, endogenous VWF limits the FVIII half-life by preventing pinocytosis and by clearing FVIII-VWF complex from the system through the VWF clearance pathway. It is believed, as shown in the examples, that endogenous VWF is the half-life limiting factor that prevents the half-life of a FVIII protein fused to a half-life extender from being longer than about two-fold of wild-type FVIII. Therefore, the present invention prevents or inhibits interaction between endogenous VWF and a FVIII protein using an adjunct moiety, thereby preventing the FVIII protein from being cleared through the VWF clearance pathway and/or inducing pinocytosis. In one embodiment, the adjunct moiety is capable of preventing or inhibiting binding of the FVIII protein with endogenous VWF and has at least one VWF-like FVIII protecting property. In addition, the adjunct moiety reduces clearance of FVIII from the system by preventing or inhibiting interaction with endogenous VWF. The adjunct moieties of the present invention bind to or are associated with (e.g., via non-covalent bonding) a FVIII protein and/or physically or chemically block the VWF binding site on the FVIII protein. The FVIII protein associated with the adjunct moiety is thus cleared from the circulation more slowly by one or more VWF clearance receptors, as compared to wild type FVIII or FVIII not associated with an adjunct moiety.

Examples of the adjunct moieties of the present invention include, e.g., polypeptides or chemical or physical modifications, additions, deletions, or variations of the FVIII protein. The adjunct moiety useful in the present invention can comprise a polypeptide, a non-polypeptide moiety, or both. Non-limiting examples of the polypeptide useful as an adjunct moiety include, e.g., a VWF fragment described herein, an immunoglobulin constant region or a portion thereof, transferrin or a fragment thereof, albumin or a fragment thereof, an albumin binding moiety, a HAP sequence, a PAS sequence, or any combinations thereof. Non-limiting examples of the non-polypeptide moiety includes polyethylene glycol (PEG), polysialic acid, hydroxyethyl starch (HES), a derivative thereof, or any combination thereof. Other such moieties useful in present invention are known in the art.

In one embodiment, the adjunct moiety is associated (or linked) with the FVIII protein by a covalent or a non-covalent bond. In some instances, however, the physical blockage or chemical association (e.g., non-covalent bonding) between the adjunct moiety and the FVIII protein may not be strong enough to provide a stable complex comprising the FVIII protein and the adjunct moiety in the presence of endogenous VWF. For example, a VWF fragment forming a non-covalent bond with a FVIII protein without any other connections may readily be dissociated in vivo from the FVIII protein in the presence of endogenous VWF, replacing the VWF fragment (e.g., recombinant VWF, i.e., rVWF) with endogenous VWF. Therefore, the FVIII protein non-covalently bound to endogenous VWF would undergo the VWF clearance pathway and be cleared from the system. In order to prevent the dissociation of the adjunct moiety with the FVIII protein, in some embodiments, the linkage between the FVIII protein and the adjunct moiety is a covalent bond, e.g., a peptide bond, one or more amino acids, or a disulfide bond. In certain embodiments, the association (i.e., linkage) between the adjunct moiety and the FVIII protein is a peptide bond or a linker between the FVIII protein and the adjunct moiety ("FVIII/AM linker"). Non-limiting examples of the linker is described elsewhere herein. In some embodiments, the adjunct moiety is a polypeptide comprising, consisting essentially of, or consisting of at least about 10, 100, 200, 300, 400, 500, 600, 700, 800, 900, 1000, 1100, 1200, 1300, 1400, 1500, 1600, 1700, 1800, 1900, 2000, 2500, 3000, or 4000 amino acids. In other embodiments, the adjunct moiety is a polypeptide comprising, consisting essentially of, or consisting of about 100 to about 200 amino acids, about 200 to about 300 amino acids, about 300 to about 400 amino acids, about 400 to about 500 amino acids, about 500 to about 600 amino acids, about 600 to about 700 amino acids, about 700 to about 800 amino acids, about 800 to about 900 amino acids, or about 900 to about 1000 amino acids. In some embodiments, the adjunct moiety covalently associated with the FVIII protein is a VWF fragment described elsewhere herein.

In certain embodiments, the adjunct moiety chemically (e.g., non-covalently) binds to or physically blocks one or more VWF binding sites on a FVIII protein. The VWF binding site on a FVIII protein is located within the A3 domain or the C2 domain of the FVIII protein. In still other embodiments, the VWF binding site on a FVIII protein is located within the A3 domain and C2 domain. For example, the VWF binding site on a FVIII protein can correspond to amino acids 1669 to 1689 and/or 2303 to 2332 of SEQ ID NO: 16 [full-length mature FVIII].

In other embodiments, a chimeric protein of the invention comprises a FVIII protein linked to an adjunct moiety, wherein the adjunct moiety is a VWF molecule, e.g. a VWF fragment comprising a D' domain and a D3 domain, but not containing the VWF clearance receptor binding site, and shields or protects the VWF binding site on the FVIII protein, thereby inhibiting or preventing interaction of the FVIII protein with endogenous VWF. In certain embodiments, the adjunct moiety is a VWF fragment. The VWF fragment useful for the present invention contains the D' domain and the D3 domain, still providing one or more advantages of VWF-like property to the FVIII protein, but the VWF fragment does not undergo the VWF clearance pathway. The FVIII protein and the adjunct moiety can be covalently associated by a linker (e.g., FVIII/AM linker). In one embodiment, the linker can be a cleavable linker. Non-limiting examples of the linkers are disclosed elsewhere herein.

In still other embodiments, a chimeric protein of the invention comprises a FVIII protein and an immunoglobulin constant region or a portion thereof (i.e., an adjunct moiety), wherein the immunoglobulin constant region or a portion thereof shields or protects the VWF binding site on the FVIII protein, thereby inhibiting or preventing interaction of the FVIII protein with endogenous VWF. In yet other embodiments, the immunoglobulin constant region or a portion thereof is an Fc region.

In one aspect, the present invention is directed to a chimeric or fusion protein or hybrid comprising one or more of the VWF fragments disclosed herein and uses of the same. The chimeric or fusion protein can be fused or linked to one or more heterologous moiety (sometimes indicated herein as H or H1). In one embodiment, the heterologous moiety (H1) is a heterologous peptide or a heterologous polypeptide that would not naturally occur with and/or is linked to the VWF fragment. In another embodiment, the heterologous moiety (H1) is a non-polypeptide moiety, e.g., chemical modification or a combination of a peptide or polypeptide and a non-polypeptide moiety. In some embodiments, the VWF fragments are linked or connected to the heterologous moiety (H1) by a linker (also referred to herein as "VWF linker"). In one embodiment, the VWF linker is a cleavable linker. Non-limiting examples of the linker between the VWF fragment and the heterologous moiety (H1) are disclosed elsewhere herein.

In one embodiment, the heterologous moiety (H1) useful in the invention improves one or more pharmacokinetic properties of the VWF fragments without significantly affecting the VWF fragments' biological activity or function (e.g., its binding to or association with a FVIII protein). In another embodiment, the heterologous moiety (H1) linked to the VWF fragment can extend the half-life of the VWF fragments. Non-limiting examples of the heterologous polypeptide moiety comprises an immunoglobulin constant region or a portion thereof, albumin or a fragment thereof, an albumin binding moiety, a PAS sequence, a HAP sequence, transferrin or a fragment thereof, or two or more combinations thereof. Non-limiting examples of the heterologous non-polypeptide moiety include polyethylene glycol (PEG), polysialic acid, hydroxyethyl starch (HES), a derivative thereof, or any combinations thereof.

In some embodiments, a heterologous moiety (H1) can be used to connect the VWF fragment and the FVIII protein by a covalent bond. Examples of the heterologous moiety that can provide the covalently linkage include, but are not limited to, an immunoglobulin constant region or a portion thereof comprising a hinge region, e.g., an Fc region or an FcRn binding partner. In a specific example, the FVIII protein is linked to a first Fc region, and the VWF fragment is linked to a second Fc region, wherein the first Fc region and the second Fc region form one or more disulfide bond.

In some embodiments, the heterologous moiety (sometimes indicated herein by "H" or "H1") is an immunoglobulin constant region or a portion thereof. Non-limiting examples of the immunoglobulin constant region or a portion thereof can be selected from the group consisting of a CH1 domain, a CH2 domain, a CH3 domain, a CH4 domain, a hinge domain, and two or more combinations thereof. In one embodiment, the immunoglobulin constant region or a portion thereof comprises at least one CH1 domain, at least one CH2 domain, at least one CH3 domain, at least one CH4 domain, or the functional fragments thereof. In another embodiment, the immunoglobulin constant region or a portion thereof comprises at least one hinge domain or a portion thereof and at least one CH2 domain or a portion thereof (e.g., in the hinge-CH2 orientation). In other embodiments, the immunoglobulin constant domain or a portion thereof comprises at least one CH2 domain or a portion thereof and at least one CH3 domain or a portion thereof (e.g., in the CH2-CH3 orientation.) Examples of the combination include, but are not limited to, a CH2 domain, a CH3 domain, and a hinge domain, which are also known as an Fc region (or Fc domain), e.g., a first Fc region. In other embodiments, the heterologous moiety (H1) is linked to the VWF fragment by a linker. In certain embodiments, the heterologous moiety (H1) is an FcRn binding partner as described elsewhere herein. In other embodiments, the heterologous moiety (H1) is a hinge region.

In certain embodiments, the chimeric protein further comprises a second (or additional) heterologous moiety (sometimes indicated herein by "H2"). It is noted that the first heterologous moiety (H1) and the second heterologous moiety (H2) can be used interchangeably and can be the same or different. The second heterologous moiety (H2) can be linked to the FVIII protein or elsewhere in the chimeric protein by a peptide bond, one or more amino acids, or by a linker (e.g., FVIII linker if linked to FVIII). Such constructs can sometimes be referred to as FVIII/VWF heterodimer. In one embodiment, the heterologous moiety (H2) comprises a heterologous polypeptide. In another embodiment, the heterologous moiety (H2) comprises a non-polypeptide moiety. In other embodiments, the heterologous moiety (H2) comprises a combination of a heterologous moiety and a non-polypeptide moiety. The second heterologous moiety (H2) can be a half-life extender. Non-limiting examples of the second heterologous polypeptide moiety (H2) include an immunoglobulin constant region or a portion thereof, albumin or a fragment thereof, an albumin binding moiety, a PAS sequence, a HAP sequence, transferrin or a fragment thereof, or two or more combinations thereof. Non-limiting examples of the heterologous non-polypeptide moiety include polyethylene glycol (PEG), polysialic acid, hydroxyethyl starch (HES), a derivative thereof, or any combinations thereof. In certain embodiments, the first heterologous moiety (H1) and the second heterologous moiety are the same or different. Either or both of the first heterologous moiety (H1) and the second heterologous moiety (H2) can confer half-life extension to the FVIII protein in a chimeric protein, provide a connection stronger than non-covalent association, i.e., by one or more covalent bonds between the FVIII protein and the VWF fragment in a chimeric protein, or both. Once the VWF fragment fused or linked to the first heterologous moiety (H1) removes the half-life ceiling by preventing or inhibiting interaction between the FVIII protein and the endogenous VWF protein, the FVIII protein fused to the heterologous moieties can reach to its full potential and can have a half-life of longer than two-fold compared to wild type FVIII.

In certain embodiments, the first heterologous moiety (e.g., a first Fc region) linked to the VWF fragment and the second heterologous moiety (e.g., a second Fc region) linked to the FVIII protein are associated with each other such that the association prevents replacement of the VWF fragment by endogenous VWF in vivo. In one embodiment, the second heterologous moiety is a second Fc region, wherein the second Fc region is linked to or associated with the first heterologous moiety, e.g., the first Fc region, by a covalent bond, e.g., disulfide bond, a peptide bond, or a linker (one or more amino acids). For example, the second heterologous moiety (e.g., the second Fc region) linked to the FVIII protein at one end can be further linked to the first heterologous moiety (e.g., the first Fc region) linked to the VWF fragment by a linker (e.g., scFc linker) or associated with the first heterologous moiety by a covalent or non-covalent bond. In another embodiment, the second heterologous moiety (e.g., the second Fc region) is linked to the VWF fragment that is already linked to first heterologous moiety. In some embodiments, the chimeric protein comprises a first polypeptide chain comprising a VWF fragment and a first heterologous moiety and a second polypeptide chain comprising a FVIII protein and a second heterologous moiety, wherein the first polypeptide chain and the second polypeptide chain are associated, wherein the association between the first polypeptide chain comprising the first heterologous moiety and the second polypeptide chain comprising the second heterologous moiety is a covalent bond, thus allowing the VWF fragment and the FVIII protein maintain its interaction with each other. At the same time, endogenous VWF, which can form a non-covalent bond with the FVIII protein cannot replace the covalently linked polypeptide chain comprising the VWF fragment.

The linker between the first heterologous moiety (H1) and the VWF fragment (e.g., VWF linker) can be a cleavable linker, e.g., a thrombin cleavable linker. The cleavable linkers can be cleaved by a protease selected from the group consisting of factor XIa, factor XIIa, kallikrein, factor VIIa, factor IXa, factor Xa, factor IIa (thrombin), Elastase-2, Granzyme-B, TEV, Enterokinase, Protease 3C, Sortase A, MMP-12, MMP-13, MMP-17, MMP-20, and any combinations thereof. These cleavable linkers allow the VWF fragment to be cleaved and dissociated from the FVIII protein upon activation of the clotting cascade, resulting in a FVIII protein with full activity potential.

In other embodiments, the chimeric protein is produced as a single polypeptide chain comprising a VWF fragment, a cleavable linker, a first heterologous moiety (H1), a processable linker, a FVIII protein, and a second heterologous moiety (H2) in any order. After synthesis, the processable linker can be cleaved by an intracellular protease enzyme before secretion, thus making two polypeptide chains as described above. In the single chain construct before secretion, the second heterologous moiety (e.g., the second Fc region) can be linked to the VWF fragment by a processable linker. In certain embodiments, one or more linkers can comprise one or more cleavage sites.

In some embodiments, the chimeric protein of the invention further comprises a third heterologous moiety (sometimes indicated herein by "H3"). The third heterologous moiety (H3) can be a half-life extender. The heterologous moiety (H3) can comprise a heterologous polypeptide, a non-polypeptide moiety, or a combination of both. Non-limiting examples of the third heterologous moiety (H3) include an immunoglobulin constant region or a portion thereof, albumin or a fragment thereof, an albumin binding moiety, a PAS sequence, a HAP sequence, transferrin or a fragment thereof, any derivatives or variants thereof, or two or more combinations thereof. Non-limiting examples of the non-polypeptide moiety include polyethylene glycol (PEG), polysialic acid, hydroxyethyl starch (HES), a derivative thereof, or any combinations thereof. The first heterologous moiety (H1) linked to the VWF fragment, the second heterologous moiety (H2) linked to the FVIII protein, and the third heterologous moiety (H3) can be the same or different. In one embodiment, the first heterologous moiety (H1) is identical to the second heterologous moiety (H2), but is different from the third heterologous moiety (H3). In another embodiment, the third heterologous moiety (H3) is fused or linked to a FVIII protein or a VWF fragment of the chimeric protein. In some embodiments, the third heterologous moiety is inserted within one or more domains of the FVIII protein or between two domains of the FVIII protein.

In one embodiment, a chimeric protein comprises a first polypeptide chain and a second polypeptide chain, wherein the first chain comprises a FVIII protein linked to a first heterologous moiety (H1), e.g., a first Fc region, by an optional linker (e.g., FVIII linker) and the second chain comprises a VWF fragment linked to a second heterologous moiety (H2), e.g., a second Fc region, by an optional linker (e.g., VWF linker). The FVIII protein can further comprise a third heterologous moiety (H3), e.g., any half-life extending moiety, e.g., albumin, or a PAS sequence, between FVIII heavy chain and FVIII light chain (i.e., amino acid residue 1648 of SEQ ID NO: 16), thus being a single chain FVIII protein. Alternatively, the FVIII protein can be a dual chain protein, i.e., the FVIII heavy chain and the FVIII light chain associated with each other by a covalent or non-covalent bond (e.g., a metal bond), wherein the heavy chain is further linked to a third heterologous moiety (H3), e.g., a non-structural half-life extending polypeptide, albumin or a fragment thereof or a PAS sequence. In another embodiment, a chimeric protein comprises a first polypeptide chain and a second polypeptide chain, wherein the first chain comprises a FVIII protein linked to a first heterologous moiety (H1), e.g., a first Fc region, by an optional linker (e.g, FVIII linker) and the second chain comprises a VWF fragment linked to a third heterologous moiety (H3), e.g., a non-structural half-life extending polypeptide, albumin or a PAS sequence, which is linked to a second heterologous moiety (H2), e.g., a second Fc region, by an optional linker. In some embodiments, the third heterologous moiety (H3) (e.g., a half-life extending polypeptide) can be linked to the C-terminus or N-terminus of the FVIII protein or inserted between two domains of the FVIII protein or between two amino acids in a domain of the FVIII protein.

In other embodiments, the chimeric protein of the invention further comprises a fourth heterologous moiety (sometimes indicated herein by "H4") and/or a fifth heterologous moiety (sometimes indicated herein by "H5"). The fourth or fifth heterologous moiety can also be a half-life extender. The fourth heterologous moiety and/or the fifth heterologous moiety can be the same or different from the third heterologous moiety. The heterologous moiety can comprise a heterologous polypeptide, a non-polypeptide moiety, or a combination of both. Non-limiting examples of the fourth or fifth heterologous moiety include an immunoglobulin constant region or a portion thereof, albumin or a fragment thereof, an albumin binding moiety, a PAS sequence, a HAP sequence, transferrin or a fragment thereof, any derivatives or variants thereof, or two or more combinations thereof. Non-limiting examples of the non-polypeptide moiety include polyethylene glycol (PEG), polysialic acid, hydroxyethyl starch (HES), a derivative thereof, or any combinations thereof. The first heterologous moiety, the second heterologous moiety, the third heterologous moiety, the fourth heterologous moiety, and the fifth heterologous moiety can be the same or different. In some embodiments, the fourth heterologous moiety (e.g., a half-life extending polypeptide) can be linked to the C-terminus or N-terminus of the FVIII protein or inserted between two domains of the FVIII protein or between two amino acids in a domain of the FVIII protein. In other embodiments, the fifth heterologous moiety (e.g., a half-life extending polypeptide) can also be linked to the C-terminus or N-terminus of the FVIII protein or inserted between two domains of the FVIII protein or between two amino acids in a domain of the FVIII protein.

In certain embodiments, the chimeric protein comprises a FVIII protein, a VWF fragment, a first heterologous moiety, a second heterologous moiety, a third heterologous moiety, a fourth heterologous moiety, and a fifth heterologous moiety, wherein the first heterologous moiety and the second heterologous moiety forms a bond (e.g., a covalent bond) between the chain comprising the FVIII protein and the chain comprising the VWF fragment, and the third heterologous moiety, the fourth heterologous moiety, and the fifth heterologous moiety are half-life extenders, and wherein the bond between the chain comprising the FVIII protein and the chain comprising the VWF fragment is stronger than the non-covalent interaction between the FVIII and the VWF fragment, thereby preventing binding of endogenous VWF to the FVIII protein in vivo, in vitro, or ex vivo.

In other embodiments, the chimeric protein comprises a FVIII protein, a VWF fragment, a first heterologous moiety, a second heterologous moiety, a third heterologous moiety, a fourth heterologous moiety, a fifth heterologous moiety, and a sixth heterologous moiety (sometimes indicated herein as "H6"), wherein the first heterologous moiety and the second heterologous moiety forms a bond between the chain comprising the FVIII protein and the chain comprising the VWF fragment, and the third heterologous moiety, the fourth heterologous moiety, the fifth heterologous moiety, and the sixth heterologous moiety are half-life extenders, and wherein the bond between the chain comprising the FVIII protein and the chain comprising the VWF fragment is stronger than the interaction between the FVIII and the VWF fragment, thereby preventing binding of endogenous VWF to the FVIII protein in vivo, in vitro, or ex vivo.

In some embodiments, a chimeric protein comprises a formula selected from the group consisting of:
(aa) V-L1-H1-L2-H2,
(bb) H2-L2-H1-L1-V,
(cc) H1-L1-V-L2-H2, and
(dd) H2-L2-V-L1-H1,
wherein V comprises a VWF fragment described herein;
Each of L1 and L2 comprises an optional linker; and
H1 comprises a first heterologous moiety; and
H2 comprises an optional second heterologous moiety.
Either or both of the first heterologous moiety and the second heterologous moiety can be a half-life extending moiety. In one embodiment, H1 comprises a polypeptide, a non-polypeptide moiety, or both. The polypeptide useful as H1 can comprise an immunoglobulin constant region or a portion thereof, albumin or a fragment thereof, an albumin binding moiety, a PAS sequence, a HAP sequence, any derivatives or variants, or any combinations thereof. The non-polypeptide moiety can comprise polyethylene glycol (PEG), polysialic acid, and hydroxyethyl starch (HES), a derivative or variant thereof, or any combinations thereof. In another embodiment, H2 comprises a polypeptide, a non-polypeptide moiety, or both. The polypeptide useful as H2 can comprise an immunoglobulin constant region or a portion thereof, albumin or a fragment thereof, an albumin binding moiety, a PAS sequence, a HAP sequence, any derivatives or variants, or any combinations thereof. The non-polypeptide moiety can comprise polyethylene glycol (PEG), polysialic acid, hydroxyethyl starch (HES), a derivative or variant thereof, or any combinations thereof. In certain embodiments, the linker between H1 and H2 in formulas (aa) and (bb) is a processable linker. In other embodiments, the linker between the VWF fragment and H1 in formulas (aa) and (bb) is a cleavable linker, e.g., a thrombin cleavable linker that can be cleaved by thrombin.

The orientation of the polypeptide formulas herein is listed from N-terminus (left) to C-terminus (right). For example, formula H-L-V means formula NH2-H-L-V-COOH. In one embodiment, the formulas described herein can comprise additional sequences between the two moieties. For example, formula V-L1-H1-L2-H2 can further comprise sequences at the N-terminus of V, between V and L1, between L1 and H1, between H1 or L2, between L2 or H2, or at the C-terminus of H2 unless otherwise specified. In another embodiment, the hyphen (-) indicates a peptide bond or one or more amino acids.

In specific embodiments, a chimeric protein comprises, consists essentially of, or consists of one or more formulas selected from the group consisting of (a1) V-H, (a2) H-V, (a3) V-L-H, (a4) H-L-V, (a5) V-L1-H1-H2, (a6) H2-H1-L1-V, (a7) V-L1-H1:H2, (a8) H2:H1-L1-V, (a9) V-H1:H2, (b1) H2:H1-V, (b2) V-L1-H1-L2-H2, (b3) H2-L2-H1-L1-V, (b4) H1-V-H2, (b5) H1-L1-V-L2-H2, and (b6) H2-L2-V-L1-H1, wherein V comprises one or more of the VWF fragments described herein, L, L1, or L2 comprises a linker, H or H1 comprises a first heterologous moiety. In one embodiment, the first heterologous moiety (H1) can be a polypeptide, a non-polypeptide moiety, or both. The heterologous polypeptide moiety can comprises an immunoglobulin constant region or a portion thereof, albumin or a fragment thereof, an albumin binding moiety, a PAS sequence, a HAP sequence, or any combinations thereof. Non-limiting examples of the non-polypeptide moiety useful as H1 include polyethylene glycol (PEG), polysialic acid, hydroxyethyl starch (HES), a derivative thereof, or any combinations thereof. In another embodiment, H2 comprises a second heterologous moiety. The second heterologous moiety can be a polypeptide, a non-polypeptide moiety, or both. The heterologous polypeptide moiety can comprises an immunoglobulin constant region or a portion thereof, albumin or a fragment thereof, an albumin binding moiety, a PAS sequence, a HAP sequence, or any combinations thereof. Non-limiting examples of the non-polypeptide moiety useful as H1 include polyethylene glycol (PEG), polysialic acid, hydroxyethyl starch (HES), a derivative thereof, or any combinations thereof. In certain embodiments, the linker between the first heterologous moiety and the second heterologous moiety is a processable linker. In other embodiments, the linker between the VWF fragment and the first heterologous moiety or the second heterologous moiety is a cleavable linker, which comprises one or more cleavage sites, e.g., a thrombin cleavable linker.

The chimeric protein of the present invention comprises a formula selected from the group consisting of (aa), (bb), (cc), (dd), (a1), (a2), (a3), (a4), (a5), (a6), (a7), (a8), (a9), (b1), (b2), (b3), (b4), (b5), and (b6) and a FVIII protein, which is covalently linked to or covalently associated with the VWF fragment, the first heterologous moiety (e.g., a first Fc region), or the second heterologous moiety (e.g., a second Fc region) of the formula. In one embodiment, the FVIII protein is linked to or associated with the VWF fragment by a covalent or non-covalent bond or by a linker. In another embodiment, the FVIII protein can be linked to the first heterologous moiety or the second heterologous moiety by a covalent or non-covalent bond or by a linker.

In one embodiment, a chimeric protein of the present invention comprises a VWF fragment described herein covalently linked to or covalently associated with a FVIII protein. For example, the chimeric protein can comprise a VWF fragment and a FVIII protein, wherein the VWF fragment and the FVIII protein are bound by a covalent non-peptide bond, a peptide bond, a non-covalent bond, or by a linker, e.g., a cleavable linker. In a specific embodiment, the VWF fragment and the FVIII protein are bound to or interact with each other by one or more disulfide bonds. In another specific embodiment, the VWF fragment is bound to or interacts with the FVIII protein at the A3 domain of FVIII, the C2 domain of FVIII, or both the A3 domain and the C2 domain of FVIII by a non-covalent bond. In another embodiment, the VWF fragment bound to or interacting with the FVIII protein is linked or fused to a first heterologous moiety. In other embodiments, the FVIII protein bound to or interacting with the VWF fragment is further linked to a second heterologous moiety. In some embodiments, the VWF fragment bound to or interacting with the FVIII protein is further linked to a first heterologous moiety and the FVIII protein is further linked to a second heterologous moiety. In certain embodiments, the first polypeptide chain comprising the VWF fragment and the first heterologous moiety and the second polypeptide chain comprising the FVIII protein and the second heterologous moiety are associated with each other such that the association does not allow interaction of the FVIII protein with other moieties, e.g., endogenous VWF. In one embodiment, the association is a covalent bond, e.g., a disulfide bond.

Each of the VWF fragment or the FVIII protein can be joined or connected to the first and second heterologous moiety by a linker, e.g., a cleavable linker, e.g., a thrombin cleavable linker. The linker between the VWF fragment and the first heterologous moiety can be denoted herein as a VWF linker. The linker between the FVIII protein and the second heterologous moiety can be denoted herein as a FVIII linker. Or, both of the VWF fragment or the FVIII protein can be joined or connected to the first and second heterologous moiety by a linker, e.g., a cleavable linker, e.g., a thrombin cleavable linker. In certain embodiments, the first heterologous moiety linked to the VWF fragment comprises a polypeptide, a non-polypeptide moiety, or both. Non-limiting examples of the first heterologous polypeptide moiety includes an immunoglobulin constant region or a portion thereof, albumin or a fragment thereof, an albumin binding moiety, a PAS sequence, a HAP sequence, transferrin or a fragment thereof, or two or more combinations thereof. Non-limiting examples of the non-polypeptide moiety includes polyethylene glycol (PEG), polysialic acid, hydroxyethyl starch (HES or HAES), a derivative or variant thereof, or any combinations thereof. In other embodiments, the second heterologous moiety linked to the FVIII protein comprises a polypeptide, a non-polypeptide moiety, or both. Non-limiting examples of the second heterologous moiety includes an immunoglobulin constant region or a portion thereof, albumin or a fragment thereof, an albumin binding moiety, a PAS sequence, a HAP sequence, transferrin or a fragment thereof, or two or more combinations thereof. Non-limiting examples of the non-polypeptide moiety includes polyethylene glycol (PEG), polysialic acid, hydroxyethyl starch (HES or HAES), a derivative or variant thereof, or any combinations thereof. In some embodiments, the VWF fragment is attached to FVIII using sortase mediated in vitro protein ligation. In some embodiments, a sortase recognition motif is used.

In one embodiment, the first heterologous moiety is an immunoglobulin constant region or a portion thereof. In a particular embodiment, the first heterologous moiety is a first Fc region. In some embodiments, the second heterologous moiety is an immunoglobulin constant region or a portion thereof. In a specific embodiment, the second heterologous moiety is a second Fc region. In a particular embodiment, the chimeric protein comprises a VWF fragment described herein and a FVIII protein, wherein the VWF fragment is linked to an immunoglobulin constant region or a portion thereof, which is an Fc region. In another embodiment, the chimeric protein comprises a VWF fragment described herein and a FVIII protein, wherein the FVIII protein is linked to an immunoglobulin constant region or a portion thereof, which is an Fc region. In other embodiments, a chimeric protein comprises a VWF fragment described herein and a FVIII protein, wherein the VWF fragment is linked to a first immunoglobulin constant region, which is a first Fc region, and the FVIII protein is linked to a second immunoglobulin constant region, which is a second Fc region, and wherein the VWF fragment and the FVIII protein is bound to or interact with each other by a non-covalent bond or the first Fc region or the second Fc region are associated with each other by a covalent bond. In still other embodiments, the VWF fragment linked to the first heterologous moiety is further linked to the second heterologous moiety, e.g., a second Fc region, by a linker, e.g., a processable linker. In one aspect, the VWF fragment is linked to the first heterologous moiety by a linker, e.g., VWF linker, e.g., a cleavable linker. In another aspect, the FVIII protein is linked to the second heterologous moiety by a linker, e.g., FVIII linker, e.g., a cleavable linker Non-limiting examples of the heterologous moieties are disclosed elsewhere herein, e.g., immunoglobulin constant region or a portion thereof, albumin, fragment or variant thereof, HAP sequences, transferrin, fragments, or variants thereof, polymer, e.g., polyethylene glycol, HES, or PSA and PAS sequences.

In some embodiments, a chimeric protein of the present invention comprises, consists essentially of, or consists of a formula selected from the group consisting of:
(a) V-L1-H1-L3-C-L2-H2,
(b) H2-L2-C-L3-H1-L1-V,
(c) C-L2-H2-L3-V-L1-H1,
(d) H1-L1-V-L3-H2-L2-C,
(e) H1-L1-V-L3-C-L2-H2,
(g) H2-L2-C-L3-V-L1-H1,
(g) V-L1-H1-L3-H2-L2-C,
(g) C-L2-H2-L3-H1-L1-V,
(i) H2-L3-H1-L1-V-L2-C,
(j) C-L2-V-L1-H1-L3-H2,
(k) V-L2-C-L1-H1-L3-H2, and
(l) H2-L3-H1-L1-C-L2-V,
  wherein V is a VWF fragment described herein;
  each of L1 or L2 is an optional linker, e.g., a cleavable linker, e.g., a thrombin cleavable linker;
  L3 is an optional linker, e.g., a processable linker
  each of H1 and H2 is an optional heterologous moiety;
  C is a FVIII protein; and
  (-) is a peptide bond or one or more amino acids.

In other aspects, a chimeric protein of the invention comprises a formula selected from the group consisting of:
(m) V-L1-H1: H2-L2-C,
(n) V-L1-H1:C-L2-H2;
(o) H1-L1-V:H2-L2-C;
(p) H1-L1-V:C-L2-H2;
(q) V:C-L1-H1:H2;
(r) V:H1-L1-C:H2;
(s) H2:H1-L1-C:V,
(t) C:V-L1-H1:H2, and
(u) C:H1-L1-V:H2.
wherein V is a VWF fragment described herein;
each of L1 or L2, is an optional linker, e.g., a thrombin cleavable linker;
each of H1 or H2 is an optional heterologous moiety;
(-) is a peptide bond or one or more amino acids; and
C is a FVIII protein; and (:) is a chemical or physical association between H1 and H2.

In one embodiment, one or more of the heterologous moieties are a half-life extender. Half-life extenders are known in the art, and non-limiting examples of such half-life extenders include an immunoglobulin constant region or a portion thereof, albumin or fragment thereof, an albumin binding moiety, a PAS sequence, a HAP sequence, transferrin or a fragment thereof, a derivative or variant thereof, or two or more combinations thereof. The non-polypeptide moiety can comprise polyethylene glycol (PEG), polysialic acid, hydroxyethyl starch (HES), a derivative thereof, or any combinations thereof.

In one embodiment, (:) in formulas (m) to (u) represents a chemical association, e.g., at least one non-peptide bond. In certain embodiments, the chemical association, i.e., (:) is a covalent bond. In other embodiments, the chemical association, i.e., (:) is a non-covalent interaction, e.g., an ionic interaction, a hydrophobic interaction, a hydrophilic interaction, a Van der Waals interaction, a hydrogen bond. In other embodiments, (:) is a non-peptide covalent bond. In still other embodiments, (:) is a peptide bond. In yet other embodiments, (:) in formulas (m) to (u) represents a physical association between two sequences, wherein a portion of a first sequence is in close proximity to a second sequence such that the first sequence shields or blocks a portion of the second sequence from interacting with another moiety, and further that this physical association is maintained without allowing the second sequence to interact with other moieties.

Formulas (a)-(u) are included herein merely as non-limiting examples of constructs of the present invention. The orientation of the polypeptide formulas is shown from N-terminus (left) to C-terminus (right). For example, formula V-L1-H1-L3-C-L2-H2 means formula NH2-V-L1-H1-L3-C-L2-H2-COOH. In addition, (:) can be an association or interaction between two polypeptide chains by a covalent bond or a non-covalent bond between any part of the first chain and any part of the second chain unless otherwise noted. For example, formula V-H1:H2-C has two polypeptide chains, the first chain being V-H1 and the second chain being C-H2, wherein V in the first chain interacts or associates with C in the second chain and/or H1 in the first chain interacts or associates with H2 in the second chain. In some embodiments, (:) means a covalent, non-peptide bond or non-covalent bond.

In certain embodiments, a chimeric protein comprises, consists essentially of, or consists of a formula selected from the group consisting of:
(1) V:C, (2) H-V:C or C:V-H,
(3) V:C-H or H-C:V, (4) V-H1:H2-C or H1-V:C-H2,
(5) V:C-H1:H2 or H2:H1-C:V, (6) H2:H1-V:C or C:V-H1:H2,
(7) H-L-V:C or C:V-L-H, (8) V:C-L-H or H-L-C:V,
(9) V-C or C-V, (10) H-V-C or C-V-H,
(11) V-H-C or C-H-V, (12) V-C-H or H-C-V,
(13) V-H1-C-H2 or H2-C-H1-V, (14) H1-V-C-H2 or H2-C-V-H1,
(15) H1-V-H2-C or C-H2-V-H1, (16) V-H1-H2-C or C-H2-H1-V,
(17) V-L-C or C-L-V, (18) H-L-V-C or C-V-L-H,
(19) H-V-L-C or C-L-V-H, (20) V-L-H-C or C-H-L-V,
(21) V-H-L-C or C-L-H-V, (22) V-L-C-H or H-C-L-V,
(23) V-C-L-H or H-L-C-V, (24) H-L1-V-L2-C or C-L2-V-L1-H,
(25) V-L-H1:H2-C or C-H2:H1-L-V,
(26) V-H1:H2-L-C or C-L-H2:H1-V,
(27) V:C-H1-H2 or H2-H1-C:V,
(28) H2-H1-V:C or C:V-H1-H2,
(29) V:C-L-H1:H2 or H2:H1-L-C:V,
(30) H2:H1-L-V:C or C:V-L-H1:H2,
(31) V-L1-H1:H2-L2-C or L-L2-H2:H1-L1-V,
(32) V:C-L-H1-H2 or H2-H1-L-C:V,
(33) V:C-H1-L-H2 or H2-L-H1-C:V,
(34) V:C-L1-H1-L2-H2 or H2-L2-H1-L1-C:V,
(35) H2-H1-V:C or C:V-H1-H2,
(36) H2-H1-L-V:C or C:V-L-H1-H2,
(37) H2-L-H1-V:C or C:V-H1-L-H2,
(38) H2-L2-H1-L1-V:C or C:V-L1-H1-L2-H2,
(39) V-L1-H-L2-C or C-L2-H-L1-V,
(40) V-L1-C-L2-H or H-L2-C-L1-V,
(41) V-L-H1-C-H2 or H2-C-H1-L-V,
(42) V-H1-C-L-H2 or H2-L-C-H1-V,
(43) V-H1-L-C-H2 or H2-C-L-H1-V,
(44) H1-L-V-C-H2 or H2-C-V-L-H1,

(45) H1-V-L-C-H2 or H2-C-L-V-H1,
(46) H1-V-C-L-H or H-L-C-V-H1,
(47) H1-L-V-H2-C or C-H2-V-L-H1,
(48) H1-V-L-H2-C or C-H2-L-V-H1,
(49) H1-V-H2-L-C or C-L-H2-V-H1,
(50) V-L-H1-H2-C or C-H2-H1-L-V,
(51) V-H1-L-H2-C or C-H2-L-H1-V,
(52) V-H1-H2-L-C or C-L-H2-H1-V,
(53) V-L1-H1-L2-C-H2 or H2-C-L2-H1-L1-V,
(54) V-L1-H1-C-L2-H2 or H2-L2-C-H1-L1-V,
(55) V-L1-H1-L2-C-L3-H2 or H2-L3-C-L2-H1-L1-V,
(56) V-H1-L1-C-L2-H2 or H2-L2-C-L1-H1-V,
(57) H1-L1-V-L2-C-H2 or H2-C-L2-V-L1-H1,
(58) H1-L1-V-C-L2-H2 or H2-L2-C-V-L1-H1,
(59) H1-L1-V-L2-C-L3-H2 or H2-L3-C-L2-V-L1-H1,
(60) H1-V-L1-C-L2-H2 or H2-L2-C-L1-V-H1,
(61) H1-L1-V-L2-H2-C or C-H2-L2-V-L1-H1,
(62) H1-L1-V-H2-L2-C or C-L2-H2-V-L1-H1,
(63) H1-L1-V-L2-H2-L3-C or C-L3-H2-L2-V-L1-H1,
(64) H1-V-L1-H2-L2-C or C-L2-H2-L1-V-H1,
(65) V-L1-H1-L2-H2-C or C-H2-L2-H1-L1-V,
(66) V-L1-H1-H2-L2-C or C-L2-H2-H1-L1-V,
(67) V-L1-H1-L2-H2-L3-C or C-L3-H2-L2-H1-L1-V, and
(68) V-H1-L1-H2-L2-C or C-L2-H2-L1-H1-V, V is a VWF fragment described herein;
C is a FVIII protein;
H or H1 is a heterologous moiety or a first heterologous moiety;
H2 is a second heterologous moiety; the first and second heterologous moieties can be the same or different;
Each of L, L1 or L2 is an optional linker;
(-) is a peptide bond or one or more amino acids; and
(:) is a chemical or physical association. The linkers can each be the same or different and each can be a cleavable linker, comprising one or more enzymatic cleavage site. The heterologous moieties can be a half-life extension technology that is known in the art, a polypeptide, a non-polypeptide moiety, or both. A polypeptide moiety can comprise an immunoglobulin constant region or a portion thereof, albumin or a fragment thereof, an albumin binding moiety, a PAS sequence, a HAP sequence, any derivatives or variants thereof, or any combinations thereof (e.g., an Fc region). A non-polypeptide moiety can comprise polyethylene glycol (PEG), polysialic acid, hydroxyethyl starch (HES), a derivative or variant thereof, or any combinations thereof. Each of the H, H1, or H2 can be individually selected based on the characteristics and can be all the same, or each one different. Non-limiting examples of the heterologous moieties are disclosed elsewhere herein, e.g., immunoglobulin constant region or a portion thereof, albumin or fragment or variant thereof, polymer, e.g., polyethylene glycol, and PAS sequences. Formulas (1)-(68) are included herein merely as non-limiting examples of constructs of the present invention.

In one embodiment, (:) represents a chemical association, e.g., at least one non-peptide bond. In certain embodiments, the chemical association, i.e., (:) is a covalent bond. In other embodiments, the chemical association, i.e., (:) is a non-covalent interaction, e.g., an ionic interaction, a hydrophobic interaction, a hydrophilic interaction, a Van der Waals interaction, a hydrogen bond. In other embodiments, (:) is a non-peptide covalent bond. In still other embodiments, (:) is a peptide bond. In yet other embodiments, (:) represents a physical association between two sequences, wherein a portion of a first sequence is in close proximity to a second sequence such that the first sequence shields or blocks a portion of the second sequence from interacting with another moiety, and further that this physical association is maintained without allowing the second sequence to interact with other moieties.

In one embodiment, the first heterologous moiety (H or H1) linked to the VWF fragment in the chimeric protein is a first Fc region. In another embodiment, the second heterologous moiety (or H2) linked to the FVIII protein in the chimeric protein is a second Fc region.

In certain embodiments, a chimeric protein of the invention comprises two polypeptide chains, a first chain comprising, consisting essentially of, or consisting of an amino acid sequence encoding FVIII (e.g., single chain FVIII) and a first heterologous moiety (e.g., a first Fc region) and a second chain comprising, consisting essentially of, or consisting of an amino acid sequence encoding a VWF fragment comprising D' domain and D3 domain, a second heterologous moiety (e.g., a second Fc region), and a linker between the VWF fragment and the second Fc domain (e.g., VWF linker). The linker between the VWF fragment and the second Fc domain can be a thrombin cleavable linker. In some embodiments, the single chain FVIII protein comprises a third heterologous moiety, e.g., a half-life extender, which is linked to the N-terminus, C-terminus, or one or more sites within the FVIII sequence.

In other embodiments, a chimeric protein of the invention comprises three polypeptide chains, wherein a first chain comprises, consists essentially of, or consists of a heavy chain of FVIII, a second chain comprises, consists essentially of, or consists of a light chain of FVIII fused to a first heterologous moiety (e.g., a first Fc region), and a third polypeptide chain comprises, consists essentially of, or consists of a VWF fragment comprising the D' domain and the D3 domain, a second heterologous moiety (e.g, a second Fc region), and a linker. The linker between the VWF fragment and the second heterologous moiety can be a thrombin cleavable linker. In some embodiments, the heavy chain FVIII is linked to a third heterologous moiety, e.g., a half-life extender, which can be linked to the N-terminus, C-terminus, or one or more sites within the FVIII sequence.

In yet other embodiments, a chimeric protein of the invention comprises two polypeptide chains, a first chain comprising, consisting essentially of, or consisting of a heavy chain of FVIII and a second chain comprising, consisting essentially of, or consisting of a light chain of FVIII, a first heterologous moiety (e.g., a first Fc region), a first linker (e.g., a protease cleavage site comprising one or more intracellular processing sites), a VWF fragment, a second linker (e.g., a thrombin cleavable linker), and a second heterologous moiety (e.g., a second Fc region), wherein the light chain of FVIII is linked to the first heterologous moiety (e.g., the first Fc region), which is further linked to the VWF fragment by the first linker (e.g. a processable linker having a protease cleavage site comprising one or more intracellular processing sites), and wherein the VWF fragment is linked to the second Fc region by the second linker (e.g., a thrombin cleavable linker). In certain embodiments, the first linker and the second linker are identical or different.

In certain embodiments, a chimeric protein of the invention comprises one polypeptide chain, which comprises a single chain FVIII protein, a first heterologous moiety (e.g., a first Fc region), a first linker (e.g., a thrombin cleavable linker), a VWF fragment, a second linker (e.g., a thrombin cleavable linker), and a second heterologous moiety (e.g., a second Fc region), wherein the single chain FVIII protein is linked to the first heterologous moiety, which is also linked to the VWF fragment by the first linker, and the VWF fragment is linked to the second Fc region by the second linker. In one embodiment, the first linker is a cleavable linker comprising a first cleavable site and a second cleavable site. In another embodiment, the second linker is a cleavable linker comprising one or two cleavable sites. In a specific embodiment, the second linker is a thrombin cleavable linker. The linker useful in the invention can be any length, e.g., at least 10, 50, 100, 200, 300, 400, 500, 600, or 700 amino acids. For example, the linker can be 20 amino acids, 35 amino acids, 42 amino acids, 73 amino acids, or 98 amino acids.

In certain embodiments, the VWF fragment is directly linked to the FVIII protein by a peptide bond or a linker. As one way of linking the VWF fragment and the FVIII protein directly or through a linker, an enzymatic ligation (e.g., sortase) can be employed. For example, sortase refers to a group of prokaryotic enzymes that modify surface proteins by recognizing and cleaving a carboxyl-terminal sorting signal. For most substrates of sortase enzymes, the recognition signal consists of the motif LPXTG (Leu-Pro-any-Thr-Gly (SEQ ID NO: 106), then a highly hydrophobic transmembrane sequence, then a cluster of basic residues such as arginine. Cleavage occurs between the Thr and Gly, with transient attachment through the Thr residue to the active site Cys residue of a ligation partner, followed by transpeptidation that attaches the protein covalently to the cell wall. In some embodiments, the ligation partner contains Gly(n).

In one embodiment, a VWF fragment linked to a sortase recognition motif by an optional linker can be fused to a FVIII protein linked to Gly(n) by a sortase, wherein n can be any integer. A ligation construct comprises the VWF fragment (N-terminal portion of the construct) and the FVIII protein (C-terminal portion of the construct), wherein the sortase recognition motif is inserted in between. An exemplary construct is shown in FIG. 24(A). Another ligation construct comprises the VWF fragment (N-terminal portion of the construct, the linker, the sortase recognition motif, and the FVIII protein (C-terminal portion of the construct) (e.g., FIG. 24(C)). In another embodiment, a FVIII protein linked to a sortase recognition motif by an optional linker can be fused to a VWF fragment linked to Gly(n) by a sortase, wherein n is any integer. A resulting ligation construct comprises the FVIII protein (N-terminal portion of the construct) and the VWF fragment (C-terminal portion of the construct), wherein the sortase recognition motif is inserted in between. An exemplary construct is shown in FIG. 24(B). Another resulting ligation construct comprises the FVIII protein (N-terminal portion of the construct), the linker, the sortase recognition motif, and the VWF fragment (C-terminal portion of the construct) (e.g., FIG. 24(D)). In other embodiments, a VWF fragment linked to a sortase recognition motif by a first optional linker can be fused to a heterologous moiety, e.g., an immunoglobulin constant region or a portion thereof, e.g., an Fc region, linked to a thrombin cleavage site by a second optional linker. A resulting construct can comprise the VWF fragment (N-terminal portion), the first linker, the sortase recognition motif, the protease cleavage site, the second optional linker, and the heterologous moiety (e.g., FIG. 24(E)). In certain embodiments, this resulting construct is a part of a chimeric protein comprising the FVIII protein and a second heterologous moiety, e.g., an immunoglobulin constant region or a portion thereof, e.g., a second Fc region. In one example, In another example, a chimeric comprises three polypeptide chains, the first chain comprising a VWF fragment, the first linker, the sortase recognition motif, the protease cleavage site, the second optional linker, the first heterologous moiety, the second chain comprising the light chain of the FVIII protein and the second heterologous moiety, and the third chain comprising the heavy chain of the FVIII protein.

In still other embodiments, the chimeric protein of the invention comprising a VWF fragment and a FVIII protein, wherein the VWF fragment and the FVIII protein are covalently associated with each other or covalently linked to each other has less immunogenicity than a FVIII protein without the VWF fragment. The reduced immunogenicity includes, but is not limited to, less humoral immune response, e.g., less neutralizing antibody titer, or less cell-mediated immune response against FVIII, e.g., production of various cytokines.

In yet other embodiments, as a result of the invention the half-life of the FVIII protein (or a chimeric protein) is extended compared to a FVIII protein without the VWF fragment or wildtype FVIII. The half-life of the FVIII protein is at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the half-life of a FVIII protein without the VWF fragment. In one embodiment, the half-life of FVIII is about 1.5-fold to about 20-fold, about 1.5 fold to about 15 fold, or about 1.5 fold to about 10 fold longer than the half-life of wild-type FVIII. In another embodiment, the half-life of the FVIII is extended about 2-fold to about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, about 2-fold to about 3-fold, about 2.5-fold to about 10-fold, about 2.5-fold to about 9-fold, about 2.5-fold to about 8-fold, about 2.5-fold to about 7-fold, about 2.5-fold to about 6-fold, about 2.5-fold to about 5-fold, about 2.5-fold to about 4-fold, about 2.5-fold to about 3-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 3-fold to about 4-fold, about 4-fold to about 6 fold, about 5-fold to about 7-fold, or about 6-fold to about 8 fold as compared to wild-type FVIII or a FVIII protein without the VWF fragment. In other embodiments, the half-life of FVIII is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours. In still other embodiments, the half-life of FVIII is about 15 hours to about two weeks, about 16 hours to about one week, about 17 hours to about one week, about 18 hours to about one week, about 19 hours to about one week, about 20 hours to about one week, about 21 hours to about one week, about 22 hours to about one week, about 23 hours to about one week, about 24 hours to about one week, about 36 hours to about one week, about 48 hours to about one week, about 60 hours to about one week, about 24 hours to about six days, about 24 hours to about five days, about 24 hours to about four days, about 24 hours to about three days, or about 24 hours to about two days.

In some embodiments, the average half-life of the FVIII protein per subject is about 15 hours, about 16 hours, about 17 hours, about 18 hours, about 19 hours, about 20 hours, about 21 hours, about 22 hours, about 23 hours, about 24 hours (1 day), about 25 hours, about 26 hours, about 27 hours, about 28 hours, about 29 hours, about 30 hours, about 31 hours, about 32 hours, about 33 hours, about 34 hours, about 35 hours, about 36 hours, about 40 hours, about 44 hours, about 48 hours (2 days), about 54 hours, about 60 hours, about 72 hours (3 days), about 84 hours, about 96 hours (4 days), about 108 hours, about 120 hours (5 days), about six days, about seven days (one week), about eight days, about nine days, about 10 days, about 11 days, about 12 days, about 13 days, or about 14 days.

In certain embodiments, the half-life of the FVIII protein covalently linked to the VWF fragment is extendable in FVIII/VWF double knockout ("DKO") mice compared to a polypeptide consisting of FVIII or a FVIII monomer-dimer hybrid.

A) Von Willebrand Factor (VWF) Fragments

VWF (also known as F8VWF) is a large multimeric glycoprotein present in blood plasma and produced constitutively in endothelium (in the Weibel-Palade bodies), megakaryocytes (α-granules of platelets), and subendothelian connective tissue. The basic VWF monomer is a 2813 amino acid protein. Every monomer contains a number of specific domains with a specific function, the D' and D3 domains (which together bind to Factor VIII), the A1 domain (which binds to platelet GPIb-receptor, heparin, and/or possibly collagen), the A3 domain (which binds to collagen), the C1 domain (in which the RGD domain binds to platelet integrin α IIbβ3 when this is activated), and the "cysteine knot" domain at the C-terminal end of the protein (which VWF shares with platelet-derived growth factor (PDGF), transforming growth factor-β (TGFβ) and β-human chorionic gonadotropin (βHCG)).

The 2813 monomer amino acid sequence for human VWF is reported as Accession Number_NP_000543.2_in Genbank. The nucleotide sequence encoding the human VWF is reported as Accession Number_NM_000552.3 in Genbank. The nucleotide sequence of human VWF is designated as SEQ ID NO: 1. SEQ ID NO: 2 is the amino acid sequence encoded by SEQ ID NO: 1. Each domain of VWF is listed in Table 1.

TABLE 1

VWF domains

| | Amino acid Sequence | | |
|---|---|---|---|
| VWF Signal Peptide (Amino acids 1 to 22 of SEQ ID NO: 2) | 1 MIPARFAGVL LALALILPGT LC | | 22 |
| VWF D1D2 region (Amino acids 23 to 763 of SEQ ID NO: 2) | 23 DFVNTFDGSM | AEGTRGRS | STARCSLFGS |
| | 51 YSFAGYCSYL LAGGCQKRSF SIIGDFQNGK RVSLSVYLGE FFDIHLFVNG | | |
| | 101 TVTQGDQRVS MPYASKGLYL ETEAGYYKLS GEAYGFVARI GSGNFQVLL | | |
| | 151 SDRYFNKTCG LCGNFNIFAE DDFMTQEGTL TSDPYDFANS WALSSGEQWC | | |
| | 201 ERASPPSSSC NISSGEMQKG LWEQCQLLKS TSVFARCHPL VDPEPFVALC | | |
| | 251 EKTLCECAGG LECACPALLE YARTCAQEGM VLYGWTDHSA CSPVCPAGME | | |
| | 301 YRQCVSPCAR TCQSLHINEM CQERCVDGCS CPEGQLLDEG LCVESTECPC | | |
| | 351 VHSGKRYPPG TSLSRDCNTC ICRNSQWICS NEECPGECLV TGQSHFKSFD | | |
| | 401 NRYFTFSGIC QYLLARDCQD HSFSIVIETV QCADDRDAVC TRSVTVRLPG | | |
| | 451 LHNSLVKLKH GAGVAMDGQD IQLPLLKGDL RIQHTVTASV RLSYGEDLQM | | |
| | 501 DWDGRGRLLV KLSPVYAGKT CGLCGNYNGN QGDDFLTPSG LAEPRVEDFG | | |
| | 551 NAWKLHGDCQ DLQKQHSDPC ALNPRMTRFS EEACAVLTSP TFEACHRAVS | | |
| | 601 PLPYLRNCRY DVCSCSDGRE CLCGALASYA AACAGRGVRV AWREPGRCEL | | |
| | 651 NCPKGQVYLQ CGTPCNLTCR SLSYPDEECN EACLEGCFCP PGLYMDERGD | | |
| | 701 CVPKAQCPCY YDGEIFQPED IFSDHHTMCY CEDGFMHCTM SGVPGSLLPD | | |
| | 751 AVLSSPLSHR SKR | | 763 |
| VWF D' Domain (Amino acids 764 to 866 of SEQ ID NO: 2) | 764 TCQNYDLECM | SLSCRPP MVKLVCPADN LRAEGLECTK | |
| | 801 SMGCVSGCLC PPGMVRHENR CVALERCPCF HQGKEYAPGE TVKIGCNTCV | | |
| | 851 CRDRKWNCTD HVCDAT | | 866 |

TABLE 1-continued

| VWF domains | | |
|---|---|---|
| VWF D3 Domain (Amino acids 867 to 1240 of SEQ ID NO: 2) | 867 | CSTI GMAHYLTFDG LKYLFPGECQ YVLVQDYCGS |
| | 901 | NPGTFRILVG NKGCSHPSVK CKKRVTILVE GGEIELFDGE VNVKRPMKDE |
| | 951 | THFEVVESGR YIILLLGKAL SVVWDRHLSI SVVLKQTYQE KVCGLCGNFD |
| | 1001 | GIQNNDLTSS NLQVEEDPVD FGNSWKVSSQ CADTRKVPLD SSPATCHNNI |
| | 1051 | MKQTMVDSSC RILTSDVFQD CNKLVDPEPY LDVCIYDTCS CESIGDCACF |
| | 1101 | CDTIAAYAHV CAQHGKVVTW RTATLCPQSC EERNLRENGY ECEWRYNSCA |
| | 1151 | PACQVTCQHP EPLACPVQCV EGCHAHCPPG KILDELLQTC VDPEDCPVCE |
| | 1201 | VAGRRFASGK KVTLNPSDPE HCQICHCDVV NLTCEACQEP |
| | 1240 | |
| VWF A1 Domain (Amino acids 1241 to 1479 of SEQ ID NO: 2) | 1241 | GGLVVPPTDA |
| | 1251 | PVSPTTLYVE DISEPPLHDF YCSRLLDLVF LLDGSSRLSE AEFEVLKAFV |
| | 1301 | VDMMERLRIS QKWVRVAVVE YHDGSHAYIG LKDRKRPSEL RRIASQVKYA |
| | 1351 | GSQVASTSEV LKYTLFQIFS KIDRPEASRI ALLLMASQEP QRMSRNFVRY |
| | 1401 | VQGLKKKKVI VIPVGIGPHA NLKQIRLIEK QAPENKAFVL SSVDELEQQR |
| | 1451 | DEIVSYLCDL APEAPPPTLP PDMAQVTVG 1479 |
| | 1480 | P GLLGVSTLGP KRNSMVLDVA |
| | 1501 | FVLEGSDKIG EADFNRSKEF MEEVIQRMDV GQDSIHVTVL QYSYMVTVEY |
| | 1551 | PFSEAQSKGD ILQRVREIRY QGGNRTNTGL ALRYLSDHSF LVSQGDREQA 1600 |
| | 1601 | PNLVYMVTGN PASDEIKRLP GDIQVVPIGV GPNANVQELE RIGWPNAPIL |
| | 1651 | IQDFETLPRE APDLVLQRCC SGEGLQIPTL SPAPDCSQPL DVILLLDGSS |
| | 1701 | SFPASYFDEM KSFAKAFISK ANIGPRLTQV SVLQYGSITT IDVPWNVVPE |
| | 1751 | KAHLLSLVDV MQREGGPSQI GDALGFAVRY LTSEMHGARP GASKAVVILV |
| | 1801 | TDVSVDSVDA AADAARSNRV TVFPIGIGDR YDAAQLRILA GPAGDSNVVK |
| | 1851 | LQRIEDLPTM VTLGNSFLHK LCSGFVRICM DEDGNEKRPG DVWTLPDQCH |
| | 1901 | TVTCQPDGQT LLKSHRVNCD RGLRPSCPNS QSPVKVEETC GCRWTCPCVC |
| | 1951 | TGSSTRHIVT FDGQNFKLTG SCSYVLFQNK EQDLEVILHN GACSPGARQG |
| | 2001 | CMKSIEVKHS ALSVEXHSDM EVTVNGRLVS VPYVGGNMEV NVYGAIMHEV |
| | 2051 | RFNHLGHIFT FTPQNNEFQL QLSPKTFASK TYGLCGICDE NGANDFMLRD |
| | 2101 | GTVTTDWKTL VQEWTVQRPG QTCQPILEEQ CLVPDSSHCQ VLLLPLFAEC |
| | 2151 | HKVLAPATFY AICQQDSCHQ EQVCEVIASY AHLCRTNGVC VDWRTPDFCA |
| | 2201 | MSCPPSLVYN HCEHGCPRHC DGNVSSCGDH PSEGCFCPPD KVMLEGSCVP |
| | 2251 | EEACTQCIGE DGVQHQFLEA WVPDHQPCQI CTCLSGRKVN CTTQPCPTAK |
| | 2301 | APTCGLCEVA RLRQNADQCC PEYECVCDPV SCDLPPVPHC ERGLQPTLTN |
| | 2351 | PGECRPNFTC ACRKEECKRV SPPSCPPHRL PTLRKTQCCD EYECACNCVN |
| | 2401 | STVSCPLGYL ASTATNDCGC TTTTCLPDKV CVHRSTIYPV GQFWEEGCDV |
| | 2451 | CTCTDMEDAV MGLRVAQCSQ KPCEDSCRSG FTYVLHEGEC CGRCLPSACE |
| | 2501 | VVTGSPRGDS QSSWKSVGSQ WASPENPCLI NECVRVKEEV FIQQRNVSCP |
| | 2551 | QLEVPVCPSG FQLSCKTSAC CPSCRCERME ACMLNGTVIG PGKTVMIDVC |

TABLE 1-continued

VWF domains

```
2601 TTCRCMVQVG VISGFKLECR KTTCNPCPLG YKEENNTGEC
     CGRCLPTACT
2651 IQLRGGQIMT LKRDETLQDG CDTHFCKVNE RGEYFWEKRV
     TGCPPFDEHK
2701 CLAEGGKIMK IPGTCCDTCE EPECNDITAR LQYVKVGSCK
     SEVEVDIHYC
2751 QGKCASKAMY SIDINDVQDQ CSCCSPTRTE PMQVALHCTN
     GSVVYHEVLN
2801 AMECKCSPRK CSK
```

Nucleotide Sequence

Full-length VWF (SEQ ID NO: 1)

```
ATGATTCCTG CCAGATTTGC CGGGGTGCTG CTTGCTCTGG CCCTCATTTT
GCCAGGGACC CTTTGTGCAG AAGGAACTCG CGGCAGGTCA TCCACGGCCC
TACTAAGGAC GGTCTAAACG GCCCCACGAC GAACGAGACG GGGAGTAAAA
CGGTCCCTGG GAAACACGTC TTCCTTGAGC GCCGTCCAGT AGGTGCCGGG
GATGCAGCCT TTTCGGAAGT GACTTCGTCA ACACCTTTGA TGGGAGCATG
TACAGCTTTG CGGGATACTG CAGTTACCTC CTGGCAGGGG GCTGCCAGAA
CTACGTCGGA AAAGCCTTCA CTGAAGCAGT TGTGGAAACT ACCCTCGTAC
ATGTCGAAAC GCCCTATGAC GTCAATGGAG GACCGTCCCC CGACGGTCTT
ACGCTCCTTC TCGATTATTG GGGACTTCCA GAATGGCAAG AGAGTGAGCC
TCTCCGTGTA TCTTGGGGAA TTTTTTGACA TCCATTTGTT TGTCAATGGT
TGCGAGGAAG AGCTAATAAC CCCTGAAGGT CTTACCGTTC TCTCACTCGG
AGAGGCACAT GAACCCCTT AAAAAACTGT AGGTAAACAA ACAGTTACCA
ACCGTGACAC AGGGGGACCA AAGAGTCTCC ATGCCCTATG CCTCCAAAGG
GCTGTATCTA GAAACTGAGG CTGGGTACTA CAAGCTGTCC GGTGAGGCCT
TGGCACTGTG TCCCCCTGGT TTCTCAGAGG TACGGGATAC GGAGGTTTCC
CGACATAGAT CTTTGACTCC GACCCATGAT GTTCGACAGG CCACTCCGGA
ATGGCTTTGT GGCCAGGATC GATGGCAGCG GCAACTTTCA AGTCCTGCTG
TCAGACAGAT ACTTCAACAA GACCTGCGGG CTGTGTGGCA ACTTTAACAT
TACCGAAACA CCGGTCCTAG CTACCGTCGC CGTTGAAAGT TCAGGACGAC
AGTCTGTCTA TGAAGTTGTT CTGGACGCCC GACACACCGT TGAAATTGTA
CTTTGCTGAA GATGACTTTA TGACCCAAGA AGGGACCTTG ACCTCGGACC
CTTATGACTT TGCCAACTCA TGGGCTCTGA GCAGTGGAGA ACAGTGGTGT
GAAACGACTT CTACTGAAAT ACTGGGTTCT TCCCTGGAAC TGGAGCCTGG
GAATACTGAA ACGGTTGAGT ACCCGAGACT CGTCACCTCT TGTCACCACA
GAACGGGCAT CTCCTCCCAG CAGCTCATGC AACATCTCCT CTGGGGAAAT
GCAGAAGGGC CTGTGGGAGC AGTGCCAGCT TCTGAAGAGC ACCTCGGTGT
CTTGCCCGTA GAGGAGGGTC GTCGAGTACG TTGTAGAGGA GACCCCTTTA
CGTCTTCCCG GACACCCTCG TCACGGTCGA AGACTTCTCG TGGAGCCACA
TTGCCCGCTG CCACCCTCTG GTGGACCCCG AGCCTTTTGT GGCCCTGTGT
GAGAAGACTT TGTGTGAGTG TGCTGGGGGG CTGGAGTGCG CCTGCCCTGC
AACGGGCGAC GGTGGGAGAC CACCTGGGGC TCGGAAAACA CCGGGACACA
CTCTTCTGAA ACACACTCAC ACGACCCCCC GACCTCACGC GGACGGGACG
CCTCCTGGAG TACGCCCGGA CCTGTGCCCA GGAGGGAATG GTGCTGTACG
GCTGGACCGA CCACAGCGCG TGCAGCCCAG TGTGCCCTGC TGGTATGGAG
GGAGGACCTC ATGCGGGCCT GGACACGGGT CCTCCCTTAC CACGACATGC
CGACCTGGCT GGTGTCGCGC ACGTCGGGTC ACACGGGACG ACCATACCTC
TATAGGCAGT GTGTGTCCCC TTGCGCCAGG ACCTGCCAGA GCCTGCACAT
CAATGAAATG TGTCAGGAGC GATGCGTGGA TGGCTGCAGC TGCCCTGAGG
ATATCCGTCA CACACAGGGG AACGCGGTCC TGGACGGTCT CGGACGTGTA
GTTACTTTAC ACAGTCCTCG CTACGCACCT ACCGACGTCG ACGGGACTCC
GACAGCTCCT GGATGAAGGC CTCTGCGTGG AGAGCACCGA GTGTCCCTGC
GTGCATTCCG GAAAGCGCTA CCCTCCCGGC ACCTCCCTCT CTCGAGACTG
CTGTCGAGGA CCTACTTCCG GAGACGCACC TCTCGTGGCT CACAGGGACG
CACGTAAGGC CTTTCGCGAT GGGAGGGCCG TGGAGGGAGA GAGCTCTGAC
CAACACCTGC ATTTGCCGAA ACAGCCAGTG GATCTGCAGC AATGAAGAAT
GTCCAGGGGA GTGCCTTGTC ACTGGTCAAT CCCACTTCAA GAGCTTTGAC
GTTGTGGACG TAAACGGCTT TGTCGGTCAC CTAGACGTCG TTACTTCTTA
CAGGTCCCCT CACGGAACAG TGACCAGTTA GGGTGAAGTT CTCGAAACTG
AACAGATACT TCACCTTCAG TGGGATCTGC CAGTACCTGC TGGCCCGGGA
TTGCCAGGAC CACTCCTTCT CCATTGTCAT TGAGACTGTC CAGTGTGCTG
TTGTCTATGA AGTGGAAGTC ACCCTAGACG TCATGGACG ACCGGGCCCT
AACGGTCCTG GTGAGGAAGA GGTAACAGTA ACTCTGACAG GTCACACGAC
ATGACCGCGA CGCTGTGTGC ACCCGCTCCG TCACCGTCCG GCTGCCTGGC
CTGCACAACA GCCTTGTGAA ACTGAAGCAT GGGGCAGGAG TTGCCATGGA
TACTGGCGCT GCGACACACG TGGGCGAGGC AGTGGCAGGC CGACGGACCG
GACGTGTTGT CGGAACACTT TGACTTCGTA CCCCGTCCTC AACGGTACCT
TGGCCAGGAG ATCCAGCTCC CCCTCCTGAA AGGTGACCTC CGCATCCAGC
ATACAGTGAC GGCCTCCGTG CGCCTCAGCT ACGGGGAGGA CCTGCAGATG
ACCGGTCCTG TAGGTCGAGG GGAGGACTT CCACTGGAG GCGTAGGTCG
TATGTCACTG CCGGAGGCAC GCGGAGTCGA TGCCCCTCCT GGACGTCTAC
GACTGGGATG GCCGCGGGAG GCTGCTGGTG AAGCTGCCC CCGTCTATGC
CGGGAAGACC TGCGGCCTGT GTGGGAATTA CAATGGCAAC CAGGGCGACG
CTGACCCTAC CGGCGCCCTC CGACGACCAC TTCGACAGGG GCAGATACG
GCCCTTCTGG ACGCCGGACA CACCCTTAAT GTTACCGTTG GTCCCGCTGC
ACTTCCTTAC CCCTCTGGG CTGGCRGAGC CCCGGGTGGA GGACTTCGGG
AACGCCTGGA AGCTGCACGG GGACTGCCAG GACCTGCAGA AGCAGCACAG
```

TABLE 1-continued

VWF domains

TGAAGGAATG GGGGAGACCC GACCGYCTCG GGGCCCACCT CCTGAAGCCC
TTGCGGACCT TCGACGTGCC CCTGACGGTC CTGGACGTCT TCGTCGTGTC
CGATCCCTGC GCCCTCAACC CGCGCATGAC CAGGTTCTCC GAGGAGGCGT
GCGCGGTCCT GACGTCCCCC ACATTCGAGG CCTGCCATCG TGCCGTCAGC
GCTAGGGACG CGGGAGTTGG GCGCGTACTG GTCCAAGAGG CTCCTCCGCA
CGCGCCAGGA CTGCAGGGGG TGTAAGCTCC GGACGGTAGC ACGGCAGTCG
CCGCTGCCCT ACCTGCGGAA CTGCCGCTAC GACGTGTGCT CCTGCTCGGA
CGGCCGCGAG TGCCTGTGCG GCGCCCTGGC CAGCTATGCC GCGGCCTGCG
GGCGACGGGA TGGACGCCTT GACGGCGATG CTGCACACGA GGACGAGCCT
GCCGGCGCTC ACGGACACGC CGCGGGACCG GTCGATACGG CGCCGGACGC
CGGGGAGAGG CGTGCGCGTC GCGTGGCGCG AGCCAGGCCG CTGTGAGCTG
AACTGCCCGA AAGGCCAGGT GTACCTGCAG TGCGGGACCC CCTGCAACCT
GCCCCTCTCC GCACGCGCAG CGCACCGCGC TCGGTCCGGC GACACTCGAC
TTGACGGGCT TTCCGGTCCA CATGGACGTC ACGCCCTGGG GGACGTTGGA
GACCTGCCGC TCTCTCTCTT ACCCGGATGA GGAATGCAAT GAGGCCTGAC
TGGAGGGCTG CTTCTGCCCC CCAGGGCTCT ACATGGATGA GAGGGGGGAC
CTGGACGGCG AGAGAGAGAA TGGGCCTACT CCTTACGTTA CTCCGGACGG
ACCTCCCGAC GAAGACGGGG GGTCCCGAGA TGTACCTACT CTCCCCCCTG
TGCGTGCCCA AGGCCCAGTG CCCCTGTTAC TATGACGGTG AGATCTTCCA
GCCAGAAGAC ATCTTCTCAG ACCATCACAC CATGTGCTAC TGTGAGGATG
ACGCACGGGT TCCGGGTCAC GGGGACAATG ATACTGCCAC TCTAGAAGGT
CGGTCTTCTG TAGAAGAGTC TGGTAGTGTG GTACACGATG ACACTCCTAC
GCTTCATGCA CTGTACCATG AGTGGAGTCC CCGGAAGCTT GCTGCCTGAC
GCTGTCCTCA GCAGTCCCCT GTCTCATCGC AGCAAAAGGA GCCTATCCTG
CGAAGTACGT GACATGGTAC TCACCTCAGG GGCCTTCGAA CGACGGACTG
CGACAGGAGT CGTCAGGGGA CAGAGTAGCG TCGTTTTCCT CGGATAGGAC
TCGGCCCCCC ATGGTCAAGC TGGTGTGTCC CGCTGACAAC CTGCGGGCTG
AAGGGCTCGA GTGTACCAAA ACGTGCCAGA ACTATGACCT GGAGTGCATG
AGCCGGGGGG TACCAGTTCG ACCACACAGG GCGACTGTTG GACGCCCGAC
TTCCCGAGCT CACATGGTTT TGCACGGTCT TGATACTGGA CCTCACGTAC
AGCATGGGCT GTGTCTCTGG CTGCCTCTGC CCCCCGGGCA TGGTCCGGCA
TGAGAACAGA TGTGTGGCCC TGGAAAGGTG TCCCTGCTTC CATCAGGGCA
TCGTACCCGA CACAGAGACC GACGGAGACG GGGGGCCCGT ACCAGGCCGT
ACTCTTGTCT ACACACCGGG ACCTTTCCAC AGGGACGAAG GTAGTCCCGT
AGGAGTATGC CCCTGGAGAA ACAGTGAAGA TTGGCTGCAA CACTTGTGTC
TGTCGGGACC GGAAGTGGAA CTGCACAGAC CATGTGTGTG ATGCCACGTG
TCCTCATACG GGGACCTCTT TGTCACTTCT AACCGACGTT GTGAACACAG
ACAGCCCTGG CCTTCACCTT GACGTGTCTG GTACACACAC TACGGTGCAC
CTCCACGATC GGCATGGCCC ACTACCTCAC CTTCGACGGG CTCAAATACC
TGTTCCCCGG GGAGTGCCAG TACGTTCTGG TGCAGGATTA CTGCGGCAGT
GAGGTGCTAG CCGTACCGGG TGATGGAGTG GAAGCTGCCC GAGTTTATGG
ACAAGGGGCC CCTCACGGTC ATGCAAGACC ACGTCCTAAT GACGCCGTCA
AACCCTGGGA CCTTTCGGAT CCTAGTGGGA ATAAGGGAT GCAGCCACCC
CTCAGTGAAA TGCAAGAAAC GGGTCACCAT CCTGGTGGGA GGAGGAGAGA
TTGGGACCCT GGAAAGCCTA GGATCACCCC TTATTCCCTA CGTCGGTGGG
GAGTCACTTT ACGTTCTTTG CCCAGTGGTA GGACCACCTC CCTCCTCTCT
TTGAGCTGTT TGACGGGGAG GTGAATGTGA AGAGGCCCAT GAAGGATGAG
ACTCACTTTG AGGTGGTGGA GTCTGGCCGG TACATCATTC TGCTGCTGGG
AACTCGACAA ACTGCCCCTC CACTTACACT TCTCCGGGTA CTTCCTACTC
TGAGTGAAAC TCCACCACCT CAGACCGGCC ATGTAGTAAG ACGACGACCC
CAAAGCCCTC TCCGTGGTCT GGGACCGCCA CCTGAGCATC TCCGTGGTCC
TGAAGCAGAC ATACCAGGAG AAAGTGTGTG GCCTGTGTGG GAATTTTGAT
GTTTCGGGAG AGGCACCAGA CCCTGGCGGT GGACTCGTAG AGGCACCAGG
ACTTCGTCTG TATGGTCCTC TTTCACACAC CGGACACACC CTTAAAACTA
GGCATCCAGA ACAATGACCT CACCAGCAGC AACCTCCAAG TGGAGGAAGA
CCCTGTGGAC TTTGGGAACT CCTGGAAAGT GAGCTCGCAG TGTGCTGACA
CCGTAGGTCT TGTTACTGGA GTGGTCGTCG TTGGAGGTTC ACCTCCTTCT
GGGACACCTG AAACCCTTGA GGACTTTTCA CTCGAGCGTC ACACGACTGT
CCAGAAAAGT GCCTCTGGAC TCATCCCCTG CCACCTGCCA TAACAACATC
ATGAAGCAGA CGATGGTGGA TTCCTCCTGT AGAATCCTTA CCAGTGACGT
GGTCTTTTCA CGGAGACCTG AGTAGGGGAC GGTGGACGGT ATTGTTGTAG
TACTTCGTCT GCTACCACCT AAGGAGGACA TCTTAGGAAT GGTCACTGCA
CTTCCAGGAC TGCAACAAGC TGGTGGACCC CGAGCCATAT CTGGATGTCT
GCATTTACGA CACCTGCTCC TGTGAGTCCA TTGGGGACTG CGCCTGCTTC
GAAGGTCCTG ACGTTGTTCG ACCACCTGGG GCTCGGTATA GACCTACAGA
CGTAAATGCT GTGGACGAGG ACACTCAGGT AACCCCTGAC GCGGACGAAG
TGCGACACCA TTGCTGCCTA TGCCCACGTG TGTGCCCAGC ATGGCAAGGT
GGTGACCTGG AGGACGGCCA CATTGTGCCC CCAGAGCTGC GAGGAGAGGA
ACGCTGTGGT AACGACGGAT ACGGGTGCAC ACACGGGTCG TACCGTTCCA
CCCACTGGACC TCCTGCCGGT GTAACACGGG GGTCTCGACG CTCCTCTCCT
ATCTCCGGGA GAACGGGTAT GAGTGTGAGT GGCGCTATAA CAGCTGTGCA
CCTGCCTGTC AAGTCACGTG TCAGCACCCT GAGCCACTGG CCTGCCCTGT
TAGAGGCCCT CTTGCCCATA CTCACACTCA CCGCGATATT GTCGACACGT
GGACGGACAG TTCAGTGCAC AGTCGTGGGA CTCGGTGACC GGACGGGACA
GCAGTGTGTG GAGGGCTGCC ATGCCCACTG CCCTCCAGGG AAAATCCTGG
ATGAGCTTTT GCAGACCTGC GTTGACCCTG AAGACTGTCC AGTGTGTGAG
CGTCACACAC CTCCCGACGG TACGGGTGAC GGGAGGTCCC TTTTAGGACC
TACTCGAAAA CGTCTGGACG CAACTGGGAC TTCTGACAGG TCACACACTC

TABLE 1-continued

VWF domains

GTGGCTGGCC GGCGTTTTGC CTCAGGAAAG AAAGTCACCT TGAATCCCAG
TGACCCTGAG CACTGCCAGA TTTGCCACTG TGATGTTGTC AACCTCACCT
CACCGACCGG CCGCAAAACG GAGTCCTTTC TTTCAGTGGA ACTTAGGGTC
ACTGGGACTC GTGACGGTCT AAACGGTGAC ACTACAACAG TTGGAGTGGA
GTGAAGCCTG CCAGGAGCCG GGAGGCCTGG TGGTGCCTCC CACAGATGCC
CCGGTGAGCC CCACCACTCT GTATGTGGAG GACATCTCGG AACCGCCGTT
CACTTCGGAC GGTCCTCGGC CCTCCGGACC ACCACGGAGG GTGTCTACGG
GGCCACTCGG GGTGGTGAGA CATACACCTC CTGTAGAGCC TTGGCGGCAA
GCACGATTTC TACTGCAGCA GGCTACTGGA CCTGGTCTTC CTGCTGGATG
GCTCCTCCAG GCTGTCCGAG GCTGAGTTTG AAGTGCTGAA GGCCTTTGTG
CGTGCTAAAG ATGACGTCGT CCGATGACCT GGACCAGAAG GACGACCTAC
CGAGGAGGTC CGACAGGCTC CGACTCAAAC TTCACGACTT CCGGAAACAC
GTGGACATGA TGGAGCGGCT GCGCATCTCC CAGAAGTGGG TCCGCGTGGC
CGTGGTGGAG TACCACGACG GCTCCCACGC CTACATCGGG CTCAAGGACC
CACCTGTACT ACCTCGCCGA CGCGTAGAGG GTCTTCACCC AGGCGCACCG
GCACCACCTC ATGGTGCTGC CGAGGGTGCG GATGTAGCCC GAGTTCCTGG
GGAAGCGACC GTCAGAGCTG CGGCGCATTG CCAGCCAGGT GAAGTATGCG
GGCAGCCAGG TGGCCTCCAC CAGCGAGGTC TTGAAATACA CACTGTTCCA
CCTTCGCTGG CAGTCTCGAC GCCGCGTAAC GGTCGGTCCA CTTCATACGC
CCGTCGGTCC ACCGGAGGTG GTCGCTCCAG AACTTTATGT GTGACAAGGT
AATCTTCAGC AAGATCGACC GCCCTGAAGC CTCCCGCATC GCCCTGCTCC
TGATGGCCAG CCAGGAGCCC AACGGATGT CCCGGAACTT TGTCCGCTAC
TTAGAAGTCG TTCTAGCTGG CGGGACTTCG GAGGGCGTAG CGGGACGAGG
ACTACCGGTC GGTCCTCGGG GTTGCCTACA GGGCCTTGAA ACAGGCGATG
GTCCAGGGCC TGAAGAAGAA GAAGGTCATT GTGATCCCGG TGGGCATTGG
GCCCCATGCC AACCTCAAGC AGATCCGCCT CATCGAGAAG CAGGCCCCTG
CAGGTCCCGG ACTTCTTCTT CTTCCAGTAA CACTAGGGCC ACCCGTAACC
CGGGGTACGG TTGGAGTTCG TCTAGGCGGA GTAGCTCTTC GTCCGGGGAC
AGAACAAGGC CTTCGTGCTG AGCAGTGTGG ATGAGCTGGA GCAGCAAAGG
GACGAGATCG TTAGCTACCT CTGTGACCTT GCCCCTGAAG CCCCTCCTCC
TCTTGTTCCG GAAGCACGAC TCGTCACACC TACTCGACCT CGTCGTTTCC
CTGCTCTAGC AATCGATGGA GACACTGGAA CGGGGACTTC GGGGAGGAGG
TACTCTGCCC CCCGACATGG CACAAGTCAC TGTGGGCCCG GGGCTCTTGG
GGGTTTCGAC CCTGGGGCCC AAGAGGAACT CCATGGTTCT GGATGTGGCG
ATGAGACGGG GGGCTGTACC GTGTTCAGTG ACACCCGGGC CCCGAGAACC
CCCAAAGCTG GGACCCCGGG TTCTCCTTGA GGTACCAAGA CCTACACCGC
TTCGTCCTGG AAGGATCGGA CAAAATTGGT GAAGCCGACT TCAACAGGAG
CAAGGAGTTC ATGGAGGAGG TGATTCAGCG GATGGATGTG GCCAGGACA
AAGCAGGACC TTCCTAGCCT GTTTTAACCA CTTCGGCTGA AGTTGTCCTC
GTTCCTCAAG TACCTCCTCC ACTAAGTCGC CTACCTACAC CCGGTCCTGT
GCATCCACGT CACGGTGCTG CAGTACTCCT ACATGGTGAC CGTGGAGTAC
CCCTTCAGCG AGGCACAGTC CAAAGGGGAC ATCCTGCAGC GGGTGCGAGA
CGTAGGTGCA GTGCCACGAC GTCATGAGGA TGTACCACTG GCACCTCATG
GGGAAGTCGC TCCGTGTCAG GTTTCCCCTG TAGGACGTCG CCCACGCTCT
GATCCGCTAC CAGGGCGGCA ACAGGACCAA CACTGGGCTG GCCCTGCGGT
ACCTCTCTGA CCACAGCTTC TTGGTCAGCC AGGGTGACCG GGAGCAGGCG
CTAGGCGATG GTCCCGCCGT TGTCCTGGTT GTGACCCGAC CGGGACGCCA
TGGAGAGACT GGTGTCGAAG AACCAGTCGG TCCCACTGGC CCTCGTCCGC
CCCAACCTGG TCTACATGGT CACCGGAAAT CCTGCCTCTG ATGAGATCAA
GAGGCTGCCT GGAGACATCC AGGTGGTGCC CATTGGAGTG GCCCTAATG
GGGTTGGACC AGATGTACCA GTGGCCTTTA GGACGGAGAC TACTCTAGTT
CTCCGACGGA CCTCTGTAGG TCCACCACGG GTAACCTCAC CCGGGATTAC
CCAACGTGCA GGAGCTGGAG AGGATTGGCT GGCCCAATGC CCCTATCCTC
ATCCAGGACT TTGAGACGCT CCCCGAGAG GCTCCTGACC TGGTGCTGCA
GGTTGCACGT CCTCGACCTC TCCTAACCGA CCGGGTTACG GGGATAGGAG
TAGGTCCTGA AACTCTGCGA GGGGGCTCTC CGAGGACTGG ACCACGACGT
GAGGTGCTGC TCCGGAGAGG GGCTGCAGAT CCCCACCCTC TCCCCTGCAC
CTGACTGCAG CCAGCCCCTG GACGTGATCC TTCTCCTGGA TGGCTCCTCC
CTCCACGACG AGGCCTCTCC CCGACGTCTA GGGGTGGGAG AGGGGACGTG
GACTGACGTC GGTCGGGGAC CTGCACTAGG AAGAGGACCT ACCGAGGAGG
AGTTTCCCAG CTTCTTATTT TGATGAAATG AAGAGTTTCG CCAAGGCTTT
CATTTCAAAA GCCAATATAG GGCCTCGTCT CACTCAGGTG TCAGTGCTGC
TCAAAGGGTC GAAGAATAAA ACTACTTTAC TTCTCAAAGC GGTTCCGAAA
GTAAAGTTTT CGGTTATATC CCGGAGCAGA GTGAGTCCAC AGTCACGACG
AGTATGAAG CATCACCACC ATTGACGTGC CATGGAACGT GGTCCCGGAG
AAAGCCCATT TGCTGAGCCT TGTGGACGTC ATGCAGCGGG AGGGAGGCCC
TCATACCTTC GTAGTGGTGG TAACTGCACG GTACCTTGCA CCAGGGCCTC
TTTCGGGTAA ACGACTCGGA ACACCTGCAG TACGTCGCCC TCCCTCCGGG
CAGCCAAATC GGGGATGCCT TGGGCTTTGC TGTGCGATAC TTGACTTCAG
AAATGCATGG TGCCAGGCCG GGAGCCTCAA AGGCGGTGGT CATCCTGGTC
GTCGGTTTAG CCCCTACGGA ACCCGAAACG ACACGCTATG AACTGAAGTC
TTTACGTACC ACGGTCCGGC CCTCGGAGTT TCCGCCACCA GTAGGACCAG
ACGGACGTCT CTGTGGATTC AGTGGATGCA GCAGTGGTCA CCGCCAGGTC
CAACAGAGTG ACAGTGTTCC CTATTGGAAT TGGAGATCGC TACGATGCAG
TGCCTGCAGA GACACCTAAG TCACCTACGT CGTCGACTAC GGCGGTCCAG
GTTGTCTCAC TGTCACAAGG GATAACCTTA ACCTCTAGCG ATGCTACGTC
CCCAGCTACG GATCTTGGCA GGCCCAGCAG GCGACTCCAA CGTGGTGAAG
CTCCAGCGAA TCGAAGACCT CCCTACCATG GTCACCTTGG GCAATTCCTT

TABLE 1-continued

VWF domains

```
GGGTCGATGC CTAGAACCGT CCGGGTCGTC CGCTGAGGTT GCACCACTTC
GAGGTCGCTT AGCTTCTGGA GGGATGGTAC CAGTGGAACC CGTTAAGGAA
CCTCCACAAA CTGTGCTCTG GATTTGTTAG GATTTGCATG GATGAGGATG
GGAATGAGAA GAGGCCCGGG GACGTCTGGA CCTTGCCAGA CCAGTGCCAC
GGAGGTGTTT GACACGAGAC CTAAACAATC CTAAACGTAC CTACTCCTAC
CCTTACTCTT CTCCGGGCCC CTGCAGACCT GGAACGGTCT GGTCACGGTG
ACCGTGACTT GCCAGCCAGA TGGCCAGACC TTGCTGAAGA GTCATCGGGT
CAACTGTGAC CGGGGGCTGA GGCCTTCGTG CCCTAACAGC CAGTCCCCTG
TGGCACTGAA CGGTCGGTCT ACCGGTCTGG AACGACTTCT CAGTAGCCCA
GTTGACACTG GCCCCCGACT CCGGAAGCAC GGGATTGTCG GTCAGGGGAC
TTAAAGTGGA AGAGACCTGT GGCTGCCGCT GGACCTGCCC CTGYGTGTGC
ACAGGCAGCT CCACTCGGCA CATCGTGACC TTTGATGGGC AGAATTTCAA
AATTTCACCT TCTCTGGACA CCGACGGCGA CCTGGACGGG GACRCACACG
TGTCCGTCGA GGTGAGCCGT GTAGCACTGA AAACTACCCG TCTTAAAGTT
GCTGACTGGC AGCTGTTCTT ATGTCCTATT TCAAAACAAG GAGCAGGACC
TGGAGGTGAT TCTCCATAAT GGTGCCTGCA GCCCTGGAGC AAGGCAGGGC
CGACTGACCG TCGACAAGAA TACAGGATAA AGTTTTGTTC CTCGTCCTGG
ACCTCCACTA AGAGGTATTA CCACGGACGT CGGGACCTCG TTCCGTCCCG
TGCATGAAAT CCATCGAGGT GAAGCACAGT GCCCTCTCCG TCGAGSTGCA
CAGTGACATG GAGGTGACGG TGAATGGGAG ACTGGTCTCT GTTCCTTACG
ACGTACTTTA GGTAGCTCCA CTTCGTGTCA CGGGAGAGGC AGCTCSACGT
GTCACTGTAC CTCCACTGCC ACTTACCCTC TGACCAGAGA CAAGGAATGC
TGGGTGGGAA CATGGAAGTC AACGTTTATG GTGCCATCAT GCATGAGGTC
AGATTCAATC ACCTTGGTCA CATCTTCACA TTCACTCCAC AAAACAATGA
ACCCACCCTT GTACCTTCAG TTGCAAATAC CACGGTAGTA CGTACTCCAG
TCTAAGTTAG TGGAACCAGT GTAGAAGTGT AAGTGAGGTG TTTTGTTACT
GTTCCAACTG CAGCTCAGCC CCAAGACTTT TGCTTCAAAG ACGTATGGTC
TGTGTGGGAT CTGTGATGAG AACGGAGCCA ATGACTTCAT GCTGAGGGAT
CAAGGTTGAC GTCGAGTCGG GGTTCTGAAA ACGAAGTTTC TGCATACCAG
ACACACCCTA GACACTACTC TTGCCTCGGT TACTGAAGTA CGACTCCCTA
GGCACAGTCA CCACAGACTG GAAAACACTT GTTCAGGAAT GGACTGTGCA
GCGGCCAGGG CAGACGTGCC AGCCCATCCT GGAGGAGCAG TGTCTTGTCC
CCGTGTCAGT GGTGTCTGAC CTTTTGTGAA CAAGTCCTTA CCTGACACGT
CGCCGGTCCC GTCTGCACGG TCGGGTAGGA CCTCCTCGTC ACAGAACAGG
CCGACAGCTC CCACTGCCAG GTCCTCCTCT TACCACTGTT TGCTGAATGC
CACAAGGTCC TGGCTCCAGC CACATTCTAT GCCATCTGCC AGCAGGACAG
GGCTGTCGAG GGTGACGGTC CAGGAGGAGA ATGGTGACAA ACGACTTACG
GTGTTCCAGG ACCGAGGTCG GTGTAAGATA CGGTAGACGG TCGTCCTGTC
TTGCCACCAG GAGCAAGTGT GTGAGGTGAT CGCCTCTTAT GCCCACCTCT
GTCGGACCAA CGGGGTCTGC GTTGACTGGA GGACACCTGA TTTCTGTGCT
AACGGTGGTC CTCGTTCACA CACTCCACTA GCGGAGAATA CGGGTGGAGA
CAGCCTGGTT GCCCCAGACG CAACTGACCT CCTGTGGACT AAAGACACGA
ATGTCATGCC CACCATCTCT GGTCTACAAC CACTGTGAGC ATGGCTGTCC
CCGGCACTGT GATGGCAACG TGAGCTCCTG TGGGGACCAT CCCTCCGAAG
TACAGTACGG GTGGTAGAGA CCAGATGTTG GTGACACTCG TACCGACAGG
GGCCGTGACA CTACCGTTGC ACTCGAGGAC ACCCCTGGTA GGGAGGCTTC
GCTGTTTCTG CCCTCCAGAT AAAGTCATGT TGGAAGGCAG CTGTGTCCCT
GAAGAGGCCT GCACTCAGTG CATTGGTGAG GATGGAGTCC AGCACCAGTT
CGACAAAGAC GGGAGGTCTA TTTCAGTACA ACCTTCCGTC GACACAGGGA
CTTCTCCGGA CGTGAGTCAC GTAACCACTC CTACCTCAGG TCGTGGTCAA
CCTGGAAGCC TGGGTCCCGG ACCACCAGCC CTGTCAGATC TGCACATGCC
TCAGCGGGCG GAAGGTCAAC TGCACAACGC AGCCCTGCCC CACGGCCAAA
GGACCTTCGG ACCCAGGGCC TGGTGGTCGG GACAGTCTAG ACGTGTACGG
AGTCGCCCGC CTTCCAGTTG ACGTGTTGCG TCGGGACGGG GTGCCGGTTT
GCTCCCACGT GTGGCCTGTG TGAAGTAGCC CGCCTCCGCC AGAATGCAGA
CCAGTGCTGC CCCGAGTATG AGTGTGTGTG TGACCCAGTG AGCTGTGACC
CGAGGGTGCA CACCGGACAC ACTTCATCGG GCGGAGGCGG TCTTACGTCT
GGTCACGACG GGGCTCATAC TCACACACAC ACTGGGTCAC TCGACACTGG
TGCCCCCAGT GCCTCACTGT GAACGTGGCC TCCAGCCCAC ACTGACCAAC
CCTGGCGAGT GCAGACCCAA CTTCACCTGC GCCTGCAGGA AGGAGGAGTG
ACGGGGGTCA CGGAGTGACA CTTGCACCGG AGGTCGGGTG TGACTGGTTG
GGACCGCTCA CGTCTGGGTT GAAGTGGACG CGGACGTCCT TCCTCCTCAC
CAAAAGAGTG TCCCCACCCT CCTGCCCCCC GCACCGTTTG CCCACCCTTC
GGAAGACCCA GTGCTGTGAT GAGTATGAGT GTGCCTGCAA CTGTGTCAAC
GTTTTCTCAC AGGGGTGGGA GGACGGGGGG CGTGGCAAAC GGGTGGGAAG
CCTTCTGGGT CACGACACTA CTCATACTCA CACGGACGTT GACACAGTTG
TCCACAGTGA GCTGTCCCCT TGGGTACTTG GCCTCAACCG CCACCAATGA
CTGTGGCTGT ACCACAACCA CCTGCCTTCC CGACAAGGTG TGTGTCCACC
AGGTGTCACT CGACAGGGGA ACCCATGAAC CGGAGTTGGC GGTGGTTACT
GACACCGACA TGGTGTTGGT GGACGGAAGG GCTGTTCCAC ACACAGGTGG
GAAGCACCAT CTACCCTGTG GGCCAGTTCT GGGAGGAGGG CTGCGATGTG
TGCACCTGCA CCGACATGGA GGATGCCGTG ATGGGCCTCC GCGTGGCCCA
CTTCGTGGTA GATGGGACAC CCGGTCAAGA CCCTCCTCCC GACGCTACAC
ACGTGGACGT GGCTGTACCT CCTACGGCAC TACCCGGAGG CGCACCGGGT
GTGCTCCCAG AAGCCCTGTG AGGACAGCTG TCGGTCGGGC TTCACTTACG
TTCTGCATGA AGGCGAGTGC TGTGGAAGGT GCCTGCCATC TGCCTGTGAG
CACGAGGGTC TTCGGGACAC TCCTGTCGAC AGCCAGCCCG AAGTGAATGC
AAGACGTACT TCCGCTCACG ACACCTTCCA CGGACGGTAG ACGGACACTC
```

TABLE 1-continued

VWF domains

```
GTGGTGACTG GCTCACCGCG GGGGGACTCC CAGTCTTCCT GGAAGAGTGT
CGGCTCCCAG TGGGCCTCCC CGGAGAACCC CTGCCTCATC AATGAGTGTG
CACCACTGAC CGAGTGGCGC CCCCCTGAGG GTCAGAAGGA CCTTCTCACA
GCCGAGGGTC ACCCGGAGGG GCCTCTTGGG GACGGAGTAG TTACTCACAC
TCCGAGTGAA GGAGGAGGTC TTTATACAAC AAAGGAACGT CTCCTGCCCC
CAGCTGGAGG TCCCTGTCTG CCCCTCGGGC TTTCAGCTGA GCTGTAAGAC
AGGCTCACTT CCTCCTCCAG AAATATGTTG TTTCCTTGCA GAGGACGGGG
GTCGACCTCC AGGGACAGAC GGGGAGCCCG AAAGTCGACT CGACATTCTG
CTCAGCGTGC TGCCCAAGCT GTCGCTGTGA GCGCATGGAG GCCTGCATGC
TCAATGGCAC TGTCATTGGG CCCGGGAAGA CTGTGATGAT CGATGTGTGC
GAGTCGCACG ACGGGTTCGA CAGCGACACT CGCGTACCTC CGGACGTACG
AGTTACCGTG ACAGTAACCC GGGCCCTTCT GACACTACTA GCTACACACG
ACGACCTGCC GCTGCATGGT GCAGGTGGGG GTCATCTCTG GATTCAAGCT
GGAGTGCAGG AAGACCACCT GCAACCCCTG CCCCCTGGGT TACAAGGAAG
TGCTGGACGG CGACGTACCA CGTCCACCCC CAGTAGAGAC CTAAGTTCGA
CCTCACGTCC TTCTGGTGGA CGTTGGGGAC GGGGGACCCA ATGTTCCTTC
AAAATAACAC AGGTGAATGT TGTGGGAGAT GTTTGCCTAC GGCTTGCACC
ATTCAGCTAA GAGGAGGACA GATCATGACA CTGAAGCGTG ATGAGACGCT
TTTTATTGTG TCCACTTACA ACACCCTCTA CAAACGGATG CCGAACGTGG
TAAGTCGATT CTCCTCCTGT CTAGTACTGT GACTTCGCAC TACTCTGCGA
CCAGGATGGC TGTGATACTC ACTTCTGCAA GGTCAATGAG AGAGGAGAGT
ACTTCTGGGA GAAGAGGGTC ACAGGCTGCC CACCCTTTGA TGAACACAAG
GGTCCTACCG ACACTATGAG TGAAGACGTT CCAGTTACTC TCTCCTCTCA
TGAAGACCCT CTTCTCCCAG TGTCCGACGG GTGGGAAACT ACTTGTGTTC
TGTCTTGCTG AGGGAGGTAA AATTATGAAA ATTCCAGGCA CCTGCTGTGA
CACATGTGAG GAGCCTGAGT GCAACGACAT CACTGCCAGG CTGCAGTATG
ACAGAACGAC TCCCTCCATT TTAATACTTT TAAGGTCCGT GGACGACACT
GTGTACACTC CTCGGACTCA CGTTGCTGTA GTGACGGTCC GACGTCATAC
TCAAGGTGGG AAGCTGTAAG TCTGAAGTAG AGGTGGATAT CCACTACTGC
CAGGGCAAAT GTGCCAGCAA AGCCATGTAC TCCATTGACA TCAACGATGT
AGTTCCACCC TTCGACATTC AGACTTCATC TCCACCTATA GGTGATGACG
GTCCCGTTTA CACGGTCGTT TCGGTACATG AGGTAACTGT AGTTGCTACA
GCAGGACCAG TGCTCCTGCT GCTCTCCGAC ACGGACGGAG CCCATGCAGG
TGGCCCTGCA CTGCACCAAT GGCTCTGTTG TGTACCATGA GGTTCTCAAT
CGTCCTGGTC ACGAGGACGA CGAGAGGCTG TGCCTGCCTC GGGTACGTCC
ACCGGGACGT GACGTGGTTA CCGAGACAAC ACATGGTACT CCAAGAGTTA
GCCATGGAGT GCAAATGCTC CCCCAGGAAG TGCAGCAAGT GA
```

The present invention is directed to a von Willebrand Factor (VWF) fragment comprising a D' domain and a D3 domain of VWF, wherein the VWF fragment inhibits binding of endogenous VWF (full-length VWF) to a FVIII protein. In one embodiment, the VWF fragment binds to or is associated with a FVIII protein. By binding to or associating with a FVIII protein, a VWF fragment of the invention protects FVIII from protease cleavage and FVIII activation, stabilizes the heavy chain and light chain of FVIII, and prevents clearance of FVIII by scavenger receptors. In another embodiment, the VWF fragment binds to or associates with a FVIII protein and blocks or prevents binding of the FVIII protein to phospholipid and activated Protein C. By preventing or inhibiting binding of the FVIII protein with endogenous, full-length VWF, the VWF fragment of the invention reduces the clearance of FVIII by VWF clearance receptors and thus extends the half-life of FVIII. The half-life extension of a FVIII protein is thus due to the binding of or associating with the VWF fragment lacking a VWF clearance receptor binding site to the FVIII protein and shielding or protecting of the FVIII protein by the VWF fragment from endogenous VWF which contains the VWF clearance receptor binding site. The FVIII protein bound to or protected by the VWF fragment can also allow recycling of a FVIII protein. Therefore, the VWF fragment cannot be full-length mature VWF. By eliminating the VWF clearance pathway receptor binding sites contained in the full length VWF molecule, the FVIII/VWF heterodimers of the invention are uncoupled from the VWF clearance pathway, which allows the further extending FVIII half-life.

The VWF fragment comprising the D' domain and the D3 domain can further comprise a VWF domain selected from the group consisting of an A1 domain, an A2 domain, an A3 domain, a D1 domain, a D2 domain, a D4 domain, a B1 domain, a B2 domain, a B3 domain, a C1 domain, a C2 domain, a CK domain, one or more fragments thereof, and any combinations thereof. In one embodiment, a VWF fragment comprises, consists essentially of, or consists of: (1) the D' and D3 domains of VWF or fragments thereof; (2) the D1, D', and D3 domains of VWF or fragments thereof; (3) the D2, D', and D3 domains of VWF or fragments thereof; (4) the D1, D2, D', and D3 domains of VWF or fragments thereof; or (5) the D1, D2, D', D3, and A1 domains of VWF or fragments thereof. The VWF fragment described herein does not contain a site binding to a VWF clearance receptor. In another embodiment, the VWF fragment described herein is not amino acids 764 to 1274 of SEQ ID NO: 2. The VWF fragment of the present invention can comprise any other sequences linked to or fused to the VWF fragment, but is not the full-length VWF. For example, a VWF fragment described herein can further comprise a signal peptide.

In one embodiment, a VWF fragment of the present invention comprises the D' domain and the D3 domain of VWF, wherein the D' domain is at least 60%, 70%, 80%, 85%, 90%, 95%, 96%, 97%, 98%, 99%, or 100% identical to amino acids 764 to 866 of SEQ ID NO: 2, wherein the VWF fragment binds to a FVIII protein, shields, inhibits or prevents binding of endogenous VWF fragment to a FVIII protein. In another embodiment, a VWF fragment comprises the D' domain and the D3 domain of VWF, wherein the D3 domain is at least 60%, 70%, 80%, 85%, 90%, 95%, 96%, 97%, 98%, 99%, or 100% identical to amino acids 867 to 1240 of SEQ ID NO: 2, wherein the VWF fragment binds to a FVIII protein or inhibits or prevents binding of endogenous VWF fragment to a FVIII protein. In some embodiments, a VWF fragment described herein comprises, consists essentially of, or consists of the D' domain and D3 domain of VWF, which are at least 60%, 70%, 80%, 85%, 90%, 95%, 96%, 97%, 98%, 99%, or 100% identical to amino acids 764 to 1240 of SEQ ID NO: 2, wherein the VWF fragment binds to a FVIII protein or inhibits or prevents binding of endogenous VWF fragment to a FVIII protein. In other embodiments, a VWF fragment comprises, consists essentially of, or consists of the D1, D2, D', and D3 domains at least 60%, 70%, 80%, 85%, 90%, 95%, 96%, 97%, 98%, 99%, or 100% identical to amino acids 23 to 1240 of SEQ ID NO: 2, wherein the VWF fragment binds to a FVIII protein or inhibits or prevents binding of endogenous VWF fragment to a FVIII protein. In still other embodiments, the VWF fragment further comprises a signal peptide operably linked thereto.

In some embodiments, a VWF fragment of the invention consists essentially of or consists of (1) the D'D3 domain, the D1D'D3 domain, D2D'D3 domain, or D1D2D'D3 domain and (2) an additional VWF sequence up to about 10 amino acids (e.g., any sequences from amino acids 764 to 1240 of SEQ ID NO: 2 to amino acids 764 to 1250 of SEQ ID NO: 2), up to about 15 amino acids (e.g., any sequences from amino acids 764 to 1240 of SEQ ID NO: 2 to amino acids 764 to 1255 of SEQ ID NO: 2), up to about 20 amino acids (e.g., any sequences from amino acids 764 to 1240 of SEQ ID NO: 2 to amino acids 764 to 1260 of SEQ ID NO: 2), up to about 25 amino acids (e.g., any sequences from amino acids 764 to 1240 of SEQ ID NO: 2 to amino acids 764 to 1265 of SEQ ID NO: 2), or up to about 30 amino acids (e.g., any sequences from amino acids 764 to 1240 of SEQ ID NO: 2 to amino acids 764 to 1260 of SEQ ID NO: 2). In a particular embodiment, the VWF fragment comprising or consisting essentially of the D' domain and the D3 domain is neither amino acids 764 to 1274 of SEQ ID NO: 2 nor the full-length mature VWF.

In other embodiments, the VWF fragment comprising the D'D3 domains linked to the D1D2 domains further comprises an intracellular cleavage site, e.g., (a cleavage site by PACE or PC5), allowing cleavage of the D1D2 domains from the D'D3 domains upon expression. Non-limiting examples of the intracellular cleavage site are disclosed elsewhere herein.

In yet other embodiments, a VWF fragment comprises the D' domain and the D3 domain, but does not comprise an amino acid sequence selected from the group consisting of (1) amino acids 1241 to 2813 of SEQ ID NO: 2, (2) amino acids 1270 to amino acids 2813 of SEQ ID NO: 2, (3) amino acids 1271 to amino acids 2813 of SEQ ID NO: 2, (4) amino acids 1272 to amino acids 2813 of SEQ ID NO: 2, (5) amino acids 1273 to amino acids 2813 of SEQ ID NO: 2, and (6) amino acids 1274 to amino acids 2813 of SEQ ID NO: 2.

In still other embodiments, a VWF fragment of the present invention comprises, consists essentially of, or consists of an amino acid sequence corresponding to the D' domain, D3 domain, and A1 domain, wherein the amino acid sequence is at least 60%, 70%, 75%, 80%, 85%, 90%, 95%, 96%, 97%, 98%, 99%, or 100% identical to amino acid 764 to 1479 of SEQ ID NO: 2, wherein the VWF binds to FVIII. In a particular embodiment, the VWF fragment is not amino acids 764 to 1274 of SEQ ID NO: 2.

In some embodiments, a VWF fragment of the invention comprises the D' domain and the D3 domain, but does not comprise at least one VWF domain selected from the group consisting of (1) an A1 domain, (2) an A2 domain, (3) an A3 domain, (4) a D4 domain, (5) a B1 domain, (6) a B2 domain, (7) a B3 domain, (8) a C1 domain, (9) a C2 domain, (10) a CK domain, (11) a CK domain and C2 domain, (12) a CK domain, a C2 domain, and a C1 domain, (13) a CK domain, a C2 domain, a C1 domain, a B3 domain, (14) a CK domain, a C2 domain, a C1 domain, a B3 domain, a B2 domain, (15) a CK domain, a C2 domain, a C1 domain, a B3 domain, a B2 domain, and a B1 domain, (16) a CK domain, a C2 domain, a C1 domain, a B3 domain, a B2 domain, a B1 domain, and a D4 domain, (17) a CK domain, a C2 domain, a C1 domain, a B3 domain, a B2 domain, a B1 domain, a D4 domain, and an A3 domain, (18) a CK domain, a C2 domain, a C1 domain, a B3 domain, a B2 domain, a B1 domain, a D4 domain, an A3 domain, and an A2 domain, (19) a CK domain, a C2 domain, a C1 domain, a B3 domain, a B2 domain, a B1 domain, a D4 domain, an A3 domain, an A2 domain, and an A1 domain, and (20) any combinations thereof.

In yet other embodiments, the VWF fragment comprises the D'D3 domains and one or more domains or modules. Examples of such domains or modules include, but are not limited to, the domains and modules disclosed in Zhour et al., Blood published online Apr. 6, 2012: DOI 10.1182/blood-2012-01-405134. For example, the VWF fragment can comprise the D'D3 domain and one or more domains or modules selected from the group consisting of A1 domain, A2 domain, A3 domain, D4N module, VWD4 module, C8-4 module, TIL-4 module, C1 module, C2 module, C3 module, C4 module, C5 module, C5 module, C6 module, and any combinations thereof.

In still other embodiments, the VWF fragment is linked to a heterologous moiety, wherein the heterologous moiety is linked to the N-terminus or the C-terminus of the VWF fragment or inserted between two amino acids in the VWF fragment. For example, the insertion sites for the heterologous moiety in the VWF fragment can be in the D' domain, the D3 domain, or both. The heterologous moiety can be a half-life extender.

In certain embodiments, a VWF fragment of the invention forms a multimer, e.g., dimer, trimer, tetramer, pentamer, hexamer, heptamer, or the higher order multimers. In other embodiments, the VWF fragment is a monomer having only one VWF fragment. In some embodiments, the VWF fragment of the present invention can have one or more amino acid substitutions, deletions, additions, or modifications. In one embodiment, the VWF fragment can include amino acid substitutions, deletions, additions, or modifications such that the VWF fragment is not capable of forming a disulfide bond or forming a dimer or a multimer. In another embodiment, the amino acid substitution is within the D' domain and the D3 domain. In a particular embodiment, a VWF fragment of the invention contains at least one amino acid substitution at a residue corresponding to residue 1099, residue 1142, or both residues 1099 and 1142 of SEQ ID NO: 2. The at least one amino acid substitution can be any amino acids that are not occurring naturally in the wild type VWF. For example, the amino acid substitution can be any amino acids other than cysteine, e.g., Isoleucine, Alanine, Leucine, Asparagine, Lysine, Aspartic acid, Methionine, Phenylalanine, Glutamic acid, Threonine, Glutamine, Tryptophan, Glycine, Valine, Proline, Serine, Tyrosine, Arginine, or Histidine. In another example, the amino acid substitution has one or more amino acids that prevent or inhibit the VWF fragments from forming multimers.

In certain embodiments, the VWF fragment useful herein can be further modified to improve its interaction with FVIII, e.g., to improve binding affinity to FVIII. As a non-limiting example, the VWF fragment comprises a serine residue at the residue corresponding to amino acid 764 of SEQ ID NO: 2 and a lysine residue at the residue corresponding to amino acid 773 of SEQ ID NO: 2. Residues 764 and/or 773 can contribute to the binding affinity of the VWF fragments to FVIII. In other embodiments, the VWF fragment can have other modifications, e.g., the fragment can be pegylated, glycosylated, hesylated, or polysialylated.

B) Heterologous Moieties

The heterologous moiety can be a heterologous polypeptide or a heterologous non-polypeptide moiety. In certain embodiments, the heterologous moiety is a half-life extending molecule which is known in the art and comprises a polypeptide, a non-polypeptide moiety, or the combination of both. The heterologous polypeptide moiety can comprise an immunoglobulin constant region or a portion thereof, albumin or a fragment thereof, an albumin binding moiety, transferrin or a fragment thereof, a PAS sequence, a HAP sequence, a derivative or variant thereof, or any combinations thereof. In some embodiments, the non-polypeptide binding moiety comprises polyethylene glycol (PEG), polysialic acid, hydroxyethyl starch (HES), a derivative thereof, or any combinations thereof. In certain embodiments, there can be one, two, three or more heterologous moieties, which can each be the same or different molecules.

1) Immunoglobulin Constant Region or Portion Thereof

An immunoglobulin constant region is comprised of domains denoted CH (constant heavy) domains (CH1, CH2, etc.). Depending on the isotype, (i.e. IgG, IgM, IgA IgD, or IgE), the constant region can be comprised of three or four CH domains. Some isotypes (e.g. IgG) constant regions also contain a hinge region. See Janeway et al. 2001, *Immunobiology*, Garland Publishing, N.Y., N.Y.

An immunoglobulin constant region or a portion thereof for producing the chimeric protein of the present invention may be obtained from a number of different sources. In preferred embodiments, an immunoglobulin constant region or a portion thereof is derived from a human immunoglobulin. It is understood, however, that the immunoglobulin constant region or a portion thereof may be derived from an immunoglobulin of another mammalian species, including for example, a rodent (e.g. a mouse, rat, rabbit, guinea pig) or non-human primate (e.g. chimpanzee, macaque) species. Moreover, the immunoglobulin constant region or a portion thereof may be derived from any immunoglobulin class, including IgM, IgG, IgD, IgA and IgE, and any immunoglobulin isotype, including IgG1, IgG2, IgG3 and IgG4. In one embodiment, the human isotype IgG1 is used.

A variety of the immunoglobulin constant region gene sequences (e.g. human constant region gene sequences) are available in the form of publicly accessible deposits. Constant region domains sequence can be selected having a particular effector function (or lacking a particular effector function) or with a particular modification to reduce immunogenicity. Many sequences of antibodies and antibody-encoding genes have been published and suitable Ig constant region sequences (e.g. hinge, CH2, and/or CH3 sequences, or portions thereof) can be derived from these sequences using art recognized techniques. The genetic material obtained using any of the foregoing methods may then be altered or synthesized to obtain polypeptides of the present invention. It will further be appreciated that the scope of this invention encompasses alleles, variants and mutations of constant region DNA sequences.

The sequences of the immunoglobulin constant region or a portion thereof can be cloned, e.g., using the polymerase chain reaction and primers which are selected to amplify the domain of interest. To clone a sequence of the immunoglobulin constant region or a portion thereof from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. Methods Enzymol. 217:270). PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250). The cloning of antibody sequences is further described in Newman et al., U.S. Pat. No. 5,658,570, filed Jan. 25, 1995, which is incorporated by reference herein.

An immunoglobulin constant region used herein can include all domains and the hinge region or portions thereof. In one embodiment, the immunoglobulin constant region or a portion thereof comprises CH2 domain, CH3 domain, and a hinge region, i.e., an Fc region or an FcRn binding partner.

As used herein, the term "Fc region" is defined as the portion of a polypeptide which corresponds to the Fc region of native immunoglobulin, i.e., as formed by the dimeric association of the respective Fc domains of its two heavy chains. A native Fc region forms a homodimer with another Fc region. In contrast, the term "genetically-fused Fc region" or "single-chain Fc region" (scFc region), as used herein, refers to a synthetic dimeric Fc region comprised of Fc domains genetically linked within a single polypeptide chain (i.e., encoded in a single contiguous genetic sequence).

In one embodiment, the "Fc region" refers to the portion of a single immunoglobulin heavy chain beginning in the hinge region just upstream of the papain cleavage site (i.e. residue 216 in IgG, taking the first residue of heavy chain constant region to be 114) and ending at the C-terminus of the antibody. Accordingly, a complete Fc domain comprises at least a hinge domain, a CH2 domain, and a CH3 domain.

The Fc region of an immunoglobulin constant region, depending on the immunoglobulin isotype can include the CH2, CH3, and CH4 domains, as well as the hinge region. Chimeric proteins comprising an Fc region of an immunoglobulin bestow several desirable properties on a chimeric protein including increased stability, increased serum half-life (see Capon et al., 1989, *Nature* 337:525) as well as binding to Fc receptors such as the neonatal Fc receptor (FcRn) (U.S. Pat. Nos. 6,086,875, 6,485,726, 6,030,613; WO 03/077834; US2003-0235536A1), which are incorporated herein by reference in their entireties.

An immunoglobulin constant region or a portion thereof can be an FcRn binding partner. FcRn is active in adult epithelial tissues and expressed in the lumen of the intestines, pulmonary airways, nasal surfaces, vaginal surfaces, colon and rectal surfaces (U.S. Pat. No. 6,485,726). An FcRn binding partner is a portion of an immunoglobulin that binds to FcRn.

The FcRn receptor has been isolated from several mammalian species including humans. The sequences of the human FcRn, monkey FcRn, rat FcRn, and mouse FcRn are known (Story et al. 1994, J. Exp. Med. 180:2377). The FcRn receptor binds IgG (but not other immunoglobulin classes such as IgA, IgM, IgD, and IgE) at relatively low pH, actively transports the IgG transcellularly in a luminal to serosal direction, and then releases the IgG at relatively higher pH found in the interstitial fluids. It is expressed in adult epithelial tissue (U.S. Pat. Nos. 6,485,726, 6,030,613, 6,086,875; WO 03/077834; US2003-0235536A1) including lung and intestinal epithelium (Israel et al. 1997, Immunology 92:69) renal proximal tubular epithelium (Kobayashi et al. 2002, Am. J. Physiol. Renal Physiol. 282:F358) as well as nasal epithelium, vaginal surfaces, and biliary tree surfaces.

FcRn binding partners useful in the present invention encompass molecules that can be specifically bound by the FcRn receptor including whole IgG, the Fc fragment of IgG, and other fragments that include the complete binding region of the FcRn receptor. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The FcRn binding partners include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U.S. Department of Public Health, Bethesda, Md.

Fc regions or FcRn binding partners bound to FcRn can be effectively shuttled across epithelial barriers by FcRn, thus providing a non-invasive means to systemically administer a desired therapeutic molecule. Additionally, fusion proteins comprising an Fc region or an FcRn binding partner are endocytosed by cells expressing the FcRn. But instead of being marked for degradation, these fusion proteins are recycled out into circulation again, thus increasing the in vivo half-life of these proteins. In certain embodiments, the portions of immunoglobulin constant regions are an Fc region or an FcRn binding partner that typically associates, via disulfide bonds and other non-specific interactions, with another Fc region or another FcRn binding partner to form dimers and higher order multimers.

Two FcRn receptors can bind a single Fc molecule. Crystallographic data suggest that each FcRn molecule binds a single polypeptide of the Fc homodimer. In one embodiment, linking the FcRn binding partner, e.g., an Fc fragment of an IgG, to a biologically active molecule provides a means of delivering the biologically active molecule orally, buccally, sublingually, rectally, vaginally, as an aerosol administered nasally or via a pulmonary route, or via an ocular route. In another embodiment, the chimeric protein can be administered invasively, e.g., subcutaneously, intravenously.

An FcRn binding partner region is a molecule or a portion thereof that can be specifically bound by the FcRn receptor with consequent active transport by the FcRn receptor of the Fc region. Specifically bound refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant KA is higher than $10^6$ $M^{-1}$, or higher than $10^8$ $M^{-1}$. If necessary, non-specific binding can be reduced without substantially affecting specific binding by varying the binding conditions. The appropriate binding conditions such as concentration of the molecules, ionic strength of the solution, temperature, time allowed for binding, concentration of a blocking agent (e.g. serum albumin, milk casein), etc., may be optimized by a skilled artisan using routine techniques.

In certain embodiments, a chimeric protein of the invention comprises one or more truncated Fc regions that are nonetheless sufficient to confer Fc receptor (FcR) binding properties to the Fc region. For example, the portion of an Fc region that binds to FcRn (i.e., the FcRn binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc region of the invention may comprise or consist of an FcRn binding portion. FcRn binding portions may be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used.

In another embodiment, the "Fc region" includes an amino acid sequence of an Fc domain or derived from an Fc domain. In certain embodiments, an Fc region comprises at least one of: a hinge (e.g., upper, middle, and/or lower hinge region) domain (about amino acids 216-230 of an antibody Fc region according to EU numbering), a CH2 domain (about amino acids 231-340 of an antibody Fc region according to EU numbering), a CH3 domain (about amino acids 341-438 of an antibody Fc region according to EU numbering), a CH4 domain, or a variant, portion, or fragment thereof. In other embodiments, an Fc region comprises a complete Fc domain (i.e., a hinge domain, a CH2 domain, and a CH3 domain). In some embodiments, an Fc region comprises, consists essentially of, or consists of a hinge domain (or a portion thereof) fused to a CH3 domain (or a portion thereof), a hinge domain (or a portion thereof) fused to a CH2 domain (or a portion thereof), a CH2 domain (or a portion thereof) fused to a CH3 domain (or a portion thereof), a CH2 domain (or a portion thereof) fused to both a hinge domain (or a portion thereof) and a CH3 domain (or a portion thereof). In still other embodiments, an Fc region lacks at least a portion of a CH2 domain (e.g., all or part of a CH2 domain). In a particular embodiment, an Fc region comprises or consists of amino acids corresponding to EU numbers 221 to 447.

The Fc regions denoted as F, F1, or F2 herein may be obtained from a number of different sources. In one embodiment, an Fc region of the polypeptide is derived from a human immunoglobulin. It is understood, however, that an Fc region may be derived from an immunoglobulin of another mammalian species, including for example, a rodent (e.g. a mouse, rat, rabbit, guinea pig) or non-human primate (e.g. chimpanzee, macaque) species. Moreover, the polypeptide of the Fc domains or portions thereof may be derived from any immunoglobulin class, including IgM, IgG, IgD, IgA and IgE, and any immunoglobulin isotype, including IgG1, IgG2, IgG3 and IgG4. In another embodiment, the human isotype IgG1 is used.

In certain embodiments, the Fc variant confers a change in at least one effector function imparted by an Fc region comprising said wild-type Fc domain (e.g., an improvement or reduction in the ability of the Fc region to bind to Fc receptors (e.g. FcγRI, FcγRII, or FcγRIII) or complement proteins (e.g. C1q), or to trigger antibody-dependent cytotoxicity (ADCC), phagocytosis, or complement-dependent cytotoxicity (CDCC)). In other embodiments, the Fc variant provides an engineered cysteine residue.

The Fc regions of the invention may employ art-recognized Fc variants which are known to impart a change (e.g., an enhancement or reduction) in effector function and/or FcR or FcRn binding. Specifically, a binding molecule of the invention may include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; 7,404,956, and 7,317,091, each of which is incorporated by reference herein. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) may be made.

The Fc region or FcRn binding partner of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example, the following single amino acid residues in human IgG1 Fc (Fcγ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wild type proline substituted by alanine at position number 238. As an example, a specific embodiment incorporates the N297A mutation, removing a highly conserved N-glycosylation site. In addition to alanine other amino acids may be substituted for the wild type amino acids at the positions specified above. Mutations may be introduced singly into Fc giving rise to more than one hundred Fc regions distinct from the native Fc. Additionally, combinations of two, three, or more of these individual mutations may be introduced together, giving rise to hundreds more Fc regions. Moreover, one of the Fc region of a construct of the invention may be mutated and the other Fc region of the construct not mutated at all, or they both may be mutated but with different mutations.

Certain of the above mutations may confer new functionality upon the Fc region or FcRn binding partner. For example, one embodiment incorporates N297A, removing a highly conserved N-glycosylation site. The effect of this mutation is to reduce immunogenicity, thereby enhancing circulating half-life of the Fc region, and to render the Fc region incapable of binding to FcγRI, FcγRIIA, FcγRIIB, and FcγRIIIA, without compromising affinity for FcRn (Routledge et al. 1995, Transplantation 60:847; Friend et al. 1999, Transplantation 68:1632; Shields et al. 1995, J. Biol. Chem. 276:6591). As a further example of new functionality arising from mutations described above affinity for FcRn may be increased beyond that of wild type in some instances. This increased affinity may reflect an increased "on" rate, a decreased "off" rate or both an increased "on" rate and a decreased "off" rate. Examples of mutations believed to impart an increased affinity for FcRn include, but not limited to, T256A, T307A, E380A, and N434A (Shields et al. 2001, J. Biol. Chem. 276:6591).

Additionally, at least three human Fc gamma receptors appear to recognize a binding site on IgG within the lower hinge region, generally amino acids 234-237. Therefore, another example of new functionality and potential decreased immunogenicity may arise from mutations of this region, as for example by replacing amino acids 233-236 of human IgG1 "ELLG" to the corresponding sequence from IgG2 "PVA" (with one amino acid deletion). It has been shown that FcγRI, FcγRII, and FcγRIII, which mediate various effector functions will not bind to IgG1 when such mutations have been introduced. Ward and Ghetie 1995, Therapeutic Immunology 2:77 and Armour et al. 1999, Eur. J. Immunol. 29:2613.

In one embodiment, the immunoglobulin constant region or a portion thereof, e.g, an Fc region, is a polypeptide including the sequence PKNSSMISNTP (SEQ ID NO: 3) and optionally further including a sequence selected from HQSLGTQ (SEQ ID NO: 4), HQNLSDGK (SEQ ID NO: 5), HQNISDGK (SEQ ID NO: 6), or VISSHLGQ (SEQ ID NO: 7) (U.S. Pat. No. 5,739,277).

In another embodiment, the immunoglobulin constant region or a portion thereof comprises an amino acid sequence in the hinge region or a portion thereof that forms one or more disulfide bonds with another immunoglobulin constant region or a portion thereof. The disulfide bond by the immunoglobulin constant region or a portion thereof places the first polypeptide comprising FVIII and the second polypeptide comprising the VWF fragment together so that endogenous VWF does not replace the VWF fragment and does not bind to the FVIII. Therefore, the disulfide bond between the first immunoglobulin constant region or a portion thereof and a second immunoglobulin constant region or a portion thereof prevents interaction between endogenous VWF and the FVIII protein. This inhibition of interaction between the VWF and the FVIII protein allows the half-life of the FVIII protein to go beyond the two fold limit. The hinge region or a portion thereof can further be linked to one or more domains of CH1, CH2, CH3, a fragment thereof, and any combinations thereof. In a particular example, an immunoglobulin constant region or a portion thereof comprises a hinge region and CH2 region (e.g., amino acids 221-340 of an Fc region).

In certain embodiments, the immunoglobulin constant region or a portion thereof is hemi-glycosylated. For example, the chimeric protein comprising two Fc regions or FcRn binding partners may contain a first, glycosylated, Fc region (e.g., a glycosylated CH2 region) or FcRn binding partner and a second, aglycosylated, Fc region (e.g., an aglycosylated CH2 region) or FcRn binding partner. In one embodiment, a linker may be interposed between the glycosylated and aglycosylated Fc regions. In another embodiment, the Fc region or FcRn binding partner is fully glycosylated, i.e., all of the Fc regions are glycosylated. In other embodiments, the Fc region may be aglycosylated, i.e., none of the Fc moieties are glycosylated.

In certain embodiments, a chimeric protein of the invention comprises an amino acid substitution to an immunoglobulin constant region or a portion thereof (e.g., Fc variants), which alters the antigen-independent effector functions of the Ig constant region, in particular the circulating half-life of the protein.

Such proteins exhibit either increased or decreased binding to FcRn when compared to proteins lacking these substitutions and, therefore, have an increased or decreased half-life in serum, respectively. Fc variants with improved affinity for FcRn are anticipated to have longer serum half-lives, and such molecules have useful applications in methods of treating mammals where long half-life of the administered polypeptide is desired, e.g., to treat a chronic disease or disorder (see, e.g, U.S. Pat. Nos. 7,348,004, 7,404,956, and 7,862,820). In contrast, Fc variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting polypeptide has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired. In one exemplary embodiment, the chimeric protein of the invention exhibit reduced transport across the epithelium of kidney glomeruli from the vasculature. In another embodiment, the chimeric protein of the invention exhibit reduced transport across the blood brain barrier (BBB) from the brain, into the vascular space. In one embodiment, a protein with altered FcRn binding comprises at least one Fc region or FcRn binding partner (e.g, one or two Fc regions or FcRn binding partners) having one or more amino acid substitutions within the "FcRn binding loop" of an Ig constant region. The FcRn binding loop is comprised of amino acid residues 280-299 (according to EU numbering) of a wild-type, full-length, Fc region. In other embodiments, an Ig constant region or a portion thereof in a chimeric protein of the invention having altered FcRn binding affinity comprises at least one Fc region or FcRn binding partner having one or more amino acid substitutions within the 15 Å FcRn "contact zone." As used herein, the term 15 Å FcRn "contact zone" includes residues at the following positions of a wild-type, full-length Fc moiety: 243-261, 275-280, 282-293, 302-319, 336-348, 367, 369, 372-389, 391, 393, 408, 424, 425-440 (EU numbering). In other embodiments, a Ig constant region or a portion thereof of the invention having altered FcRn binding affinity comprises at least one Fc region or FcRn binding partner having one or more amino acid substitutions at an amino acid position corresponding to any one of the following EU positions: 256, 277-281, 283-288, 303-309, 313, 338, 342, 376, 381, 384, 385, 387, 434 (e.g., N434A or N434K), and 438. Exemplary amino acid substitutions which altered FcRn binding activity are disclosed in International PCT Publication No. WO05/047327 which is incorporated by reference herein.

An Fc region or FcRn binding partner used in the invention may also comprise an art recognized amino acid substitution which alters the glycosylation of the chimeric protein. For example, the Fc region or FcRn binding partner of the chimeric protein linked to a VWF fragment or a FVIII protein may comprise an Fc region having a mutation leading to reduced glycosylation (e.g., N- or O-linked glycosylation) or may comprise an altered glycoform of the wild-type Fc moiety (e.g., a low fucose or fucose-free glycan).

In one embodiment, an unprocessed chimeric protein of the invention may comprise a genetically fused Fc region (i.e., scFc region) having two or more of its constituent Ig constant region or a portion thereof independently selected from the Ig constant region or a portion thereof described herein. In one embodiment, the Fc regions of a dimeric Fc region are the same. In another embodiment, at least two of the Fc regions are different. For example, the Fc regions or FcRn binding partners of the proteins of the invention comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In yet other embodiments, the Fc regions or FcRn binding partners of the protein of the invention may differ in sequence at one or more amino acid positions. For example, at least two of the Fc regions or FcRn binding partners may differ at about 5 amino acid positions (e.g., 1, 2, 3, 4, or 5 amino acid positions), about 10 positions, about 15 positions, about 20 positions, about 30 positions, about 40 positions, or about 50 positions).

2) Albumin or Fragment, or Variant Thereof

In certain embodiments, the heterologous moiety linked to the VWF fragment or linked to a FVIII protein is albumin or a functional fragment thereof. In other embodiments, a chimeric protein of the invention comprises a FVIII protein and albumin or a fragment thereof, wherein the albumin or a fragment thereof shields or protects the VWF binding site on the FVIII protein, thereby inhibiting or preventing interaction of the FVIII protein with endogenous VWF.

Human serum albumin (HSA, or HA), a protein of 609 amino acids in its full-length form, is responsible for a significant proportion of the osmotic pressure of serum and also functions as a carrier of endogenous and exogenous ligands. The term "albumin" as used herein includes full-length albumin or a functional fragment, variant, derivative, or analog thereof.

In one embodiment, the chimeric protein comprises the VWF fragment described herein and albumin, fragment, or variant thereof, wherein the VWF fragment is linked to albumin or a fragment or variant thereof. In another embodiment, the chimeric protein comprises the VWF fragment and a FVIII protein, which are bound to each other, wherein the VWF fragment is linked to albumin or a fragment or variant thereof, the protein having VIII activity is linked to albumin or a fragment or variant thereof, or both the VWF fragment and the protein having VIII activity are linked to albumin or a fragment or variant thereof. In other embodiments, the chimeric protein comprises the VWF fragment linked to albumin or a fragment or variant thereof is further linked to a heterologous moiety selected from the group consisting of an immunoglobulin constant region or a portion thereof (e.g., an Fc region), a PAS sequence, HES, and PEG. In still other embodiments, the chimeric protein comprises the VWF fragment and a FVIII protein, which are bound to each other, wherein the FVIII protein is linked to albumin or a fragment or variant thereof and further linked to a heterologous moiety selected from the group consisting of an immunoglobulin constant region or a portion thereof (e.g., an Fc region), a PAS sequence, HES, and PEG. In yet other embodiments, the chimeric protein comprises the VWF fragment linked to albumin or a fragment or variant thereof and a FVIII protein linked to albumin or a fragment or variant thereof, which are bound to each other, wherein the VWF fragment activity is further linked to a first heterologous moiety selected from the group consisting of an immunoglobulin constant region or a portion thereof (e.g., an Fc region), a PAS sequence, HES, and PEG and wherein the FVIII protein activity is further linked to a second heterologous moiety selected from the group consisting of an immunoglobulin constant region or a portion thereof (e.g., an Fc region), a PAS sequence, HES, and PEG.

In other embodiments, the heterologous moiety linked to the VWF fragment or the FVIII protein is albumin or a fragment or variant thereof, which extends (or is capable of extending) the half-life of the VWF fragment or the FVIII protein. Further examples of albumin or the fragments or variants thereof are disclosed in US Pat. Publ. Nos. 2008/0194481A1, 2008/0004206 A1, 2008/0161243 A1, 2008/0261877 A1, or 2008/0153751 A1 or PCT Appl. Publ. Nos. 2008/033413 A2, 2009/058322 A1, or 2007/021494 A2.

3) Albumin Binding Moiety

In certain embodiments, the heterologous moiety linked to the VWF fragment or the FVIII protein is an albumin binding moiety, which comprises an albumin binding peptide, a bacterial albumin binding domain, an albumin-binding antibody fragment, or any combinations thereof. For example, the albumin binding protein can be a bacterial albumin binding protein, an antibody or an antibody fragment including domain antibodies (see U.S. Pat. No. 6,696,245). An albumin binding protein, for example, can be a bacterial albumin binding domain, such as the one of streptococcal protein G (Konig, T. and Skerra, A. (1998) *J. Immunol. Methods* 218, 73-83). Other examples of albumin binding peptides that can be used as conjugation partner are, for instance, those having a Cys-Xaa$_1$-Xaa$_2$-Xaa$_3$-Xaa$_4$-Cys consensus sequence, wherein Xaa$_1$ is Asp, Asn, Ser, Thr, or Trp; Xaa$_2$ is Asn, Gln, His, Ile, Leu, or Lys; Xaa$_3$ is Ala, Asp, Phe, Trp, or Tyr; and Xaa$_4$ is Asp, Gly, Leu, Phe, Ser, or Thr as described in US patent application 2003/0069395 or Dennis et al. (Dennis et al. (2002) *J. Biol. Chem.* 277, 35035-35043).

4) PAS Sequence

In other embodiments, the heterologous moiety linked to the VWF fragment or to the FVIII protein is a PAS sequence. In one embodiment, the chimeric protein comprises a VWF fragment described herein and a PAS sequence, wherein the VWF fragment is linked to the PAS sequence. In another embodiment, a chimeric protein of the invention comprises a FVIII protein and a PAS sequence, wherein the PAS sequence shields or protects the VWF binding site on the FVIII protein, thereby inhibiting or preventing interaction of the FVIII protein with endogenous VWF.

A PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the chimeric protein. Yet, the skilled person is aware that an amino acid polymer also may form random coil conformation when residues other than alanine, serine, and proline are added as a minor constituent in the PAS sequence. The term "minor constituent" as used herein means that amino acids other than alanine, serine, and proline may be added in the PAS sequence to a certain degree, e.g., up to about 12%, i.e., about 12 of 100 amino acids of the PAS sequence, up to about 10%, i.e. about 10 of 100 amino acids of the PAS sequence, up to about 9%, i.e., about 9 of 100 amino acids, up to about 8%, i.e., about 8 of 100 amino acids, about 6%, i.e., about 6 of 100 amino acids, about 5%, i.e., about 5 of 100 amino acids, about 4%, i.e., about 4 of 100 amino acids, about 3%, i.e., about 3 of 100 amino acids, about 2%, i.e., about 2 of 100 amino acids, about 1%, i.e., about 1 of 100 of the amino acids. The amino acids different from alanine, serine and proline may be selected from the group consisting of Arg, Asn, Asp, Cys, Gln, Glu, Gly, His, Ile, Leu, Lys, Met, Phe, Thr, Trp, Tyr, and Val.

Under physiological conditions, the PAS sequence stretch forms a random coil conformation and thereby can mediate an increased in vivo and/or in vitro stability to the VWF factor or the protein of coagulation activity. Since the random coil domain does not adopt a stable structure or function by itself, the biological activity mediated by the VWF fragment or the FVIII protein to which it is fused is essentially preserved. In other embodiments, the PAS sequences that form random coil domain are biologically inert, especially with respect to proteolysis in blood plasma, immunogenicity, isoelectric point/electrostatic behavior, binding to cell surface receptors or internalization, but are still biodegradable, which provides clear advantages over synthetic polymers such as PEG.

Non-limiting examples of the PAS sequences forming random coil conformation comprise an amino acid sequence selected from the group consisting of ASPAAPA-PASPAAPAPSAPA (SEQ ID NO: 8), AAPASPAPAAP-SAPAPAAPS (SEQ ID NO: 9), APSSPSP-SAPSSPSPASPSS (SEQ ID NO: 10), APSSPSPSAPSSPSPASPS (SEQ ID NO: 11), SSP-SAPSPSSPASPSPSSPA (SEQ ID NO: 12), AASPAAPSAP-PAAASPAAPSAPPA (SEQ ID NO: 13) and ASAAAPAAASAAASAPSAAA (SEQ ID NO: 14) or any combinations thereof. Additional examples of PAS sequences are known from, e.g., US Pat. Publ. No. 2010/0292130 A1 and PCT Appl. Publ. No. WO 2008/155134 A1.

5) HAP Sequence

In certain embodiments, the heterologous moiety linked to the VWF fragment or the FVIII protein is a glycine-rich homo-amino-acid polymer (HAP). The HAP sequence can comprise a repetitive sequence of glycine, which has at least 50 amino acids, at least 100 amino acids, 120 amino acids, 140 amino acids, 160 amino acids, 180 amino acids, 200 amino acids, 250 amino acids, 300 amino acids, 350 amino acids, 400 amino acids, 450 amino acids, or 500 amino acids in length. In one embodiment, the HAP sequence is capable of extending half-life of a moiety fused to or linked to the HAP sequence. Non-limiting examples of the HAP sequence includes, but are not limited to (Gly)$_n$, (Gly$_4$Ser)$_n$ or S(Gly$_4$Ser)$_n$, wherein n is 1, 2, 3, 4, 5, 6, 7, 8, 9, 10, 11, 12, 13, 14, 15, 16, 17, 18, 19, or 20. In one embodiment, n is 20, 21, 22, 23, 24, 25, 26, 26, 28, 29, 30, 31, 32, 33, 34, 35, 36, 37, 38, 39, or 40. In another embodiment, n is 50, 60, 70, 80, 90, 100, 110, 120, 130, 140, 150, 160, 170, 180, 190, or 200. See, e.g., Schlapschy M et al., Protein Eng. Design Selection, 20: 273-284 (2007).

6) Transferrin or Fragment Thereof

In certain embodiments, the heterologous moiety linked to the VWF fragment or the FVIII protein is transferrin or a fragment thereof. Any transferrin may be used to make the chimeric proteins of the invention. As an example, wild-type human Tf (Tf) is a 679 amino acid protein, of approximately 75 KDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and S95936 (www.ncbi.nlm.nih.gov/), all of which are herein incorporated by reference in their entirety. Transferrin comprises two domains, N domain and C domain. N domain comprises two subdomains, N1 domain and N2 domain, and C domain comprises two subdomains, C1 domain and C2 domain.

In one embodiment, the transferrin portion of the chimeric protein includes a transferrin splice variant. In one example, a transferrin splice variant can be a splice variant of human transferrin, e.g., Genbank Accession AAA61140. In another embodiment, the transferrin portion of the chimeric protein includes one or more domains of the transferrin sequence, e.g., N domain, C domain, N1 domain, N2 domain, C1 domain, C2 domain or any combinations thereof.

7) Polymer, e.g., Polyethylene Glycol (PEG)

In other embodiments, the heterologous moiety attached to the VWF fragment or the protein having clotting activity, e.g. FVIII activity, is a soluble polymer known in the art, including, but not limited to, polyethylene glycol, ethylene glycol/propylene glycol copolymers, carboxymethylcellulose, dextran, or polyvinyl alcohol. The heterologous moiety such as soluble polymer can be attached to any positions within the VWF fragment or the FVIII protein or the N- or C-terminus. In still other embodiments, a chimeric protein of the invention comprises a FVIII protein and PEG, wherein PEG shields or protects the VWF binding site on the FVIII protein, thereby inhibiting or preventing interaction of the FVIII protein with endogenous VWF.

In certain embodiments, the chimeric protein comprises the VWF fragment described herein and PEG, wherein the VWF fragment is linked to PEG. In another embodiment, the chimeric protein comprises the VWF fragment and a FVIII protein, which are bound to each other, wherein the VWF fragment is linked to PEG, the FVIII protein is linked to PEG, or both the VWF fragment and the FVIII protein are linked to PEG. In other embodiments, the chimeric protein comprising the VWF fragment linked to PEG is further linked to a heterologous moiety selected from the group consisting of an immunoglobulin constant region or a portion thereof (e.g., an Fc region), a PAS sequence, HES, and albumin, fragment, or variant thereof. In still other embodiments, the chimeric protein comprises the VWF fragment and a FVIII protein, which are bound to each other, wherein the FVIII protein is further linked to a heterologous moiety selected from the group consisting of an immunoglobulin constant region or a portion thereof (e.g., an Fc region), a PAS sequence, HES, and albumin, fragment, or variant thereof. In yet other embodiments, the chimeric protein comprises the VWF fragment linked to PEG and a FVIII protein linked to PEG, which are bound to each other, wherein the VWF fragment activity is further linked to a first heterologous moiety selected from the group consisting of an immunoglobulin constant region or a portion thereof (e.g., an Fc region), a PAS sequence, HES, and albumin, fragment, or variant thereof and wherein the FVIII protein activity is further linked to a second heterologous moiety selected from the group consisting of an immunoglobulin constant region or a portion thereof (e.g., an Fc region), a PAS sequence, HES, and albumin, fragment, or variant thereof.

Also provided by the invention are chemically modified derivatives of the chimeric protein of the invention which may provide additional advantages such as increased solubility, stability and circulating time of the polypeptide, or decreased immunogenicity (see U.S. Pat. No. 4,179,337). The chemical moieties for modification can be selected from the group consisting of water soluble polymers including, but not limited to, polyethylene glycol, ethylene glycol/propylene glycol copolymers, carboxymethylcellulose, dextran, and polyvinyl alcohol. The chimeric protein may be modified at random positions within the molecule or at the N- or C-terminus, or at predetermined positions within the molecule and may include one, two, three or more attached chemical moieties.

The polymer can be of any molecular weight, and can be branched or unbranched. For polyethylene glycol, in one embodiment, the molecular weight is between about 1 kDa and about 100 kDa for ease in handling and manufacturing. Other sizes may be used, depending on the desired profile (e.g., the duration of sustained release desired, the effects, if any on biological activity, the ease in handling, the degree or lack of antigenicity and other known effects of the polyethylene glycol to a protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80,000, 85,000, 90,000, 95,000, or 100,000 kDa.

In some embodiments, the polyethylene glycol may have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), each of which is incorporated herein by reference in its entirety.

The number of polyethylene glycol moieties attached to each chimeric protein, the VWF fragment, or the FVIII protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., *Crit. Rev. Thera. Drug Carrier Sys.* 9:249-304 (1992).

In some embodiments, the FVIII protein may be PEGylated. PEGylated Factor VIII can refer to a conjugate formed between Factor VIII and at least one polyethylene glycol (PEG) molecule.

In other embodiments, a FVIII protein used in the invention is conjugated to one or more polymers. The polymer can be water-soluble and covalently or non-covalently attached to Factor VIII or other moieties conjugated to Factor VIII. Non-limiting examples of the polymer can be poly(alkylene oxide), poly(vinyl pyrrolidone), poly(vinyl alcohol), polyoxazoline, or poly(acryloylmorpholine). Additional types of polymer-conjugated FVIII are disclosed in U.S. Pat. No. 7,199,223.

8) Hydroxyethyl Starch (HES)

In certain embodiments, the heterologous moiety linked to the VWF fragment or the FVIII protein is a polymer, e.g., hydroxyethyl starch (HES) or a derivative thereof. In one embodiment, a chimeric protein comprises a VWF fragment described herein and HES, wherein the VWF fragment is linked to HES. In other embodiments, a chimeric protein of the invention comprises a FVIII protein fused to hydroxyethyl starch (HES), wherein the hydroxyethyl starch or a derivative thereof shields or protects the VWF binding site on the FVIII protein from endogenous VWF, thereby inhibiting or preventing interaction of the FVIII protein with endogenous VWF.

Hydroxyethyl starch (HES) is a derivative of naturally occurring amylopectin and is degraded by alpha-amylase in the body. HES is a substituted derivative of the carbohydrate polymer amylopectin, which is present in corn starch at a concentration of up to 95% by weight. HES exhibits advantageous biological properties and is used as a blood volume replacement agent and in hemodilution therapy in the clinics (Sommermeyer et al., *Krankenhauspharmazie,* 8(8), 271-278 (1987); and Weidler et al., *Arzneim.-Forschung/Drug Res.,* 41, 494-498 (1991)).

Amylopectin contains glucose moieties, wherein in the main chain alpha-1,4-glycosidic bonds are present and at the branching sites alpha-1,6-glycosidic bonds are found. The physical-chemical properties of this molecule are mainly determined by the type of glycosidic bonds. Due to the nicked alpha-1,4-glycosidic bond, helical structures with about six glucose-monomers per turn are produced. The physico-chemical as well as the biochemical properties of the polymer can be modified via substitution. The introduction of a hydroxyethyl group can be achieved via alkaline hydroxyethylation. By adapting the reaction conditions it is possible to exploit the different reactivity of the respective hydroxy group in the unsubstituted glucose monomer with respect to a hydroxyethylation. Owing to this fact, the skilled person is able to influence the substitution pattern to a limited extent.

HES is mainly characterized by the molecular weight distribution and the degree of substitution. The degree of substitution, denoted as DS, relates to the molar substitution, is known to the skilled people. See Sommermeyer et al., *Krankenhauspharmazie,* 8(8), 271-278 (1987), as cited above, in particular p. 273.

In one embodiment, hydroxyethyl starch has a mean molecular weight (weight mean) of from 1 to 300 kD, from 2 to 200 kD, from 3 to 100 kD, or from 4 to 70 kD. hydroxyethyl starch can further exhibit a molar degree of substitution of from 0.1 to 3, preferably 0.1 to 2, more preferred, 0.1 to 0.9, preferably 0.1 to 0.8, and a ratio between C2:C6 substitution in the range of from 2 to 20 with respect to the hydroxyethyl groups. A non-limiting example of HES having a mean molecular weight of about 130 kD is a HES with a degree of substitution of 0.2 to 0.8 such as 0.2, 0.3, 0.4, 0.5, 0.6, 0.7, or 0.8, preferably of 0.4 to 0.7 such as 0.4, 0.5, 0.6, or 0.7. In a specific embodiment, HES with a mean molecular weight of about 130 kD is VOLUVEN® from Fresenius. VOLUVEN® is an artificial colloid, employed, e.g., for volume replacement used in the therapeutic indication for therapy and prophylaxis of hypovolaemia. The characteristics of VOLUVEN® are a mean molecular weight of 130,000+/−20,000 D, a molar substitution of 0.4 and a C2:C6 ratio of about 9:1. In other embodiments, ranges of the mean molecular weight of hydroxyethyl starch are, e.g., 4 to 70 kD or 10 to 70 kD or 12 to 70 kD or 18 to 70 kD or 50 to 70 kD or 4 to 50 kD or 10 to 50 kD or 12 to 50 kD or 18 to 50 kD or 4 to 18 kD or 10 to 18 kD or 12 to 18 kD or 4 to 12 kD or 10 to 12 kD or 4 to 10 kD. In still other embodiments, the mean molecular weight of hydroxyethyl starch employed is in the range of from more than 4 kD and below 70 kD, such as about 10 kD, or in the range of from 9 to 10 kD or from 10 to 11 kD or from 9 to 11 kD, or about 12 kD, or in the range of from 11 to 12 kD) or from 12 to 13 kD or from 11 to 13 kD, or about 18 kD, or in the range of from 17 to 18 kD or from 18 to 19 kD or from 17 to 19 kD, or about 30 kD, or in the range of from 29 to 30, or from 30 to 31 kD, or about 50 kD, or in the range of from 49 to 50 kD or from 50 to 51 kD or from 49 to 51 kD.

In certain embodiments, the heterologous moiety can be mixtures of hydroxyethyl starches having different mean molecular weights and/or different degrees of substitution and/or different ratios of C2: C6 substitution. Therefore, mixtures of hydroxyethyl starches may be employed having different mean molecular weights and different degrees of substitution and different ratios of C2: C6 substitution, or having different mean molecular weights and different degrees of substitution and the same or about the same ratio of C2:C6 substitution, or having different mean molecular weights and the same or about the same degree of substitution and different ratios of C2:C6 substitution, or having the same or about the same mean molecular weight and different degrees of substitution and different ratios of C2:C6 substitution, or having different mean molecular weights and the same or about the same degree of substitution and the same or about the same ratio of C2:C6 substitution, or having the same or about the same mean molecular weights and different degrees of substitution and the same or about the same ratio of C2:C6 substitution, or having the same or about the same mean molecular weight and the same or about the same degree of substitution and different ratios of C2: C6 substitution, or having about the same mean molecular weight and about the same degree of substitution and about the same ratio of C2:C6 substitution.

9) Polysialic Acids (PSA)

In certain embodiments, the non-polypeptide heterologous moiety linked to the VWF fragment or the FVIII protein is a polymer, e.g., polysialic acids (PSAs) or a derivative thereof. Polysialic acids (PSAs) are naturally occurring unbranched polymers of sialic acid produced by certain bacterial strains and in mammals in certain cells Roth J., et al. (1993) in *Polysialic Acid: From Microbes to Man,* eds Roth J., Rutishauser U., Troy F. A. (Birkhäuser Verlag, Basel, Switzerland), pp 335-348. They can be produced in various degrees of polymerization from n=about 80 or more sialic acid residues down to n=2 by limited acid hydrolysis or by digestion with neuraminidases, or by fractionation of the natural, bacterially derived forms of the polymer. The composition of different polysialic acids also varies such that there are homopolymeric forms i.e. the alpha-2,8-linked polysialic acid comprising the capsular polysaccharide of *E. coli* strain K1 and the group-B meningococci, which is also found on the embryonic form of the neuronal cell adhesion molecule (N-CAM). Heteropolymeric forms also exist—such as the alternating alpha-2,8 alpha-2,9 polysialic acid of *E. coli* strain K92 and group C polysaccharides of *N. meningitidis*. Sialic acid may also be found in alternating copolymers with monomers other than sialic acid such as group W135 or group Y of *N. meningitidis*. Polysialic acids have important biological functions including the evasion of the immune and complement systems by pathogenic bacteria and the regulation of glial adhesiveness of immature neurons during foetal development (wherein the polymer has an anti-adhesive function) Cho and Troy, *P.N.A.S., USA*, 91 11427-11431, although there are no known receptors for polysialic acids in mammals. The alpha-2,8-linked polysialic acid of *E. coli* strain K1 is also known as 'colominic acid' and is used (in various lengths) to exemplify the present invention. Various methods of attaching or conjugating polysialic acids to a polypeptide have been described (for example, see U.S. Pat. No. 5,846,951; WO-A-0187922, and US 2007/0191597 A1, which are incorporated herein by reference in their entireties.

C) FVIII Protein

"A FVIII protein" as used herein means a functional FVIII polypeptide in its normal role in coagulation, unless otherwise specified. The term a FVIII protein includes a functional fragment, variant, analog, or derivative thereof that retains the function of full-length wild-type Factor VIII in the coagulation pathway. "A FVIII protein" is used interchangeably with FVIII polypeptide (or protein) or FVIII. Examples of the FVIII functions include, but not limited to, an ability to activate coagulation, an ability to act as a cofactor for factor IX, or an ability to form a tenase complex with factor IX in the presence of Ca2+ and phospholipids, which then converts Factor X to the activated form Xa. The FVIII protein can be the human, porcine, canine, rat, or murine FVIII protein. In addition, comparisons between FVIII from humans and other species have identified conserved residues that are likely to be required for function (Cameron et al., *Thromb. Haemost.* 79:317-22 (1998); U.S. Pat. No. 6,251,632).

A number of tests are available to assess the function of the coagulation system: activated partial thromboplastin time (aPTT) test, chromogenic assay, ROTEM assay, prothrombin time (PT) test (also used to determine INR), fibrinogen testing (often by the Clauss method), platelet count, platelet function testing (often by PFA-100), TCT, bleeding time, mixing test (whether an abnormality corrects if the patient's plasma is mixed with normal plasma), coagulation factor assays, antiphosholipid antibodies, D-dimer, genetic tests (e.g. factor V Leiden, prothrombin mutation G20210A), dilute Russell's viper venom time (dRVVT), miscellaneous platelet function tests, thromboelastography (TEG or Sonoclot), thromboelastometry (TEM®, e.g, ROTEM®), or euglobulin lysis time (ELT).

The aPTT test is a performance indicator measuring the efficacy of both the "intrinsic" (also referred to the contact activation pathway) and the common coagulation pathways. This test is commonly used to measure clotting activity of commercially available recombinant clotting factors, e.g., FVIII or FIX. It is used in conjunction with prothrombin time (PT), which measures the extrinsic pathway.

ROTEM analysis provides information on the whole kinetics of haemostasis: clotting time, clot formation, clot stability and lysis. The different parameters in thromboelastometry are dependent on the activity of the plasmatic coagulation system, platelet function, fibrinolysis, or many factors which influence these interactions. This assay can provide a complete view of secondary haemostasis.

The FVIII polypeptide and polynucleotide sequences are known, as are many functional fragments, mutants and modified versions. Examples of human FVIII sequences (full-length) are shown as subsequences in SEQ ID NO: 16 or 18.

TABLE 2

Full-length FVIII (FVIII signal peptide underlined;
FVIII heavy chain is double underlined;
B domain is italicized; and FVIII light chain is in plain text)

Signal Peptide: (SEQ ID NO: 15)
MQIELSTCFFLCLLRFCFS

Mature Factor VIII (SEQ ID NO: 16)*
ATRRYYLGAVELSWDYMQSDLGELPVDARFPPRVPKSFPFNTSVVYKKTLFVEFTDHLFNIAKPRPPWMGLL
GPTIQAEVYDTVVITLKNMASHPVSLHAVGVSYWKASEGAEYDDQTSQREKEDDKVFPGGSHTYVWQVLKEN
GPMASDPLCLTYSYLSHVDLVKDLNSGLIGALLVCREGSLAKEKTQTLHKFILLFAVFDEGKSWHSETKNSL
MQDRDAASARAWPKMHTVNGYVNRSLPGLIGCHRKSVYWHVIGMGTTPEVHSIFLEGHTFLVRNHRQASLEI
SPITFLTAQTLLMDLGQFLLFCHISSHQHDGMEAYVKDSCPEEDPQLRMKNNEEAEDYDDDLTDSEMDVVRF
DDDNSPSFIQIRSVAKKHPKTWVHYIAAEEEDWDYAPLVLAPDDRSYKSQYLNNGPQRIGRKYKKVRFMAYT
DETFKTREAIQHESGILGPLLYGEVGDTLLIIFKNQASRPYNIYPHGITDVRPLYSRRLPKGVKHLKDFPIL
PGEIFKYKWTVTVEDGPTKSDPRCLTRYYSSFVNMERDLASGLIGPLLICYKESVDQRGNQIMSDKRNVILF
SVFDENRSWYLTENIQRFLPNPAGVQLEDPEFQASNIMHSINGYVFDSLQLSVCLHEVAYWYILSIGAQTDF
LSVFFSGYTFKHKMVYEDTLTLFPFSGETVFMSMENPGLWILGCHNSDFRNRGMTALLKVSSCDKNTGDYYE
DSYEDISAYLLSKNNAIEPR*SFSQNSRHPSTRQKQFNATTIPENDIEKTDPWFAHRTPMPKIQNVSSSDLLM*
*LLRQSPTPHGLSLSDLQEAKYETFSDDPSPGAIDSNNSLSEMTHFRPQLHHSGDMVFTPESGLQLRLNEKLG*
*TTAATELKKLDFKVSSTSNNLISTIPSDNLAAGTDNTSSLGPPSMPVHYDSQLDTTLFGKKSSPLTESGGPL*
*SLSEENNDSKLLESGLMNSQESSWGKNVSSTESGRLFKGKRAHGPALLTKDNALFKVSISLLKTNKTSNNSA*
*TNRKTHIDGPSLLIENSPSVWQNILESDTEFKKVTPLIHDRMLMDKNATALRLNHMSNKTTSSKNMEMVQQK*
*KEGPIPPDAQNPDMSFFKMLFLPESARWIQRTHGKNSLNSGQGPSPKQLVSLGPEKSVEGQNFLSEKNKVVV*
*GKGEFTKDVGLKEMVFPSSRNLFLTNLDNLHENNTHNQEKKIQEEIEKKETLIQENVVLPQIHTVTGTKNFM*
*KNLFLLSTRQNVEGSYDGAYAPVLQDFRSLNDSTNRTKKHTAHFSKKGEEENLEGLGNQTKQIVEKYACTTR*
*ISPNTSQQNFVTQRSKRALKQFRLPLEETELEKRIIVDDTSTQWSKNMKHLTPSTLTQIDYNEKEKGAITQS*
*PLSDCLTRSHSIPQANRSPLPIAKVSSFPSIRPIYLTRVLFQDNSSHLPAASYRKKDSGVQESSHFLQGAKK*
*NNLSLAILTLEMTGDQREVGSLGTSATNSVTYKKVENTVLPKPDLPKTSGKVELLPKVHIYQKDLFPTETSN*
*GSPGHLDLVEGSLLQGTEGAIKWNEANRPGKVPFLRVATESSAKTPSKLLDPLAWDNHYGTQIPKEEWKSQE*

TABLE 2-continued

Full-length FVIII (FVIII signal peptide underlined;
FVIII heavy chain is double underlined;
B domain is italicized; and FVIII light chain is in plain text)

*KSPEKTAFKKKDTILSLNACESNHAIAAINEGQNKPEIEVTWAKQGRTERLCSQNPPVLKRHQR*EITRTTLQ
SDQEEIDYDDTISVEMKKEDFDIYDEDENQSPRSFQKKTRHYFIAAVERLWDYGMSSSPHVLRNRAQSGSVP
QFKKVVFQEFTDGSFTQPLYRGELNEHLGLLGPYIRAEVEDNIMVTFRNQASRPYSFYSSLISYEEDQRQGA
EPRKNFVKPNETKTYFWKVQHHMAPTKDEFDCKAWAYFSDVDLEKDVHSGLIGPLLVCHTNTLNPAHGRQVT
VQEFALFFTIFDETKSWYFTENMERNCRAPCNIQMEDPTFKENYRFHAINGYIMDTLPGLVMAQDQRIRWYL
LSMGSNENIHSIHFSGHVFTVRKKEEYKMALYNLYPGVFETVEMLPSKAGIWRVECLIGEHLHAGMSTLFLV
YSNKCQTPLGMASGHIRDFQITASGQYGQWAPKLARLHYSGSINAWSTKEPFSWIKVDLLAPMIIHGIKTQG
ARQKFSSLYISQFIIMYSLDGKKWQTYRGNSTGTLMVFFGNVDSSGIKHNIFNPPIIARYIRLHPTHYSIRS
TLRMELMGCDLNSCSMPLGMESKAISDAQITASSYFTNMFATWSPSKARLHLQGRSNAWRPQVNNPKEWLQV
DFQKTMKVTGVTTQGVKSLLTSMYVKEFLISSSQDGHQWTLFFQNGKVKVFQGNQDSFTPVVNSLDPPLLTR
YLRIHPQSWVHQIALRMEVLGCEAQDLY

TABLE 3

| Nucleotide Sequence Encoding Full-Length FVIII (SEQ ID NO: 17)* |
|---|
| 661 <u>ATG CAAATAGAGC TCTCCACCTG</u> |
| 721 <u>CTTCTTTCTG TGCCTTTTGC GATTCTGCTT TAGT</u>GCCACC AGAAGATACT ACCTGGGTGC |
| 781 AGTGGAACTG TCATGGGACT ATATGCAAAG TGATCTCGGT GAGCTGCCTG TGGACGCAAG |
| 841 ATTTCCTCCT AGAGTGCCAA ATCTTTTCC ATTCAACACC TCAGTCGTGT ACAAAAAGAC |
| 901 TCTGTTTGTA GAATTCACGG ATCACCTTTT CAACATCGCT AAGCCAAGGC CACCCTGGAT |
| 961 GGGTCTGCTA GGTCCTACCA TCCAGGCTGA GGTTTATGAT ACAGTGGTCA TTACACTTAA |
| 1021 GAACATGGCT TCCCATCCTG TCAGTCTTCA TGCTGTTGGT GTATCCTACT GGAAAGCTTC |
| 1081 TGAGGGAGCT GAATATGATG ATCAGACCAG TCAAAGGGAG AAAGAAGATG ATAAAGTCTT |
| 1141 CCCTGGTGGA AGCCATACAT ATGTCTGGCA GGTCCTGAAA GAGAATGGTC CAATGGCCTC |
| 1201 TGACCCACTG TGCCTTACCT ACTCATATCT TTCTCATGTG GACCTGGTAA AAGACTTGAA |
| 1261 TTCAGGCCTC ATTGGAGCCC TACTAGTATG TAGAGAAGGG AGTCTGGCCA AGGAAAAGAC |
| 1321 ACAGACCTTG CACAAATTTA TACTACTTTT TGCTGTATTT GATGAAGGGA AAAGTTGGCA |
| 1381 CTCAGAAACA AAGAACTCCT TGATGCAGGA TAGGGATGCT GCATCTGCTC GGGCCTGGCC |
| 1441 TAAAATGCAC ACAGTCAATG GTTATGTAAA CAGGTCTCTG CCAGGTCTGA TTGGATGCCA |
| 1501 CAGGAAATCA GTCTATTGGC ATGTGATTGG AATGGGCACC ACTCCTGAAG TGCACTCAAT |
| 1561 ATTCCTCGAA GGTCACACAT TTCTTGTGAG GAACCATCGC CAGGCGTCCT TGGAAATCTC |
| 1621 GCCAATAACT TTCCTTACTG CTCAAACACT CTTGATGGAC CTTGGACAGT TTCTACTGTT |
| 1681 TTGTCATATC TCTTCCCACC AACATGATGG CATGGAAGCT TATGTCAAAG TAGACAGCTG |
| 1741 TCCAGAGGAA CCCCAACTAC GAATGAAAAA TAATGAAGAA GCGGAAGACT ATGATGATGA |
| 1801 TCTTACTGAT TCTGAAATGG ATGTGGTCAG GTTTGATGAT GACAACTCTC CTTCCTTTAT |
| 1861 CCAAATTCGC TCAGTTGCCA AGAAGCATCC TAAAACTTGG GTACATTACA TTGCTGCTGA |
| 1921 AGAGGAGGAC TGGGACTATG CTCCCTTAGT CCTCGCCCCC GATGACAGAA GTTATAAAAG |
| 1981 TCAATATTTG AACAATGGCC CTCAGCGGAT TGGTAGGAAG TACAAAAAAG TCCGATTTAT |
| 2041 GGCATACACA GATGAAACCT TTAAGACTCG TGAAGCTATT CAGCATGAAT CAGGAATCTT |
| 2101 GGGACCTTTA CTTTATGGGG AAGTTGGAGA CACACTGTTG ATTATATTTA AGAATCAAGC |
| 2161 AAGCAGACCA TATAACATCT ACCCTCACGG AATCACTGAT GTCCGTCCTT TGTATTCAAG |
| 2221 GAGATTACCA AAAGGTGTAA AACATTTGAA GGATTTTCCA ATTCTGCCAG GAGAAATATT |
| 2281 CAAATATAAA TGGACAGTGA CTGTAGAAGA TGGGCCAACT AAATCAGATC CTCGGTGCCT |
| 2341 GACCCGCTAT TACTCTAGTT TCGTTAATAT GGAGAGAGAT CTAGCTTCAG GACTCATTGG |

TABLE 3-continued

Nucleotide Sequence Encoding Full-Length FVIII (SEQ ID NO: 17)*

```
2401  CCCTCTCCTC ATCTGCTACA AAGAATCTGT AGATCAAAGA GGAAACCAGA TAATGTCAGA
2461  CAAGAGGAAT GTCATCCTGT TTTCTGTATT TGATGAGAAC CGAAGCTGGT ACCTCACAGA
2521  GAATATACAA CGCTTTCTCC CCAATCCAGC TGGAGTGCAG CTTGAGGATC CAGAGTTCCA
2581  AGCCTCCAAC ATCATGCACA GCATCAATGG CTATGTTTTT GATAGTTTGC AGTTGTCAGT
2641  TTGTTTGCAT GAGGTGGCAT ACTGGTACAT TCTAAGCATT GGAGCACAGA CTGACTTCCT
2701  TTCTGTCTTC TTCTCTGGAT ATACCTTCAA ACACAAAATG GTCTATGAAG ACACACTCAC
2761  CCTATTCCCA TTCTCAGGAG AAACTGTCTT CATGTCGATG GAAAACCCAG GTCTATGGAT
2821  TCTGGGGTGC CACAACTCAG ACTTTCGGAA CAGAGGCATG ACCGCCTTAC TGAAGGTTTC
2881  TAGTTGTGAC AAGAACACTG GTGATTATTA CGAGGACAGT TATGAAGATA TTTCAGCATA
2941  CTTGCTGAGT AAAAACAATG CCATTGAACC AAGAAGCTTC TCCCAGAATT CAAGACACCC
3001  TAGCACTAGG CAAAAGCAAT TTAATGCCAC CACAATTCCA GAAAATGACA TAGAGAAGAC
3061  TGACCCTTGG TTTGCACACA GAACACCTAT GCCTAAAATA CAAAATGTCT CCTCTAGTGA
3121  TTTGTTGATG CTCTTGCGAC AGAGTCCTAC TCCACATGGG CTATCCTTAT CTGATCTCCA
3181  AGAAGCCAAA TATGAGACTT TTTCTGATGA TCCATCACCT GGAGCAATAG ACAGTAATAA
3241  CAGCCTGTCT GAAATGACAC ACTTCAGGCC ACAGCTCCAT ACAGTGGGG ACATGGTATT
3301  TACCCCTGAG TCAGGCCTCC AATTAAGATT AAATGAGAAA CTGGGGACAA CTGCAGCAAC
3361  AGAGTTGAAG AAACTTGATT TCAAAGTTTC TAGTACATCA AATAATCTGA TTTCAACAAT
3421  TCCATCAGAC AATTTGGCAG CAGGTACTGA TAATACAAGT TCCTTAGGAC CCCCAAGTAT
3481  GCCAGTTCAT TATGATAGTC AATTAGATAC CACTCTATTT GGCAAAAAGT CATCTCCCCT
3541  TACTGAGTCT GGTGGACCTC TGAGCTTGAG TGAAGAAAAT AATGATTCAA AGTTGTTAGA
3601  ATCAGGTTTA ATGAATAGCC AAGAAAGTTC ATGGGGAAAA ATGTATCGT CAACAGAGAG
3661  TGGTAGGTTA TTTAAAGGGA AAAGAGCTCA TGGACCTGCT TTGTTGACTA AGATAATGC
3721  CTTATTCAAA GTTAGCATCT CTTTGTTAAA GACAAACAAA ACTTCCAATA ATTCAGCAAC
3781  TAATAGAAAG ACTCACATTG ATGGCCCATC ATTATTAATT GAGAATAGTC CATCAGTCTG
3841  GCAAAATATA TTAGAAAGTG ACACTGAGTT TAAAAAAGTG ACACCTTTGA TTCATGACAG
3901  AATGCTTATG GACAAAAATG CTACAGCTTT GAGGCTAAAT CATATGTCAA ATAAAACTAC
3961  TTCATCAAAA AACATGGAAA TGGTCCAACA GAAAAAAGAG GGCCCCATTC CACCAGATGC
4021  ACAAAATCCA GATATGTCGT TCTTTAAGAT GCTATTCTTG CCAGAATCAG CAAGGTGGAT
4081  ACAAAGGACT CATGGAAAGA ACTCTCTGAA CTCTGGGCAA GGCCCCAGTC CAAAGCAATT
4141  AGTATCCTTA GGACCAGAAA AAGTTGGAGA GGTCAGAAT TTCTTGTCTG AGAAAACAA
4201  AGTGGTAGTA GGAAAGGGTG AATTTACAAA GGACGTAGGA CTCAAAGAGA TGGTTTTTCC
4261  AAGCAGCAGA AACCTATTTC TTACTAACTT GGATAATTTA CATGAAAATA ATACACACAA
4321  TCAAGAAAAA AAAATTCAGG AAGAAATAGA AAAGAAGGAA ACATTAATCC AAGAGAATGT
4381  AGTTTTGCCT CAGATACATA CAGTGACTGG CACTAAGAAT TTCATGAAGA ACCTTTTCTT
4441  ACTGAGCACT AGGCAAAATG TAGAAGGTTC ATATGACGGG GCATATGCTC CAGTACTTCA
4501  AGATTTTAGG TCATTAAATG ATTCAACAAA TAGAACAAAG AAACACACAG CTCATTTCTC
4561  AAAAAAAGGG GAGGAAGAAA ACTTGGAAGG CTTGGGAAAT CAAACCAAGC AAATTGTAGA
4621  GAAATATGCA TGCACCACAA GGATATCTCC TAATACAAGC CAGCAGAATT TTGTCACGCA
4681  ACGTAGTAAG AGAGCTTTGA AACAATTCAG ACTCCCACTA GAAGAAACAG AACTTGAAAA
```

TABLE 3-continued

| Nucleotide Sequence Encoding Full-Length FVIII (SEQ ID NO: 17)* |
|---|

```
4741  AAGGATAATT GTGGATGACA CCTCAACCCA GTGGTCCAAA AACATGAAAC ATTTGACCCC
4801  GAGCACCCTC ACACAGATAG ACTACAATGA GAAGGAGAAA GGGGCCATTA CTCAGTCTCC
4861  CTTATCAGAT TGCCTTACGA GGAGTCATAG CATCCCTCAA GCAAATAGAT CTCCATTACC
4921  CATTGCAAAG GTATCATCAT TTCCATCTAT TAGACCTATA TATCTGACCA GGGTCCTATT
4981  CCAAGACAAC TCTTCTCATC TTCCAGCAGC ATCTTATAGA AGAAAGATT CTGGGGTCCA
5041  AGAAAGCAGT CATTTCTTAC AAGGAGCCAA AAAAAATAAC CTTTCTTTAG CCATTCTAAC
5101  CTTGGAGATG ACTGGTGATC AAAGAGAGGT TGGCTCCCTG GGGACAAGTG CCACAAATTC
5161  AGTCACATAC AAGAAAGTTG AGAACACTGT TCTCCCGAAA CCAGACTTGC CCAAAACATC
5221  TGGCAAAGTT GAATTGCTTC CAAAAGTTCA CATTTATCAG AAGGACCTAT TCCCTACGGA
5281  AACTAGCAAT GGGTCTCCTG GCCATCTGGA TTTCAGGGAA GGGAGCCTTC TTCAGGGAAC
5341  AGAGGGAGCG ATTAAGTGGA ATGAAGCAAA CAGACCTGGA AAAGTTCCCT TTCTGAGAGT
5401  AGCAACAGAA AGCTCTGCAA AGACTCCCTC CAAGCTATTG GATCCTCTTG CTTGGGATAA
5461  CCACTATGGT ACTCAGATAC AAAAGAAGA GTGGAAATCC AAGAGAAGT CACCAGAAAA
5521  AACAGCTTTT AAGAAAAAGG ATACCATTTT GTCCCTGAAC GCTTGTGAAA GCAATCATGC
5581  AATAGCAGCA ATAAATGAGG GACAAAATAA GCCCGAAATA GAAGTCACCT GGGCAAAGCA
5641  AGGTAGGACT GAAAGGCTGT GCTCTCAAAA CCCACCAGTC TTGAAACGCC ATCAACGGGA
5701  AATAACTCGT ACTACTCTTC AGTCAGATCA AGAGGAAATT GACTATGATG ATACCATATC
5761  AGTTGAAATG AAGAAGGAAG ATTTTGACAT TTATGATGAG GATGAAAATC AGAGCCCCCG
5821  CAGCTTTCAA AAGAAAACAC GACACTATTT TATTGCTGCA GTGGAGAGGC TCTGGGATTA
5881  TGGGATGAGT AGCTCCCCAC ATGTTCTAAG AAACAGGGCT CAGAGTGGCA GTGTCCCTCA
5941  GTTCAAGAAA GTTGTTTTCC AGGAATTTAC TGATGGCTCC TTTACTCAGC CCTTATACCG
6001  TGGAGAACTA AATGAACATT TGGGACTCCT GGGGCCATAT ATAAGAGCAG AAGTTGAAGA
6061  TAATATCATG GTAACTTTCA GAAATCAGGC CTCTCGTCCC TATTCCTTCT ATTCTAGCCT
6121  TATTTCTTAT GAGGAAGATC AGAGGCAAGG AGCAGAACCT AGAAAAAACT TTCTCCAGCC
6181  TAATGAAACC AAAACTTACT TTTGGAAAGT GCAACATCAT ATGGCACCCA CTAAAGATGA
6241  GTTTGACTGC AAAGCCTGGG CTTATTTCTC TGATGTTGAC CTGGAAAAAG ATGTGCACTC
6301  AGGCCTGATT GGACCCCTTC TGGTCTGCCA CACTAACACA CTGAACCCTG CTCATGGGAG
6361  ACAAGTGACA GTACAGGAAT TTGCTCTGTT TTTCACCATC TTTGATGAGA CCAAAAGCTG
6421  GTACTTCACT GAAAATATGG AAAGAAACTG CAGGGCTCCC TGCAATATCC AGATGGAAGA
6481  TCCCACTTTT AAAGAGAATT ATCGCTTCCA TGCAATCAAT GGCTACATAA TGGATACACT
6541  ACCTGGCTTA GTAATGGCTC AGGATCAAAG GATTCGATGG TATCTGCTCA GCATGGGCAG
6601  CAATGAAAAC ATCCATTCTA TTCATTTCAG TGGACATGTG TTCACTGTAC GAAAAAAAGA
6661  GGAGTATAAA ATGGCACTGT ACAATCTCTA TCCAGGTGTT TTTGAGACAG TGGAAATGTT
6721  ACCATCCAAA GCTGGAATTT GGCGGGTGGA ATGCCTTATT GGCGAGCATC TACATGCTGG
6781  GATGAGCACA CTTTTTCTGG TGTACAGCAA TAAGTGTCAG ACTCCCCTGG GAATGGCTTC
6841  TGGACACATT AGAGATTTTC AGATTACAGC TTCAGGACAA TATGGACAGT GGGCCCCAAA
6901  GCTGGCCAGA CTTCATTATT CCGGATCAAT CAATGCCTGG AGCACCAAGG AGCCCTTTTC
6961  TTGGATCAAG GTGGATCTGT TGGCACCAAT GATTATTCAC GGCATCAAGA CCCAGGGTGC
7021  CCGTCAGAAG TTCTCCAGCC TCTACATCTC TCAGTTTATC ATCATGTATA GTCTTGATGG
```

TABLE 3-continued

Nucleotide Sequence Encoding Full-Length FVIII (SEQ ID NO: 17)*

```
7081   GAAGAAGTGG CAGACTTATC GAGGAAATTC CACTGGAACC TTAATGGTCT TCTTTGGCAA

7141   TGTGGATTCA TCTGGGATTA AACACAATAT TTTTAACCCT CCAATTATTG CTCGATACAT

7201   CCGTTTGCAC CCAACTCATT ATAGCATTCG CAGCACTCTT CGCATGGAGT TGATGGGCTG

7261   TGATTTAAAT AGTTGCAGCA TGCCATTGGG AATGGAGAGT AAAGCAATAT CAGATGCACA

7321   GATTACTGCT TCATCCTACT TTACCAATAT GTTTGCCACC TGGTCTCCTT CAAAAGCTCG

7381   ACTTCACCTC CAAGGGAGGA GTAATGCCTG GAGACCTCAG GTGAATAATC CAAAAGAGTG

7441   GCTGCAAGTG GACTTCCAGA AGACAATGAA AGTCACAGGA GTAACTACTC AGGGAGTAAA

7501   ATCTCTGCTT ACCAGCATGT ATGTGAAGGA GTTCCTCATC TCCAGCAGTC AAGATGGCCA

7561   TCAGTGGACT CTCTTTTTTC AGAATGGCAA AGTAAAGGTT TTTCAGGGAA ATCAAGACTC

7621   CTTCACACCT GTGGTGAACT CTCTAGACCC ACCGTTACTG ACTCGCTACC TTCGAATTCA

7681   CCCCCAGAGT TGGGTGCACC AGATTGCCCT GAGGATGGAG GTTCTGGGCT GCGAGGCACA

7741   GGACCTCTAC
```

*The underlined nucleic acids encode a signal peptide.

FVIII polypeptides include full-length FVIII, full-length FVIII minus Met at the N-terminus, mature FVIII (minus the signal sequence), mature FVIII with an additional Met at the N-terminus, and/or FVIII with a full or partial deletion of the B domain. In certain embodiments, FVIII variants include B domain deletions, whether partial or full deletions.

The human FVIII gene was isolated and expressed in mammalian cells (Toole, J. J., et al., Nature 312:342-347 (1984); Gitschier, J., et al., Nature 312:326-330 (1984); Wood, W. I., et al., Nature 312:330-337 (1984); Vehar, G. A., et al., Nature 312:337-342 (1984); WO 87/04187; WO 88/08035; WO 88/03558; and U.S. Pat. No. 4,757,006). The FVIII amino acid sequence was deduced from cDNA as shown in U.S. Pat. No. 4,965,199. In addition, partially or fully B-domain deleted FVIII is shown in U.S. Pat. Nos. 4,994,371 and 4,868,112. In some embodiments, the human FVIII B-domain is replaced with the human Factor V B-domain as shown in U.S. Pat. No. 5,004,803. The cDNA sequence encoding human Factor VIII and amino acid sequence are shown in SEQ ID NOs: 17 and 16, respectively, of US Application Publ. No. 2005/0100990.

The porcine FVIII sequence is published in Toole, J. J., et al., Proc. Natl. Acad. Sci. USA 83:5939-5942 (1986). Further, the complete porcine cDNA sequence obtained from PCR amplification of FVIII sequences from a pig spleen cDNA library has been reported in Healey, J. F., et al., Blood 88:4209-4214 (1996). Hybrid human/porcine FVIII having substitutions of all domains, all subunits, and specific amino acid sequences were disclosed in U.S. Pat. No. 5,364,771 by Lollar and Runge, and in WO 93/20093. More recently, the nucleotide and corresponding amino acid sequences of the A1 and A2 domains of porcine FVIII and a chimeric FVIII with porcine A1 and/or A2 domains substituted for the corresponding human domains were reported in WO 94/11503. U.S. Pat. No. 5,859,204, Lollar, J. S., also discloses the porcine cDNA and deduced amino acid sequences. U.S. Pat. No. 6,458,563 discloses a B-domain-deleted porcine FVIII.

U.S. Pat. No. 5,859,204 to Lollar, J. S. reports functional mutants of FVIII having reduced antigenicity and reduced immunoreactivity. U.S. Pat. No. 6,376,463 to Lollar, J. S. also reports mutants of FVIII having reduced immunoreactivity. US Appl. Publ. No. 2005/0100990 to Saenko et al. reports functional mutations in the A2 domain of FVIII.

In one embodiment, the FVIII (or FVIII portion of a chimeric protein) may be at least 50%, 60%, 70%, 80%, 90%, 95%, 96%, 97%, 98%, 99%, or 100% identical to a FVIII amino acid sequence of amino acids 1 to 1438 of SEQ ID NO: 18 or amino acids 1 to 2332 of SEQ ID NO: 16 (without a signal sequence) or a FVIII amino acid sequence of amino acids −19 to 1438 of SEQ ID NO: 15 and SEQ ID NO: 18 or amino acids −19 to 2332 of SEQ ID NO: 15 and SEQ ID NO: 16 (with a signal sequence), wherein the FVIII has a clotting activity, e.g., activates Factor IX as a cofactor to convert Factor X to activated Factor X. The FVIII (or FVIII portion of a chimeric protein) may be identical to a FVIII amino acid sequence of amino acids 1 to 1438 of SEQ ID NO: 18 or amino acids 1 to 2332 of SEQ ID NO: 16 (without a signal sequence). The FVIII may further comprise a signal sequence.

The "B-domain" of FVIII, as used herein, is the same as the B-domain known in the art that is defined by internal amino acid sequence identity and sites of proteolytic cleavage, e.g., residues Ser741-Arg1648 of full-length human FVIII. The other human FVIII domains are defined by the following amino acid residues: A1, residues Ala1-Arg372; A2, residues Ser373-Arg740; A3, residues Ser1690-Asn2019; C1, residues Lys2020-Asn2172; C2, residues Ser2173-Tyr2332. The A3-C1-C2 sequence includes residues Ser1690-Tyr2332. The remaining sequence, residues Glu1649-Arg1689, is usually referred to as the a3 acidic region. The locations of the boundaries for all of the domains, including the B-domains, for porcine, mouse and canine FVIII are also known in the art. In one embodiment, the B domain of FVIII is deleted ("B-domain-deleted factor VIII" or "BDD FVIII"). An example of a BDD FVIII is REFACTO® (recombinant BDD FVIII), which has the same sequence as the Factor VIII portion of the sequence in Table 4. (BDD FVIII heavy chain is double underlined; B domain is italicized; and BDD FVIII light chain is in plain text).

TABLE 4

BDD FVIII (SEQ ID NO: 18)
ATRRYYLGAVELSWDYMQSDLGELPVDARFPPRVPKSFPFNTSVVYKKTLFVEFTDHLFNIAKPRPPWMGLL
GPTIQAEVYDTVVITLKNMASHPVSLHAVGVSYWKASEGAEYDDQTSQREKEDDKVFPGGSHTYVWQVLKEN
GPMASDPLCLTYSYLSHVDLVKDLNSGLIGALLVCREGSLAKEKTQTLHKFILLFAVFDEGKSWHSETKNSL
MQDRDAASARAWPKMHTVNGYVNRSLPGLIGCHRKSVYWHVIGMGTTPEVHSIFLEGHTFLVRNHRQASLEI
SPITFLTAQTLLMDLGQFLLFCHISSHQHDGMEAYVKVDSCPEEPQLRMKNNEEAEDYDDDLTDSEMDVVRF
DDDNSPSFIQIRSVAKKHPKTWVHYIAAEEEDWDYAPLVLAPDDRSYKSQYLNNGPQRIGRKYKKVRFMAYT
DETFKTREAIQHESGILGPLLYGEVGDTLLIIFKNQASRPYNIYPHGITDVRPLYSRRLPKGVKHLKDRPIL
PGEIFKYKWTVTVEDGPTKSDPRCLTRYYSSFVNMERDLASGLIGPLLICYKESVDQRGNQIMSDKRNVILF
SVFDENRSWYLTENIQRFLPNPAGVQLEDPEFQASNIMHSINGYVFDSLQLSVCLHEVAYWYILSIGAQTDF
LSVFFSGYTFKHKMVYEDTLTLFPFSGETVFMSMENPGLWILGCHNSDFRNRGMTALLKVSSCDKNTGDYYE
DSYEDISAYLLSKNNAIEPR*SFSQNPPVLKRHQ*REITRTTLQSDQEEIDYDDTISVEMKKEDFDIYDEDENQ
SPRSFQKKTRHYFIAAVERLWDYGMSSSPHVLRNRAQSGSVPQFKKVVFQEFTDGSFTQPLYRGELNEHLGL
LGPYIRAEVEDNIMVTFRNQASRPYSFYSSLISYEEDQRQGAEPRKNFVKPNETKTYFWKVQHHMAPTKDEF
DCKAWAYFSDVDLEKDVHSGLIGPLLVCHTNTLNPAHGRQVTVQEFALFFTIFDETKSWYFTENMERNCRAP
CNIQMEDPTFKENYRFHAINGYIMDTLPGLVMAQDQRIRWYLLSMGSNENIHSIHFSGHVFTVRKKEEYKMA
LYNLYPGVFETVEMLPSKAGIWRVECLIGEHLHAGMSTLFLVYSNKCQTPLGMASGHIRDFQITASGQYGQW
APKLARLHYSGSINAWSTKEPFSWIKVDLLAPMIIHGIKTQGARQKFSSLYISQFIIMYSLDGKKWQTYRGN
STGTLMVFFGNVDSSGIKHNIFNPPIIARYIRLHPTHYSIRSTLRMELMGCDLNSCSMPLGMESKAISDAQI
TASSYFTNMFATWSPSKARLHLQGRSNAWRPQVNNPKEWLQVDFQKTMKVTGVTTQGVKSLLTSMYVKEFLI
SSSQDGHQWTLFFQNGKVKVFQGNQDSFTPVVNSLDPPLLTRYLRIHPQSWVHQIALRMEVLGCEAQDLY

TABLE 5

| Nucleotide Sequence Encoding BDD FVIII (SEQ ID NO: 19)* | | | | | |
|---|---|---|---|---|---|
| 661 | | | A TGCAAATAGA | GCTCTCCACC | TGCTTCTTTC |
| 721 | TGTGCCTTTT | GCGATTCTGC | TTTAGTGCCA | CCAGAAGATA | CTACCTGGGT GCAGTGGAAC |
| 781 | TGTCATGGGA | CTATATGCAA | AGTGATCTCG | GTGAGCTGCC | TGTGGACGCA AGATTTCCTC |
| 841 | CTAGAGTGCC | AAAATCTTTT | CCATTCAACA | CCTCAGTCGT | GTACAAAAAG ACTCTGTTTG |
| 901 | TAGAATTCAC | GGATCACCTT | TCAACATCG | CTAAGCCAAG | GCCACCCTGG ATGGGTCTGC |
| 961 | TAGGTCCTAC | CATCCAGGCT | GAGGTTTATG | ATACAGTGGT | CATTACACTT AAGAACATGG |
| 1021 | CTTCCCATCC | TGTCAGTCTT | CATGCTGTTG | GTGTATCCTA | CTGGAAAGCT TCTGAGGGAG |
| 1081 | CTGAATATGA | TGATCAGACC | AGTCAAAGGG | AGAAAGAAGA | TGATAAAGTC TTCCCTGGTG |
| 1141 | GAAGCCATAC | ATATGTCTGG | CAGGTCCTGA | AGAGAATGG | TCCAATGGCC TCTGACCCAC |
| 1201 | TGTGCCTTAC | CTACTCATAT | CTTTCTCATG | TGGACCTGGT | AAAAGACTTG AATTCAGGCC |
| 1261 | TCATTGGAGC | CCTACTAGTA | TGTAGAGAAG | GGAGTCTGGC | CAAGGAAAAG ACACAGACCT |
| 1321 | TGCACAAATT | TATACTACTT | TTTGCTGTAT | TTGATGAAGG | GAAAAGTTGG CACTCAGAAA |
| 1381 | CAAAGAACTC | CTTGATGCAG | GATAGGGATG | CTGCATCTGC | TCGGGCCTGG CCTAAAATGC |
| 1441 | ACACAGTCAA | TGGTTATGTA | AACAGGTCTC | TGCCAGGTCT | GATTGGATGC CACAGGAAAT |
| 1501 | CAGTCTATTG | GCATGTGATT | GGAATGGGCA | CCACTCCTGA | AGTGCACTCA ATATTCCTCG |
| 1561 | AAGGTCACAC | ATTTCTTGTG | AGGAACCATC | GCCAGGCGTC | CTTGGAAATC TCGCCAATAA |

TABLE 5-continued

Nucleotide Sequence Encoding BDD FVIII (SEQ ID NO: 19)*

| | |
|---|---|
| 1621 | CTTTCCTTAC TGCTCAAACA CTCTTGATGG ACCTTGGACA GTTTCTACTG TTTTGTCATA |
| 1681 | TCTCTTCCCA CCAACATGAT GGCATGGAAG CTTATGTCAA AGTAGACAGC TGTCCAGAGG |
| 1741 | AACCCCAACT ACGAATGAAA ATAATGAAG AAGCGGAAGA CTATGATGAT GATCTTACTG |
| 1801 | ATTCTGAAAT GGATGTGGTC AGGTTTGATG ATGACAACTC TCCTTCCTTT ATCCAAATTC |
| 1861 | GCTCAGTTGC CAAGAAGCAT CCTAAAACTT GGGTACATTA CATTGCTGCT GAAGAGGAGG |
| 1921 | ACTGGGACTA TGCTCCCTTA GTCCTCGCCC CCGATGACAG AAGTTATAAA AGTCAATATT |
| 1981 | TGAACAATGG CCCTCAGCGG ATTGGTAGGA AGTACAAAAA AGTCCGATTT ATGGCATACA |
| 2041 | CAGATGAAAC CTTTAAGACT CGTGAAGCTA TTCAGCATGA ATCAGGAATC TTGGGACCTT |
| 2101 | TACTTTATGG GGAAGTTGGA GACACACTGT TGATTATATT TAAGAATCAA GCAAGCAGAC |
| 2161 | CATATAACAT CTACCCTCAC GGAATCACTG ATGTCCGTCC TTTGTATTCA AGGAGATTAC |
| 2221 | CAAAAGGTGT AAAACATTTG AAGGATTTTC CAATTCTGCC AGGAGAAATA TTCAAATATA |
| 2281 | AATGGACAGT GACTGTAGAA GATGGGCCAA CTAAATCAGA TCCTCGGTGC CTGACCCGCT |
| 2341 | ATTACTCTAG TTTCGTTAAT ATGGAGAGAG ATCTAGCTTC AGGACTCATT GGCCCTCTCC |
| 2401 | TCATCTGCTA CAAAGAATCT GTAGATCAAA GAGGAAACCA GATAATGTCA GACAAGAGGA |
| 2461 | ATGTCATCCT GTTTTCTGTA TTTGATGAGA ACCGAAGCTG GTACCTCACA GAGAATATAC |
| 2521 | AACGCTTTCT CCCCAATCCA GCTGGAGTGC AGCTTGAGGA TCCAGAGTTC CAAGCCTCCA |
| 2581 | ACATCATGCA CAGCATCAAT GGCTATGTTT TTGATAGTTT GCAGTTGTCA GTTTGTTTGC |
| 2641 | ATGAGGTGGC ATACTGGTAC ATTCTAAGCA TTGGAGCACA GACTGACTTC CTTTCTGTCT |
| 2701 | TCTTCTCTGG ATATACCTTC AAACACAAAA TGGTCTATGA AGACACACTC ACCCTATTCC |
| 2761 | CATTCTCAGG AGAAACTGTC TTCATGTCGA TGGAAAACCC AGGTCTATGG ATTCTGGGGT |
| 2821 | GCCACAACTC AGACTTTCGG AACAGAGGCA TGACCGCCTT ACTGAAGGTT TCTAGTTGTG |
| 2881 | ACAAGAACAC TGGTGATTAT TACGAGGACA GTTATGAAGA TATTTCAGCA TACTTGCTGA |
| 2941 | GTAAAAACAA TGCCATTGAA CCAAGAAGCT TCTCTCAAAA CCCACCAGTC TTGAAACGCC |
| 3001 | ATCAACGGGA ATAACTCGT ACTACTCTTC AGTCAGATCA AGAGGAAATT GACTATGATG |
| 3061 | ATACCATATC AGTTGAAATG AAGAAGGAAG ATTTTGACAT TTATGATGAG GATGAAAATC |
| 3121 | AGAGCCCCCG CAGCTTTCAA AAGAAAACAC GACACTATTT TATTGCTGCA GTGGAGAGGC |
| 3181 | TCTGGGATTA TGGGATGAGT AGCTCCCCAC ATGTTCTAAG AAACAGGGCT CAGAGTGGCA |
| 3241 | GTGTCCCTCA GTTCAAGAAA GTTGTTTTCC AGGAATTTAC TGATGGCTCC TTTACTCAGC |
| 3301 | CCTTATACCG TGGAGAACTA AATGAACATT TGGGACTCCT GGGGCCATAT ATAAGAGCAG |
| 3361 | AAGTTGAAGA TAATATCATG GTAACTTTCA GAAATCAGGC CTCTCGTCCC TATTCCTTCT |
| 3421 | ATTCTAGCCT TATTTCTTAT GAGGAAGATC AGAGGCAAGG AGCAGAACCT AGAAAAAACT |
| 3481 | TTGTCAAGCC TAATGAAACC AAAACTTACT TTTGGAAAGT GCAACATCAT ATGGCACCCA |
| 3541 | CTAAAGATGA GTTTGACTGC AAAGCCTGGG CTTATTTCTC TGATGTTGAC CTGGAAAAAG |
| 3601 | ATGTGCACTC AGGCCTGATT GGACCCCTTC TGGTCTGCCA CACTAACACA CTGAACCCTG |
| 3661 | CTCATGGGAG ACAAGTGACA GTACAGGAAT TGCTCTGTT TTTCACCATC TTTGATGAGA |
| 3721 | CCAAAAGCTG GTACTTCACT GAAATATGG AAAGAACTG CAGGGCTCCC TGCAATATCC |
| 3781 | AGATGGAAGA TCCCACTTTT AAAGAGAATT ATCGCTTCCA TGCAATCAAT GGCTACATAA |
| 3841 | TGGATACACT ACCTGGCTTA GTAATGGCTC AGGATCAAAG GATTCGATGG TATCTGCTCA |
| 3901 | GCATGGGCAG CAATGAAAAC ATCCATTCTA TTCATTTCAG TGGACATGTG TTCACTGTAC |

TABLE 5-continued

Nucleotide Sequence Encoding BDD FVIII (SEQ ID NO: 19)*

```
3961    GAAAAAAGA GGAGTATAAA ATGGCACTGT ACAATCTCTA TCCAGGTGTT TTTGAGACAG

4021    TGGAAATGTT ACCATCCAAA GCTGGAATTT GGCGGGTGGA ATGCCTTATT GGCGAGCATC

4081    TACATGCTGG GATGAGCACA CTTTTTCTGG TGTACAGCAA TAAGTGTCAG ACTCCCCTGG

4141    GAATGGCTTC TGGACACATT AGAGATTTTC AGATTACAGC TTCAGGACAA TATGGACAGT

4201    GGGCCCCAAA GCTGGCCAGA CTTCATTATT CCGGATCAAT CAATGCCTGG AGCACCAAGG

4261    AGCCCTTTTC TTGGATCAAG GTGGATCTGT TGGCACCAAT GATTATTCAC GGCATCAAGA

4321    CCCAGGGTGC CCGTCAGAAG TTCTCCAGCC TCTACATCTC TCAGTTTATC ATCATGTATA

4381    GTCTTGATGG GAAGAAGTGG CAGACTTATC GAGGAAATTC CACTGGAACC TTAATGGTCT

4441    TCTTTGGCAA TGTGGATTCA TCTGGGATAA AACACAATAT TTTTAACCCT CCAATTATTG

4501    CTCGATACAT CCGTTTGCAC CCAACTCATT ATAGCATTCG CAGCACTCTT CGCATGGAGT

4561    TGATGGGCTG TGATTTAAAT AGTTGCAGCA TGCCATTGGG AATGGAGAGT AAAGCAATAT

4621    CAGATGCACA GATTACTGCT TCATCCTACT TTACCAATAT GTTTGCCACC TGGTCTCCTT

4681    CAAAAGCTCG ACTTCACCTC CAAGGGAGGA GTAATGCCTG GAGACCTCAG GTGAATAATC

4741    CAAAAGAGTG GCTGCAAGTG GACTTCCAGA AGACAATGAA AGTCACAGGA GTAACTACTC

4801    AGGGAGTAAA ATCTCTGCTT ACCAGCATGT ATGTGAAGGA GTTCCTCATC TCCAGCAGTC

4861    AAGATGGCCA TCAGTGGACT CTCTTTTTTC AGAATGGCAA AGTAAAGGTT TTTCAGGGAA

4921    ATCAAGACTC CTTCACACCT GTGGTGAACT CTCTAGACCC ACCGTTACTG ACTCGCTACC

4981    TTCGAATTCA CCCCCAGAGT TGGGTGCACC AGATTGCCCT GAGGATGGAG GTTCTGGGCT

5041    GCGAGGCACA GGACCTCTAC
```

*The underlined nucleic acids encode a signal peptide.

A "B-domain-deleted FVIII" may have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563. In some embodiments, a B-domain-deleted FVIII sequence of the present invention comprises any one of the deletions disclosed at col. 4, line 4 to col. 5, line 28 and Examples 1-5 of U.S. Pat. No. 6,316,226 (also in U.S. Pat. No. 6,346,513). In another embodiment, a B-domain deleted Factor VIII is the 5743/Q1638 B-domain deleted Factor VIII (SQ BDD FVIII) (e.g., Factor VIII having a deletion from amino acid 744 to amino acid 1637, e.g., Factor VIII having amino acids 1-743 and amino acids 1638-2332 of SEQ ID NO: 16, i.e., SEQ ID NO: 18). In some embodiments, a B-domain-deleted FVIII of the present invention has a deletion disclosed at col. 2, lines 26-51 and examples 5-8 of U.S. Pat. No. 5,789,203 (also U.S. Pat. Nos. 6,060,447, 5,595,886, and 6,228,620). In some embodiments, a B-domain-deleted Factor VIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563.

In some embodiments, a B-domain-deleted FVIII has a deletion of most of the B domain, but still contains amino-terminal sequences of the B domain that are essential for in vivo proteolytic processing of the primary translation product into two polypeptide chain, as disclosed in WO 91/09122. In some embodiments, a B-domain-deleted FVIII is constructed with a deletion of amino acids 747-1638, i.e., virtually a complete deletion of the B domain. Hoeben R. C., et al. *J. Biol. Chem.* 265 (13): 7318-7323 (1990). A B-domain-deleted Factor VIII may also contain a deletion of amino acids 771-1666 or amino acids 868-1562 of FVIII. Meulien P., et al. *Protein Eng.* 2(4): 301-6 (1988). Additional B domain deletions that are part of the invention include: deletion of amino acids 982 through 1562 or 760 through 1639 (Toole et al., *Proc. Natl. Acad. Sci. U.S.A.* 83, 5939-5942)), 797 through 1562 (Eaton, et al. Biochemistry (1986) 25:8343-8347)), 741 through 1646 (Kaufman (PCT published application No. WO 87/04187)), 747-1560 (Sarver, et al., *DNA* (1987) 6:553-564)), 741 through 1648 (Pasek (PCT application No. 88/00831)), or 816 through 1598 or 741 through 1648 (Lagner (Behring Inst. Mitt. (1988) No 82:16-25, EP 295597)). In other embodiments, BDD FVIII includes a FVIII polypeptide containing fragments of the B-domain that retain one or more N-linked glycosylation sites, e.g., residues 757, 784, 828, 900, 963, or optionally 943, which correspond to the amino acid sequence of the full-length FVIII sequence. Examples of the B-domain fragments include 226 amino acids or 163 amino acids of the B-domain as disclosed in Miao, H. Z., et al., *Blood* 103(a): 3412-3419 (2004), Kasuda, A, et al., *J. Thromb. Haemost.* 6: 1352-1359 (2008), and Pipe, S. W., et al., *J. Thromb. Haemost.* 9: 2235-2242 (2011) (i.e., the first 226 amino acids or 163 amino acids of the B domain are retained). In some embodiments, the FVIII with a partial B-domain is FVIII198 (SEQ ID NO: 105). FVIII198 is a partial B-domain containing single chain FVIIIFc molecule-226N6. 226 represents the N-terminus 226 amino acid of the FVIII B-domain, and N6 represents six N-glycosylation sites in the B-domain. In still other embodiments, BDD FVIII further comprises a point mutation at residue 309 (from Phe to Ser) to improve expression of the BDD FVIII protein. See Miao, H. Z., et al., Blood 103(a): 3412-3419 (2004). In still other embodiments, the BDD FVIII includes a FVIII polypeptide containing a portion of the B-domain, but not containing one or more furin cleavage sites (e.g., Arg1313 and Arg 1648). See Pipe, S. W., et al., *J. Thromb. Haemost.* 9: 2235-2242 (2011). Each of the foregoing deletions may be made in any FVIII sequence.

A FVIII protein useful in the present invention can include FVIII having one or more additional heterologous sequences or chemical or physical modifications therein, which do not affect the FVIII coagulation activity. Such heterologous sequences or chemical or physical modifications can be fused to the C-terminus or N-terminus of the FVIII protein or inserted between one or more of the two amino acid residues in the FVIII protein. Such insertions in the FVIII protein do not affect the FVIII coagulation activity or FVIII function. In one embodiment, the insertions improve pharmacokinetic properties of the FVIII protein (e.g., half-life). In another embodiment, the insertions can be more than two, three, four, five, or six sites.

In one embodiment, FVIII is cleaved right after Arginine at amino acid 1648 (in full-length Factor VIII or SEQ ID NO: 16), amino acid 754 (in the 5743/Q1638 B-domain deleted Factor VIII or SEQ ID NO: 16), or the corresponding Arginine residue (in other variants), thereby resulting in a heavy chain and a light chain. In another embodiment, FVIII comprises a heavy chain and a light chain, which are linked or associated by a metal ion-mediated non-covalent bond.

In other embodiments, FVIII is a single chain FVIII that has not been cleaved right after Arginine at amino acid 1648 (in full-length FVIII or SEQ ID NO: 16), amino acid 754 (in the 5743/Q1638 B-domain-deleted FVIII or SEQ ID NO: 18), or the corresponding Arginine residue (in other variants). A single chain FVIII may comprise one or more amino acid substitutions. In one embodiment, the amino acid substitution is at a residue corresponding to residue 1648, residue 1645, or both of full-length mature Factor VIII polypeptide (SEQ ID NO: 16) or residue 754, residue 751, or both of SQ BDD Factor VIII (SEQ ID NO: 18). The amino acid substitution can be any amino acids other than Arginine, e.g., isoleucine, leucine, lysine, methionine, phenylalanine, threonine, tryptophan, valine, alanine, asparagine, aspartic acid, cysteine, glutamic acid, glutamine, glycine, proline, selenocysteine, serine, tyrosine, histidine, ornithine, pyrrolysine, or taurine.

FVIII can further be cleaved by thrombin and then activated as FVIIIa, serving as a cofactor for activated Factor IX (FIXa). And the activated FIX together with activated FVIII forms a Xase complex and converts Factor X to activated Factor X (FXa). For activation, FVIII is cleaved by thrombin after three Arginine residues, at amino acids 372, 740, and 1689 (corresponding to amino acids 372, 740, and 795 in the B-domain deleted FVIII sequence), the cleavage generating FVIIIa having the 50 kDa A1, 43 kDa A2, and 73 kDa A3-C1-C2 chains. In one embodiment, the FVIII protein useful for the present invention is non-active FVIII. In another embodiment, the FVIII protein is an activated FVIII.

The protein having FVIII polypeptide linked to or associated with the VWF fragment can comprise a sequence at least 50%, 60%, 70%, 80%, 90%, 95%, 96%, 97%, 98%, 99%, or 100% identical to SEQ ID NO: 16 or 18, wherein the sequence has the FVIII clotting activity, e.g., activating Factor IX as a cofactor to convert Factor X to activated Factor X (FXa).

"Hybrid" polypeptides and proteins, as used herein, means a combination of a first polypeptide chain, e.g., the VWF fragment, optionally fused to a first heterologous moiety, with a second polypeptide chain, e.g., a FVIII protein, optionally fused to a second heterologous moiety, thereby forming a heterodimer. In one embodiment, the first polypeptide and the second polypeptide in a hybrid are associated with each other via protein-protein interactions, such as charge-charge or hydrophobic interactions. In another embodiment, the first polypeptide and the second polypeptide in a hybrid are associated with each other via disulfide or other covalent bond(s). Hybrids are described, for example, in US 2004/101740 and US 2006/074199. The second polypeptide may be an identical copy of the first polypeptide or a non-identical polypeptide. In one embodiment, the first polypeptide is a VWF fragment-Fc fusion protein, and the second polypeptide is a polypeptide comprising, consisting essentially of, or consisting of an FcRn binding domain, wherein the first polypeptide and the second polypeptide are associated with each other. In another embodiment, the first polypeptide comprises a VWF fragment-Fc fusion protein, and the second polypeptide comprises FVIII-Fc fusion protein, making the hybrid a heterodimer. The first polypeptide and the second polypeptide can be associated through a covalent bond, e.g., a disulfide bond, between the first Fc region and the second Fc region. The first polypeptide and the second polypeptide can further be associated with each other by binding between the VWF fragment and the FVIII protein.

D) Linkers

The chimeric protein of the present invention further comprises a linker. One or more linkers can be present between any two proteins, e.g., between the adjunct moiety and the FVIII protein (sometimes also referred to as "FVIII/AM linker"), between the VWF fragment and a first heterologous moiety (sometime also referred to as "VWF linker"), e.g., a first Fc region, between a FVIII protein and a second heterologous moiety (sometimes also referred to as "FVIII linker"), e.g., a second Fc region, between the VWF fragment and a FVIII protein (e.g., FVIII/AM linker), between the VWF fragment and a second heterologous moiety, and/or between a FVIII protein and a first heterologous moiety. Each of the linkers can have the same or different sequence. In one embodiment, the linker is a polypeptide linker. In another embodiment, the linker is a non-polypeptide linker.

The linker useful in the present invention can comprise any organic molecule. In one embodiment, the linker is a polymer, e.g., polyethylene glycol (PEG) or hydroxyethyl starch (HES). In another embodiment, the linker is an amino acid sequence (e.g., a polypeptide linker). The polypeptide linker can comprise at least about 10, 20, 30, 40, 50, 60, 70, 80, 90, 100, 150, 200, 300, 400, 500, 600, 700, 800, 900, 1000, 1100, 1200, 1300, 1400, 1500, 1600, 1700, 1800, 1900, or 2000 amino acids. The linker can comprise 1-5 amino acids, 1-10 amino acids, 1-20 amino acids, 10-50 amino acids, 50-100 amino acids, 100-200 amino acids, 200-300 amino acids, 300-400 amino acids, 400-500 amino acids, 500-600 amino acids, 600-700 amino acids, 700-800 amino acids, 800-900 amino acids, or 900-1000 amino acids.

Examples of polypeptide linkers are well known in the art. In one embodiment, the linker comprises the sequence G. The linker can comprise the sequence (GA)$_n$. The linker can comprise the sequence (GGS)$_n$. In other embodiments, the linker comprises (GGGS)$_n$ (SEQ ID NO: 20). In still other embodiments, the linker comprises the sequence (GGS)$_n$ (GGGGS)$_n$ (SEQ ID NO: 21). In these instances, n may be an integer from 1-100. In other instances, n may be an integer from 1-20, i.e., 1, 2, 3, 4, 5, 6, 7, 8, 9, 10, 11, 12, 13, 14, 15, 16, 17, 18, 19, or 20. Examples of linkers include, but are not limited to, GGG, SGGSGGS (SEQ ID NO: 22), GGSGGSGGSGGSGGG (SEQ ID NO: 23), GGSGGSGGGGSGGGS (SEQ ID NO: 24), GGSGGSGGSGGSGGSGGS (SEQ ID NO: 25), GGGGSGGGGSGGGGS (SEQ ID NO: 26), the linkers in Table 13 (SEQ ID NOs: 92, 93, and 94), and the linkers in Table 14A (SEQ ID NOs: 95, 96 and 97). The linker does not eliminate or diminish the VWF fragment activity or the clotting activity of Factor VIII. Optionally, the linker enhances the VWF fragment activity or the clotting activity of Factor VIII protein, e.g., by further diminishing the effects of steric hindrance and making the VWF fragment or Factor VIII portion more accessible to its target binding site.

In one embodiment, the linker useful for the chimeric protein is 15-25 amino acids long. In another embodiment, the linker useful for the chimeric protein is 15-20 amino acids long. In some embodiments, the linker for the chimeric protein is 10-25 amino acids long. In other embodiments, the linker for the chimeric protein is 15 amino acids long. In still other embodiments, the linker for the chimeric protein is (GGGGS)$_n$ (SEQ ID NO: 27) where G represents glycine, S represents serine and n is an integer from 1-20.

E) Cleavage Sites

The linker may also incorporate a moiety capable of being cleaved either chemically (e.g., hydrolysis of an ester bond), enzymatically (i.e., incorporation of a protease cleavage sequence), or photolytically (e.g., a chromophore such as 3-amino-3-(2-nitrophenyl) proprionic acid (ANP)) in order to release one molecule from another.

In one embodiment, the linker is a cleavable linker. The cleavable linkers can comprise one or more cleavage sites at the N-terminus or C-terminus or both. In another embodiment, the cleavable linker consists essentially of or consists of one or more cleavable sites. In other embodiments, the cleavable linker comprises heterologous amino acid linker sequences described herein or polymers and one or more cleavable sites.

In certain embodiments, a cleavable linker comprises one or more cleavage sites that can be cleaved in a host cell (i.e., intracellular processing sites). Non limiting examples of the cleavage site include RRRR (SEQ ID NO: 52), RKRRKR (SEQ ID NO: 53), and RRRRS (SEQ ID NO: 54).

In other embodiments, a cleavable linker comprises one or more cleavage sites that are cleaved by a protease after a chimeric protein comprising the cleavable linker is administered to a subject. In one embodiment, the cleavage site is cleaved by a protease selected from the group consisting of factor XIa, factor XIIa, kallikrein, factor VIIa, factor IXa, factor Xa, factor IIa (thrombin), Elastase-2, MMP-12, MMP-13, MMP-17, and MMP-20. In another embodiment, the cleavage site is selected from the group consisting of a FXIa cleavage site (e.g., KLTR↓AET (SEQ ID NO: 29)), a FXIa cleavage site (e.g, DFTR↓VVG (SEQ ID NO: 30)), a FXIIa cleavage site (e.g., TMTR↓IVGG (SEQ ID NO: 31)), a Kallikrein cleavage site (e.g., SPFR↓STGG (SEQ ID NO: 32)), a FVIIa cleavage site (e.g., LQVR↓IVGG (SEQ ID NO: 33)), a FIXa cleavage site (e.g., PLGR↓IVGG (SEQ ID NO: 34)), a FXa cleavage site (e.g., IEGR↓TVGG (SEQ ID NO: 35)), a FIIa (thrombin) cleavage site (e.g, LTPR↓SLLV (SEQ ID NO: 36)), a Elastase-2 cleavage site (e.g, LGPV↓SGVP (SEQ ID NO: 37)), a Granzyme-B cleavage (e.g, VAGD↓SLEE (SEQ ID NO: 38)), a MMP-12 cleavage site (e.g., GPAG↓LGGA (SEQ ID NO: 39)), a MMP-13 cleavage site (e.g., GPAG↓LRGA (SEQ ID NO: 40)), a MMP-17 cleavage site (e.g., APLG↓LRLR (SEQ ID NO: 41)), a MMP-20 cleavage site (e.g., PALP↓LVAQ (SEQ ID NO: 42)), a TEV cleavage site (e.g., ENLYFQ↓G (SEQ ID NO: 43)), a Enterokinase cleavage site (e.g., DDDK↓IVGG (SEQ ID NO: 44)), a Protease 3C (PRESCISSION™) cleavage site (e.g., LEVLFQ↓GP (SEQ ID NO: 45)), and a Sortase A cleavage site (e.g., LPKT↓GSES) (SEQ ID NO: 46). In certain embodiments, the FXIa cleavage sites include, but are not limited to, e.g., TQSFNDFTR (SEQ ID NO: 47) and SVSQTSKLTR (SEQ ID NO: 48). Non-limiting exemplary thrombin cleavage sites include, e.g., DFLAEGGGVR (SEQ ID NO: 49), TTKIKPR (SEQ ID NO: 50), or LVPRG (SEQ ID NO: 55), and a sequence comprising, consisting essentially of, or consisting of ALRPR (e.g., ALRPRVVGGA (SEQ ID NO: 51)).

In a specific embodiment, the cleavage site is TLDPRSFLLRNPNDKYEPFWEDEEK (SEQ ID NO: 56).

Polynucleotides, Vectors, Host Cells, and Methods of Making

Also provided in the invention is a polynucleotide encoding a VWF fragment described herein, a chimeric protein comprising the VWF fragment and a heterologous moiety, a chimeric protein comprising a FVIII protein and an adjunct moiety, or a chimeric protein comprising a VWF fragment and a FVIII protein. When a VWF fragment is linked to a heterologous moiety or a FVIII protein in a chimeric protein as a single polypeptide chain, the invention is drawn to a polynucleotide encoding the VWF fragment linked to the heterologous moiety or the FVIII protein. When the chimeric protein comprises a first and a second polypeptide chains, the first polypeptide chain comprising a VWF fragment and a first heterologous moiety (e.g., a first Fc region) and the second polypeptide chain comprising a second heterologous moiety (e.g., a second Fc region), wherein the first polypeptide chain and the second polypeptide chain are associated with each other, a polynucleotide can comprise the first nucleotide sequence and the second nucleotide sequence. In one embodiment, the first nucleotide sequence and the second nucleotide sequence are on the same polynucleotide. In another embodiment, the first nucleotide sequence and the second nucleotide sequence are on two different polynucleotides (e.g., different vectors). In certain embodiments, the present invention is directed to a set of polynucleotides comprising a first nucleotide chain and a second nucleotide chain, wherein the first nucleotide chain encodes the VWF fragment of the chimeric protein and the second nucleotide chain encodes the FVIII protein.

In other embodiments, the set of the polynucleotides further comprises an additional nucleotide chain (e.g., a second nucleotide chain when the chimeric polypeptide is encoded by a single polynucleotide chain or a third nucleotide chain when the chimeric protein is encoded by two polynucleotide chains) which encodes a protein convertase. The protein convertase can be selected from the group consisting of proprotein convertase subtilisin/kexin type 5 (PCSK5 or PC5), proprotein convertase subtilisin/kexin type 7 (PCSK7 or PC5), a yeast Kex 2, proprotein convertase subtilisin/kexin type 3 (PACE or PCSK3), and two or more combinations thereof. In some embodiments, the protein convertase is PACE, PC5, or PC7. In a specific embodiment, the protein convertase is PC5 or PC7. See International Application no. PCT/US2011/043568, which is incorporated herein by reference. In another embodiment, the protein convertase is PACE/Furin.

In certain embodiments, the invention includes a set of the polynucleotides comprising a first nucleotide sequence encoding a VWF fragment comprising a D' domain and a D3 domain of VWF, a second nucleotide sequence encoding a FVIII protein, and a third nucleotide sequence encoding a D1 domain and D2 domain of VWF. In this embodiment, the D1 domain and D2 domain are separately expressed (not linked to the D'D3 domain of the VWF fragment) in order for the proper disulfide bond formation and folding of the D'D3 domains. The D1D2 domain expression can either be in cis or trans.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Expression vectors of the invention will include polynucleotides encoding the VWF fragment or the chimeric protein comprising the VWF fragment.

In one embodiment, a coding sequence for the VWF fragment, the second heterologous moiety (e.g., a second Fc region), or the FVIII protein is operably linked to an expression control sequence. As used herein, two nucleic acid sequences are operably linked when they are covalently linked in such a way as to permit each component nucleic acid sequence to retain its functionality. A coding sequence and a gene expression control sequence are said to be operably linked when they are covalently linked in such a way as to place the expression or transcription and/or translation of the coding sequence under the influence or control of the gene expression control sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding nucleic acid sequence if the gene expression sequence were capable of effecting transcription of that coding nucleic acid sequence such that the resulting transcript is translated into the desired protein or polypeptide.

A gene expression control sequence as used herein is any regulatory nucleotide sequence, such as a promoter sequence or promoter-enhancer combination, which facilitates the efficient transcription and translation of the coding nucleic acid to which it is operably linked. The gene expression control sequence may, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression control sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined coding nucleic acid. The gene expression sequences optionally include enhancer sequences or upstream activator sequences as desired.

Viral vectors include, but are not limited to, nucleic acid sequences from the following viruses: retrovirus, such as Moloney murine leukemia virus, Harvey murine sarcoma virus, murine mammary tumor virus, and Rous sarcoma virus; adenovirus, adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

In one embodiment, the virus is an adeno-associated virus, a double-stranded DNA virus. The adeno-associated virus can be engineered to be replication-deficient and is capable of infecting a wide range of cell types and species. It further has advantages such as heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, Calif.). Other plasmids are well-known to those of ordinary skill in the art. Additionally, plasmids may be custom designed using standard molecular biology techniques to remove and/or add specific fragments of DNA.

In one insect expression system that may be used to produce the proteins of the invention, *Autographa californica* nuclear polyhidrosis virus (AcNPV) is used as a vector to express the foreign genes. The virus grows in *Spodoptera frugiperda* cells. A coding sequence may be cloned into non-essential regions (for example, the polyhedron gene) of the virus and placed under control of an ACNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed. (see, e.g., Smith et al. (1983) *J Virol* 46:584; U.S. Pat. No. 4,215,051). Further examples of this expression system may be found in Ausubel et al., eds. (1989) Current Protocols in Molecular Biology, Vol. 2, Greene Publish. Assoc. & Wiley Interscience.

Another system which can be used to express the proteins of the invention is the glutamine synthetase gene expression system, also referred to as the "GS expression system" (Lonza Biologics PLC, Berkshire UK). This expression system is described in detail in U.S. Pat. No. 5,981,216.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. See, e.g., Logan & Shenk (1984) *Proc Natl Acad Sci USA* 81:3655). Alternatively, the vaccinia 7.5 K promoter may be used. See, e.g., Mackett et al. (1982) *Proc Natl Acad Sci USA* 79:7415; Mackett et al. (1984) *J Virol* 49:857; Panicali et al. (1982) *Proc Natl Acad Sci USA* 79:4927.

To increase efficiency of production, the polynucleotides can be designed to encode multiple units of the protein of the invention separated by enzymatic cleavage sites. The resulting polypeptide can be cleaved (e.g., by treatment with the appropriate enzyme) in order to recover the polypeptide units. This can increase the yield of polypeptides driven by a single promoter. When used in appropriate viral expression systems, the translation of each polypeptide encoded by the mRNA is directed internally in the transcript; e.g., by an internal ribosome entry site, IRES. Thus, the polycistronic construct directs the transcription of a single, large polycistronic mRNA which, in turn, directs the translation of multiple, individual polypeptides. This approach eliminates the production and enzymatic processing of polyproteins and may significantly increase the yield of polypeptides driven by a single promoter.

Vectors used in transformation will usually contain a selectable marker used to identify transformants. In bacterial systems, this can include an antibiotic resistance gene such as ampicillin or kanamycin. Selectable markers for use in cultured mammalian cells include genes that confer resistance to drugs, such as neomycin, hygromycin, and methotrexate. The selectable marker may be an amplifiable selectable marker. One amplifiable selectable marker is the dihydrofolate reductase (DHFR) gene. Simonsen C C et al. (1983) *Proc Natl Acad Sci USA* 80:2495-9. Selectable markers are reviewed by Thilly (1986) Mammalian Cell Technology, Butterworth Publishers, Stoneham, Mass., and the choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, U.S. Pat. No. 4,713,339).

The expression vectors can encode for tags that permit easy purification of the recombinantly produced protein. Examples include, but are not limited to, vector pUR278 (Ruther et al. (1983) *EMBO J.* 2:1791), in which coding sequences for the protein to be expressed may be ligated into the vector in frame with the lac z coding region so that a tagged fusion protein is produced; pGEX vectors may be used to express proteins of the invention with a glutathione S-transferase (GST) tag. These proteins are usually soluble and can easily be purified from cells by adsorption to glutathione-agarose beads followed by elution in the presence of free glutathione. The vectors include cleavage sites (thrombin or Factor Xa protease or PRESCISSION PROTEASE™ (Pharmacia, Peapack, N.J.)) for easy removal of the tag after purification.

The expression vector or vectors are then transfected or co-transfected into a suitable target cell, which will express the polypeptides. Transfection techniques known in the art include, but are not limited to, calcium phosphate precipitation (Wigler et al. (1978) *Cell* 14:725), electroporation (Neumann et al. (1982) *EMBO J.* 1:841), and liposome-based reagents. A variety of host-expression vector systems may be utilized to express the proteins described herein including both prokaryotic and eukaryotic cells. These include, but are not limited to, microorganisms such as bacteria (e.g., *E. coli*) transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems, including mammalian cells (e.g., HEK 293, CHO, Cos, HeLa, HKB11, and BHK cells).

In one embodiment, the host cell is a eukaryotic cell. As used herein, a eukaryotic cell refers to any animal or plant cell having a definitive nucleus. Eukaryotic cells of animals include cells of vertebrates, e.g., mammals, and cells of invertebrates, e.g., insects. Eukaryotic cells of plants specifically can include, without limitation, yeast cells. A eukaryotic cell is distinct from a prokaryotic cell, e.g., bacteria.

In certain embodiments, the eukaryotic cell is a mammalian cell. A mammalian cell is any cell derived from a mammal. Mammalian cells specifically include, but are not limited to, mammalian cell lines. In one embodiment, the mammalian cell is a human cell. In another embodiment, the mammalian cell is a HEK 293 cell, which is a human embryonic kidney cell line. HEK 293 cells are available as CRL-1533 from American Type Culture Collection, Manassas, Va., and as 293-H cells, Catalog No. 11631-017 or 293-F cells, Catalog No. 11625-019 from Invitrogen (Carlsbad, Calif.). In some embodiments, the mammalian cell is a PER.C6 ® cell, which is a human cell line derived from retina. PER.C6® cells are available from Crucell (Leiden, The Netherlands). In other embodiments, the mammalian cell is a Chinese hamster ovary (CHO) cell. CHO cells are available from American Type Culture Collection, Manassas, Va. (e.g., CHO-K1; CCL-61). In still other embodiments, the mammalian cell is a baby hamster kidney (BHK) cell. BHK cells are available from American Type Culture Collection, Manassas, Va. (e.g., CRL-1632). In some embodiments, the mammalian cell is a HKB11 cell, which is a hybrid cell line of a HEK293 cell and a human B cell line. Mei et al., *Mol. Biotechnol.* 34(2): 165-78 (2006).

In one embodiment, a plasmid encoding the VWF fragment or the chimeric protein of the invention further includes a selectable marker, e.g., zeocin resistance, and is transfected into HEK 293 cells, for production of the VWF fragment or the chimeric protein.

In another embodiment, a first plasmid comprising a Factor VIII-Fc fusion coding sequence and a first selectable marker, e.g., a zeocin resistance gene, and a second plasmid comprising a VWF fragment-Fc coding sequence and a second selectable marker, e.g., a neomycin resistance gene, are cotransfected into HEK 293 cells, for production of Factor VIII-Fc and VWF-Fc hybrid. The first and second plasmids can be introduced in equal amounts (i.e., 1:1 ratio), or they can be introduced in unequal amounts.

In some embodiments, a first plasmid including a Factor VIII-Fc fusion coding sequence and a first selectable marker, e.g., a zeocin resistance gene, and a second plasmid including a VWF fragment-Fc coding sequence and a second selectable marker, e.g., a neomycin resistance gene, and a third plasmid including a protein convertase coding sequence (e.g., PC5 or Furin) and a third selectable marker, e.g., a hygromycin resistance gene, are cotransfected into HEK 293 cells, for production of Factor VIII-VWF fragment hybrid. The first and second plasmids can be introduced in equal amounts (i.e., 1:1 molar ratio), or they can be introduced in unequal amounts. In certain embodiments, a first plasmid, including a Factor VIII-Fc fusion coding sequence, a VWF fragment-Fc coding sequence, and a first selectable marker, e.g., a zeocin resistance gene, and a second plasmid including a protein convertase coding sequence (e.g., PC5 or Furin) and a second selectable marker, e.g., a hygromycin resistance gene, are cotransfected into HEK 293 cells, for production of Factor VIII-VWF-fragment hybrid. In one embodiment, the nucleotide sequence encoding the FVIII-Fc sequence and the VWF fragment-Fc sequence can be connected to encode one single polypeptide. In another embodiment, the nucleotide sequence encoding the FVIII-Fc sequence and the VWF fragment-Fc sequence can be encoded as two polypeptide chains. The promoters for the Factor VIII-Fc fusion coding sequence and the VWF fragment-Fc coding sequence can be different or they can be the same.

In some embodiments, a plasmid comprising Furin is co-transfected with the plasmid containing the Factor VIII-Fc coding sequence and/or VWF fragment-Fc coding sequence. In some embodiments, the Furin protein is on the same plasmid comprising the Factor VIII-Fc fusion coding sequence. In some embodiments, the Furin protein is on the same plasmid comprising the VWF fragment-Fc coding sequence. In some embodiments, the Furin protein is on a separate plasmid.

In still other embodiments, transfected cells are stably transfected. These cells can be selected and maintained as a stable cell line, using conventional techniques known to those of skill in the art.

Host cells containing DNA constructs of the protein are grown in an appropriate growth medium. As used herein, the term "appropriate growth medium" means a medium containing nutrients required for the growth of cells. Nutrients required for cell growth may include a carbon source, a nitrogen source, essential amino acids, vitamins, minerals, and growth factors. Optionally, the media can contain one or more selection factors. Optionally the media can contain bovine calf serum or fetal calf serum (FCS). In one embodiment, the media contains substantially no IgG. The growth medium will generally select for cells containing the DNA construct by, for example, drug selection or deficiency in an essential nutrient which is complemented by the selectable marker on the DNA construct or co-transfected with the DNA construct. Cultured mammalian cells are generally grown in commercially available serum-containing or serum-free media (e.g., MEM, DMEM, DMEM/F12). In one embodiment, the medium is CD293 (Invitrogen, Carlsbad, Calif.). In another embodiment, the medium is CD17 (Invitrogen, Carlsbad, Calif.). Selection of a medium appropriate for the particular cell line used is within the level of those ordinary skilled in the art.

In order to co-express the VWF fragment and a second heterologous moiety or a FVIII protein, the host cells are cultured under conditions that allow expression of both the VWF fragment and a second heterologous moiety or a FVIII protein. As used herein, culturing refers to maintaining living cells in vitro for at least a definite time. Maintaining can, but need not include, an increase in population of living cells. For example, cells maintained in culture can be static in population, but still viable and capable of producing a desired product, e.g., a recombinant protein or recombinant fusion protein. Suitable conditions for culturing eukaryotic cells are well known in the art and include appropriate selection of culture media, media supplements, temperature, pH, oxygen saturation, and the like. For commercial purposes, culturing can include the use of any of various types of scale-up systems including shaker flasks, roller bottles, hollow fiber bioreactors, stirred-tank bioreactors, airlift bioreactors, Wave bioreactors, and others.

The cell culture conditions are also selected to allow association of the VWF fragment with the second heterologous moiety or a FVIII protein. Conditions that allow expression of the VWF fragment and/or the FVIII protein, may include the presence of a source of vitamin K. For example, in one embodiment, stably transfected HEK 293 cells are cultured in CD293 media (Invitrogen, Carlsbad, Calif.) or OptiCHO media (Invitrogen, Carlsbad, Calif.) supplemented with 4 mM glutamine.

In one aspect, the present invention is directed to a method of expressing, making, or producing the VWF fragment of the invention comprising a) transfecting a host cell with a polynucleotide encoding the VWF fragment and b) culturing the host cell in a culture medium under a condition suitable for expressing the VWF fragment, wherein the VWF fragment is expressed. In one embodiment, the invention is drawn to a method of producing a mature VWF protein or a fragment thereof comprising a) transfecting a host cell with a first polynucleotide encoding the VWF protein or a fragment thereof, which is fused to a propeptide of VWF, and a second polynucleotide encoding a protein convertase, e.g., PC5, PC7, or Furin and b) culturing the host cell in a culture medium under a condition suitable for expressing the mature VWF protein or fragment thereof. The polynucleotide encoding the VWF protein or a fragment thereof can also be fused to a prepeptide of VWF. The prepeptide sequence can be cleaved during insertion to the endoplasmic reticulum before secretion.

In another aspect, the invention is directed to a method of expressing, making, or producing a chimeric protein comprising the VWF fragment linked to or associated with a heterologous moiety or a FVIII protein comprising a) transfecting one or more host cells with a polynucleotide or a set of polynucleotides encoding the chimeric protein and b) culturing the host cell in a culture medium under conditions suitable for expressing the chimeric protein. In one embodiment, the invention is drawn to a method of expressing, making, or producing a chimeric protein comprising a) transfecting a host cell with a first polynucleotide encoding a VWF fragment linked to a heterologous moiety and a second polynucleotide encoding a FVIII protein linked to a heterologous moiety and b) culturing the host cell in a culture medium under conditions suitable for expressing the chimeric protein. The first polynucleotide and the second polynucleotide can be in one vector or two vectors. In another embodiment, the invention is drawn to a method of expressing, making, or producing a chimeric protein comprising a) transfecting a host cell with a first polynucleotide encoding a VWF fragment linked to a heterologous moiety, a second polynucleotide encoding a FVIII protein linked to a heterologous moiety, and a third polynucleotide encoding a protein convertase, and b) culturing the host cell in a culture medium under conditions suitable for expressing the chimeric protein. In other embodiments, the invention is drawn to a method of expressing, making, or producing a chimeric protein comprising a) transfecting a host cell with a first polynucleotide encoding a VWF fragment comprising a D' domain and a D3 domain linked to a heterologous moiety, a second polynucleotide encoding a FVIII protein linked to a heterologous moiety, and a third polynucleotide encoding a D1 domain and a D2 domain of VWF, and b) culturing the host cell in a culture medium under conditions suitable for expressing the chimeric protein. In one embodiment, the first polynucleotide, the second polynucleotide, and the third polynucleotide can be in one vector or separate vectors. In another embodiment, the first polynucleotide and the second polynucleotide can be in one vector, and the third polynucleotide can be another vector. In other embodiments, the first polynucleotide and the third polynucleotide can be in one vector, and the second polynucleotide can be another vector. In some embodiments, the second polynucleotide and the third polynucleotide can be in one vector and the first polynucleotide can be in another vector.

In further embodiments, the protein product containing the VWF fragment or the chimeric protein comprising the VWF fragment is secreted into the media. Media is separated from the cells, concentrated, filtered, and then passed over two or three affinity columns, e.g., a protein A column and one or two anion exchange columns.

In certain aspects, the present invention relates to the VWF fragment or the chimeric polypeptide produced by the methods described herein.

In vitro production allows scale-up to give large amounts of the desired altered polypeptides of the invention. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, hydrophobic interaction chromatography (HIC, chromatography over DEAE-cellulose or affinity chromatography.

Pharmaceutical Composition

Compositions containing the VWF fragment or the chimeric protein of the present invention may contain a suitable pharmaceutically acceptable carrier. For example, they may contain excipients and/or auxiliaries that facilitate processing of the active compounds into preparations designed for delivery to the site of action.

The pharmaceutical composition can be formulated for parenteral administration (i.e. intravenous, subcutaneous, or intramuscular) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, e.g., pyrogen free water.

Suitable formulations for parenteral administration also include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances, which increase the viscosity of the suspension, including, for example, sodium carboxymethyl cellulose, sorbitol and dextran. Optionally, the suspension may also contain stabilizers. Liposomes also can be used to encapsulate the molecules of the invention for delivery into cells or interstitial spaces. Exemplary pharmaceutically acceptable carriers are physiologically compatible solvents, dispersion media, coatings, antibacterial and antifungal agents, isotonic and absorption delaying agents, water, saline, phosphate buffered saline, dextrose, glycerol, ethanol and the like. In some embodiments, the composition comprises isotonic agents, for example, sugars, polyalcohols such as mannitol, sorbitol, or sodium chloride. In other embodiments, the compositions comprise pharmaceutically acceptable substances such as wetting agents or minor amounts of auxiliary substances such as wetting or emulsifying agents, preservatives or buffers, which enhance the shelf life or effectiveness of the active ingredients.

Compositions of the invention may be in a variety of forms, including, for example, liquid (e.g., injectable and infusible solutions), dispersions, suspensions, semi-solid and solid dosage forms. The preferred form depends on the mode of administration and therapeutic application.

The composition can be formulated as a solution, micro emulsion, dispersion, liposome, or other ordered structure suitable to high drug concentration. Sterile injectable solutions can be prepared by incorporating the active ingredient in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The active ingredient can be formulated with a controlled-release formulation or device. Examples of such formulations and devices include implants, transdermal patches, and microencapsulated delivery systems. Biodegradable, biocompatible polymers can be used, for example, ethylene vinyl acetate, polyanhydrides, polyglycolic acid, collagen, polyorthoesters, and polylactic acid. Methods for the preparation of such formulations and devices are known in the art. See e.g., Sustained and Controlled Release Drug Delivery Systems, J. R. Robinson, ed., Marcel Dekker, Inc., New York, 1978.

Injectable depot formulations can be made by forming microencapsulated matrices of the drug in biodegradable polymers such as polylactide-polyglycolide. Depending on the ratio of drug to polymer, and the nature of the polymer employed, the rate of drug release can be controlled. Other exemplary biodegradable polymers are polyorthoesters and polyanhydrides. Depot injectable formulations also can be prepared by entrapping the drug in liposomes or microemulsions.

Supplementary active compounds can be incorporated into the compositions. In one embodiment, the VWF fragment or the chimeric protein of the invention is formulated with another clotting factor, or a variant, fragment, analogue, or derivative thereof. For example, the clotting factor includes, but is not limited to, factor V, factor VII, factor VIII, factor IX, factor X, factor XI, factor XII, factor XIII, prothrombin, fibrinogen, von Willebrand factor or recombinant soluble tissue factor (rsTF) or activated forms of any of the preceding. The clotting factor of hemostatic agent can also include anti-fibrinolytic drugs, e.g., epsilon-aminocaproic acid, tranexamic acid.

Dosage regimens may be adjusted to provide the optimum desired response. For example, a single bolus may be administered, several divided doses may be administered over time, or the dose may be proportionally reduced or increased as indicated by the exigencies of the therapeutic situation. It is advantageous to formulate parenteral compositions in dosage unit form for ease of administration and uniformity of dosage. See, e.g., Remington's Pharmaceutical Sciences (Mack Pub. Co., Easton, Pa. 1980).

In addition to the active compound, the liquid dosage form may contain inert ingredients such as water, ethyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols, and fatty acid esters of sorbitan.

Non-limiting examples of suitable pharmaceutical carriers are also described in Remington's Pharmaceutical Sciences by E. W. Martin. Some examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain pH buffering reagents, and wetting or emulsifying agents.

For oral administration, the pharmaceutical composition can take the form of tablets or capsules prepared by conventional means. The composition can also be prepared as a liquid for example a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring and sweetening agents. Alternatively, the composition can be presented as a dry product for constitution with water or another suitable vehicle.

For buccal administration, the composition may take the form of tablets or lozenges according to conventional protocols.

For administration by inhalation, the compounds for use according to the present invention are conveniently delivered in the form of a nebulized aerosol with or without excipients or in the form of an aerosol spray from a pressurized pack or nebulizer, with optionally a propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can also be formulated for rectal administration as a suppository or retention enema, e.g., containing conventional suppository bases such as cocoa butter or other glycerides.

Gene Therapy

A VWF fragment or chimeric protein thereof of the invention can be produced in vivo in a mammal, e.g., a human patient, using a gene therapy approach to treatment of a bleeding disease or disorder selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath would be therapeutically beneficial. In one embodiment, the bleeding disease or disorder is hemophilia. In another embodiment, the bleeding disease or disorder is hemophilia A. This involves administration of a suitable VWF fragment or chimeric protein-encoding nucleic acid operably linked to suitable expression control sequences. In certain embodiment, these sequences are incorporated into a viral vector. Suitable viral vectors for such gene therapy include adenoviral vectors, lentiviral vectors, baculoviral vectors, Epstein Barr viral vectors, papovaviral vectors, vaccinia viral vectors, herpes simplex viral vectors, and adeno associated virus (AAV) vectors. The viral vector can be a replication-defective viral vector. In other embodiments, a adenoviral vector has a deletion in its E1 gene or E3 gene. When an adenoviral vector is used, the mammal may not be exposed to a nucleic acid encoding a selectable marker gene. In other embodiments, the sequences are incorporated into a non-viral vector known to those skilled in the art.

Methods of Using VWF Fragment or Chimeric Protein

One aspect of the present invention is directed to preventing or inhibiting FVIII interaction with endogenous VWF by blocking or shielding the VWF binding site on the FVIII from endogenous VWF. In one embodiment, the invention is directed to a method of constructing a FVIII protein having half-life longer than wild-type FVIII or a FVIII monomer-dimer hybrid, the method comprising covalently associating an adjunct moiety with the FVIII protein, thereby making a chimeric protein comprising the FVIII protein and the adjunct moiety, wherein the adjunct moiety shields or prevents the FVIII protein interaction with endogenous VWF. The chimeric protein useful in the method includes any one or more chimeric protein described herein.

Another aspect of the invention includes a method of administering to a subject in need thereof a FVIII protein having half-life longer than wild-type FVIII or a FVIII monomer-dimer hybrid, which consists of two polypeptide chains, a first chain consisting of an amino acid sequence encoding FVIII and an Fc region and a second chain consisting of an Fc region, wherein the method comprises administering the VWF fragment described herein or the chimeric protein described herein to the subject. The FVIII amino acid sequence in the monomer-dimer hybrid can be SQ FVIII or wild-type FVIII.

In one embodiment, the invention is directed to a method of using an adjunct moiety, e.g., a VWF fragment described herein or a chimeric protein comprising the VWF fragment, to prevent or inhibit endogenous VWF interaction with a FVIII protein. In another embodiment, a FVIII protein that is capable of interacting with the VWF fragment is endogenous FVIII. In other embodiments, a FVIII protein that is capable of interacting with the VWF fragment is a FVIII composition separately administered to a subject before or after or simultaneously with the VWF fragment or the chimeric protein comprising the VWF fragment. In other embodiments, a FVIII protein that is capable of binding to the VWF fragment is a FVIII composition administered to a subject together with the VWF fragment or the chimeric protein. In still other embodiments, a FVIII protein that is capable of binding to the VWF fragment is FVIII present with the VWF fragment or associated with the VWF fragment in the chimeric protein. The VWF fragment or the chimeric protein comprising the VWF fragment binds to, or is associated with, the FVIII protein and thus extends the half-life of the FVIII protein bound to the VWF fragment or the chimeric protein. The FVIII protein bound to the VWF fragment or the chimeric protein is shielded or protected from the clearance pathway of VWF and thus has reduced clearance compared to the FVIII protein not bound to the VWF fragment or the chimeric protein. The shielded FVIII protein thus has a longer half-life than a FVIII protein not bound to or associated with the VWF fragment or the chimeric protein. In certain embodiments, the FVIII protein associated with or protected by a VWF fragment or a chimeric protein of the invention is not cleared by a VWF clearance receptor. In other embodiments, the FVIII protein associated with or protected by a VWF fragment or a chimeric protein is cleared from the system slower than the FVIII protein that is not associated with or protected by the VWF fragment.

In one aspect, the VWF fragment of this invention or the chimeric protein comprising the same has reduced clearance from circulation as the VWF fragment or the chimeric protein does not contain a VWF clearance receptor binding site. The VWF fragment prevents or inhibits clearance of FVIII bound to or associated with the VWF fragment from the system through the VWF clearance pathway. The VWF fragments useful for the present invention can also provide at least one or more VWF-like FVIII protection properties that are provided by endogenous VWF. In certain embodiments, the VWF fragments can also mask one or more FVIII clearance receptor binding site, thereby preventing clearance of FVIII by its own clearance pathway.

In another aspect, the VWF fragment or chimeric protein of the invention can be used to treat or prevent a disease or disorder associated with a Type 2N von Willebrand disease (VWD). Type 2N VWD is a qualitative VWF defect resulting from defective VWF binding to FVIII and consequently resulting in low levels of circulating FVIII. Therefore, the VWF fragment or chimeric protein of the invention by binding to or being bound to the FVIII protein not only stabilizes the FVIII protein, but also prevents clearance of the FVIII protein from the circulation.

In some embodiments, the prevention or inhibition of a FVIII protein binding to endogenous VWF by the VWF fragment or chimeric protein can be in vitro or in vivo.

Also provided is a method of increasing the half-life of a FVIII protein comprising administering the VWF fragment or the chimeric protein comprising the VWF fragment and a FVIII protein to a subject in need thereof. The half-life of non-activated FVIII bound to or associated with full-length VWF is about 12 to 14 hours in plasma. In VWD type 3, wherein there is almost no VWF in circulation, the half-life of FVIII is only about six hours, leading to symptoms of mild to moderate hemophilia A in such patients due to decreased concentrations of FVIII. The half-life of the FVIII protein linked to or associated with the VWF fragment of the present invention can increase at least about 1.5 times, 1.6 times, 1.7 times, 1.8 times, 1.9 times, 2.0 times, 2.1 times, 2.2 times, 2.3 times, 2.4 times, 2.6 times, 2.7. times, 2.8 times, 2.9 times, 3.0 times, 3.1 times, 3.2 times, 3.3 times, 3.4 times, 3.5 times, 3.6 times, 3.7 times, 3.8 times, 3.9 times, or 4.0 times higher than the half-life of the non-activated FVIII bound to or associated with full-length VWF. In one embodiment, the half-life of the FVIII protein linked to or associated with the VWF fragment in the chimeric protein increases at least about 2 times, 2.5 times, 3.0 times, 3.5 times, 4.0 times, 4.5 times, 5.0 times, 5.5 times, 6.0 times, 7 times, 8 times, 9 times, or 10 times higher than the half-life of the non-activated FVIII bound to or associated with full-length VWF. In another embodiment, the half-life of the FVIII protein linked to or associated with the VWF fragment in the chimeric protein increases about 2 to about 5 times, about 3 to about 10 times, about 5 to about 15 times, about 10 to about 20 times, about 15 to about 25 times, about 20 to about 30 times, about 25 to about 35 times, about 30 to about 40 times, about 35 to about 45 times higher than the half-life of the non-activated FVIII bound to or associated with full-length VWF. In a specific embodiment, the half-life of the FVIII protein linked to or associated with the VWF fragment in the chimeric protein increases at least about 30, 31, 32, 33, 34, 35, 36, 37, 38, 39, or 40 times higher than the half-life of the wild type FVIII in a FVIII and VWF double knockout mouse. In some embodiments, the half-life of the chimeric protein comprising the VWF fragment fused to a first heterologous moiety, e.g., a first Fc region, and a FVIII protein linked to a second heterologous moiety, e.g., a second Fc region is longer than the half-life of a chimeric protein comprising a FVIII protein and two Fc regions, wherein the FVIII protein is linked to one of the two Fc regions (i.e., FVIII monomer-dimer hybrid). In other embodiments, the half-life of the chimeric protein comprising the VWF fragment fused to a first heterologous moiety, e.g., a first Fc region, and a FVIII protein linked to a second heterologous moiety, e.g., a second Fc region is at least about 1.5 times, 2 times, 2.5 times, 3.5 times, 3.6 times, 3.7 times, 3.8 times, 3.9 times, 4.0 times, 4.5 times, or 5.0 times the half-life of a chimeric protein comprising a FVIII protein and two Fc regions, wherein the FVIII protein is linked to one of the two Fc regions (i.e., FVIII monomer-dimer hybrid).

In some embodiments, as a result of the invention the half-life of the FVIII protein is extended compared to a FVIII protein without the VWF fragment or wildtype FVIII. The half-life of the FVIII protein is at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the half-life of a FVIII protein without the VWF fragment. In one embodiment, the half-life of FVIII is about 1.5-fold to about 20-fold, about 1.5 fold to about 15 fold, or about 1.5 fold to about 10 fold longer than the half-life of wild-type FVIII. In another embodiment, the half-life of the FVIII is extended about 2-fold to about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, about 2-fold to about 3-fold, about 2.5-fold to about 10-fold, about 2.5-fold to about 9-fold, about 2.5-fold to about 8-fold, about 2.5-fold to about 7-fold, about 2.5-fold to about 6-fold, about 2.5-fold to about 5-fold, about 2.5-fold to about 4-fold, about 2.5-fold to about 3-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 3-fold to about 4-fold, about 4-fold to about 6 fold, about 5-fold to about 7-fold, or about 6-fold to about 8 fold as compared to wild-type FVIII or a FVIII protein without the VWF fragment. In other embodiments, the half-life of FVIII is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours. In still other embodiments, the half-life of FVIII is about 15 hours to about two weeks, about 16 hours to about one week, about 17 hours to about one week, about 18 hours to about one week, about 19 hours to about one week, about 20 hours to about one week, about 21 hours to about one week, about 22 hours to about one week, about 23 hours to about one week, about 24 hours to about one week, about 36 hours to about one week, about 48 hours to about one week, about 60 hours to about one week, about 24 hours to about six days, about 24 hours to about five days, about 24 hours to about four days, about 24 hours to about three days, or about 24 hours to about two days.

In some embodiments, the average half-life of the FVIII protein per subject is about 15 hours, about 16 hours, about 17 hours, about 18 hours, about 19 hours, about 20 hours, about 21 hours, about 22 hours, about 23 hours, about 24 hours (1 day), about 25 hours, about 26 hours, about 27 hours, about 28 hours, about 29 hours, about 30 hours, about 31 hours, about 32 hours, about 33 hours, about 34 hours, about 35 hours, about 36 hours, about 40 hours, about 44 hours, about 48 hours (2 days), about 54 hours, about 60 hours, about 72 hours (3 days), about 84 hours, about 96 hours (4 days), about 108 hours, about 120 hours (5 days), about six days, about seven days (one week), about eight days, about nine days, about 10 days, about 11 days, about 12 days, about 13 days, or about 14 days.

In a specific embodiment, a half-life of the chimeric protein of the invention is about two fold longer than the half-life of wild-type FVIII or BDD FVIII. In another embodiment, a half-life of the chimeric protein is about three fold longer than the half-life of wild-type FVIII or BDD FVIII.

In addition, the invention provides a method of treating or preventing a bleeding disease or disorder comprising administering an effective amount of the VWF fragment or the chimeric protein (e.g., a chimeric protein comprising the VWF fragment linked to a first heterologous moiety, e.g., a first Fc region, and a FVIII protein linked to a second heterologous moiety, e.g., a second Fc region, wherein the VWF fragment is bound to or associated with the FVIII protein). In one embodiment, the bleeding disease or disorder is selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath. In a specific embodiment, the bleeding disease or disorder is hemophilia A.

The VWF fragment and the chimeric protein comprising an adjunct moiety, e.g., the VWF fragment described herein and a FVIII protein prepared by the invention has many uses as will be recognized by one skilled in the art, including, but not limited to methods of treating a subject having a hemostatic disorder and methods of treating a subject in need of a general hemostatic agent. In one embodiment, the invention relates to a method of treating a subject having a hemostatic disorder comprising administering a therapeutically effective amount of the VWF fragment or the chimeric protein.

The FVIII protein portion in the chimeric protein treats or prevents a hemostatic disorder by serving as a cofactor to Factor IX on a negatively charged phospholipid surface, thereby forming a Xase complex. The binding of activated coagulation factors to a phospholipid surface localizes this process to sites of vascular damage. On a phospholipid surface, Factor VIIIa increases the maximum velocity of Factor X activation by Factor IXa, by approximately 200.000-fold, leading to the large second burst of thrombin generation.

The chimeric protein comprising an adjunct moiety, e.g., a VWF fragment, and a FVIII protein can be used to treat any hemostatic disorder. The hemostatic disorders that may be treated by administration of the chimeric protein of the invention include, but are not limited to, hemophilia A, as well as deficiencies or structural abnormalities relating to Factor VIII. In one embodiment, the hemostatic disorder is hemophilia A.

The chimeric protein comprising an adjunct moiety, e.g., a VWF fragment, and a FVIII protein can be used prophylactically to treat a subject with a hemostatic disorder. The chimeric protein of the invention can be used to treat an acute bleeding episode in a subject with a hemostatic disorder. In another embodiment, the hemostatic disorder can be the result of a defective clotting factor, e.g., von Willebrand's factor. In one embodiment, the hemostatic disorder is an inherited disorder. In another embodiment, the hemostatic disorder is an acquired disorder. The acquired disorder can result from an underlying secondary disease or condition. The unrelated condition can be, as an example, but not as a limitation, cancer, an auto-immune disease, or pregnancy. The acquired disorder can result from old age or from medication to treat an underlying secondary disorder (e.g. cancer chemotherapy).

The invention also relates to methods of treating a subject that does not have a congenital hemostatic disorder, but has a secondary disease or condition resulting in acquisition of a hemostatic disorder, e.g., due to development of an anti-FVIII antibody or a surgery. The invention thus relates to a method of treating a subject in need of a general hemostatic agent comprising administering a therapeutically effective amount of the chimeric protein comprising the VWF fragment and a FVIII protein prepared by the present methods.

The present invention is also related to methods of reducing immunogenicity of FVIII or inducing less immunogenicity against FVIII comprising administering an effective amount of the VWF fragment, the chimeric proteins described herein, or the polynucleotides encoding the same.

In one embodiment, the subject in need of a general hemostatic agent is undergoing, or is about to undergo, surgery. The chimeric protein comprising the VWF fragment and a FVIII protein can be administered prior to, during, or after surgery as a prophylactic regimen. The chimeric protein comprising the VWF fragment and a FVIII protein can be administered prior to, during, or after surgery to control an acute bleeding episode.

The chimeric protein comprising the VWF fragment and a FVIII protein can be used to treat a subject having an acute bleeding episode who does not have a hemostatic disorder. The acute bleeding episode can result from severe trauma, e.g., surgery, an automobile accident, wound, laceration gun shot, or any other traumatic event resulting in uncontrolled bleeding. Non limiting examples of bleeding episodes include a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath, and any combinations thereof.

In prophylactic applications, one or more compositions containing the chimeric protein or the VWF fragment of the invention or a cocktail thereof are administered to a patient not already in the disease state to enhance the patient's resistance or reduce symptoms associated with a disease or disorder. Such an amount is defined to be a "prophylactic effective dose." In therapeutic applications, a relatively high dosage (e.g., from about 1 to 400 mg/kg of polypeptide per dose, with dosages of from 5 to 25 mg being more commonly used for radioimmunoconjugates and higher doses for cytotoxin-drug modified polypeptides) at relatively short intervals is sometimes required until progression of the disease is reduced or terminated, and until the patient shows partial or complete amelioration of symptoms of disease. Thereafter, the patient can be administered a prophylactic regime.

In some embodiments, a chimeric protein, a VWF fragment, or a composition of the invention is used for on-demand treatment, which includes treatment for a bleeding episode, hemarthrosis, muscle bleed, oral bleed, hemorrhage, hemorrhage into muscles, oral hemorrhage, trauma, trauma capitis (head trauma), gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. The subject may be in need of surgical prophylaxis, peri-operative management, or treatment for surgery. Such surgeries include, e.g., minor surgery, major surgery, tooth extraction, tonsillectomy, inguinal herniotomy, synovectomy, total knee replacement, craniotomy, osteosynthesis, trauma surgery, intracranial surgery, intra-abdominal surgery, intrathoracic surgery, or joint replacement surgery.

In one embodiment, the chimeric protein comprising the VWF fragment and a FVIII protein is administered intravenously, subcutaneously, intramuscularly, or via any mucosal surface, e.g., orally, sublingually, buccally, nasally, rectally, vaginally or via pulmonary route. The chimeric protein comprising the VWF fragment and a FVIII protein can be implanted within or linked to a biopolymer solid support that allows for the slow release of the chimeric protein to the site of bleeding or implanted into bandage/dressing. The dose of the chimeric protein comprising the VWF fragment and a FVIII protein will vary depending on the subject and upon the particular route of administration used. Dosages can range from 0.1 to 100,000 µg/kg body weight. In one embodiment, the dosing range is 0.1-1,000 µg/kg. In another embodiment, the dosing range is 0.1-500 µg/kg. The protein can be administered continuously or at specific timed intervals. In vitro assays may be employed to determine optimal dose ranges and/or schedules for administration. In vitro assays that measure clotting factor activity are known in the art, e.g., STA-CLOT VIIa-rTF clotting assay or ROTEM clotting assay. Additionally, effective doses may be extrapolated from dose-response curves obtained from animal models, e.g., a hemophiliac dog (Mount et al. 2002, *Blood* 99(8):2670).

Having now described the present invention in detail, the same will be more clearly understood by reference to the following examples, which are included herewith for purposes of illustration only and are not intended to be limiting of the invention. All patents and publications referred to herein are expressly incorporated by reference.

EXAMPLES

Throughout the examples, the following materials and methods were used unless otherwise stated.

Materials and Methods

In general, the practice of the present invention employs, unless otherwise indicated, conventional techniques of chemistry, biophysics, molecular biology, recombinant DNA technology, immunology (especially, e.g., antibody technology), and standard techniques in electrophoresis. See, e.g., Sambrook, Fritsch and Maniatis, Molecular Cloning Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., CS.H.L. Press, Pub. (1999); and Current Protocols in Molecular Biology, eds. Ausubel et al., John Wiley & Sons (1992).

Example 1

Cloning Different VWF Domains (FIG. 1)

(a) Cloning pSYN-VWF-001, 002, 003 and 004 pSYN-VWF-001 through 004 contain nucleotide sequences encoding VWF fragments, which are amino acids 1-276 (001), amino acids 1-477 (002), amino acids 1-511 (003) and amino acids 1-716 (004) VWF-D'D3A protein sequence. Amino acid numbering represents the mature VWF sequence without propeptide and corresponds to amino acids 764-1039 (001), amino acids 764-1240 (002), amino acids 764-1274 (003), and amino acids 764-1479 (004) of SEQ ID NO: 2, respectively. All four constructs have the FVIII signal peptide at N-terminus, which allows proper secretion of the synthesized protein and followed by a 6×His tag at C-terminus, which is used for protein purification. Above constructs were synthesized by using following primer combinations:

```
pSYN VWF-001:
ESC48-Fwd-VWF-D'D3 with VIII signal and BsiW1 site
                                         (SEQ ID NO: 57)
TCGCGACGTACGGCCGCCACCATGCAAATAGAGCTCTCCACCTGCTTCTT
TCTGTGCCTTTTGCGATTCTGCTTTAGCCTATCCTGTCGGCCCCCCATG ESC50-Rev-VWF-partial D'D3 (1-276 amino acid) with
6 His and Not1 site
                                         (SEQ ID NO: 58)
TGACCTCGAGCGGCCGCTCAGTGGTGATGGTGATGATGCAGAGGCACTTT
TCTGGTGTCAGCACACTG pSYN VWF-002:
ESC48-Fwd-VWF-D'D3 with VIII signal and BsiW1 site
                                         (SEQ ID NO: 59)
TCGCGACGTACGGCCGCCACCATGCAAATAGAGCTCTCCACCTGCTTCTT
TCTGTGCCTTTTGCGATTCTGCTTTAGCCTATCCTGTCGGCCCCCCATG ESC51-Rev-VWF D'D3 (1-477 amino acid) with 6His
and Not 1 site
                                         (SEQ ID NO: 60)
TGACCTCGAGCGGCCGCTCAGTGGTGATGGTGATGATGCGGCTCCTGGCA
GGCTTCACAGGTGAGGTTGACAAC pSYN VWF-003:
ESC48-Fwd-VWF-D'D3 with VIII signal and BsiW1 site
                                         (SEQ ID NO: 61)
TCGCGACGTACGGCCGCCACCATGCAAATAGAGCTCTCCACCTGCTTCTT
TCTGTGCCTTTTGCGATTCTGCTTTAGCCTATCCTGTCGGCCCCCCATG ESC52-Rev-VWF-D'D3 Partial A1 (1-511 amino acids)
with 6His and Not1 site
                                         (SEQ ID NO: 62)
TGACCTCGAGCGGCCGCTCAGTGGTGATGGTGATGATGCCTGCTGCAGTA
GAAATCGTGCAACGGCGGTTC pSYN VWF-004:
ESC48-Fwd-VWF-D'D3 with VIII signal and BsiW1 site
                                         (SEQ ID NO: 63)
TCGCGACGTACGGCCGCCACCATGCAAATAGAGCTCTCCACCTGCTTCTT
TCTGTGCCTTTTGCGATTCTGCTTTAGCCTATCCTGTCGGCCCCCCATG ESC53-Rev-VWF-D'D3A1 (1-716 amino acids) with 6His
and Not1 site
                                         (SEQ ID NO: 64)
TGACCTCGAGCGGCCGCTCAGTGGTGATGGTGATGATGGCCCACAGTGAC
TTGTGCCATGTGGGG
```

Proteins from VWF-001, 002, 003 and 004 constructs are supposed to exists as a monomer.

A 50 μl PCR reaction was carried out with ESC 48/ESC50, ESC 48/ESC 51, ESC 48/ESC52, ESC48/ESC53 primer combinations and full length VWF plasmid as the template, using the 2 step PCR amplification cycle: 94° C. 2 minutes; 21 cycles of (96° C. 30 seconds, 68° C. 2 minute). Correct sized bands (~960 bp for VWF 001; 1460 for VWF 002, 1520 bp for VWF 003; and 2150 bp for VWF 004) were gel purified with a Gel Extraction kit (Qiagen, Valencia, Calif.) and cloned into the BsiWI and Not1 restriction sites of pcDNA 4 to generate pSYN-VWF 001,002,003 and 004, respectively.

(b) Cloning pSYN-VWF-006 pSYN-VWF-006 contains D1D2D'D3-CK (cysteine knot) domain of VWF. To clone this construct, synthesis of DNA fragment containing a portion of D3 domain and CK domain was outsourced (Genscript-sequence id number 122026, shown below). A fragment of Genscript construct was sub-cloned into the BamHI/EcoRV digested pSYN-VWF 008, i.e., the vector coding full-length VWF.

```
Genscript-Sequence number-122026
                                         (SEQ ID NO: 65)
GGATCCTAGTGGGGAATAAGGGATGCAGCCACCCCTCAGT-
GAAATGCAAGAA
ACGGGTCACCATCCTGGTGGAGGGAGGAGAGATTGAGCTGTTTGACGGG-
GAG
GTGAATGTGAAGAGGCCCATGAAGGATGAGACTCACTTTGAGGTGGTG-
GAGT
CTGGCCGGTACATCAT-
TCTGCTGCTGGGCAAAGCCCTCTCCGTGGTCTGGGA
CCGCCACCTGAGCATCTCCGTGGTCCTGAAGCAGACATACCAG-
GAGAAAGTG
TGTGGCCTGTGTGGGAATTTTGATGGCATCCAGAACAATGACCT-
CACCAGCA
GCAACCTCCAAGTGGAGGAAGACCCTGTGGACTTTGGGAACTCCTG-
GAAAGT
GAGCTGCAGTGTGCTGACACCAGAAAAGTGCCTCTGGACT-
CATCCCCTGCC
ACCTGCCATAACAACATCATGAAGCAGACGATGGTGGAT-
TCCTCCTGTAGAA
TCCT-
TACCAGTGACGTCTTCCAGGACTGCAACAAGCTGGTGGACCCCGAGCC
ATATCTGGATGTCTGCATTTACGACACCTGCTCCTGTGAGTCCAT-
TGGGGAC
TGCCCTGCTTCTGCGACACCATTGCTGCCTATGCC-
CACGTGTGTGCCCAGC
ATGGCAAGGTGGTGACCTGGAGGACGGCCACAT-
TGTGCCCCAGAGCTGCGA
GGAGAGGAATCTCCGGGAGAACGGGTATGAGTGTGAGTGGCGC-
TATAACAGC
TGTGCACCTGCCTGTCAAGTCACGTGTCAGCACCCTGAGC-
CACTGGCCTGCC
CTGTGCAGTGTGTGGAGGGCTGCCATGCCCACTGCCCTCCAGG-
GAAAATCCT
GGATGAGCTTTTGCAGACCTGCGTTGACCCTGAAGACTGTCCAGTGTGT-
GAG
GTGGCTGGCCGGCGTTTTGCCTCAGGAAAGAAAGTCACCTT-
GAATCCCAGTG
ACCCTGAGCACTGCCAGATTTGCCACTGTGATGTTGTCAACCT-
CACCTGTGA
AGCCTGCCAGGAGCCGGGAGGCCTGGTGGTGCCTCCCACA-
GATGCCCCGGTG
AGCCCCACCACTCTGTATGTGGATGAGACGCTCCAGGATGGCTGTGA-
TACTC
```

```
-continued
ACTTCTGCAAGGTCAATGAGAGAGGAGAGTACTTCTGGGAGAAGAGGGT-
CAC
AGGCTGCCCACCCTTTGATGAACACAAGTGTCTTGCTGAGG-
GAGGTAAAATT
ATGAAAATTCCAGGCACCTGCTGTGACACATGTGAGGAGCCT-
GAGTGCAACG
ACATCACTGCCAGGCTGCAGTATGTCAAGGTGGGAAGCTGTAAGTCT-
GAAGT
AGAGGTGGATATC
```

(c) Cloning pSYN-VWF-009, 010, 011, 012 and 013 pSYN VWF 008 construct contains the full-length VWF sequence in pcDNA 3.1 (amino acids 1-2813 of SEQ ID NO: 2). It includes 763 amino acid propeptide (i.e., D1D2 domains) followed by remaining 2050 amino acids sequence of mature VWF. pSYN-VWF-009, 010, 011 and 012 contain the same coding sequences as VWF 001, 002, 003 and 004, respectively, but additionally has D1D2 domains (VWF propeptide) at the N-terminus instead of the FVIII signal peptide. pSYN-VWF-008 has a BamH1 site at Arg907 and Not1 site at the end of coding region (after stop codon). pSYN-VWF-008, 001, 002, 003 and 004 were digested with BamH1 and Not1 restriction enzymes. Inserts from pSYN-VWF-001 (423 bp), pSYN-VWF-002 (1026 bp), pSYN-VWF-003 (1128 bp) and pSYN-VWF-004 (1743 bp) were ligated into bamH1/Not1 digested pSYN-VWF-008 (8242 bp) to obtain pSYN-VWF-009 (D1D2D'D3: amino acid 1-1039 of SEQ ID NO: 2); pSYN-VWF-010 (D1D2D'D3: amino acid 1-1240 of SEQ ID NO: 2); pSYN-VWF-011 (D1D2D'D3: amino acid 1-1274 of SEQ ID NO: 2); pSYN-VWF-012 (D1D2D'D3: amino acid 1-1479). All 4 constructs have 6×His tag at the C-terminus. In transfected cells, pSYN-VWF-009, 010, 011, and 012 are synthesized with propeptide, but due to intracellular processing, the secreted products do not contain any propeptide (D1D2). The protein expressed from the VWF-009 construct exists as a monomer and the proteins expressed from the VWF-010, 011, and 012 constructs are supposed to exist as dimers, as shown in FIG. 6 and FIG. 7 using VWF-009 and VWF-010 as examples, respectively.

pSYN-VWF-010 was used to generate pSYN-VWF-013, which has two point mutations at C336A and C379A corresponding to SEQ ID NO: 73 (amino acid numbering represents mature VWF sequence without D1D2 domain-VWF sequence 2). These mutations are predicted to prevent dimerization of VWF D'D3 domain.

(d) Cloning pSYN-VWF-025 and 029 pSYN-VWF-025 contains wild type D1D2D'D3 sequences of full-length VWF in pLIVE vector while pSYN-VWF-029 contains D1D2D'D3 domains with C336A/C379A mutations in pLIVE vector. For cloning pSYN-VWF-025 and 029, the following primer combination was used:

```
ESC 89-fwd with Nhe1 site =
                                    (SEQ ID NO: 66)
    CTCACTATAGGGAGACCCAAGCTGGCTAGCCG ESC 91-rev with Sal1 =
                                    (SEQ ID NO: 67)
    CTGGATCCCGGGAGTCGACTCGTCAGTGGTGATGGTGATGATG
```

A 50 µl PCR reaction was carried out with ESC 89/ESC91 primer combinations and either pSYN-VWF-010 (for pSYN-VWF-025) or pSYN-VWF-013 (for pSYN-VWF-029) plasmid as the template using the 3 step PCR amplification cycle: 94° C.-2 minutes; 21 cycles of (96° C.-30 seconds, 55° C.-30 second, 68° C.-4 minutes). The expected sized band (~3800 bp) was gel purified with a Gel Extraction kit (Qiagen, Valencia, Calif.) and cloned into the Nhe1 and Sal1 restriction sites of pLIVE-Mirus vector (Invitrogen, Carlsbad, Calif.) to generate pSYN-VWF-025 and 029.

(e) Cloning pSYN-VWF-031 pSYN-VWF-031 is a D1D2D'D3(C336A/C379A)-Fc construct which has a 48 amino acid long thrombin cleavable linker (8×GGGGS (SEQ ID NO: 110)+ thrombin site) in between the VWF D1D2D'D3(C336A/C379A) and the Fc sequences. To make this construct, VWF-Fc region was amplified from construct pSYN-FVIII-064 (refer FVIII-VWF construct below). pSYN-FVIII-VWF was digested with Xba1 and Nhe1. The resulting insert region of 4165 bp, containing the VWF fragment and Fc region, was used as a template for amplifying the VWF and Fc region by primer combinations LW 22/LW23.

```
LW 22-FWD-VWF-D'D3 with FVIII signal sequence and
BsiW1 site
                                    (SEQ ID NO: 68)
GCGCCGGCCGTACGATGCAAATAGAGCTCTCCACCTGCTTCTTTCTGTG
CCTTTTGCGATTCTGCTTTAGCCTATCCTGTCGGCCCCCATG LW 23-Rev-Fc with stop codon and Not1 site
                                    (SEQ ID NO: 69)
TCATCAATGTATCTTATCATGTCTGAATTCGCGGCCGCTCATTTACC
```

Nucleotide Sequence of VWF 031 (SEQ ID NO: 108)

```
  1 ATGATTCCTG CCAGATTTGC CGGGGTGCTG CTTGCTCTGG
    CCCTCATTTT

51 GCCAGGGACC CTTTGTGCAG AAGGAACTCG CGGCAGGTCA
    TCCACGGCCC

101 GATGCAGCCT TTTCGGAAGT GACTTCGTCA ACACCTTTGA
    TGGGAGCATG

151 TACAGCTTTG CGGGATACTG CAGTTACCTC CTGGCAGGGG
    GCTGCCAGAA

201 ACGCTCCTTC TCGATTATTG GGGACTTCCA GAATGGCAAG
    AGAGTGAGCC

251 TCTCCGTGTA TCTTGGGGAA TTTTTTGACA TCCATTTGTT
    TGTCAATGGT

301 ACCGTGACAC AGGGGGACCA AAGAGTCTCC ATGCCCTATG
    CCTCCAAAGG

351 GCTGTATCTA GAAACTGAGG CTGGGTACTA CAAGCTGTCC
    GGTGAGGCCT

401 ATGGCTTTGT GGCCAGGATC GATGGCAGCG GCAACTTTCA
    AGTCCTGCTG

451 TCAGACAGAT ACTTCAACAA GACCTGCGGG CTGTGTGGCA
    ACTTTAACAT

501 CTTTGCTGAA GATGACTTTA TGACCCAAGA AGGGACCTTG
    ACCTCGGACC

551 CTTATGACTT TGCCAACTCA TGGGCTCTGA GCAGTGGAGA
    ACAGTGGTGT

601 GAACGGGCAT CTCCTCCCAG CAGCTCATGC AACATCTCCT
    CTGGGGAAAT

651 GCAGAAGGGC CTGTGGGAGC AGTGCCAGCT TCTGAAGAGC
    ACCTCGGTGT

701 TTGCCCGCTG CCACCCTCTG GTGGACCCCG AGCCTTTTGT
    GGCCCTGTGT
```

```
 751  GAGAAGACTT TGTGTGAGTG TGCTGGGGGG CTGGAGTGCG
      CCTGCCCTGC

801  CCTCCTGGAG TACGCCCGGA CCTGTGCCCA GGAGGGAATG
      GTGCTGTACG

851  GCTGGACCGA CCACAGCGCG TGCAGCCCAG TGTGCCCTGC
      TGGTATGGAG

901  TATAGGCAGT GTGTGTCCCC TTGCGCCAGG ACCTGCCAGA
      GCCTGCACAT

951  CAATGAAATG TGTCAGGAGC GATGCGTGGA TGGCTGCAGC
      TGCCCTGAGG

1001  GACAGCTCCT GGATGAAGGC CTCTGCGTGG AGAGCACCGA
      GTGTCCCTGC

1051  GTGCATTCCG GAAAGCGCTA CCCTCCCGGC ACCTCCCTCT
      CTCGAGACTG

1101  CAACACCTGC ATTTGCCGAA ACAGCCAGTG GATCTGCAGC
      AATGAAGAAT

1151  GTCCAGGGGA GTGCCTTGTC ACTGGTCAAT CCCACTTCAA
      GAGCTTTGAC

1201  AACAGATACT TCACCTTCAG TGGGATCTGC CAGTACCTGC
      TGGCCCGGGA

1251  TTGCCAGGAC CACTCCTTCT CCATTGTCAT TGAGACTGTC
      CAGTGTGCTG

1301  ATGACCGCGA CGCTGTGTGC ACCCGCTCCG TCACCGTCCG
      GCTGCCTGGC

1351  CTGCACAACA GCCTTGTGAA ACTGAAGCAT GGGGCAGGAG
      TTGCCATGGA

1401  TGGCCAGGAC ATCCAGCTCC CCTCCTGAA AGGTGACCTC
      CGCATCCAGC

1451  ATACAGTGAC GGCCTCCGTG CGCCTCAGCT ACGGGGAGGA
      CCTGCAGATG

1501  GACTGGGATG GCCGCGGGAG GCTGCTGGTG AAGCTGTCCC
      CCGTCTATGC

1551  CGGGAAGACC TGCGGCCTGT GTGGGAATTA CAATGGCAAC
      CAGGGCGACG

1601  ACTTCCTTAC CCCCTCTGGG CTGGCGGAGC CCCGGGTGGA
      GGACTTCGGG

1651  AACGCCTGGA AGCTGCACGG GGACTGCCAG GACCTGCAGA
      AGCAGCACAG

1701  CGATCCCTGC GCCCTCAACC CGCGCATGAC CAGGTTCTCC
      GAGGAGGCGT

1751  GCGCGGTCCT GACGTCCCCC ACATTCGAGG CCTGCCATCG
      TGCCGTCAGC

1801  CCGCTGCCCT ACCTGCGGAA CTGCCGCTAC GACGTGTGCT
      CCTGCTCGGA

1851  CGGCCGCGAG TGCCTGTGCG GCGCCCTGGC CAGCTATGCC
      GCGGCCTGCG

1901  CGGGGAGAGG CGTGCGCGTC GCGTGGCGCG AGCCAGGCCG
      CTGTGAGCTG

1951  AACTGCCCGA AAGGCCAGGT GTACCTGCAG TGCGGGACCC
      CCTGCAACCT

2001  GACCTGCCGC TCTCTCTCTT ACCCGGATGA GGAATGCAAT
      GAGGCCTGCC

2051  TGGAGGGCTG CTTCTGCCCC CCAGGGCTCT ACATGGATGA
      GAGGGGGGAC
```

```
2101  TGCGTGCCCA AGGCCCAGTG CCCCTGTTAC TATGACGGTG
      AGATCTTCCA

2151  GCCAGAAGAC ATCTTCTCAG ACCATCACAC CATGTGCTAC
      TGTGAGGATG

2201  GCTTCATGCA CTGTACCATG AGTGGAGTCC CCGGAAGCTT
      GCTGCCTGAC

2251  GCTGTCCTCA GCAGTCCCCT GTCTCATCGC AGCAAAAGGA
      GCCTATCCTG

2301  TCGGCCCCCC ATGGTCAAGC TGGTGTGTCC CGCTGACAAC
      CTGCGGGCTG

2351  AAGGGCTCGA GTGTACCAAA ACGTGCCAGA ACTATGACCT
      GGAGTGCATG

2401  AGCATGGGCT GTGTCTCTGG CTGCCTCTGC CCCCCGGGCA
      TGGTCCGGCA

2451  TGAGAACAGA TGTGTGGCCC TGGAAAGGTG TCCCTGCTTC
      CATCAGGGCA

2501  AGGAGTATGC CCCTGGAGAA ACAGTGAAGA TTGGCTGCAA
      CACTTGTGTC

2551  TGTCGGGACC GGAAGTGGAA CTGCACAGAC CATGTGTGTG
      ATGCCACGTG

2601  CTCCACGATC GGCATGGCCC ACTACCTCAC CTTCGACGGG
      CTCAAATACC

2651  TGTTCCCCGG GGAGTGCCAG TACGTTCTGG TGCAGGATTA
      CTGCGGCAGT

2701  AACCCTGGGA CCTTTCGGAT CCTAGTGGGG AATAAGGGAT
      GCAGCCACCC

2751  CTCAGTGAAA TGCAAGAAAC GGGTCACCAT CCTGGTGGAG
      GGAGGAGAGA

2801  TTGAGCTGTT TGACGGGGAG GTGAATGTGA AGAGGCCCAT
      GAAGGATGAG

2851  ACTCACTTTG AGGTGGTGGA GTCTGGCCGG TACATCATTC
      TGCTGCTGGG

2901  CAAAGCCCTC TCCGTGGTCT GGGACCGCCA CCTGAGCATC
      TCCGTGGTCC

2951  TGAAGCAGAC ATACCAGGAG AAAGTGTGTG GCCTGTGTGG
      GAATTTTGAT

3001  GGCATCCAGA ACAATGACCT CACCAGCAGC AACCTCCAAG
      TGGAGGAAGA

3051  CCCTGTGGAC TTTGGGAACT CCTGGAAAGT GAGCTCGCAG
      TGTGCTGACA

3101  CCAGAAAAGT GCCTCTGGAC TCATCCCCTG CCACCTGCCA
      TAACAACATC

3151  ATGAAGCAGA CGATGGTGGA TTCCTCCTGT AGAATCCTTA
      CCAGTGACGT

3201  CTTCCAGGAC TGCAACAAGC TGGTGGACCC CGAGCCATAT
      CTGGATGTCT

3251  GCATTTACGA CACCTGCTCC TGTGAGTCCA TTGGGGACTG
      CGCCGCATTC

3301  TGCGACACCA TTGCTGCCTA TGCCCACGTG TGTGCCCAGC
      ATGGCAAGGT

3351  GGTGACCTGG AGGACGGCCA CATTGTGCCC CCAGAGCTGC
      GAGGAGAGGA

3401  ATCTCCGGGA GAACGGGTAT GAGGCTGAGT GGCGCTATAA
      CAGCTGTGCA
```

```
3451  CCTGCCTGTC AAGTCACGTG TCAGCACCCT GAGCCACTGG
      CCTGCCCTGT

3501  GCAGTGTGTG GAGGGCTGCC ATGCCCACTG CCCTCCAGGG
      AAAATCCTGG

3551  ATGAGCTTTT GCAGACCTGC GTTGACCCTG AAGACTGTCC
      AGTGTGTGAG

3601  GTGGCTGGCC GGCGTTTTGC CTCAGGAAAG AAAGTCACCT
      TGAATCCCAG

3651  TGACCCTGAG CACTGCCAGA TTTGCCACTG TGATGTTGTC
      AACCTCACCT

3701  GTGAAGCCTG CCAGGAGCCG ATATCTGGCG GTGGAGGTTC
      CGGTGGCGGG

3751  GGATCCGGCG GTGGAGGTTC CGGCGGTGGA GGTTCCGGTG
      GCGGGGGATC

3801  CGGTGGCGGG GGATCCCTGG TCCCCCGGGG CAGCGGCGGT
      GGAGGTTCCG

3851  GTGGCGGGGG ATCCGACAAA ACTCACACAT GCCCACCGTG
      CCCAGCTCCA

3901  GAACTCCTGG GCGGACCGTC AGTCTTCCTC TTCCCCCCAA
      AACCCAAGGA

3951  CACCCTCATG ATCTCCCGGA CCCCTGAGGT CACATGCGTG
      GTGGTGGACG

4001  TGAGCCACGA AGACCCTGAG GTCAAGTTCA ACTGGTACGT
      GGACGGCGTG

4051  GAGGTGCATA ATGCCAAGAC AAAGCCGCGG GAGGAGCAGT
      ACAACAGCAC

4101  GTACCGTGTG GTCAGCGTCC TCACCGTCCT GCACCAGGAC
      TGGCTGAATG

4151  GCAAGGAGTA CAAGTGCAAG GTCTCCAACA AAGCCCTCCC
      AGCCCCCATC

4201  GAGAAAACCA TCTCCAAAGC CAAAGGGCAG CCCCGAGAAC
      CACAGGTGTA

4251  CACCCTGCCC CCATCCCGGG ATGAGCTGAC CAAGAACCAG
      GTCAGCCTGA

4301  CCTGCCTGGT CAAAGGCTTC TATCCCAGCG ACATCGCCGT
      GGAGTGGGAG

4351  AGCAATGGGC AGCCGGAGAA CAACTACAAG ACCACGCCTC
      CCGTGTTGGA

4401  CTCCGACGGC TCCTTCTTCC TCTACAGCAA GCTCACCGTG
      GACAAGAGCA

4451  GGTGGCAGCA GGGGAACGTC TTCTCATGCT CCGTGATGCA
      TGAGGCTCTG

4501  CACAACCACT ACACGCAGAA GAGCCTCTCC CTGTCTCCGG
      GTAAATGA
```

Protein Sequence of VWF 031 (SEQ ID NO: 109)

```
   1  MIPARFAGVL LALALILPGT LCAEGTRGRS STARCSLFGS
      DFVNTFDGSM

51  YSFAGYCSYL LAGGCQKRSF SIIGDFQNGK RVSLSVYLGE
      FFDIHLFVNG

101  TVTQGDQRVS MPYASKGLYL ETEAGYYKLS GEAYGFVARI
      DGSGNFQVLL

151  SDRYFNKTCG LCGNFNIFAE DDFMTQEGTL TSDPYDFANS
      WALSSGEQWC

201  ERASPPSSSC NISSGEMQKG LWEQCQLLKS TSVFARCHPL
      VDPEPFVALC

251  EKTLCECAGG LECACPALLE YARTCAQEGM VLYGWTDHSA
      CSPVCPAGME

301  YRQCVSPCAR TCQSLHINEM CQERCVDGCS CPEGQLLDEG
      LCVESTECPC

351  VHSGKRYPPG TSLSRDCNTC ICRNSQWICS NEECPGECLV
      TGQSHFKSFD

401  NRYFTFSGIC QYLLARDCQD HSFSIVIETV QCADDRDAVC
      TRSVTVRLPG

451  LHNSLVKLKH GAGVAMDGQD IQLPLLKGDL RIQHTVTASV
      RLSYGEDLQM

501  DWDGRGRLLV KLSPVYAGKT CGLCGNYNGN QGDDFLTPSG
      LAEPRVEDFG

551  NAWKLHGDCQ DLQKQHSDPC ALNPRMTRFS EEACAVLTSP
      TFEACHRAVS

601  PLPYLRNCRY DVCSCSDGRE CLCGALASYA AACAGRGVRV
      AWREPGRCEL

651  NCPKGQVYLQ CGTPCNLTCR SLSYPDEECN EACLEGCFCP
      PGLYMDERGD

701  CVPKAQCPCY YDGEIFQPED IFSDHHTMCY CEDGFMHCTM
      SGVPGSLLPD

751  AVLSSPLSHR SKRSLSCRPP MVKLVCPADN LRAEGLECTK
      TCQNYDLECM

801  SMGCVSGCLC PPGMVRHENR CVALERCPCF HQGKEYAPGE
      TVKIGCNTCV

851  CRDRKWNCTD HVCDATCSTI GMAHYLTFDG LKYLFPGECQ
      YVLVQDYCGS

901  NPGTFRILVG NKGCSHPSVK CKKRVTILVE GGEIELFDGE
      VNVKRPMKDE

951  THFEVVESGR YIILLLGKAL SVVWDRHLSI SVVLKQTYQE
      KVCGLCGNFD

1001  GIQNNDLTSS NLQVEEDPVD FGNSWKVSSQ CADTRKVPLD
      SSPATCHNNI

1051  MKQTMVDSSC RILTSDVFQD CNKLVDPEPY LDVCIYDTCS
      CESIGDCAAF

1101  CDTIAAYAHV CAQHGKVVTW RTATLCPQSC EERNLRENGY
      EAEWRYNSCA

1151  PACQVTCQHP EPLACPVQCV EGCHAHCPPG KILDELLQTC
      VDPEDCPVCE

1201  VAGRRFASGK KVTLNPSDPE HCQICHCDVV NLTCEACQEP
      ISGGGGSGGG

1251  GSGGGGSGGG GSGGGGSGGG GSLVPRGSGG GGSGGGGSDK
      THTCPPCPAP

1301  ELLGGPSVFL FPPKPKDTLM ISRTPEVTCV VVDVSHEDPE
      VKFNWYVDGV

1351  EVHNAKTKPR EEQYNSTYRV VSVLTVLHQD WLNGKEYKCK
      VSNKALPAPI

1401  EKTISKAKGQ PREPQVYTLP PSRDELTKNQ VSLTCLVKGF
      YPSDIAVEWE
```

```
1451 SNGQPENNYK TTPPVLDSDG SFFLYSKLTV DKSRWQQGNV
     FSCSVMHEAL

1501 HNHYTQKSLS LSPGK*
```

| DNA construct | Linker between VWF and Fc |
|---|---|
| VWF035 | 73 aa = IS{11X(GGGGS)} LVPRGSGGGSGGGGS (SEQ ID NO: 96) |
| VWF036 | 98 aa = IS{16X(GGGGS)} LVPRGSGGGSGGGGS (SEQ ID NO: 97) |

VWF = D'D3 (1-477aa with C336A/C379A)

The PCR product obtained from LW22/LW23 amplification (~2300 bp) was cloned in BsiW1/Not1 digested pSYN-VWF-002 to obtain pSYN-VWF-014 intermediate. pSYN-VWF-014 contains FVIII signal peptide-D'D3-20 amino acid thrombin cleavable linker followed by the Fc region.

To generate the D1D2D'D3-Fc construct, the D1D2D'D3 region was amplified from pSYN-VWF-013 using primer combination LW24/LW27 by standard PCR method.

```
LW24-Fwd-VWF D1D2D'D3 cloning oligo with BsiW1 site
                                     (SEQ ID NO: 70)
GCGCCGGCCGTACGATGATTCCTGCCAGATTTGCCGGGGTG LW27-Rev-VWF D'D3 oligo with EcoRV
                                     (SEQ ID NO: 71)
CCACCGCCAGATATCGGCTCCTGGCAGGCTTCACAGGTGAG
```

The PCR product obtained from LW22/LW23 amplification (~3750 bp) was cloned in BsiW1/EcoRV digested pSYN-VWF-014 to obtain pSYN-VWF-015 intermediate. The linker length between the VWF fragment and Fc region was changed to obtain pSYN-VWF-031.

Full length VWF protein sequence is shown at Table 1.

VWF-D1D2D'D3 Protein Sequence 1 b (SEQ ID NO: 72)

```
   1 MIPARFAGVL LALALILPGT LCAEGTRGRS STARCSLFGS
     DFVNTFDGSM

51 YSFAGYCSYL LAGGCQKRSF SIIGDFQNGK RVSLSVYLGE
     FFDIHLFVNG

101 TVTQGDQRVS MPYASKGLYL ETEAGYYKLS GEAYGFVARI
     DGSGNFQVLL

151 SDRYFNKTCG LCGNFNIFAE DDFMTQEGTL TSDPYDFANS
     WALSSGEQWC

201 ERASPPSSSC NISSGEMQKG LWEQCQLLKS TSVFARCHPL
     VDPEPFVALC

251 EKTLCECAGG LECACPALLE YARTCAQEGM VLYGWTDHSA
     CSPVCPAGME

301 YRQCVSPCAR TCQSLHINEM CQERCVDGCS CPEGQLLDEG
     LCVESTECPC

351 VHSGKRYPPG TSLSRDCNTC ICRNSQWICS NEECPGECLV
     TGQSHFKSFD

401 NRYFTFSGIC QYLLARDCQD HSFSIVIETV QCADDRDAVC
     TRSVTVRLPG

451 LHNSLVKLKH GAGVAMDGQD IQLPLLKGDL RIQHTVTASV
     RLSYGEDLQM
```

-continued

```
 501 DWDGRGRLLV KLSPVYAGKT CGLCGNYNGN QGDDFLTPSG
     LAEPRVEDFG

551 NAWKLHGDCQ DLQKQHSDPC ALNPRMTRFS EEACAVLTSP
     TFEACHRAVS

601 PLPYLRNCRY DVCSCSDGRE CLCGALASYA AACAGRGVRV
     AWREPGRCEL

651 NCPKGQVYLQ CGTPCNLTCR SLSYPDEECN EACLEGCFCP
     PGLYMDERGD

701 CVPKAQCPCY YDGEIFQPED IFSDHHTMCY CEDGFMHCTM
     SGVPGSLLPD

751 AVLSSPLSHR SKRSLSCRPP MVKLVCPADN LRAEGLECTK
     TCQNYDLECM

801 SMGCVSGCLC PPGMVRHENR CVALERCPCF HQGKEYAPGE
     TVKIGCNTCV

851 CRDRKWNCTD HVCDATCSTI GMAHYLTFDG LKYLFPGECQ
     YVLVQDYCGS

901 NPGTFRILVG NKGCSHPSVK CKKRVTILVE GGEIELFDGE
     VNVKRPMKDE

951 THFEVVESGR YIILLLGKAL SVVWDRHLSI SVVLKQTYQE
     KVCGLCGNFD

1001 GIQNNDLTSS NLQVEEDPVD FGNSWKVSSQ CADTRKVPLD
     SSPATCHNNI

1051 MKQTMVDSSC RILTSDVFQD CNKLVDPEPY LDVCIYDTCS
     CESIGDCACF

1101 CDTIAAYAHV CAQHGKVVTW RTATLCPQSC EERNLRENGY
     ECEWRYNSCA

1157 PACQVTCQHP EPLACPVQCV EGCHAHCPPG KILDELLQTC
     VDPEDCPVCE

1201 VAGRRFASGK KVTLNPSDPE HCQICHCDVV NLTCEACQEP*
```

VWF-D'D3 Protein Sequence 2 (SEQ ID NO: 73)

```
   1 SLSCRPPMVK LVCPADNLRA EGLECTKTCQ NYDLECMSMG
     CVSGCLCPPG

51 MVRHENRCVA LERCPCFHQG KEYAPGETVK IGCNTCVCRD
     RKWNCTDHVC

101 DATCSTIGMA HYLTFDGLKY LFPGECQYVL VQDYCGSNPG
     TFRILVGNKG

151 CSHPSVKCKK RVTILVEGGE IELFDGEVNV KRPMKDETHF
     EVVESGRYII

201 LLLGKALSVV WDRHLSISVV LKQTYQEKVC GLCGNFDGIQ
     NNDLTSSNLQ

251 VEEDPVDFGN SWKVSSQCAD TRKVPLDSSP ATCHNNIMKQ
     TMVDSSCRIL

301 TSDVFQDCNK LVDPEPYLDV CIYDTCSCES IGDCACFCDT
     IAAYAHVCAQ

351 HGKVVTWRTA TLCPQSCEER NLRENGYECE WRYNSCAPAC
     QVTCQHPEPL
```

```
401 ACPVQCVEGC HAHCPPGKIL DELLQTCVDP EDCPVCEVAG
    RRFASGKKVT

451 LNPSDPEHCQ ICHCDVVNLT CEACQEP
```

Example 2

Heterodimeric Constructs Comprising FVIII-Fc and VWF-D'D3 Domain at the Amino Terminus of the Second Fc Chain (FVIII-VWF-Fc Heterodimer, FIG. 2)

(a) Cloning of pSYN-FVIII-064

The FVIII-064 plasmid comprises a single chain FC (scFc) scaffold with enzyme cleavage sites which are processed during synthesis in a cell. The construct has a FVIII binding domain of full-length VWF (D'D3).

Plasmid (pSYN-FVIII-064) was designed for the expression FVIII-Fc and VWF-Fc heterodimer, where the D'D3 domains to bind FVIII and prevents FVIII interaction with phospholipids and activated protein C and/or preventing or inhibiting binding to endogenous VWF. Protein from pSYN-FVIII-064 is expressed in the cell as a single polypeptide where the C-terminus of the FVIII-Fc subunit is linked to the N-terminus of the VWF D'D3-Fc subunit by a 6× (GGGGS) polypeptide linker (SEQ ID NO: 74). In addition, RRRRS (SEQ ID NO: 75) and RKRRKR (SEQ ID NO: 76) sequences were inserted at the 5' and 3' end of the polypeptide linker, respectively, for intracellular cleavage by pro-protein convertases following the last Arg at each sequence. Hence, the cells can express a double chain FVIII-Fc/D'D3-Fc heterodimer where the FVIII-Fc chain has a RRRRS sequence (SEQ ID NO: 75) at the C-terminus, but the remainder of the linker sequence has been removed. Another 3× (GGGGS) polypeptide linker (SEQ ID NO: 28) along with a thrombin cleavage site is introduced in between the VWF domains and the Fc region to facilitate release of the VWF fragment from FVIII once the FVIII-VWF heterodimeric protein is activated by thrombin allowing interaction of FVIII with other clotting factors.

Synthesis of the DNA fragments containing a portion of the first Fc region followed by a 6× (GGGGS) (SEQ ID NO: 74), the VWF-D'D3 domain (1-477aa; C336A/C379A mutation), 3× (GGGGS) (SEQ ID NO:28), the thrombin cleavage site and a portion of the second Fc was outsourced (Genscript-sequence number 103069, shown below). A fragment of Genscript construct was sub cloned into the SalI/RsRII digested pSYN-FVIII-049, which is FVIII-Fc construct with a cleavable linker in between two Fc domains.

Genscript-Sequence Number 103069 (SEQ ID NO: 82):

```
CCGTCGACAAGAGCAGGTGGCAGCAGGGGAACGTCTTCTCATGCTCCGT-
GAT
GCATGAGGCTCTGCACAACCACTA-
CACGCAGAAGAGCCTCTCCCTGTCTCCG
GGTAAACGGCGCCGCCGGAGCGGTGGCGGCGGATCAGGTGGGGGTG-
GATCAG
GCGGTGGAGGTTCCGGTGGCGGGGGATCCGGCGGTG-
GAGGTTCCGGTGGGGG
TGGATCAAGGAAGAGGAGGAAGAGAAGCCTATCCTGTCGGCCCCC-
CATGGTC
AAGCTGGTGTGTCCCGCTGACAACCTGCGGGCT-
GAAGGGCTCGAGTGTACCA
AAACGTGCCAGAACTATGACCTGGAGTGCATGAG-
CATGGGCTGTGTCTCTGG
CTGCCTCTGCCCCCGGGCATGGTCCGGCATGAGAATC-
GATGTGTGGCCCTG
GAAAGGTGTCCCTGCTTCCATCAGGGCAAGGAGTATGCCCCTG-
GAGAAACAG
TGAAGATTGGCTGCAACACTTGTGTCTGTCGGGACCGGAAGTG-
GAACTGCAC
AGACCATGTGTGTGATGCCACGTGCTCCACGATCGGCATGGCCCAC-
TACCTC
ACCTTCGACGGGCTCAAATACCTGTTCCCCGGG-
GAGTGCCAGTACGTTCTGG
TGCAGGATTACTGCGGCAGTAACCCTGGGACCTTTCGGATCCTAGTGGG-
GAA
TAAGGGATGCAGCCACCCCTCAGTGAAATGCAAGAAACGGGTCAC-
CATCCTG
GTGGAGGGAGGAGAGATTGAGCTGTTTGACGGGGAGGTGAATGT-
GAAGAGGC
CCATGAAGGATGAGACTCACTTTGAGGTGGTGGAGTCTGGCCGGTACAT-
CAT
TCTGCTGCTGGGCAAAGCCCTCTCCGTGGTCTGGGACCGCCACCTGAG-
CATC
TCCGTGGTCCTGAAGCAGACATACCAG-
GAGAAAGTGTGTGGCCTGTGTGGGA
ATTTTGATGGCATCCAGAACAATGACCTCACCAGCAGCAACCTC-
CAAGTGGA
GGAAGACCCTGTGGACTTTGGGAACTCCTGGAAAGT-
GAGCTCGCAGTGTGCT
GACACCAGAAAAGTGCCTCTGGACTCATCCCCTGCCACCTGCCAT-
AACAACA
TCATGAAGCAGACGATGGTGGATTCCTCCTGTAGAATCCT-
TACCAGTGACGT
CTTCCAGGACTGCAACAAGCTGGTGGACCCCGAGCCATATCTG-
GATGTCTGC
ATTTACGACACCTGCTCCTGTGAGTCCATTGGGGACTGCGCCGCAT-
TCTGCG
ACACCATTGCTGCCTATGCCCACGTGTGTGCCCAG-
CATGGCAAGGTGGTGAC
CTGGAGGACGGCCACATTGTGCCCCCAGAGCTGCGAGGAGAG-
GAATCTCCGG
GAGAACGGGTATGAGGCTGAGTGGCGC-
TATAACAGCTGTGCACCTGCCTGTC
AAGTCACGTGTCAGCACCCTGAGC-
CACTGGCCTGCCCTGTGCAGTGTGTGGA
GGGCTGCCATGCCCACTGCCCTCCAGGGAAAATCCTGGAT-
GAGCTTTTGCAG
ACCTGCGTTGACCCTGAAGACTGTCCAGTGTGT-
GAGGTGGCTGGCCGGCGTT
TTGCCTCAGGAAAGAAAGTCACCTTGAATCCCAGTGACCCT-
GAGCACTGCCA
GATTTGCCACTGTGATGTTGTCAACCTCACCTGTGAAGCCTGCCAG-
GAGCCG
ATCGATGGCGGTGGAGGTTCCGGTGGCGGGG-
GATCCCTGGTCCCCCGGGCA
GCGGAGGCGACAAAACTCACACATGCC-
CACCGTGCCCAGCTCCAGAACTCCT
GGGCGGACCGTCA
```

(b) Cloning of pSYN-FVIII-065

The FVIII-065 plasmid comprises the first 276 amino acids of the D'D3 domain of VWF attached to a second Fc region. The VWF fragment was PCR amplified from full-length VWF plasmid pSYN-VWF-008 by using primer combinations ESC17 and ESC41.

```
ESC17-Fwd-VWF cloning oligo with Cla1
                                (SEQ ID NO: 77)
GTCCGGCATGAGAATCGATGTGTG ESC41-Rev-VWF with EcoRV
                                (SEQ ID NO: 78)
CCTCCACCGCCAGATATCAGAGGCACTTTTC
```

The expected sized band (~692 bp) was gel purified with a Gel Extraction kit (Qiagen, Valencia, Calif.) and cloned into the Cla1 and EcoRV sites of pSYN-FVIII-064 to generate pSYN-FVIII-065.

Example 3

Cloning of pSYN-FVIII-159, 160, 178, 179 (FIG. 3)

In order to vary the linker length between the VWF fragment and Fc region, an EcoRV site was introduced at the junction of VWF and the beginning of 20 amino acid linker in pSYN-FVIII-064, variable size linkers were then used to replace the 20 aa linker in PSYN-FVIII-064. The new DNA constructs are: pSYN-FVIII-159, 160, 178, and 179 which contains 35 aa, 48 aa, 73 aa and 98 aa linkers, respectively.

To insert a 35 amino acid linker in pSYN-FVIII-159, two oligos (ESC78-105 bp and ESC79-107 bp) were ordered from Integrated DNA Technologies, Inc (Coralville, Iowa). Oligos were annealed and extended using a standard PCR method:
Primers:

```
ESC78-Fwd with EcoRV site
                                    (SEQ ID NO: 79)
AAAGTGCCTCTGATATCTGGCGGTGGAGGTTCCGGTGGCGGGGGATCCG
GTGGCGGGGGATCCGGTGGCGGGGGATCCGGTGGCGGGGGATCCCTGGT
CCCCCGG ESC79-Rev with RsRII site
                                    (SEQ ID NO: 80)
GAAGAGGAAGACTGACGGTCCGCCCAGGAGTTCTGGAGCTGGGCACGGT
GGGCATGTGTGAGTTTTGTCGCCTCCGCTGCCCCGGGGGACCAGGGATC
CCCCGCCAC
```

A 50 µl PCR oligo annealing and extension reaction was carried out with ESC78/ESC79 primer combo using the 3 step PCR amplification cycle: 25 cycles of (96° C. 30 seconds, 55° C. 30 seconds, 68° C. 30 seconds). The expected sized band (~186 bp) was gel purified with a Gel Extraction kit (Qiagen, Valencia, Calif.) and cloned into the EcoRV and RsRII restriction sites of pSYN-FVIII-064 to generate pSYN-FVIII-159.

(b) Cloning pSYN-FVIII-160, 178, and 179 pSYN-VIII-160 has a 48 amino acids linker in between the VWF fragment and the Fc region. Synthesis of DNA fragment coding for 48 amino acids linker (ISGG GGGSGGGGSGGGGSGGGGSGGGGSGGGGSLVPRGSG GGGSGGGGS) (SEQ ID NO: 81) and a portion of the Fc region was outsourced (Genscript-Sequence no-132601, shown below). A fragment of the Genscript construct was sub cloned into the EcoRV/RsRII digested pSYN-FVIII-0159 (mentioned above).
Genscript-Sequence No-132601 (SEQ ID NO: 83)

```
AAAGTGCCTCTGATATCTGGCGGTGGAGGTTCCGGTGGCGGGGGATCCG
GCGGTGGAGGTTCCGGCGGTGGAGGTTCCGGTGGCGGGGGATCCGGTGG
CGGGGGATCCCTGGTCCCCCGGGGCAGCGGCGGTGGAGGTTCCGGTGGC
GGGGGATCCGACAAAACTCACACATGCCCACCGTGCCCAGCTCCAGAAC
TCCTGGGCGGACCGTCAGTCTTCC
``` pSYN-VIII-178 has a 73 amino acids linker in between the VWF fragment and the Fc region. Synthesis of DNA fragment coding for 73 amino acids linker (ISGGGGSGGGGSGGGGSGGGGSGGGGSGGGGSGGG GSGGGGSGGGGSGGGGSGGGGSLVP RGSGGGGSGGGGS) (SEQ ID NO: 84) and a portion of Fc region was outsourced (Genscript-Sequence no-144849, shown below). A fragment of Genscript construct was sub cloned into the EcoRV/RsRII digested pSYN-FVIII-0159 (mentioned above).
Genscript-Sequence #-144849 (SEQ ID NO: 85)

```
GCCTGCCAGGAGCCGATATCTGGCGGTGGAGGTTCCGGTGGCGGGGGATCC
GGCGGTGGAGGTTCCGGCGGTGGAGGTTCCGGTGGCGGGGGATCCGGCGGT
GGAGGTTCCGGTGGCGGGGGATCCGGCGGTGGAGGTTCCGGCGGTGGAGGT
TCCGGTGGCGGGGGATCCGGTGGCGGGGGATCCCTGGTCCCCCGGGGCAGC
GGCGGTGGAGGTTCCGGTGGCGGGGGATCCGACAAAACTCACACATGCCCC
CGTGCCCAGCTCCAGAACTCCTGGGCGGACCGTCAGTCTTCCTC
``` pSYN-VIII-179 has a 98 amino acids linker in between the VWF fragment and the Fc region. Synthesis of DNA fragment coding for 98 amino acids linker (IS-GGGGSGGGGSGGGGSGGGGSGGGGSGGGGSGGGG SGGGGSGGGGSGGGGSGGGGSGG GGSGGGGSGGGGSGGGGSGGGGSLVPRGSGGGGSG GGGS) (SEQ ID NO: 86) and a portion of Fc region was outsourced (Genscript-Sequence no-144849 shown below). A fragment of Genscript construct was sub cloned into the EcoRV/RsRII digested pSYN-FVIII-0159 (mentioned above).
Genscript-Sequence #-144849 (SEQ ID NO:87)

```
GCCTGCCAGGAGCCGATATCTGGCGGTGGAGGTTCCGGTGGCGGGGGAT
CCGGCGGTGGAGGTTCCGGCGGTGGAGGTTCCGGTGGCGGGGGATCCGG
CGGTGGAGGTTCCGGTGGCGGGGGATCCGGCGGTGGAGGTTCCGGCGGT
GGAGGTTCCGGTGGCGGGGGATCCGGCGGTGGAGGTTCCGGTGGCGGGG
GATCCGGCGGTGGAGGTTCCGGCGGTGGAGGTTCCGGTGGCGGGGGATC
CGGTGGCGGGGGATCCCTGGTCCCCCGGGGCAGCGGCGGTGGAGGTTCC
GGTGGCGGGGGATCCGACAAAACTCACACATGCCCACCGTGCCCAGCTC
CAGAACTCCTGGGCGGACCGTCAGTCTTCCTCTTCCC
```

Cloning of pSYN-FVIII-180, 181, and 182 pSYN-FVIII-180, 181, and 182 were constructed from pSYN-FVIII-160. K2093A or F2093A or K2093A/F2093A mutations were introduced into the C1 domain of FVIII in pSYN-FVIII-160 to form pSYN-FVIII-180, pSYN-FVIII-181 and pSYN-FVIII-182 respectively.
FVIII-VWF-Fc Heterodimer Protein Sequence (SEQ ID NO: 88)

(FVIII sequence amino acid position 1-1457; underlined region represents Fc region; curvy underline represents cleavable linker in between first Fc and VWF fragment; double underlined region represents VWF fragment; bold region represents variable length cleavable linker in between VWF fragment and Fc. The linker length varies in FVIII-064, 159, 160, 178, and 179 constructs).

```
  1 MQIELSTCFF LCLLRFCFSA TRRYYLGAVE LSWDYMQSDL
    GELPVDARFP

51 PRVPKSFPFN TSVVYKKTLF VEFTDHLFNI AKPRPPWMGL
    LGPTIQAEVY

101 DTVVITLKNM ASHPVSLHAV GVSYWKASEG AEYDDQTSQR
    EKEDDKVFPG

151 GSHTYVWQVL KENGPMASDP LCLTYSYLSH VDLVKDLNSG
    LIGALLVCRE

201 GSLAKEKTQT LHKFILLFAV FDEGKSWHSE TKNSLMQDRD
    AASARAWPKM

251 HTVNGYVNRS LPGLIGCHRK SVYWHVIGMG TTPEVHSIFL
    EGHTFLVRNH

301 RQASLEISPI TFLTAQTLLM DLGQFLLFCH ISSHQHDGME
    AYVKVDSCPE

351 EPQLRMKNNE EAEDYDDDLT DSEMDVVRFD DDNSPSFIQI
    RSVAKKHPKT

401 WVHYIAAEEE DWDYAPLVLA PDDRSYKSQY LNNGPQRIGR
    KYKKVRFMAY

451 TDETFKTREA IQHESGILGP LLYGEVGDTL LIIFKNQASR
    PYNIYPHGIT
```

```
 501 DVRPLYSRRL PKGVKHLKDF PILPGEIFKY KWTVTVEDGP
     TKSDPRCLTR

551 YYSSFVNMER DLASGLIGPL LICYKESVDQ RGNQIMSDKR
     NVILFSVFDE

601 NRSWYLTENI QRFLPNPAGV QLEDPEFQAS NIMHSINGYV
     FDSLQLSVCL

651 HEVAYWYILS IGAQTDFLSV FFSGYTFKHK MVYEDTLTLF
     PFSGETVFMS

701 MENPGLWILG CHNSDFRNRG MTALLKVSSC DKNTGDYYED
     SYEDISAYLL

751 SKNNAIEPRS FSQNPPVLKR HQREITRTTL QSDQEEIDYD
     DTISVEMKKE

801 DFDIYDEDEN QSPRSFQKKT RHYFIAAVER LWDYGMSSSP
     HVLRNRAQSG

851 SVPQFKKVVF QEFTDGSFTQ PLYRGELNEH LGLLGPYIRA
     EVEDNIMVTF

901 RNQASRPYSF YSSLISYEED QRQGAEPRKN FVKPNETKTY
     FWKVQHHMAP

951 TKDEFDCKAW AYFSDVDLEK DVHSGLIGPL LVCHTNTLNP
     AHGRQVTVQE

1001 FALFFTIFDE TKSWYFTENM ERNCRAPCNI QMEDPTFKEN
     YRFHAINGYI

1051 MDTLPGLVMA QDQRIRWYLL SMGSNENIHS IHFSGHVFTV
     RKKEEYKMAL

1101 YNLYPGVFET VEMLPSKAGI WRVECLIGEH LHAGMSTLFL
     VYSNKCQTPL

1151 GMASGHIRDF QITASGQYGQ WAPKLARLHY SGSINAWSTK
     EPFSWIKVDL

1201 LAPMIIHGIK TQGARQKFSS LYISQFIIMY SLDGKKWQTY
     RGNSTGTLMV

1251 FFGNVDSSGI KHNIFNPPII ARYIRLHPTH YSIRSTLRME
     LMGCDLNSCS

1301 MPLGMESKAI SDAQITASSY FTNMFATWSP SKARLHLQGR
     SNAWRPQVNN

1351 PKEWLQVDFQ KTMKVTGVTT QGVKSLLTSM YVKEFLISSS
     QDGHQWTLFF

1401 QNGKVKVFQG NQDSFTPVVN SLDPPLLTRY LRIHPQSWVH
     QIALRMEVLG

1451 CEAQDLYDKT HTCPPCPAPE LLGGPSVFLF PPKPKDTLMI
     SRTPEVTCVV

1501 VDVSHEDPEV KFNWYVDGVE VHNAKTKPRE EQYNSTYRVV
     SVLTVLHQDW

1551 LNGKEYKCKV SNKALPAPIE KTISKAKGQP REPQVYTLPP
     SRDELTKNQV

1601 SLTCLVKGFY PSDIAVEWES NGQPENNYKT TPPVLDSDGS
     FFLYSKLTVD

1651 KSRWQQGNVF SCSVMHEALH NHYTQKSLSL SPGKRRRRSG
     GGGSGGGSG

1701 GGGSGGGSG GGGSGGGSR KRRKRSLSCR PPMVKLVCPA
     DNLRAEGLEC

1751 TKTCQNYDLE CMSMGCVSGC LCPPGMVRHE NRCVALERCP
     CFHQGKEYAP

1801 GETVKIGCNT CVCRDRKWNC TDHVCDATCS TIGMAHYLTF
     DGLKYLFPGE

1851 CQYVLVQDYC GSNPGTFRIL VGNKGCSHPS VKCKKRVTIL
     VEGGEIELFD

1901 GEVNVKRPMK DETHFEVVES GRYIILLLGK ALSVVWDRHL
     SISVVLKQTY

1951 QEKVCGLCGN FDGIQNNDLT SSNLQVEEDP VDFGNSWKVS
     SQCADTRKVP

2001 LDSSPATCHN NIMKQTMVDS SCRILTSDVF QDCNKLVDPE
     PYLDVCIYDT

2051 CSCESIGDCA AFCDTIAAYA HVCAQHGKVV TWRTATLCPQ
     SCEERNLREN

2101 GYEAEWRYNS CAPACQVTCQ HPEPLACPVQ CVEGCHAHCP
     PGKILDELLQ

2151 TCVDPEDCPV CEVAGRRFAS GKKVTLNPSD PEHCQICHCD
     VVNLTCEACQ

2201 EPIDGGGGSG GGGSLVPRGS GGDKTHTCPP CPAPELLGGP
     SVFLFPPKPK

2251 DTLMISRTPE VTCVVVDVSH EDPEVKFNWY VDGVEVHNAK
     TKPREEQYNS

2301 TYRVVSVLTV LHQDWLNGKE YKCKVSNKAL PAPIEKTISK
     AKGQPREPQV

2351 YTLPPSRDEL TKNQVSLTCL VKGFYPSDIA VEWESNGQPE
     NNYKTTPPVL

2401 DSDGSFFLYS KLTVDKSRWQ QGNVFSCSVM HEALHNHYTQ
     KSLSLSPGK
```

Example 4

Example of FVIII-VWF DNA Constructs (FIG. 4)

The VWF fragment and FVIII protein can be linked together by a linker or another protein or a polypeptide using conventional recombinant DNA techniques, as show in FIG. 4. In FIG. 4A, the D1D2D'D3 domains of VWF is linked to the FVIII protein by a 48aa linker-IS-GGGGSGGGGSGGGGSGGGGSGGGGSGGGGSLVPRG SGGGGSGGGGS (SEQ ID NO: 89) and protects FVIII from premature clearance. To further enhance the FVIII protecting activity of D'D3, another protein or polypeptide that has half-life extension potential such as albumin or a PAS sequence (heterologous moieties) can be incorporated into the construct. The heterologous moiety, e.g., albumin protein or PAS sequence, can be incorporated into different positions of the FVIII molecule; a few examples were shown in FIG. 4B-4D: at the N-termini of FVIII (4B), at the C-termini of FVIII (4C), or in the B region (4D). In those constructs, the additional protein sequences could enhance the D'D3 protecting activity and further extend FVIII half-life.

In addition, a heterologous moiety, e.g., albumin or PAS sequence, can also be incorporated into the FVIII/VWF heterodimer constructs as shown in FIG. 4E-4G. In FIG. 4E, a heterologous moiety, e.g., albumin or PAS sequence, is incorporated into the FVIII B domain region of FVIII-148; In FIG. 4F, a heterologous moiety, e.g., albumin or PAS sequence, is incorporated into the FVIII B domain region of FVIII-136; In FIG. 4G, a heterologous moiety, e.g., albumin or PAS sequence, is used as a linker to connect D'D3 fragment and Fc. In those configurations, a synergetic effect of D'D3, Fc, and heterologous moiety that is a half-life extender (e.g., albumin/PAS sequence) is expected on FVIII half-life extension.

Example 5

Plasmid Construction of Co-transfection System for FVIIIFc-VWF Heterodimer (FIG. 5)

A co-transfection system was generated for FVIIIFc-VWF heterodimer production, which contains three DNA constructs. The first DNA construct-pSYN-FVIII-155 is encoding a FVIII-Fc fusion protein in which a single chain FVIII protein was directly fused to a single Fc fragment, and the second DNA construct is pSYN-VWF-031, which encodes a D'D3-Fc fusion protein (mentioned above in example 1). HEK293F cells were transfected with the two plasmids along with a third plasmid (PC5) at a 80:15:5 ratio. Co-transfection with PC5 is to ensure full propeptide processing of the D1 and D2 regions so that we have mature D'D3 domains. The synthesized proteins were secreted as FVIIIFc/D'D3Fc heterodimer and D'D3Fc homodimer and the FVIIIFc/D'D3Fc heterodimer was separated from the D'D3Fc homodimer by protein purification.

pSYN-FVIII-155 Mature Protein Sequencing (SEQ ID NO: 90):

ATRRYYLGAVELSWDYMQSDLGELPVDARFPPRVPKSFPFNTSVVYK

KTLFVEFTDHLFNIAKPRPPWMGLLGPTIQAEVYDTVVITLKNMASH

PVSLHAVGVSYWKASEGAEYDDQTSQREKEDDKVFPGGSHTYVWQVL

KENGPMASDPLCLTYSYLSHVDLVKDLNSGLIGALLVCREGSLAKEK

TQTLHKFILLFAVFDEGKSWHSETKNSLMQDRDAASARAWPKMHTVN

GYVNRSLPGLIGCHRKSVYWHVIGMGTTPEVHSIFLEGHTFLVRNHR

QASLEISPITFLTAQTLLMDLGQFLLFCHISSHQHDGMEAYVKVDSC

PEEPQLRMKNNEEAEDYDDDLTDSEMDVVRFDDDNSPSFIQIRSVAK

KHPKTWVHYIAAEEEDWDYAPLVLAPDDRSYKSQYLNNGPQRIGRKY

KKVRFMAYTDETFKTREAIQHESGILGPLLYGEVGDTLLIIFKNQAS

RPYNIYPHGITDVRPLYSRRLPKGVKHLKDFPILPGEIFKYKWTVTV

EDGPTKSDPRCLTRYYSSFVNMERDLASGLIGPLLICYKESVDQRGN

SQIMSDKRNVILFVFDENRSWYLTENIQRFLPNPAGVQLEDPEFQAS

NIMHSINGYVFDSLQLSVCLHEVAYWYILSIGAQTDFLSVFFSGYTF

KHKMVYEDTLTLFPPFSGETVFMSMENPGLWILGCHNSDFRNRGMTAL

LKVSSCDKNTGDYYEDSYEDISAYLLSKNNAIEPRSFSQNPPVLKAH

QAEITRTTLQSDQEEIDYDDTISVEMKKEDFDIYDEDENQSPRSFQK

KTRHYFIAAVERLWDYGMSSSPHVLRNRAQSGSVPQFKKVVFQEFTD

GSFTQPLYRGELNEHLGLLGPYIRAEVEDNIMVTFRNQASRPYSFYS

SLISYEEDQRQGAEPRKNFVKPNETKTYFWKVQHHMAPTKDEFDCKA

WAYFSDVDLEKDVHSGLIGPLLVCHTNTLNPAHGRQVTVQEFALFFT

IFDETKSWYFTENMERNCRAPCNIQMEDPTFKENYRFHAINGYIMDT

LPGLVMAQDQRIRWYLLSMGSNENIHSIHFSGHVFTVRKKEEYKMAL

YNLYPGVFETVEMLPSKAGIWRVECLIGEHLHAGMSTLFLVYSNKCQ

TPLGMASGHIRDFQITASGQYGQWAPKLARLHYSGSINAWSTKEPFS

WIKVDLLAPMIIHGIKTQGARQKFSSLYISQFIIMYSLDGKKWQTYR

GNSTGTLMVFFGNVDSSGIKHNIFNPPIIARYIRLHPTHYSIRSTLR

MELMGCDLNSCSMPLGMESKAISDAQITASSYFTNMFATWSPSKARL

HLQGRSNAWRPQVNNPKEWLQVDFQKTMKVTGVTTQGVKSLLTSMYV

SKEFLISSQDGHQWTLFFQNGKVKVFQGNQDSFTPVVNSLDPPLLTR

YLRIHPQSWVHQIALRMEVLGCEAQDLYDKTHTCPPCPAPELLGGPS

VFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIE

KTISKAKGQPREPQVYTLPPSRDELTKNQVSLTCLVKGFYPSDIAVE

WESNGQPENNYKTTPPVLDSDGSFFLYSKLTVDKSRWQQGNVFSCSV

MHEALHNHYTQKSLSLSPGK pSYN-FVIII-155 DNA Sequencing (SEQ ID NO: 91):

ATGCAAATAGAGCTCTCCACCTGCTTCTTTCTGTGCCTTTTGCGATTCTGCTTTAGTGCCACCAGAAGATAC

TACCTGGGTGCAGTGGAACTGTCATGGGACTATATGCAAAGTGATCTCGGTGAGCTGCCTGTGGACGCAAGA

TTTCCTCCTAGAGTGCCAAAATCTTTTCCATTCAACACCTCAGTCGTGTACAAAAAGACTCTGTTTGTAGAA

TTCACGGATCACCTTTTCAACATCGCTAAGCCAAGGCCACCCTGGATGGGTCTGCTAGGTCCTACCATCCAG

GCTGAGGTTTATGATACAGTGGTCATTACACTTAAGAACATGGCTTCCCATCCTGTCAGTCTTCATGCTGTT

GGTGTATCCTACTGGAAAGCTTCTGAGGGAGCTGAATATGATGATCAGACCAGTCAAAGGGAGAAAGAAGAT

GATAAAGTCTTCCCTGGTGGAAGCCATACATATGTCTGGCAGGTCCTGAAAGAGAATGGTCCAATGGCCTCT

GACCCACTGTGCCTTACCTACTCATATCTTTCTCATGTGGACCTGGTAAAAGACTTGAATTCAGGCCTCATT

GGAGCCCTACTAGTATGTAGAGAAGGGAGTCTGGCCAAGGAAAAGACACAGACCTTGCACAAATTTATACTA

CTTTTTGCTGTATTTGATGAAGGGAAAAGTTGGCACTCAGAAACAAAGAACTCCTTGATGCAGGATAGGGAT

GCTGCATCTGCTCGGGCCTGGCCTAAAATGCACACAGTCAATGGTTATGTAAACAGGTCTCTGCCAGGTCTG

ATTGGATGCCACAGGAAATCAGTCTATTGGCATGTGATTGGAATGGGCACCACTCCTGAAGTGCACTCAATA

TTCCTCGAAGGTCACACATTTCTTGTGAGGAACCATCGCCAGGCGTCCTTGGAAATCTCGCCAATAACTTTC

-continued

```
CTTACTGCTCAAACACTCTTGATGGACCTTGGACAGTTTCTACTGTTTTGTCATATCTCTTCCCACCAACAT

GATGGCATGGAAGCTTATGTCAAAGTAGACAGCTGTCCAGAGGAACCCCAACTACGAATGAAAAATAATGAA

GAAGCGGAAGACTATGATGATGATCTTACTGATTCTGAAATGGATGTGGTCAGGTTTGATGATGACAACTCT

CCTTCCTTTATCCAAATTCGCTCAGTTGCCAAGAAGCATCCTAAAACTTGGGTACATTACATTGCTGCTGAA

GAGGAGGACTGGGACTATGCTCCCTTAGTCCTCGCCCCCGATGACAGAAGTTATAAAAGTCAATATTTGAAC

AATGGCCCTCAGCGGATTGGTAGGAAGTACAAAAAAGTCCGATTTATGGCATACACAGATGAAACCTTTAAG

ACTCGTGAAGCTATTCAGCATGAATCAGGAATCTTGGGACCTTTACTTTATGGGGAAGTTGGAGACACACTG

TTGATTATATTTAAGAATCAAGCAAGCAGACCATATAACATCTACCCTCACGGAATCACTGATGTCCGTCCT

TTGTATTCAAGGAGATTACCAAAAGGTGTAAAACATTTGAAGGATTTTCCAATTCTGCCAGGAGAAATATTC

AAATATAAATGGACAGTGACTGTAGAAGATGGGCCAACTAAATCAGATCCTCGGTGCCTGACCCGCTATTAC

TCTAGTTTCGTTAATATGGAGAGAGATCTAGCTTCAGGACTCATTGGCCCTCTCCTCATCTGCTACAAAGAA

TCTGTAGATCAAAGAGGAAACCAGATAATGTCAGACAAGAGGAATGTCATCCTGTTTTCTGTATTTGATGAG

AACCGAAGCTGGTACCTCACAGAGAATATACAACGCTTTCTCCCCAATCCAGCTGGAGTGCAGCTTGAGGAT

CCAGAGTTCCAAGCCTCCAACATCATGCACAGCATCAATGGCTATGTTTTTGATAGTTTGCAGTTGTCAGTT

TGTTTGCATGAGGTGGCATACTGGTACATTCTAAGCATTGGAGCACAGACTGACTTCCTTTCTGTCTTCTTC

TCTGGATATACCTTCAAACACAAAATGGTCTATGAAGACACACTCACCCTATTCCCATTCTCAGGAGAAACT

GTCTTCATGTCGATGGAAAACCCAGGTCTATGGATTCTGGGGTGCCACAACTCAGACTTTCGGAACAGAGGC

ATGACCGCCTTACTGAAGGTTTCTAGTTGTGACAAGAACACTGGTGATTATTACGAGGACAGTTATGAAGAT

ATTTCAGCATACTTGCTGAGTAAAAACAATGCCATTGAACCAAGAAGCTTCTCTCAAAACCCACCAGTCTTG

AAAGCCCATCAGGCGGAAATAACTCGTACTACTCTTCAGTCAGATCAAGAGGAAATTGACTATGATGATACC

ATATCAGTTGAAATGAAGAAGGAAGATTTTGACATTTATGATGAGGATGAAAATCAGAGCCCCCGCAGCTTT

CAAAAGAAAACACGACACTATTTTATTGCTGCAGTGGAGAGGCTCTGGGATTATGGGATGAGTAGCTCCCCA

CATGTTCTAAGAAACAGGGCTCAGAGTGGCAGTGTCCCTCAGTTCAAGAAAGTTGTTTTCCAGGAATTTACT

GATGGCTCCTTTACTCAGCCCTTATACCGTGGAGAACTAAATGAACATTTGGGACTCCTGGGGCCATATATA

AGAGCAGAAGTTGAAGATAATATCATGGTAACTTTCAGAAATCAGGCCTCTCGTCCCTATTCCTTCTATTCT

AGCCTTATTTCTTATGAGGAAGATCAGAGGCAAGGAGCAGAACCTAGAAAAAACTTTGTCAAGCCTAATGAA

ACCAAAACTTACTTTTGGAAAGTGCAACATCATATGGCACCCACTAAAGATGAGTTTGACTGCAAAGCCTGG

GCTTATTTCTCTGATGTTGACCTGGAAAAAGATGTGCACTCAGGCCTGATTGGACCCCTTCTGGTCTGCCAC

ACTAACACACTGAACCCTGCTCATGGGAGACAAGTGACAGTACAGGAATTTGCTCTGTTTTTCACCATCTTT

GATGAGACCAAAAGCTGGTACTTCACTGAAAATATGGAAAGAAACTGCAGGGCTCCCTGCAATATCCAGATG

GAAGATCCCACTTTTAAAGAGAATTATCGCTTCCATGCAATCAATGGCTACATAATGGATACACTACCTGGC

TTAGTAATGGCTCAGGATCAAAGGATTCGATGGTATCTGCTCAGCATGGGCAGCAATGAAAACATCCATTCT

ATTCATTTCAGTGGACATGTGTTCACTGTACGAAAAAAAGAGGAGTATAAAATGGCACTGTACAATCTCTAT

CCAGGTGTTTTTGAGACAGTGGAAATGTTACCATCCAAAGCTGGAATTTGGCGGGTGGAATGCCTTATTGGC

GAGCATCTACATGCTGGGATGAGCACACTTTTTCTGGTGTACAGCAATAAGTGTCAGACTCCCCTGGGAATG

GCTTCTGGACACATTAGAGATTTTCAGATTACAGCTTCAGGACAATATGGACAGTGGGCCCCAAAGCTGGCC

AGACTTCATTATTCCGGATCAATCAATGCCTGGAGCACCAAGGAGCCCTTTTCTTGGATCAAGGTGGATCTG

TTGGCACCAATGATTATTCACGGCATCAAGACCCAGGGTGCCCGTCAGAAGTTCTCCAGCCTCTACATCTCT

CAGTTTATCATCATGTATAGTCTTGATGGGAAGAAGTGGCAGACTTATCGAGGAAATTCCACTGGAACCTTA

ATGGTCTTCTTTGGCAATGTGGATTCATCTGGGATAAAACACAATATTTTTAACCCTCCAATTATTGCTCGA
```

```
                         -continued
TACATCCGTTTGCACCCAACTCATTATAGCATTCGCAGCACTCTTCGCATGGAGTTGATGGGCTGTGATTTA

AATAGTTGCAGCATGCCATTGGGAATGGAGAGTAAAGCAATATCAGATGCACAGATTACTGCTTCATCCTAC

TTTACCAATATGTTTGCCACCTGGTCTCCTTCAAAAGCTCGACTTCACCTCCAAGGGAGGAGTAATGCCTGG

AGACCTCAGGTGAATAATCCAAAAGAGTGGCTGCAAGTGGACTTCCAGAAGACAATGAAAGTCACAGGAGTA

ACTACTCAGGGAGTAAAATCTCTGCTTACCAGCATGTATGTGAAGGAGTTCCTCATCTCCAGCAGTCAAGAT

GGCCATCAGTGGACTCTCTTTTTTCAGAATGGCAAAGTAAAGGTTTTTCAGGGAAATCAAGACTCCTTCACA

CCTGTGGTGAACTCTCTAGACCCACCGTTACTGACTCGCTACCTTCGAATTCACCCCCAGAGTTGGGTGCAC

CAGATTGCCCTGAGGATGGAGGTTCTGGGCTGCGAGGCACAGGACCTCTACGACAAAACTCACACATGCCCA

CCGTGCCCAGCTCCAGAACTCCTGGGCGGACCGTCAGTCTTCCTCTTCCCCCCAAAACCCAAGGACACCCTC

ATGATCTCCCGGACCCCTGAGGTCACATGCGTGGTGGTGGACGTGAGCCACGAAGACCCTGAGGTCAAGTTC

AACTGGTACGTGGACGGCGTGGAGGTGCATAATGCCAAGACAAAGCCGCGGGAGGAGCAGTACAACAGCACG

TACCGTGTGGTCAGCGTCCTCACCGTCCTGCACCAGGACTGGCTGAATGGCAAGGAGTACAAGTGCAAGGTC

TCCAACAAAGCCCTCCCAGCCCCCATCGAGAAAACCATCTCCAAAGCCAAAGGGCAGCCCCGAGAACCACAG

GTGTACACCCTGCCCCCATCCCGGGATGAGCTGACCAAGAACCAGGTCAGCCTGACCTGCCTGGTCAAAGGC

TTCTATCCCAGCGACATCGCCGTGGAGTGGGAGAGCAATGGGCAGCCGGAGAACAACTACAAGACCACGCCT

CCCGTGTTGGACTCCGACGGCTCCTTCTTCCTCTACAGCAAGCTCACCGTGGACAAGAGCAGGTGGCAGCAG

GGGAACGTCTTCTCATGCTCCGTGATGCATGAGGCTCTGCACAACCACTACACGCAGAAGAGCCTCTCCCTG

TCTCCGGGTAAA
```

Additional VWF fragments and FVIIIFC-VWF heterodimers that have been constructed are listed below.

TABLE 6

VWF Fragments and FVIII/VWF Heterodimer Constructs

| Construct | Description | Vector |
|---|---|---|
| VWF | | |
| pSYN-VWF-001 | FVIII signal peptide D'D3 region (1-276 amino acids long 6x His) | pcDNA 4 |
| pSYN-VWF-002 | FVIII signal peptide D'D3 region (1-477 amino acids long 6x His) | pcDNA 4 |
| pSYN-VWF-003 | FVIII signal peptide D'D3 region partial A1 (1-511 amino acids long 6x His) | pcDNA 4 |
| pSYN-VWF-004 | FVIII signal peptide D'D3A1 region (1-716 amino acids long 6x His) | pcDNA 4 |
| pSYN-VWF-006 | D1D2D'D3-linker-CK1 | pcDNA 3.1 |
| pSYN-VWF-008 | Full length WT-VWF | pcDNA 3.1 |
| pSYN-VWF-009 | D1D2D'D3 region (1-276 aa, 6x His) | pcDNA 3.1 |
| pSYN-VWF-010 | D1D2D'D3 region (1-477 aa, 6x His) | pcDNA 3.1 |
| pSYN-VWF-011 | D1D2D'D3 region partial A1 (1-511 aa, 6x His) | pcDNA 3.1 |
| pSYN-VWF-012 | D1D2D'D3A1 region (1-716 aa, 6x His) | pcDNA 3.1 |
| pSYN-VWF-013 | D1D2D'D3 region (1-477 aa, C336A/C379A, 6x His) | pcDNA 3.1 |
| pSYN-VWF-014 | FVIII signal peptide-D'D3 (1-477aa, C336A/C379A)-single Fc with 20aa linker containing thrombin site | pcDNA 4 |
| pSYN-VWF-015 | D1D2D'D3 (1-477aa, C336A/C379A)-single Fc with 20aa linker containing thrombin site | pcDNA 4 |
| pSYN-VWF-016 | FVIII signal peptide-D'D3 (1-477aa, WT)-single Fc with 20aa linker containing thrombin site | pcDNA 4 |
| pSYN-VWF-017 | D1D2D'D3 (1-477aa, WT)-single Fc with 20aa linker containing thrombin site | pcDNA 4 |
| pSYN-VWF-025 | D1D2D'D3 region (1-477 aa, 6x His) in pLIVE | pLIVE |
| pSYN-VWF-029 | D1D2D'D3 region (1-477 aa, C336A/C379A, 6x His) in pLIVE | pLIVE |
| pSYN-VWF-030 | FVIII signal peptide-D'D3 (1-477aa, C336A/C379A)-single Fc with 48aa linker containing thrombin site | pcDNA 4 |
| pSYN-VWF-031 | D1D2D'D3 (1-477aa, C336A/C379A)-single Fc with 48aa linker containing thrombin site | pcDNA 4 |
| pSYN-VWF-032 | FVIII signal peptide-D'D3 (1-477aa, WT)-single Fc with 48aa linker containing thrombin site | pcDNA 4 |

TABLE 6-continued

VWF Fragments and FVIII/VWF Heterodimer Constructs

| Construct | Description | Vector |
|---|---|---|
| pSYN-VWF-033 | FVIII signal peptide-D'D3 (1-477aa, WT)-single Fc with 35 aa linker containing thrombin site | pcDNA 4 |

FVIII

| Construct | Description | Vector |
|---|---|---|
| pSYN-FVIII-055 | BDD-FVIII scFc with R336I and Y1680F | pBUD |
| pSYN-FVIII-056 | BDD-FVIII scFc with R336I, R562 and Y1680F | pBUD |
| pSYN-FVIII-057 | BDD-FVIII scFc with Y1680F | pBUD |
| pSYN-FVIII-058 | BDD-FVIII scFc with S488A | pBUD |
| pSYN-FVIII-059 | BDD-FVIII scFc with R336I, R562K, S488A | pBUD |
| pSYN-FVIII-060 | BDD-FVIII scFc with R336I, R562K, Y1680F | pBUD |
| pSYN-FVIII-061 | BDD-FVIII scFc with R336I, R562K, S488A, Y1680F | pBUD |
| pSYN-FVIII-064 | BDD-FVIII cleavable scFc with VWF D'D3 (1-477aa, C336A/C379A) on second Fc & 20aa thrombin cleavable linker in between | pBUD |
| pSYN-FVIII-065 | BDD-FVIII cleavable scFc with VWF D'D3 (1-276aa) on second Fc & 20aa thrombin cleavable linker in between | pBUD |
| pSYN-FVIII-083 | BDD-FVIII scFc with R336I, S488A, R562K, Y1680F, E1984V | pBUD |
| pSYN-FVIII-086 | BDD-FVIII scFc with 6x(GGGGS) linker in between C2 of FVIII and Fc | pBUD |
| pSYN-FVIII-095 | BDD-FVIII scFc with S104C, R562K, Y1680F, G1960C | pBUD |
| pSYN-FVIII-101 | BDD-FVIII scFc from FVIII-041 into pcDNA 3.3. Topo | pcDNA 3.3 Topo |
| pSYN-FVIII-102 | BDD-FVIII (M662C/D1828C for disulfide binding; APC cleavage mutations R336I/R562K; along with Y1680F mutation for VWF binding) | pBUD |
| pSYN-FVIII-103 | BDD-FVIII scFc (Y662C/T1828C) | pBUD |
| pSYN-FVIII-104 | BDD-FVIII scFc (G655C/ST1788C) | pBUD |
| pSYN-FVIII-113 | BDD-FVIII (R490A/H497A) cleavable scFc with VWF D'D3 (1-477aa, C336A/C379A) on second Fc & 20aa thrombin cleavable linker in between | pBUD |
| pSYN-FVIII-114 | BDD-FVIII (R490A/H497A) cleavable scFc with VWF D'D3 (1-276) on second Fc & 20aa thrombin cleavable linker in between | pBUD |
| pSYN-FVIII-126 | BDD-FVIII scFc (M662C/D1828C) | pcDNA 3.3 Topo |
| pSYN-FVIII-127 | BDD-FVIII scFc (M662C/D1828C for disulfide binding; APC cleavage mutations R336I/R562K; along with Y1680F mutation for VWF binding) | pcDNA 3.3 |
| pSYN-FVIII-128 | BDD-FVIII scFc (Y664C/T1826C) | pcDNA 3.3 Topo |
| pSYN-FVIII-129 | mutation of R336I R562K R490A H497A N1224A in the background of pSYN-VIII-64 | pBUD |
| pSYN-FVIII-130 | mutation of R336I R562K R490A H497A N1224A in the background of pSYN-VIII-65 | pBUD |
| pSYN-FVIII-131 | mutation of R471A Y487A R490A H497A N1224A in the background of p SYN-VIII-64 | pBUD |
| pSYN-FVIII-132 | mutation of R471A Y487A R490A H497A N1224A in the background of pSYN-VIII-65 | pBUD |
| pSYN-FVIII-135 | BDD-FVIII scFc with R1645A/R1648A | pcDNA 3.3 Topo |
| pSYN-FVIII-136 | BDD-FVIII cleavable scFc with VWF D'D3 (1-477aa, C336A/C379A) on second Fc & 20aa thrombin cleavable linker in between | pcDNA 3.3 Topo |
| pSYN-FVIII-137 | BDD-FVIII cleavable scFc with VWF D'D3 (1-276aa) on second Fc & 20aa thrombin cleavable linker in between | pcDNA 3.3 Topo |
| pSYN-FVIII-145 | BDD-FVIII scFc with R471A/Y487A, R490A/H497A | pcDNA 3.3 Topo |
| pSYN-FVIII-146 | BDD-FVIII cleavable scFc (R471A/Y487A) with VWF D'D3 (1-477aa, C336A/C379A) on second Fc & 20aa thrombin cleavable linker | pcDNA 3.3 Topo |
| pSYN-FVIII-147 | BDD-FVIII cleavable scFc (R471A/Y487A) with VWF D'D3 (1-276aa) on second Fc & 20aa thrombin cleavable linker in between | pcDNA 3.3 Topo |
| pSYN-FVIII-148 | BDD-FVIII cleavable scFc (R1645A/R1648A) with VWF D'D3 (1-477aa, C336A/C379A) on second Fc & 20aa thrombin cleavable linker | pcDNA 3.3 Topo |
| pSYN-FVIII-149 | BDD-FVIII cleavable scFc (R1645A/R1648A) with VWF D'D3 (1-276aa) on second Fc & 20aa thrombin cleavable linker | pcDNA 3.3 Topo |
| pSYN-FVIII-155 | BDD-FVIII fused to single Fc (R1645A/R1648A) | pcDNA 4 |
| pSYN-FVIII-159 | BDD-FVIII cleavable scFc with VWF D'D3 (1-477aa, C336A/C379A) on second Fc & 35 aa thrombin cleavable linker in between | pBUD |

TABLE 6-continued

VWF Fragments and FVIII/VWF Heterodimer Constructs

| Construct | Description | Vector |
|---|---|---|
| pSYN-FVIII-160 | BDD-FVIII cleavable scFc with VWF D'D3 ( 1-477aa, C336A/C379A) on second Fc & 48 aa thrombin cleavable linker in between | pBUD |
| pSYN-FVIII-164 | BDD-FVIII cleavable scFc (R490A/H497A, R1645A/R1648A) with VWF D'D3 ( 1-477aa, C336A/C379A) on second Fc & 20aa thrombin cleavable linker | pcDNA 3.3 Topo |
| pSYN-FVIII-165 | BDD-FVIII cleavable scFc (R336I/R562K, R490A/H497A, R1645A/R1648A) with VWF D'D3 ( 1-477aa, C336A/C379A) on second Fc & 20aa thrombin cleavable linker | pcDNA 3.3 Topo |
| pSYN-FVIII-178 | BDD-FVIII cleavable scFc with VWF D'D3 ( 1-477aa, C336A/C379A) on second Fc & 73 aa thrombin cleavable linker in between | pBUD |
| pSYN-FVIII-179 | BDD-FVIII cleavable scFc with VWF D'D3 ( 1-477aa, C336A/C379A) on second Fc & 98 aa thrombin cleavable linker in between | pBUD |
| pSYN-FVIII-180 | BDD-FVIII (K2092A) cleavable scFc with VWF D'D3 ( 1-477aa, C336A/C379A) on second Fc & 48 aa thrombin cleavable linker in between | pBUD |
| pSYN-FVIII-181 | BDD-FVIII (F2093A) cleavable scFc with VWF D'D3 ( 1-477aa, C336A/C379A) on second Fc & 48 aa thrombin cleavable linker in between | pBUD |
| pSYN-FVIII-182 | BDD-FVIII (K2092A/F2093A) cleavable scFc with VWF D'D3 ( 1-477aa, C336A/C379A) on second Fc & 48 aa thrombin cleavable linker in between | pBUD |

Example 6

Protein Purification

Protein Purification of VWF Fragments

The VWF fragments were purified through a two-step purification method. A

Nickel Sulfate charged IMAC (Immobilized Metal Affinity Chromatography) column was used for the primary purification, a Fractogel DEAE ion exchange column was used for the final purification. The detail purification method is described below.

(a) Primary Purification of VWF Fragment on Nickel IMAC

A 14 mL Nickel IMAC Sepharose HP column [XK26/3] was equilibrated with 25 mM HEPES, 500 mM NaCl, 10 mM Imidazole, and 0.05% Tween-20 @ pH 7.5. Approximately 7.2 L of VWF conditioned media was adjusted with 100 mL of 1M HEPES @ pH 7.5 and 600 mL of 5M NaCl. Then 80 mL of 1M Imidazole (@ pH 7.5) was added to a final concentration of 10 mM. The 7.8 L of the adjusted VWF conditioned media was then loaded onto the column at 2-8° C. at 10 mL/min [113 cm/hour]. The wash steps were performed at 13.3 mL/minute [150 cm/hour]. First, a 2× Column Volume (CV) wash was performed with 25 mM HEPES, 500 mM NaCl, 10 mM Imidazole, and 0.05% Tween-20 @ pH 7.5 in normal flow {"DownFlow"}. Next, a 3×CV wash was performed with 25 mM HEPES, 500 mM NaCl, 10 mM Imidazole, and 0.05% Tween-20 @ pH 7.5 in reverse flow {"UpFlow"}. Lastly, A 3×CV wash was performed with 25 mM HEPES, 500 mM NaCl, 10 mM Imidazole, and 0.05% Tween-20 @ pH 7.5 in normal flow {"DownFlow"}. The elution was performed as a 10xCV gradient to 50% B1 (25 mM HEPES, 500 mM NaCl, 500 mM Imidazole, and 0.05% Tween-20 @ pH 7.5). The fraction volume was set to 10 mL. Then, the column was stripped with 100% B1. This was followed by a wash with 25 mM HEPES, 500 mM NaCl, 10 mM Imidazole, and 0.05% Tween-20 @ pH 7.5. A second Strip was performed with 1N NaOH. Then the column was flushed with 1M TRIS, 1M NaCl @ pH 7.8, followed by 25 mM HEPES, 500 mM NaCl, 10 mM Imidazole, and 0.05% Tween-20 @ pH 7.5. Finally, the column was flushed with 5 CV's of DPBS+ 20% Ethanol and stored at 4° C.

(b) Secondary Purification of VWF Fragment on Fractogel DEAE

Secondary purification of VWF fragment was performed on Fractogel DEAE @ pH 7.5. Firstly, 20 mL of VWF Nickel IMAC eluate (corresponding to the VWF fragment peak) was adjusted with 200 mg of Zwittergent 3-14 zwitterionic detergent in an attempt to disrupt aggregated species without using denaturing or reducing excipients. After the detergent was dissolved, the protein was left at RT for approximately 15 minutes. Then, the protein was adjusted with 4 grams of trehalose, 1 mL of 10% Tween-20, 5 mL of 1M HEPES @ pH 7.5 and 174 mL of "Milli-Q" water. The equilibration buffer "A12" was 25 mM HEPES, 50 mM NaCl, 1% Trehalose, 0.05% Tween-20 @ pH 7.5. The elution buffer "B1" was 25 mM HEPES, 1000 mM NaCl, 1% Trehalose, 0.05% Tween-20 @ pH 7.5. The elution was performed as a 10 CV gradient to 50% B1, with a 5+CV hold followed by a step to 100% B1. Then the column was stripped with 0.85% Phosphoric Acid, followed by 1M TRIS, 1M NaCl @ pH 7.5. Then the column was stripped with 1N NaOH, 2M NaCl followed by 1M TRIS, 1M NaCl @ pH 7.5. Then the column was flushed with 25 mM HEPES, 100 mM NaCl+20% Ethanol @ pH 7.5 for storage.

(c) Protein Purification of FVIII-VWF Heterodimer

The FVIII-VWF heterodimer was first purified by an affinity column (GE VIIISelect), then followed by a Fractogal TMAE ion exchange column. (McCue J T, Selvitelli K, Walker J, J Chromatogr A. 2009 Nov. 6; 1216(45):7824-30. Epub 2009 Sep. 23.)

For the purification of FVIII-155/VWF-31, a tangential flow filtration (TFF) step was used to buffer exchange the clarified conditioned media. The targeted proteins in the filtrate were then captured using affinity chromatography. A weak anion exchange chromatography step was followed to reduce HMW species. Both the purity and size of the molecule were accessed by HPLC-SEC and SDS-PAGE.

The presence of different domains of FVIII-155/VWF-31 was further confirmed by western blotting. The specific activity of the molecule was comparable to B-domain deleted FVIII.

(d) Thrombin Digestion of FVIII-VWF Heterodimer (FIG. 8)

FVIII-VWF-Fc heterodimer or FVIII-Fc (control) was mixed with thrombin in 1:10 ratio in thrombin cleavage buffer (50 mM Tris, pH 7.4, 150 mM NaCl, 2 mM CaCl2, 5% Glycerol). The reaction was incubated at 37° C. for 20 minutes. Digested product was run on 4-12% reducing tris-glycine gel. Undigested protein was used as a control. Bands were visualized by coomassie stain.

(e) Evaluation of the VWF Binding Ability of FVIII-155/VWF-031 by Octet Assay

The VWF binding ability of FVIII-155/VWF-031 was determined by Bio-Layer Interferometry (BL1) based measurements (Octet assay) at 25° C. with a ForteBio Octet 384 instrument using Tris binding buffer (50 mM Tris, pH 7.2, 150 mM NaCl, 5 mM $CaCl_2$). The Octet assay for determining FVIII binding was based on the hydrophobic immobilization of human von Willebrand Factor (hVWF) (Haematologic Technologies Catalog No. HCVWF-0191) onto the APS Biosensor, followed by binding of 1.0% Bovine Serum Albumin (Jackson ImmunoResearch Catalog No. 001-000-161). Briefly, hVWF (38.5 nM) was diluted in Tris buffer and loaded across APS Biosensors for 600 sec, yielding approximately 3.0-3.5 nm binding on the reaction probes. Control APS probes were loaded with 1.0% BSA in the absence of hVWF for reference subtraction. After loading, all probes were incubated in Tris buffer for 300 sec to establish a new baseline. Subsequently, biosensor probes were incubated in solutions of FVIII-155/VWF-031, FVIIIFc Drug Substance, or rFVIII (60 nM) for 5 min at room temperature, followed by a 5 min dissociation step. Using the Octet data analysis software, the binding response (nm) was derived from the subtracted data (Reaction probe minus Reference probe). As shown in FIG. 15, compared to the VWF binding affinity of rFVIIIFc and rFVIII, the VWF binding affinity of FVIII-155/VWF-031 was severely impaired. This indicates successful shielding of FVIII from full length VWF by the D'D3 fragment within the FVIIIFc/VWF heterodimer.

Example 7

VWF-FVIII Interaction is a Limiting Factor for FVIII Half-life Extension

The majority of the circulating FVIII exists as a FVIII-VWF complex (>95% of plasma FVIII). This FVIII-VWF interaction promotes FVIII clearance through the VWF clearance pathway, thus making the VWF half-life (T1/2) a limitation of the FVIII half-life extension. To evaluate this hypothesis, the limitation of FVIII half-life extension by Fc technology was tested in FVIII deficient mice (HemA mice, which have intact VWF gene) and FVIII/VWF deficient (FVIII-VWF Double Knockout (DKO)) mice.

The HemA mice or FVIII-VWF DKO mice were treated with a single intravenous dose of rFVIII or rFVIIIFc at 125 IU/kg in HemA mice or 200 IU/kg in DKO mice. Blood samples were collected up to 72 hrs in the HemA mice or up to 8 hrs in the FVIII/VWF DKO mice. Plasma sample's FVIII activity was then measured by a FVIII chromogenic assay. The pharmacokinetic (PK) profile of the two rFVIII variance was analyzed using WinNonline program.

As shown in Table 7 and FIG. 9, in the FVIII/VWF DKO mice, rFVIIIFc showed about 4.8 fold longer $T_{1/2}$ (i.e., $T_{1/2}$ of 1.2 hr) compared to $T_{1/2}$ of rFVIII (i.e., $T_{1/2}$ of 0.25 hr). In contrast, when tested in HemA mice, rFVIIIFc only had 1.8 fold longer $T_{1/2}$ compare to rFVIII. The $T_{1/2}$ of rFVIIIFc was 13.7 hr, which is in line with the endogenous murine VWF half-life. This indicates that the FVIII-VWF interaction is a limiting factor for FVIII half-life extension. In order to achieve more than 2 fold FVIII half-life extension, the FVIII-VWF interaction will have to be eliminated.

TABLE 7

FVIII PK in HemA and FVIII/VWF DKO mice

| Test Molecule | FVIII-deficient Mice | | FVIII/VWF-deficient Mice | |
|---|---|---|---|---|
| | $T_{1/2}$ (hr) | $T_{1/2}$ Ratio vs rFVIII | $T_{1/2}$ (hr) | $T_{1/2}$ Ratio |
| rFVIII | 7.6 | 1 | 0.25 | 1 |
| rFVIIIFc | 13.7 | 1.8 | 1.2 | 4.8 |

FVIII Chromogenic Assay

The FVIII activity was measured using the COATEST SP FVIII kit from DiaPharma (lot# N089019) and all incubations were performed on a 37° C. plate heater with shaking The range of rFVIII standard was from 100 mIU/mL to 0.78 mIU/mL. A pooled normal human plasma assay control and plasma samples (diluted with 1× Coatest buffer) were added into Immulon 2HB 96-well plates in duplicate (25 µL/well). Freshly prepared IXa/FX/Phospholipid mix (50 µL), 25 µL of 25 mM $CaCl_2$, and 50 µL of FXa substrate were added sequentially into each well with 5 minutes incubation between each addition. After incubating with the substrate, 25 µL of 20% Acetic Acid was added to terminate the color reaction, and the absorbance of OD405 was measured with a SpectraMAX plus (Molecular Devices) instrument. Data were analyzed with SoftMax Pro software (version 5.2). The Lowest Level of Quantification (LLOQ) is 7.8 mIU/mL.

Example 8

VWF D'D3 Dimer Protects FVIII from FVIII Proteolysis and Clearance (FIG. 10)

The FVIII protection activity of the VWF fragments was evaluated by their ability to protect endogenous murine FVIII from its clearance in VWF deficient mice. Different VWF fragment as listed in Table 8 Column 1 (FIG. 1, Example 1) were introduced into the blood circulation of the VWF deficient mice by Hydrodynamic injection of their corresponding DNA constructs at 100 µg/mouse. The plasma samples were collected at 48 hrs post injection, and murine FVIII plasma activity was measured by a FVIII chromogenic assay. VWF expression level was measured by VWF ELISA.

Four different lengths of the VWF fragments that have been tested are 276, 477, 511, and 716 amino acids. The 276 to 716 amino acid range was tested to find out the length of the VWF fragments required for FVIII binding (276aa) without VWF's clearance receptor's binding domain (716aa). The full length VWF and the D1D2D'D3CK multimer were used as the positive control for FVIII protection. In blood circulation, the VWF fragments synthesized with the D1D2 domain exist as a dimer and exist as monomers when they are synthesized without the D1D2 domain.

The increase of murine FVIII activity in plasma post hydrodynamic injection measures the FVIII protection effect of the VWF fragments. As shown in Table 8 and FIG. 10A-B, the first 276aa of the D'D3 fragment had no FVIII protection activity as demonstrated by the similar pre/post injection FVIII plasma level (FIG. 10A). However, the introduction of the other VWF fragments induced a significant increase on FVIII plasma level, indicating that those VWF fragments can protect FVIII from its clearance pathway.

TABLE 8

FVIII/VWF DKO mice murine FVIII plasma level Pre/post introduction of VWF fragments (DNA constructs were illustrated in FIG. 1)

| DNA CONSTRUCT | Encoding VWF Fragment | FVIII Activity-Pre (mIU/mL) | | FVIII Activity-48 hr (mIU/mL) | | VWF Antigen-48 hr (nM/mL) | |
|---|---|---|---|---|---|---|---|
| | | Avg. | SD | Avg. | SD | Avg. | SD |
| VWF-001 | D'D3$_{276aa}$ | 53 | 31 | 86 | 16 | 2.8 | 1.9 |
| VWF 009 | D1D2D'D3$_{276aa}$ | 45 | 20 | 65 | 17 | 1.8 | 1.3 |
| VWF-002 | D'D3$_{477aa}$ | 56 | 3 | 257 | 38 | 17.0 | 0.5 |
| VWF 010 | D1D2D'D3$_{477aa}$ | 42 | 11 | 387 | 22 | 8.2 | 1.6 |
| VWF-003 | D'D3A1$_{511aa}$ | 88 | 21 | 253 | 47 | 12.9 | 2.2 |
| VWF-011 | D1D2D'D3A1$_{511aa}$ | 63 | 42 | 360 | 15 | 9.3 | 2.3 |
| VWF-004 | D'D3A1$_{716aa}$ | 87 | 8 | 239 | 56 | | |
| VWF-012 | D1D2D'D3A1$_{716aa}$ | 64 | 22 | 307 | 29 | | |
| VWF-006 | D1D2D'D3CK | 38 | 10 | 249 | 20 | 2.4 | 1.0 |
| VWF-008 | Full length VWF | 51 | 8 | 380 | 41 | 10.6 | 2.3 |

The ratio of post injection plasma FVIII activity and the plasma antigen level of the VWF fragments that contain the D'D3 domain of full-length VWF were listed in Table 8. Similar post injection FVIII/VWF ratio was observed from the full length VWF and the two dimer forms of the VWF fragments, meaning that those two VWF fragment dimers provide the same FVIII protection as the full length VWF. In addition, threefold higher FVIII/VWF ratio was observed from the VWF fragment dimer isoforms compare to their corresponding monomers: the D'D3 (477aa) dimer has the FVIII/VWF ratio of 38.7 mIU/nmol; the D'D3 (477aa) monomer has the FVIII/VWF ration of 11.6 mIU/nmol: the D'D3A1 (511aa) dimer has the FVIII/VWF ratio of 32.9 mIU/nmol; and the D'D3 (511aa) monomer has the FVIII/VWF ratio of 13.8 mIU/nmol, indicating the dimer isoforms of the VWF fragments provides better FVIII protections compare to their corresponding monomers.

TABLE 9

FVIII protection effect of full length D'D3 fragment

| DNA Construct | Encoding VWF Fragment | Multimer State | FVIII/VWF (mIU/nmol) | |
|---|---|---|---|---|
| | | | Mean | (SD) |
| VWF-002 | D'D3$_{477aa}$ | Monomer | 11.6 | (4.4) |
| VWF-010 | D1D2D'D3$_{477aa}$ | Dimer | 38.7 | (11.7) |
| VWF-003 | D'D3A1$_{511aa}$ | Monomer | 13.8 | (1.3) |
| VWF-011 | D1D2D'D3A1$_{511aa}$ | Dimer | 32.9 | (5.5) |
| VWF-008 | Full length VWF | Multimer | 31.1 | (6.7) |

Hydrodynamic Injection:

Hydrodynamic Injection is an efficient and safe non-viral gene delivery method to the liver in small animals, such as mice and rats. It was originally described as a rapid injection of a naked plasmid DNA/saline solution free of endotoxin at a tenth volume of the animal's body weight in about 5-7 seconds. The naked plasmid DNA contains the gene of interest and the liver produced targeted protein from the injected DNA can be detected within 24 hours post-injection. Plasma samples were then collected to study the therapeutic property of the expressed protein.

For all the hydrodynamic injections that were performed herein in this patent application, 2 ml of plasmid DNA in 0.9% sterile saline solution was delivered via intravenous tail vein injection within about 4-7 seconds to mice weighing 20-35 grams. The mice were closely monitored for the first couple of hours until the normal activity resumed. After the blood samples were collected via retro orbital blood collection, plasma samples were then obtained and stored at −80° C. for further analysis.

VWF ELISA:

Goat anti-human VWF antibody (Affinity purified, affinity biological, GAVWF-AP) was used as the capture antibody at 0.5 ug/well and VWF-EIA-D (Affinity Biologicals, VWF-EIA-D, 1:100 dilution) was used as the detecting antibody for the VWF ELISA. ELISA assay was performed following the standard ELISA procedure, TMB was used as the HRP substrate, PBST/1.5% BSA/0.5M NaCl buffer was used as blocking and binding buffer. The assay standard range is 100 ng to 0.78 ng, and the assay's lowest limit of quantification (LLOQ) is 7.8 ng/mL.

Example 9

Co-administration of Full Length VWF D'D3 Fragment Extend rBDD-FVIII Half-life in FVIII-VWF DKO Mice (FIG. 11)

Example 8 has demonstrated that full length D'D3 fragment can protect endogenous FVIII from its clearance pathway. In order to further evaluate the FVIII protection activity of D'D3 protein, FVIII-VWF DKO mice were co-administered with B domain deleted FVIII (rBDD-FVIII) and D'D3 dimer (VWF-010) or rBDD-FVIII and D'D3 monomer (VWF-002), via intravenous injection at 200 IU/kg for rBDD-FVIII, 770 µg/kg for D'D3 dimer and 590 µg/kg for D'D3 monomer. The PK profile of rBDD-FVIII was then monitored by its post injection plasma activity. Due to the short in vivo half-life of the D'D3 fragments, at three hour post the initial co-injection, another dose of D'D3 was administered through the same route to maintain a desirable D'D3 plasma level.

For PK analysis, plasma sample was obtained via retro-orbital blood collection at 5 min, 30 min, 1 hour, 2 hour, 4 hour and 6 hour post injection, plasma FVIII activity and D'D3 antigen level was analyzed by FVIII chromogenic assay and VWF ELISA.

As shown in FIG. 11 and Table 10, the D'D3 monomer prolonged rBDD-FVIII half-life by 2.5 fold and improved its recovery by 1.8 fold. The D'D3 dimer prolonged rBDD-FVIII half-life by 4.1 fold and improved its recovery by 3.5 fold. Improved mean residency time, clearance and AUC were also observed from both of the D'D3 isoforms. The D'D3 dimer, however, achieved better results in all the PK parameters compared to its monomer form.

In summary, co-injection of full length D'D3 protects FVIII from its clearance pathway, as show in the improved PK profile of rBDD-FVIII. The potential clinical value of this finding needs to be further evaluated.

TABLE 10

BDD-FVIII PK parameter in FVIII-VWF DKO mice when co-administered with D'D3 fragments

| Treatment | 5 min Recovery (%) | $T_{1/2}$ (hr) | MRT (hr) | Cl (mL/hr/kg) | Vss (mL/kg) | AUC_D (hr * kg * mIU/ mL/mIU) | $T_{1/2}$ Fold Increase | Recovery Fold Increase |
|---|---|---|---|---|---|---|---|---|
| rBDD-FVIII | 25 | 0.23 | 0.24 | 407.72 | 133.14 | 0.0025 | | |
| rBDD-FVIII VWF-002 | 44 | 0.57 | 0.58 | 151.93 | 124.63 | 0.0066 | 2.5 | 1.8 |
| rBDD-FVIII VWF-010 | 87 | 0.95 | 0.98 | 71.48 | 97.54 | 0.014 | 4.1 | 3.5 |

Example 10

The D'D3 Monomer Synthesized with D1D2 Domain and its Dimer Isoform have Same FVIII Protection Activity and Further Extended FVIIIFc's Half-life by ~4 Fold in FVIII-VWF DKO Mice (FIG. 12)

In order to quantify the FVIII protection ability of the D'D3 domains and determine if the D'D3 dimerization is necessary for its FVIII protection activity, each of two DNA constructs (i.e., VWF-025 (containing DNA sequence encoding D1D2D'D3) and VWF-029 (containing D1D2D'D3 codon DNA with C336A and C379A mutation)) was administered into FVIII/VWF DKO mice by hydrodynamic injection. This injection resulted in D'D3 dimer (VWF-025) or monomer expression (VWF-029) in the FVIII/VWF DKO mice. At day5 post hydrodynamic injection, a single intravenous dose of rFVIIIFc was administered at 200 IU/kg, and plasma samples was collected at 5 min, 4, 8,16, 24, 31, 40, 55, 66 hrs post rFVIIIFc IV injection. An rFVIIIFc PK study that was performed in naïve FVIII-VWF DKO mice at the same dose was used as the rFVIIIFc half-life base line. Plasma FVIII activity was analyzed by a FVIII chromogenic assay. Plasma D'D3 level was measured by VWF ELISA, and rFVIIIFc PK profile was analyzed using WinNonlin program.

As shown in Table 11 and FIG. 12, with the VWF D'D3 fragments in the circulation, rFVIIIFc's initial recovery increased from 42% to 75% with D'D3 dimer and 60% with D'D3 monomer. rFVIIIFc's $T_{1/2}$ was also increased from 2.5 hrs to 9.3 hrs and 9.2 hrs, respectively. Similar to $T_{1/2}$, improved mean residency time, clearance, and volume distribution were also observed from the D'D3 monomer and dimer expressing mice. Overall, we see about 8 fold improvements on the rFVIIIFc's half-life and 6 fold improvements on AUC in both D'D3 monomer and dimer expressing mice. Same as its dimer isoform, the D'D3 monomer of full-length VWF that was synthesized with propeptide (D1D2) of VWF is sufficient to provide the full FVIII protection effect as the full length VWF molecule.

In FVIII/VWF DKO mice, WT-FVIII has a 0.25 hr $T_{1/2}$. The Fc fusion technology increased FVIII $T_{1/2}$ to 1.2 hour, which is about 4.8 fold increase. When the Fc fusion technology was combined with the D'D3 domains, the FVIII $T_{1/2}$ was increased to 9.3 hr (D'D3 dimer) and 9.2 hr (D'D3 monomer), which are about 37 fold increases in total. (Table 10) This result demonstrated the synergistic effect of the Fc fusion and D'D3 VWF fragment on the FVIII half-life extension.

TABLE 11 rFVIIIFc PK parameter with/without D'D3 fragment in blood circulation

| Treatment | 5 min Recovery (%) | $T_{1/2}$ (hr) | MRT (hr) | Cl (mL/hr/kg) | Vss (mL/kg) | AUC_D (hr * kg * mIU/ mL/mIU) | $T_{1/2}$ Fold Increase | AUC D Fold Increase |
|---|---|---|---|---|---|---|---|---|
| rFVIIIFc | 43 | 1.2 | 0.76 | 39.5 | 67.0 | 0.025 | | |
| rFVIIIFc VWF-025 | 75 | 9.3 | 11.1 | 6.1 | 67.6 | 0.164 | 7.8 | 6.6 |
| rFVIIIFc VWF-029 | 60 | 9.2 | 11.3 | 6.7 | 75.7 | 0.149 | 7.7 | 6.0 |

Example 11

FVIII-VWF Heterodimer PK in HemA Mice

The PK profile of the lead candidates of FVIII-VWF heterodimer (such as FVIII-155/VWF-031) will be tested in HemA mice to evaluate their ability of shielding FVIII from the endogenous VWF and their ability for FVIII half-life extension.

HemA mice will be treated with a single intravenous dose of the lead candidates at 200 IU/kg, plasma samples will then be collected at 5 min, 4 hr, 8 hr, 24 hr, 48 hr, 72 hr, 96 hr and 120 hr, plasma activity will be tested by FVIII chromogenic assay, and FVIII variance half-life will be calculated by WinNonlin program.

In an optimal FVIII/VWF heterodimer configuration, the FVIII binding to the endogenous VWF will be completely inhibited, therefor the base line half-life of rFVIII will be decreased from 7.6 hr to 0.25 hr as shown in example 7. When D'D3 fragment non-covalently associated with FVIII, about 8 fold of half-life benefit was observed (example 9). In the lead candidates of the FVIII/VWF heterodimer, the VWF fragment is covalently associated with the FVIII molecule, better FVIII protection might be able to be achieved. The invention of this application opened the door to further extend FVIII half-life beyond the two fold ceiling, with the combination of the available half-life extension technologies, HemA patients could expect a better long acting FVIII variance in the near future.

The PK profile of FVIII-155/VWF-031 was tested in HemA and FVIII/VWF DKO mice to evaluate the ability of the D'D3 fragment to shield the FVIII moiety from the endogenous VWF. HemA or FVIII/VWF DKO mice were treated with a single intravenous dose of FVIII-155/VWF-031 at 200 IU/kg, plasma samples were then collected at 5 min, 8 hrs, 24 hrs, and 48 hours post dosing. The FVIII activity of the plasma sample was tested by a FVIII chromogenic assay, and the half-life of FVIII-155/VWF-031 was calculated using WinNonlin program.

Severely impaired binding to immobilized VWF was detected by biolayer interferometry (FIG. 15, Octet; ForteBio Inc., Menlo Park, Calif.) for FVIII-155/VWF-031 compared to rFVIIIFc and rFVIII. This shows the D'D3 domain in the molecule had successfully blocked the FVIII binding to native VWF molecules. Therefore, similar half-life of rFVIII-155/VWF-031 was expected in the two different mouse strains. Study results are listed in FIG. 16 and Table 12A. As predicted, rFVIII-155/VWF-031 had comparable PK profile in both HemA and FVIII/VWF DKO mice, indicating that the half-life of FVIIIFc/VWF heterodimer is independent from the half-life of endogenous VWF. The results show that inhibition of the interaction between the rFVIIIFc with endogenous VWF by the VWF D'D3 domains allows elimination of the FVIII half-life ceiling and opens up the possibility of extending FVIII half-life beyond the half-life achievable without the VWF D'D3 domains (about two fold of the wild type FVIII).

TABLE 12A

FVIII-155/VWF-031 PK in FVIII/VWF DKO mice and HemA mice

| Treatment | 5 min Recovery (%) | $T_{1/2}$ (hr) | MRT (hr) | Cl (mL/hr/kg) | Vss (mL/kg) | AUC_D (hr * kg * mIU/mL/mIU) |
|---|---|---|---|---|---|---|
| FVIII-155/VWF-031 DKO | 49 | 9.9 | 6.9 | 11.6 | 80.5 | 0.09 |
| FVIII-155/VWF-031 HemA | 69 | 10.8 | 707 | 11.9 | 92.1 | 0.08 |

The FVIII protecting ability of the D'D3 domains was evaluated by comparing the $t_{1/2}$ of FVIII-155/VWF-031 with FVIIIFc in FVIII/VWF DKO mice. After a single IV administration, blood samples were collected at 5 min, 8 hrs, 24 hrs and 48 hrs for FVIII-155/VWF-031, and at 5 min, 1 hrs, 2 hrs, 4 hrs, 6 hrs and 8 hrs for FVIIIFc. The FVIII activity of plasma sample was tested by a FVIII chromogenic assay, and the half-life of FVIII-155/VWF-031 was calculated using WinNonlin program.

FIG. 16B and Table 12B show a significantly improved PK profile for FVIII-155/VWF-031 compared to rFVIIIFc in DKO mice: about 6 fold increases on $t_{1/2}$; and about 5 fold increases in clearance and AUC. This result demonstrates that the D'D3 domain in FVIIIFc/VWF heterodimer protects the FVIII moiety from some clearance pathways, thus providing some of the protection normally provided by full length VWF. This conclusion is also confirmed in HemA mice. When compared to rFVIIIFc in HemA mice, rFVIII-155/VWF-031 has shown shorter $t_{1/2}$ and lesser AUC, meaning in this configuration, the D'D3 domains (VWF-031) successfully prevents binding of the FVIII protein (rFVIII-155) to endogenous VWF, which has half-life extending properties to some degree, as well as a FVIII half-life limiting property. Full length VWF is 250 kDa, and forms multimers such that endogenous VWF can be up to 2 MDa, and therefore it is consistent with this hypothesis that the 55 kDa D'D3 region of VWF does not provide the same protection normally afforded by the much large endogenous VWF in this context. Since the VWF fragment prevents endogenous VWF from binding rFVIII-155/VWF-031, in this particular construct the half-life is decreased in the HemA mouse. Therefore, the results in Table 12B indicate that the rFVIII-155/VWF-031 molecule is capable of preventing the FVIII half-life extender (endogenous VWF) from binding the rFVIII-155/VWF-031. However, the experiment shows that removing the FVIII half-life limiting factor has opened up the possibility of extending a half-life of the FVIII protein beyond 1.5 fold or 2 fold shown previously. When FVIII is combined with other half-life extension elements as shown in FIG. 4, a breakthrough of the 2 fold half-life extension ceiling of FVIII could be achieved.

TABLE 12B

FVIII-155/VWF-031 and FVIIIFc PK in FVIII/VWF DKO mice

| Treatment | 5 min Recovery (%) | $T_{1/2}$ (hr) | MRT (hr) | Cl (mL/hr/kg) | Vss (mL/kg) | AUC_D (hr * kg * mIU/mL/mIU) |
|---|---|---|---|---|---|---|
| FVIIIFc DKO | 43 | 1.6 | 1.9 | 63.9 | 123.2 | 0.02 |
| FVIII-155/VWF-031 DKO | 49 | 9.9 | 6.9 | 11.6 | 80.5 | 0.09 |
| Fold Increase | | 6.2 | 3.6 | 5.5 | | 4.5 |
| FVIII-155/VWF-031 HemA | 69 | 10.8 | 7.7 | 11.9 | 92.1 | 0.08 |
| FVIIIFc HemA | 86 | 16.4 | 20.3 | 2.9 | 57.7 | 0.35 |

Example 12

Optimization of the D'D3-Fc Linker of FVIII/D'D3 Heterodimer (FIG. 13)

To allow rFVIIIFc to escape the VWF clearance pathway and eliminate the 2 fold FVIII half-life extension ceiling, the VWF D'D3 fragment has been incorporated into the rFVIIIFc molecule (FIG. 2), resulting in an FVIIIFc/VWF heterodimer. In order to eliminate the interaction between rFVIIIFc and endogenous VWF and maximize the D'D3 FVIII protection potential, the linker between the D'D3 domain and the Fc region was adjusted to allow the optimal FVIII/D'D3 binding. A more optimal linker will allow the D'D3 domain to have greater FVIII protection than a less optimal linker construct does. This can be tested by hydrodynamic injection of the DNA constructs in FVIII/VWF DKO mice. A more optimal construct will yield higher steady state protein expression of the FVIIIFc/D'D3 heterodimer.

Three different FVIIIFc/D'D3 heterodimers (FIG. 3, Example 3) were engineered for optimal linker selection. The possible linkers between the D'D3 domains and the Fc region were listed in Table 13. Those DNA constructs were administered into FVIII/VWF DKO mice by hydrodynamic injection ("HDI") at 100 μg/mouse, and plasma samples were collected 48 hr post HDI. Circulating FVIIIFc/D'D3 heterodimer activity was analyzed by a FVIII chromogenic assay. The study result was shown in FIG. 13. 48 hours post HDI, similar expression level were reached by FVIII-064 and FVIII-159, indicating the 20aa linker and the 35aa linker promote similar level of FVIII/D'D3 interaction. In another hand, FVIII-160 showed significantly higher expression than FVIII-064, meaning that the 48aa linker allows better FVIII/D'D3 binding compare to the 20aa and 35aa linkers.

An optimal linker between the VWF fragment and the Fc region is one of the key elements of the FVIIIFc/VWF heterodimer. Finding the best linker will allow the optimal interaction between FVIII and the VWF fragment, prevent FVIII binding to endogenous VWF, enable FVIII to escape the VWF clearance pathway, and extend the FVIII half-life beyond the plasma VWF half-life.

TABLE 13

Different linkers between D'D3 and Fc fragment

| DNA construct | Linker between D'D3 and Fc |
|---|---|
| FVIII-064 (SEQ ID NO: 92) | 20 aa = I D G G G G S G G G G S L V P R G S G G |
| FVIII-159 (SEQ ID NO: 93) | 35 aa = I S G G G G S G G G G S G G G G S G G G S G G G G S L V P R G S G G |
| FVIII-160 (SEQ ID NO: 94) | 48 aa = I S G G G G S G G G G S G G G G S G G S G G G G S G G G G S L V P R G S G G G G S G G G G S |

Example 13

Single Chain FVIII Stability

The Single chain FVIII protein might be more stable than its dual chain isoform.

To test this hypothesis, two DNA constructs were made: FVIII-136 (processable FVIIIFc with the D'D3 domain) and FVIII-148 (Single Chain (SC) FVIIIFc with the D'D3 domain, which contains R1645A/R1648A mutation to prevent cleavage between FVIII heavy chain and light chain).

Both plasmids were administered into FVIII/VWF DKO mice by hydrodynamic injection. Plasma samples were collected 24 hr and 48 hr post injections to measure the expression level of the two FVIIIFc/D'D3 isoforms. As shown in FIG. 14, at both time points, a trend of better expression was observed by the SC-FVIIIFc/D'D3 construct (FVIII-148) (p=0.12, p=0.19), indicating single chain FVIII might be more stable or better expressed than its dual chain isoform (FVIII-136). The PK profile of the two FVIII isoforms and their cell culture expression levels will be further investigated. The single chain FVIII isoform could be potentially used to replace the conventional dual chain isoform to achieve better protein production and better in vivo FVIII half-life.

Example 14

PEGylation

One or more polyethylene glycol (PEG) molecules can be attached within any regions of the FVIII protein, the VWF fragment, or both. As FVIII does not have a free cysteine at its surface based on crystal structure (PDB:2R7E, Shen et al., Blood 111:1240 (2008); PDB:3CDZ, Ngo, Structure, 16:597-606 (2008)), one approach is to insert a cysteine containing peptide (e.g., GGGSGCGGGS) (SEQ ID NO: 107) into or link it to the FVIII protein, the VWF fragment, or both. PEG molecules containing maleimide can then be conjugated specifically to the cysteine introduced on the recombinant FVIII protein. Briefly, the recombinant FVIII protein containing the Cys insertion can be constructed by standard molecular technology, and the recombinant FVIII protein expressed in mammalian expression system (e.g., HEK293, CHO, BHK21, PER.C6, and CAP cells) can be purified via affinity and ion exchange chromatography. The purified recombinant FVIII protein is reduced by Tris(2-carboxyethyl)phosphine (TCEP) to expose the thiol group of the introduced cysteine and then reacted with maleimide PEG. The resulting recombinant FVIII protein is tested for procoagulant activity and extended half-life.

PEG is attached to at least one of the locations disclosed in U.S. Appl. No. 61/670,553, which is incorporated herein by reference in its entirety, or other suitable insertion sites. The FVIII activity of the PEGylated recombinant FVIII protein is analyzed using a FVIII chromogenic assay. The PK of the PEGylated recombinant FVIII protein is analyzed in HemA mice and FVIII-VWF DKO Mice as described above.

Example 15

FVIII Stability in HemA and FVIII/VWF Double Knockout (DKO) Plasma

Plasma stability of different FVIIIFc fusions was tested in HemA or FVIII/VWF double knockout (DKO) plasma. For stability assay, 5 IU/ml of various FVIIIFc proteins were incubated with either mouse HemA or DKO plasma at 37° C. Aliquots were collected at different time points to measure activity by FVIII chromogenic assay. Activity at each time point was measured in duplicate and average activity was plotted as a function of time.

For the FVIIIFc immuno-precipitation assay, 5 µg FVIIIFc was incubated with either 250 µl of PBS or mouse DKO plasma for 24 hrs at 37° C. FVIIIFc was immuno-precipitated by adding 5 µg sheep anti-FVIII polyclonal antibody (ab61370) for 1 hr at room temperature and 100 µl protein A beads. After 4×1 ml PBS washes, beads were re-suspended in 50 µl 1× reducing SDS-PAGE buffer. After boiling, 20 µl sample (i.e. ~1 µg FVIIIFc) was loaded on to 4-15% Bio-Rad stain free gel. Gel was imaged by Bio-rad system followed by western analysis with FVIII anti heavy chain antibody (GMA012).

Activity of FVIIIFc (dual chain FVIII molecule, which has separate FVIII heavy and light chains, held together by non-covalent interactions) decreases with time in both HemA and DKO plasma (FIG. 18A). Due to lack of VWF mediated protection, loss in FVIIIFc activity was more pronounced in DKO plasma. This loss in FVIII activity was mainly due to dissociation or degradation of FVIII heavy chain (HC). About a 75% reduction in FVIIIFc heavy chain was observed after a 24 hr incubation in DKO plasma (FIG. 18B). No significant reduction was observed for either light chain (LC) (data not shown) or non-processed/single chain FVIIIFc (i.e. FVIII molecule in which light chain and heavy chain are still held together covalently-top band in the gel picture) (FIG. 18B).

As VWF is proposed to increase the stability of FVIII in vivo, we tested if chimeric protein-FVIII-VWF heterodimer (FVIII155:VWF31, which has VWF D'D3 covalently, attached to FVIII through Fc) was more stable in Hem A and DKO plasma. From plasma stability data shown in FIG. 19, the presence of D'D3 increased the stability of FVIIIFc, both in HemA and DKO plasma. Single chain FVIIIFc without D'D3 was used as control in these experiments (scFVIII). From FIG. 19, single chain FVIII was more stable than dual chain FVIIIFc; however the presence of D'D3 significantly increased the plasma stability of single chain FVIIIFc molecule further. This suggests that D'D3 stabilizes FVIII, not just by holding heavy and light chain together but also through some other unknown mechanisms.

Example 16

Use of Furin/PACE for VWF Processing

VWF is a unique protein in the sense that it contains a very large pro-peptide (i.e.D1D2 domain of VWF, ~85 kDa). The VWF pro-peptide serves as an internal chaperone for proper folding of VWF molecule. Two enzymes were tested for VWF processing-PC5 and Furin (PACE). VWF031 construct (D1D2D'D3Fc) was transiently co-transfected in HEK293 cells with various concentrations of either PC5 or PACE. After four days, the tissue culture media was collected and subjected to protein A pull down. Even at a lower concentration (2.5%), furin (PACE) was more efficient than 10% PC5, in removing the pro-peptide (D1D2) from D'D3Fc (FIG. 20). Removal of D1D2 is important, as the presence of D1D2 has been implicated in preventing interaction of D'D3 with FVIII.

Example 17

VWF Fragment in FVIII-VWF Heterodimer Prevents FVIII Interaction with Full Length VWF A ForteBio octet instrument was used to test FVIII construct 155/VWF31 heterodimer binding to full length VWF (FIG. 21A). For the binding assay, full length VWF was captured by using APS sensor, followed by blocking with 1% BSA. After blocking, different FVIII constructs were tested for VWF binding. As predicted, wild type FVIII and FVIIIFc bound strongly to the VWF sensors. FVIII Y1680F mutant, which is known to have low or no affinity for VWF showed significantly reduced VWF binding. FVIII155/VWF31 heterodimer did not bind at all to full length VWF, confirming shielding of FVIII with D'D3 in FVIII-VWF heterodimer.

The same experiment was performed in reverse orientation to determine if the D'D3 portion in the FVIII-VWF heterodimer can interact with other FVIII molecules not covalently attached to D'D3. As shown in FIG. 21B, the VWF31 (D'D3Fc) construct alone when immobilized on protein G sensor can bind strongly to FVIII, however the D'D3 in FVIII155:VWF31 heterodimer did not show any binding to FVIII. Protein G alone with FVIII was used as control. These binding experiments confirmed that D'D3 in heterodimer can interact with only one FVIII molecule which is covalently attached to it and prevent FVIII from interacting with full length wild type VWF molecules.

To determine the exact binding affinity of VWF D'D3 for FVIII molecule, surface plasma resonance experiments were performed with VWF031 (FIG. 22). VWF031 construct (D'D3Fc) was captured by using anti-human IgG and B-domain deleted FVIII was passed over D'D3Fc containing chip. A $K_D$ of about 10 nM was observed for FVIII. This affinity is about 25-fold lower compare to full length wild type VWF molecule and is similar to what is reported previously in literature.

Example 18

Effect of Different Linker Length in Between D'D3 and Fc on Heterodimer Activity and PK To check if varying the length of thrombin cleavable linker in between D'D3 and Fc has any effect on the PK and activity of FVIII-VWF heterodimer, different VWF constructs were co-expressed along with FVIII 155. Three different linker lengths constructs listed in Table 14A were tested (VWF031, VWF035 and VWF036). Each plasmid was mixed with FVIII155 plasmid (Example 5) and transfected into HEK293 cells. At day four post transfection, cell culture media was harvested and concentrated to 10 IU/ml FVIII chromogenic activity.

Concentrated cell media was then administered into 8-12 weeks old FVIII/VWF DKO mice at 100 IU/10 mL/kg dose. Plasma samples were collected at 5 min, 8 hr, 16 hr, 24 hr, 32 hr and 48 hr post dosing. FVIII activity of the plasma samples were analyzed by FVIII chromogenic assay and half-life was calculated using WinNonlin-Phoenix program.

As shown in FIG. 23, when the linker length between D'D3 and Fc fragment was increased from 48 aa to 73aa or 98aa, the half-life of the corresponding FVIIIFc/VWF heterodimer increased and reached 12.2 hr and 13.3 hr respectively. This represents a 1.5 to 1.6 fold increase over 48aa long variant. To date, the 98aa linker is the most optimal linker to utilize the FVIII protection activity of the D'D3 fragment, and it will be incorporated into FVIIIFc/VWF heterodimer to further improve its half-life.

To compare the effect of linker on FVIII activity, FVIII chromogenic and aPTT assay were performed on tissue culture media from cells expressing different FVIII-VWF heterodimers. Though aPTT activity was 2-fold reduced compare to chromogenic activity for heterodimer constructs, no significant difference was seen between various linkers, except when the linker also contain a PAR1 site next to thrombin site (Table 14B).

TABLE 14A

Sequence of Variable Linker in between VWF D'D3 and Fc

| DNA construct | Linker between D'D3 and Fc |
|---|---|
| VWF031 | 48 aa = I S G G G G S G G G G S G G G G S G G G G S G G G G S G G G G S L V P R G S G G G G S G G G G S (SEQ ID NO: 95) |
| VWF035 | 73 aa = I S G G G G S G G G G S G G G G S G G G G S G G G G S G G G G S G G G G S G G G G S G G G G S G G G G S L V P R G S G G G G S G G G G S (SEQ ID NO: 96) |
| VWF036 | 98 aa = I G G G G S G G G G S G G G G S G G G G S G G G G S G G G G S G G G G S G G G G S G G G G S G G G G S G G G G S G G G G S G G G G S G G G G S L V P R G S G G G S G G G G S (SEQ ID NO: 97) |

TABLE 14B

Heterodimer activity with different linker length

| Sample ID | Sample description | Linker length between D'D3 and Fc (aa) | Chromogenic IU/mL | aPTT IU/mL | Chromogenic/ aPTT |
|---|---|---|---|---|---|
| 1 | FVIII Fc 155 + VWF15 | 20 | 1.81 | 0.85 | 2.14 |
| 2 | FVIII Fc 155 + VWF31 | 48 | 2.32 | 1.05 | 2.21 |
| 3 | FVIII Fc 155 + VWF33 | 35 | 2.21 | 1.02 | 2.16 |
| 4 | FVIII Fc 155 + VWF35 | 73 | 2.65 | 1.24 | 2.14 |
| 5 | FVIII Fc 155 + VWF36 | 98 | 2.75 | 1.11 | 2.47 |
| 6 | FVIII Fc 155 + VWF39 | 26 (thrombin + PAR1) | 1.85 | 1.21 | 1.53 |

Example 19

Linking FVIII with VWF Fragment Using Sortase Enzyme

In another aspect, a VWF fragment (e.g. D1D2D'D3 or D'D3 domain) is attached to FVIII by using sortase mediated in vitro protein ligation method. In one example, *Staphylococcus aureus* sortase A (LPXTG) recognition motif was introduced at the C-terminus of VWF fragment and Gly(n) residue at the N-terminus of FVIII (where the number of glycine residues is variable). The FVIII molecule used can be either single chain or dual chain. The sortase catalyzed trans-peptidation reaction will covalently attach the VWF fragment to FVIII. Reverse orientation of recognition motif can also be used to link these two proteins, where we have FVIII at the N-terminus with LPXTG motif and VWF fragment at the C-terminus with Gly(n) (See FIG. 24—example of sortase ligation for reference). The LPXTG motif and Glycine residues can be replaced with other sortase recognition sequences.

VWF fragment containing sortase A recognition sequence Fc fusion protein was also made. For Fc fusion constructs, VWF D1D2D'D3 fragment was fused with Fc region of IgG through a GS linker that contains a sortase recognition sequence and a thrombin cleavage site (Table 15 and 16). Once protein is expressed and purified on Protein A column, the Fc region can be removed by thrombin cleavage. Resulting VWF fragment with sortase A recognition site can then be used for ligation with FVIII molecule (FIG. 24—Example of sortase ligation for reference—row E).

pSYN-VWF-051 has a 54 amino acids linker with sortase and thrombin site in between the VWF fragment and the Fc region. Synthesis of DNA fragment coding for 54 amino acids linker (ISGGGGSGGG GSGGGGSGGG GSGGGGSGGG GSLPETGALR PRVVGGGGSG GGGS) (SEQ ID NO: 98) and a portion of the Fc region was outsourced (Genewiz Sequence no-10-210746313, shown below). A fragment of the Genewiz construct was sub cloned into the EcoRV/RsRII digested pSYN-VWF-031.

Genewiz-Sequence no-10-210746313(SEQ ID NO: 99)

AGGAGCCGATATCTGGCGGTGGAGGTTCCGGTGGCGGGGGATCCGGCGGT

GGAGGTTCCGGCGGTGGAGGTTCCGGTGGCGGGGGATCCGGTGGCGGGGG

ATCCTTACCTGAAACTGGAGCCCTGCGGCCCCGGGTCGTCGGCGGTGGAG

GTTCCGGTGGCGGGGGATCCGACAAAACTCACACATGCCCACCGTGCCCA

GCTCCAGAACTCCTGGGCGGACCGTCAGTCTT

The sequence of N-terminus pentaglycine containing single chain FVIII is shown in Table 17 and 18.

TABLE 15

Nucleotide sequence of pSYN-VWF051 (VWF D1D2D'D3Fc with sortase A recognition motif and thrombin cleavable linker in between VWF fragment and Fc)

(SEQ ID NO: 100)

```
   1 ATGATTCCTG CCAGATTTGC CGGGGTGCTG CTTGCTCTGG CCCTCATTTT
  51 GCCAGGGACC CTTTGTGCAG AAGGAACTCG CGGCAGGTCA TCCACGGCCC
 101 GATGCAGCCT TTTCGGAAGT GACTTCGTCA ACACCTTTGA TGGGAGCATG
 151 TACAGCTTTG CGGGATACTG CAGTTACCTC CTGGCAGGGG GCTGCCAGAA
 201 ACGCTCCTTC TCGATTATTG GGGACTTCCA GAATGGCAAG AGAGTGAGCC
 251 TCTCCGTGTA TCTTGGGGAA TTTTTTGACA TCCATTTGTT TGTCAATGGT
 301 ACCGTGACAC AGGGGGACCA AAGAGTCTCC ATGCCCTATG CCTCCAAAGG
 351 GCTGTATCTA GAAACTGAGG CTGGGTACTA CAAGCTGTCC GGTGAGGCCT
 401 ATGGCTTTGT GGCCAGGATC GATGGCAGCG GCAACTTTCA GTCCTGCTG
 451 TCAGACAGAT ACTTCAACAA GACCTGCGGG CTGTGTGGCA ACTTTAACAT
 501 CTTTGCTGAA GATGACTTTA TGACCCAAGA AGGGACCTTG ACCTCGGACC
 551 CTTATGACTT TGCCAACTCA TGGGCTCTGA GCAGTGGAGA ACAGTGGTGT
 601 GAACGGGCAT CTCCTCCCAG CAGCTCATGC AACATCTCCT CTGGGGAAAT
 651 GCAGAAGGGC CTGTGGGAGC AGTGCCAGCT TCTGAAGAGC ACCTCGGTGT
 701 TTGCCCGCTG CCACCCTCTG GTGGACCCCG AGCCTTTTGT GGCCCTGTGT
 751 GAGAAGACTT TGTGTGAGTG TGCTGGGGGG CTGGAGTGCG CCTGCCCTGC
 801 CCTCCTGGAG TACGCCCGGA CCTGTGCCCA GGAGGGAATG GTGCTGTACG
 851 GCTGGACCGA CCACAGCGCG TGCAGCCCAG TGTGCCCTGC TGGTATGGAG
 901 TATAGGCAGT GTGTGTCCCC TTGCGCCAGG ACCTGCCAGA GCCTGCACAT
 951 CAATGAAATG TGTCAGGAGC GATGCGTGGA TGGCTGCAGC TGCCCTGAGG
1001 GACAGCTCCT GGATGAAGGC CTCTGCGTGG AGAGCACCGA GTGTCCCTGC
1051 GTGCATTCCG GAAAGCGCTA CCCTCCCGGC ACCTCCCTCT CTCGAGACTG
1101 CAACACCTGC ATTTGCCGAA ACAGCCAGTG GATCTGCAGC AATGAAGAAT
1151 GTCCAGGGGA GTGCCTTGTC ACTGGTCAAT CCCACTTCAA GAGCTTTGAC
1201 AACAGATACT TCACCTTCAG TGGGATCTGC CAGTACCTGC TGGCCCGGGA
1251 TTGCCAGGAC CACTCCTTCT CCATTGTCAT TGAGACTGTC CAGTGTGCTG
1301 ATGACCGCGA CGCTGTGTGC ACCCGCTCCG TCACCGTCCG GCTGCCTGGC
1351 CTGCACAACA GCCTTGTGAA ACTGAAGCAT GGGGCAGGAG TTGCCATGGA
1401 TGGCCAGGAC ATCCAGCTCC CCCTCCTGAA AGGTGACCTC CGCATCCAGC
1451 ATACAGTGAC GGCCTCCGTG CGCCTCAGCT ACGGGGAGGA CCTGCAGATG
1501 GACTGGGATG GCCGCGGGAG GCTGCTGGTG AAGCTGTCCC CCGTCTATGC
1551 CGGAAAGACC TGCGGCCTGT GTGGGAATTA CAATGGCAAC CAGGGCGACG
1601 ACTTCCTTAC CCCCTCTGGG CTGGCGGAGC CCCGGGTGGA GGACTTCGGG
1651 AACGCCTGGA AGCTGCACGG GGACTGCCAG GACCTGCAGA AGCAGCACAG
1701 CGATCCCTGC GCCCTCAACC CGCGCATGAC CAGGTTCTCC GAGGAGGCGT
1751 GCGCGGTCCT GACGTCCCCC ACATTCGAGG CCTGCCATCG TGCCGTCAGC
```

TABLE 15-continued

Nucleotide sequence of pSYN-VWF051 (VWF D1D2D'D3Fc with s

TABLE 15-continued

Nucleotide sequence of pSYN-VWF051 (VWF D1D2D'D3Fc with sortase A recognition motif and thrombin cleavable linker in between VWF fragment and Fc)

```
3701  GTGAAGCCTG CCAGGAGCCG ATATCTGGCG GTGGAGGTTC CGGTGGCGGG
3751  GGATCCGGCG GTGGAGGTTC CGGCGGTGGA GGTTCCGGTG GCGGGGGATC
3801  CGGTGGCGGG GGATCCTTAC CTGAAACTGG AGCCCTGCGG CCCCGGGTCG
3851  TCGGCGGTGG AGGTTCCGGT GGCGGGGGAT CCGACAAAAC TCACACATGC
3901  CCACCGTGCC CAGCTCCAGA ACTCCTGGGC GGACCGTCAG TCTTCCTCTT
3951  CCCCCCAAAA CCCAAGGACA CCCTCATGAT CTCCCGGACC CCTGAGGTCA
4001  CATGCGTGGT GGTGGACGTG AGCCACGAAG ACCCTGAGGT CAAGTTCAAC
4051  TGGTACGTGG ACGGCGTGGA GGTGCATAAT GCCAAGACAA AGCCGCGGGA
4101  GGAGCAGTAC AACAGCACGT ACCGTGTGGT CAGCGTCCTC ACCGTCCTGC
4151  ACCAGGACTG GCTGAATGGC AAGGAGTACA AGTGCAAGGT CTCCAACAAA
4201  GCCCTCCCAG CCCCCATCGA GAAAACCATC TCCAAAGCCA AGGGCAGCC
4251  CCGAGAACCA CAGGTGTACA CCCTGCCCCC ATCCCGGGAT GAGCTGACCA
4301  AGAACCAGGT CAGCCTGACC TGCCTGGTCA AAGGCTTCTA TCCCAGCGAC
4351  ATCGCCGTGG AGTGGGAGAG CAATGGGCAG CCGGAGAACA ACTACAAGAC
4401  CACGCCTCCC GTGTTGGACT CCGACGGCTC CTTCTTCCTC TACAGCAAGC
4451  TCACCGTGGA CAAGAGCAGG TGGCAGCAGG GGAACGTCTT CTCATGCTCC
4501  GTGATGCATG AGGCTCTGCA CAACCACTAC ACGCAGAAGA GCCTCTCCCT
4551  GTCTCCGGGT AAATGA
```

TABLE 16

Protein sequence of VWF051 (VWF D1D2D'D3Fc with sortase A recognition motif and thrombin cleavable linker in between VWF fragment and Fc; sortase A site shown in bold)

(SEQ ID NO: 101)

```
  1  MIPARFAGVL LALALILPGT LCAEGTRGRS STARCSLFGS DFVNTFDGSM
 51  YSFAGYCSYL LAGGCQKRSF SIIGDFQNGK RVSLSVYLGE FFDIHLFVNG
101  TVTQGDQRVS MPYASKGLYL ETEAGYYKLS GEAYGFVARI DGSGNFQVLL
151  SDRYFNKTCG LCGNFNIFAE DDFMTQEGTL TSDPYDFANS WALSSGEQWC
201  ERASPPSSSC NISSGEMQKG LWEQCQLLKS TSVFARCHPL VDPEPFVALC
251  EKTLCECAGG LECACPALLE YARTCAQEGM VLYGWTDHSA CSPVCPAGME
301  YRQCVSPCAR TCQSLHINEM CQERCVDGCS CPEGQLLDEG LCVESTECPC
351  VHSGKRYPPG TSLSRDCNTC ICRNSQWICS NEECPGECLV TGQSHFKSFD
401  NRYFTFSGIC QYLLARDCQD HSFSIVIETV QCADDRDAVC TRSVTVRLPG
451  LHNSLVKLKH GAGVAMDGQD IQLPLLKGDL RIQHTVTASV RLSYGEDLQM
501  DWDGRGRLLV KLSPVYAGKT CGLCGNYNGN QGDDFLTPSG LAEPRVEDFG
551  NAWKLHGDCQ DLQKQHSDPC ALNPRMTRFS EEACAVLTSP TFEACHRAVS
601  PLPYLRNCRY DVCSCSDGRE CLCGALASYA AACAGRGVRV AWREPGRCEL
651  NCPKGQVYLQ CGTPCNLTCR SLSYPDEECN EACLEGCFCP PGLYMDERGD
701  CVPKAQCPCY YDGEIFQPED IFSDHHTMCY CEDGFMHCTM SGVPGSLLPD
```

TABLE 16-continued

Protein sequence of VWF051 (VWF D1D2D'D3Fc with sortase A recognition motif and thrombin cleavable linker in between VWF fragment and Fc; sortase A site shown in bold)

```
 751  AVLSSPLSHR SKRSLSCRPP MVKLVCPADN LRAEGLECTK TCQNYDLECM
 801  SMGCVSGCLC PPGMVRHENR CVALERCPCF HQGKEYAPGE TVKIGCNTCV
 851  CRDRKWNCTD HVCDATCSTI GMAHYLTFDG LKYLFPGECQ YVLVQDYCGS
 901  NPGTFRILVG NKGCSHPSVK CKKRVTILVE GGEIELFDGE VNVKRPMKDE
 951  THFEVVESGR YIILLLGKAL SVVWDRHLSI SVVLKQTYQE KVCGLCGNFD
1001  GIQNNDLTSS NLQVEEDPVD FGNSWKVSSQ CADTRKVPLD SSPATCHNNI
1051  MKQTMVDSSC RILTSDVFQD CNKLVDPEPY LDVCIYDTCS CESIGDCAAF
1101  CDTIAAYAHV CAQHGKVVTW RTATLCPQSC EERNLRENGY EAEWRYNSCA
1151  PACQVTCQHP EPLACPVQCV EGCHAHCPPG KILDELLQTC VDPEDCPVCE
1201  VAGRRFASGK KVTLNPSDPE HCQICHCDVV NLTCEACQEP ISGGGGSGGG
1251  GSGGGGSGGG GSGGGGSGGG GSLPETGALR PRVVGGGGSG GGGSDKTHTC
1301  PPCPAPELLG GPSVFLFPPK PKDTLMISRT PEVTCVVVDV SHEDPEVKFN
1351  WYVDGVEVHN AKTKPREEQY NSTYRVVSVL TVLHQDWLNG KEYKCKVSNK
1401  ALPAPIEKTI SKAKGQPREP QVYTLPPSRD ELTKNQVSLT CLVKGFYPSD
1451  IAVEWESNGQ PENNYKTTPP VLDSDGSFFL YSKLTVDKSR WQQGNVFSCS
1501  VMHEALHNHY TQKSLSLSPG K*
```

TABLE 17

Nucleotide sequence of FVIII 265 (FVIII single chain molecule with pentaglycines at N-terminus)

(SEQ ID NO: 102)
```
  1  ATGCAAATAG AGCTCTCCAC CTGCTTCTTT CTGTGCCTTT TGCGATTCTG
 51  CTTTAGTGGA GGAGGAGGAG GAGCCACCAG AAGATACTAC CTGGGTGCAG
101  TGGAACTGTC ATGGGACTAT ATGCAAAGTG ATCTCGGTGA GCTGCCTGTG
151  GACGCAAGAT TTCCTCCTAG AGTGCCAAAA CTTTTTCCAT TCAACACCTC
201  AGTCGTGTAC AAAAAGACTC TGTTTGTAGA ATTCACGGAT CACCTTTTCA
251  ACATCGCTAA GCCAAGGCCA CCCTGGATGG GTCTGCTAGG TCCTACCATC
301  CAGGCTGAGG TTTATGATAC AGTGGTCATT ACACTTAAGA ACATGGCTTC
351  CCATCCTGTC AGTCTTCATG CTGTTGGTGT ATCCTACTGG AAAGCTTCTG
401  AGGGAGCTGA ATATGATGAT CAGACCAGTC AAAGGGAGAA AGAAGATGAT
451  AAAGTCTTCC CTGGTGGAAG CCATACATAT GTCTGGCAGG TCCTGAAAGA
501  GAATGGTCCA ATGGCCTCTG ACCCACTGTG CCTTACCTAC TCATATCTTT
551  CTCATGTGGA CCTGGTAAAA GACTTGAATT CAGGCCTCAT TGGAGCCCTA
601  CTAGTATGTA GAGAAGGGAG TCTGGCCAAG GAAAAGACAC AGACCTTGCA
651  CAAATTTATA CTACTTTTTG CTGTATTTGA TGAAGGGAAA AGTTGGCACT
701  CAGAAACAAA GAACTCCTTG ATGCAGGATA GGGATGCTGC ATCTGCTCGG
751  GCCTGGCCTA AAATGCACAC AGTCAATGGT TATGTAAACA GGTCTCTGCC
801  AGGTCTGATT GGATGCCACA GGAAATCAGT CTATTGGCAT GTGATTGGAA
```

TABLE 17-continued

Nucleotide sequence of FVIII 265 (FVIII single chain
molecule with pentaglycines at N-terminus)

```
 851  TGGGCACCAC TCCTGAAGTG CACTCAATAT TCCTCGAAGG TCACACATTT
 901  CTTGTGAGGA ACCATCGCCA GGCGTCCTTG GAAATCTCGC CAATAACTTT
 951  CCTTACTGCT CAAACACTCT TGATGGACCT TGGACAGTTT CTACTGTTTT
1001  GTCATATCTC TTCCCACCAA CATGATGGCA TGGAAGCTTA TGTCAAAGTA
1051  GACAGCTGTC CAGAGGAACC CCAACTACGA ATGAAAAATA ATGAAGAAGC
1101  GGAAGACTAT GATGATGATC TTACTGATTC TGAAATGGAT GTGGTCAGGT
1151  TTGATGATGA CAACTCTCCT TCCTTTATCC AAATTCGCTC AGTTGCCAAG
1201  AAGCATCCTA AACTTGGGT ACATTACATT GCTGCTGAAG AGGAGGACTG
1251  GGACTATGCT CCCTTAGTCC TCGCCCCCGA TGACAGAAGT TATAAAAGTC
1301  AATATTTGAA CAATGGCCCT CAGCGGATTG GTAGGAAGTA CAAAAAAGTC
1351  CGATTTATGG CATACACAGA TGA7ACCTTT AAGACTCGTG AAGCTATTCA
1401  GCATGAATCA GGAATCTTGG GACCTTTACT TTATGGGGAA GTTGGAGACA
1451  CACTGTTGAT TATATTTAAG AATCAAGCAA GCAGACCATA TAACATCTAC
1501  CCTCACGGAA TCACTGATGT CCGTCCTTTG TATTCAAGGA GATTACCAAA
1551  AGGTGTAAAA CATTTGAAGG ATTTTCCAAT TCTGCCAGGA GAAATATTCA
1601  AATATAAATG GACAGTGACT GTAGAAGATG GCCAACTAA ATCAGATCCT
1651  CGGTGCCTGA CCCGCTATTA CTCTAGTTTC GTTAATATGG AGAGAGATCT
1701  AGCTTCAGGA CTCATTGGCC CTCTCCTCAT CTGCTACAAA GAATCTGTAG
1751  ATCAAAGAGG AAACCAGATA ATGTCAGACA AGAGGAATGT CATCCTGTTT
1801  TCTGTATTTG ATGAGAACCG AAGCTGGTAC CTCACAGAGA ATATACAACG
1851  CTTTCTCCCC AATCCAGCTG GAGTGCAGCT TGAGGATCCA GAGTTCCAAG
1901  CCTCCAACAT CATGCACAGC ATCAATGGCT ATGTTTTTGA TAGTTTGCAG
1951  TTGTCAGTTT GTTTGCATGA GGTGGCATAC TGGTACATTC TAAGCATTGG
2001  AGCACAGACT GACTTCCTTT CTGTCTTCTT CTCTGGATAT ACCTTCAAAC
2051  ACAAAATGGT CTATGAAGAC ACACTCACCC TATTCCCATT CTCAGGAGAA
2101  ACTGTCTTCA TGTCGATGGA AAACCCAGGT CTATGGATTC TGGGGTGCCA
2151  CAACTCAGAC TTTCGGAACA GAGGCATGAC CGCCTTACTG AAGGTTTCTA
2201  GTTGTGACAA GAACACTGGT GATTATTACG AGGACAGTTA TGAAGATATT
2251  TCAGCATACT TGCTGAGTAA AAACAATGCC ATTGAACCAA GAAGCTTCTC
2301  TCAAAACCCA CCAGTCTTGA AGGCCCATCA GGCCGAAATA ACTCGTACTA
2351  CTCTTCAGTC AGATCAAGAG GAAATTGACT ATGATGATAC CATATCAGTT
2401  GAAATGAAGA AGGAAGATTT TGACATTTAT GATGAGGATG AAGATCAGAG
2451  CCCCCGCAGC TTTCAAAAGA AAACACGACA CTATTTTATT GCTGCAGTGG
2501  AGAGGCTCTG GGATTATGGG ATGAGTAGCT CCCCACATGT TCTAAGAAAC
2551  AGGGCTCAGA GTGGCAGTGT CCCTCAGTTC AAGAAAGTTG TTTTCCAGGA
2601  ATTTACTGAT GGCTCCTTTA CTCAGCCCTT ATACCGTGGA GAACTAAATG
2651  AACATTTGGG CCTCCTCGGC CCATATATAA GAGCAGAAGT TGAAGATAAT
2701  ATCATGGTAA CTTTCAGAAA TCAGGCCTCT CGTCCCTATT CCTTCTATTC
2751  TAGCCTTATT TCTTATGAGG AAGATCAGAG GCAAGGAGCA GAACCTAGAA
```

TABLE 17-continued

Nucleotide sequence of FVIII 265 (FVIII single chain
molecule with pentaglycines at N-terminus)

```
2801  AAAACTTTGT CAAGCCTAAT GAAACCAAAA CTTACTTTTG GAAAGTGCAA
2851  CATCATATGG CACCCACTAA AGATGAGTTT GACTGCAAAG CCTGGGCTTA
2901  TTTCTCTGAT GTTGACCTGG AAAAAGATGT GCACTCAGGC CTGATTGGAC
2951  CCCTTCTGGT CTGCCACACT AACACACTGA ACCCTGCTCA TGGGAGACAA
3001  GTGACAGTAC AGGAATTTGC TCTGTTTTTC ACCATCTTTG ATGAGACCAA
3051  AAGCTGGTAC TTCACTGAAA ATATGGAAAG AAACTGCAGG GCTCCCTGCA
3101  ATATCCAGAT GGAAGATCCC ACTTTTAAAG AGAATTATCG CTTCCATGCA
3151  ATCAATGGCT ACATAATGGA TACACTACCT GGCTTAGTAA TGGCTCAGGA
3201  TCAAAGGATT CGATGGTATC TGCTCAGCAT GGGCAGCAAT GAAAACATCC
3251  ATTCTATTCA TTTCAGTGGA CATGTGTTCA CTGTACGAAA AAAAGAGGAG
3301  TATAAAATGG CACTGTACAA TCTCTATCCA GGTGTTTTTG AGACAGTGGA
3351  AATGTTACCA TCCAAAGCTG GAATTTGGCG GGTGGAATGC CTTATTGGCG
3401  AGCATCTACA TGCTGGGATG AGCACACTTT TTCTGGTGTA CAGCAATAAG
3451  TGTCAGACTC CCCTGGGAAT GGCTTCTGGA CACATTAGAG ATTTTCAGAT
3501  TACAGCTTCA GGACAATATG GACAGTGGGC CCCAAAGCTG GCCAGACTTC
3551  ATTATTCCGG ATCAATCAAT GCCTGGAGCA CCAAGGAGCC CTTTTCTTGG
3601  ATCAAGGTGG ATCTGTTGGC ACCAATGATT ATTCACGGCA TCAAGACCCA
3651  GGGTGCCCGT CAGAAGTTCT CCAGCCTCTA CATCTCTCAG TTTATCATCA
3701  TGTATAGTCT TGATGGGAAG AAGTGGCAGA CTTATCGAGG AAATTCCACT
3751  GGAACCTTAA TGGTCTTCTT TGGCAATGTG GATTCATCTG GGATAAAACA
3801  CAATATTTTT AACCCTCCAA TTATTGCTCG ATACATCCGT TTGCACCCAA
3851  CTCATTATAG CATTCGCAGC ACTCTTCGCA TGGAGTTGAT GGGCTGTGAT
3901  TTAAATAGTT GCAGCATGCC ATTGGGAATG GAGAGTAAAG CAATATCAGA
3951  TGCACAGATT ACTGCTTCAT CCTACTTTAC CAATATGTTT GCCACCTGGT
4001  CTCCTTCAAA AGCTCGACTT CACCTCCAAG GGAGGAGTAA TGCCTGGAGA
4051  CCTCAGGTGA ATAATCCAAA AGAGTGGCTG CAAGTGGACT TCCAGAAGAC
4101  AATGAAAGTC ACAGGAGTAA CTACTCAGGG AGTAAAATCT CTGCTTACCA
4151  GCATGTATGT GAAGGAGTTC CTCATCTCCA GCAGTCAAGA TGGCCATCAG
4201  TGGACTCTCT TTTTTCAGAA TGGCAAAGTA AAGGTTTTTC AGGGAAATCA
4251  AGACTCCTTC ACACCTGTGG TGAACTCTCT AGACCCACCG TTACTGACTC
4301  GCTACCTTCG AATTCACCCC CAGAGTTGGG TGCACCAGAT TGCCCTGAGG
4351  ATGGAGGTTC TGGGCTGCGA GGCACAGGAC CTCTACTGA
```

TABLE 18

Protein sequence of FVIII 265 (FVIII single chain molecule
with pentaglycines at N-terminus; pentaglycine shown
in bold)

(SEQ ID NO: 103)
```
  1  MQIELSTCFF LCLLRFCFSG GGGGATRRYY LGAVELSWDY MQSDLGELPV
 51  DARFPPRVPK SFPFNTSVVY KKTLFVEFTD HLFNIAKPRP PWMGLLGPTI
```

TABLE 18-continued

Protein sequence of FVIII 265 (FVIII single chain molecule with pentaglycines at N-terminus; pentaglycine shown in bold)

```
 101    QAEVYDTVVI TLKNMASHPV SLHAVGVSYW KASEGAEYDD QTSQREKEDD
 151    KVFPGGSHTY VWQVLKENGP MASDPLCLTY SYLSHVDLVK DLNSGLIGAL
 201    LVCREGSLAK EKTQTLHKFI LLFAVFDEGK SWHSETKNSL MQDRDAASAR
 251    AWPKMHTVNG YVNRSLPGLI GCHRKSVYWH VIGMGTTPEV HSIFLEGHTF
 301    LVRNHRQASL EISPITFLTA QTLLMDLGQF LLFCHISSHQ HDGMEAYVKV
 351    DSCPEEPQLR MKNNEEAEDY DDDLTDSEMD VVRFDDDNSP SFIQIRSVAK
 401    KHPKTWVHYI AAEEEDWDYA PLVLAPDDRS YKSQYLNNGP QRIGRKYKKV
 451    RFMAYTDETF KTREAIQHES GILGPLLYGE VGDTLLIIFK NQASRPYNIY
 501    PHGITDVRPL YSRRLPKGVK HLKDFPILPG EIFKYKWTVT VEDGPTKSDP
 551    RCLTRYYSSF VNMERDLASG LIGPLLICYK ESVDQRGNQI MSDKRNVILF
 601    SVFDENRSWY LTENIQRFLP NPAGVQLEDP EFQASNIMHS INGYVFDSLQ
 651    LSVCLHEVAY WYILSIGAQT DFLSVFFSGY TFKHKMVYED TLTLFPFSGE
 701    TVFMSMENPG LWILGCHNSD FRNRGMTALL KVSSCDKNTG DYYEDSYEDI
 751    SAYLLSKNNA IEPRSFSQNP PVLKAHQAEI TRTTLQSDQE EIDYDDTISV
 801    EMKKEDFDIY DEDENQSPRS FQKKTRHYFI AAVERLWDYG MSSSPHVLRN
 851    RAQSGSVPQF KKVVFQEFTD GSFTQPLYRG ELNEHLGLLG PYIRAEVEDN
 901    IMVTFRNQAS RPYSFYSSLI SYEEDQRQGA EPRKNFVKPN ETKTYFWKVQ
 951    HHMAPTKDEF DCKAWAYFSD VDLEKDVHSG LIGPLLVCHT NTLNPAHGRQ
1001    VTVQEFALFF TIFDETKSWY FTENMERNCR APCNIQMEDP TFKENYRFHA
1051    INGYIMDTLP GLVMAQDQRI RWYLLSMGSN ENIHSIHFSG HVFTVRKKEE
1101    YKMALYNLYP GVFETVEMLP SKAGIWRVEC LIGEHLHAGM STLFLVYSNK
1151    CQTPLGMASG HIRDFQITAS GQYGQWAPKL ARLHYSGSIN AWSTKEPFSW
1201    IKVDLLAPMI IHGIKTQGAR QKFSSLYISQ FIIMYSLDGK KWQTYRGNST
1251    GTLMVFFGNV DSSGIKHNIF NPPIIARYIR LHPTHYSIRS TLRMELMGCD
1301    LNSCSMPLGM ESKAISDAQI TASSYFTNMF ATWSPSKARL HLQGRSNAWR
1351    PQVNNPKEWL QVDFQKTMKV TGVTTQGVKS LLTSMYVKEF LISSSQDGHQ
1401    WTLFFQNGKV KVFQGNQDSF TPVVNSLDPP LLTRYLRIHP QSWVHQIALR
1451    MEVLGCEAQD LY*
```

Example 20

Plasma Stability and PK of FVIII198 in HemA and FVIII/VWF Double Knockout (DKO) Plasma The Plasma stability of FVIII 198 (which is a partial B-domain containing single chain FVIIIFc molecule-226N6; where 226 represents the N-terminus 226 amino acids of FVIII B-domain and N6 represents six N-glycosylation sites in the B-domain) was compared to single chain FVIIIFc (FVIII 155/Fc) in FVIII/VWF double knockout (DKO) plasma. Schematic representation of FVIII155 and FVIII198 can be seen in FIG. 25.

For the stability assay, 5 IU/ml of FVIII 198 or FVIIIFc proteins was incubated with mouse or DKO plasma at 37° C. Aliquots were collected at different time points for activity measurement by FVIII chromogenic assay. Activity at each time point was measured in duplicate and average activity was plotted as a function of time. In the stability assay, the presence of partial B-domain increased the stability of single chain FVIIIFc (FIG. 26A).

The half-life of FVIII 198 (single chain-B226N6) was also compared with FVIII155 (single chain B-domain deleted FVIII) in DKO mice. FVIII 198 has at least about a 1.5 fold longer half-life compared to FVIII155 (FIG. 26B). These experiments suggest that there might be a co-relation between FVIII stability and its in-vivo half-life.

FVIII198 Nucleotide Sequence (FVIIIFc with Partial B-Domain, 226N6) (SEQ ID NO: 104)

```
   1  ATGCAAATAG AGCTCTCCAC CTGCTTCTTT CTGTGCCTTTT GCGATTCTG
  51  CTTTAGTGCC ACCAGAAGAT ACTACCTGGG TGCAGTGGAAC TGTCATGGG
 101  ACTATATGCA AAGTGATCTC GGTGAGCTGC CTGTGGACGCA AGATTTCCT
 151  CCTAGAGTGC AAAATCTTT TCCATTCAAC ACCTCAGTCGT GTACAAAAA
 201  GACTCTGTTT GTAGAATTCA CGGATCACCT TTTCAACATCG CTAAGCCAA
 251  GGCCACCCTG GATGGGTCTG CTAGGTCCTA CCATCCAGGCT GAGGTTTAT
 301  GATACAGTGG TCATTACACT TAAGAACATG GCTTCCCATCC TGTCAGTCT
 351  TCATGCTGTT GGTGTATCCT ACTGGAAAGC TTCTGAGGGAG CTGAATATG
 401  ATGATCAGAC CAGTCAAAGG GAGAAAGAAG ATGATAAAGTC TTCCCTGGT
 451  GGAAGCCATA CATATGTCTG GCAGGTCCTG AAAGAGAATGG TCCAATGGC
 501  CTCTGACCCA CTGTGCCTTA CCTACTCATA TCTTTCTCATG TGGACCTGG
 551  TAAAAGACTT GAATTCAGGC CTCATTGGAG CCCTACTAGTA TGTAGAGAA
 601  GGGAGTCTGG CCAAGGAAAA GACACAGACC TTGCACAAATT TATACTACT
 651  TTTTGCTGTA TTTGATGAAG GGAAAAGTTG GCACTCAGAAA CAAAGAACT
 701  CCTTGATGCA GGATAGGGAT GCTGCATCTG CTCGGGCCTGG CCTAAAATG
 751  CACACAGTCA ATGGTTATGT AAACAGGTCT CTGCCAGGTCT GATTGGATG
 801  CCACAGGAAA TCAGTCTATT GGCATGTGAT TGGAATGGGCA CCACTCCTG
 851  AAGTGCACTC AATATTCCTC GAAGGTCACA CATTTCTTGTG AGGAACCAT
 901  CGCCAGGCGT CCTTGGAAAT CTCGCCAATA ACTTTCCTTAC TGCTCAAAC
 951  ACTCTTGATG GACCTTGGAC AGTTTCTACT GTTTTGTCATA TCTCTTCCC
1001  ACCAACATGA TGGCATGGAA GCTTATGTCA AGTAGACAGC TGTCCAGAG
1051  GAACCCCAAC TACGAATGAA AATAATGAA GAAGCGGAAGA CTATGATGA
1101  TGATCTTACT GATTCTGAAA TGGATGTGGT CAGGTTTGATG ATGACAACT
1151  CTCCTTCCTT TATCCAAATT CGCTCAGTTG CCAAGAAGCAT CCTAAAACT
1201  TGGGTACATT ACATTGCTGC TGAAGAGGAG GACTGGGACTA TGCTCCCTT
1251  AGTCCTCGCC CCCGATGACA GAAGTTATAA AGTCAATATT TGAACAATG
1301  GCCCTCAGCG GATTGGTAGG AAGTACAAAA AAGTCCGATTT ATGGCATAC
1351  ACAGATGAAA CCTTTAAGAC TCGTGAAGCT ATTCAGCATGA ATCAGGAAT
1401  CTTGGGACCT TTACTTTATG GGGAAGTTGG AGACACACTGT TGATTATAT
1451  TTAAGAATCA AGCAAGCAGA CCATATAACA TCTACCCTCAC GGAATCACT
1501  GATGTCCGTC CTTTGTATTC AAGGAGATTA CCAAAAGGTGT AAAACATTT
1551  GAAGGATTTT CCAATTCTGC CAGGAGAAAT ATTCAAATATA AATGGACAG
1601  TGACTGTAGA AGATGGGCCA ACTAAATCAG ATCCTCGGTGC CTGACCCGC
1651  TATTACTCTA GTTTCGTTAA TATGGAGAGA GATCTAGCTTC AGGACTCAT
1701  TGGCCCTCTC CTCATCTGCT ACAAAGAATC TGTAGATCAAA GAGGAAACC
1751  AGATAATGTC AGACAAGAGG AATGTCATCC TGTTTTCTGTA TTTGATGAG
1801  AACCGAAGCT GGTACCTCAC AGAGAATATA CAACGCTTTCT CCCCAATCC
1851  AGCTGGAGTG CAGCTTGAGG ATCCAGAGTT CCAAGCCTCCA ACATCATGC
1901  ACAGCATCAA TGGCTATGTT TTTGATAGTT TGCAGTTGTCA GTTTGTTTG
1951  CATGAGGTGG CATACTGGTA CATTCTAAGC ATTGGAGCACA GACTGACTT
2001  CCTTTCTGTC TTCTTCTCTG GATATACCTT CAAACACAAAA TGGTCTATG
```

```
2051  AAGACACACT CACCCTATTC CCATTCTCAG GAGAAACTGTC TTCATGTCG
2101  ATGGAAAACC CAGGTCTATG GATTCTGGGG TGCCACAACTC AGACTTTCG
2151  GAACAGAGGC ATGACCGCCT TACTGAAGGT TTCTAGTTGTG ACAAGAACA
2201  CTGGTGATTA TTACGAGGAC AGTTATGAAG ATATTTCAGCA TACTTGCTG
2251  AGTAAAAACA ATGCCATTGA ACCAAGAAGC TTCTCTCAGAA TTCAAGACA
2301  CCCTAGCACT AGGCAAAAGC AATTTAATGC CACCACAATTC CAGAAAATG
2351  ACATAGAGAA GACTGACCCT TGGTTTGCAC ACAGAACACCT ATGCCTAAA
2401  ATACAAAATG TCTCCTCTAG TGATTTGTTG ATGCTCTTGCG ACAGAGTCC
2451  TACTCCACAT GGGCTATCCT TATCTGATCT CCAAGAAGCCA AATATGAGA
2501  CTTTTTCTGA TGATCCATCA CCTGGAGCAA TAGACAGTAAT AACAGCCTG
2551  TCTGAAATGA CACACTTCAG GCCACAGCTC CATCACAGTGG GGACATGGT
2601  ATTTACCCCT GAGTCAGGCC TCCAATTAAG ATTAAATGAGA AACTGGGGA
2651  CAACTGCAGC AACAGAGTTG AAGAAACTTG ATTTCAAAGTT CTAGTACA
2701  TCAAATAATC TGATTTCAAC AATTCCATCA GACAATTTGGC AGCAGGTAC
2751  TGATAATACA AGTTCCTTAG GACCCCCAAG TATGCCAGTTC ATTATGATA
2801  GTCAATTAGA TACCACTCTA TTTGGCAAAA AGTCATCTCCC CTTACTGAG
2851  TCTGGTGGAC CTCTGAGCTT GAGTGAAGAA ATAATGATTC AAAGTTGTT
2901  AGAATCAGGT TTAATGAATA GCCAAGAAAG TTCATGGGGAA AAAATGTAT
2951  CGTCAGAAAT AACTCGTACT ACTCTTCAGT CAGATCAAGAG GAAATTGAC
3001  TATGATGATA CCATATCAGT TGAAATGAAG AAGGAAGATTT TGACATTTA
3051  TGATGAGGAT GAAAATCAGA GCCCCCGCAG CTTTCAAAAGA AAACACGAC
3101  ACTATTTTAT TGCTGCAGTG GAGAGGCTCT GGGATTATGGG ATGAGTAGC
3151  TCCCCACATG TTCTAAGAAA CAGGGCTCAG AGTGGCAGTGT CCCTCAGTT
3201  CAAGAAAGTT GTTTTCCAGG AATTTACTGA TGGCTCCTTTA CTCAGCCCT
3251  TATACCGTGG AGAACTAAAT GAACATTTGG GACTCCTGGGG CCATATATA
3301  AGAGCAGAAG TTGAAGATAA TATCATGGTA ACTTTCAGAAA TCAGGCCTC
3351  TCGTCCCTAT TCCTTCTATT CTAGCCTTAT TTCTTATGAGG AAGATCAGA
3401  GGCAAGGAGC AGAACCTAGA AAAAACTTTG TCAAGCCTAAT GAAACCAAA
3451  ACTTACTTTT GGAAAGTGCA ACATCATATG GCACCCACTAA AGATGAGTT
3501  TGACTGCAAA GCCTGGGCTT ATTTCTCTGA TGTTGACCTGG AAAAAGATG
3551  TGCACTCAGG CCTGATTGGA CCCCTTCTGG TCTGCCACACT AACACACTG
3601  AACCCTGCTC ATGGGAGACA AGTGACAGTA CAGGAATTTGC TCTGTTTTT
3651  CACCATCTTT GATGAGACCA AAAGCTGGTA CTTCACTGAAA ATATGGAAA
3701  GAAACTGCAG GGCTCCCTGC AATATCCAGA TGGAAGATCCC ACTTTTAAA
3751  GAGAATTATC GCTTCCATGC AATCAATGGC TACATAATGGA TACACTACC
3801  TGGCTTAGTA ATGGCTCAGG ATCAAAGGAT TCGATGGTATC TGCTCAGCA
3851  TGGGCAGCAA TGAAACATC CATTCTATTC ATTTCAGTGGA CATGTGTTC
3901  ACTGTACGAA AAAAGAGGA GTATAAAATG GCACTGTACAA TCTCTATCC
3951  AGGTGTTTTT GAGACAGTGG AAATGTTACC ATCCAAAGCTG GAATTTGGC
4001  GGGTGGAATG CCTTATTGGC GAGCATCTAC ATGCTGGGATG AGCACACTT
```

-continued

```
4051 TTTCTGGTGT ACAGCAATAA GTGTCAGACT CCCCTGGGAAT GGCTTCTGG

4101 ACACATTAGA GATTTTCAGA TTACAGCTTC AGGACAATATG ACAGTGGG

4151 CCCCAAAGCT GGCCAGACTT CATTATTCCG GATCAATCAAT GCCTGGAGC

4201 ACCAAGGAGC CCTTTTCTTG GATCAAGGTG GATCTGTTGGC ACCAATGAT

4251 TATTCACGGC ATCAAGACCC AGGGTGCCCG TCAGAAGTTCT CCAGCCTCT

4301 ACATCTCTCA GTTTATCATC ATGTATAGTC TTGATGGGAAG AAGTGGCAG

4351 ACTTATCGAG GAAATTCCAC TGGAACCTTA ATGGTCTTCTT TGGCAATGT

4401 GGATTCATCT GGGATAAAAC ACAATATTTT TAACCCTCCAA TTATTGCTC

4451 GATACATCCG TTTGCACCCA ACTCATTATA GCATTCGCAGC ACTCTTCGC

4501 ATGGAGTTGA TGGGCTGTGA TTTAAATAGT TGCAGCATGCC ATTGGGAAT

4551 GGAGAGTAAA GCAATATCAG ATGCACAGAT TACTGCTTCAT CCTACTTTA

4601 CCAATATGTT TGCCACCTGG TCTCCTTCAA AAGCTCGACTT CACCTCCAA

4651 GGGAGGAGTA ATGCCTGGAG ACCTCAGGTG AATAATCCAAA AGAGTGGCT

4701 GCAAGTGGAC TTCCAGAAGA CAATGAAAGT CACAGGAGTAA CTACTCAGG

4751 GAGTAAAATC TCTGCTTACC AGCATGTATG TGAAGGAGTTC CTCATCTCC

4801 AGCAGTCAAG ATGGCCATCA GTGGACTCTC TTTTTTCAGAA TGGCAAAGT

4851 AAAGGTTTTT CAGGGAAATC AAGACTCCTT CACACCTGTGG TGAACTCTC

4901 TAGACCCACC GTTACTGACT CGCTACCTTC GAATTCACCCC CAGAGTTGG

4951 GTGCACCAGA TTGCCCTGAG GATGGAGGTT CTGGGCTGCGA GGCACAGGA

5001 CCTCTACGAC AAAACTCACA CATGCCCACC GTGCCCAGCTC CAGAACTCC

5051 TGGGCGGACC GTCAGTCTTC CTCTTCCCCC CAAAACCCAAG GACACCCTC

5101 ATGATCTCCC GGACCCCTGA GGTCACATGC GTGGTGGTGGA CGTGAGCCA

5151 CGAAGACCCT GAGGTCAAGT TCAACTGGTA CGTGGACGGCG TGGAGGTGC

5201 ATAATGCCAA GACAAAGCCG CGGGAGGAGC AGTACAACAGC ACGTACCGT

5251 GTGGTCAGCG TCCTCACCGT CCTGCACCAG GACTGGCTGAA TGGCAAGGA

5301 GTACAAGTGC AAGGTCTCCA ACAAAGCCCT CCCAGCCCCA TCGAGAAAA

5351 CCATCTCCAA AGCCAAAGGG CAGCCCCGAG AACCACAGGTG TACACCCTG

5401 CCCCCATCCC GGGATGAGCT GACCAAGAAC CAGGTCAGCCT GACCTGCCT

5451 GGTCAAAGGC TTCTATCCCA GCGACATCGC CGTGGAGTGGG AGAGCAATG

5501 GGCAGCCGGA GAACAACTAC AAGACCACGC CTCCCGTGTTG GACTCCGAC

5551 GGCTCCTTCT TCCTCTACAG CAAGCTCACC GTGGACAAGAG CAGGTGGCA

5601 GCAGGGGAAC GTCTTCTCAT GCTCCGTGAT GCATGAGGCTC TGCACAACC

5651 ACTACACGCA GAAGAGCCTC TCCCTGTCTC CGGGTAAATGA
```

FVIII 198 Protein Sequence (SEQ ID NO: 105)

```
  1 MQIELSTCFF LCLLRFCFSA TRRYYLGAVE LSWDYMQSDL GELPVDARFP

51 PRVPKSFPFN TSVVYKKTLF VEFTDHLFNI AKPRPPWMGL LGPTIQAEVY

101 DTVVITLKNM ASHPVSLHAV GVSYWKASEG AEYDDQTSQR EKEDDKVFPG

151 GSHTYVWQVL KENGPMASDP LCLTYSYLSH VDLVKDLNSG LIGALLVCRE

201 GSLAKEKTQT LHKFILLFAV FDEGKSWHSE TKNSLMQDRD AASARAWPKM

251 HTVNGYVNRS LPGLIGCHRK SVYWHVIGMG TTPEVHSIFL EGHTFLVRNH
```

```
301 RQASLEISPI TFLTAQTLLM DLGQFLLFCH ISSHQHDGME AYVKVDSCPE

351 EPQLRMKNNE EAEDYDDDLT DSEMDVVRFD DDNSPSFIQI RSVAKKHPKT

401 WVHYIAAEEE DWDYAPLVLA PDDRSYKSQY LNNGPQRIGR KYKKVRFMAY

451 TDETFKTREA IQHESGILGP LLYGEVGDTL LIIFKNQASR PYNIYPHGIT

501 DVRPLYSRRL PKGVKHLKDF PILPGEIFKY KWTVTVEDGP TKSDPRCLTR

551 YYSSFVNMER DLASGLIGPL LICYKESVDQ RGNQIMSDKR NVILFSVFDE

601 NRSWYLTENI QRFLPNPAGV QLEDPEFQAS NIMHSINGYV FDSLQLSVCL

651 HEVAYWYILS IGAQTDFLSV FFSGYTFKHK MVYEDTLTLF PFSGETVFMS

701 MENPGLWILG CHNSDFRNRG MTALLKVSSC DKNTGDYYED SYEDISAYLL

751 SKNNAIEPRS FSQNSRHPST RQKQFNATTI PENDIEKTDP WFAHRTPMPK

801 IQNVSSSDLL MLLRQSPTPH GLSLSDLQEA KYETFSDDPS PGAIDSNNSL

851 SEMTHFRPQL HHSGDMVFTP ESGLQLRLNE KLGTTAATEL KKLDFKVSST

901 SNNLISTIPS DNLAAGTDNT SSLGPPSMPV HYDSQLDTTL FGKKSSPLTE

951 SGGPLSLSEE NNDSKLLESG LMNSQESSWG KNVSSEITRT TLQSDQEEID

1001 YDDTISVEMK KEDFDIYDED ENQSPRSFQK KTRHYFIAAV ERLWDYGMSS

1051 SPHVLRNRAQ SGSVPQFKKV VFQEFTDGSF TQPLYRGELN EHLGLLGPYI

1101 RAEVEDNIMV TFRNQASRPY SFYSSLISYE EDQRQGAEPR KNFVKPNETK

1151 TYFWKVQHHM APTKDEFDCK AWAYFSDVDL EKDVHSGLIG PLLVCHTNTL

1201 NPAHGRQVTV QEFALFFTIF DETKSWYFTE NMERNCRAPC NIQMEDPTFK

1251 ENYRFHAING YIMDTLPGLV MAQDQRIRWY LLSMGSNENI HSIHFSGHVF

1301 TVRKKEEYKM ALYNLYPGVF ETVEMLPSKA GIWRVECLIG EHLHAGMSTL

1351 FLVYSNKCQT PLGMASGHIR DFQITASGQY GQWAPKLARL HYSGSINAWS

1401 TKEPFSWIKV DLLAPMIIHG IKTQGARQKF SSLYISQFII MYSLDGKKWQ

1451 TYRGNSTGTL MVFFGNVDSS GIKHNIFNPP IIARYIRLHP THYSIRSTLR

1501 MELMGCDLNS CSMPLGMESK AISDAQITAS SYFTNMFATW SPSKARLHLQ

1551 GRSNAWRPQV NNPKEWLQVD FQKTMKVTGV TTQGVKSLLT SMYVKEFLIS

1601 SSQDGHQWTL FFQNGKVKVF QGNQDSFTPV VNSLDPPLLT RYLRIHPQSW

1651 VHQIALRMEV LGCEAQDLYD KTHTCPPCPA PELLGGPSVF LFPPKPKDTL

1701 MISRTPEVTC VVVDVSHEDP EVKFNWYVDG VEVHNAKTKP REEQYNSTYR

1751 VVSVLTVLHQ DWLNGKEYKC KVSNKALPAP IEKTISKAKG QPREPQVYTL

1801 PPSRDELTKN QVSLTCLVKG FYPSDIAVEW ESNGQPENNY KTTPPVLDSD

1851 GSFFLYSKLT VDKSRWQQGN VFSCSVMHEA LHNHYTQKSL SLSPGK*
```

Example 21

Expression of D1D2 Protein of VWF

Proper folding of D'D3 domain is essential for its binding to FVIII. VWF propeptide (D1D2-amino acids 1-763) is required for efficient disulfide bond formation and folding of D'D3. It acts as an internal chaperone for D'D3 folding. VWF constructs making VWF fragments can either be expressed where VWF propeptide (i.e. D1D2 domain) is directly attached to D'D3 domain and removed during the regular intracellular processing of D'D3 (i.e. in cis) or, it can either be expressed from other plasmid i.e. in trans. We designed FVIII-VWF heterodimer in such a way where D1D2 can either be expressed in cis or trans.

Cloning VWF 053: VWF 053 clone expresses VWF propeptide (D1D2 domain) for in trans expression of D1D2. VWF propeptide was PCR amplified from full length using ESC 54 and ESC124.

ESC54-VWF forward with BsiW1 site
(SEQ ID NO: 111)
(CGCTTCGCGACGTACGGCCGCCACCATGATTCCTGCCAGATTTGCC
GGGGTGCTGCTTGCTC)

ESC 124-D1D2 cloning oligo with Not1 site-reverse
(SEQ ID NO: 112)
(CTAGACTCGAGCGGCCGCTCACCTTTTGCTGCGATGAGACAGGGGAC
TGCTGAGGACAGC)

PCR product was digested with BsiW1 and Not1 and ligated into BsiW1/Not1 digested pcDNA 4.

Nucleotide Sequence of VWF 053 (VWF D1D2-Propeptide) (SEQ ID NO: 113)

```
   1  ATGATTCCTG CCAGATTTGC CGGGGTGCTG CTTGCTCTGG CCCTCATTTT
  51  GCCAGGGACC CTTTGTGCAG AAGGAACTCG CGGCAGGTCA TCCACGGCCC
 101  GATGCAGCCT TTTCGGAAGT GACTTCGTCA ACACCTTTGA TGGGAGCATG
 151  TACAGCTTTG CGGGATACTG CAGTTACCTC CTGGCAGGGG GCTGCCAGAA
 201  ACGCTCCTTC TCGATTATTG GGACTTCCA GAATGGCAAG AGAGTGAGCC
 251  TCTCCGTGTA TCTTGGGGAA TTTTTTGACA TCCATTTGTT TGTCAATGGT
 301  ACCGTGACAC AGGGGACCA AAGAGTCTCC ATGCCCTATG CCTCCAAAGG
 351  GCTGTATCTA GAAACTGAGG CTGGGTACTA CAAGCTGTCC GGTGAGGCCT
 401  ATGGCTTTGT GGCCAGGATC GATGGCAGCG GCAACTTTCA AGTCCTGCTG
 451  TCAGACAGAT ACTTCAACAA GACCTGCGGG CTGTGTGGCA ACTTTAACAT
 501  CTTTGCTGAA GATGACTTTA TGACCCAAGA AGGGACCTTG ACCTCGGACC
 551  CTTATGACTT TGCCAACTCA TGGGCTCTGA GCAGTGGAGA ACAGTGGTGT
 601  GAACGGGCAT CTCCTCCCAG CAGCTCATGC AACATCTCCT CTGGGGAAAT
 651  GCAGAAGGGC CTGTGGGAGC AGTGCCAGCT TCTGAAGAGC ACCTCGGTGT
 701  TTGCCCGCTG CCACCCTCTG GTGGACCCCG AGCCTTTTGT GGCCCTGTGT
 751  GAGAAGACTT TGTGTGAGTG TGCTGGGGGG CTGGAGTGCG CCTGCCCTGC
 801  CCTCCTGGAG TACGCCCGGA CCTGTGCCCA GGAGGGAATG GTGCTGTACG
 851  GCTGGACCGA CCACAGCGCG TGCAGCCCAG TGTGCCCTGC TGGTATGGAG
 901  TATAGGCAGT GTGTGTCCCC TTGCGCCAGG ACCTGCCAGA GCCTGCACAT
 951  CAATGAAATG TGTCAGGAGC GATGCGTGGA TGGCTGCAGC TGCCCTGAGG
1001  GACAGCTCCT GGATGAAGGC CTCTGCGTGG AGAGCACCGA GTGTCCCTGC
1051  GTGCATTCCG GAAAGCGCTA CCCTCCCGGC ACCTCCCTCT CTCGAGACTG
1101  CAACACCTGC ATTTGCCGAA ACAGCCAGTG GATCTGCAGC AATGAAGAAT
1151  GTCCAGGGGA GTGCCTTGTC ACTGGTCAAT CCCACTTCAA GAGCTTTGAC
1201  AACAGATACT TCACCTTCAG TGGGATCTGC CAGTACCTGC TGGCCCGGGA
1251  TTGCCAGGAC CACTCCTTCT CCATTGTCAT TGAGACTGTC CAGTGTGCTG
1301  ATGACCGCGA CGCTGTGTGC ACCCGCTCCG TCACCGTCCG GCTGCCTGGC
1351  CTGCACAACA GCCTTGTGAA ACTGAAGCAT GGGGCAGGAG TTGCCATGGA
1401  TGGCCAGGAC ATCCAGCTCC CCCTCCTGAA AGGTGACCTC CGCATCCAGC
1451  ATACAGTGAC GGCCTCCGTG CGCCTCAGCT ACGGGGAGGA CCTGCAGATG
1501  GACTGGGATG GCCGCGGGAG GCTGCTGGTG AAGCTGTCCC CCGTCTATGC
1551  CGGGAAGACC TGCGGCCTGT GTGGGAATTA CAATGGCAAC CAGGGCGACG
1601  ACTTCCTTAC CCCCTCTGGG CTGGCGGAGC CCCGGGTGGA GGACTTCGGG
1651  AACGCCTGGA AGCTGCACGG GGACTGCCAG GACCTGCAGA AGCAGCACAG
1701  CGATCCCTGC GCCCTCAACC CGCGCATGAC CAGGTTCTCC GAGGAGGCGT
1751  GCGCGGTCCT GACGTCCCCC ACATTCGAGG CCTGCCATCG TGCCGTCAGC
1801  CCGCTGCCCT ACCTGCGGAA CTGCCGCTAC GACGTGTGCT CCTGCTCGGA
```

```
1851   CGGCCGCGAG TGCCTGTGCG GCGCCCTGGC CAGCTATGCC GCGGCCTGCG

1901   CGGGGAGAGG CGTGCGCGTC GCGTGGCGCG AGCCAGGCCG CTGTGAGCTG

1951   AACTGCCCGA AAGGCCAGGT GTACCTGCAG TGCGGGACCC CCTGCAACCT

2001   GACCTGCCGC TCTCTCTCTT ACCCGGATGA GGAATGCAAT GAGGCCTGCC

2051   TGGAGGGCTG CTTCTGCCCC CCAGGGCTCT ACATGGATGA GAGGGGGGAC

2101   TGCGTGCCCA AGGCCCAGTG CCCCTGTTAC TATGACGGTG AGATCTTCCA

2151   GCCAGAAGAC ATCTTCTCAG ACCATCACAC CATGTGCTAC TGTGAGGATG

2201   GCTTCATGCA CTGTACCATG AGTGGAGTCC CCGGAAGCTT GCTGCCTGAC

2251   GCTGTCCTCA GCAGTCCCCT GTCTCATCGC AGCAAAAGG
```

Protein Sequence of VWF 053 (VWF D1D2-Propeptide)
(SEQ ID NO: 114)

```
  1    MIPARFAGVL LALALILPGT LCAEGTRGRS STARCSLFGS DFVNTFDGSM

51    YSFAGYCSYL LAGGCQKRSF SIIGDFQNGK RVSLSVYLGE FFDIHLFVNG

101    TVTQGDQRVS MPYASKGLYL ETEAGYYKLS GEAYGFVARI DGSGNFQVLL

151    SDRYFNKTCG LCGNFNIFAE DDFMTQEGTL TSDPYDFANS WALSSGEQWC

201    ERASPPSSSC NISSGEMQKG LWEQCQLLKS TSVFARCHPL VDPEPFVALC

251    EKTLCECAGG LECACPALLE YARTCAQEGM VLYGWTDHSA CSPVCPAGME

301    YRQCVSPCAR TCQSLHINEM CQERCVDGCS CPEGQLLDEG LCVESTECPC

351    VHSGKRYPPG TSLSRDCNTC ICRNSQWICS NEECPGECLV TGQSHFKSFD

401    NRYFTFSGIC QYLLARDCQD HSFSIVIETV QCADDRDAVC TRSVTVRLPG

451    LHNSLVKLKH GAGVAMDGQD IQLPLLKGDL RIQHTVTASV RLSYGEDLQM

501    DWDGRGRLLV KLSPVYAGKT CGLCGNYNGN QGDDFLTPSG LAEPRVEDFG

551    NAWKLHGDCQ DLQKQHSDPC ALNPRMTRFS EEACAVLTSP TFEACHRAVS

601    PLPYLRNCRY DVCSCSDGRE CLCGALASYA AACAGRGVRV AWREPGRCEL

651    NCPKGQVYLQ CGTPCNLTCR SLSYPDEECN EACLEGCFCP PGLYMDERGD

701    CVPKAQCPCY YDGEIFQPED IFSDHHTMCY CEDGFMHCTM SGVPGSLLPD

751    AVLSSPLSHR SKR
```

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are incorporated by reference herein in their entirety.

What is claimed is:

1. A pharmaceutical composition comprising a chimeric protein and a pharmaceutically acceptable carrier,
wherein the chimeric protein comprises a first polypeptide and a second polypeptide;
wherein the first polypeptide comprises:
  (a) a Factor VIII ("FVIII") protein comprising amino acid residues 1 to 743 of SEQ ID NO: 16 and a B-domain deletion; and
  (b) a first immunoglobulin constant region,
wherein the second polypeptide comprises:
  (a) a von Willebrand Factor (VWF) fragment comprising a D' and a D3 domain of VWF, wherein the VWF fragment comprises an alanine substitution for cysteine at residues corresponding to residue 1099 and residue 1142 of SEQ ID NO: 2;
  (b) a second immunoglobulin constant region; and
  (c) a cleavable linker located between the VWF fragment and the second immunoglobulin constant region,
wherein the first polypeptide and the second polypeptide are linked by a disulfide bond between the first and second immunoglobulin constant regions.

2. The pharmaceutical composition of claim 1, wherein the first immunoglobulin constant region or portion thereof is a first Fc region and wherein the second immunoglobulin constant region or portion thereof is a second Fc region.

3. The pharmaceutical composition of claim 1, wherein the pharmaceutical composition is in powder form for constitution with a suitable vehicle.

4. The pharmaceutical composition of claim 1, wherein the FVIII protein comprises an a3 acidic region, an A3 region, a C1 region, and a C2 region of FVIII comprising amino acids 1649 to 2332 of SEQ ID NO: 16.

5. The pharmaceutical composition of claim 1, wherein both the first and second immunoglobulin constant region is the Fc fragment of IgG1.

6. The pharmaceutical composition of claim 1, wherein both the first and second immunoglobulin constant regions are glycosylated.

7. The pharmaceutical composition of claim 1, wherein the pharmaceutical composition is freeze dried.

8. The pharmaceutical composition of claim 1, wherein the first polypeptide and the second polypeptide are linked by two disulfide bonds between the first and second immunoglobulin constant regions.

9. The pharmaceutical composition of claim 1, wherein the cleavable linker is a thrombin cleavable linker.

10. The pharmaceutical composition of claim 1, wherein the B-domain deletion is a partial deletion of the B domain.

11. The pharmaceutical composition of claim 1, wherein the VWF fragment consists of a D' and a D3 domain of VWF.

12. The pharmaceutical composition of claim 1, wherein the VWF fragment does not include the A1 domain, the A2 domain, the A3 domain, the D4 domain, the B1 domain, the B2 domain, the B3 domain, the C1 domain, the C2 domain, or the CK domain of VWF.

13. The pharmaceutical composition of claim 4, wherein both the first and second immunoglobulin constant region is the Fc fragment of IgG1.

14. The pharmaceutical composition of claim 13, wherein the cleavable linker is a thrombin cleavable linker.

15. The pharmaceutical composition of claim 14, wherein the VWF fragment consists of a D' and a D3 domain of VWF.

16. A pharmaceutical composition comprising a chimeric protein and a pharmaceutically acceptable carrier,
wherein the chimeric protein comprises a first polypeptide and a second polypeptide;
wherein the first polypeptide comprises:
  (a) a Factor VIII ("FVIII") protein comprising amino acid residues 1 to 743 of SEQ ID NO: 16 and a B-domain deletion; and
  (b) a first immunoglobulin constant region,
wherein the second polypeptide comprises:
  (a) a von Willebrand Factor (VWF) fragment comprising a D' and a D3 domain of VWF, wherein the VWF fragment comprises an alanine substitution for cysteine at residues corresponding to residue 1099 and residue 1142 of SEQ ID NO: 2;
  (b) a second immunoglobulin constant region; and
  (c) a cleavable linker located between the VWF fragment and the second immunoglobulin constant region,
wherein the FVIII protein is a single chain FVIII protein;
wherein the VWF fragment is prevented or inhibited from forming multimers;
wherein the VWF fragment binds to the FVIII protein and does not bind endogenous human VWF;
wherein the first polypeptide and the second polypeptide are linked by a disulfide bond between the first and second immunoglobulin constant regions; and
wherein the pharmaceutical composition is freeze-dried.

17. The pharmaceutical composition of claim 16, wherein the first immunoglobulin constant region or portion thereof is a first Fc region and wherein the second immunoglobulin constant region or portion thereof is a second Fc region.

18. The pharmaceutical composition of claim 16, wherein the pharmaceutical composition is in powder form for constitution with a suitable vehicle.

19. The chimeric protein of claim 16, wherein the FVIII protein comprises an a3 acidic region, an A3 region, a C1 region, and a C2 region of FVIII comprising amino acids 1649 to 2332 of SEQ ID NO: 16.

20. The pharmaceutical composition of claim 16, wherein both the first and second immunoglobulin constant region is the Fc fragment of IgG1.

21. The pharmaceutical composition of claim 16, wherein both the first and second immunoglobulin constant regions are glycosylated.

22. The pharmaceutical composition of claim 16, wherein the first polypeptide and the second polypeptide are linked by two disulfide bonds between the first and second immunoglobulin constant regions.

23. The pharmaceutical composition of claim 16, wherein the cleavable linker is a thrombin cleavable linker.

24. The pharmaceutical composition of claim 19, wherein both the first and second immunoglobulin constant region is the Fc fragment of IgG1.

25. The pharmaceutical composition of claim 24, wherein the first polypeptide and the second polypeptide are linked by two disulfide bonds between the first and second immunoglobulin constant regions.

26. A pharmaceutical composition comprising a chimeric protein and a pharmaceutically acceptable carrier,
wherein the chimeric protein comprises a first polypeptide and a second polypeptide;
wherein the first polypeptide comprises:
  (a) a Factor VH ("FVIII") protein comprising amino acid residues 1 to 740 of SEQ ID NO: 16 and a B-domain deletion; and
  (b) a first immunoglobulin constant region,
wherein the second polypeptide comprises:
  (a) a von Willebrand Factor (VWF) fragment comprising a D' and a D3 domain of VWF, wherein the VWF fragment comprises an alanine substitution for cysteine at residues corresponding to residue 1099 and residue 1142 of SEQ ID NO: 2;
  (b) a second immunoglobulin constant region; and
  (c) a cleavable linker located between the VWF fragment and the second immunoglobulin constant region,
wherein the first polypeptide and the second polypeptide are linked by a disulfide bond between the first and second immunoglobulin constant regions.

27. The pharmaceutical composition of claim 26, wherein the pharmaceutical composition is in powder form for constitution with a suitable vehicle.

28. The pharmaceutical composition of claim 26, wherein the FVIII protein comprises an a3 acidic region, an A3 region, a C1 region, and a C2 region of FV111 comprising amino acids 1649 to 2332 of SEQ ID NO: 16.

29. The pharmaceutical composition of claim 26, wherein both the first and second immunoglobulin constant region is the Fc fragment of IgG1.

30. The pharmaceutical composition of claim 26, wherein both the first and second immunoglobulin constant regions are glycosylated.

31. The pharmaceutical composition of claim 26, wherein the pharmaceutical composition is freeze dried.

32. The pharmaceutical composition of claim 26, wherein the first polypeptide and the second polypeptide are linked by two disulfide bonds between the first and second immunoglobulin constant regions.

33. The pharmaceutical composition of claim 26, wherein the cleavable linker is a thrombin cleavable linker.

34. The pharmaceutical composition of claim 26, wherein the B-domain deletion is a partial deletion of the B domain.

35. The pharmaceutical composition of claim 26, wherein the VWF fragment consists of a D' and a D3 domain of VWF.

36. The pharmaceutical composition of claim 26, wherein the VWF fragment does not include the A1 domain, the A2 domain, the A3 domain, the D4 domain, the B1 domain, the B2 domain, the B3 domain, the C1 domain, the C2 domain, or the CK domain of VWF.

37. The pharmaceutical composition of claim 28, wherein both the first and second immunoglobulin constant region is the Fc fragment of IgG1.

38. The pharmaceutical composition of claim 37, wherein the cleavable linker is a thrombin cleavable linker.

39. The pharmaceutical composition of claim 38, wherein the VWF fragment consists of a D' and a D3 domain of VWF.

40. A pharmaceutical composition comprising a chimeric protein and a pharmaceutically acceptable carrier,
wherein the chimeric protein comprises a first polypeptide and a second polypeptide;
wherein the first polypeptide comprises:
  (a) a Factor VII ("FVIII") protein comprising amino acid residues 1 to 740 of SEQ ID NO: 16 and a B-domain deletion; and
  (b) a first immunoglobulin constant region, wherein the second polypeptide comprises:
(a) a von Willebrand Factor (VWF) fragment comprising a D' and a D3 domain of VWF, wherein the VWF fragment comprises an alanine substitution for cysteine at residues corresponding to residue 1099 and residue 1142 of SEQ ID NO: 2;
(b) a second immunoglobulin constant region; and
(c) a cleavable linker located between the VWF fragment and the second immunoglobulin constant region,
wherein the FVII protein is a single chain FVIII protein;
wherein the VWF fragment is prevented or inhibited from forming multimers;
wherein the VWF fragment binds to the FVIII protein and does not bind endogenous human VWF;
wherein the first polypeptide and the second polypeptide are linked by a disulfide bond between the first and second immunoglobulin constant regions; and
wherein the pharmaceutical composition is freeze-dried.

41. The pharmaceutical composition of claim 40, wherein the pharmaceutical composition is in powder form for constitution with a suitable vehicle.

42. The chimeric protein of claim 40, wherein the FVII protein comprises an a3 acidic region, an A3 region, a C1 region, and a C2 region of FVIII comprising amino acids 1649 to 2332 of SEQ ID NO: 16.

43. The pharmaceutical composition of claim 40, wherein both the first and second immunoglobulin constant region is the Fc fragment of IgG1.

44. The pharmaceutical composition of claim 40, wherein both the first and second immunoglobulin constant regions are glycosylated.

45. The pharmaceutical composition of claim 40, wherein the first polypeptide and the second polypeptide are linked by two disulfide bonds between the first and second immunoglobulin constant regions.

46. The pharmaceutical composition of claim 42, wherein the cleavable linker is a thrombin cleavable linker.

47. The pharmaceutical composition of claim 40, wherein both the first and second immunoglobulin constant region is the Fc fragment of IgG1.

48. The pharmaceutical composition of claim 47, wherein the first polypeptide and the second polypeptide are linked by two disulfide bonds between the first and second immunoglobulin constant regions.

* * * * *

SEQUENCE LISTING

<160> NUMBER OF SEQ ID NOS: 114

<210> SEQ ID NO 1

<211> LENGTH: 16842
<212> TYPE: DNA
<213> ORGANISM: Homo sapiens

<400> SEQUENCE: 1

| | | | | | |
|---|---|---|---|---|---|
| atgattcctg | ccagatttgc | cggggtgctg | cttgctctgg | ccctcatttt | gccagggacc | 60 |
| ctttgtgcag | aaggaactcg | cggcaggtca | tccacggccc | tactaaggac | ggtctaaacg | 120 |
| gccccacgac | gaacgagacc | gggagtaaaa | cggtccctgg | gaaacacgtc | ttccttgagc | 180 |
| gccgtccagt | aggtgccggg | gatgcagcct | tttcggaagt | gacttcgtca | acacctttga | 240 |
| tgggagcatg | tacagctttg | cgggatactg | cagttacctc | ctggcagggg | gctgccagaa | 300 |
| ctacgtcgga | aaagccttca | ctgaagcagt | tgtggaaact | accctcgtac | atgtcgaaac | 360 |
| gccctatgac | gtcaatggag | gaccgtcccc | cgacggtctt | acgctccttc | tcgattattg | 420 |
| gggacttcca | gaatggcaag | agagtgagcc | tctccgtgta | tcttgggaa | ttttttgaca | 480 |
| tccatttgtt | tgtcaatggt | tgcgaggaag | agctaataac | ccctgaaggt | cttaccgttc | 540 |
| tctcactcgg | agaggcacat | agaaccccctt | aaaaaactgt | aggtaaacaa | acagttacca | 600 |
| accgtgacac | aggggacca | aagagtctcc | atgccctatg | cctccaaagg | gctgtatcta | 660 |
| gaaactgagg | ctgggtacta | caagctgtcc | ggtgaggcct | tggcactgtg | tccccctggt | 720 |
| ttctcagagg | tacgggatac | ggaggtttcc | cgacatagat | ctttgactcc | gacccatgat | 780 |
| gttcgacagg | ccactccgga | atggctttgt | ggccaggatc | gatggcagcg | gcaactttca | 840 |
| agtcctgctg | tcagacagat | acttcaacaa | gacctgcggg | ctgtgtggca | actttaacat | 900 |
| taccgaaaca | ccgtcctag | ctaccgtcgc | cgttgaaagt | tcaggacgac | agtctgtcta | 960 |
| tgaagttgtt | ctggacgccc | gacacaccgt | tgaaattgta | ctttgctgaa | gatgacttta | 1020 |
| tgacccaaga | agggaccttg | acctcggacc | cttatgactt | tgccaactca | tgggctctga | 1080 |
| gcagtggaga | acagtggtgt | gaaacgactt | ctactgaaat | actgggttct | tccctggaac | 1140 |
| tggagcctgg | gaatactgaa | acggttgagt | acccgagact | cgtcacctct | tgtcaccaca | 1200 |
| gaacgggcat | ctcctcccag | cagctcatgc | aacatctcct | ctggggaaat | gcagaagggc | 1260 |
| ctgtgggagc | agtgccagct | tctgaagagc | acctcggtgt | cttgcccgta | gaggagggtc | 1320 |
| gtcgagtacg | ttgtagagga | gaccccttta | cgtcttcccg | gacaccctcg | tcacggtcga | 1380 |
| agacttctcg | tggagccaca | ttgcccgctg | ccaccctctg | gtggaccccg | agccttttgt | 1440 |
| ggccctgtgt | gagaagactt | tgtgtgagtg | tgctgggggg | ctggagtgcg | cctgccctgc | 1500 |
| aacgggcgac | ggtgggagac | cacctggggc | tcggaaaaca | ccgggacaca | ctcttctgaa | 1560 |
| acacactcac | acgaccccccc | gacctcacgc | ggacgggacg | cctcctggag | tacgcccgga | 1620 |
| cctgtgccca | ggagggaatg | gtgctgtacg | gctggaccga | ccacagcgcg | tgcagcccag | 1680 |
| tgtgccctgc | tggtatggag | ggaggacctc | atgcgggcct | ggacacgggt | cctcccttac | 1740 |
| cacgacatgc | cgacctggct | ggtgtcgcgc | acgtcgggtc | acacgggacg | accataccct | 1800 |
| tataggcagt | gtgtgtcccc | ttgcgccagg | acctgccaga | gcctgcacat | caatgaaatg | 1860 |
| tgtcaggagc | gatgcgtgga | tggctgcagc | tgccctgagg | atatccgtca | cacacagggg | 1920 |
| aacgcggtcc | tggacggtct | cggacgtgta | gttactttac | acagtcctcg | ctacgcacct | 1980 |
| accgacgtcg | acgggactcc | gacagctcct | ggatgaaggc | ctctgcgtgg | agagcaccga | 2040 |
| gtgtccctgc | gtgcattccg | gaaagcgcta | ccctcccggc | acctccctct | ctcgagactg | 2100 |
| ctgtcgagga | cctacttccg | gagacgcacc | tctcgtggct | cacagggacg | cacgtaaggc | 2160 |
| ctttcgcgat | gggagggccg | tggagggaga | gagctctgac | caacacctgc | atttgccgaa | 2220 |

```
acagccagtg gatctgcagc aatgaagaat gtccagggga gtgccttgtc actggtcaat    2280
cccacttcaa gagctttgac gttgtggacg taaacggctt tgtcggtcac ctagacgtcg    2340
ttacttctta caggtcccct cacggaacag tgaccagtta gggtgaagtt ctcgaaactg    2400
aacagatact tcaccttcag tgggatctgc cagtacctgc tggcccggga ttgccaggac    2460
cactccttct ccattgtcat tgagactgtc cagtgtgctg ttgtctatga agtggaagtc    2520
accctagacg gtcatggacg accgggccct aacggtcctg gtgaggaaga ggtaacagta    2580
actctgacag gtcacacgac atgaccgcga cgctgtgtgc acccgctccg tcaccgtccg    2640
gctgcctggc ctgcacaaca gccttgtgaa actgaagcat ggggcaggag ttgccatgga    2700
tactggcgct gcgacacacg tgggcgaggc agtggcaggc cgacggaccg gacgtgttgt    2760
cggaacactt tgacttcgta ccccgtcctc aacggtacct tggccaggac atccagctcc    2820
ccctcctgaa aggtgacctc cgcatccagc atacagtgac ggcctccgtg cgcctcagct    2880
acggggagga cctgcagatg accggtcctg taggtcgagg gggaggactt tccactggag    2940
gcgtaggtcg tatgtcactg ccggaggcac gcggagtcga tgcccctcct ggacgtctac    3000
gactgggatg gccgcgggag gctgctggtg aagctgtccc ccgtctatgc cgggaagacc    3060
tgcggcctgt gtgggaatta caatggcaac cagggcgacg ctgaccctac cggcgccctc    3120
cgacgaccac ttcgacaggg ggcagatacg gcccttctgg acgccggaca cacccttaat    3180
gttaccgttg gtcccgctgc acttccttac cccctctggg ctggcrgagc cccgggtgga    3240
ggacttcggg aacgcctgga agctgcacgg ggactgccag gacctgcaga agcagcacag    3300
tgaaggaatg ggggagaccc gaccgyctcg gggcccacct cctgaagccc ttgcggacct    3360
tcgacgtgcc cctgacggtc ctggacgtct tcgtcgtgtc cgatccctgc gccctcaacc    3420
cgcgcatgac caggttctcc gaggaggcgt gcgcggtcct gacgtccccc acattcgagg    3480
cctgccatcg tgccgtcagc gctagggacg cgggagttgg gcgcgtactg gtccaagagg    3540
ctcctccgca cgcgccagga ctgcaggggg tgtaagctcc ggacggtagc acggcagtcg    3600
ccgctgccct acctgcggaa ctgccgctac gacgtgtgct cctgctcgga cggccgcgag    3660
tgcctgtgcg gcgccctggc cagctatgcc gcggcctgcg ggcgacggga tggacgcctt    3720
gacggcgatg ctgcacacga ggacgagcct gccggcgctc acggacacgc gcgggaccg    3780 gtcgatacgg cgccggacgc cggggagagg cgtgcgcgtc gcgtggcgcg agccaggccg    3840
ctgtgagctg aactgcccga aaggccaggt gtacctgcag tgcgggaccc cctgcaacct    3900 gccccctctcc gcacgcgcag cgcaccgcgc tcggtccggc gacactcgac ttgacgggct    3960
ttccggtcca catggacgtc acgccctggg ggacgttgga gacctgccgc tctctctctt    4020
acccggatga ggaatgcaat gaggcctgcc tggaggctg cttctgcccc caggctct    4080 acatggatga gggggggac ctggacggcg agagagagaa tgggcctact ccttacgtta    4140
ctccggacgg acctcccgac gaagacgggg ggtcccgaga tgtacctact ctcccccctg    4200
tgcgtgccca aggcccagtg cccctgttac tatgacggtg agatcttcca gccagaagac    4260
atcttctcag accatcacac catgtgctac tgtgaggatg acgcacgggt tccgggtcac    4320
ggggacaatg atactgccac tctagaaggt cggtcttctg tagaagagtc tggtagtgtg    4380
gtacacgatg acactcctac gcttcatgca ctgtaccatg agtggagtcc ccggaagctt    4440
gctgcctgac gctgtcctca gcagtcccct gtctcatcgc agcaaaagga gcctatcctg    4500
cgaagtacgt gacatggtac tcacctcagg ggccttcgaa cgacggactg cgacaggagt    4560
```

-continued

| | | | | | |
|---|---|---|---|---|---|
| cgtcagggga | cagagtagcg | tcgttttcct | cggataggac | tcggccccccc | atggtcaagc | 4620 |
| tggtgtgtcc | cgctgacaac | ctgcgggctg | aagggctcga | gtgtaccaaa | acgtgccaga | 4680 |
| actatgacct | ggagtgcatg | agccgggggg | taccagttcg | accacacagg | gcgactgttg | 4740 |
| gacgcccgac | ttcccgagct | cacatggttt | tgcacggtct | tgatactgga | cctcacgtac | 4800 |
| agcatgggct | gtgtctctgg | ctgcctctgc | ccccgggca | tggtccggca | tgagaacaga | 4860 |
| tgtgtggccc | tggaaaggtg | tccctgcttc | catcagggca | tcgtacccga | cacagagacc | 4920 |
| gacggagacg | gggggcccgt | accaggccgt | actcttgtct | acacaccggg | acctttccac | 4980 |
| agggacgaag | gtagtcccgt | aggagtatgc | ccctggagaa | acagtgaaga | ttggctgcaa | 5040 |
| cacttgtgtc | tgtcgggacc | ggaagtggaa | ctgcacagac | catgtgtgtg | atgccacgtg | 5100 |
| tcctcatacg | gggacctctt | tgtcacttct | aaccgacgtt | gtgaacacag | acagccctgg | 5160 |
| ccttcacctt | gacgtgtctg | gtacacacac | tacggtgcac | ctccacgatc | ggcatggccc | 5220 |
| actacctcac | cttcgacggg | ctcaaatacc | tgttccccgg | ggagtgccag | tacgttctgg | 5280 |
| tgcaggatta | ctgcggcagt | gaggtgctag | ccgtaccggg | tgatggagtg | gaagctgccc | 5340 |
| gagtttatgg | acaaggggcc | ctcacggtc | atgcaagacc | acgtcctaat | gacgccgtca | 5400 |
| aaccctggga | ccttcggat | cctagtgggg | aataagggat | gcagccaccc | tcagtgaaa | 5460 |
| tgcaagaaac | gggtcaccat | cctggtggag | ggaggagaga | ttgggaccct | ggaaagccta | 5520 |
| ggatcacccc | ttattcccta | cgtcggtggg | gagtcacttt | acgttctttg | cccagtggta | 5580 |
| ggaccacctc | cctcctctct | ttgagctgtt | tgacggggag | gtgaatgtga | agaggcccat | 5640 |
| gaaggatgag | actcactttg | aggtggtgga | gtctggccgg | tacatcattc | tgctgctggg | 5700 |
| aactcgacaa | actgcccctc | cacttacact | tctccgggta | cttcctactc | tgagtgaaac | 5760 |
| tccaccacct | cagaccggcc | atgtagtaag | acgacgaccc | caaagccctc | tccgtggtct | 5820 |
| gggaccgcca | cctgagcatc | tccgtggtcc | tgaagcagac | ataccaggag | aaagtgtgtg | 5880 |
| gcctgtgtgg | gaattttgat | gtttcgggag | aggcaccaga | ccctggcggt | ggactcgtag | 5940 |
| aggcaccagg | acttcgtctg | tatggtcctc | tttcacacac | cggacacacc | cttaaaacta | 6000 |
| ggcatccaga | acaatgacct | caccagcagc | aacctccaag | tggaggaaga | ccctgtggac | 6060 |
| tttgggaact | cctggaaagt | gagctcgcag | tgtgctgaca | ccgtaggtct | tgttactgga | 6120 |
| gtggtcgtcg | ttgagggttc | acctccttct | gggacacctg | aaacccttga | ggacctttca | 6180 |
| ctcgagcgtc | acacgactgt | ccagaaaagt | gcctctggac | tcatcccctg | ccacctgcca | 6240 |
| taacaacatc | atgaagcaga | cgatggtgga | ttcctcctgt | agaatcctta | ccagtgacgt | 6300 |
| ggtcttttca | cggagacctg | agtaggggac | ggtggacggt | attgttgtag | tacttcgtct | 6360 |
| gctaccacct | aaggaggaca | tcttaggaat | ggtcactgca | cttccaggac | tgcaacaagc | 6420 |
| tggtggaccc | cgagccatat | ctggatgtct | gcatttacga | cacctgctcc | tgtgagtcca | 6480 |
| ttggggactg | cgcctgcttc | gaaggtcctg | acgttgttcg | accacctggg | gctcggtata | 6540 |
| gacctacaga | cgtaaatgct | gtggacgagg | acactcagga | aaccctgac | gcggacgaag | 6600 |
| tgcgacacca | ttgctgccta | tgcccacgtg | tgtgcccagc | atggcaaggt | ggtgacctgg | 6660 |
| aggacggcca | cattgtgccc | ccagagctgc | gaggagagga | acgctgtggt | aacgacggat | 6720 |
| acgggtgcac | acacgggtcg | taccgttcca | ccactggacc | tcctgccggt | gtaacacggg | 6780 |
| ggtctcgacg | ctcctctcct | atctccggga | gaacgggtat | gagtgtgagt | ggcgctataa | 6840 |
| cagctgtgca | cctgcctgtc | aagtcacgtg | tcagcaccct | gagccactgg | cctgccctgt | 6900 |
| tagaggccct | cttgcccata | ctcacactca | ccgcgatatt | gtcgacacgt | ggacggacag | 6960 |

```
ttcagtgcac agtcgtggga ctcggtgacc ggacgggaca gcagtgtgtg gagggctgcc   7020
atgcccactg ccctccaggg aaaatcctgg atgagctttt gcagacctgc gttgaccctg   7080
aagactgtcc agtgtgtgag cgtcacacac ctcccgacgg tacgggtgac gggaggtccc   7140
tttttaggacc tactcgaaaa cgtctggacg caactggacg ttctgacagg tcacacactc   7200
gtggctggcc ggcgttttgc ctcaggaaag aaagtcacct tgaatcccag tgaccctgag   7260
cactgccaga tttgccactg tgatgttgtc aacctcacct caccgaccgg ccgcaaaacg   7320
gagtcctttc tttcagtgga acttagggtc actgggactc gtgacggtct aaacggtgac   7380
actacaacag ttggagtgga gtgaagcctg ccaggagccg ggaggcctgg tggtgcctcc   7440
cacagatgcc ccggtgagcc ccaccactct gtatgtggag gacatctcgg aaccgccgtt   7500
cacttcggac ggtcctcggc cctccggacc accacggagg gtgtctacgg ggccactcgg   7560
ggtggtgaga catacacctc ctgtagagcc ttggcggcaa gcacgatttc tactgcagca   7620
ggctactgga cctggtcttc ctgctggatg gctcctccag gctgtccgag gctgagtttg   7680
aagtgctgaa ggcctttgtg cgtgctaaag atgacgtcgt ccgatgacct ggaccagaag   7740
gacgacctac cgaggaggtc cgacaggctc cgactcaaac ttcacgactt ccggaaacac   7800
gtggacatga tggagcggct gcgcatctcc cagaagtggg tccgcgtggc cgtggtggag   7860
taccacgacg gctcccacgc ctacatcggg ctcaaggacc cacctgtact acctcgccga   7920
cgcgtagagg gtcttcaccc aggcgcaccg gcaccacctc atggtgctgc cgagggtgcg   7980
gatgtagccc gagttcctgg ggaagcgacc gtcagagctg cggcgcattg ccagccaggt   8040
gaagtatgcg ggcagccagg tggcctccac cagcgaggtc ttgaaataca cactgttcca   8100
ccttcgctgg cagtctcgac gccgcgtaac ggtcggtcca cttcatacgc ccgtcggtcc   8160
accggaggtg gtcgctccag aactttatgt gtgacaaggt aatcttcagc aagatcgacc   8220
gccctgaagc ctcccgcatc gccctgctcc tgatggccag ccaggagccc caacggatgt   8280
cccggaactt tgtccgctac ttagaagtcg ttctagctgg cgggacttcg gagggcgtag   8340
cgggacgagg actaccggtc ggtcctcggg gttgcctaca gggccttgaa acaggcgatg   8400
gtccagggcc tgaagaagaa gaaggtcatt gtgatcccgg tgggcattgg gccccatgcc   8460
aacctcaagc agatccgcct catcgagaag caggcccctg caggtcccgg acttcttctt   8520
cttccagtaa cactagggcc acccgtaacc cggggtacgg ttggagttcg tctaggcgga   8580
gtagctcttc gtccggggac agaacaaggc cttcgtgctg agcagtgtgg atgagctgga   8640
gcagcaaagg gacgagatcg ttagctacct ctgtgacctt gccctgaag ccctcctcc   8700
tcttgttccg gaagcacgac tcgtcacacc tactcgacct cgtcgtttcc ctgctctagc   8760
aatcgatgga gacactggaa cggggacttc ggggaggagg tactctgccc cccgacatgg   8820
cacaagtcac tgtgggcccg gggctcttgg gggtttcgac cctggggccc aagaggaact   8880
ccatggttct ggatgtggcg atgagacggg gggctgtacc gtgttcagtg acacccgggc   8940
cccgagaacc cccaaagctg ggaccccggg ttctccttga ggtaccaaga cctacaccgc   9000
ttcgtcctgg aaggatcgga caaaattggt gaagccgact tcaacaggag caaggagttc   9060
atggaggagg tgattcagcg gatggatgtg ggccaggaca aagcaggacc ttcctagcct   9120
gtttttaacca cttcggctga agttgtcctc gttcctcaag tacctcctcc actaagtcgc   9180
ctacctacac ccggtcctgt gcatccacgt cacggtgctg cagtactcct acatggtgac   9240
cgtggagtac cccttcagcg aggcacagtc caaagggac atcctgcagc gggtgcgaga   9300
```

```
cgtaggtgca gtgccacgac gtcatgagga tgtaccactg gcacctcatg ggaagtcgc   9360
tccgtgtcag gtttcccctg taggacgtcg cccacgctct gatccgctac cagggcggca   9420
acaggaccaa cactgggctg gccctgcggt acctctctga ccacagcttc ttggtcagcc   9480
agggtgaccg ggagcaggcg ctaggcgatg gtcccgccgt tgtcctggtt gtgacccgac   9540
cgggacgcca tggagagact ggtgtcgaag aaccagtcgg tcccactggc cctcgtccgc   9600
cccaacctgg tctacatggt caccggaaat cctgcctctg atgagatcaa gaggctgcct   9660
ggagacatcc aggtggtgcc cattggagtg ggccctaatg gggttggacc agatgtacca   9720
gtggccttta ggacggagac tactctagtt ctccgacgga cctctgtagg tccaccacgg   9780
gtaacctcac ccgggattac caacgtgca ggagctggag aggattggct ggcccaatgc    9840
ccctatcctc atccaggact ttgagacgct ccccgagag gctcctgacc tggtgctgca    9900
ggttgcacgt cctcgacctc tcctaaccga ccgggttacg gggataggag taggtcctga   9960
aactctgcga gggggctctc cgaggactgg accacgacgt gaggtgctgc tccggagagg  10020
ggctgcagat ccccacccte tccectgcac ctgactgcag ccagcccctg gacgtgatcc  10080
ttctcctgga tggctcctcc ctccacgacg aggcctctcc ccgacgtcta ggggtgggag  10140
aggggacgtg gactgacgtc ggtcgggac ctgcactagg aagaggacct accgaggagg   10200
agtttcccag cttcttattt tgatgaaatg aagagtttcg ccaaggcttt catttcaaaa  10260
gccaatatag ggcctcgtct cactcaggtg tcagtgctgc tcaaagggtc gaagaataaa  10320
actactttac ttctcaaagc ggttccgaaa gtaaagtttt cggttatatc ccggagcaga  10380
gtgagtccac agtcacgacg agtatggaag catcaccacc attgacgtgc catggaacgt  10440
ggtcccggag aaagcccatt tgctgagcct tgtggacgtc atgcagcggg agggaggccc  10500
tcataccttc gtagtggtgg taactgcacg gtaccttgca ccaggcctc tttcgggtaa   10560
acgactcgga acacctgcag tacgtcgccc tccctccggg cagccaaatc ggggatgcct  10620
tgggctttgc tgtgcgatac ttgacttcag aaatgcatgg tgccaggccg ggagcctcaa  10680
aggcggtggt catcctggtc gtcggtttag cccctacgga acccgaaacg acacgctatg  10740
aactgaagtc tttacgtacc acggtccggc cctcggagtt ccgccacca gtaggaccag   10800
acggacgtct ctgtggattc agtggatgca gcagctgatg ccgccaggtc aacagagtg   10860
acagtgttcc ctattggaat tggagatcgc tacgatgcag tgcctgcaga cacctaag    10920
tcacctacgt cgtcgactac ggcggtccag gttgtctcac tgtcacaagg gataaccta    10980
acctctagcg atgctacgtc cccagctacg atcttggca ggcccagcag gcgactccaa   11040
cgtggtgaag ctccagcgaa tcgaagacct ccctaccatg gtcaccttgg gcaattcctt  11100
gggtcgatgc ctagaaccgt ccgggtcgtc cgctgaggtt gcaccacttc gaggtcgctt  11160
agcttctgga gggatggtac cagtggaacc cgttaaggaa cctccacaaa ctgtgctctg  11220
gatttgttag gatttgcatg gatgaggatg ggaatgagaa gaggcccggg gacgtctgga  11280
ccttgccaga ccagtgccac ggaggtgttt gacacgagac ctaaacaatc ctaaacgtac  11340
ctactcctac ccttactctt ctccgggccc ctgcagacct ggaacggtct ggtcacggtg  11400
accgtgactt gccagccaga tggccagacc ttgctgaaga gtcatcgggt caactgtgac  11460
cgggggctga ggccttcgtg ccctaacagc cagtcccctg tggcactgaa cggtcggtct  11520
accggtctgg aacgacttct cagtagccca gttgacactg gccccgact ccggaagcac   11580
gggattgtcg gtcaggggac ttaaagtgga agagacctgt ggctgccgct ggacctgccc  11640
ctgygtgtgc acaggcagct ccactcggca catcgtgacc tttgatgggc agaatttcaa  11700
```

```
aatttcacct tctctggaca ccgacggcga cctggacggg gacrcacacg tgtccgtcga  11760
ggtgagccgt gtagcactgg aaactacccg tcttaaagtt gctgactggc agctgttctt  11820
atgtcctatt tcaaaacaag gagcaggacc tggaggtgat tctccataat ggtgcctgca  11880
gccctggagc aaggcagggc cgactgaccg tcgacaagaa tacaggataa agttttgttc  11940
ctcgtcctgg acctccacta agaggtatta ccacggacgt cgggacctcg ttccgtcccg  12000
tgcatgaaat ccatcgaggt gaagcacagt gccctctccg tcgagstgca cagtgacatg  12060
gaggtgacgg tgaatgggag actggtctct gttccttacg acgtacttta ggtagctcca  12120
cttcgtgtca cggagagggc agctcsacgt gtcactgtac ctccactgcc acttaccctc  12180
tgaccagaga caaggaatgc tgggtgggaa catggaagtc aacgtttatg gtgccatcat  12240
gcatgaggtc agattcaatc accttggtca catcttcaca ttcactccac aaaacaatga  12300
acccaccctt gtaccttcag ttgcaaatac cacggtagta cgtactccag tctaagttag  12360
tggaaccagt gtagaagtgt aagtgaggtg ttttgttact gttccaactg cagctcagcc  12420
ccaagacttt tgcttcaaag acgtatggtc tgtgtgggat ctgtgatgag aacggagcca  12480
atgacttcat gctgagggat caaggttgac gtcgagtcgg ggttctgaaa acgaagtttc  12540
tgcataccag acacacccta gacactactc ttgcctcggt tactgaagta cgactcccta  12600
ggcacagtca ccacagactg gaaaacactt gttcaggaat ggactgtgca gcggccaggg  12660
cagacgtgcc agcccatcct ggaggagcag tgtcttgtcc ccgtgtcagt ggtgtctgac  12720
cttttgtgaa caagtcctta cctgacacgt cgccggtccc gtctgcacgg tcgggtagga  12780
cctcctcgtc acagaacagg ccgacagctc ccactgccag gtcctcctct taccactgtt  12840
tgctgaatgc cacaaggtcc tggctccagc cacattctat gccatctgcc agcaggacag  12900
ggctgtcgag ggtgacggtc caggaggaga atggtgacaa acgacttacg gtgttccagg  12960
accgaggtcg gtgtaagata cggtagacgg tcgtcctgtc ttgccaccag gagcaagtgt  13020
gtgaggtgat cgcctcttat gcccacctct gtcggaccaa cggggtctgc gttgactgga  13080
ggacacctga tttctgtgct aacggtggtc ctcgttcaca cactccacta gcggagaata  13140
cgggtggaga cagcctggtt gccccagacg caactgacct cctgtggact aaagacacga  13200
atgtcatgcc caccatctct ggtctacaac cactgtgagc atggctgtcc ccggcactgt  13260
gatggcaacg tgagctcctg tggggaccat ccctccgaag tacagtacgg gtggtagaga  13320
ccagatgttg gtgacactcg taccgacagg ggccgtgaca ctaccgttgc actcgaggac  13380
acccctggta gggaggcttc gctgtttctg ccctccagat aaagtcatgt tggaaggcag  13440
ctgtgtccct gaagaggcct gcactcagtg cattggtgag gatggagtcc agcaccagtt  13500
cgacaaagac gggaggtcta tttcagtaca accttccgtc gacacaggga cttctccgga  13560
cgtgagtcac gtaaccactc ctacctcagg tcgtggtcaa cctggaagcc tgggtcccgg  13620
accaccagcc ctgtcagatc tgcacatgcc tcagcgggcg aaggtcaac tgcacaacgc  13680
agccctgccc cacggccaaa ggaccttcgg acccagggcc tggtggtcgg gacagtctag  13740
acgtgtacgg agtcgcccgc cttccagttg acgtgttgcg tcgggacggg gtgccggttt  13800
gctcccacgt gtggcctgtg tgaagtagcc cgcctccgcc agaatgcaga ccagtgctgc  13860
cccgagtatg agtgtgtgtg tgacccagtg agctgtgacc cgagggtgca caccggacac  13920
acttcatcgg gcggaggcgg tcttacgtct ggtcacgacg gggctcatac tcacacacac  13980
actgggtcac tcgacactgg tgcccccagt gcctcactgt gaacgtggcc tccagcccac  14040
```

```
actgaccaac cctggcgagt gcagacccaa cttcacctgc gcctgcagga aggaggagtg    14100 acggggtca cggagtgaca cttgcaccgg aggtcgggtg tgactggttg ggaccgctca    14160
cgtctgggtt gaagtggacg cggacgtcct tcctcctcac caaaagagtg tccccaccct    14220 cctgccccc gcaccgtttg cccacccttc ggaagaccca gtgctgtgat gagtatgagt    14280
gtgcctgcaa ctgtgtcaac gttttctcac aggggtggga ggacggggg cgtggcaaac    14340 gggtgggaag ccttctgggt cacgacacta ctcatactca cacggacgtt gacacagttg    14400
tccacagtga gctgtcccct tgggtacttg gcctcaaccg ccaccaatga ctgtggctgt    14460
accacaacca cctgccttcc cgacaaggtg tgtgtccacc aggtgtcact cgacagggga    14520
acccatgaac cggagttggc ggtggttact gacaccgaca tggtgttggt ggacggaagg    14580
gctgttccac acacaggtgg gaagcaccat ctaccctgtg ggccagttct gggaggaggg    14640
ctgcgatgtg tgcacctgca ccgacatgga ggatgccgtg atgggcctcc gcgtggccca    14700
cttcgtggta gatgggacac ccggtcaaga ccctcctccc gacgctacac acgtggacgt    14760
ggctgtacct cctacggcac tacccggagg cgcaccgggt gtgctcccag aagccctgtg    14820
aggacagctg tcggtcgggc ttcacttacg ttctgcatga aggcgagtgc tgtggaaggt    14880
gcctgccatc tgcctgtgag cacgagggtc ttcgggacac tcctgtcgac agccagcccg    14940
aagtgaatgc aagacgtact tccgctcacg acaccttcca cggacggtag acggacactc    15000
gtggtgactg gctcaccgcg ggggactcc cagtcttcct ggaagagtgt cggctcccag    15060
tgggcctccc cggagaaccc ctgcctcatc aatgagtgtg caccactgac cgagtggcgc    15120 cccctgagg gtcagaagga ccttctcaca gccgagggtc acccggaggg gcctcttggg    15180
gacggagtag ttactcacac tccgagtgaa ggaggaggtc tttatacaac aaaggaacgt    15240
ctcctgcccc cagctggagg tccctgtctg cccctcgggc tttcagctga gctgtaagac    15300
aggctcactt cctcctccag aaatatgttg tttccttgca gaggacgggg gtcgacctcc    15360
agggacagac ggggagcccg aaagtcgact cgacattctg ctcagcgtgc tgcccaagct    15420
gtcgctgtga gcgcatggag gcctgcatgc tcaatggcac tgtcattggg cccgggaaga    15480
ctgtgatgat cgatgtgtgc gagtcgcacg acgggttcga cagcgacact cgcgtacctc    15540
cggacgtacg agttaccgtg acagtaaccc gggcccttct gacactacta gctacacacg    15600
acgacctgcc gctgcatggt gcaggtgggg gtcatctctg gattcaagct ggagtgcagg    15660
aagaccacct gcaacccctg cccctgggt tacaaggaag tgctggacgg cgacgtacca    15720
cgtccacccc cagtagagac ctaagttcga cctcacgtcc ttctggtgga cgttggggac    15780
gggggaccca atgttccttc aaaataacac aggtgaatgt tgtgggagat gtttgcctac    15840
ggcttgcacc attcagctaa gaggaggaca gatcatgaca ctgaagcgtg atgagacgct    15900
ttttattgtg tccacttaca acaccctcta caaacggatg ccgaacgtgg taagtcgatt    15960
ctcctcctgt ctagtactgt gacttcgcac tactctgcga ccaggatggc tgtgatactc    16020
acttctgcaa ggtcaatgag agaggagagt acttctggga gaagagggtc acaggctgcc    16080
caccctttga tgaacacaag ggtcctaccg acactatgag tgaagacgtt ccagttactc    16140
tctcctctca tgaagaccct cttctcccag tgtccgacgg gtgggaaact acttgtgttc    16200
tgtcttgctg agggaggtaa aattatgaaa attccaggca cctgctgtga cacatgtgag    16260
gagcctgagt gcaacgacat cactgccagg ctgcagtatg acagaacgac tccctccatt    16320
ttaatacttt taaggtccgt ggacgacact gtgtacactc ctcggactca cgttgctgta    16380
gtgacggtcc gacgtcatac tcaaggtggg aagctgtaag tctgaagtag aggtggatat    16440
```

```
ccactactgc cagggcaaat gtgccagcaa agccatgtac tccattgaca tcaacgatgt   16500
agttccaccc ttcgacattc agacttcatc tccacctata ggtgatgacg gtcccgttta   16560
cacggtcgtt tcggtacatg aggtaactgt agttgctaca gcaggaccag tgctcctgct   16620
gctctccgac acgacggag cccatgcagg tggccctgca ctgcaccaat ggctctgttg    16680
tgtaccatga ggttctcaat cgtcctggtc acgaggacga cgagaggctg tgcctgcctc   16740
gggtacgtcc accgggacgt gacgtggtta ccgagacaac acatggtact ccaagagtta   16800
gccatggagt gcaaatgctc ccccaggaag tgcagcaagt ga                      16842
```

<210> SEQ ID NO 2
<211> LENGTH: 2813
<212> TYPE: PRT
<213> ORGANISM: Homo sapiens
<220> FEATURE:
<221> NAME/KEY: misc_feature
<222> LOCATION: (1)..(22)
<223> OTHER INFORMATION: VWF Signal Peptide
<220> FEATURE:
<221> NAME/KEY: misc_feature
<222> LOCATION: (23)..(763)
<223> OTHER INFORMATION: VWF D1D2 region
<220> FEATURE:
<221> NAME/KEY: misc_feature
<222> LOCATION: (764)..(866)
<223> OTHER INFORMATION: VWF D'Domain
<220> FEATURE:
<221> NAME/KEY: misc_feature
<222> LOCATION: (867)..(1240)
<223> OTHER INFORMATION: VWF D3 Domain
<220> FEATURE:
<221> NAME/KEY: misc_feature
<222> LOCATION: (1241)..(1479)
<223> OTHER INFORMATION: VWF A1 Domain
<220> FEATURE:
<221> NAME/KEY: misc_feature
<222> LOCATION: (2016)..(2016)
<223> OTHER INFORMATION: Xaa can be any naturally occurring amino acid

<400> SEQUENCE: 2

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
                20                  25                  30

Ala Arg Cys Ser Leu Phe Gly Ser Asp Phe Val Asn Thr Phe Asp Gly
            35                  40                  45

Ser Met Tyr Ser Phe Ala Gly Tyr Cys Ser Tyr Leu Leu Ala Gly Gly
        50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175
```

```
Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590
```

```
Glu Ala Cys His Arg Ala Val Ser Pro Leu Pro Tyr Leu Arg Asn Cys
            595                 600                 605

Arg Tyr Asp Val Cys Ser Cys Ser Asp Gly Arg Glu Cys Leu Cys Gly
        610                 615                 620

Ala Leu Ala Ser Tyr Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
    850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
    930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp Gly Ile Gln Asn Asn Asp Leu Thr
        995                 1000                1005

Ser Ser Asn Leu Gln Val Glu Glu Asp Pro Val Asp Phe Gly Asn
```

```
            1010                1015                1020
Ser Trp Lys Val Ser Ser Gln Cys Ala Asp Thr Arg Lys Val Pro
    1025                1030                1035

Leu Asp Ser Ser Pro Ala Thr Cys His Asn Asn Ile Met Lys Gln
    1040                1045                1050

Thr Met Val Asp Ser Ser Cys Arg Ile Leu Thr Ser Asp Val Phe
    1055                1060                1065

Gln Asp Cys Asn Lys Leu Val Asp Pro Glu Pro Tyr Leu Asp Val
    1070                1075                1080

Cys Ile Tyr Asp Thr Cys Ser Cys Glu Ser Ile Gly Asp Cys Ala
    1085                1090                1095

Cys Phe Cys Asp Thr Ile Ala Ala Tyr Ala His Val Cys Ala Gln
    1100                1105                1110

His Gly Lys Val Val Thr Trp Arg Thr Ala Thr Leu Cys Pro Gln
    1115                1120                1125

Ser Cys Glu Glu Arg Asn Leu Arg Glu Asn Gly Tyr Glu Cys Glu
    1130                1135                1140

Trp Arg Tyr Asn Ser Cys Ala Pro Ala Cys Gln Val Thr Cys Gln
    1145                1150                1155

His Pro Glu Pro Leu Ala Cys Pro Val Gln Cys Val Glu Gly Cys
    1160                1165                1170

His Ala His Cys Pro Pro Gly Lys Ile Leu Asp Glu Leu Leu Gln
    1175                1180                1185

Thr Cys Val Asp Pro Glu Asp Cys Pro Val Cys Glu Val Ala Gly
    1190                1195                1200

Arg Arg Phe Ala Ser Gly Lys Lys Val Thr Leu Asn Pro Ser Asp
    1205                1210                1215

Pro Glu His Cys Gln Ile Cys His Cys Asp Val Val Asn Leu Thr
    1220                1225                1230

Cys Glu Ala Cys Gln Glu Pro Gly Gly Leu Val Val Pro Pro Thr
    1235                1240                1245

Asp Ala Pro Val Ser Pro Thr Thr Leu Tyr Val Glu Asp Ile Ser
    1250                1255                1260

Glu Pro Pro Leu His Asp Phe Tyr Cys Ser Arg Leu Leu Asp Leu
    1265                1270                1275

Val Phe Leu Leu Asp Gly Ser Ser Arg Leu Ser Glu Ala Glu Phe
    1280                1285                1290

Glu Val Leu Lys Ala Phe Val Val Asp Met Met Glu Arg Leu Arg
    1295                1300                1305

Ile Ser Gln Lys Trp Val Arg Val Ala Val Val Glu Tyr His Asp
    1310                1315                1320

Gly Ser His Ala Tyr Ile Gly Leu Lys Asp Arg Lys Arg Pro Ser
    1325                1330                1335

Glu Leu Arg Arg Ile Ala Ser Gln Val Lys Tyr Ala Gly Ser Gln
    1340                1345                1350

Val Ala Ser Thr Ser Glu Val Leu Lys Tyr Thr Leu Phe Gln Ile
    1355                1360                1365

Phe Ser Lys Ile Asp Arg Pro Glu Ala Ser Arg Ile Ala Leu Leu
    1370                1375                1380

Leu Met Ala Ser Gln Glu Pro Gln Arg Met Ser Arg Asn Phe Val
    1385                1390                1395

Arg Tyr Val Gln Gly Leu Lys Lys Lys Lys Val Ile Val Ile Pro
    1400                1405                1410
```

```
Val Gly Ile Gly Pro His Ala Asn Leu Lys Gln Ile Arg Leu Ile
    1415            1420                1425

Glu Lys Gln Ala Pro Glu Asn Lys Ala Phe Val Leu Ser Ser Val
    1430            1435                1440

Asp Glu Leu Glu Gln Gln Arg Asp Glu Ile Val Ser Tyr Leu Cys
    1445            1450                1455

Asp Leu Ala Pro Glu Ala Pro Pro Thr Leu Pro Pro Asp Met
    1460            1465                1470

Ala Gln Val Thr Val Gly Pro Gly Leu Leu Gly Val Ser Thr Leu
    1475            1480                1485

Gly Pro Lys Arg Asn Ser Met Val Leu Asp Val Ala Phe Val Leu
    1490            1495                1500

Glu Gly Ser Asp Lys Ile Gly Glu Ala Asp Phe Asn Arg Ser Lys
    1505            1510                1515

Glu Phe Met Glu Glu Val Ile Gln Arg Met Asp Val Gly Gln Asp
    1520            1525                1530

Ser Ile His Val Thr Val Leu Gln Tyr Ser Tyr Met Val Thr Val
    1535            1540                1545

Glu Tyr Pro Phe Ser Glu Ala Gln Ser Lys Gly Asp Ile Leu Gln
    1550            1555                1560

Arg Val Arg Glu Ile Arg Tyr Gln Gly Gly Asn Arg Thr Asn Thr
    1565            1570                1575

Gly Leu Ala Leu Arg Tyr Leu Ser Asp His Ser Phe Leu Val Ser
    1580            1585                1590

Gln Gly Asp Arg Glu Gln Ala Pro Asn Leu Val Tyr Met Val Thr
    1595            1600                1605

Gly Asn Pro Ala Ser Asp Glu Ile Lys Arg Leu Pro Gly Asp Ile
    1610            1615                1620

Gln Val Val Pro Ile Gly Val Gly Pro Asn Ala Asn Val Gln Glu
    1625            1630                1635

Leu Glu Arg Ile Gly Trp Pro Asn Ala Pro Ile Leu Ile Gln Asp
    1640            1645                1650

Phe Glu Thr Leu Pro Arg Glu Ala Pro Asp Leu Val Leu Gln Arg
    1655            1660                1665

Cys Cys Ser Gly Glu Gly Leu Gln Ile Pro Thr Leu Ser Pro Ala
    1670            1675                1680

Pro Asp Cys Ser Gln Pro Leu Asp Val Ile Leu Leu Leu Asp Gly
    1685            1690                1695

Ser Ser Ser Phe Pro Ala Ser Tyr Phe Asp Glu Met Lys Ser Phe
    1700            1705                1710

Ala Lys Ala Phe Ile Ser Lys Ala Asn Ile Gly Pro Arg Leu Thr
    1715            1720                1725

Gln Val Ser Val Leu Gln Tyr Gly Ser Ile Thr Thr Ile Asp Val
    1730            1735                1740

Pro Trp Asn Val Val Pro Glu Lys Ala His Leu Leu Ser Leu Val
    1745            1750                1755

Asp Val Met Gln Arg Glu Gly Gly Pro Ser Gln Ile Gly Asp Ala
    1760            1765                1770

Leu Gly Phe Ala Val Arg Tyr Leu Thr Ser Glu Met His Gly Ala
    1775            1780                1785

Arg Pro Gly Ala Ser Lys Ala Val Val Ile Leu Val Thr Asp Val
    1790            1795                1800
```

```
Ser Val Asp Ser Val Asp Ala Ala Asp Ala Ala Arg Ser Asn
    1805            1810            1815

Arg Val Thr Val Phe Pro Ile Gly Ile Gly Asp Arg Tyr Asp Ala
    1820            1825            1830

Ala Gln Leu Arg Ile Leu Ala Gly Pro Ala Gly Asp Ser Asn Val
    1835            1840            1845

Val Lys Leu Gln Arg Ile Glu Asp Leu Pro Thr Met Val Thr Leu
    1850            1855            1860

Gly Asn Ser Phe Leu His Lys Leu Cys Ser Gly Phe Val Arg Ile
    1865            1870            1875

Cys Met Asp Glu Asp Gly Asn Glu Lys Arg Pro Gly Asp Val Trp
    1880            1885            1890

Thr Leu Pro Asp Gln Cys His Thr Val Thr Cys Gln Pro Asp Gly
    1895            1900            1905

Gln Thr Leu Leu Lys Ser His Arg Val Asn Cys Asp Arg Gly Leu
    1910            1915            1920

Arg Pro Ser Cys Pro Asn Ser Gln Ser Pro Val Lys Val Glu Glu
    1925            1930            1935

Thr Cys Gly Cys Arg Trp Thr Cys Pro Cys Val Cys Thr Gly Ser
    1940            1945            1950

Ser Thr Arg His Ile Val Thr Phe Asp Gly Gln Asn Phe Lys Leu
    1955            1960            1965

Thr Gly Ser Cys Ser Tyr Val Leu Phe Gln Asn Lys Glu Gln Asp
    1970            1975            1980

Leu Glu Val Ile Leu His Asn Gly Ala Cys Ser Pro Gly Ala Arg
    1985            1990            1995

Gln Gly Cys Met Lys Ser Ile Glu Val Lys His Ser Ala Leu Ser
    2000            2005            2010

Val Glu Xaa His Ser Asp Met Glu Val Thr Val Asn Gly Arg Leu
    2015            2020            2025

Val Ser Val Pro Tyr Val Gly Gly Asn Met Glu Val Asn Val Tyr
    2030            2035            2040

Gly Ala Ile Met His Glu Val Arg Phe Asn His Leu Gly His Ile
    2045            2050            2055

Phe Thr Phe Thr Pro Gln Asn Asn Glu Phe Gln Leu Gln Leu Ser
    2060            2065            2070

Pro Lys Thr Phe Ala Ser Lys Thr Tyr Gly Leu Cys Gly Ile Cys
    2075            2080            2085

Asp Glu Asn Gly Ala Asn Asp Phe Met Leu Arg Asp Gly Thr Val
    2090            2095            2100

Thr Thr Asp Trp Lys Thr Leu Val Gln Glu Trp Thr Val Gln Arg
    2105            2110            2115

Pro Gly Gln Thr Cys Gln Pro Ile Leu Glu Glu Gln Cys Leu Val
    2120            2125            2130

Pro Asp Ser Ser His Cys Gln Val Leu Leu Leu Pro Leu Phe Ala
    2135            2140            2145

Glu Cys His Lys Val Leu Ala Pro Ala Thr Phe Tyr Ala Ile Cys
    2150            2155            2160

Gln Gln Asp Ser Cys His Gln Glu Gln Val Cys Glu Val Ile Ala
    2165            2170            2175

Ser Tyr Ala His Leu Cys Arg Thr Asn Gly Val Cys Val Asp Trp
    2180            2185            2190

Arg Thr Pro Asp Phe Cys Ala Met Ser Cys Pro Pro Ser Leu Val
```

```
                2195                2200                2205
Tyr Asn His Cys Glu His Gly Cys Pro Arg His Cys Asp Gly Asn
    2210                2215                2220
Val Ser Ser Cys Gly Asp His Pro Ser Glu Gly Cys Phe Cys Pro
    2225                2230                2235
Pro Asp Lys Val Met Leu Glu Gly Ser Cys Val Pro Glu Glu Ala
    2240                2245                2250
Cys Thr Gln Cys Ile Gly Glu Asp Gly Val Gln His Gln Phe Leu
    2255                2260                2265
Glu Ala Trp Val Pro Asp His Gln Pro Cys Gln Ile Cys Thr Cys
    2270                2275                2280
Leu Ser Gly Arg Lys Val Asn Cys Thr Thr Gln Pro Cys Pro Thr
    2285                2290                2295
Ala Lys Ala Pro Thr Cys Gly Leu Cys Glu Val Ala Arg Leu Arg
    2300                2305                2310
Gln Asn Ala Asp Gln Cys Cys Pro Glu Tyr Glu Cys Val Cys Asp
    2315                2320                2325
Pro Val Ser Cys Asp Leu Pro Pro Val Pro His Cys Glu Arg Gly
    2330                2335                2340
Leu Gln Pro Thr Leu Thr Asn Pro Gly Glu Cys Arg Pro Asn Phe
    2345                2350                2355
Thr Cys Ala Cys Arg Lys Glu Glu Cys Lys Arg Val Ser Pro Pro
    2360                2365                2370
Ser Cys Pro Pro His Arg Leu Pro Thr Leu Arg Lys Thr Gln Cys
    2375                2380                2385
Cys Asp Glu Tyr Glu Cys Ala Cys Asn Cys Val Asn Ser Thr Val
    2390                2395                2400
Ser Cys Pro Leu Gly Tyr Leu Ala Ser Thr Ala Thr Asn Asp Cys
    2405                2410                2415
Gly Cys Thr Thr Thr Thr Cys Leu Pro Asp Lys Val Cys Val His
    2420                2425                2430
Arg Ser Thr Ile Tyr Pro Val Gly Gln Phe Trp Glu Glu Gly Cys
    2435                2440                2445
Asp Val Cys Thr Cys Thr Asp Met Glu Asp Ala Val Met Gly Leu
    2450                2455                2460
Arg Val Ala Gln Cys Ser Gln Lys Pro Cys Glu Asp Ser Cys Arg
    2465                2470                2475
Ser Gly Phe Thr Tyr Val Leu His Glu Gly Glu Cys Cys Gly Arg
    2480                2485                2490
Cys Leu Pro Ser Ala Cys Glu Val Val Thr Gly Ser Pro Arg Gly
    2495                2500                2505
Asp Ser Gln Ser Ser Trp Lys Ser Val Gly Ser Gln Trp Ala Ser
    2510                2515                2520
Pro Glu Asn Pro Cys Leu Ile Asn Glu Cys Val Arg Val Lys Glu
    2525                2530                2535
Glu Val Phe Ile Gln Gln Arg Asn Val Ser Cys Pro Gln Leu Glu
    2540                2545                2550
Val Pro Val Cys Pro Ser Gly Phe Gln Leu Ser Cys Lys Thr Ser
    2555                2560                2565
Ala Cys Cys Pro Ser Cys Arg Cys Glu Arg Met Glu Ala Cys Met
    2570                2575                2580
Leu Asn Gly Thr Val Ile Gly Pro Gly Lys Thr Val Met Ile Asp
    2585                2590                2595
```

```
Val Cys Thr Thr Cys Arg Cys Met Val Gln Val Gly Val Ile Ser
    2600                2605                2610

Gly Phe Lys Leu Glu Cys Arg Lys Thr Thr Cys Asn Pro Cys Pro
    2615                2620                2625

Leu Gly Tyr Lys Glu Glu Asn Asn Thr Gly Glu Cys Cys Gly Arg
    2630                2635                2640

Cys Leu Pro Thr Ala Cys Thr Ile Gln Leu Arg Gly Gly Gln Ile
    2645                2650                2655

Met Thr Leu Lys Arg Asp Glu Thr Leu Gln Asp Gly Cys Asp Thr
    2660                2665                2670

His Phe Cys Lys Val Asn Glu Arg Gly Glu Tyr Phe Trp Glu Lys
    2675                2680                2685

Arg Val Thr Gly Cys Pro Pro Phe Asp Glu His Lys Cys Leu Ala
    2690                2695                2700

Glu Gly Gly Lys Ile Met Lys Ile Pro Gly Thr Cys Cys Asp Thr
    2705                2710                2715

Cys Glu Glu Pro Glu Cys Asn Asp Ile Thr Ala Arg Leu Gln Tyr
    2720                2725                2730

Val Lys Val Gly Ser Cys Lys Ser Glu Val Glu Val Asp Ile His
    2735                2740                2745

Tyr Cys Gln Gly Lys Cys Ala Ser Lys Ala Met Tyr Ser Ile Asp
    2750                2755                2760

Ile Asn Asp Val Gln Asp Gln Cys Ser Cys Cys Ser Pro Thr Arg
    2765                2770                2775

Thr Glu Pro Met Gln Val Ala Leu His Cys Thr Asn Gly Ser Val
    2780                2785                2790

Val Tyr His Glu Val Leu Asn Ala Met Glu Cys Lys Cys Ser Pro
    2795                2800                2805

Arg Lys Cys Ser Lys
    2810

<210> SEQ ID NO 3
<211> LENGTH: 11
<212> TYPE: PRT
<213> ORGANISM: Artificial Sequence
<220> FEATURE:
<223> OTHER INFORMATION: polypeptide

<400> SEQUENCE: 3

Pro Lys Asn Ser Ser Met Ile Ser Asn Thr Pro
1               5                   10

<210> SEQ ID NO 4
<211> LENGTH: 7
<212> TYPE: PRT
<213> ORGANISM: Artificial
<220> FEATURE:
<223> OTHER INFORMATION: polypeptide

<400> SEQUENCE: 4

His Gln Ser Leu Gly Thr Gln
1               5

<210> SEQ ID NO 5
<211> LENGTH: 8
<212> TYPE: PRT
<213> ORGANISM: Artificial
<220> FEATURE:
<223> OTHER INFORMATION: polypeptide
```

<400> SEQUENCE: 5

His Gln Asn Leu Ser Asp Gly Lys
1               5

<210> SEQ ID NO 6
<211> LENGTH: 8
<212> TYPE: PRT
<213> ORGANISM: Artificial
<220> FEATURE:
<223> OTHER INFORMATION: polypeptide

<400> SEQUENCE: 6

His Gln Asn Ile Ser Asp Gly Lys
1               5

<210> SEQ ID NO 7
<211> LENGTH: 8
<212> TYPE: PRT
<213> ORGANISM: Artificial
<220> FEATURE:
<223> OTHER INFORMATION: polypeptide

<400> SEQUENCE: 7

Val Ile Ser Ser His Leu Gly Gln
1               5

<210> SEQ ID NO 8
<211> LENGTH: 20
<212> TYPE: PRT
<213> ORGANISM: Artificial
<220> FEATURE:
<223> OTHER INFORMATION: PAS sequence

<400> SEQUENCE: 8

Ala Ser Pro Ala Ala Pro Ala Pro Ala Ser Pro Ala Ala Pro Ala Pro
1               5                   10                  15

Ser Ala Pro Ala
            20

<210> SEQ ID NO 9
<211> LENGTH: 20
<212> TYPE: PRT
<213> ORGANISM: Artificial
<220> FEATURE:
<223> OTHER INFORMATION: PAS sequence

<400> SEQUENCE: 9

Ala Ala Pro Ala Ser Pro Ala Pro Ala Ala Pro Ser Ala Pro Ala Pro
1               5                   10                  15

Ala Ala Pro Ser
            20

<210> SEQ ID NO 10
<211> LENGTH: 20
<212> TYPE: PRT
<213> ORGANISM: Artificial
<220> FEATURE:
<223> OTHER INFORMATION: PAS sequence

<400> SEQUENCE: 10

Ala Pro Ser Ser Pro Ser Pro Ser Ala Pro Ser Ser Pro Ser Pro Ala
1               5                   10                  15

Ser Pro Ser Ser
            20

```
<210> SEQ ID NO 11
<211> LENGTH: 19
<212> TYPE: PRT
<213> ORGANISM: Artificial
<220> FEATURE:
<223> OTHER INFORMATION: PAS sequence

<400> SEQUENCE: 11

Ala Pro Ser Ser Pro Ser Pro Ser Ala Pro Ser Ser Pro Ser Pro Ala
1               5                   10                  15

Ser Pro Ser

<210> SEQ ID NO 12
<211> LENGTH: 20
<212> TYPE: PRT
<213> ORGANISM: Artificial
<220> FEATURE:
<223> OTHER INFORMATION: PAS sequence

<400> SEQUENCE: 12

Ser Ser Pro Ser Ala Pro Ser Pro Ser Ser Pro Ala Ser Pro Ser Pro
1               5                   10                  15

Ser Ser Pro Ala
            20

<210> SEQ ID NO 13
<211> LENGTH: 24
<212> TYPE: PRT
<213> ORGANISM: Artificial
<220> FEATURE:
<223> OTHER INFORMATION: PAS sequence

<400> SEQUENCE: 13

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 14
<211> LENGTH: 20
<212> TYPE: PRT
<213> ORGANISM: Artificial
<220> FEATURE:
<223> OTHER INFORMATION: PAS sequence

<400> SEQUENCE: 14

Ala Ser Ala Ala Ala Pro Ala Ala Ala Ser Ala Ala Ala Ser Ala Pro
1               5                   10                  15

Ser Ala Ala Ala
            20

<210> SEQ ID NO 15
<211> LENGTH: 19
<212> TYPE: PRT
<213> ORGANISM: Artificial
<220> FEATURE:
<223> OTHER INFORMATION: FVIII signal peptide

<400> SEQUENCE: 15

Met Gln Ile Glu Leu Ser Thr Cys Phe Phe Leu Cys Leu Leu Arg Phe
1               5                   10                  15

Cys Phe Ser
```

<210> SEQ ID NO 16
<211> LENGTH: 2332
<212> TYPE: PRT
<213> ORGANISM: Homo sapiens

<400> SEQUENCE: 16

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asn Ser Pro Ser Phe
        355                 360                 365

Ile Gln Ile Arg Ser Val Ala Lys Lys His Pro Lys Thr Trp Val His
    370                 375                 380
```

```
Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
            405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
            485                 490                 495

His Leu Lys Asp Phe Pro Ile Leu Pro Gly Glu Ile Phe Lys Tyr Lys
        500                 505                 510

Trp Thr Val Thr Val Glu Asp Gly Pro Thr Lys Ser Asp Pro Arg Cys
    515                 520                 525

Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
            565                 570                 575

Ser Val Phe Asp Glu Asn Arg Ser Trp Tyr Leu Thr Glu Asn Ile Gln
        580                 585                 590

Arg Phe Leu Pro Asn Pro Ala Gly Val Gln Leu Glu Asp Pro Glu Phe
    595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
            645                 650                 655

Thr Phe Lys His Lys Met Val Tyr Glu Asp Thr Leu Thr Leu Phe Pro
        660                 665                 670

Phe Ser Gly Glu Thr Val Phe Met Ser Met Glu Asn Pro Gly Leu Trp
    675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
            725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
    770                 775                 780

Val Ser Ser Ser Asp Leu Leu Met Leu Leu Arg Gln Ser Pro Thr Pro
785                 790                 795                 800
```

-continued

His Gly Leu Ser Leu Ser Asp Leu Gln Glu Ala Lys Tyr Glu Thr Phe
            805                 810                 815

Ser Asp Asp Pro Ser Pro Gly Ala Ile Asp Ser Asn Asn Ser Leu Ser
        820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
    850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
            885                 890                 895

Gly Thr Asp Asn Thr Ser Ser Leu Gly Pro Pro Ser Met Pro Val His
        900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
            965                 970                 975

Arg Ala His Gly Pro Ala Leu Leu Thr Lys Asp Asn Ala Leu Phe Lys
        980                 985                 990

Val Ser Ile Ser Leu Leu Lys Thr Asn Lys Thr Ser Asn Asn Ser Ala
        995                 1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Gln Lys Lys Glu Gly
    1070                1075                1080

Pro Ile Pro Pro Asp Ala Gln Asn Pro Asp Met Ser Phe Phe Lys
    1085                1090                1095

Met Leu Phe Leu Pro Glu Ser Ala Arg Trp Ile Gln Arg Thr His
    1100                1105                1110

Gly Lys Asn Ser Leu Asn Ser Gly Gln Gly Pro Ser Pro Lys Gln
    1115                1120                1125

Leu Val Ser Leu Gly Pro Glu Lys Ser Val Glu Gly Gln Asn Phe
    1130                1135                1140

Leu Ser Glu Lys Asn Lys Val Val Val Gly Lys Gly Glu Phe Thr
    1145                1150                1155

Lys Asp Val Gly Leu Lys Glu Met Val Phe Pro Ser Ser Arg Asn
    1160                1165                1170

Leu Phe Leu Thr Asn Leu Asp Asn Leu His Glu Asn Asn Thr His
    1175                1180                1185

Asn Gln Glu Lys Lys Ile Gln Glu Glu Ile Glu Lys Lys Glu Thr
    1190                1195                1200

Leu Ile Gln Glu Asn Val Val Leu Pro Gln Ile His Thr Val Thr

```
            1205                1210                1215
Gly Thr Lys Asn Phe Met Lys Asn Leu Phe Leu Leu Ser Thr Arg
            1220                1225                1230
Gln Asn Val Glu Gly Ser Tyr Asp Gly Ala Tyr Ala Pro Val Leu
            1235                1240                1245
Gln Asp Phe Arg Ser Leu Asn Asp Ser Thr Asn Arg Thr Lys Lys
            1250                1255                1260
His Thr Ala His Phe Ser Lys Lys Gly Glu Glu Asn Leu Glu
            1265                1270                1275
Gly Leu Gly Asn Gln Thr Lys Gln Ile Val Glu Lys Tyr Ala Cys
            1280                1285                1290
Thr Thr Arg Ile Ser Pro Asn Thr Ser Gln Gln Asn Phe Val Thr
            1295                1300                1305
Gln Arg Ser Lys Arg Ala Leu Lys Gln Phe Arg Leu Pro Leu Glu
            1310                1315                1320
Glu Thr Glu Leu Glu Lys Arg Ile Ile Val Asp Asp Thr Ser Thr
            1325                1330                1335
Gln Trp Ser Lys Asn Met Lys His Leu Thr Pro Ser Thr Leu Thr
            1340                1345                1350
Gln Ile Asp Tyr Asn Glu Lys Glu Lys Gly Ala Ile Thr Gln Ser
            1355                1360                1365
Pro Leu Ser Asp Cys Leu Thr Arg Ser His Ser Ile Pro Gln Ala
            1370                1375                1380
Asn Arg Ser Pro Leu Pro Ile Ala Lys Val Ser Ser Phe Pro Ser
            1385                1390                1395
Ile Arg Pro Ile Tyr Leu Thr Arg Val Leu Phe Gln Asp Asn Ser
            1400                1405                1410
Ser His Leu Pro Ala Ala Ser Tyr Arg Lys Lys Asp Ser Gly Val
            1415                1420                1425
Gln Glu Ser Ser His Phe Leu Gln Gly Ala Lys Lys Asn Asn Leu
            1430                1435                1440
Ser Leu Ala Ile Leu Thr Leu Glu Met Thr Gly Asp Gln Arg Glu
            1445                1450                1455
Val Gly Ser Leu Gly Thr Ser Ala Thr Asn Ser Val Thr Tyr Lys
            1460                1465                1470
Lys Val Glu Asn Thr Val Leu Pro Lys Pro Asp Leu Pro Lys Thr
            1475                1480                1485
Ser Gly Lys Val Glu Leu Leu Pro Lys Val His Ile Tyr Gln Lys
            1490                1495                1500
Asp Leu Phe Pro Thr Glu Thr Ser Asn Gly Ser Pro Gly His Leu
            1505                1510                1515
Asp Leu Val Glu Gly Ser Leu Leu Gln Gly Thr Glu Gly Ala Ile
            1520                1525                1530
Lys Trp Asn Glu Ala Asn Arg Pro Gly Lys Val Pro Phe Leu Arg
            1535                1540                1545
Val Ala Thr Glu Ser Ser Ala Lys Thr Pro Ser Lys Leu Leu Asp
            1550                1555                1560
Pro Leu Ala Trp Asp Asn His Tyr Gly Thr Gln Ile Pro Lys Glu
            1565                1570                1575
Glu Trp Lys Ser Gln Glu Lys Ser Pro Glu Lys Thr Ala Phe Lys
            1580                1585                1590
Lys Lys Asp Thr Ile Leu Ser Leu Asn Ala Cys Glu Ser Asn His
            1595                1600                1605
```

```
Ala Ile Ala Ala Ile Asn Glu Gly Gln Asn Lys Pro Glu Ile Glu
    1610            1615                1620

Val Thr Trp Ala Lys Gln Gly Arg Thr Glu Arg Leu Cys Ser Gln
    1625            1630                1635

Asn Pro Pro Val Leu Lys Arg His Gln Arg Glu Ile Thr Arg Thr
    1640            1645                1650

Thr Leu Gln Ser Asp Gln Glu Glu Ile Asp Tyr Asp Asp Thr Ile
    1655            1660                1665

Ser Val Glu Met Lys Lys Glu Asp Phe Asp Ile Tyr Asp Glu Asp
    1670            1675                1680

Glu Asn Gln Ser Pro Arg Ser Phe Gln Lys Lys Thr Arg His Tyr
    1685            1690                1695

Phe Ile Ala Ala Val Glu Arg Leu Trp Asp Tyr Gly Met Ser Ser
    1700            1705                1710

Ser Pro His Val Leu Arg Asn Arg Ala Gln Ser Gly Ser Val Pro
    1715            1720                1725

Gln Phe Lys Lys Val Val Phe Gln Glu Phe Thr Asp Gly Ser Phe
    1730            1735                1740

Thr Gln Pro Leu Tyr Arg Gly Glu Leu Asn Glu His Leu Gly Leu
    1745            1750                1755

Leu Gly Pro Tyr Ile Arg Ala Glu Val Glu Asp Asn Ile Met Val
    1760            1765                1770

Thr Phe Arg Asn Gln Ala Ser Arg Pro Tyr Ser Phe Tyr Ser Ser
    1775            1780                1785

Leu Ile Ser Tyr Glu Glu Asp Gln Arg Gln Gly Ala Glu Pro Arg
    1790            1795                1800

Lys Asn Phe Val Lys Pro Asn Glu Thr Lys Thr Tyr Phe Trp Lys
    1805            1810                1815

Val Gln His His Met Ala Pro Thr Lys Asp Glu Phe Asp Cys Lys
    1820            1825                1830

Ala Trp Ala Tyr Phe Ser Asp Val Asp Leu Glu Lys Asp Val His
    1835            1840                1845

Ser Gly Leu Ile Gly Pro Leu Leu Val Cys His Thr Asn Thr Leu
    1850            1855                1860

Asn Pro Ala His Gly Arg Gln Val Thr Val Gln Glu Phe Ala Leu
    1865            1870                1875

Phe Phe Thr Ile Phe Asp Glu Thr Lys Ser Trp Tyr Phe Thr Glu
    1880            1885                1890

Asn Met Glu Arg Asn Cys Arg Ala Pro Cys Asn Ile Gln Met Glu
    1895            1900                1905

Asp Pro Thr Phe Lys Glu Asn Tyr Arg Phe His Ala Ile Asn Gly
    1910            1915                1920

Tyr Ile Met Asp Thr Leu Pro Gly Leu Val Met Ala Gln Asp Gln
    1925            1930                1935

Arg Ile Arg Trp Tyr Leu Leu Ser Met Gly Ser Asn Glu Asn Ile
    1940            1945                1950

His Ser Ile His Phe Ser Gly His Val Phe Thr Val Arg Lys Lys
    1955            1960                1965

Glu Glu Tyr Lys Met Ala Leu Tyr Asn Leu Tyr Pro Gly Val Phe
    1970            1975                1980

Glu Thr Val Glu Met Leu Pro Ser Lys Ala Gly Ile Trp Arg Val
    1985            1990                1995
```

| | | | | | | | | | |
|---|---|---|---|---|---|---|---|---|---|
| Glu | Cys | Leu | Ile | Gly | Glu | His | Leu | His | Ala | Gly | Met | Ser | Thr | Leu |
| 2000 | | | | 2005 | | | | 2010 | |

Phe Leu Val Tyr Ser Asn Lys Cys Gln Thr Pro Leu Gly Met Ala
2015                    2020                    2025

Ser Gly His Ile Arg Asp Phe Gln Ile Thr Ala Ser Gly Gln Tyr
2030                    2035                    2040

Gly Gln Trp Ala Pro Lys Leu Ala Arg Leu His Tyr Ser Gly Ser
2045                    2050                    2055

Ile Asn Ala Trp Ser Thr Lys Glu Pro Phe Ser Trp Ile Lys Val
2060                    2065                    2070

Asp Leu Leu Ala Pro Met Ile Ile His Gly Ile Lys Thr Gln Gly
2075                    2080                    2085

Ala Arg Gln Lys Phe Ser Ser Leu Tyr Ile Ser Gln Phe Ile Ile
2090                    2095                    2100

Met Tyr Ser Leu Asp Gly Lys Lys Trp Gln Thr Tyr Arg Gly Asn
2105                    2110                    2115

Ser Thr Gly Thr Leu Met Val Phe Phe Gly Asn Val Asp Ser Ser
2120                    2125                    2130

Gly Ile Lys His Asn Ile Phe Asn Pro Pro Ile Ile Ala Arg Tyr
2135                    2140                    2145

Ile Arg Leu His Pro Thr His Tyr Ser Ile Arg Ser Thr Leu Arg
2150                    2155                    2160

Met Glu Leu Met Gly Cys Asp Leu Asn Ser Cys Ser Met Pro Leu
2165                    2170                    2175

Gly Met Glu Ser Lys Ala Ile Ser Asp Ala Gln Ile Thr Ala Ser
2180                    2185                    2190

Ser Tyr Phe Thr Asn Met Phe Ala Thr Trp Ser Pro Ser Lys Ala
2195                    2200                    2205

Arg Leu His Leu Gln Gly Arg Ser Asn Ala Trp Arg Pro Gln Val
2210                    2215                    2220

Asn Asn Pro Lys Glu Trp Leu Gln Val Asp Phe Gln Lys Thr Met
2225                    2230                    2235

Lys Val Thr Gly Val Thr Thr Gln Gly Val Lys Ser Leu Leu Thr
2240                    2245                    2250

Ser Met Tyr Val Lys Glu Phe Leu Ile Ser Ser Ser Gln Asp Gly
2255                    2260                    2265

His Gln Trp Thr Leu Phe Phe Gln Asn Gly Lys Val Lys Val Phe
2270                    2275                    2280

Gln Gly Asn Gln Asp Ser Phe Thr Pro Val Val Asn Ser Leu Asp
2285                    2290                    2295

Pro Pro Leu Leu Thr Arg Tyr Leu Arg Ile His Pro Gln Ser Trp
2300                    2305                    2310

Val His Gln Ile Ala Leu Arg Met Glu Val Leu Gly Cys Glu Ala
2315                    2320                    2325

Gln Asp Leu Tyr
2330

<210> SEQ ID NO 17
<211> LENGTH: 7053
<212> TYPE: DNA
<213> ORGANISM: Homo sapiens

<400> SEQUENCE: 17
atgcaaatag agctctccac ctgcttcttt ctgtgccttt tgcgattctg ctttagtgcc      60

-continued

```
accagaagat actacctggg tgcagtggaa ctgtcatggg actatatgca aagtgatctc      120
ggtgagctgc ctgtggacgc aagatttcct cctagagtgc caaaatcttt tccattcaac      180
acctcagtcg tgtacaaaaa gactctgttt gtagaattca cggatcacct tttcaacatc      240
gctaagccaa ggccaccctg gatgggtctg ctaggtccta ccatccaggc tgaggtttat      300
gatacagtgg tcattacact taagaacatg gcttcccatc ctgtcagtct tcatgctgtt      360
ggtgtatcct actggaaagc ttctgaggga gctgaatatg atgatcagac cagtcaaagg      420
gagaaagaag atgataaagt cttccctggt ggaagccata catatgtctg gcaggtcctg      480
aaagagaatg gtccaatggc ctctgaccca ctgtgcctta cctactcata tctttctcat      540
gtggacctgg taaaagactt gaattcaggc ctcattggag ccctactagt atgtagagaa      600
gggagtctgg ccaaggaaaa gacacagacc ttgcacaaat ttatactact ttttgctgta      660
tttgatgaag ggaaaagttg gcactcagaa acaaagaact ccttgatgca ggataggat       720 gctgcatctg ctcgggcctg gcctaaaatg cacacagtca atggttatgt aaacaggtct      780
ctgccaggtc tgattggatg ccacaggaaa tcagtctatt ggcatgtgat tggaatgggc      840
accactcctg aagtgcactc aatattcctc gaaggtcaca catttcttgt gaggaaccat      900
cgccaggcgt ccttggaaat ctcgccaata actttcctta ctgctcaaac actcttgatg      960
gaccttggac agtttctact gttttgtcat atctcttccc accaacatga tggcatggaa     1020
gcttatgtca aagtagacag ctgtccagag aaccccaac tacgaatgaa aaataatgaa       1080
gaagcggaag actatgatga tgatcttact gattctgaaa tggatgtggt caggtttgat     1140
gatgacaact ctccttcctt tatccaaatt cgctcagttg ccaagaagca tcctaaaact     1200
tgggtacatt acattgctgc tgaagaggag gactgggact atgctcccctt agtcctcgcc    1260 cccgatgaca gaagttataa aagtcaatat ttgaacaatg ccctcagcg gattggtagg      1320 aagtacaaaa aagtccgatt tatggcatac acagatgaaa cctttaagac tcgtgaagct     1380
attcagcatg aatcaggaat cttgggacct ttactttatg gggaagttgg agacacactg     1440
ttgattatat ttaagaatca agcaagcaga ccatataaca tctaccctca cggaatcact     1500
gatgtccgtc ctttgtattc aaggagatta ccaaaaggtg taaaacattt gaaggatttt     1560
ccaattctgc caggagaaat attcaaatat aaatggacag tgactgtaga agatgggcca     1620
actaaatcag atcctcggtg cctgacccgc tattactcta gtttcgttaa tatggagaga     1680
gatctagctt caggactcat tggccctctc ctcatctgct acaaagaatc tgtagatcaa     1740
agaggaaacc agataatgtc agacaagagg aatgtcatcc tgttttctgt atttgatgag     1800
aaccgaagct ggtacctcac agagaatata caacgctttc tccccaatcc agctggagtg     1860
cagcttgagg atccagagtt ccaagcctcc aacatcatgc acagcatcaa tggctatgtt     1920
tttgatagtt tgcagttgtc agtttgtttg catgaggtgg catactggta cattctaagc     1980
attggagcac agactgactt cctttctgtc ttcttctctg atatacctt caaacacaaa      2040 atggtctatg aagacacact caccctattc ccattctcag agaaactgt cttcatgtcg      2100 atggaaaacc caggtctatg gattctgggg tgccacaact cagactttcg gaacagaggc     2160
atgaccgcct tactgaaggt ttctagttgt gacaagaaca ctggtgatta ttacgaggac     2220
agttatgaag atatttcagc atacttgctg agtaaaaaca tgccattga accaagaagc     2280 ttctcccaga attcaagaca ccctagcact aggcaaaagc aatttaatgc caccacaatt     2340
ccagaaaatg acatagagaa gactgaccct tggtttgcac acagaacacc tatgcctaaa     2400
atacaaaatg tctcctctag tgatttgttg atgctcttgc gacagagtcc tactccacat    2460
```

```
gggctatcct tatctgatct ccaagaagcc aaatatgaga cttttctga tgatccatca    2520 cctggagcaa tagacagtaa taacagcctg tctgaaatga cacacttcag gccacagctc    2580
catcacagtg gggacatggt atttaccct gagtcaggcc tccaattaag attaaatgag     2640
aaactgggga caactgcagc aacagagttg aagaaacttg atttcaaagt ttctagtaca    2700
tcaaataatc tgatttcaac aattccatca gacaatttgg cagcaggtac tgataataca    2760
agttccttag accccaag tatgccagtt cattatgata gtcaattaga taccactcta      2820
tttggcaaaa agtcatctcc ccttactgag tctggtggac ctctgagctt gagtgaagaa    2880
aataatgatt caaagttgtt agaatcaggt ttaatgaata gccaagaaag ttcatgggga    2940
aaaaatgtat cgtcaacaga gagtggtagg ttatttaaag ggaaaagagc tcatggacct    3000
gctttgttga ctaaagataa tgccttattc aaagttagca tctctttgtt aaagacaaac    3060
aaaacttcca ataattcagc aactaataga aagactcaca ttgatggccc atcattatta    3120
attgagaata gtccatcagt ctggcaaaat atattagaaa gtgacactga gtttaaaaaa    3180 gtgacaccttt tgattcatga cagaatgctt atggacaaaa atgctacagc tttgaggcta   3240
aatcatatgt caaataaaac tacttcatca aaaaacatgg aaatggtcca acagaaaaaa    3300
gagggcccca ttccaccaga tgcacaaaat ccagatatgt cgttctttaa gatgctattc    3360
ttgccagaat cagcaaggtg gatacaaagg actcatggaa agaactctct gaactctggg    3420
caaggcccca gtccaaagca attagtatcc ttaggaccag aaaaatctgt ggaaggtcag    3480
aatttcttgt ctgagaaaaa caaagtggta gtaggaaagg gtgaatttac aaaggacgta    3540
ggactcaaag agatggtttt tccaagcagc agaaacctat ttcttactaa cttggataat    3600
ttacatgaaa ataatacaca caatcaagaa aaaaaattc aggaagaaat agaaagaag    3660 gaaacattaa tccaagagaa tgtagttttg cctcagatac atacagtgac tggcactaag    3720
aatttcatga agaaccttt cttactgagc actaggcaaa atgtagaagg ttcatatgac    3780
ggggcatatg ctccagtact tcaagatttt aggtcattaa atgattcaac aaatagaaca    3840
aagaaacaca cagctcattt ctcaaaaaaa ggggaggaag aaaacttgga aggcttggga    3900
aatcaaacca agcaaattgt agagaaatat gcatgcacca aaggatatc tcctaataca     3960 agccagcaga tttttgtcac gcaacgtagt aagagagctt tgaaacaatt cagactccca    4020
ctagaagaaa cagaacttga aaaaggata attgtggatg acacctcaac ccagtggtcc     4080
aaaaacatga acatttgac cccgagcacc ctcacacaga tagactacaa tgagaaggag    4140
aaaggggcca ttactcagtc tcccttatca gattgcctta cgaggagtca tagcatccct    4200
caagcaaata gatctccatt acccattgca aaggtatcat catttccatc tattagacct    4260
atatatctga ccagggtcct attccaagac aactcttctc atcttccagc agcatcttat    4320
agaaagaaag attctggggt ccaagaaagc agtcatttct tacaaggagc caaaaaaaat    4380
aacctttctt tagccattct aaccttggag atgactggtg atcaaagaga ggttggctcc    4440
ctggggacaa gtgccacaaa ttcagtcaca tacaagaaag ttgagaacac tgttctcccg    4500
aaaccagact tgcccaaaac atctggcaaa gttgaattgc ttccaaaagt tcacatttat    4560
cagaaggacc tattcctac ggaaactagc aatgggtctc ctggccatct ggatctcgtg     4620
gaagggagcc ttcttcaggg aacagaggga gcgattaagt ggaatgaagc aaacagacct    4680
ggaaaagttc cctttctgag agtagcaaca gaaagctctg caaagactcc ctccaagcta    4740
ttggatcctc ttgcttggga taaccactat ggtactcaga taccaaaaga agagtggaaa    4800
```

-continued

```
tcccaagaga agtcaccaga aaaaacagct tttaagaaaa aggataccat tttgtccctg    4860
aacgcttgtg aaagcaatca tgcaatagca gcaataaatg agggacaaaa taagcccgaa    4920
atagaagtca cctgggcaaa gcaaggtagg actgaaaggc tgtgctctca aacccacca     4980
gtcttgaaac gccatcaacg ggaataact cgtactactc ttcagtcaga tcaagaggaa     5040
attgactatg atgataccat atcagttgaa atgaagaagg aagattttga catttatgat    5100
gaggatgaaa atcagagccc ccgcagcttt caaaagaaaa cacgacacta ttttattgct    5160
gcagtggaga ggctctggga ttatgggatg agtagctccc cacatgttct aagaaacagg    5220
gctcagagtg gcagtgtccc tcagttcaag aaagttgttt tccaggaatt tactgatggc    5280
tcctttactc agcccttata ccgtggagaa ctaaatgaac atttgggact cctggggcca    5340
tatataagag cagaagttga agataatatc atggtaactt tcagaaatca ggcctctcgt    5400
ccctattcct tctattctag ccttatttct tatgaggaag atcagaggca aggagcagaa    5460
cctagaaaaa actttgtcaa gcctaatgaa accaaaactt acttttggaa agtgcaacat    5520
catatggcac ccactaaaga tgagtttgac tgcaaagcct gggcttattt ctctgatgtt    5580
gacctggaaa aagatgtgca ctcaggcctg attggacccc ttctggtctg ccacactaac    5640
acactgaacc ctgctcatgg gagacaagtg acagtacagg aatttgctct gtttttcacc    5700
atctttgatg agaccaaaag ctggtacttc actgaaaata tggaaagaaa ctgcagggct    5760
ccctgcaata tccagatgga agatcccact tttaaagaga attatcgctt ccatgcaatc    5820
aatggctaca ataatggatac actacctggc ttagtaatgg ctcaggatca aaggattcga    5880
tggtatctgc tcagcatggg cagcaatgaa acatccatt ctattcattt cagtggacat    5940
gtgttcactg tacgaaaaaa agaggagtat aaaatggcac tgtacaatct ctatccaggt    6000
gttttttgaga cagtggaaat gttaccatcc aaagctggaa tttggcgggt ggaatgcctt    6060
attggcgagc atctacatgc tgggatgagc acacttttttc tggtgtacag caataagtgt    6120
cagactcccc tggaatggc ttctggacac attagagatt ttcagattac agcttcagga    6180
caatatggac agtgggcccc aaagctggcc agacttcatt attccggatc aatcaatgcc    6240
tggagcacca aggagcccctt ttcttggatc aaggtggatc tgttggcacc aatgattatt    6300
cacggcatca agacccaggg tgcccgtcag aagttctcca gcctctacat ctctcagttt    6360
atcatcatgt atagtcttga tgggaagaag tggcagactt atcgaggaaa ttccactgga    6420
accttaatgg tcttctttgg caatgtggat tcatctggga taaaacacaa tattttttaac    6480
cctccaatta ttgctcgata catccgtttg cacccaactc attatagcat tcgcagcact    6540
cttcgcatgg agttgatggg ctgtgattta aatagttgca gcatgccatt gggaatggag    6600
agtaaagcaa tatcagatgc acagattact gcttcatcct actttaccaa tatgtttgcc    6660
acctggtctc cttcaaaagc tcgacttcac ctccaaggga ggagtaatgc ctggagacct    6720
caggtgaata atccaaaaga gtggctgcaa gtggacttcc agaagacaat gaaagtcaca    6780
ggagtaacta ctcagggagt aaaatctctg cttaccagca tgtatgtgaa ggagttcctc    6840
atctccagca gtcaagatgg ccatcagtgg actctctttt ttcagaatgg caaagtaaag    6900
gttttttcagg gaaatcaaga ctccttcaca cctgtggtga actctctaga cccaccgtta    6960
ctgactcgct accttcgaat tcaccccag agttgggtgc accagattgc cctgaggatg    7020
gaggttctgg gctgcgaggc acaggacctc tac                                 7053
```

<210> SEQ ID NO 18
<211> LENGTH: 1438

```
<212> TYPE: PRT
<213> ORGANISM: Artificial
<220> FEATURE:
<223> OTHER INFORMATION: BDD FVIII

<400> SEQUENCE: 18
```

| | | | | | | | | | | | | | | |
|---|---|---|---|---|---|---|---|---|---|---|---|---|---|---|
| Ala | Thr | Arg | Arg | Tyr | Tyr | Leu | Gly | Ala | Val | Glu | Leu | Ser | Trp | Asp | Tyr |
| 1 | | | | 5 | | | | | 10 | | | | | 15 |
| Met | Gln | Ser | Asp | Leu | Gly | Glu | Leu | Pro | Val | Asp | Ala | Arg | Phe | Pro | Pro |
| | | | 20 | | | | | 25 | | | | | 30 | | |
| Arg | Val | Pro | Lys | Ser | Phe | Pro | Phe | Asn | Thr | Ser | Val | Val | Tyr | Lys | Lys |
| | | 35 | | | | | 40 | | | | | 45 | | | |
| Thr | Leu | Phe | Val | Glu | Phe | Thr | Asp | His | Leu | Phe | Asn | Ile | Ala | Lys | Pro |
| 50 | | | | | 55 | | | | | 60 | | | | | |
| Arg | Pro | Pro | Trp | Met | Gly | Leu | Leu | Gly | Pro | Thr | Ile | Gln | Ala | Glu | Val |
| 65 | | | | 70 | | | | | 75 | | | | | 80 | |
| Tyr | Asp | Thr | Val | Val | Ile | Thr | Leu | Lys | Asn | Met | Ala | Ser | His | Pro | Val |
| | | | | 85 | | | | | 90 | | | | | 95 | |
| Ser | Leu | His | Ala | Val | Gly | Val | Ser | Tyr | Trp | Lys | Ala | Ser | Glu | Gly | Ala |
| | | | 100 | | | | | 105 | | | | | 110 | | |
| Glu | Tyr | Asp | Asp | Gln | Thr | Ser | Gln | Arg | Glu | Lys | Glu | Asp | Asp | Lys | Val |
| | | 115 | | | | | 120 | | | | | 125 | | | |
| Phe | Pro | Gly | Gly | Ser | His | Thr | Tyr | Val | Trp | Gln | Val | Leu | Lys | Glu | Asn |
| 130 | | | | | 135 | | | | | 140 | | | | | |
| Gly | Pro | Met | Ala | Ser | Asp | Pro | Leu | Cys | Leu | Thr | Tyr | Ser | Tyr | Leu | Ser |
| 145 | | | | | 150 | | | | | 155 | | | | | 160 |
| His | Val | Asp | Leu | Val | Lys | Asp | Leu | Asn | Ser | Gly | Leu | Ile | Gly | Ala | Leu |
| | | | | 165 | | | | | 170 | | | | | 175 | |
| Leu | Val | Cys | Arg | Glu | Gly | Ser | Leu | Ala | Lys | Glu | Lys | Thr | Gln | Thr | Leu |
| | | | 180 | | | | | 185 | | | | | 190 | | |
| His | Lys | Phe | Ile | Leu | Leu | Phe | Ala | Val | Phe | Asp | Glu | Gly | Lys | Ser | Trp |
| | | | 195 | | | | | 200 | | | | | 205 | | |
| His | Ser | Glu | Thr | Lys | Asn | Ser | Leu | Met | Gln | Asp | Arg | Asp | Ala | Ala | Ser |
| | | 210 | | | | | 215 | | | | | 220 | | | |
| Ala | Arg | Ala | Trp | Pro | Lys | Met | His | Thr | Val | Asn | Gly | Tyr | Val | Asn | Arg |
| 225 | | | | | 230 | | | | | 235 | | | | | 240 |
| Ser | Leu | Pro | Gly | Leu | Ile | Gly | Cys | His | Arg | Lys | Ser | Val | Tyr | Trp | His |
| | | | | 245 | | | | | 250 | | | | | 255 | |
| Val | Ile | Gly | Met | Gly | Thr | Thr | Pro | Glu | Val | His | Ser | Ile | Phe | Leu | Glu |
| | | | 260 | | | | | 265 | | | | | 270 | | |
| Gly | His | Thr | Phe | Leu | Val | Arg | Asn | His | Arg | Gln | Ala | Ser | Leu | Glu | Ile |
| | | 275 | | | | | 280 | | | | | 285 | | | |
| Ser | Pro | Ile | Thr | Phe | Leu | Thr | Ala | Gln | Thr | Leu | Leu | Met | Asp | Leu | Gly |
| 290 | | | | | 295 | | | | | 300 | | | | | |
| Gln | Phe | Leu | Leu | Phe | Cys | His | Ile | Ser | Ser | His | Gln | His | Asp | Gly | Met |
| 305 | | | | | 310 | | | | | 315 | | | | | 320 |
| Glu | Ala | Tyr | Val | Lys | Val | Asp | Ser | Cys | Pro | Glu | Glu | Pro | Gln | Leu | Arg |
| | | | | 325 | | | | | 330 | | | | | 335 | |
| Met | Lys | Asn | Asn | Glu | Glu | Ala | Glu | Asp | Tyr | Asp | Asp | Asp | Leu | Thr | Asp |
| | | | 340 | | | | | 345 | | | | | 350 | | |
| Ser | Glu | Met | Asp | Val | Val | Arg | Phe | Asp | Asp | Asp | Asn | Ser | Pro | Ser | Phe |
| | | 355 | | | | | 360 | | | | | 365 | | | |
| Ile | Gln | Ile | Arg | Ser | Val | Ala | Lys | Lys | His | Pro | Lys | Thr | Trp | Val | His |
| 370 | | | | | 375 | | | | | 380 | | | | | |

-continued

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
        405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
            485                 490                 495

His Leu Lys Asp Phe Pro Ile Leu Pro Gly Glu Ile Phe Lys Tyr Lys
        500                 505                 510

Trp Thr Val Thr Val Glu Asp Gly Pro Thr Lys Ser Asp Pro Arg Cys
    515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
            565                 570                 575

Ser Val Phe Asp Glu Asn Arg Ser Trp Tyr Leu Thr Glu Asn Ile Gln
        580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
            645                 650                 655

Thr Phe Lys His Lys Met Val Tyr Glu Asp Thr Leu Thr Leu Phe Pro
        660                 665                 670

Phe Ser Gly Glu Thr Val Phe Met Ser Met Glu Asn Pro Gly Leu Trp
    675                 680                 685

Ile Leu Gly Cys His Asn Ser Asp Phe Arg Asn Arg Gly Met Thr Ala
690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
            725                 730                 735

Ile Glu Pro Arg Ser Phe Ser Gln Asn Pro Pro Val Leu Lys Arg His
        740                 745                 750

Gln Arg Glu Ile Thr Arg Thr Thr Leu Gln Ser Asp Gln Glu Glu Ile
        755                 760                 765

Asp Tyr Asp Asp Thr Ile Ser Val Glu Met Lys Lys Glu Asp Phe Asp
    770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly

```
                    805                 810                 815
Met Ser Ser Ser Pro His Val Leu Arg Asn Arg Ala Gln Ser Gly Ser
                820                 825                 830

Val Pro Gln Phe Lys Lys Val Val Phe Gln Glu Phe Thr Asp Gly Ser
                835                 840                 845

Phe Thr Gln Pro Leu Tyr Arg Gly Glu Leu Asn Glu His Leu Gly Leu
    850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
                900                 905                 910

Val Lys Pro Asn Glu Thr Lys Thr Tyr Phe Trp Lys Val Gln His His
                915                 920                 925

Met Ala Pro Thr Lys Asp Glu Phe Asp Cys Lys Ala Trp Ala Tyr Phe
            930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
                980                 985                 990

Lys Ser Trp Tyr Phe Thr Glu Asn Met Glu Arg Asn Cys Arg Ala Pro
                995                1000                1005

Cys Asn Ile Gln Met Glu Asp Pro Thr Phe Lys Glu Asn Tyr Arg
    1010                1015                1020

Phe His Ala Ile Asn Gly Tyr Ile Met Asp Thr Leu Pro Gly Leu
    1025                1030                1035

Val Met Ala Gln Asp Gln Arg Ile Arg Trp Tyr Leu Leu Ser Met
    1040                1045                1050

Gly Ser Asn Glu Asn Ile His Ser Ile His Phe Ser Gly His Val
    1055                1060                1065

Phe Thr Val Arg Lys Lys Glu Glu Tyr Lys Met Ala Leu Tyr Asn
    1070                1075                1080

Leu Tyr Pro Gly Val Phe Glu Thr Val Glu Met Leu Pro Ser Lys
    1085                1090                1095

Ala Gly Ile Trp Arg Val Glu Cys Leu Ile Gly Glu His Leu His
    1100                1105                1110

Ala Gly Met Ser Thr Leu Phe Leu Val Tyr Ser Asn Lys Cys Gln
    1115                1120                1125

Thr Pro Leu Gly Met Ala Ser Gly His Ile Arg Asp Phe Gln Ile
    1130                1135                1140

Thr Ala Ser Gly Gln Tyr Gly Gln Trp Ala Pro Lys Leu Ala Arg
    1145                1150                1155

Leu His Tyr Ser Gly Ser Ile Asn Ala Trp Ser Thr Lys Glu Pro
    1160                1165                1170

Phe Ser Trp Ile Lys Val Asp Leu Leu Ala Pro Met Ile Ile His
    1175                1180                1185

Gly Ile Lys Thr Gln Gly Ala Arg Gln Lys Phe Ser Ser Leu Tyr
    1190                1195                1200

Ile Ser Gln Phe Ile Ile Met Tyr Ser Leu Asp Gly Lys Lys Trp
    1205                1210                1215
```

```
Gln Thr Tyr Arg Gly Asn Ser Thr Gly Thr Leu Met Val Phe Phe
    1220            1225                1230
Gly Asn Val Asp Ser Ser Gly Ile Lys His Asn Ile Phe Asn Pro
1235                1240                1245
Pro Ile Ile Ala Arg Tyr Ile Arg Leu His Pro Thr His Tyr Ser
    1250                1255                1260
Ile Arg Ser Thr Leu Arg Met Glu Leu Met Gly Cys Asp Leu Asn
1265                1270                1275
Ser Cys Ser Met Pro Leu Gly Met Glu Ser Lys Ala Ile Ser Asp
    1280                1285                1290
Ala Gln Ile Thr Ala Ser Ser Tyr Phe Thr Asn Met Phe Ala Thr
1295                1300                1305
Trp Ser Pro Ser Lys Ala Arg Leu His Leu Gln Gly Arg Ser Asn
    1310                1315                1320
Ala Trp Arg Pro Gln Val Asn Asn Pro Lys Glu Trp Leu Gln Val
1325                1330                1335
Asp Phe Gln Lys Thr Met Lys Val Thr Gly Val Thr Thr Gln Gly
    1340                1345                1350
Val Lys Ser Leu Leu Thr Ser Met Tyr Val Lys Glu Phe Leu Ile
1355                1360                1365
Ser Ser Ser Gln Asp Gly His Gln Trp Thr Leu Phe Phe Gln Asn
    1370                1375                1380
Gly Lys Val Lys Val Phe Gln Gly Asn Gln Asp Ser Phe Thr Pro
1385                1390                1395
Val Val Asn Ser Leu Asp Pro Pro Leu Leu Thr Arg Tyr Leu Arg
    1400                1405                1410
Ile His Pro Gln Ser Trp Val His Gln Ile Ala Leu Arg Met Glu
1415                1420                1425
Val Leu Gly Cys Glu Ala Gln Asp Leu Tyr
    1430                1435

<210> SEQ ID NO 19
<211> LENGTH: 4371
<212> TYPE: DNA
<213> ORGANISM: Artificial
<220> FEATURE:
<223> OTHER INFORMATION: BDD FVIII

<400> SEQUENCE: 19
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc aaaatctttt ccattcaac     180 acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgg tcattacact taagaacatg gcttcccatc ctgtcagtct tcatgctgtt     360
ggtgtatcct actggaaagc ttctgaggga gctgaatatg atgatcagac cagtcaaagg     420
gagaaagaag atgataaagt cttccctggt ggaagccata catatgtctg gcaggtcctg     480
aaagagaatg gtccaatggc ctctgaccca ctgtgcctta cctactcata tctttctcat     540
gtggacctgg taaagacttg aattcaggc ctcattggag ccctactagt atgtagagaa     600
gggagtctgg ccaaggaaaa gacacagacc ttgcacaaat ttatactact ttttgctgta     660
tttgatgaag ggaaaagttg gcactcagaa acaaagaact ccttgatgca ggatagggat     720
```

```
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag aaccccaac tacgaatgaa aaataatgaa    1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt ccttttctgtc ttcttctctg gatataccct caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctctcaaa acccaccagt cttgaaacgc atcaacgggg aaataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctgggatt atgggatgag tagctcccca   2520
catgttctaa gaaacagggc tcagagtggc agtgtccctc agttcaagaa agttgttttc   2580
caggaattta ctgatggctc ctttactcag cccttatacc gtggagaact aaatgaacat   2640
ttgggactcc tggggccata taagagcag aagttgaag ataatatcat ggtaactttc    2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
ttttggaaag tgcaacatca tatggcaccc actaaagatg agtttgactg caaagcctgg   2880
gcttatttct ctgatgttga cctggaaaaa gatgtgcact caggcctgat tggaccccctt  2940 ctggtctgcc acactaacac actgaaccct gctcatggga gacaagtgac agtacaggaa   3000
tttgctctgt ttttcaccat ctttgatgag accaaaagct ggtacttcac tgaaaatatg   3060
```

| | | |
|---|---|---|
| gaaagaaact gcagggctcc ctgcaatatc cagatggaag atcccacttt taaagagaat | 3120 | |
| tatcgcttcc atgcaatcaa tggctacata atggatacac tacctggctt agtaatggct | 3180 | |
| caggatcaaa ggattcgatg gtatctgctc agcatgggca gcaatgaaaa catccattct | 3240 | |
| attcatttca gtggacatgt gttcactgta cgaaaaaaag aggagtataa aatggcactg | 3300 | |
| tacaatctct atccaggtgt ttttgagaca gtggaaatgt taccatccaa agctggaatt | 3360 | |
| tggcgggtgg aatgccttat tggcgagcat ctacatgctg ggatgagcac acttttctg | 3420 | |
| gtgtacagca ataagtgtca gactcccctg ggaatggctt ctggacacat tagagatttt | 3480 | |
| cagattacag cttcaggaca atatggacag tgggccccaa agctggccag acttcattat | 3540 | |
| tccggatcaa tcaatgcctg gagcaccaag gagccctttt cttggatcaa ggtggatctg | 3600 | |
| ttggcaccaa tgattattca cggcatcaag acccagggtg cccgtcagaa gttctccagc | 3660 | |
| ctctacatct ctcagtttat catcatgtat agtcttgatg gaagaagtg gcagacttat | 3720 | |
| cgaggaaatt ccactggaac cttaatggtc ttctttggca atgtggattc atctgggata | 3780 | |
| aaacacaata ttttaaccc tccaattatt gctcgataca tccgtttgca cccaactcat | 3840 | |
| tatagcattc gcagcactct tcgcatggag ttgatgggct gtgatttaaa tagttgcagc | 3900 | |
| atgccattgg gaatggagag taaagcaata tcagatgcac agattactgc ttcatcctac | 3960 | |
| tttaccaata tgtttgccac ctggtctcct tcaaaagctc gacttcacct ccaagggagg | 4020 | |
| agtaatgcct ggagacctca ggtgaataat ccaaaagagt ggctgcaagt ggacttccag | 4080 | |
| aagacaatga agtcacagg agtaactact cagggagtaa aatctctgct taccagcatg | 4140 | |
| tatgtgaagg agttcctcat ctccagcagt caagatggcc atcagtggac tctcttttt | 4200 | |
| cagaatggca agtaaaggt ttttcaggga aatcaagact ccttcacacc tgtggtgaac | 4260 | |
| tctctagacc caccgttact gactcgctac cttcgaattc accccagag ttgggtgcac | 4320 | |
| cagattgccc tgaggatgga ggttctgggc tgcgaggcac aggacctcta c | 4371 | |

<210> SEQ ID NO 20
<211> LENGTH: 500
<212> TYPE: PRT
<213> ORGANISM: Artificial
<220> FEATURE:
<223> OTHER INFORMATION: linker

<400> SEQUENCE: 20

```
Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
            20                  25                  30
Gly Gly Ser Gly Gly Gly Gly Ser Gly Gly Gly Gly Ser Gly Gly Gly
        35                  40                  45
Gly Ser Gly Gly Gly Gly Ser Gly Gly Gly Gly Ser Gly Gly Gly Gly
    50                  55                  60
Ser Gly Gly Gly Gly Ser Gly Gly Gly Gly Ser Gly Gly Gly Gly Ser
65                  70                  75                  80
Gly Gly Gly Gly Ser Gly Gly Gly Gly Ser Gly Gly Gly Gly Ser Gly
                85                  90                  95
Gly Gly Gly Ser Gly Gly Gly Gly Ser Gly Gly Gly Gly Ser Gly Gly
            100                 105                 110
Gly Gly Ser Gly Gly Gly Gly Ser Gly Gly Gly Gly Ser Gly Gly Gly
        115                 120                 125
Gly Ser Gly Gly Gly Gly Ser Gly Gly Gly Gly Ser Gly Gly Gly Gly
```

```
            130                 135                 140
Ser Gly Gly Gly Ser Gly Gly Gly Ser Gly Gly Gly Ser
145                 150                 155                 160

Gly Gly Gly Gly Ser Gly Gly Gly Ser Gly Gly Gly Ser Gly
                165                 170                 175

Gly Gly Gly Ser Gly Gly Gly Ser Gly Gly Gly Ser Gly Gly
            180                 185                 190

Gly Gly Ser Gly Gly Gly Ser Gly Gly Gly Ser Gly Gly Gly
        195                 200                 205

Gly Ser Gly Gly Gly Ser Gly Gly Gly Ser Gly Gly Gly Gly
    210                 215                 220

Ser Gly Gly Gly Gly Ser Gly Gly Gly Ser Gly Gly Gly Ser
225                 230                 235                 240

Gly Gly Gly Gly Ser Gly Gly Gly Ser Gly Gly Gly Ser Gly
                245                 250                 255

Gly Gly Gly Ser Gly Gly Gly Ser Gly Gly Gly Ser Gly Gly
            260                 265                 270

Gly Gly Ser Gly Gly Gly Ser Gly Gly Gly Ser Gly Gly Gly
        275                 280                 285

Gly Ser Gly Gly Gly Ser Gly Gly Gly Ser Gly Gly Gly Gly
    290                 295                 300

Ser Gly Gly Gly Ser Gly Gly Gly Ser Gly Gly Gly Ser
305                 310                 315                 320

Gly Gly Gly Gly Ser Gly Gly Gly Ser Gly Gly Gly Ser Gly
                325                 330                 335

Gly Gly Gly Ser Gly Gly Gly Ser Gly Gly Gly Ser Gly Gly
            340                 345                 350

Gly Gly Ser Gly Gly Gly Ser Gly Gly Gly Ser Gly Gly Gly
        355                 360                 365

Gly Ser Gly Gly Gly Ser Gly Gly Gly Ser Gly Gly Gly Gly
    370                 375                 380

Ser Gly Gly Gly Gly Ser Gly Gly Gly Ser Gly Gly Gly Ser
385                 390                 395                 400

Gly Gly Gly Gly Ser Gly Gly Gly Ser Gly Gly Gly Ser Gly
                405                 410                 415

Gly Gly Gly Ser Gly Gly Gly Ser Gly Gly Gly Ser Gly Gly
            420                 425                 430

Gly Gly Ser Gly Gly Gly Ser Gly Gly Gly Ser Gly Gly Gly
        435                 440                 445

Gly Ser Gly Gly Gly Ser Gly Gly Gly Ser Gly Gly Gly Gly
    450                 455                 460

Ser Gly Gly Gly Gly Ser Gly Gly Gly Ser Gly Gly Gly Ser
465                 470                 475                 480

Gly Gly Gly Gly Ser Gly Gly Gly Ser Gly Gly Gly Ser Gly
                485                 490                 495

Gly Gly Gly Ser
            500

<210> SEQ ID NO 21
<211> LENGTH: 800
<212> TYPE: PRT
<213> ORGANISM: Artificial
<220> FEATURE:
<223> OTHER INFORMATION: linker
<220> FEATURE:
```

```
<221> NAME/KEY: REPEAT
<222> LOCATION: (1)..(300)
<223> OTHER INFORMATION: Gly-Gly-Ser repeats 1 to 100 times
<220> FEATURE:
<221> NAME/KEY: REPEAT
<222> LOCATION: (301)..(800)
<223> OTHER INFORMATION: Gly-Gly-Gly-Gly-Ser repeats 1 to 100 times

<400> SEQUENCE: 21
```

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser Gly Gly Ser Gly Gly Ser
        35                  40                  45

Gly Gly Ser Gly Gly Ser Gly Gly Ser Gly Gly Ser Gly Gly Ser Gly
    50                  55                  60

Gly Ser Gly Gly Ser Gly Gly Ser Gly Gly Ser Gly Gly Ser Gly Gly
65                  70                  75                  80

Ser Gly Gly Ser Gly Gly Ser Gly Gly Ser Gly Gly Ser Gly Gly Ser
            85                  90                  95

Gly Gly Ser Gly Gly Ser Gly Gly Ser Gly Gly Ser Gly Gly Ser Gly
            100                 105                 110

Gly Ser Gly Gly Ser Gly Gly Ser Gly Gly Ser Gly Gly Ser Gly Gly
        115                 120                 125

Ser Gly Gly Ser Gly Gly Ser Gly Gly Ser Gly Gly Ser Gly Gly Ser
    130                 135                 140

Gly Gly Ser Gly Gly Ser Gly Gly Ser Gly Gly Ser Gly Gly Ser Gly
145                 150                 155                 160

Gly Ser Gly Gly Ser Gly Gly Ser Gly Gly Ser Gly Gly Ser Gly Gly
            165                 170                 175

Ser Gly Gly Ser Gly Gly Ser Gly Gly Ser Gly Gly Ser Gly Gly Ser
        180                 185                 190

Gly Gly Ser Gly Gly Ser Gly Gly Ser Gly Gly Ser Gly Gly Ser Gly
    195                 200                 205

Gly Ser Gly Gly Ser Gly Gly Ser Gly Gly Ser Gly Gly Ser Gly Gly
210                 215                 220

Ser Gly Gly Ser Gly Gly Ser Gly Gly Ser Gly Gly Ser Gly Gly Ser
225                 230                 235                 240

Gly Gly Ser Gly Gly Ser Gly Gly Ser Gly Gly Ser Gly Gly Ser Gly
            245                 250                 255

Gly Ser Gly Gly Ser Gly Gly Ser Gly Gly Ser Gly Gly Ser Gly Gly
        260                 265                 270

Ser Gly Gly Ser Gly Gly Ser Gly Gly Ser Gly Gly Ser Gly Gly Ser
    275                 280                 285

Gly Gly Ser Gly Gly Ser Gly Gly Ser Gly Gly Ser Gly Gly Gly Gly
290                 295                 300

Ser Gly Gly Gly Gly Ser Gly Gly Gly Gly Ser Gly Gly Gly Gly Ser
305                 310                 315                 320

Gly Gly Gly Gly Ser Gly Gly Gly Gly Ser Gly Gly Gly Gly Ser Gly
            325                 330                 335

Gly Gly Gly Ser Gly Gly Gly Gly Ser Gly Gly Gly Gly Ser Gly Gly
        340                 345                 350

Gly Gly Ser Gly Gly Gly Gly Ser Gly Gly Gly Gly Ser Gly Gly Gly
    355                 360                 365

-continued

Gly Ser Gly Gly Gly Gly Ser Gly Gly Gly Gly Ser Gly Gly Gly Gly
    370                 375                 380

Ser Gly Gly Gly Ser Gly Gly Gly Ser Gly Gly Gly Ser
385                 390                 395                 400

Gly Gly Gly Gly Ser Gly Gly Gly Gly Ser Gly Gly Gly Gly Ser Gly
                405                 410                 415

Gly Gly Gly Ser Gly Gly Gly Gly Ser Gly Gly Gly Gly Ser Gly Gly
            420                 425                 430

Gly Gly Ser Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Gly Gly Gly Gly Ser Gly Gly Gly Gly Ser Gly Gly Gly Gly Ser
465                 470                 475                 480

Gly Gly Gly Gly Ser Gly Gly Gly Gly Ser Gly Gly Gly Gly Ser Gly
                485                 490                 495

Gly Gly Gly Ser Gly Gly Gly Gly Ser Gly Gly Gly Gly Ser Gly Gly
            500                 505                 510

Gly Gly Ser Gly Gly Gly Gly Ser Gly Gly Gly Gly Ser Gly Gly Gly
        515                 520                 525

Gly Ser Gly Gly Gly Gly Ser Gly Gly Gly Gly Ser Gly Gly Gly Gly
    530                 535                 540

Ser Gly Gly Gly Gly Ser Gly Gly Gly Gly Ser Gly Gly Gly Gly Ser
545                 550                 555                 560

Gly Gly Gly Gly Ser Gly Gly Gly Gly Ser Gly Gly Gly Gly Ser Gly
                565                 570                 575

Gly Gly Gly Ser Gly Gly Gly Gly Ser Gly Gly Gly Gly Ser Gly Gly
            580                 585                 590

Gly Gly Ser Gly Gly Gly Gly Ser Gly Gly Gly Gly Ser Gly Gly Gly
        595                 600                 605

Gly Ser Gly Gly Gly Ser Gly Gly Gly Gly Ser Gly Gly Gly Gly
    610                 615                 620

Ser Gly Gly Gly Gly Ser Gly Gly Gly Gly Ser Gly Gly Gly Gly Ser
625                 630                 635                 640

Gly Gly Gly Gly Ser Gly Gly Gly Gly Ser Gly Gly Gly Gly Ser Gly
                645                 650                 655

Gly Gly Gly Ser Gly Gly Gly Gly Ser Gly Gly Gly Gly Ser Gly Gly
            660                 665                 670

Gly Gly Ser Gly Gly Gly Gly Ser Gly Gly Gly Gly Ser Gly Gly Gly
        675                 680                 685

Gly Ser Gly Gly Gly Gly Ser Gly Gly Gly Gly Ser Gly Gly Gly Gly
    690                 695                 700

Ser Gly Gly Gly Gly Ser Gly Gly Gly Gly Ser Gly Gly Gly Gly Ser
705                 710                 715                 720

Gly Gly Gly Gly Ser Gly Gly Gly Gly Ser Gly Gly Gly Gly Ser Gly
                725                 730                 735

Gly Gly Gly Ser Gly Gly Gly Gly Ser Gly Gly Gly Gly Ser Gly Gly
            740                 745                 750

Gly Gly Ser Gly Gly Gly Gly Ser Gly Gly Gly Gly Ser Gly Gly Gly
        755                 760                 765

Gly Ser Gly Gly Gly Gly Ser Gly Gly Gly Ser Gly Gly Gly Gly
    770                 775                 780

Ser Gly Gly Gly Gly Ser Gly Gly Gly Gly Ser Gly Gly Gly Gly Ser

```
<210> SEQ ID NO 22
<211> LENGTH: 7
<212> TYPE: PRT
<213> ORGANISM: Artificial
<220> FEATURE:
<223> OTHER INFORMATION: linker

<400> SEQUENCE: 22

Ser Gly Gly Ser Gly Gly Ser
1               5

<210> SEQ ID NO 23
<211> LENGTH: 15
<212> TYPE: PRT
<213> ORGANISM: Artificial
<220> FEATURE:
<223> OTHER INFORMATION: linker

<400> SEQUENCE: 23

Gly Gly Ser Gly Gly Ser Gly Gly Ser Gly Gly Ser Gly Gly Gly
1               5                   10                  15

<210> SEQ ID NO 24
<211> LENGTH: 16
<212> TYPE: PRT
<213> ORGANISM: Artificial
<220> FEATURE:
<223> OTHER INFORMATION: linker

<400> SEQUENCE: 24

Gly Gly Ser Gly Gly Ser Gly Gly Gly Ser Gly Gly Gly Gly Ser
1               5                   10                  15

<210> SEQ ID NO 25
<211> LENGTH: 18
<212> TYPE: PRT
<213> ORGANISM: Artificial
<220> FEATURE:
<223> OTHER INFORMATION: linker

<400> SEQUENCE: 25

Gly Gly Ser Gly Gly Ser Gly Gly Ser Gly Gly Ser Gly Gly Ser Gly
1               5                   10                  15

Gly Ser

<210> SEQ ID NO 26
<211> LENGTH: 15
<212> TYPE: PRT
<213> ORGANISM: Artificial
<220> FEATURE:
<223> OTHER INFORMATION: linker
<220> FEATURE:
<221> NAME/KEY: REPEAT
<222> LOCATION: (1)..(15)
<223> OTHER INFORMATION: Gly-Gly-Gly-Gly-Ser repeats 1 to 3 times

<400> SEQUENCE: 26

Gly Gly Gly Gly Ser Gly Gly Gly Gly Ser Gly Gly Gly Gly Ser
1               5                   10                  15

<210> SEQ ID NO 27
<211> LENGTH: 100
<212> TYPE: PRT
<213> ORGANISM: Artificial
<220> FEATURE:
```

(Note: SEQ ID NO 24 sequence as shown: Gly Gly Ser Gly Gly Ser Gly Gly Gly Ser Gly Gly Gly Gly Ser — but the image shows "Gly Gly Ser Gly Gly Ser Gly Gly Gly Gly Ser Gly Gly Gly Gly Ser" - reproducing exactly)

```
<223> OTHER INFORMATION: linker
<220> FEATURE:
<221> NAME/KEY: REPEAT
<222> LOCATION: (1)..(100)
<223> OTHER INFORMATION: Gly-Gly-Gly-Gly-Ser repeats 1 to 20 times

<400> SEQUENCE: 27

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser
            100

<210> SEQ ID NO 28
<211> LENGTH: 15
<212> TYPE: PRT
<213> ORGANISM: Artificial
<220> FEATURE:
<223> OTHER INFORMATION: linker
<220> FEATURE:
<221> NAME/KEY: REPEAT
<222> LOCATION: (1)..(15)
<223> OTHER INFORMATION: Gly-Gly-Gly-Gly-Ser is repeated 1 to 3 times

<400> SEQUENCE: 28

Gly Gly Gly Gly Ser Gly Gly Gly Gly Ser Gly Gly Gly Gly Ser
1               5                   10                  15

<210> SEQ ID NO 29
<211> LENGTH: 7
<212> TYPE: PRT
<213> ORGANISM: Artificial
<220> FEATURE:
<223> OTHER INFORMATION: cleavable linker
<220> FEATURE:
<221> NAME/KEY: MISC_FEATURE
<222> LOCATION: (4)..(5)
<223> OTHER INFORMATION: FXIa cleavage site

<400> SEQUENCE: 29

Lys Leu Thr Arg Ala Glu Thr
1               5

<210> SEQ ID NO 30
<211> LENGTH: 7
<212> TYPE: PRT
<213> ORGANISM: Artificial
<220> FEATURE:
<223> OTHER INFORMATION: cleavable linker
<220> FEATURE:
<221> NAME/KEY: MISC_FEATURE
<222> LOCATION: (4)..(5)
<223> OTHER INFORMATION: FXIa cleavage site

<400> SEQUENCE: 30

Asp Phe Thr Arg Val Val Gly
1               5
```

```
<210> SEQ ID NO 31
<211> LENGTH: 8
<212> TYPE: PRT
<213> ORGANISM: Artificial
<220> FEATURE:
<223> OTHER INFORMATION: cleavable linker
<220> FEATURE:
<221> NAME/KEY: MISC_FEATURE
<222> LOCATION: (4)..(5)
<223> OTHER INFORMATION: FXIIa cleavage site

<400> SEQUENCE: 31

Thr Met Thr Arg Ile Val Gly Gly
1               5

<210> SEQ ID NO 32
<211> LENGTH: 8
<212> TYPE: PRT
<213> ORGANISM: Artificial
<220> FEATURE:
<223> OTHER INFORMATION: cleavable linker
<220> FEATURE:
<221> NAME/KEY: MISC_FEATURE
<222> LOCATION: (4)..(5)
<223> OTHER INFORMATION: Kallikrein cleavage site

<400> SEQUENCE: 32

Ser Pro Phe Arg Ser Thr Gly Gly
1               5

<210> SEQ ID NO 33
<211> LENGTH: 8
<212> TYPE: PRT
<213> ORGANISM: Artificial
<220> FEATURE:
<223> OTHER INFORMATION: cleavable linker
<220> FEATURE:
<221> NAME/KEY: misc_feature
<222> LOCATION: (4)..(5)
<223> OTHER INFORMATION: FVIIa cleavage site

<400> SEQUENCE: 33

Leu Gln Val Arg Ile Val Gly Gly
1               5

<210> SEQ ID NO 34
<211> LENGTH: 8
<212> TYPE: PRT
<213> ORGANISM: Artificial
<220> FEATURE:
<223> OTHER INFORMATION: cleavable linker
<220> FEATURE:
<221> NAME/KEY: misc_feature
<222> LOCATION: (4)..(5)
<223> OTHER INFORMATION: FIXa cleavage site

<400> SEQUENCE: 34

Pro Leu Gly Arg Ile Val Gly Gly
1               5

<210> SEQ ID NO 35
<211> LENGTH: 8
<212> TYPE: PRT
<213> ORGANISM: Artificial
<220> FEATURE:
<223> OTHER INFORMATION: cleavable linker
<220> FEATURE:
<221> NAME/KEY: misc_feature
<222> LOCATION: (4)..(5)
```

```
<223> OTHER INFORMATION: FXa cleavage site

<400> SEQUENCE: 35

Ile Glu Gly Arg Thr Val Gly Gly
1               5

<210> SEQ ID NO 36
<211> LENGTH: 8
<212> TYPE: PRT
<213> ORGANISM: Artificial
<220> FEATURE:
<223> OTHER INFORMATION: cleavable linker
<220> FEATURE:
<221> NAME/KEY: misc_feature
<222> LOCATION: (4)..(5)
<223> OTHER INFORMATION: FIIa (thrombin) cleavage site

<400> SEQUENCE: 36

Leu Thr Pro Arg Ser Leu Leu Val
1               5

<210> SEQ ID NO 37
<211> LENGTH: 8
<212> TYPE: PRT
<213> ORGANISM: Artificial
<220> FEATURE:
<223> OTHER INFORMATION: cleavable linker
<220> FEATURE:
<221> NAME/KEY: misc_feature
<222> LOCATION: (4)..(5)
<223> OTHER INFORMATION: Elastase-2 cleavage site

<400> SEQUENCE: 37

Leu Gly Pro Val Ser Gly Val Pro
1               5

<210> SEQ ID NO 38
<211> LENGTH: 8
<212> TYPE: PRT
<213> ORGANISM: Artificial
<220> FEATURE:
<223> OTHER INFORMATION: cleavable linker
<220> FEATURE:
<221> NAME/KEY: misc_feature
<222> LOCATION: (4)..(5)
<223> OTHER INFORMATION: Granzyme-B cleavage site

<400> SEQUENCE: 38

Val Ala Gly Asp Ser Leu Glu Glu
1               5

<210> SEQ ID NO 39
<211> LENGTH: 8
<212> TYPE: PRT
<213> ORGANISM: Artificial
<220> FEATURE:
<223> OTHER INFORMATION: cleavable linker
<220> FEATURE:
<221> NAME/KEY: misc_feature
<222> LOCATION: (4)..(5)
<223> OTHER INFORMATION: MMP-12 cleavage site

<400> SEQUENCE: 39

Gly Pro Ala Gly Leu Gly Gly Ala
1               5

<210> SEQ ID NO 40
<211> LENGTH: 8
<212> TYPE: PRT
```

```
<213> ORGANISM: Artificial
<220> FEATURE:
<223> OTHER INFORMATION: cleavable linker
<220> FEATURE:
<221> NAME/KEY: misc_feature
<222> LOCATION: (4)..(5)
<223> OTHER INFORMATION: MMP-13 cleavage site

<400> SEQUENCE: 40

Gly Pro Ala Gly Leu Arg Gly Ala
1               5

<210> SEQ ID NO 41
<211> LENGTH: 8
<212> TYPE: PRT
<213> ORGANISM: Artificial
<220> FEATURE:
<223> OTHER INFORMATION: cleavable linker
<220> FEATURE:
<221> NAME/KEY: misc_feature
<222> LOCATION: (4)..(5)
<223> OTHER INFORMATION: MMP-17 cleavage site

<400> SEQUENCE: 41

Ala Pro Leu Gly Leu Arg Leu Arg
1               5

<210> SEQ ID NO 42
<211> LENGTH: 8
<212> TYPE: PRT
<213> ORGANISM: Artificial
<220> FEATURE:
<223> OTHER INFORMATION: cleavable linker
<220> FEATURE:
<221> NAME/KEY: misc_feature
<222> LOCATION: (4)..(5)
<223> OTHER INFORMATION: MMP-20 cleavage site

<400> SEQUENCE: 42

Pro Ala Leu Pro Leu Val Ala Gln
1               5

<210> SEQ ID NO 43
<211> LENGTH: 7
<212> TYPE: PRT
<213> ORGANISM: Artificial
<220> FEATURE:
<223> OTHER INFORMATION: cleavable linker
<220> FEATURE:
<221> NAME/KEY: misc_feature
<222> LOCATION: (6)..(7)
<223> OTHER INFORMATION: TEV cleavage site

<400> SEQUENCE: 43

Glu Asn Leu Tyr Phe Gln Gly
1               5

<210> SEQ ID NO 44
<211> LENGTH: 8
<212> TYPE: PRT
<213> ORGANISM: Artificial
<220> FEATURE:
<223> OTHER INFORMATION: cleavable linker
<220> FEATURE:
<221> NAME/KEY: misc_feature
<222> LOCATION: (4)..(5)
<223> OTHER INFORMATION: Enterokinase cleavage site

<400> SEQUENCE: 44

Asp Asp Asp Lys Ile Val Gly Gly
```

```
<210> SEQ ID NO 45
<211> LENGTH: 8
<212> TYPE: PRT
<213> ORGANISM: Artificial
<220> FEATURE:
<223> OTHER INFORMATION: cleavable linker
<220> FEATURE:
<221> NAME/KEY: misc_feature
<222> LOCATION: (6)..(7)
<223> OTHER INFORMATION: Protease C (PRESCISSION) cleavage site

<400> SEQUENCE: 45

Leu Glu Val Leu Phe Gln Gly Pro
1               5

<210> SEQ ID NO 46
<211> LENGTH: 8
<212> TYPE: PRT
<213> ORGANISM: Artificial
<220> FEATURE:
<223> OTHER INFORMATION: cleavable linker
<220> FEATURE:
<221> NAME/KEY: misc_feature
<222> LOCATION: (4)..(5)
<223> OTHER INFORMATION: Sortase A

<400> SEQUENCE: 46

Leu Pro Lys Thr Gly Ser Glu Ser
1               5

<210> SEQ ID NO 47
<211> LENGTH: 9
<212> TYPE: PRT
<213> ORGANISM: Artificial
<220> FEATURE:
<223> OTHER INFORMATION: cleavable linker

<400> SEQUENCE: 47

Thr Gln Ser Phe Asn Asp Phe Thr Arg
1               5

<210> SEQ ID NO 48
<211> LENGTH: 10
<212> TYPE: PRT
<213> ORGANISM: Artificial
<220> FEATURE:
<223> OTHER INFORMATION: cleavage site

<400> SEQUENCE: 48

Ser Val Ser Gln Thr Ser Lys Leu Thr Arg
1               5                   10

<210> SEQ ID NO 49
<211> LENGTH: 10
<212> TYPE: PRT
<213> ORGANISM: Artificial
<220> FEATURE:
<223> OTHER INFORMATION: cleavage site

<400> SEQUENCE: 49

Asp Phe Leu Ala Glu Gly Gly Gly Val Arg
1               5                   10

<210> SEQ ID NO 50
<211> LENGTH: 7
<212> TYPE: PRT
```

```
<213> ORGANISM: Artificial
<220> FEATURE:
<223> OTHER INFORMATION: cleavage site

<400> SEQUENCE: 50

Thr Thr Lys Ile Lys Pro Arg
1               5

<210> SEQ ID NO 51
<211> LENGTH: 10
<212> TYPE: PRT
<213> ORGANISM: Artificial
<220> FEATURE:
<223> OTHER INFORMATION: cleavge site

<400> SEQUENCE: 51

Ala Leu Arg Pro Arg Val Val Gly Gly Ala
1               5                   10

<210> SEQ ID NO 52
<211> LENGTH: 4
<212> TYPE: PRT
<213> ORGANISM: Artificial
<220> FEATURE:
<223> OTHER INFORMATION: cleavage site

<400> SEQUENCE: 52

Arg Arg Arg Arg
1

<210> SEQ ID NO 53
<211> LENGTH: 6
<212> TYPE: PRT
<213> ORGANISM: Artificial
<220> FEATURE:
<223> OTHER INFORMATION: cleavage site

<400> SEQUENCE: 53

Arg Lys Arg Arg Lys Arg
1               5

<210> SEQ ID NO 54
<211> LENGTH: 5
<212> TYPE: PRT
<213> ORGANISM: Artificial
<220> FEATURE:
<223> OTHER INFORMATION: cleavage site

<400> SEQUENCE: 54

Arg Arg Arg Arg Ser
1               5

<210> SEQ ID NO 55
<211> LENGTH: 5
<212> TYPE: PRT
<213> ORGANISM: Artificial
<220> FEATURE:
<223> OTHER INFORMATION: cleavage site

<400> SEQUENCE: 55

Leu Val Pro Arg Gly
1               5

<210> SEQ ID NO 56
<211> LENGTH: 25
<212> TYPE: PRT
<213> ORGANISM: Artificial
```

<220> FEATURE:
<223> OTHER INFORMATION: cleavage and linker site

<400> SEQUENCE: 56

Thr Leu Asp Pro Arg Ser Phe Leu Leu Arg Asn Pro Asn Asp Lys Tyr
1               5                   10                  15

Glu Pro Phe Trp Glu Asp Glu Glu Lys
            20                  25

<210> SEQ ID NO 57
<211> LENGTH: 99
<212> TYPE: DNA
<213> ORGANISM: Artificial
<220> FEATURE:
<223> OTHER INFORMATION: ESC48-Fwd-VWF-D'D3 with VIII signal and BsiW1
      site for pSYN VWF-001

<400> SEQUENCE: 57
tcgcgacgta cggccgccac catgcaaata gagctctcca cctgcttctt tctgtgcctt    60
ttgcgattct gctttagcct atcctgtcgg ccccccatg                          99

<210> SEQ ID NO 58
<211> LENGTH: 68
<212> TYPE: DNA
<213> ORGANISM: Artificial
<220> FEATURE:
<223> OTHER INFORMATION: ESC50- Rev- VWF- partial D'D3 (1-276 amino
      acid) with 6 His and Not1 site for pSYN VWF- 001

<400> SEQUENCE: 58
tgacctcgag cggccgctca gtggtgatgg tgatgatgca gaggcacttt tctggtgtca    60
gcacactg                                                            68

<210> SEQ ID NO 59
<211> LENGTH: 99
<212> TYPE: DNA
<213> ORGANISM: Artificial
<220> FEATURE:
<223> OTHER INFORMATION: ESC48- Fwd - VWF-D'D3 with VIII signal and
      BsiW1 site for pSYN VWF- 002

<400> SEQUENCE: 59
tcgcgacgta cggccgccac catgcaaata gagctctcca cctgcttctt tctgtgcctt    60
ttgcgattct gctttagcct atcctgtcgg ccccccatg                          99

<210> SEQ ID NO 60
<211> LENGTH: 71
<212> TYPE: DNA
<213> ORGANISM: Artificial
<220> FEATURE:
<223> OTHER INFORMATION: ESC51- Rev- VWF D'D3 (1-477 amino acid) with
      6His and Not 1 site for pSYN VWF- 002

<400> SEQUENCE: 60
tgacctcgag cggccgctca gtggtgatgg tgatgatgcc tgctgcagta gaaatcgtgc    60
aacggcggtt c                                                        71

<210> SEQ ID NO 61
<211> LENGTH: 99
<212> TYPE: DNA
<213> ORGANISM: Artificial
<220> FEATURE:
<223> OTHER INFORMATION: ESC48- Fwd - VWF-D'D3 with VIII signal and
      BsiW1 site for pSYN VWF- 003

<400> SEQUENCE: 61

```
tcgcgacgta cggccgccac catgcaaata gagctctcca cctgcttctt tctgtgcctt    60
ttgcgattct gctttagcct atcctgtcgg ccccccatg                            99
```

<210> SEQ ID NO 62
<211> LENGTH: 65
<212> TYPE: DNA
<213> ORGANISM: Artificial
<220> FEATURE:
<223> OTHER INFORMATION: ESC52- Rev-VWF-D'D3 Partial A1 (1-511 amino acids) with 6His and Not1 site for pSYN VWF- 003

<400> SEQUENCE: 62

```
tgacctcgag cggccgctca gtggtgatgg tgatgatggc ccacagtgac ttgtgccatg    60
tgggg                                                                65
```

<210> SEQ ID NO 63
<211> LENGTH: 99
<212> TYPE: DNA
<213> ORGANISM: Artificial
<220> FEATURE:
<223> OTHER INFORMATION: ESC48- Fwd - VWF-D'D3 with VIII signal and BsiW1 site for pSYN VWF- 004

<400> SEQUENCE: 63

```
tcgcgacgta cggccgccac catgcaaata gagctctcca cctgcttctt tctgtgcctt    60
ttgcgattct gctttagcct atcctgtcgg ccccccatg                            99
```

<210> SEQ ID NO 64
<211> LENGTH: 65
<212> TYPE: DNA
<213> ORGANISM: Artificial
<220> FEATURE:
<223> OTHER INFORMATION: ESC53-Rev- VWF-D'D3A1 (1-716 amino acids) with 6His and Not1 site for pSYN VWF- 004

<400> SEQUENCE: 64

```
tgacctcgag cggccgctca gtggtgatgg tgatgatggc ccacagtgac ttgtgccatg    60
tgggg                                                                65
```

<210> SEQ ID NO 65
<211> LENGTH: 1313
<212> TYPE: DNA
<213> ORGANISM: Artificial
<220> FEATURE:
<223> OTHER INFORMATION: cloned vector

<400> SEQUENCE: 65

```
ggatcctagt ggggaataag ggatgcagcc acccctcagt gaaatgcaag aaacgggtca     60
ccatcctggt ggagggagga gagattgagc tgtttgacgg ggaggtgaat gtgaagaggc    120
ccatgaagga tgagactcac tttgaggtgg tggagtctgg ccggtacatc attctgctgc    180
tgggcaaagc cctctccgtg gtctgggacc gccacctgag catctccgtg gtcctgaagc    240
agacatacca ggagaaagtg tgtggcctgt gtgggaattt tgatggcatc cagaacaatg    300
acctcaccag cagcaacctc caagtggagg aagaccctgt ggactttggg aactcctgga    360
aagtgagctc gcagtgtgct gacaccagaa aagtgcctct ggactcatcc cctgccacct    420
gccataacaa catcatgaag cagacgatgg tggattcctc ctgtagaatc cttaccagtg    480
acgtcttcca ggactgcaac aagctggtgg accccgagcc atatctggat gtctgcattt    540
```

```
acgacacctg ctcctgtgag tccattgggg actgcgcctg cttctgcgac accattgctg    600
cctatgccca cgtgtgtgcc cagcatggca aggtggtgac ctggaggacg gccacattgt    660
gcccccagag ctgcgaggag aggaatctcc gggagaacgg gtatgagtgt gagtggcgct    720
ataacagctg tgcacctgcc tgtcaagtca cgtgtcagca ccctgagcca ctggcctgcc    780
ctgtgcagtg tgtggagggc tgccatgccc actgccctcc agggaaaatc ctggatgagc    840
ttttgcagac ctgcgttgac cctgaagact gtccagtgtg tgaggtggct ggccggcgtt    900
ttgcctcagg aaagaaagtc accttgaatc ccagtgaccc tgagcactgc cagatttgcc    960
actgtgatgt tgtcaacctc acctgtgaag cctgccagga gccggaggc ctggtggtgc   1020 ctcccacaga tgccccggtg agccccacca ctctgtatgt ggatgagacg ctccaggatg   1080
gctgtgatac tcacttctgc aaggtcaatg agagaggaga gtacttctgg gagaagaggg   1140
tcacaggctg cccacccttt gatgaacaca gtgtcttgc tgagggaggt aaaattatga    1200
aaattccagg cacctgctgt gacacatgtg aggagcctga gtgcaacgac atcactgcca   1260
ggctgcagta tgtcaaggtg ggaagctgta agtctgaagt agaggtggat atc          1313

<210> SEQ ID NO 66
<211> LENGTH: 32
<212> TYPE: DNA
<213> ORGANISM: Artificial
<220> FEATURE:
<223> OTHER INFORMATION: ESC 89-fwd with NheIsite

<400> SEQUENCE: 66
ctcactatag ggagacccaa gctggctagc cg                                 32

<210> SEQ ID NO 67
<211> LENGTH: 43
<212> TYPE: DNA
<213> ORGANISM: Artificial
<220> FEATURE:
<223> OTHER INFORMATION: ESC 91-rev with SalI

<400> SEQUENCE: 67
ctggatcccg ggagtcgact cgtcagtggt gatggtgatg atg                     43

<210> SEQ ID NO 68
<211> LENGTH: 92
<212> TYPE: DNA
<213> ORGANISM: Artificial
<220> FEATURE:
<223> OTHER INFORMATION: LW 22-FWD-VWF-D'D3 with FVIII signal sequence
      and BsiWI site

<400> SEQUENCE: 68
gcgccggccg tacgatgcaa atagagctct ccacctgctt ctttctgtgc cttttgcgat    60
tctgctttag cctatcctgt cggccccca tg                                  92

<210> SEQ ID NO 69
<211> LENGTH: 47
<212> TYPE: DNA
<213> ORGANISM: Artificial
<220> FEATURE:
<223> OTHER INFORMATION: LW 23-Rev- Fc with stop codon and NotI site

<400> SEQUENCE: 69
tcatcaatgt atcttatcat gtctgaattc gcggccgctc atttacc                 47
```

```
<210> SEQ ID NO 70
<211> LENGTH: 41
<212> TYPE: DNA
<213> ORGANISM: Artificial
<220> FEATURE:
<223> OTHER INFORMATION: LW24- Fwd- VWF D1D2D'D3 cloning oligo with
      BsiW1 site

<400> SEQUENCE: 70
gcgccggccg tacgatgatt cctgccagat ttgccggggt g                    41

<210> SEQ ID NO 71
<211> LENGTH: 41
<212> TYPE: DNA
<213> ORGANISM: Artificial
<220> FEATURE:
<223> OTHER INFORMATION: LW27-Rev-VWF  D'D3 oligo with EcoRV

<400> SEQUENCE: 71
ccaccgccag atatcggctc ctggcaggct tcacaggtga g                    41

<210> SEQ ID NO 72
<211> LENGTH: 1240
<212> TYPE: PRT
<213> ORGANISM: Artificial
<220> FEATURE:
<223> OTHER INFORMATION: VWF-D1D2D'D3

<400> SEQUENCE: 72

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240
```

-continued

Val Asp Pro Glu Pro Phe Val Ala Leu Cys Glu Lys Thr Leu Cys Glu
            245                 250                 255

Cys Ala Gly Gly Leu Glu Cys Ala Cys Pro Ala Leu Leu Glu Tyr Ala
        260                 265                 270

Arg Thr Cys Ala Gln Glu Gly Met Val Leu Tyr Gly Trp Thr Asp His
    275                 280                 285

Ser Ala Cys Ser Pro Val Cys Pro Ala Gly Met Glu Tyr Arg Gln Cys
290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
            325                 330                 335

Leu Asp Glu Gly Leu Cys Val Glu Ser Thr Glu Cys Pro Cys Val His
        340                 345                 350

Ser Gly Lys Arg Tyr Pro Pro Gly Thr Ser Leu Ser Arg Asp Cys Asn
    355                 360                 365

Thr Cys Ile Cys Arg Asn Ser Gln Trp Ile Cys Ser Asn Glu Glu Cys
370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
            405                 410                 415

Asp Cys Gln Asp His Ser Phe Ser Ile Val Ile Glu Thr Val Gln Cys
        420                 425                 430

Ala Asp Asp Arg Asp Ala Val Cys Thr Arg Ser Val Thr Val Arg Leu
    435                 440                 445

Pro Gly Leu His Asn Ser Leu Val Lys Leu Lys His Gly Ala Gly Val
450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
            485                 490                 495

Asp Leu Gln Met Asp Trp Asp Gly Arg Gly Arg Leu Leu Val Lys Leu
        500                 505                 510

Ser Pro Val Tyr Ala Gly Lys Thr Cys Gly Leu Cys Gly Asn Tyr Asn
    515                 520                 525

Gly Asn Gln Gly Asp Asp Phe Leu Thr Pro Ser Gly Leu Ala Glu Pro
530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
            565                 570                 575

Thr Arg Phe Ser Glu Glu Ala Cys Ala Val Leu Thr Ser Pro Thr Phe
        580                 585                 590

Glu Ala Cys His Arg Ala Val Ser Pro Leu Pro Tyr Leu Arg Asn Cys
    595                 600                 605

Arg Tyr Asp Val Cys Ser Cys Ser Asp Gly Arg Glu Cys Leu Cys Gly
610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
            645                 650                 655

Val Tyr Leu Gln Cys Gly Thr Pro Cys Asn Leu Thr Cys Arg Ser Leu

-continued

```
                660                 665                 670
Ser Tyr Pro Asp Glu Cys Asn Glu Ala Cys Leu Glu Gly Cys Phe
            675                 680                 685

Cys Pro Pro Gly Leu Tyr Met Asp Glu Arg Gly Asp Cys Val Pro Lys
            690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
                740                 745                 750

Leu Ser Ser Pro Leu Ser His Arg Ser Lys Arg Ser Leu Ser Cys Arg
            755                 760                 765

Pro Pro Met Val Lys Leu Val Cys Pro Ala Asp Asn Leu Arg Ala Glu
            770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
            835                 840                 845

Cys Val Cys Arg Asp Arg Lys Trp Asn Cys Thr Asp His Val Cys Asp
850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
            915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
            995                 1000                1005

Ser Ser  Asn Leu Gln Val Glu  Glu Asp Pro Val Asp  Phe Gly Asn
        1010                1015                1020

Ser Trp  Lys Val Ser Ser Gln  Cys Ala Asp Thr Arg  Lys Val Pro
        1025                1030                1035

Leu Asp  Ser Ser Pro Ala Thr  Cys His Asn Asn Ile  Met Lys Gln
        1040                1045                1050

Thr Met  Val Asp Ser Ser Cys  Arg Ile Leu Thr Ser  Asp Val Phe
        1055                1060                1065

Gln Asp  Cys Asn Lys Leu Val  Asp Pro Glu Pro Tyr  Leu Asp Val
        1070                1075                1080
```

Cys Ile Tyr Asp Thr Cys Ser Cys Glu Ser Ile Gly Asp Cys Ala
1085                1090                1095

Cys Phe Cys Asp Thr Ile Ala Ala Tyr Ala His Val Cys Ala Gln
1100                1105                1110

His Gly Lys Val Val Thr Trp Arg Thr Ala Thr Leu Cys Pro Gln
1115                1120                1125

Ser Cys Glu Glu Arg Asn Leu Arg Glu Asn Gly Tyr Glu Cys Glu
1130                1135                1140

Trp Arg Tyr Asn Ser Cys Ala Pro Ala Cys Gln Val Thr Cys Gln
1145                1150                1155

His Pro Glu Pro Leu Ala Cys Pro Val Gln Cys Val Glu Gly Cys
1160                1165                1170

His Ala His Cys Pro Pro Gly Lys Ile Leu Asp Glu Leu Leu Gln
1175                1180                1185

Thr Cys Val Asp Pro Glu Asp Cys Pro Val Cys Glu Val Ala Gly
1190                1195                1200

Arg Arg Phe Ala Ser Gly Lys Lys Val Thr Leu Asn Pro Ser Asp
1205                1210                1215

Pro Glu His Cys Gln Ile Cys His Cys Asp Val Val Asn Leu Thr
1220                1225                1230

Cys Glu Ala Cys Gln Glu Pro
1235                1240

<210> SEQ ID NO 73
<211> LENGTH: 477
<212> TYPE: PRT
<213> ORGANISM: Artificial
<220> FEATURE:
<223> OTHER INFORMATION: VWF-D'D3

<400> SEQUENCE: 73

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
                20                  25                  30

Asp Leu Glu Cys Met Ser Met Gly Cys Val Ser Gly Cys Leu Cys Pro
            35                  40                  45

Pro Gly Met Val Arg His Glu Asn Arg Cys Val Ala Leu Glu Arg Cys
        50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

-continued

```
Val Glu Ser Gly Arg Tyr Ile Ile Leu Leu Gly Lys Ala Leu Ser
            195                 200                 205
Val Val Trp Asp Arg His Leu Ser Ile Ser Val Val Leu Lys Gln Thr
    210                 215                 220
Tyr Gln Glu Lys Val Cys Gly Leu Cys Gly Asn Phe Asp Gly Ile Gln
225                 230                 235                 240
Asn Asn Asp Leu Thr Ser Ser Asn Leu Gln Val Glu Glu Asp Pro Val
                245                 250                 255
Asp Phe Gly Asn Ser Trp Lys Val Ser Ser Gln Cys Ala Asp Thr Arg
            260                 265                 270
Lys Val Pro Leu Asp Ser Ser Pro Ala Thr Cys His Asn Asn Ile Met
        275                 280                 285
Lys Gln Thr Met Val Asp Ser Ser Cys Arg Ile Leu Thr Ser Asp Val
    290                 295                 300
Phe Gln Asp Cys Asn Lys Leu Val Asp Pro Glu Pro Tyr Leu Asp Val
305                 310                 315                 320
Cys Ile Tyr Asp Thr Cys Ser Cys Glu Ser Ile Gly Asp Cys Ala Cys
                325                 330                 335
Phe Cys Asp Thr Ile Ala Ala Tyr Ala His Val Cys Ala Gln His Gly
            340                 345                 350
Lys Val Val Thr Trp Arg Thr Ala Thr Leu Cys Pro Gln Ser Cys Glu
        355                 360                 365
Glu Arg Asn Leu Arg Glu Asn Gly Tyr Glu Cys Glu Trp Arg Tyr Asn
    370                 375                 380
Ser Cys Ala Pro Ala Cys Gln Val Thr Cys Gln His Pro Glu Pro Leu
385                 390                 395                 400
Ala Cys Pro Val Gln Cys Val Glu Gly Cys His Ala His Cys Pro Pro
                405                 410                 415
Gly Lys Ile Leu Asp Glu Leu Leu Gln Thr Cys Val Asp Pro Glu Asp
            420                 425                 430
Cys Pro Val Cys Glu Val Ala Gly Arg Arg Phe Ala Ser Gly Lys Lys
        435                 440                 445
Val Thr Leu Asn Pro Ser Asp Pro Glu His Cys Gln Ile Cys His Cys
    450                 455                 460
Asp Val Val Asn Leu Thr Cys Glu Ala Cys Gln Glu Pro
465                 470                 475

<210> SEQ ID NO 74
<211> LENGTH: 30
<212> TYPE: PRT
<213> ORGANISM: Artificial
<220> FEATURE:
<223> OTHER INFORMATION: VWF-D'D3 domain (1-477aa; C336A/C379A mutation)
<220> FEATURE:
<221> NAME/KEY: REPEAT
<222> LOCATION: (1)..(30)
<223> OTHER INFORMATION: Gly-Gly-Gly-Gly-Ser repeats 6 times

<400> SEQUENCE: 74

Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser
            20                  25                  30

<210> SEQ ID NO 75
<211> LENGTH: 5
<212> TYPE: PRT
```

```
<213> ORGANISM: Artificial
<220> FEATURE:
<223> OTHER INFORMATION: linker

<400> SEQUENCE: 75

Arg Arg Arg Arg Ser
1               5

<210> SEQ ID NO 76
<211> LENGTH: 6
<212> TYPE: PRT
<213> ORGANISM: Artificial
<220> FEATURE:
<223> OTHER INFORMATION: linker

<400> SEQUENCE: 76

Arg Lys Arg Arg Lys Arg
1               5

<210> SEQ ID NO 77
<211> LENGTH: 24
<212> TYPE: DNA
<213> ORGANISM: Artificial
<220> FEATURE:
<223> OTHER INFORMATION: ESC17-Fwd- VWF cloning oligo with Cla1

<400> SEQUENCE: 77
gtccggcatg agaatcgatg tgtg                                           24

<210> SEQ ID NO 78
<211> LENGTH: 31
<212> TYPE: DNA
<213> ORGANISM: Artificial
<220> FEATURE:
<223> OTHER INFORMATION: ESC41- Rev-VWF with EcoRV

<400> SEQUENCE: 78
cctccaccgc cagatatcag aggcactttt c                                   31

<210> SEQ ID NO 79
<211> LENGTH: 105
<212> TYPE: DNA
<213> ORGANISM: Artificial
<220> FEATURE:
<223> OTHER INFORMATION: ESC78- Fwd with EcoRV site

<400> SEQUENCE: 79
aaagtgcctc tgatatctgg cggtggaggt tccggtggcg ggggatccgg tggcggggga    60
tccggtggcg ggggatccgg tggcggggga tccctggtcc cccgg                   105

<210> SEQ ID NO 80
<211> LENGTH: 107
<212> TYPE: DNA
<213> ORGANISM: Artificial
<220> FEATURE:
<223> OTHER INFORMATION: ESC79- Rev with RsRII site

<400> SEQUENCE: 80
gaagaggaag actgacggtc cgcccaggag ttctggagct gggcacggtg ggcatgtgtg    60
agttttgtcg cctccgctgc ccggggggac cagggatccc ccgccac                 107

<210> SEQ ID NO 81
<211> LENGTH: 48
<212> TYPE: PRT
<213> ORGANISM: Artificial
```

<220> FEATURE:
<223> OTHER INFORMATION: linker

<400> SEQUENCE: 81

Ile Ser Gly Gly Gly Ser Gly Gly Gly Ser Gly Gly Gly Gly
1               5                   10                  15

Ser Gly Gly Gly Gly Ser Gly Gly Gly Ser Gly Gly Gly Ser
            20                  25                  30

Leu Val Pro Arg Gly Ser Gly Gly Gly Ser Gly Gly Gly Ser
            35                  40                  45

<210> SEQ ID NO 82
<211> LENGTH: 1781
<212> TYPE: DNA
<213> ORGANISM: Artificial
<220> FEATURE:
<223> OTHER INFORMATION: pSYN-FVIII-049, which is FVIII-Fc construct
      with a cleavable linker in between two Fc domains; Genscript-
      Sequence number 103069

<400> SEQUENCE: 82

```
ccgtcgacaa gagcaggtgg cagcagggga acgtcttctc atgctccgtg atgcatgagg      60
ctctgcacaa ccactacacg cagaagagcc tctccctgtc tccgggtaaa cggcgccgcc     120
ggagcggtgg cggcggatca ggtggggtg  gatcaggcgg tggaggttcc ggtggcgggg     180
gatccggcgg tggaggttcc ggtggggtg  gatcaaggaa gaggaggaag agaagcctat     240
cctgtcggcc ccccatggtc aagctggtgt gtcccgctga caacctgcgg gctgaagggc     300
tcgagtgtac caaaacgtgc cagaactatg acctggagtg catgagcatg ggctgtgtct     360
ctggctgcct ctgccccccg ggcatggtcc ggcatgagaa tcgatgtgtg ccctggaaa      420
ggtgtccctg cttccatcag gcaaggagt  atgcccctgg agaaacagtg aagattggct     480
gcaacacttg tgtctgtcgg accggaagt  ggaactgcac agaccatgtg tgtgatgcca     540
cgtgctccac gatcggcatg cccactacc  tcaccttcga cgggctcaaa tacctgttcc     600
ccgggagtg  ccagtacgtt ctggtgcagg attactgcgg cagtaaccct gggacctttc     660
ggatcctagt ggggaataag ggatgcagcc acccctcagt gaaatgcaag aaacgggtca     720
ccatcctggt ggagggagga gagattgagc tgtttgacgg ggaggtgaat gtgaagaggc     780
ccatgaagga tgagactcac tttgaggtgg tggagtctgg ccgtacatc  attctgctgc     840
tgggcaaagc cctctccgtg gtctgggacc gccacctgag catctccgtg gtcctgaagc     900
agacatacca ggagaaagtg tgtggcctgt gtgggaattt tgatggcatc cagaacaatg     960
acctcaccag cagcaacctc caagtggagg aagaccctgt ggactttggg aactcctgga    1020
aagtgagctc gcagtgtgct gacaccagaa aagtgcctct ggactcatcc cctgccacct    1080
gccataacaa catcatgaag cagacgatgg tggattcctc ctgtagaatc cttaccagtg    1140
acgtcttcca ggactgcaac aagctggtgg accccgagcc atatctggat gtctgcattt    1200
acgacacctg ctcctgtgag tccattgggg actgcgccgc attctgcgac accattgctg    1260
cctatgccca cgtgtgtgcc cagcatggca aggtggtgac ctggaggacg ccacattgt    1320
gcccccagag ctgcgaggag aggaatctcc gggagaacgg tatgaggct  gagtggcgct    1380
ataacagctg tgcacctgcc tgtcaagtca cgtgtcagca ccctgagcca ctggcctgcc    1440
ctgtgcagtg tgtggagggc tgccatgccc actgccctcc agggaaaatc ctggatgagc    1500
ttttgcagac ctgcgttgac cctgaagact gtccagtgtg tgaggtggct ggccggcgtt    1560
tgcctcagg aaagaaagtc accttgaatc ccagtgaccc tgagcactgc cagatttgcc    1620
```

```
actgtgatgt tgtcaacctc acctgtgaag cctgccagga gccgatcgat ggcggtggag      1680
gttccggtgg cggggggatcc ctggtccccc ggggcagcgg aggcgacaaa actcacacat    1740
gcccaccgtg cccagctcca gaactcctgg gcggaccgtc a                          1781
```

```
<210> SEQ ID NO 83
<211> LENGTH: 220
<212> TYPE: DNA
<213> ORGANISM: Artificial
<220> FEATURE:
<223> OTHER INFORMATION: A fragment of the Genscript construct was sub
      cloned into the EcoRV/RsRII digested pSYN-FVIII-0159; Genscript-
      Sequence no-132601

<400> SEQUENCE: 83
```

```
aaagtgcctc tgatatctgg cggtggaggt tccggtggcg ggggatccgg cggtggaggt      60
tccggcggtg gaggttccgg tggcggggga tccggtggcg ggggatccct ggtccccggg    120
ggcagcggcg gtggaggttc cgtggcggg gatccgaca aaactcacac atgcccaccg      180
tgcccagctc cagaactcct gggcggaccg tcagtcttcc                           220
```

```
<210> SEQ ID NO 84
<211> LENGTH: 73
<212> TYPE: PRT
<213> ORGANISM: Artificial
<220> FEATURE:
<223> OTHER INFORMATION: pSYN-VIII-178 has a 73 amino acids linker in
      between the VWF fragment and the Fc region; synthesis of DNA
      fragment coding for 73 amino acids linker

<400> SEQUENCE: 84
```

```
Ile Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser Gly Gly Gly Gly Ser Gly
        35                  40                  45

Gly Gly Gly Ser Gly Gly Gly Gly Ser Leu Val Pro Arg Gly Ser Gly
    50                  55                  60

Gly Gly Gly Ser Gly Gly Gly Gly Ser
65                  70
```

```
<210> SEQ ID NO 85
<211> LENGTH: 299
<212> TYPE: DNA
<213> ORGANISM: Artificial
<220> FEATURE:
<223> OTHER INFORMATION: Genscript-Sequence #-144849

<400> SEQUENCE: 85
```

```
gcctgccagg agccgatatc tggcggtgga ggttccggtg cgggggatc cggcggtgga       60 ggttccggcg gtggaggttc cggtggcggg ggatccggcg gtggaggttc cggtggcggg    120
ggatccggcg gtggaggttc cggcggtgga ggttccggtg cgggggatc cggtggcggg    180 ggatccctgg tccccgggg cagcggcggt ggaggttccg gtggcggggg atccgacaaa    240
actcacacat gccccgtgc ccagctccag aactcctggg cggaccgtca gtcttcctc      299
```

```
<210> SEQ ID NO 86
<211> LENGTH: 98
<212> TYPE: PRT
<213> ORGANISM: Artificial
```

<220> FEATURE:
<223> OTHER INFORMATION: linker

<400> SEQUENCE: 86

Ile Ser Gly Gly Gly Ser Gly Gly Gly Ser Gly Gly Gly Gly Gly
1               5                   10                  15

Ser Gly Gly Gly Gly Ser Gly Gly Gly Ser Gly Gly Gly Gly Ser
            20                  25                  30

Gly Gly Gly Gly Ser Gly Gly Gly Ser Gly Gly Gly Ser Gly
        35                  40                  45

Gly Gly Gly Ser Gly Gly Gly Ser Gly Gly Gly Ser Gly Gly
    50                  55                  60

Gly Gly Ser Gly Gly Gly Ser Gly Gly Gly Ser Gly Gly Gly
65                  70                  75                  80

Gly Ser Leu Val Pro Arg Gly Ser Gly Gly Ser Gly Gly Gly
                85                  90                  95

Gly Ser

<210> SEQ ID NO 87
<211> LENGTH: 380
<212> TYPE: DNA
<213> ORGANISM: Artificial
<220> FEATURE:
<223> OTHER INFORMATION: Genscript-Sequence #-144849

<400> SEQUENCE: 87
gcctgccagg agccgatatc tggcggtgga ggttccggtg gcgggggatc cggcggtgga      60
ggttccggcg gtggaggttc cggtggcggg ggatccggcg gtggaggttc cggtggcggg     120
ggatccggcg gtggaggttc cggcggtgga ggttccggtg gcgggggatc cggcggtgga     180
ggttccggtg gcgggggatc cggcggtgga ggttccggcg gtggaggttc cggtggcggg     240
ggatccggtg gcgggggatc cctggtcccc cggggcagcg gcggtggagg ttccggtggc     300
gggggatccg acaaaactca cacatgccca ccgtgcccag ctccagaact cctgggcgga     360
ccgtcagtct tcctcttccc                                                 380

<210> SEQ ID NO 88
<211> LENGTH: 2449
<212> TYPE: PRT
<213> ORGANISM: Artificial
<220> FEATURE:
<223> OTHER INFORMATION: FVIII-VWF-Fc heterodimer

<400> SEQUENCE: 88

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

```
His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
                180                 185                 190

Gly Ala Leu Leu Val Cys Arg Glu Gly Ser Leu Ala Lys Glu Lys Thr
                195                 200                 205

Gln Thr Leu His Lys Phe Ile Leu Leu Phe Ala Val Phe Asp Glu Gly
            210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
            275                 280                 285

Phe Leu Glu Gly His Thr Phe Leu Val Arg Asn His Arg Gln Ala Ser
            290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
                340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asp Asn Ser
            370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
            450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
            515                 520                 525
```

```
Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
```

```
                    945               950               955               960
Ala Tyr Phe Ser Asp Val Asp Leu Glu Lys Asp Val His Ser Gly Leu
                965               970               975
Ile Gly Pro Leu Leu Val Cys His Thr Asn Thr Leu Asn Pro Ala His
                980               985               990
Gly Arg Gln Val Thr Val Gln Glu Phe Ala Leu Phe Phe Thr Ile Phe
                995              1000              1005
Asp Glu Thr Lys Ser Trp Tyr Phe Thr Glu Asn Met Glu Arg Asn
     1010              1015              1020
Cys Arg Ala Pro Cys Asn Ile Gln Met Glu Asp Pro Thr Phe Lys
     1025              1030              1035
Glu Asn Tyr Arg Phe His Ala Ile Asn Gly Tyr Ile Met Asp Thr
     1040              1045              1050
Leu Pro Gly Leu Val Met Ala Gln Asp Gln Arg Ile Arg Trp Tyr
     1055              1060              1065
Leu Leu Ser Met Gly Ser Asn Glu Asn Ile His Ser Ile His Phe
     1070              1075              1080
Ser Gly His Val Phe Thr Val Arg Lys Lys Glu Glu Tyr Lys Met
     1085              1090              1095
Ala Leu Tyr Asn Leu Tyr Pro Gly Val Phe Glu Thr Val Glu Met
     1100              1105              1110
Leu Pro Ser Lys Ala Gly Ile Trp Arg Val Glu Cys Leu Ile Gly
     1115              1120              1125
Glu His Leu His Ala Gly Met Ser Thr Leu Phe Leu Val Tyr Ser
     1130              1135              1140
Asn Lys Cys Gln Thr Pro Leu Gly Met Ala Ser Gly His Ile Arg
     1145              1150              1155
Asp Phe Gln Ile Thr Ala Ser Gly Gln Tyr Gly Gln Trp Ala Pro
     1160              1165              1170
Lys Leu Ala Arg Leu His Tyr Ser Gly Ser Ile Asn Ala Trp Ser
     1175              1180              1185
Thr Lys Glu Pro Phe Ser Trp Ile Lys Val Asp Leu Leu Ala Pro
     1190              1195              1200
Met Ile Ile His Gly Ile Lys Thr Gln Gly Ala Arg Gln Lys Phe
     1205              1210              1215
Ser Ser Leu Tyr Ile Ser Gln Phe Ile Ile Met Tyr Ser Leu Asp
     1220              1225              1230
Gly Lys Lys Trp Gln Thr Tyr Arg Gly Asn Ser Thr Gly Thr Leu
     1235              1240              1245
Met Val Phe Phe Gly Asn Val Asp Ser Ser Gly Ile Lys His Asn
     1250              1255              1260
Ile Phe Asn Pro Pro Ile Ile Ala Arg Tyr Ile Arg Leu His Pro
     1265              1270              1275
Thr His Tyr Ser Ile Arg Ser Thr Leu Arg Met Glu Leu Met Gly
     1280              1285              1290
Cys Asp Leu Asn Ser Cys Ser Met Pro Leu Gly Met Glu Ser Lys
     1295              1300              1305
Ala Ile Ser Asp Ala Gln Ile Thr Ala Ser Ser Tyr Phe Thr Asn
     1310              1315              1320
Met Phe Ala Thr Trp Ser Pro Ser Lys Ala Arg Leu His Leu Gln
     1325              1330              1335
Gly Arg Ser Asn Ala Trp Arg Pro Gln Val Asn Asn Pro Lys Glu
     1340              1345              1350
```

```
Trp Leu Gln Val Asp Phe Gln Lys Thr Met Lys Val Thr Gly Val
    1355                1360                1365

Thr Thr Gln Gly Val Lys Ser Leu Leu Thr Ser Met Tyr Val Lys
    1370                1375                1380

Glu Phe Leu Ile Ser Ser Gln Asp Gly His Gln Trp Thr Leu
    1385                1390                1395

Phe Phe Gln Asn Gly Lys Val Lys Val Phe Gln Gly Asn Gln Asp
    1400                1405                1410

Ser Phe Thr Pro Val Val Asn Ser Leu Asp Pro Pro Leu Leu Thr
    1415                1420                1425

Arg Tyr Leu Arg Ile His Pro Gln Ser Trp Val His Gln Ile Ala
    1430                1435                1440

Leu Arg Met Glu Val Leu Gly Cys Glu Ala Gln Asp Leu Tyr Asp
    1445                1450                1455

Lys Thr His Thr Cys Pro Pro Cys Pro Ala Pro Glu Leu Leu Gly
    1460                1465                1470

Gly Pro Ser Val Phe Leu Phe Pro Pro Lys Pro Lys Asp Thr Leu
    1475                1480                1485

Met Ile Ser Arg Thr Pro Glu Val Thr Cys Val Val Val Asp Val
    1490                1495                1500

Ser His Glu Asp Pro Glu Val Lys Phe Asn Trp Tyr Val Asp Gly
    1505                1510                1515

Val Glu Val His Asn Ala Lys Thr Lys Pro Arg Glu Glu Gln Tyr
    1520                1525                1530

Asn Ser Thr Tyr Arg Val Val Ser Val Leu Thr Val Leu His Gln
    1535                1540                1545

Asp Trp Leu Asn Gly Lys Glu Tyr Lys Cys Lys Val Ser Asn Lys
    1550                1555                1560

Ala Leu Pro Ala Pro Ile Glu Lys Thr Ile Ser Lys Ala Lys Gly
    1565                1570                1575

Gln Pro Arg Glu Pro Gln Val Tyr Thr Leu Pro Pro Ser Arg Asp
    1580                1585                1590

Glu Leu Thr Lys Asn Gln Val Ser Leu Thr Cys Leu Val Lys Gly
    1595                1600                1605

Phe Tyr Pro Ser Asp Ile Ala Val Glu Trp Glu Ser Asn Gly Gln
    1610                1615                1620

Pro Glu Asn Asn Tyr Lys Thr Thr Pro Pro Val Leu Asp Ser Asp
    1625                1630                1635

Gly Ser Phe Phe Leu Tyr Ser Lys Leu Thr Val Asp Lys Ser Arg
    1640                1645                1650

Trp Gln Gln Gly Asn Val Phe Ser Cys Ser Val Met His Glu Ala
    1655                1660                1665

Leu His Asn His Tyr Thr Gln Lys Ser Leu Ser Leu Ser Pro Gly
    1670                1675                1680

Lys Arg Arg Arg Arg Ser Gly Gly Gly Ser Gly Gly Gly Gly
    1685                1690                1695

Ser Gly Gly Gly Gly Ser Gly Gly Gly Gly Ser Gly Gly Gly
    1700                1705                1710

Ser Gly Gly Gly Gly Ser Arg Lys Arg Arg Lys Arg Ser Leu Ser
    1715                1720                1725

Cys Arg Pro Pro Met Val Lys Leu Val Cys Pro Ala Asp Asn Leu
    1730                1735                1740
```

```
Arg Ala Glu Gly Leu Glu Cys Thr Lys Thr Cys Gln Asn Tyr Asp
    1745            1750            1755

Leu Glu Cys Met Ser Met Gly Cys Val Ser Gly Cys Leu Cys Pro
    1760            1765            1770

Pro Gly Met Val Arg His Glu Asn Arg Cys Val Ala Leu Glu Arg
    1775            1780            1785

Cys Pro Cys Phe His Gln Gly Lys Glu Tyr Ala Pro Gly Glu Thr
    1790            1795            1800

Val Lys Ile Gly Cys Asn Thr Cys Val Cys Arg Asp Arg Lys Trp
    1805            1810            1815

Asn Cys Thr Asp His Val Cys Asp Ala Thr Cys Ser Thr Ile Gly
    1820            1825            1830

Met Ala His Tyr Leu Thr Phe Asp Gly Leu Lys Tyr Leu Phe Pro
    1835            1840            1845

Gly Glu Cys Gln Tyr Val Leu Val Gln Asp Tyr Cys Gly Ser Asn
    1850            1855            1860

Pro Gly Thr Phe Arg Ile Leu Val Gly Asn Lys Gly Cys Ser His
    1865            1870            1875

Pro Ser Val Lys Cys Lys Lys Arg Val Thr Ile Leu Val Glu Gly
    1880            1885            1890

Gly Glu Ile Glu Leu Phe Asp Gly Glu Val Asn Val Lys Arg Pro
    1895            1900            1905

Met Lys Asp Glu Thr His Phe Glu Val Val Glu Ser Gly Arg Tyr
    1910            1915            1920

Ile Ile Leu Leu Leu Gly Lys Ala Leu Ser Val Val Trp Asp Arg
    1925            1930            1935

His Leu Ser Ile Ser Val Val Leu Lys Gln Thr Tyr Gln Glu Lys
    1940            1945            1950

Val Cys Gly Leu Cys Gly Asn Phe Asp Gly Ile Gln Asn Asn Asp
    1955            1960            1965

Leu Thr Ser Ser Asn Leu Gln Val Glu Glu Asp Pro Val Asp Phe
    1970            1975            1980

Gly Asn Ser Trp Lys Val Ser Ser Gln Cys Ala Asp Thr Arg Lys
    1985            1990            1995

Val Pro Leu Asp Ser Ser Pro Ala Thr Cys His Asn Asn Ile Met
    2000            2005            2010

Lys Gln Thr Met Val Asp Ser Ser Cys Arg Ile Leu Thr Ser Asp
    2015            2020            2025

Val Phe Gln Asp Cys Asn Lys Leu Val Asp Pro Glu Pro Tyr Leu
    2030            2035            2040

Asp Val Cys Ile Tyr Asp Thr Cys Ser Cys Glu Ser Ile Gly Asp
    2045            2050            2055

Cys Ala Ala Phe Cys Asp Thr Ile Ala Ala Tyr Ala His Val Cys
    2060            2065            2070

Ala Gln His Gly Lys Val Val Thr Trp Arg Thr Ala Thr Leu Cys
    2075            2080            2085

Pro Gln Ser Cys Glu Glu Arg Asn Leu Arg Glu Asn Gly Tyr Glu
    2090            2095            2100

Ala Glu Trp Arg Tyr Asn Ser Cys Ala Pro Ala Cys Gln Val Thr
    2105            2110            2115

Cys Gln His Pro Glu Pro Leu Ala Cys Pro Val Gln Cys Val Glu
    2120            2125            2130

Gly Cys His Ala His Cys Pro Pro Gly Lys Ile Leu Asp Glu Leu
```

```
Leu Gln Thr Cys Val Asp Pro Glu Asp Cys Pro Val Cys Glu Val
    2150            2155                2160
Ala Gly Arg Arg Phe Ala Ser Gly Lys Lys Val Thr Leu Asn Pro
    2165            2170                2175
Ser Asp Pro Glu His Cys Gln Ile Cys His Cys Asp Val Val Asn
    2180            2185                2190
Leu Thr Cys Glu Ala Cys Gln Glu Pro Ile Asp Gly Gly Gly Gly
    2195            2200                2205
Ser Gly Gly Gly Gly Ser Leu Val Pro Arg Gly Ser Gly Gly Asp
    2210            2215                2220
Lys Thr His Thr Cys Pro Pro Cys Pro Ala Pro Glu Leu Leu Gly
    2225            2230                2235
Gly Pro Ser Val Phe Leu Phe Pro Pro Lys Pro Lys Asp Thr Leu
    2240            2245                2250
Met Ile Ser Arg Thr Pro Glu Val Thr Cys Val Val Val Asp Val
    2255            2260                2265
Ser His Glu Asp Pro Glu Val Lys Phe Asn Trp Tyr Val Asp Gly
    2270            2275                2280
Val Glu Val His Asn Ala Lys Thr Lys Pro Arg Glu Glu Gln Tyr
    2285            2290                2295
Asn Ser Thr Tyr Arg Val Val Ser Val Leu Thr Val Leu His Gln
    2300            2305                2310
Asp Trp Leu Asn Gly Lys Glu Tyr Lys Cys Lys Val Ser Asn Lys
    2315            2320                2325
Ala Leu Pro Ala Pro Ile Glu Lys Thr Ile Ser Lys Ala Lys Gly
    2330            2335                2340
Gln Pro Arg Glu Pro Gln Val Tyr Thr Leu Pro Pro Ser Arg Asp
    2345            2350                2355
Glu Leu Thr Lys Asn Gln Val Ser Leu Thr Cys Leu Val Lys Gly
    2360            2365                2370
Phe Tyr Pro Ser Asp Ile Ala Val Glu Trp Glu Ser Asn Gly Gln
    2375            2380                2385
Pro Glu Asn Asn Tyr Lys Thr Thr Pro Pro Val Leu Asp Ser Asp
    2390            2395                2400
Gly Ser Phe Phe Leu Tyr Ser Lys Leu Thr Val Asp Lys Ser Arg
    2405            2410                2415
Trp Gln Gln Gly Asn Val Phe Ser Cys Ser Val Met His Glu Ala
    2420            2425                2430
Leu His Asn His Tyr Thr Gln Lys Ser Leu Ser Leu Ser Pro Gly
    2435            2440                2445
Lys

<210> SEQ ID NO 89
<211> LENGTH: 48
<212> TYPE: PRT
<213> ORGANISM: Artificial
<220> FEATURE:
<223> OTHER INFORMATION: a 48-amino acid linker

<400> SEQUENCE: 89

Ile Ser Gly Gly Gly Gly Ser Gly Gly Gly Gly Ser Gly Gly Gly Gly
1               5                   10                  15
Ser Gly Gly Gly Gly Ser Gly Gly Gly Gly Ser Gly Gly Gly Gly Ser
                20                  25                  30
```

Leu Val Pro Arg Gly Ser Gly Gly Gly Ser Gly Gly Gly Gly Ser
                35                  40                  45

<210> SEQ ID NO 90
<211> LENGTH: 1665
<212> TYPE: PRT
<213> ORGANISM: Artificial
<220> FEATURE:
<223> OTHER INFORMATION: pSYN-FVIII-155 mature protein

<400> SEQUENCE: 90

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

```
Ser Glu Met Asp Val Val Arg Phe Asp Asp Asn Ser Pro Ser Phe
        355                 360                 365

Ile Gln Ile Arg Ser Val Ala Lys Lys His Pro Lys Thr Trp Val His
370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Val Arg Phe Met Ala Tyr Thr
                420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
        450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
                515                 520                 525

Leu Thr Arg Tyr Tyr Ser Ser Phe Val Asn Met Glu Arg Asp Leu Ala
        530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
        610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Ala His
                740                 745                 750

Gln Ala Glu Ile Thr Arg Thr Thr Leu Gln Ser Asp Gln Glu Glu Ile
        755                 760                 765
```

```
Asp Tyr Asp Asp Thr Ile Ser Val Glu Met Lys Lys Glu Asp Phe Asp
770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Ser Gly Ser
            820                 825                 830

Val Pro Gln Phe Lys Lys Val Phe Gln Glu Phe Thr Asp Gly Ser
        835                 840                 845

Phe Thr Gln Pro Leu Tyr Arg Gly Glu Leu Asn Glu His Leu Gly Leu
850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
            900                 905                 910

Val Lys Pro Asn Glu Thr Lys Thr Tyr Phe Trp Lys Val Gln His His
        915                 920                 925

Met Ala Pro Thr Lys Asp Glu Phe Asp Cys Lys Ala Trp Ala Tyr Phe
930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
            980                 985                 990

Lys Ser Trp Tyr Phe Thr Glu Asn Met Glu Arg Asn Cys Arg Ala Pro
        995                 1000                1005

Cys Asn Ile Gln Met Glu Asp Pro Thr Phe Lys Glu Asn Tyr Arg
    1010                1015                1020

Phe His Ala Ile Asn Gly Tyr Ile Met Asp Thr Leu Pro Gly Leu
    1025                1030                1035

Val Met Ala Gln Asp Gln Arg Ile Arg Trp Tyr Leu Leu Ser Met
    1040                1045                1050

Gly Ser Asn Glu Asn Ile His Ser Ile His Phe Ser Gly His Val
    1055                1060                1065

Phe Thr Val Arg Lys Lys Glu Glu Tyr Lys Met Ala Leu Tyr Asn
    1070                1075                1080

Leu Tyr Pro Gly Val Phe Glu Thr Val Glu Met Leu Pro Ser Lys
    1085                1090                1095

Ala Gly Ile Trp Arg Val Glu Cys Leu Ile Gly Glu His Leu His
    1100                1105                1110

Ala Gly Met Ser Thr Leu Phe Leu Val Tyr Ser Asn Lys Cys Gln
    1115                1120                1125

Thr Pro Leu Gly Met Ala Ser Gly His Ile Arg Asp Phe Gln Ile
    1130                1135                1140

Thr Ala Ser Gly Gln Tyr Gly Gln Trp Ala Pro Lys Leu Ala Arg
    1145                1150                1155

Leu His Tyr Ser Gly Ser Ile Asn Ala Trp Ser Thr Lys Glu Pro
    1160                1165                1170

Phe Ser Trp Ile Lys Val Asp Leu Leu Ala Pro Met Ile Ile His
```

```
            1175                1180                1185

Gly Ile Lys Thr Gln Gly Ala Arg Gln Lys Phe Ser Ser Leu Tyr
    1190                1195                1200

Ile Ser Gln Phe Ile Ile Met Tyr Ser Leu Asp Gly Lys Lys Trp
    1205                1210                1215

Gln Thr Tyr Arg Gly Asn Ser Thr Gly Thr Leu Met Val Phe Phe
    1220                1225                1230

Gly Asn Val Asp Ser Ser Gly Ile Lys His Asn Ile Phe Asn Pro
    1235                1240                1245

Pro Ile Ile Ala Arg Tyr Ile Arg Leu His Pro Thr His Tyr Ser
    1250                1255                1260

Ile Arg Ser Thr Leu Arg Met Glu Leu Met Gly Cys Asp Leu Asn
    1265                1270                1275

Ser Cys Ser Met Pro Leu Gly Met Glu Ser Lys Ala Ile Ser Asp
    1280                1285                1290

Ala Gln Ile Thr Ala Ser Ser Tyr Phe Thr Asn Met Phe Ala Thr
    1295                1300                1305

Trp Ser Pro Ser Lys Ala Arg Leu His Leu Gln Gly Arg Ser Asn
    1310                1315                1320

Ala Trp Arg Pro Gln Val Asn Asn Pro Lys Glu Trp Leu Gln Val
    1325                1330                1335

Asp Phe Gln Lys Thr Met Lys Val Thr Gly Val Thr Thr Gln Gly
    1340                1345                1350

Val Lys Ser Leu Leu Thr Ser Met Tyr Val Lys Glu Phe Leu Ile
    1355                1360                1365

Ser Ser Ser Gln Asp Gly His Gln Trp Thr Leu Phe Phe Gln Asn
    1370                1375                1380

Gly Lys Val Lys Val Phe Gln Gly Asn Gln Asp Ser Phe Thr Pro
    1385                1390                1395

Val Val Asn Ser Leu Asp Pro Pro Leu Leu Thr Arg Tyr Leu Arg
    1400                1405                1410

Ile His Pro Gln Ser Trp Val His Gln Ile Ala Leu Arg Met Glu
    1415                1420                1425

Val Leu Gly Cys Glu Ala Gln Asp Leu Tyr Asp Lys Thr His Thr
    1430                1435                1440

Cys Pro Pro Cys Pro Ala Pro Glu Leu Leu Gly Gly Pro Ser Val
    1445                1450                1455

Phe Leu Phe Pro Pro Lys Pro Lys Asp Thr Leu Met Ile Ser Arg
    1460                1465                1470

Thr Pro Glu Val Thr Cys Val Val Val Asp Val Ser His Glu Asp
    1475                1480                1485

Pro Glu Val Lys Phe Asn Trp Tyr Val Asp Gly Val Glu Val His
    1490                1495                1500

Asn Ala Lys Thr Lys Pro Arg Glu Glu Gln Tyr Asn Ser Thr Tyr
    1505                1510                1515

Arg Val Val Ser Val Leu Thr Val Leu His Gln Asp Trp Leu Asn
    1520                1525                1530

Gly Lys Glu Tyr Lys Cys Lys Val Ser Asn Lys Ala Leu Pro Ala
    1535                1540                1545

Pro Ile Glu Lys Thr Ile Ser Lys Ala Lys Gly Gln Pro Arg Glu
    1550                1555                1560

Pro Gln Val Tyr Thr Leu Pro Pro Ser Arg Asp Glu Leu Thr Lys
    1565                1570                1575
```

Asn Gln Val Ser Leu Thr Cys Leu Val Lys Gly Phe Tyr Pro Ser
        1580                1585                1590

Asp Ile Ala Val Glu Trp Glu Ser Asn Gly Gln Pro Glu Asn Asn
    1595                1600                1605

Tyr Lys Thr Thr Pro Pro Val Leu Asp Ser Asp Gly Ser Phe Phe
    1610                1615                1620

Leu Tyr Ser Lys Leu Thr Val Asp Lys Ser Arg Trp Gln Gln Gly
    1625                1630                1635

Asn Val Phe Ser Cys Ser Val Met His Glu Ala Leu His Asn His
    1640                1645                1650

Tyr Thr Gln Lys Ser Leu Ser Leu Ser Pro Gly Lys
    1655                1660                1665

<210> SEQ ID NO 91
<211> LENGTH: 5052
<212> TYPE: DNA
<213> ORGANISM: Artificial
<220> FEATURE:
<223> OTHER INFORMATION: pSYN-FVIII-155

<400> SEQUENCE: 91

| | |
|---|---|
| atgcaaatag agctctccac ctgcttcttt ctgtgccttt tgcgattctg ctttagtgcc | 60 |
| accagaagat actacctggg tgcagtggaa ctgtcatggg actatatgca aagtgatctc | 120 |
| ggtgagctgc ctgtggacgc aagatttcct cctagagtgc aaaatctttt ccattcaac | 180 |
| acctcagtcg tgtacaaaaa gactctgttt gtagaattca cggatcacct tttcaacatc | 240 |
| gctaagccaa ggccaccctg gatgggtctg ctaggtccta ccatccaggc tgaggtttat | 300 |
| gatacagtgg tcattacact taagaacatg gcttcccatc ctgtcagtct tcatgctgtt | 360 |
| ggtgtatcct actggaaagc ttctgaggga gctgaatatg atgatcagac cagtcaaagg | 420 |
| gagaaagaag atgataaagt cttccctggt ggaagccata catatgtctg gcaggtcctg | 480 |
| aaagagaatg gtccaatggc ctctgaccca ctgtgcctta cctactcata tctttctcat | 540 |
| gtggacctgg taaagacttt gaattcaggc ctcattggag ccctactagt atgtagagaa | 600 |
| gggagtctgg ccaaggaaaa gacacagacc ttgcacaaat ttatactact ttttgctgta | 660 |
| tttgatgaag ggaaaagttg gcactcagaa acaaagaact ccttgatgca ggatagggat | 720 |
| gctgcatctg ctcgggcctg gcctaaaatg cacacagtca atggttatgt aaacaggtct | 780 |
| ctgccaggtc tgattggatg ccacaggaaa tcagtctatt ggcatgtgat tggaatgggc | 840 |
| accactcctg aagtgcactc aatattcctc gaaggtcaca catttcttgt gaggaaccat | 900 |
| cgccaggcgt ccttggaaat ctcgccaata actttcctta ctgctcaaac actcttgatg | 960 |
| gaccttggac agtttctact gttttgtcat atctcttccc accaacatga tggcatggaa | 1020 |
| gcttatgtca agtagacag ctgtccagag aaccccaac tacgaatgaa aaataatgaa | 1080 |
| gaagcggaag actatgatga tgatcttact gattctgaaa tggatgtggt caggtttgat | 1140 |
| gatgacaact ctccttcctt tatccaaatt cgctcagttg ccaagaagca tcctaaaact | 1200 |
| tgggtacatt acattgctgc tgaagaggag gactgggact atgctccctt agtcctcgcc | 1260 |
| cccgatgaca aagttatat aagtcaatat ttgaacaatg ccctcagcg gattggtagg | 1320 |
| aagtacaaaa aagtccgatt tatggcatac acagatgaaa cctttaagac tcgtgaagct | 1380 |
| attcagcatg aatcaggaat cttgggacct tactttatg gggaagttgg agacacactg | 1440 |
| ttgattatat ttaagaatca agcaagcaga ccatataaca tctaccctca cggaatcact | 1500 |

-continued

```
gatgtccgtc ctttgtattc aaggagatta ccaaaaggtg taaaacattt gaaggatttt    1560
ccaattctgc caggagaaat attcaaatat aaatggacag tgactgtaga agatgggcca    1620
actaaatcag atcctcggtg cctgacccgc tattactcta gtttcgttaa tatggagaga    1680
gatctagctt caggactcat tggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata aacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatataccctt caaacacaaa    2040
atggtctatg aagacacact caccctattc ccattctcag agaaactgt cttcatgtcg    2100
atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctctcaaa acccaccagt cttgaaagcc catcaggcgg aaataactcg tactactctt    2340
cagtcagatc aagaggaaat tgactatgat gataccatat cagttgaaat gaagaaggaa    2400
gattttgaca tttatgatga ggatgaaaat cagagccccc gcagctttca aaagaaaaca    2460
cgacactatt ttattgctgc agtggagagg ctctgggatt atgggatgag tagctcccca    2520
catgttctaa gaaacagggc tcagagtggc agtgtccctc agttcaagaa agttgttttc    2580
caggaattta ctgatggctc ctttactcag cccttatacc gtggagaact aaatgaacat    2640
ttgggactcc tggggccata tataagagca gaagttgaag ataatatcat ggtaactttc    2700
agaaatcagg cctctcgtcc ctattccttc tattctagcc ttatttctta tgaggaagat    2760
cagaggcaag gagcagaacc tagaaaaaac tttgtcaagc ctaatgaaac caaaacttac    2820
ttttggaaag tgcaacatca tatggcaccc actaaagatg agtttgactg caaagcctgg    2880
gcttatttct ctgatgttga cctggaaaaa gatgtgcact caggcctgat tggaccccctt    2940
ctggtctgcc acactaacac actgaaccct gctcatggga caagtgac agtacaggaa    3000
tttgctctgt ttttcaccat ctttgatgag accaaaagct ggtacttcac tgaaaatatg    3060
gaaagaaact gcagggctcc ctgcaatatc cagatggaag atcccacttt taagagaat    3120
tatcgcttcc atgcaatcaa tggctacata atggatacac tacctggctt agtaatggct    3180
caggatcaaa ggattcgatg gtatctgctc agcatgggca gcaatgaaaa catccattct    3240
attcatttca gtggacatgt gttcactgta cgaaaaaaag aggagtataa aatggcactg    3300
tacaatctct atccaggtgt ttttgagaca gtggaaatgt taccatccaa agctggaatt    3360
tggcgggtgg aatgccttat tggcgagcat ctacatgctg ggatgagcac acttttctg    3420
gtgtacagca ataagtgtca gactcccctg ggaatggctt ctggacacat tagagatttt    3480
cagattacag cttcaggaca atatggacag tgggcccca agctggccag acttcattat    3540
tccggatcaa tcaatgcctg gagcaccaag gagcccttt cttggatcaa ggtggatctg    3600
ttggcaccaa tgattattca cggcatcaag acccagggtg cccgtcagaa gttctccagc    3660
ctctacatct ctcagtttat catcatgtat agtcttgatg ggaagaagtg gcagacttat    3720
cgaggaaatt ccactggaac cttaatggtc ttctttggca atgtggattc atctgggata    3780
aaacacaata ttttttaaccc tccaattatt gctcgataca tccgtttgca cccaactcat    3840
tatagcattc gcagcactct tcgcatggag ttgatgggct gtgattaaaa tagttgcagc    3900
```

-continued

```
atgccattgg gaatggagag taaagcaata tcagatgcac agattactgc ttcatcctac    3960
tttaccaata tgtttgccac ctggtctcct tcaaaagctc gacttcacct ccaagggagg    4020
agtaatgcct ggagacctca ggtgaataat ccaaaagagt ggctgcaagt ggacttccag    4080 aagcaatga aagtcacagg agtaactact cagggagtaa aatctctgct taccagcatg     4140
tatgtgaagg agttcctcat ctccagcagt caagatggcc atcagtggac tctcttttttt   4200 cagaatggca aagtaaaggt ttttcaggga aatcaagact ccttcacacc tgtggtgaac    4260
tctctagacc caccgttact gactcgctac cttcgaattc accccagag ttgggtgcac     4320 cagattgccc tgaggatgga ggttctgggc tgcgaggcac aggacctcta cgacaaaact   4380
cacacatgcc caccgtgccc agctccagaa ctcctgggcg gaccgtcagt cttcctcttc    4440
cccccaaaac ccaaggacac cctcatgatc tcccggaccc ctgaggtcac atgcgtggtg    4500
gtggacgtga gccacgaaga ccctgaggtc aagttcaact ggtacgtgga cggcgtggag   4560
gtgcataatg ccaagacaaa gccgcgggag gagcagtaca acagcacgta ccgtgtggtc   4620
agcgtcctca ccgtcctgca ccaggactgg ctgaatggca aggagtacaa gtgcaaggtc   4680
tccaacaaag ccctcccagc ccccatcgag aaaaccatct ccaaagccaa agggcagccc   4740
cgagaaccac aggtgtacac cctgcccca tcccgggatg agctgaccaa gaaccaggtc    4800
agcctgacct gcctggtcaa aggcttctat cccagcgaca tcgccgtgga gtgggagagc   4860
aatgggcagc cggagaacaa ctacaagacc acgcctcccg tgttggactc cgacggctcc   4920
ttcttcctct acagcaagct caccgtggac aagagcaggt ggcagcaggg gaacgtcttc   4980
tcatgctccg tgatgcatga ggctctgcac aaccactaca cgcagaagag cctctccctg   5040
tctccgggta aa                                                        5052
```

<210> SEQ ID NO 92
<211> LENGTH: 19
<212> TYPE: PRT
<213> ORGANISM: Artificial
<220> FEATURE:
<223> OTHER INFORMATION: GFVIII-159

<400> SEQUENCE: 92

Ile Asp Gly Gly Gly Gly Ser Gly Gly Gly Gly Ser Leu Val Pro Arg
1               5                   10                  15

Gly Ser Gly

<210> SEQ ID NO 93
<211> LENGTH: 34
<212> TYPE: PRT
<213> ORGANISM: Artificial
<220> FEATURE:
<223> OTHER INFORMATION: GFVIII-160

<400> SEQUENCE: 93

Ile Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Leu Val Pro Arg Gly
            20                  25                  30

Ser Gly

<210> SEQ ID NO 94
<211> LENGTH: 48
<212> TYPE: PRT
<213> ORGANISM: Artificial

```
<220> FEATURE:
<223> OTHER INFORMATION: FVIII-064

<400> SEQUENCE: 94

Ile Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Leu Val Pro Arg Gly Ser Gly Gly Gly Gly Ser Gly Gly Gly Gly Ser
        35                  40                  45

<210> SEQ ID NO 95
<211> LENGTH: 48
<212> TYPE: PRT
<213> ORGANISM: Artificial Sequence
<220> FEATURE:
<223> OTHER INFORMATION: VWF031

<400> SEQUENCE: 95

Ile Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Leu Val Pro Arg Gly Ser Gly Gly Gly Gly Ser Gly Gly Gly Gly Ser
        35                  40                  45

<210> SEQ ID NO 96
<211> LENGTH: 73
<212> TYPE: PRT
<213> ORGANISM: Artificial Sequence
<220> FEATURE:
<223> OTHER INFORMATION: VWF035

<400> SEQUENCE: 96

Ile Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser Gly Gly Gly Gly Ser Gly
        35                  40                  45

Gly Gly Gly Ser Gly Gly Gly Gly Ser Leu Val Pro Arg Gly Ser Gly
    50                  55                  60

Gly Gly Gly Ser Gly Gly Gly Gly Ser
65                  70

<210> SEQ ID NO 97
<211> LENGTH: 98
<212> TYPE: PRT
<213> ORGANISM: Artificial Sequence
<220> FEATURE:
<223> OTHER INFORMATION: VWF036

<400> SEQUENCE: 97

Ile Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser Gly Gly Gly Gly Ser Gly
        35                  40                  45

Gly Gly Gly Ser Gly Gly Gly Gly Ser Gly Gly Gly Gly Ser Gly Gly
    50                  55                  60
```

Gly Gly Ser Gly Gly Gly Ser Gly Gly Gly Ser Gly Gly Gly
65                  70                  75                  80

Gly Ser Leu Val Pro Arg Gly Ser Gly Gly Gly Ser Gly Gly Gly
                85                  90                  95

Gly Ser

<210> SEQ ID NO 98
<211> LENGTH: 54
<212> TYPE: PRT
<213> ORGANISM: Artificial Sequence
<220> FEATURE:
<223> OTHER INFORMATION: pSYN-VWF-051 linker

<400> SEQUENCE: 98

Ile Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Leu Pro Glu Thr Gly Ala Leu Arg Pro Arg Val Val Gly Gly Gly
        35                  40                  45

Ser Gly Gly Gly Gly Ser
    50

<210> SEQ ID NO 99
<211> LENGTH: 232
<212> TYPE: DNA
<213> ORGANISM: Artificial Sequence
<220> FEATURE:
<223> OTHER INFORMATION: Genewiz-Sequence no-10-210746313

<400> SEQUENCE: 99
aggagccgat atctggcggt ggaggttccg gtggcggggg atccggcggt ggaggttccg      60
gcggtggagg ttccggtggc gggggatccg gtggcggggg atccttacct gaaactggag     120
ccctgcggcc ccgggtcgtc ggcggtggag gttccggtgg cggggatcc gacaaaactc      180 acacatgccc accgtgccca gctccagaac tcctgggcgg accgtcagtc tt             232

<210> SEQ ID NO 100
<211> LENGTH: 4566
<212> TYPE: DNA
<213> ORGANISM: Artificial Sequence
<220> FEATURE:
<223> OTHER INFORMATION: pSYN-VWF051

<400> SEQUENCE: 100
atgattcctg ccagatttgc cggggtgctg cttgctctgg ccctcatttt gccagggacc      60
ctttgtgcag aaggaactcg cggcaggtca tccacggccc gatgcagcct tttcggaagt     120
gacttcgtca acaccttgga tgggagcatg tacagctttg cgggatactg cagttacctc     180
ctggcagggg gctgccagaa cgctcccttc tcgattattg ggacttcca gaatggcaag      240 agagtgagcc tctccgtgta tcttggggaa ttttttgaca tccatttgtt tgtcaatggt     300
accgtgacac aggggaccaa agagtctccc atgccctatg cctccaaagg ctgtatccta     360
gaaactgagg ctgggtacta caagctgtcc ggtgaggcct atggctttgt ggccaggatc     420
gatggcagcg gcaacttca gtcctgctg tcagacagat acttcaacaa gacctgcggg     480
ctgtgtggca actttaacat ctttgctgaa gatgacttta tgacccaaga agggacttg     540 acctcggacc cttatgactt tgccaactca tgggctctga gcagtggaga acagtggtgt     600

```
gaacgggcat ctcctcccag cagctcatgc aacatctcct ctggggaaat gcagaagggc    660
ctgtgggagc agtgccagct tctgaagagc acctcggtgt ttgcccgctg ccaccctctg    720
gtggaccccg agccttttgt ggccctgtgt gagaagactt tgtgtgagtg tgctgggggg    780
ctggagtgcg cctgccctgc cctcctggag tacgcccgga cctgtgccca ggagggaatg    840
gtgctgtacg gctggaccga ccacagcgcg tgcagcccag tgtgccctgc tggtatggag    900
tataggcagt gtgtgtcccc ttgcgccagg acctgccaga gcctgcacat caatgaaatg    960
tgtcaggagc gatgcgtgga tggctgcagc tgccctgagg acagctcct ggatgaaggc    1020
ctctgcgtgg agagcaccga gtgtccctgc gtgcattccg aaagcgcta ccctcccggc    1080
acctccctct ctcgagactg caacacctgc atttgccgaa acagccagtg gatctgcagc    1140
aatgaagaat gtccagggga gtgccttgtc actggtcaat cccacttcaa gagctttgac    1200
aacagatact tcaccttcag tgggatctgc cagtacctgc tggcccggga ttgccaggac    1260
cactccttct ccattgtcat tgagactgtc cagtgtgctg atgaccgcga cgctgtgtgc    1320
acccgctccg tcaccgtccg gctgcctggc ctgcacaaca gccttgtgaa actgaagcat    1380
ggggcaggag ttgccatgga tggccaggac atccagctcc ccctcctgaa aggtgacctc    1440
cgcatccagc atacagtgac ggcctccgtg cgcctcagct acggggagga cctgcagatg    1500
gactgggatg gccgcgggag gctgctggtg aagctgtccc ccgtctatgc cgggaagacc    1560
tgcggcctgt gtgggaatta caatggcaac cagggcgacg acttccttac ccctctgggg    1620
ctggcggagc cccgggtgga ggacttcggg aacgcctgga agctgcacgg ggactgccag    1680
gacctgcaga agcagcacag cgatccctgc gccctcaacc cgcgcatgac caggttctcc    1740
gaggaggcgt gcgcggtcct gacgtccccc acattcgagg cctgccatcg tgccgtcagc    1800
ccgctgccct acctgcggaa ctgccgctac gacgtgtgct cctgctcgga cggccgcgag    1860
tgcctgtgcg gcgccctggc cagctatgcc gcggcctgcg cggggagagg cgtgcgcgtc    1920
gcgtggcgcg agccaggccg ctgtgagctg aactgcccga aggccaggt gtacctgcag    1980
tgcgggaccc cctgcaacct gacctgccgc tctctctctt acccggatga ggaatgcaat    2040
gaggcctgcc tggagggctg cttctgcccc ccagggctct acatggatga gggggggac    2100
tgcgtgccca aggcccagtg cccctgttac tatgacggtg agatcttcca gccagaagac    2160
atcttctcag accatcacac catgtgctac tgtgaggatg gcttcatgca ctgtaccatg    2220
agtggagtcc ccggaagctt gctgcctgac gctgtcctca gcagtcccct gtctcatcgc    2280
agcaaaagga gcctatcctg tcggccccc atggtcaagc tggtgtgtcc cgctgacaac    2340
ctgcgggctg aagggctcga gtgtaccaaa acgtgccaga actatgacct ggagtgcatg    2400
agcatgggct gtgtctctgg ctgcctctgc cccccgggca tggtccggca tgagaacaga    2460
tgtgtggccc tggaaaggtg tccctgcttc catcagggca aggagtatgc ccctggagaa    2520
acagtgaaga ttggctgcaa cacttgtgtc tgtcgggacc ggaagtggaa ctgcacagac    2580
catgtgtgtg atgccacgtg ctccacgatc ggcatggccc actacctcac cttcgacggg    2640
ctcaaatacc tgttccccgg ggagtgccag tacgttctgg tgcaggatta ctgcggcagt    2700
aaccctggga cctttcggat cctagtgggg aataagggat gcagccaccc ctcagtgaaa    2760
tgcaagaaac gggtcaccat cctggtggag ggaggagaga ttgagctgtt tgacggggag    2820
gtgaatgtga agaggcccat gaaggatgag actcactttg aggtggtgga gtctggccgg    2880
tacatcattc tgctgctggg caaagccctc tccgtggtct gggaccgcca cctgagcatc    2940
tccgtggtcc tgaagcagac ataccaggag aaagtgtgtg gcctgtgtgg gaattttgat    3000
```

-continued

```
ggcatccaga acaatgacct caccagcagc aacctccaag tggaggaaga ccctgtggac   3060
tttgggaact cctggaaagt gagctcgcag tgtgctgaca ccagaaaagt gcctctggac   3120
tcatcccctg ccacctgcca taacaacatc atgaagcaga cgatggtgga ttcctcctgt   3180
agaatcctta ccagtgacgt cttccaggac tgcaacaagc tggtggaccc cgagccatat   3240
ctggatgtct gcatttacga cacctgctcc tgtgagtcca ttggggactg cgccgcattc   3300
tgcgacacca ttgctgccta tgcccacgtg tgtgcccagc atggcaaggt ggtgacctgg   3360
aggacggcca cattgtgccc ccagagctgc gaggagagga atctccggga gaacgggtat   3420
gaggctgagt ggcgctataa cagctgtgca cctgcctgtc aagtcacgtg tcagcaccct   3480
gagccactgg cctgccctgt gcagtgtgtg gagggctgcc atgcccactg ccctccaggg   3540
aaaatcctgg atgagctttt gcagacctgc gttgaccctg aagactgtcc agtgtgtgag   3600
gtggctggcc ggcgttttgc ctcaggaaag aaagtcacct tgaatcccag tgaccctgag   3660
cactgccaga tttgccactg tgatgttgtc aacctcacct gtgaagcctg ccaggagccg   3720
atatctggcg gtggaggttc cggtggcggg ggatccggcg gtggaggttc cggcggtgga   3780
ggttccggtg gcgggggatc cggtggcggg ggatccttac ctgaaactgg agccctgcgg   3840
ccccgggtcg tcggcggtgg aggttccggt ggcgggggat ccgacaaaac tcacacatgc   3900
ccaccgtgcc cagctccaga actcctgggc ggaccgtcag tcttcctctt ccccccaaaa   3960
cccaaggaca ccctcatgat ctcccggacc cctgaggtca catgcgtggt ggtggacgtg   4020
agccacgaag accctgaggt caagttcaac tggtacgtgg acggcgtgga ggtgcataat   4080
gccaagacaa agccgcggga ggagcagtac aacagcacgt accgtgtggt cagcgtcctc   4140
accgtcctgc accaggactg gctgaatggc aaggagtaca agtgcaaggt ctccaacaaa   4200
gccctcccag cccccatcga gaaaaccatc tccaaagcca aagggcagcc ccgagaacca   4260
caggtgtaca ccctgccccc atcccgggat gagctgacca agaaccaggt cagcctgacc   4320
tgcctggtca aaggcttcta tcccagcgac atcgccgtgg agtgggagag caatgggcag   4380
ccggagaaca actacaagac cacgcctccc gtgttggact ccgacggctc cttcttcctc   4440
tacagcaagc tcaccgtgga caagagcagg tggcagcagg ggaacgtctt ctcatgctcc   4500
gtgatgcatg aggctctgca caaccactac acgcagaaga gcctctccct gtctccgggt   4560
aaatga                                                              4566
```

<210> SEQ ID NO 101
<211> LENGTH: 1521
<212> TYPE: PRT
<213> ORGANISM: Artificial Sequence
<220> FEATURE:
<223> OTHER INFORMATION: VWF051

<400> SEQUENCE: 101

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80
```

```
Arg Val Ser Leu Ser Val Tyr Leu Gly Glu Phe Phe Asp Ile His Leu
            85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
            115                 120                 125

Leu Ser Gly Glu Ala Tyr Gly Phe Val Ala Arg Ile Asp Gly Ser Gly
130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
            165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
            195                 200                 205

Ser Cys Asn Ile Ser Ser Gly Glu Met Gln Lys Gly Leu Trp Glu Gln
            210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
            245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
            275                 280                 285

Ser Ala Cys Ser Pro Val Cys Pro Ala Gly Met Glu Tyr Arg Gln Cys
290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
            325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
            355                 360                 365

Thr Cys Ile Cys Arg Asn Ser Gln Trp Ile Cys Ser Asn Glu Glu Cys
370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
            405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
            435                 440                 445

Pro Gly Leu His Asn Ser Leu Val Lys Leu Lys His Gly Ala Gly Val
            450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
            485                 490                 495
```

```
Asp Leu Gln Met Asp Trp Asp Gly Arg Gly Arg Leu Leu Val Lys Leu
                500                 505                 510

Ser Pro Val Tyr Ala Gly Lys Thr Cys Gly Leu Cys Gly Asn Tyr Asn
            515                 520                 525

Gly Asn Gln Gly Asp Asp Phe Leu Thr Pro Ser Gly Leu Ala Glu Pro
        530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
```

```
              915                 920                 925
    Val Glu Gly Gly Glu Ile Glu Leu Phe Asp Gly Glu Val Asn Val Lys
        930                 935                 940

Arg Pro Met Lys Asp Glu Thr His Phe Glu Val Val Glu Ser Gly Arg
    945                 950                 955                 960

Tyr Ile Ile Leu Leu Leu Gly Lys Ala Leu Ser Val Val Trp Asp Arg
                    965                 970                 975

His Leu Ser Ile Ser Val Val Leu Lys Gln Thr Tyr Gln Glu Lys Val
                980                 985                 990

Cys Gly Leu Cys Gly Asn Phe Asp Gly Ile Gln Asn Asn Asp Leu Thr
                    995                 1000                1005

Ser Ser Asn Leu Gln Val Glu Glu Asp Pro Val Asp Phe Gly Asn
        1010                1015                1020

Ser Trp Lys Val Ser Ser Gln Cys Ala Asp Thr Arg Lys Val Pro
        1025                1030                1035

Leu Asp Ser Ser Pro Ala Thr Cys His Asn Asn Ile Met Lys Gln
        1040                1045                1050

Thr Met Val Asp Ser Ser Cys Arg Ile Leu Thr Ser Asp Val Phe
        1055                1060                1065

Gln Asp Cys Asn Lys Leu Val Asp Pro Glu Pro Tyr Leu Asp Val
        1070                1075                1080

Cys Ile Tyr Asp Thr Cys Ser Cys Glu Ser Ile Gly Asp Cys Ala
        1085                1090                1095

Ala Phe Cys Asp Thr Ile Ala Ala Tyr Ala His Val Cys Ala Gln
        1100                1105                1110

His Gly Lys Val Val Thr Trp Arg Thr Ala Thr Leu Cys Pro Gln
        1115                1120                1125

Ser Cys Glu Glu Arg Asn Leu Arg Glu Asn Gly Tyr Glu Ala Glu
        1130                1135                1140

Trp Arg Tyr Asn Ser Cys Ala Pro Ala Cys Gln Val Thr Cys Gln
        1145                1150                1155

His Pro Glu Pro Leu Ala Cys Pro Val Gln Cys Val Glu Gly Cys
        1160                1165                1170

His Ala His Cys Pro Pro Gly Lys Ile Leu Asp Glu Leu Leu Gln
        1175                1180                1185

Thr Cys Val Asp Pro Glu Asp Cys Pro Val Cys Glu Val Ala Gly
        1190                1195                1200

Arg Arg Phe Ala Ser Gly Lys Lys Val Thr Leu Asn Pro Ser Asp
        1205                1210                1215

Pro Glu His Cys Gln Ile Cys His Cys Asp Val Val Asn Leu Thr
        1220                1225                1230

Cys Glu Ala Cys Gln Glu Pro Ile Ser Gly Gly Gly Gly Ser Gly
        1235                1240                1245

Gly Gly Gly Ser Gly Gly Gly Gly Ser Gly Gly Gly Gly Ser Gly
        1250                1255                1260

Gly Gly Gly Ser Gly Gly Gly Gly Ser Leu Pro Glu Thr Gly Ala
        1265                1270                1275

Leu Arg Pro Arg Val Val Gly Gly Gly Ser Gly Gly Gly Gly
        1280                1285                1290

Ser Asp Lys Thr His Thr Cys Pro Pro Cys Pro Ala Pro Glu Leu
        1295                1300                1305

Leu Gly Gly Pro Ser Val Phe Leu Phe Pro Pro Lys Pro Lys Asp
        1310                1315                1320
```

Thr Leu Met Ile Ser Arg Thr Pro Glu Val Thr Cys Val Val Val
    1325                1330                1335

Asp Val Ser His Glu Asp Pro Glu Val Lys Phe Asn Trp Tyr Val
    1340                1345                1350

Asp Gly Val Glu Val His Asn Ala Lys Thr Lys Pro Arg Glu Glu
    1355                1360                1365

Gln Tyr Asn Ser Thr Tyr Arg Val Val Ser Val Leu Thr Val Leu
    1370                1375                1380

His Gln Asp Trp Leu Asn Gly Lys Glu Tyr Lys Cys Lys Val Ser
    1385                1390                1395

Asn Lys Ala Leu Pro Ala Pro Ile Glu Lys Thr Ile Ser Lys Ala
    1400                1405                1410

Lys Gly Gln Pro Arg Glu Pro Gln Val Tyr Thr Leu Pro Pro Ser
    1415                1420                1425

Arg Asp Glu Leu Thr Lys Asn Gln Val Ser Leu Thr Cys Leu Val
    1430                1435                1440

Lys Gly Phe Tyr Pro Ser Asp Ile Ala Val Glu Trp Glu Ser Asn
    1445                1450                1455

Gly Gln Pro Glu Asn Asn Tyr Lys Thr Thr Pro Pro Val Leu Asp
    1460                1465                1470

Ser Asp Gly Ser Phe Phe Leu Tyr Ser Lys Leu Thr Val Asp Lys
    1475                1480                1485

Ser Arg Trp Gln Gln Gly Asn Val Phe Ser Cys Ser Val Met His
    1490                1495                1500

Glu Ala Leu His Asn His Tyr Thr Gln Lys Ser Leu Ser Leu Ser
    1505                1510                1515

Pro Gly Lys
    1520

<210> SEQ ID NO 102
<211> LENGTH: 4389
<212> TYPE: DNA
<213> ORGANISM: Artificial Sequence
<220> FEATURE:
<223> OTHER INFORMATION: FVIII 265

<400> SEQUENCE: 102
atgcaaatag agctctccac ctgcttcttt ctgtgccttt gcgattctg ctttagtgga      60 ggaggaggag gagccaccag aagatactac ctgggtgcag tggaactgtc atgggactat    120
atgcaaagtg atctcggtga gctgcctgtg gacgcaagat tcctcctag agtgccaaaa     180 tcttttccat tcaacacctc agtcgtgtac aaaaagactc tgtttgtaga attcacggat    240 cacctttca acatcgctaa gccaaggcca ccctggatgg gtctgctagg tcctaccatc     300
caggctgagg tttatgatac agtggtcatt acacttaaga catggcttc ccatcctgtc    360 agtcttcatg ctgttggtgt atcctactgg aaagcttctg agggagctga atatgatgat     420
cagaccagtc aaagggagaa agaagatgat aaagtcttcc ctggtggaag ccatacatat    480
gtctggcagg tcctgaaaga gaatggtcca atgcctctg acccactgtg ccttacctac    540
tcatatcttt tcatgtgga cctggtaaaa gacttgaatt caggcctcat ggagccta    600 ctagtatgta gagaagggag tctggccaag gaaaagacac agaccttgca caaatttata    660 ctacttttg ctgtatttga tgaagggaaa agttggcact cagaaacaaa gaactccttg    720
atgcaggata gggatgctgc atctgctcgg gcctggccta aaatgcacac agtcaatggt    780

```
tatgtaaaca ggtctctgcc aggtctgatt ggatgccaca ggaaatcagt ctattggcat    840
gtgattggaa tgggcaccac tcctgaagtg cactcaatat tcctcgaagg tcacacattt    900
cttgtgagga accatcgcca ggcgtccttg aaatctcgc caataacttt ccttactgct     960
caaacactct tgatggacct tggacagttt ctactgtttt gtcatatctc ttcccaccaa   1020
catgatggca tggaagctta tgtcaaagta gacagctgtc cagaggaacc ccaactacga   1080
atgaaaaata tgaagaagc ggaagactat gatgatgatc ttactgattc tgaaatggat    1140
gtggtcaggt ttgatgatga caactctcct tcctttatcc aaattcgctc agttgccaag   1200
aagcatccta aaacttgggt acattacatt gctgctgaag aggaggactg ggactatgct   1260
cccttagtcc tcgcccccga tgacagaagt tataaaagtc aatatttgaa caatggccct   1320
cagcggattg gtaggaagta caaaaaagtc cgatttatgg catacacaga tgaaaccttt   1380
aagactcgtg aagctattca gcatgaatca ggaatcttgg gacctttact ttatggggaa   1440
gttggagaca cactgttgat tatatttaag aatcaagcaa gcagaccata taacatctac   1500
cctcacggaa tcactgatgt ccgtcctttg tattcaagga gattaccaaa aggtgtaaaa   1560
catttgaagg attttccaat tctgccagga gaaatattca aatataaatg gacagtgact   1620
gtagaagatg ggccaactaa atcagatcct cggtgcctga cccgctatta ctctagtttc   1680
gttaatatgg agagagatct agcttcagga ctcattggcc ctctcctcat ctgctacaaa   1740
gaatctgtag atcaaagagg aaaccagata atgtcagaca agaggaatgt catcctgttt   1800
tctgtatttg atgagaaccg aagctggtac ctcacagaga atatacaacg ctttctcccc   1860
aatccagctg gagtgcagct tgaggatcca gagttccaag cctccaacat catgcacagc   1920
atcaatggct atgttttga tagtttgcag ttgtcagttt gtttgcatga ggtggcatac   1980
tggtacattc taagcattgg agcacagact gacttccttt ctgtcttctt ctctggatat   2040
accttcaaac acaaaatggt ctatgaagac acactcaccc tattcccatt ctcaggagaa   2100
actgtcttca tgtcgatgga aaacccaggt ctatggattc tggggtgcca caactcagac   2160
tttcggaaca gaggcatgac cgccttactg aaggtttcta gttgtgacaa gaacactggt   2220
gattattacg aggacagtta tgaagatatt tcagcatact tgctgagtaa aaacaatgcc   2280
attgaaccaa gaagcttctc tcaaaaccca ccagtcttga aggcccatca ggccgaaata   2340
actcgtacta ctcttcagtc agatcaagag gaaattgact atgatgatac catatcagtt   2400
gaaatgaaga aggaagattt tgacatttat gatgaggatg aaaatcagag cccccgcagc   2460
tttcaaaaga aaacacgaca ctattttatt gctgcagtgg agaggctctg ggattatggg   2520
atgagtagct ccccacatgt tctaagaaac agggctcaga gtggcagtgt ccctcagttc   2580
aagaaagttg ttttccagga atttactgat ggctcctttta ctcagccctt ataccgtgga   2640
gaactaaatg aacatttggg cctcctcggc ccatatataa gagcagaagt tgaagataat   2700
atcatggtaa ctttcagaaa tcaggcctct cgtccctatt ccttctattc tagccttatt   2760
tcttatgagg aagatcagag gcaaggagca gaacctagaa aaaactttgt caagcctaat   2820
gaaaccaaaa cttacttttg gaaagtgcaa catcatatgg cacccactaa agatgagttt   2880
gactgcaaag cctgggctta tttctctgat gttgacctgg aaaagatgt gcactcaggc   2940
ctgattggac cccttctggt ctgccacact aacacactga accctgctca tgggagacaa   3000
gtgacagtac aggaatttgc tctgtttttc accatctttg atgagaccaa aagctggtac   3060
ttcactgaaa atatgaaaag aaactgcagg gctccctgca atatccagat ggaagatccc   3120
acttttaaag agaattatcg cttccatgca atcaatggct acataatgga tacactacct   3180
```

```
ggcttagtaa tggctcagga tcaaaggatt cgatggtatc tgctcagcat gggcagcaat    3240
gaaaacatcc attctattca tttcagtgga catgtgttca ctgtacgaaa aaaagaggag    3300
tataaaatgg cactgtacaa tctctatcca ggtgtttttg agacagtgga aatgttacca    3360
tccaaagctg gaatttggcg ggtggaatgc cttattggcg agcatctaca tgctgggatg    3420
agcacacttt ttctggtgta cagcaataag tgtcagactc ccctgggaat ggcttctgga    3480
cacattagag attttcagat tacagcttca ggacaatatg gacagtgggc cccaaagctg    3540
gccagacttc attattccgg atcaatcaat gcctggagca ccaaggagcc ttttcttgg    3600 atcaaggtgg atctgttggc accaatgatt attcacggca tcaagaccca gggtgcccgt    3660
cagaagttct ccagcctcta catctctcag tttatcatca tgtatagtct tgatgggaag    3720
aagtggcaga cttatcgagg aaattccact ggaaccttaa tggtcttctt tggcaatgtg    3780
gattcatctg gataaaaaca caatattttt aaccctccaa ttattgctcg atacatccgt    3840
ttgcacccaa ctcattatag cattcgcagc actcttcgca tggagttgat gggctgtgat    3900
ttaaatagtt gcagcatgcc attgggaatg gagagtaaag caatatcaga tgcacagatt    3960
actgcttcat cctactttac caatatgttt gccacctggt ctccttcaaa agctcgactt    4020
cacctccaag ggaggagtaa tgcctggaga cctcaggtga ataatccaaa agagtggctg    4080
caagtggact tccagaagac aatgaaagtc acaggagtaa ctactcaggg agtaaaatct    4140
ctgcttacca gcatgtatgt gaaggagttc ctcatctcca gcagtcaaga tggccatcag    4200
tggactctct tttttcagaa tggcaaagta aaggttttc agggaaatca agactccttc    4260
acacctgtgg tgaactctct agacccaccg ttactgactc gctaccttcg aattcacccc    4320
cagagttggg tgcaccagat tgccctgagg atggaggttc tgggctgcga ggcacaggac    4380
ctctactga                                                            4389
```

<210> SEQ ID NO 103
<211> LENGTH: 1462
<212> TYPE: PRT
<213> ORGANISM: Artificial Sequence
<220> FEATURE:
<223> OTHER INFORMATION: FVIII 265

<400> SEQUENCE: 103

```
Met Gln Ile Glu Leu Ser Thr Cys Phe Phe Leu Cys Leu Leu Arg Phe
1               5                  10                  15

Cys Phe Ser Gly Gly Gly Gly Ala Thr Arg Arg Tyr Tyr Leu Gly
            20                  25                  30

Ala Val Glu Leu Ser Trp Asp Tyr Met Gln Ser Asp Leu Gly Glu Leu
        35                  40                  45

Pro Val Asp Ala Arg Phe Pro Pro Arg Val Pro Lys Ser Phe Pro Phe
    50                  55                  60

Asn Thr Ser Val Val Tyr Lys Lys Thr Leu Phe Val Glu Phe Thr Asp
65                  70                  75                  80

His Leu Phe Asn Ile Ala Lys Pro Arg Pro Pro Trp Met Gly Leu Leu
                85                  90                  95

Gly Pro Thr Ile Gln Ala Glu Val Tyr Asp Thr Val Val Ile Thr Leu
            100                 105                 110

Lys Asn Met Ala Ser His Pro Val Ser Leu His Ala Val Gly Val Ser
        115                 120                 125

Tyr Trp Lys Ala Ser Glu Gly Ala Glu Tyr Asp Asp Gln Thr Ser Gln
    130                 135                 140
```

```
Arg Glu Lys Glu Asp Asp Lys Val Phe Pro Gly Gly Ser His Thr Tyr
145                 150                 155                 160

Val Trp Gln Val Leu Lys Glu Asn Gly Pro Met Ala Ser Asp Pro Leu
            165                 170                 175

Cys Leu Thr Tyr Ser Tyr Leu Ser His Val Asp Leu Val Lys Asp Leu
            180                 185                 190

Asn Ser Gly Leu Ile Gly Ala Leu Leu Val Cys Arg Glu Gly Ser Leu
        195                 200                 205

Ala Lys Glu Lys Thr Gln Thr Leu His Lys Phe Ile Leu Leu Phe Ala
210                 215                 220

Val Phe Asp Glu Gly Lys Ser Trp His Ser Glu Thr Lys Asn Ser Leu
225                 230                 235                 240

Met Gln Asp Arg Asp Ala Ala Ser Ala Arg Ala Trp Pro Lys Met His
            245                 250                 255

Thr Val Asn Gly Tyr Val Asn Arg Ser Leu Pro Gly Leu Ile Gly Cys
            260                 265                 270

His Arg Lys Ser Val Tyr Trp His Val Ile Gly Met Gly Thr Thr Pro
        275                 280                 285

Glu Val His Ser Ile Phe Leu Glu Gly His Thr Phe Leu Val Arg Asn
    290                 295                 300

His Arg Gln Ala Ser Leu Glu Ile Ser Pro Ile Thr Phe Leu Thr Ala
305                 310                 315                 320

Gln Thr Leu Leu Met Asp Leu Gly Gln Phe Leu Leu Phe Cys His Ile
                325                 330                 335

Ser Ser His Gln His Asp Gly Met Glu Ala Tyr Val Lys Val Asp Ser
        340                 345                 350

Cys Pro Glu Glu Pro Gln Leu Arg Met Lys Asn Asn Glu Glu Ala Glu
        355                 360                 365

Asp Tyr Asp Asp Asp Leu Thr Asp Ser Glu Met Asp Val Val Arg Phe
    370                 375                 380

Asp Asp Asp Asn Ser Pro Ser Phe Ile Gln Ile Arg Ser Val Ala Lys
385                 390                 395                 400

Lys His Pro Lys Thr Trp Val His Tyr Ile Ala Ala Glu Glu Glu Asp
                405                 410                 415

Trp Asp Tyr Ala Pro Leu Val Leu Ala Pro Asp Asp Arg Ser Tyr Lys
            420                 425                 430

Ser Gln Tyr Leu Asn Asn Gly Pro Gln Arg Ile Gly Arg Lys Tyr Lys
        435                 440                 445

Lys Val Arg Phe Met Ala Tyr Thr Asp Glu Thr Phe Lys Thr Arg Glu
    450                 455                 460

Ala Ile Gln His Glu Ser Gly Ile Leu Gly Pro Leu Leu Tyr Gly Glu
465                 470                 475                 480

Val Gly Asp Thr Leu Leu Ile Ile Phe Lys Asn Gln Ala Ser Arg Pro
            485                 490                 495

Tyr Asn Ile Tyr Pro His Gly Ile Thr Asp Val Arg Pro Leu Tyr Ser
            500                 505                 510

Arg Arg Leu Pro Lys Gly Val Lys His Leu Lys Asp Phe Pro Ile Leu
        515                 520                 525

Pro Gly Glu Ile Phe Lys Tyr Lys Trp Thr Val Thr Val Glu Asp Gly
        530                 535                 540

Pro Thr Lys Ser Asp Pro Arg Cys Leu Thr Arg Tyr Tyr Ser Ser Phe
545                 550                 555                 560
```

```
Val Asn Met Glu Arg Asp Leu Ala Ser Gly Leu Ile Gly Pro Leu Leu
                565                 570                 575

Ile Cys Tyr Lys Glu Ser Val Asp Gln Arg Gly Asn Gln Ile Met Ser
                580                 585                 590

Asp Lys Arg Asn Val Ile Leu Phe Ser Val Phe Asp Glu Asn Arg Ser
                595                 600                 605

Trp Tyr Leu Thr Glu Asn Ile Gln Arg Phe Leu Pro Asn Pro Ala Gly
                610                 615                 620

Val Gln Leu Glu Asp Pro Glu Phe Gln Ala Ser Asn Ile Met His Ser
625                 630                 635                 640

Ile Asn Gly Tyr Val Phe Asp Ser Leu Gln Leu Ser Val Cys Leu His
                645                 650                 655

Glu Val Ala Tyr Trp Tyr Ile Leu Ser Ile Gly Ala Gln Thr Asp Phe
                660                 665                 670

Leu Ser Val Phe Phe Ser Gly Tyr Thr Phe Lys His Lys Met Val Tyr
                675                 680                 685

Glu Asp Thr Leu Thr Leu Phe Pro Phe Ser Gly Glu Thr Val Phe Met
                690                 695                 700

Ser Met Glu Asn Pro Gly Leu Trp Ile Leu Gly Cys His Asn Ser Asp
705                 710                 715                 720

Phe Arg Asn Arg Gly Met Thr Ala Leu Leu Lys Val Ser Ser Cys Asp
                725                 730                 735

Lys Asn Thr Gly Asp Tyr Tyr Glu Asp Ser Tyr Glu Asp Ile Ser Ala
                740                 745                 750

Tyr Leu Leu Ser Lys Asn Asn Ala Ile Glu Pro Arg Ser Phe Ser Gln
                755                 760                 765

Asn Pro Pro Val Leu Lys Ala His Gln Ala Glu Ile Thr Arg Thr Thr
770                 775                 780

Leu Gln Ser Asp Gln Glu Glu Ile Asp Tyr Asp Asp Thr Ile Ser Val
785                 790                 795                 800

Glu Met Lys Lys Glu Asp Phe Asp Ile Tyr Asp Glu Asp Glu Asn Gln
                805                 810                 815

Ser Pro Arg Ser Phe Gln Lys Lys Thr Arg His Tyr Phe Ile Ala Ala
                820                 825                 830

Val Glu Arg Leu Trp Asp Tyr Gly Met Ser Ser Ser Pro His Val Leu
                835                 840                 845

Arg Asn Arg Ala Gln Ser Gly Ser Val Pro Gln Phe Lys Lys Val Val
850                 855                 860

Phe Gln Glu Phe Thr Asp Gly Ser Phe Thr Gln Pro Leu Tyr Arg Gly
865                 870                 875                 880

Glu Leu Asn Glu His Leu Gly Leu Leu Gly Pro Tyr Ile Arg Ala Glu
                885                 890                 895

Val Glu Asp Asn Ile Met Val Thr Phe Arg Asn Gln Ala Ser Arg Pro
                900                 905                 910

Tyr Ser Phe Tyr Ser Ser Leu Ile Ser Tyr Glu Glu Asp Gln Arg Gln
                915                 920                 925

Gly Ala Glu Pro Arg Lys Asn Phe Val Lys Pro Asn Glu Thr Lys Thr
                930                 935                 940

Tyr Phe Trp Lys Val Gln His His Met Ala Pro Thr Lys Asp Glu Phe
945                 950                 955                 960

Asp Cys Lys Ala Trp Ala Tyr Phe Ser Asp Val Asp Leu Glu Lys Asp
                965                 970                 975

Val His Ser Gly Leu Ile Gly Pro Leu Leu Val Cys His Thr Asn Thr
```

-continued

```
                980             985             990
Leu Asn Pro Ala His Gly Arg Gln Val Thr Val Gln Glu Phe Ala Leu
            995                 1000                1005

Phe Phe Thr Ile Phe Asp Glu Thr Lys Ser Trp Tyr Phe Thr Glu
    1010                1015                1020

Asn Met Glu Arg Asn Cys Arg Ala Pro Cys Asn Ile Gln Met Glu
    1025                1030                1035

Asp Pro Thr Phe Lys Glu Asn Tyr Arg Phe His Ala Ile Asn Gly
    1040                1045                1050

Tyr Ile Met Asp Thr Leu Pro Gly Leu Val Met Ala Gln Asp Gln
    1055                1060                1065

Arg Ile Arg Trp Tyr Leu Leu Ser Met Gly Ser Asn Glu Asn Ile
    1070                1075                1080

His Ser Ile His Phe Ser Gly His Val Phe Thr Val Arg Lys Lys
    1085                1090                1095

Glu Glu Tyr Lys Met Ala Leu Tyr Asn Leu Tyr Pro Gly Val Phe
    1100                1105                1110

Glu Thr Val Glu Met Leu Pro Ser Lys Ala Gly Ile Trp Arg Val
    1115                1120                1125

Glu Cys Leu Ile Gly Glu His Leu His Ala Gly Met Ser Thr Leu
    1130                1135                1140

Phe Leu Val Tyr Ser Asn Lys Cys Gln Thr Pro Leu Gly Met Ala
    1145                1150                1155

Ser Gly His Ile Arg Asp Phe Gln Ile Thr Ala Ser Gly Gln Tyr
    1160                1165                1170

Gly Gln Trp Ala Pro Lys Leu Ala Arg Leu His Tyr Ser Gly Ser
    1175                1180                1185

Ile Asn Ala Trp Ser Thr Lys Glu Pro Phe Ser Trp Ile Lys Val
    1190                1195                1200

Asp Leu Leu Ala Pro Met Ile Ile His Gly Ile Lys Thr Gln Gly
    1205                1210                1215

Ala Arg Gln Lys Phe Ser Ser Leu Tyr Ile Ser Gln Phe Ile Ile
    1220                1225                1230

Met Tyr Ser Leu Asp Gly Lys Lys Trp Gln Thr Tyr Arg Gly Asn
    1235                1240                1245

Ser Thr Gly Thr Leu Met Val Phe Phe Gly Asn Val Asp Ser Ser
    1250                1255                1260

Gly Ile Lys His Asn Ile Phe Asn Pro Pro Ile Ile Ala Arg Tyr
    1265                1270                1275

Ile Arg Leu His Pro Thr His Tyr Ser Ile Arg Ser Thr Leu Arg
    1280                1285                1290

Met Glu Leu Met Gly Cys Asp Leu Asn Ser Cys Ser Met Pro Leu
    1295                1300                1305

Gly Met Glu Ser Lys Ala Ile Ser Asp Ala Gln Ile Thr Ala Ser
    1310                1315                1320

Ser Tyr Phe Thr Asn Met Phe Ala Thr Trp Ser Pro Ser Lys Ala
    1325                1330                1335

Arg Leu His Leu Gln Gly Arg Ser Asn Ala Trp Arg Pro Gln Val
    1340                1345                1350

Asn Asn Pro Lys Glu Trp Leu Gln Val Asp Phe Gln Lys Thr Met
    1355                1360                1365

Lys Val Thr Gly Val Thr Thr Gln Gly Val Lys Ser Leu Leu Thr
    1370                1375                1380
```

| Ser | Met | Tyr | Val | Lys | Glu | Phe | Leu | Ile | Ser | Ser | Gln | Asp | Gly |
|---|---|---|---|---|---|---|---|---|---|---|---|---|---|
| 1385 | | | | 1390 | | | | | 1395 | | | | |

| His | Gln | Trp | Thr | Leu | Phe | Phe | Gln | Asn | Gly | Lys | Val | Lys | Val | Phe |
|---|---|---|---|---|---|---|---|---|---|---|---|---|---|---|
| 1400 | | | | | 1405 | | | | | 1410 | | | | |

| Gln | Gly | Asn | Gln | Asp | Ser | Phe | Thr | Pro | Val | Val | Asn | Ser | Leu | Asp |
|---|---|---|---|---|---|---|---|---|---|---|---|---|---|---|
| 1415 | | | | | 1420 | | | | | 1425 | | | | |

| Pro | Pro | Leu | Leu | Thr | Arg | Tyr | Leu | Arg | Ile | His | Pro | Gln | Ser | Trp |
|---|---|---|---|---|---|---|---|---|---|---|---|---|---|---|
| 1430 | | | | | 1435 | | | | | 1440 | | | | |

| Val | His | Gln | Ile | Ala | Leu | Arg | Met | Glu | Val | Leu | Gly | Cys | Glu | Ala |
|---|---|---|---|---|---|---|---|---|---|---|---|---|---|---|
| 1445 | | | | | 1450 | | | | | 1455 | | | | |

| Gln | Asp | Leu | Tyr |
|---|---|---|---|
| 1460 | | | |

<210> SEQ ID NO 104
<211> LENGTH: 5691
<212> TYPE: DNA
<213> ORGANISM: Artificial Sequence
<220> FEATURE:
<223> OTHER INFORMATION: FVIII198

<400> SEQUENCE: 104

| | |
|---|---|
| atgcaaatag agctctccac ctgcttcttt ctgtgccttt tgcgattctg ctttagtgcc | 60 |
| accagaagat actacctggg tgcagtggaa ctgtcatggg actatatgca aagtgatctc | 120 |
| ggtgagctgc ctgtggacgc aagatttcct cctagagtgc caaaatcttt tccattcaac | 180 |
| acctcagtcg tgtacaaaaa gactctgttt gtagaattca cggatcacct tttcaacatc | 240 |
| gctaagccaa ggccaccctg gatgggtctg ctaggtccta ccatccaggc tgaggtttat | 300 |
| gatacagtgg tcattacact taagaacatg gcttcccatc ctgtcagtct tcatgctgtt | 360 |
| ggtgtatcct actggaaagc ttctgaggga ctgaatatg atgatcagac cagtcaaagg | 420 |
| gagaaagaag atgataaagt cttccctggt ggaagccata catatgtctg gcaggtcctg | 480 |
| aaagagaatg gtccaatggc ctctgaccca ctgtgcctta cctactcata tctttctcat | 540 |
| gtggacctgg taaaagactt gaattcaggc ctcattggag ccctactagt atgtagagaa | 600 |
| gggagtctgg ccaaggaaaa gacacagacc ttgcacaaat ttatactact ttttgctgta | 660 |
| tttgatgaag ggaaaagttg gcactcagaa acaaagaact ccttgatgca ggatagggat | 720 |
| gctgcatctg ctcgggcctg gcctaaaatg cacacagtca atggttatgt aaacaggtct | 780 |
| ctgccaggtc tgattggatg ccacaggaaa tcagtctatt ggcatgtgat tggaatgggc | 840 |
| accactcctg aagtgcactc aatattcctc gaaggtcaca tttcttgt gaggaaccat | 900 |
| cgccaggcgt ccttggaaat ctcgccaata actttcctta ctgctcaaac actcttgatg | 960 |
| gaccttggac agtttctact gttttgtcat atctcttccc accaacatga tggcatggaa | 1020 |
| gcttatgtca agtagacag ctgtccagag gaaccccaac tacgaatgaa aaataatgaa | 1080 |
| gaagcggaag actatgatga tgatcttact gattctgaaa tggatgtggt caggtttgat | 1140 |
| gatgacaact ctccttcctt tatccaaatt cgctcagttg ccaagaagca tcctaaaact | 1200 |
| tgggtacatt acattgctgc tgaagaggag gactgggact atgctccctt agtcctcgcc | 1260 |
| cccgatgaca aagttatata aagtcaatat ttgaacaatg ccctcagcg gattggtagg | 1320 |
| aagtacaaaa aagtccgatt tatggcatac acagatgaaa cctttaagac tcgtgaagct | 1380 |
| attcagcatg aatcaggaat cttgggacct tactttatg gggaagttgg agacacactg | 1440 |
| ttgattatat ttaagaatca agcaagcaga ccatataaca tctaccctca cggaatcact | 1500 |

```
gatgtccgtc ctttgtattc aaggagatta ccaaaaggtg taaaacattt gaaggatttt    1560
ccaattctgc caggagaaat attcaaatat aaatggacag tgactgtaga agatgggcca    1620
actaaatcag atcctcggtg cctgacccgc tattactcta gtttcgttaa tatggagaga    1680
gatctagctt caggactcat tggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata aacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg atataccctt caaacacaaa    2040
atggtctatg aagacacact caccctattc ccattctcag agaaactgt cttcatgtcg    2100 atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctctcaga attcaagaca ccctagcact aggcaaaagc aatttaatgc caccacaatt    2340
ccagaaaatg acatagagaa gactgaccct tggtttgcac acagaacacc tatgcctaaa    2400
atacaaaatg tctcctctag tgatttgttg atgctcttgc gacagagtcc tactccacat    2460
gggctatcct tatctgatct ccaagaagcc aaatatgaga ctttttctga tgatccatca    2520
cctggagcaa tagacagtaa taacagcctg tctgaaatga cacacttcag gccacagctc    2580
catcacagtg gggacatggt attttaccct gagtcaggcc tccaattaag attaaatgag    2640
aaactgggga caactgcagc aacagagttg aagaaacttg atttcaaagt ttctagtaca    2700
tcaaataatc tgatttcaac aattccatca gacaatttgg cagcaggtac tgataataca    2760
agttccttag accccaag tatgccagtt cattatgata gtcaattaga taccactcta    2820
tttggcaaaa agtcatctcc ccttactgag tctggtggac ctctgagctt gagtgaagaa    2880
aataatgatt caaagttgtt agaatcaggt ttaatgaata gccaagaaag ttcatgggga    2940
aaaaatgtat cgtcagaaat aactcgtact actcttcagt cagatcaaga ggaaattgac    3000
tatgatgata ccatatcagt tgaaatgaag aaggaagatt ttgacattta tgatgaggat    3060
gaaaatcaga gcccccgcag cttttcaaaag aaaacacgac actatttttat tgctgcagtg    3120 gagaggctct gggattatgg gatgagtagc tccccacatg ttctaagaaa cagggctcag    3180
agtggcagtg tccctcagtt caagaaagtt gttttccagg aatttactga tggctccttt    3240
actcagccct tataccgtgg agaactaaat gaacatttgg gactcctggg gccatatata    3300
agagcagaag ttgaagataa tatcatggta actttcagaa atcaggcctc tcgtccctat    3360
tccttctatt ctagccttat ttcttatgag gaagatcaga ggcaaggagc agaacctaga    3420
aaaaactttg tcaagcctaa tgaaaccaaa acttacttttt ggaaagtgca acatcatatg    3480
gcacccacta aagatgagtt tgactgcaaa gcctgggctt atttctctga tgttgacctg    3540 gaaaagatg tgcactcagg cctgattgga ccccttctgg tctgccacac taacacactg    3600
aaccctgctc atgggagaca agtgacagta caggaatttg ctctgttttt caccatcttt    3660
gatgagacca aaagctggta cttcactgaa aatatggaaa gaaactgcag ggctccctgc    3720
aatatccaga tggaagatcc cactttttaaa gagaattatc gcttccatgc aatcaatggc    3780
tacataatgg atacactacc tggcttagta atggctcagg atcaaaggat tcgatggtat    3840
ctgctcagca tgggcagcaa tgaaaacatc cattctattc atttcagtgg acatgtgttc    3900
```

```
actgtacgaa aaaaagagga gtataaaatg gcactgtaca atctctatcc aggtgttttt    3960
gagacagtgg aaatgttacc atccaaagct ggaatttggc gggtggaatg ccttattggc    4020
gagcatctac atgctgggat gagcacactt tttctggtgt acagcaataa gtgtcagact    4080
cccctgggaa tggcttctgg acacattaga gattttcaga ttacagcttc aggacaatat    4140
ggacagtggg ccccaaagct ggccagactt cattattccg gatcaatcaa tgcctggagc    4200
accaaggagc ccttttcttg atcaaggtg gatctgttgg caccaatgat tattcacggc    4260
atcaagaccc agggtgcccg tcagaagttc tccagcctct acatctctca gtttatcatc    4320
atgtatagtc ttgatgggaa gaagtggcag acttatcgag gaaattccac tggaacctta    4380
atggtcttct ttggcaatgt ggattcatct gggataaaac acaatatttt taaccctcca    4440
attattgctc gatacatccg tttgcaccca actcattata gcattcgcag cactcttcgc    4500
atggagttga tgggctgtga tttaaatagt tgcagcatgc cattgggaat ggagagtaaa    4560
gcaatatcag atgcacagat tactgcttca tcctacttta ccaatatgtt tgccacctgg    4620
tctccttcaa aagctcgact tcacctccaa gggaggagta atgcctggag acctcaggtg    4680
aataatccaa aagagtggct gcaagtggac ttccagaaga caatgaaagt cacaggagta    4740
actactcagg gagtaaaatc tctgcttacc agcatgtatg tgaaggagtt cctcatctcc    4800
agcagtcaag atgccatca gtggactctc ttttttcaga atggcaaagt aaaggttttt    4860
cagggaaatc aagactcctt cacacctgtg gtgaactctc tagacccacc gttactgact    4920
cgctaccttc gaattcaccc ccagagttgg gtgcaccaga ttgccctgag gatggaggtt    4980
ctgggctgcg aggcacagga cctctacgac aaaactcaca catgcccacc gtgcccagct    5040
ccagaactcc tgggcggacc gtcagtcttc ctcttccccc caaaacccaa ggacaccctc    5100
atgatctccc ggacccctga ggtcacatgc gtggtggtgg acgtgagcca cgaagaccct    5160
gaggtcaagt tcaactggta cgtggacggc gtggaggtgc ataatgccaa gacaaagccg    5220
cgggaggagc agtacaacag cacgtaccgt gtggtcagcg tcctcaccgt cctgcaccag    5280
gactggctga atggcaagga gtacaagtgc aaggtctcca acaaagccct cccagccccc    5340
atcgagaaaa ccatctccaa agccaaaggg cagccccgag aaccacaggt gtacaccctg    5400
cccccatccc gggatgagct gaccaagaac caggtcagcc tgacctgcct ggtcaaaggc    5460
ttctatccca gcgacatcgc cgtggagtgg gagagcaatg ggcagccgga gaacaactac    5520
aagaccacgc ctcccgtgtt ggactccgac ggctccttct tcctctacag caagctcacc    5580
gtggacaaga gcaggtggca gcaggggaac gtcttctcat gctccgtgat gcatgaggct    5640
ctgcacaacc actacacgca gaagagcctc tccctgtctc cgggtaaatg a             5691
```

<210> SEQ ID NO 105
<211> LENGTH: 1896
<212> TYPE: PRT
<213> ORGANISM: Artificial Sequence
<220> FEATURE:
<223> OTHER INFORMATION: FVIII 198

<400> SEQUENCE: 105

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

```
Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460
```

```
Ser Gly Ile Leu Gly Pro Leu Leu Tyr Gly Val Gly Asp Thr Leu
465                 470                 475                 480

Leu Ile Ile Phe Lys Asn Gln Ala Ser Arg Pro Tyr Asn Ile Tyr Pro
            485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
            530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
                675                 680                 685

Leu Phe Pro Phe Ser Gly Glu Thr Val Phe Met Ser Met Glu Asn Pro
            690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
            755                 760                 765

Ser Thr Arg Gln Lys Gln Phe Asn Ala Thr Thr Ile Pro Glu Asn Asp
            770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
            835                 840                 845

Ser Leu Ser Glu Met Thr His Phe Arg Pro Gln Leu His His Ser Gly
            850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
```

```
                885               890                895
Val Ser Ser Thr Ser Asn Asn Leu Ile Ser Thr Ile Pro Ser Asp Asn
            900                905                910

Leu Ala Ala Gly Thr Asp Asn Thr Ser Ser Leu Gly Pro Pro Ser Met
            915                920                925

Pro Val His Tyr Asp Ser Gln Leu Asp Thr Thr Leu Phe Gly Lys Lys
            930                935                940

Ser Ser Pro Leu Thr Glu Ser Gly Gly Pro Leu Ser Leu Ser Glu Glu
945                950                955                960

Asn Asn Asp Ser Lys Leu Leu Glu Ser Gly Leu Met Asn Ser Gln Glu
            965                970                975

Ser Ser Trp Gly Lys Asn Val Ser Ser Glu Ile Thr Arg Thr Thr Leu
            980                985                990

Gln Ser Asp Gln Glu Glu Ile Asp Tyr Asp Asp Thr Ile Ser Val Glu
            995                1000               1005

Met Lys Lys Glu Asp Phe Asp Ile Tyr Asp Glu Asp Glu Asn Gln
        1010               1015               1020

Ser Pro Arg Ser Phe Gln Lys Lys Thr Arg His Tyr Phe Ile Ala
        1025               1030               1035

Ala Val Glu Arg Leu Trp Asp Tyr Gly Met Ser Ser Ser Pro His
        1040               1045               1050

Val Leu Arg Asn Arg Ala Gln Ser Gly Ser Val Pro Gln Phe Lys
        1055               1060               1065

Lys Val Val Phe Gln Glu Phe Thr Asp Gly Ser Phe Thr Gln Pro
        1070               1075               1080

Leu Tyr Arg Gly Glu Leu Asn Glu His Leu Gly Leu Leu Gly Pro
        1085               1090               1095

Tyr Ile Arg Ala Glu Val Glu Asp Asn Ile Met Val Thr Phe Arg
        1100               1105               1110

Asn Gln Ala Ser Arg Pro Tyr Ser Phe Tyr Ser Ser Leu Ile Ser
        1115               1120               1125

Tyr Glu Glu Asp Gln Arg Gln Gly Ala Glu Pro Arg Lys Asn Phe
        1130               1135               1140

Val Lys Pro Asn Glu Thr Lys Thr Tyr Phe Trp Lys Val Gln His
        1145               1150               1155

His Met Ala Pro Thr Lys Asp Glu Phe Asp Cys Lys Ala Trp Ala
        1160               1165               1170

Tyr Phe Ser Asp Val Asp Leu Glu Lys Asp Val His Ser Gly Leu
        1175               1180               1185

Ile Gly Pro Leu Leu Val Cys His Thr Asn Thr Leu Asn Pro Ala
        1190               1195               1200

His Gly Arg Gln Val Thr Val Gln Glu Phe Ala Leu Phe Phe Thr
        1205               1210               1215

Ile Phe Asp Glu Thr Lys Ser Trp Tyr Phe Thr Glu Asn Met Glu
        1220               1225               1230

Arg Asn Cys Arg Ala Pro Cys Asn Ile Gln Met Glu Asp Pro Thr
        1235               1240               1245

Phe Lys Glu Asn Tyr Arg Phe His Ala Ile Asn Gly Tyr Ile Met
        1250               1255               1260

Asp Thr Leu Pro Gly Leu Val Met Ala Gln Asp Gln Arg Ile Arg
        1265               1270               1275

Trp Tyr Leu Leu Ser Met Gly Ser Asn Glu Asn Ile His Ser Ile
        1280               1285               1290
```

```
His Phe Ser Gly His Val Phe Thr Val Arg Lys Lys Glu Glu Tyr
    1295            1300                1305

Lys Met Ala Leu Tyr Asn Leu Tyr Pro Gly Val Phe Glu Thr Val
    1310            1315                1320

Glu Met Leu Pro Ser Lys Ala Gly Ile Trp Arg Val Glu Cys Leu
    1325            1330                1335

Ile Gly Glu His Leu His Ala Gly Met Ser Thr Leu Phe Leu Val
    1340            1345                1350

Tyr Ser Asn Lys Cys Gln Thr Pro Leu Gly Met Ala Ser Gly His
    1355            1360                1365

Ile Arg Asp Phe Gln Ile Thr Ala Ser Gly Gln Tyr Gly Gln Trp
    1370            1375                1380

Ala Pro Lys Leu Ala Arg Leu His Tyr Ser Gly Ser Ile Asn Ala
    1385            1390                1395

Trp Ser Thr Lys Glu Pro Phe Ser Trp Ile Lys Val Asp Leu Leu
    1400            1405                1410

Ala Pro Met Ile Ile His Gly Ile Lys Thr Gln Gly Ala Arg Gln
    1415            1420                1425

Lys Phe Ser Ser Leu Tyr Ile Ser Gln Phe Ile Ile Met Tyr Ser
    1430            1435                1440

Leu Asp Gly Lys Lys Trp Gln Thr Tyr Arg Gly Asn Ser Thr Gly
    1445            1450                1455

Thr Leu Met Val Phe Phe Gly Asn Val Asp Ser Ser Gly Ile Lys
    1460            1465                1470

His Asn Ile Phe Asn Pro Pro Ile Ile Ala Arg Tyr Ile Arg Leu
    1475            1480                1485

His Pro Thr His Tyr Ser Ile Arg Ser Thr Leu Arg Met Glu Leu
    1490            1495                1500

Met Gly Cys Asp Leu Asn Ser Cys Ser Met Pro Leu Gly Met Glu
    1505            1510                1515

Ser Lys Ala Ile Ser Asp Ala Gln Ile Thr Ala Ser Ser Tyr Phe
    1520            1525                1530

Thr Asn Met Phe Ala Thr Trp Ser Pro Ser Lys Ala Arg Leu His
    1535            1540                1545

Leu Gln Gly Arg Ser Asn Ala Trp Arg Pro Gln Val Asn Asn Pro
    1550            1555                1560

Lys Glu Trp Leu Gln Val Asp Phe Gln Lys Thr Met Lys Val Thr
    1565            1570                1575

Gly Val Thr Thr Gln Gly Val Lys Ser Leu Leu Thr Ser Met Tyr
    1580            1585                1590

Val Lys Glu Phe Leu Ile Ser Ser Ser Gln Asp Gly His Gln Trp
    1595            1600                1605

Thr Leu Phe Phe Gln Asn Gly Lys Val Lys Val Phe Gln Gly Asn
    1610            1615                1620

Gln Asp Ser Phe Thr Pro Val Val Asn Ser Leu Asp Pro Pro Leu
    1625            1630                1635

Leu Thr Arg Tyr Leu Arg Ile His Pro Gln Ser Trp Val His Gln
    1640            1645                1650

Ile Ala Leu Arg Met Glu Val Leu Gly Cys Glu Ala Gln Asp Leu
    1655            1660                1665

Tyr Asp Lys Thr His Thr Cys Pro Pro Cys Pro Ala Pro Glu Leu
    1670            1675                1680
```

```
Leu Gly Gly Pro Ser Val Phe Leu Phe Pro Pro Lys Pro Lys Asp
    1685                1690                1695

Thr Leu Met Ile Ser Arg Thr Pro Glu Val Thr Cys Val Val Val
    1700                1705                1710

Asp Val Ser His Glu Asp Pro Glu Val Lys Phe Asn Trp Tyr Val
    1715                1720                1725

Asp Gly Val Glu Val His Asn Ala Lys Thr Lys Pro Arg Glu Glu
    1730                1735                1740

Gln Tyr Asn Ser Thr Tyr Arg Val Val Ser Val Leu Thr Val Leu
    1745                1750                1755

His Gln Asp Trp Leu Asn Gly Lys Glu Tyr Lys Cys Lys Val Ser
    1760                1765                1770

Asn Lys Ala Leu Pro Ala Pro Ile Glu Lys Thr Ile Ser Lys Ala
    1775                1780                1785

Lys Gly Gln Pro Arg Glu Pro Gln Val Tyr Thr Leu Pro Pro Ser
    1790                1795                1800

Arg Asp Glu Leu Thr Lys Asn Gln Val Ser Leu Thr Cys Leu Val
    1805                1810                1815

Lys Gly Phe Tyr Pro Ser Asp Ile Ala Val Glu Trp Glu Ser Asn
    1820                1825                1830

Gly Gln Pro Glu Asn Asn Tyr Lys Thr Thr Pro Pro Val Leu Asp
    1835                1840                1845

Ser Asp Gly Ser Phe Phe Leu Tyr Ser Lys Leu Thr Val Asp Lys
    1850                1855                1860

Ser Arg Trp Gln Gln Gly Asn Val Phe Ser Cys Ser Val Met His
    1865                1870                1875

Glu Ala Leu His Asn His Tyr Thr Gln Lys Ser Leu Ser Leu Ser
    1880                1885                1890

Pro Gly Lys
    1895

<210> SEQ ID NO 106
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 106

Leu Pro Xaa Thr Gly
1               5

<210> SEQ ID NO 107
<211> LENGTH: 10
<212> TYPE: PRT
<213> ORGANISM: Artificial Sequence
<220> FEATURE:
<223> OTHER INFORMATION: cysteine containing peptide

<400> SEQUENCE: 107

Gly Gly Gly Ser Gly Cys Gly Gly Gly Ser
1               5                   10

<210> SEQ ID NO 108
<211> LENGTH: 4548
<212> TYPE: DNA
```

<213> ORGANISM: Artificial Sequence
<220> FEATURE:
<223> OTHER INFORMATION: VWF 031

<400> SEQUENCE: 108

```
atgattcctg ccagatttgc cggggtgctg cttgctctgg ccctcatttt gccagggacc      60
ctttgtgcag aaggaactcg cggcaggtca tccacggccc gatgcagcct tttcggaagt     120
gacttcgtca acacctttga tgggagcatg tacagctttg cgggatactg cagttacctc     180
ctggcagggg gctgccagaa acgctccttc tcgattattg gggacttcca gaatggcaag     240
agagtgagcc tctccgtgta tcttggggaa ttttttgaca tccatttgtt tgtcaatggt     300
accgtgacac agggggacca aagagtctcc atgccctatg cctccaaagg gctgtatcta     360
gaaactgagg ctgggtacta caagctgtcc ggtgaggcct atggctttgt ggccaggatc     420
gatggcagcg gcaactttca gtcctgctg tcagacagat acttcaacaa gacctgcggg     480
ctgtgtggca actttaacat ctttgctgaa gatgacttta tgacccaaga agggaccttg     540
acctcggacc cttatgactt tgccaactca tgggctctga cagtggaga acagtggtgt     600
gaacgggcat ctcctcccag cagctcatgc aacatctcct ctggggaaat gcagaagggc     660
ctgtgggagc agtgccagct tctgaagagc acctcggtgt ttgcccgctg ccaccctctg     720
gtggaccccg agccttttgt ggccctgtgt gagaagactt tgtgtgagtg tgctgggggg     780
ctggagtgcg cctgccctgc cctcctggag tacgcccgga cctgtgccca ggagggaatg     840
gtgctgtacg gctggaccga ccacagcgcg tgcagcccag tgtgccctgc tggtatggag     900
tataggcagt gtgtgtcccc ttgcgccagg acctgccaga gcctgcacat caatgaaatg     960
tgtcaggagc gatgcgtgga tggctgcagc tgccctgagg acagctcctg gatgaaggc     1020
ctctgcgtgg agagcaccga gtgtccctgc gtgcattccg gaaagcgcta ccctcccggc     1080
acctccctct ctcgagactg caacacctgc atttgccgaa acagccagtg gatctgcagc     1140
aatgaagaat gtccagggga gtgccttgtc actggtcaat cccacttcaa gagctttgac     1200
aacagatact tcaccttcag tgggatctgc cagtacctgc tggcccggga ttgccaggac     1260
cactccttct ccattgtcat tgagactgtc cagtgtgctg atgaccgcga cgctgtgtgc     1320
acccgctccg tcaccgtccg gctgcctggc ctgcacaaca gccttgtgaa actgaagcat     1380
ggggcaggag ttgccatgga tggccaggac atccagctcc ccctcctgaa aggtgacctc     1440
cgcatccagc atacagtgac ggcctccgtg cgcctcagct acgggaggga cctgcagatg     1500
gactgggatg gccgcgggag gctgctggtg aagctgtccc ccgtctatgc cgggaagacc     1560
tgcggcctgt gtgggaatta caatggcaac cagggcgacg acttccttac ccctctgggg     1620
ctggcggagc ccggggtgga ggacttcggg aacgcctgga agctgcacgg ggactgccag     1680
gacctgcaga agcagcacag cgatcctgc gccctcaacc cgcgcatgac caggttctcc     1740
gaggaggcgt gcgcggtcct gacgtccccc acattcgagg cctgccatcg tgccgtcagc     1800
ccgctgccct acctgcggaa ctgccgctac gacgtgtgct cctgctcgga cggccgcgag     1860
tgcctgtgcg gcgccctggc cagctatgcc gcggcctgcg cgggagagg cgtgcgcgtc     1920
gcgtggcgcg agccaggccg ctgtgagctg aactgcccga aggccaggt gtacctgcag     1980
tgcgggaccc cctgcaacct gacctgccgc tctctctctt acccggatga ggaatgcaat     2040
gaggcctgcc tggagggctg cttctgcccc ccagggctct acatggatga gggggggac     2100
tgcgtgccca aggcccagtg cccctgttac tatgacggtg agatcttcca gccagaagac     2160
atcttctcag accatcacac catgtgctac tgtgaggatg gcttcatgca ctgtaccatg     2220
```

-continued

```
agtggagtcc ccggaagctt gctgcctgac gctgtcctca gcagtcccct gtctcatcgc    2280
agcaaaagga gcctatcctg tcggcccccc atggtcaagc tggtgtgtcc cgctgacaac    2340
ctgcgggctg aagggctcga gtgtaccaaa acgtgccaga actatgacct ggagtgcatg    2400
agcatgggct gtgtctctgg ctgcctctgc cccccgggga tggtccggca tgagaacaga    2460
tgtgtggccc tggaaaggtg tccctgcttc catcagggca aggagtatgc ccctggagaa    2520
acagtgaaga ttggctgcaa cacttgtgtc tgtcgggacc ggaagtggaa ctgcacagac    2580
catgtgtgtg atgccacgtg ctccacgatc ggcatggccc actacctcac cttcgacggg    2640
ctcaaatacc tgttccccgg ggagtgccag tacgttctgg tgcaggatta ctgcggcagt    2700
aaccctggga cctttcggat cctagtgggg aataagggat gcagccaccc ctcagtgaaa    2760
tgcaagaaac gggtcaccat cctggtggag ggaggagaga ttgagctgtt tgacggggag    2820
gtgaatgtga agaggcccat gaaggatgag actcactttg aggtggtgga gtctggccgg    2880
tacatcattc tgctgctggg caaagccctc tccgtggtct gggaccgcca cctgagcatc    2940
tccgtggtcc tgaagcagac ataccaggag aaagtgtgtg gcctgtgtgg gaattttgat    3000
ggcatccaga caatgaccct caccagcagc aacctccaag tggaggaaga ccctgtggac    3060
tttgggaact cctggaaagt gagctcgcag tgtgctgaca ccagaaaagt gcctctggac    3120
tcatcccctg ccacctgcca taacaacatc atgaagcaga cgatggtgga ttcctcctgt    3180
agaatcctta ccagtgacgt cttccaggac tgcaacaagc tggtggaccc cgagccatat    3240
ctggatgtct gcatttacga cacctgctcc tgtgagtcca ttggggactg cgccgcattc    3300
tgcgacacca ttgctgccta tgcccacgtg tgtgcccagc atggcaaggt ggtgacctgg    3360
aggacggcca cattgtgccc ccagagctgc gaggagagga tctccgggga gaacgggtat    3420
gaggctgagt ggcgctataa cagctgtgca cctgcctgtc aagtcacgtg tcagcaccct    3480
gagccactgg cctgccctgt gcagtgtgtg gagggctgcc atgccactg ccctccaggg    3540
aaaatcctgg atgagctttt gcagacctgc gttgaccctg aagactgtcc agtgtgtgag    3600
gtggctggcc ggcgttttgc ctcaggaaag aaagtcacct tgaatcccag tgaccctgag    3660
cactgccaga tttgccactg tgatgttgtc aacctcacct gtgaagcctg ccaggagccg    3720
atatctggcg gtggaggttc cggtggcggg ggatccggcg gtggaggttc cggcggtgga    3780
ggttccggtg gcgggggatc cggtggcggg ggatccctgg tcccccgggg cagcggcggt    3840
ggaggttccg gtggcggggg atccgacaaa actcacacat gcccaccgtg cccagctcca    3900
gaactcctgg gcgaccgtc agtcttcctc ttccccccaa aacccaagga caccctcatg    3960
atctcccgga cccctgaggt cacatgcgtg gtggtggacg tgagccacga agaccctgag    4020
gtcaagttca actggtacgt ggacggcgtg gaggtgcata atgccaagac aaagccgcgg    4080
gaggagcagt acaacagcac gtaccgtgtg gtcagcgtcc tcaccgtcct gcaccaggac    4140
tggctgaatg gcaaggagta caagtgcaag gtctccaaca aagccctccc agcccccatc    4200
gagaaaacca tctccaaagc caaagggcag ccccgagaac cacaggtgta caccctgccc    4260
ccatcccggg atgagctgac caagaaccag gtcagcctga cctgcctggt caaaggcttc    4320
tatcccagcg acatcgccgt ggagtgggag agcaatggg agccggagaa caactacaag    4380
accacgcctc ccgtgttgga ctccgacggc tccttcttcc tctacagcaa gctcaccgtg    4440
gacaagagca ggtggcagca ggggaacgtc ttctcatgct ccgtgatgca tgaggctctg    4500
cacaaccact acacgcagaa gagcctctcc ctgtctccgg gtaaatga                 4548
```

<210> SEQ ID NO 109
<211> LENGTH: 1515
<212> TYPE: PRT
<213> ORGANISM: Artificial Sequence
<220> FEATURE:
<223> OTHER INFORMATION: VWF 031

<400> SEQUENCE: 109

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365
```

```
Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
                435                 440                 445

Pro Gly Leu His Asn Ser Leu Val Lys Leu Lys His Gly Ala Gly Val
    450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
    515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
                580                 585                 590

Glu Ala Cys His Arg Ala Val Ser Pro Leu Pro Tyr Leu Arg Asn Cys
            595                 600                 605

Arg Tyr Asp Val Cys Ser Cys Ser Asp Gly Arg Glu Cys Leu Cys Gly
            610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
                660                 665                 670

Ser Tyr Pro Asp Glu Glu Cys Asn Glu Ala Cys Leu Glu Gly Cys Phe
            675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
                755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
```

-continued

```
785                 790                 795                 800
Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
                820                 825                 830

Gly Lys Glu Tyr Ala Pro Gly Glu Thr Val Lys Ile Gly Cys Asn Thr
                835                 840                 845

Cys Val Cys Arg Asp Arg Lys Trp Asn Cys Thr Asp His Val Cys Asp
850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
                900                 905                 910

Gly Cys Ser His Pro Ser Val Lys Cys Lys Lys Arg Val Thr Ile Leu
                915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
                980                 985                 990

Cys Gly Leu Cys Gly Asn Phe Asp  Gly Ile Gln Asn Asn  Asp Leu Thr
                995                 1000                1005

Ser Ser  Asn Leu Gln Val Glu  Glu Asp Pro Val Asp  Phe Gly Asn
        1010                1015                1020

Ser Trp  Lys Val Ser Ser Gln  Cys Ala Asp Thr Arg  Lys Val Pro
        1025                1030                1035

Leu Asp  Ser Ser Pro Ala Thr  Cys His Asn Asn Ile  Met Lys Gln
        1040                1045                1050

Thr Met  Val Asp Ser Ser Cys  Arg Ile Leu Thr Ser  Asp Val Phe
        1055                1060                1065

Gln Asp  Cys Asn Lys Leu Val  Asp Pro Glu Pro Tyr  Leu Asp Val
        1070                1075                1080

Cys Ile  Tyr Asp Thr Cys Ser  Cys Glu Ser Ile Gly  Asp Cys Ala
        1085                1090                1095

Ala Phe  Cys Asp Thr Ile Ala  Ala Tyr Ala His Val  Cys Ala Gln
        1100                1105                1110

His Gly  Lys Val Val Thr Trp  Arg Thr Ala Thr Leu  Cys Pro Gln
        1115                1120                1125

Ser Cys  Glu Glu Arg Asn Leu  Arg Glu Asn Gly Tyr  Glu Ala Glu
        1130                1135                1140

Trp Arg  Tyr Asn Ser Cys Ala  Pro Ala Cys Gln Val  Thr Cys Gln
        1145                1150                1155

His Pro  Glu Pro Leu Ala Cys  Pro Val Gln Cys Val  Glu Gly Cys
        1160                1165                1170

His Ala  His Cys Pro Pro Gly  Lys Ile Leu Asp Glu  Leu Leu Gln
        1175                1180                1185

Thr Cys  Val Asp Pro Glu Asp  Cys Pro Val Cys Glu  Val Ala Gly
        1190                1195                1200
```

Arg Arg Phe Ala Ser Gly Lys Lys Val Thr Leu Asn Pro Ser Asp
1205                1210                1215

Pro Glu His Cys Gln Ile Cys His Cys Asp Val Val Asn Leu Thr
1220                1225                1230

Cys Glu Ala Cys Gln Glu Pro Ile Ser Gly Gly Gly Ser Gly
1235                1240                1245

Gly Gly Gly Ser Gly Gly Gly Ser Gly Gly Gly Ser Gly
1250                1255                1260

Gly Gly Gly Ser Gly Gly Gly Ser Leu Val Pro Arg Gly Ser
1265                1270                1275

Gly Gly Gly Gly Ser Gly Gly Gly Ser Asp Lys Thr His Thr
1280                1285                1290

Cys Pro Pro Cys Pro Ala Pro Glu Leu Leu Gly Pro Ser Val
1295                1300                1305

Phe Leu Phe Pro Pro Lys Pro Lys Asp Thr Leu Met Ile Ser Arg
1310                1315                1320

Thr Pro Glu Val Thr Cys Val Val Val Asp Val Ser His Glu Asp
1325                1330                1335

Pro Glu Val Lys Phe Asn Trp Tyr Val Asp Gly Val Glu Val His
1340                1345                1350

Asn Ala Lys Thr Lys Pro Arg Glu Glu Gln Tyr Asn Ser Thr Tyr
1355                1360                1365

Arg Val Val Ser Val Leu Thr Val Leu His Gln Asp Trp Leu Asn
1370                1375                1380

Gly Lys Glu Tyr Lys Cys Lys Val Ser Asn Lys Ala Leu Pro Ala
1385                1390                1395

Pro Ile Glu Lys Thr Ile Ser Lys Ala Lys Gly Gln Pro Arg Glu
1400                1405                1410

Pro Gln Val Tyr Thr Leu Pro Pro Ser Arg Asp Glu Leu Thr Lys
1415                1420                1425

Asn Gln Val Ser Leu Thr Cys Leu Val Lys Gly Phe Tyr Pro Ser
1430                1435                1440

Asp Ile Ala Val Glu Trp Glu Ser Asn Gly Gln Pro Glu Asn Asn
1445                1450                1455

Tyr Lys Thr Thr Pro Pro Val Leu Asp Ser Asp Gly Ser Phe Phe
1460                1465                1470

Leu Tyr Ser Lys Leu Thr Val Asp Lys Ser Arg Trp Gln Gln Gly
1475                1480                1485

Asn Val Phe Ser Cys Ser Val Met His Glu Ala Leu His Asn His
1490                1495                1500

Tyr Thr Gln Lys Ser Leu Ser Leu Ser Pro Gly Lys
1505                1510                1515

<210> SEQ ID NO 110
<211> LENGTH: 40
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)..(5)
<223> OTHER INFORMATION: Gly-Gly-Gly-Gly-Ser repeat

<400> SEQUENCE: 110

Gly Gly Gly Gly Ser Gly Gly Gly Gly Ser Gly Gly Gly Gly Ser Gly

```
1               5               10              15
Gly Gly Gly Ser Gly Gly Gly Ser Gly Gly Gly Ser Gly Gly
        20              25              30
Gly Gly Ser Gly Gly Gly Gly Ser
        35              40

<210> SEQ ID NO 111
<211> LENGTH: 62
<212> TYPE: DNA
<213> ORGANISM: Artificial Sequence
<220> FEATURE:
<223> OTHER INFORMATION: ESC54-VWF forward with BsiW1 site

<400> SEQUENCE: 111
cgcttcgcga cgtacggccg ccaccatgat tcctgccaga tttgccgggg tgctgcttgc    60
tc                                                                    62

<210> SEQ ID NO 112
<211> LENGTH: 60
<212> TYPE: DNA
<213> ORGANISM: Artificial Sequence
<220> FEATURE:
<223> OTHER INFORMATION: ESC 124 - D1D2 cloning oligo with Not1 site-
      reverse

<400> SEQUENCE: 112
ctagactcga gcggccgctc accttttgct gcgatgagac agggactgc tgaggacagc     60

<210> SEQ ID NO 113
<211> LENGTH: 2289
<212> TYPE: DNA
<213> ORGANISM: Artificial Sequence
<220> FEATURE:
<223> OTHER INFORMATION: VWF 053 (VWF D1D2-propeptide)

<400> SEQUENCE: 113
atgattcctg ccagatttgc cggggtgctg cttgctctgg ccctcatttt gccagggacc    60
ctttgtgcag aaggaactcg cggcaggtca tccacggccc gatgcagcct tttcggaagt   120
gacttcgtca acacctttga tgggagcatg tacagctttg cgggatactg cagttacctc   180
ctggcagggg gctgccagaa acgctccttc tcgattattg ggacttcca gaatggcaag    240 agagtgagcc tctccgtgta tcttggggaa ttttttgaca tccatttgtt tgtcaatggt   300
accgtgacac aggggaccaa agagtctccc atgccctatg cctccaaagg gctgtatcta   360
gaaactgagg ctgggtacta caagctgtcc ggtgaggcct atggctttgt ggccaggatc   420
gatggcagcg gcaactttca gtcctgctg tcagacagat acttcaacaa gacctgcggg   480
ctgtgtggca ctttaacat ctttgctgaa gatgacttta tgacccaaga agggaccttg    540
acctcggacc cttatgactt tgccaactca tgggctctga gcagtggaga acagtggtgt   600
gaacgggcat ctcctcccag cagctcatgc aacatctcct ctgggaaat gcagaagggc   660 ctgtgggagc agtgccagct tctgaagagc acctcggtgt tgcccgctg ccaccctctg   720 gtggaccccg agccttttgt ggccctgtgt gagaagactt gtgtgagtg tgctgggggg   780 ctggagtgcg cctgccctgc cctcctggag tacgcccgga cctgtgccca ggagggaatg   840
gtgctgtacg gctggaccga ccacagcgcg tgcagcccag tgtgcctgc tggtatggag   900 tataggcagt gtgtgtcccc ttgcgccagg acctgccaga gcctgcacat caatgaaatg   960
tgtcaggagc gatgcgtgga tggctgcagc tgccctgagg acagctcct ggatgaaggc    1020
```

```
ctctgcgtgg agagcaccga gtgtccctgc gtgcattccg gaaagcgcta ccctcccggc    1080
acctccctct ctcgagactg caacacctgc atttgccgaa acagccagtg gatctgcagc    1140
aatgaagaat gtccagggga gtgccttgtc actggtcaat cccacttcaa gagctttgac    1200
aacagatact tcaccttcag tgggatctgc agtacctgc tggcccggga ttgccaggac     1260
cactccttct ccattgtcat tgagactgtc cagtgtgctg atgaccgcga cgctgtgtgc    1320
acccgctccg tcaccgtccg gctgcctggc ctgcacaaca gccttgtgaa actgaagcat    1380
ggggcaggag ttgccatgga tggccaggac atccagctcc ccctcctgaa aggtgacctc    1440
cgcatccagc atacagtgac ggcctccgtg cgcctcagct acggggagga cctgcagatg    1500
gactgggatg ccgcgggag gctgctggtg aagctgtccc ccgtctatgc cgggaagacc     1560
tgcggcctgt gtgggaatta caatggcaac cagggcgacg acttccttac ccctctgggg    1620
ctggcggagc cccgggtgga ggacttcggg aacgcctgga gctgcacgg ggactgccag     1680
gacctgcaga gcagcacag cgatccctgc gccctcaacc cgcgcatgac caggttctcc     1740
gaggaggcgt gcgcggtcct gacgtccccc acattcgagg cctgccatcg tgccgtcagc    1800
ccgctgccct acctgcggaa ctgccgctac gacgtgtgct cctgctcgga cggccgcgag    1860
tgcctgtgcg gcgccctggc cagctatgcc gcggcctgcg cggggagagg cgtgcgcgtc    1920
gcgtggcgcg agccaggccg ctgtgagctg aactgcccga aaggccaggt gtacctgcag    1980
tgcgggaccc cctgcaacct gacctgccgc tctctctctt accggatgca ggaatgcaat    2040
gaggcctgcc tggagggctg cttctgcccc ccagggctct acatggatga gggggggac    2100
tgcgtgccca aggccagtg cccctgttac tatgacggtg agatcttcca gccagaagac    2160
atcttctcag accatcacac catgtgctac tgtgaggatg gcttcatgca ctgtaccatg    2220
agtggagtcc ccggaagctt gctgcctgac gctgtcctca gcagtccct gtctcatcgc     2280
agcaaaagg                                                              2289
```

<210> SEQ ID NO 114
<211> LENGTH: 763
<212> TYPE: PRT
<213> ORGANISM: Artificial Sequence
<220> FEATURE:
<223> OTHER INFORMATION: VWF 053 (VWF D1D2-Propeptide)

<400> SEQUENCE: 114

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
```

-continued

```
            130                 135                 140
Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Ser Ser
            195                 200                 205

Ser Cys Asn Ile Ser Ser Gly Glu Met Gln Lys Gly Leu Trp Glu Gln
210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
            275                 280                 285

Ser Ala Cys Ser Pro Val Cys Pro Ala Gly Met Glu Tyr Arg Gln Cys
            290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
            355                 360                 365

Thr Cys Ile Cys Arg Asn Ser Gln Trp Ile Cys Ser Asn Glu Glu Cys
370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
            435                 440                 445

Pro Gly Leu His Asn Ser Leu Val Lys Leu Lys His Gly Ala Gly Val
450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
            515                 520                 525

Gly Asn Gln Gly Asp Asp Phe Leu Thr Pro Ser Gly Leu Ala Glu Pro
            530                 535                 540

Arg Val Glu Asp Phe Gly Asn Ala Trp Lys Leu His Gly Asp Cys Gln
545                 550                 555                 560
```

-continued

```
Asp Leu Gln Lys Gln His Ser Asp Pro Cys Ala Leu Asn Pro Arg Met
            565                 570                 575
Thr Arg Phe Ser Glu Glu Ala Cys Ala Val Leu Thr Ser Pro Thr Phe
            580                 585                 590
Glu Ala Cys His Arg Ala Val Ser Pro Leu Pro Tyr Leu Arg Asn Cys
            595                 600                 605
Arg Tyr Asp Val Cys Ser Cys Ser Asp Gly Arg Glu Cys Leu Cys Gly
            610                 615                 620
Ala Leu Ala Ser Tyr Ala Ala Ala Cys Ala Gly Arg Gly Val Arg Val
625                 630                 635                 640
Ala Trp Arg Glu Pro Gly Arg Cys Glu Leu Asn Cys Pro Lys Gly Gln
            645                 650                 655
Val Tyr Leu Gln Cys Gly Thr Pro Cys Asn Leu Thr Cys Arg Ser Leu
            660                 665                 670
Ser Tyr Pro Asp Glu Glu Cys Asn Glu Ala Cys Leu Glu Gly Cys Phe
            675                 680                 685
Cys Pro Pro Gly Leu Tyr Met Asp Glu Arg Gly Asp Cys Val Pro Lys
            690                 695                 700
Ala Gln Cys Pro Cys Tyr Tyr Asp Gly Glu Ile Phe Gln Pro Glu Asp
705                 710                 715                 720
Ile Phe Ser Asp His His Thr Met Cys Tyr Cys Glu Asp Gly Phe Met
            725                 730                 735
His Cys Thr Met Ser Gly Val Pro Gly Ser Leu Leu Pro Asp Ala Val
            740                 745                 750
Leu Ser Ser Pro Leu Ser His Arg Ser Lys Arg
            755                 760
```